US011286518B2

(12) United States Patent
Beckman et al.

(10) Patent No.: US 11,286,518 B2
(45) Date of Patent: Mar. 29, 2022

(54) ANALYTICAL STANDARDS AND METHODS OF USING SAME

(71) Applicant: REGENTS OF THE UNIVERSITY OF MINNESOTA, Minneapolis, MN (US)

(72) Inventors: Kenneth Beckman, Saint Paul, MN (US); Daryl Gohl, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 244 days.

(21) Appl. No.: 16/099,229

(22) PCT Filed: May 5, 2017

(86) PCT No.: PCT/US2017/031271

§ 371 (c)(1),
(2) Date: Nov. 6, 2018

(87) PCT Pub. No.: WO2017/192974

PCT Pub. Date: Nov. 9, 2017

(65) Prior Publication Data

US 2019/0177781 A1 Jun. 13, 2019

Related U.S. Application Data

(60) Provisional application No. 62/332,879, filed on May 6, 2016.

(51) Int. Cl.
*C12Q 1/68* (2018.01)
*C12Q 1/6848* (2018.01)
*C12Q 1/6869* (2018.01)

(52) U.S. Cl.
CPC ............ *C12Q 1/6848* (2013.01); *C12Q 1/68* (2013.01); *C12Q 1/6869* (2013.01)

(58) Field of Classification Search
None
See application file for complete search history.

(56) References Cited

U.S. PATENT DOCUMENTS 6,277,560 B1 8/2001 Andrieu et al.
6,943,242 B2 9/2005 Samartzidou et al.
7,666,592 B2 2/2010 Ecker et al.
7,989,168 B2 8/2011 Fiss et al.
8,143,388 B2 3/2012 Söderlund et al.
8,304,194 B2 11/2012 Cantor et al.
8,691,510 B2 4/2014 Faham et al.
8,715,967 B2 5/2014 Casbon et al.
8,825,411 B2 9/2014 Govindarajan et al.
9,150,905 B2 10/2015 Robins
9,371,558 B2 * 6/2016 Robins ................ C12Q 1/6851
9,404,155 B2 8/2016 Bortner
9,523,129 B2 12/2016 Faham et al.
2004/0175719 A1 9/2004 Christians
2006/0024690 A1 2/2006 Kao et al.
2006/0211030 A1 * 9/2006 Brenner .......... C12Q 2565/125 435/6.1
2015/0017652 A1 1/2015 Robins et al.
2015/0031551 A1 1/2015 Sikora
2015/0031559 A1 1/2015 Casbon et al.
2015/0087537 A1 3/2015 Hubbell
2015/0132754 A1 5/2015 Wang et al.
2015/0211078 A1 7/2015 Apte et al.
2015/0213193 A1 7/2015 Apte et al.
2015/0329890 A9 11/2015 Tian
2016/0017415 A1 1/2016 Van Criekinge
2016/0032282 A1 2/2016 Vigneault et al.
2016/0290132 A1 10/2016 Knight et al.
2016/0319340 A1 11/2016 Robins et al.
2016/0333402 A1 11/2016 Koller et al.
2016/0355873 A1 12/2016 Dzakula

FOREIGN PATENT DOCUMENTS

CN 102344960 2/2012
CN 102517392 6/2012
CN 103589789 2/2014
CN 105331606 2/2016
JP 2000-500007 A 1/2000
JP 2015-204813 A 11/2015
JP 2015-535431 A 12/2015
WO 2013/169957 A1 11/2013
WO WO 2014/082032 A1 5/2014

OTHER PUBLICATIONS

Nelson et al. (PLoS One, 2014, 9(4):e94249, p. 1-14) (Year: 2014).*
Ibarra et al. (EMBO Journal, 2009, 28, 2794-2802) (Year: 2009).*
International Search Report and Written Opinion for PCT/US17/31271 dated Sep. 27, 2017, 13 pages.
16S Metagenomic Sequencing Library Preparation. *Illumina Tech. Note* 15044223 Rev. A.
Ahn et al., Effects of PCR cycle number and DNA polymerase type on the 16S rRNA gene pyrosequencing analysis of bacterial communities. *J Microbiol* 50, 1071-1074 (2012).
Aird et al., Analyzing and minimizing PCR amplification bias in Illumina sequencing libraries. *Genome Biol* 12, R18 (2011).
Ayyadevara et al., Discrimination of primer 3'-nucleotide mismatch by taq DNA polymerase during polymerase chain reaction. *Anal Biochem* 284, 11-18 (2000).
Bartram et al., Generation of multimillion-sequence 16S rRNA gene libraries from complex microbial communities by assembling paired-end illumina reads. *Appl Environ Microbiol* 77, 3846-3852 (2011).

(Continued)

*Primary Examiner* — Stephanie K Mummert
(74) *Attorney, Agent, or Firm* — Mueting Raasch Group

(57) ABSTRACT

Analytical standards can allow one to detect and/or measure sampling, processing, and/or amplification errors in a sample that includes a plurality of polynucleotide molecules. The analytical standards can provide an internal control to detect errors in the representation of the original sample reflected in data obtained after manipulating and/or processing of sample molecules.

19 Claims, 29 Drawing Sheets

Specification includes a Sequence Listing.

(56) References Cited

OTHER PUBLICATIONS

Bolger et al., Trimmomatic: a flexible trimmer for Illumina sequence data. *Bioinformatics* 30, 2114-2120 (2014).
Brooks et al., The truth about metagenomics: quantifying and counteracting bias in 16S rRNA studies. *BMC Microbiol* 15, 66 (2015).
Brown et al., Unusual biology across a group comprising more than 15% of domain Bacteria. *Nature* 523, 208-211 (2015).
Bru et al., Quantification of the detrimental effect of a single primer-template mismatch by real-time PCR using the 16S rRNA gene as an example. *Appl Environ Microbiol* 74, 1660-1663 (2008).
Caporaso et al., QIIME allows analysis of high-throughput community sequencing data. *Nat Methods* 7, 335-336 (2010).
Caporaso et al., Ultra-high-throughput microbial community analysis on the Illumina HiSeq and MiSeq platforms. *ISME J* 6, 1621-1624 (2012).
Cardona et al., Storage conditions of intestinal microbiota matter in metagenomic analysis. *BMC Microbiol* 12, 158 (2012).
Carlson et al., Using synthetic templates to design an unbiased multiplex PCR assay. *Nat Commun* 4, 2680 (2013).
Cho et al., The human microbiome: at the interface of health and disease. *Nat Rev Genet* 13, 260-270 (2012).
Claesson et al., Comparison of two next-generation sequencing technologies for resolving highly complex microbiota composition using tandem variable 16S rRNA gene regions. *Nucleic Acids Res* 38, e200 (2010).
Cock et al., Biopython: freely available Python tools for computational molecular biology and bioinformatics. *Bioinformatics* 25, 1422-1423 (2009).
Crooks et al., WebLogo: a sequence logo generator. *Genome Res* 14, 1188-1190 (2004).
D'Amore et al., A comprehensive benchmarking study of protocols and sequencing platforms for 16S rRNA community profiling, *BMC Genomics* 17, 55 (2016).
Degnan et al., Illumina-based analysis of microbial community diversity. *ISME J* 6, 183-194 (2012).
Desantis et al., Greengenes, a chimera-checked 16S rRNA gene database and workbench compatible with ARB. *Appl Environ Microbiol* 72, 5069-5072 (2006).
Deveson et al., Representing genetic variation with synthetic DNA standards. *Nat Methods* 13, 784-791 (2016).
Eloe-Fadrosh et al., Metagenomics uncovers gaps in amplicon-based detection of microbial diversity. *Nat Microbiol* 1, 15032 (2016).
Fadrosh et al., An improved dual-indexing approach for multiplexed 16S rRNA gene sequencing on the Illumina MiSeq platform. *Microbiome* 2, 6 (2014).
Faith et al., The long-term stability of the human gut microbiota. *Science* 341, 1237439 (2013).
Feinstein et al., Assessment of bias associated with incomplete extraction of microbial DNA from soil. *Appl Environ Microbiol* 75, 5428-5433 (2009).
Gilbert et al., The Earth Microbiome project: successes and aspirations. *BMC Biol* 12, 69 (2014).
Gloor et al., Microbiome profiling by illumina sequencing of combinatorial sequence-tagged PCR products. *PLoS One* 5, e15406 (2010).
Goodrich et al., Conducting a microbiome study. *Cell* 158, 250-262 (2014).
Haas et al., Chimeric 16S rRNA sequence formation and detection in Sanger and 454-pyrosequenced PCR amplicons. *Genome Res* 21, 494-504 (2011).
Hansen et al., Biased 16S rDNA PCR amplification caused by interference from DNA flanking the template region *FEMS Microbiol. Ecol.* 26, 141-149, (2011).
Hardwick et al., Spliced synthetic genes as internal controls in RNA sequencing experiments. *Nat Methods* 13, 792-798 (2016).
Hong et al., Polymerase chain reaction primers miss half of rRNA microbial diversity. *ISME J* 3, 1365-1373 (2009).
Human Microbiome Project "A framework for human microbiome research." 2012, *Nature* 486, 215-21.
Ishii et al., Optimization of annealing temperature to reduce bias caused by a primer mismatch in multitemplate PCR. *Appl Environ Microbiol* 67, 3753-3755 (2001).
Jones et al., Library preparation methodology can influence genomic and functional predictions in human microbiome research. *Proc Natl Acad Sci U S A* 112, 14024-14029 (2015).
Jumpstart Consortium Human Microbiome Project Data Generation Working, Evaluation of 16S rDNA-based community profiling for human microbiome research. *PLoS One* 7, e39315 (2012).
Kennedy et al., Evaluating bias of illumina-based bacterial 16S rRNA gene profiles. *Appl Environ Microbiol* 80, 5717-5722 (2014).
Kennedy et al., The impact of different DNA extraction kits and laboratories upon the assessment of human gut microbiota composition by 16S rRNA gene sequencing. *PLoS One* 9, e88982 (2014).
Klindworth et al., Evaluation of general 16S ribosomal RNA gene PCR primers for classical and next-generation sequencing-based diversity studies. *Nucleic Acids Res* 41, e1 (2013).
Kozich et al., Development of a dual-index sequencing strategy and curation pipeline for analyzing amplicon sequence data on the MiSeq Illumina sequencing platform, *Appl Environ Microbiol* 79, 5112-5120 (2013).
Kuczynski et al., Experimental and analytical tools for studying the human microbiome. *Nat Rev Genet* 13, 47-58 (2011).
Kunkel et al., DNA replication fidelity. *Annu Rev Biochem* 69, 497-529 (2000).
Lahr et al., Reducing the impact of PCR-mediated recombination in molecular evolution and environmental studies using a new-generation high-fidelity DNA polymerase. *Biotechniques* 47, 857-866 (2009).
Langmead et al., Fast gapped-read alignment with Bowtie 2. *Nat Methods* 9, 357-359 (2012).
Lee et al., Groundtruthing next-gen sequencing for microbial ecology-biases and errors in community structure estimates from PCR amplicon pyrosequencing. *PLoS One* 7, e44224 (2012).
Lundberg et al., Practical innovations for high-throughput amplicon sequencing. *Nat Methods* 10, 999-1002 (2013).
Mao et al., Coverage evaluation of universal bacterial primers using the metagenomic datasets. *BMC Microbiol* 12, 66 (2012).
Martin, "Cutadapt removes adapter sequences from high-throughput sequencing reads" *EMBnet.journal*, 2011; 17(1):10-12. Accessed online Nov. 30, 2020 <journal.embnet.org/index.php/embnetjournal/article/view/200/479>.
Masella et al., PANDAseq: paired-end assembler for illumina sequences. *BMC Bioinformatics* 13, 31 (2012).
Nelson et al., Analysis, optimization and verification of Illumina-generated 16S rRNA gene amplicon surveys. *PLoS One* 9, e94249 (2014).
Patin et al., Effects of OTU clustering and PCR artifacts on microbial diversity estimates. *Microb Ecol* 65, 709-719 (2013).
Pinto et al., PCR biases distort bacterial and archaeal community structure in pyrosequencing datasets. *PLoS One* 7, e43093 (2012).
Polz et al., Bias in template-to-product ratios in multitemplate PCR. *Appl Environ Microbiol* 64, 3724-3730 (1998).
Quail et al., Optimal enzymes for amplifying sequencing libraries. *Nat Methods* 9, 10-11 (2011).
Reysenbach et al., Differential amplification of rRNA genes by polymerase chain reaction. *Appl Environ Microbiol* 58, 3417-3418 (1992).
Sabat et al., Selective and sensitive method for PCR amplification of *Escherichia coli* 16S rRNA genes in soil. *Appl Environ Microbiol* 66, 844-849 (2000).
Salipante et al., Performance comparison of Illumina and ion torrent next-generation sequencing platforms for 16S rRNA-based bacterial community profiling. *Appl Environ Microbiol* 80, 7583-7591 (2014).
Salter et al., Reagent and laboratory contamination can critically impact sequence-based microbiome analyses. *BMC Biol* 12, 87 (2014).
Schirmer et al., Insight into biases and sequencing errors for amplicon sequencing with the Illumina MiSeq platform. *Nucleic Acids Res* 43, e37 (2015).

(56) References Cited

OTHER PUBLICATIONS

Schloss et al., Reducing the effects of PCR amplification and sequencing artifacts on 16S rRNA-based studies. *PLoS One* 6, e27310 (2011).
Schloss et al., Introducing mothur: open-source, platform-independent, community-supported software for describing and comparing microbial communities. *Appl Environ Microbiol* 75, 7537-7541 (2009).
Sinha et al., The microbiome quality control project: baseline study design and future directions. *Genome Biol* 16, 276 (2015).
Suzuki et al., Bias caused by template annealing in the amplification of mixtures of 16S rRNA genes by PCR. *Appl Environ Microbiol* 62, 625-630 (1996).
Wagner et al., Surveys of Gene Families Using Polymerase Chain Reaction: PCR Selection and PCR Drift *Syst Biol*, 43(2), 250-61 (1994).
Wang et al., The frequency of chimeric molecules as a consequence of PCR co-amplification of 16S rRNA genes from different bacterial species. *Microbiology (Reading)* 142 (Pt 5), 1107-1114 (1996).
Wang et al., Frequency of formation of chimeric molecules as a consequence of PCR coamplification of 16S rRNA genes from mixed bacterial genomes. *Appl Environ Microbiol* 63, 4645-4650 (1997).
Wu et al., Effects of polymerase, template dilution and cycle number on PCR based 16 S rRNA diversity analysis using the deep sequencing method. *BMC Microbiol* 10, 255 (2010).
Yu et al., Improved extraction of PCR-quality community DNA from digesta and fecal samples. *Biotechniques* 36, 808-812 (2004).
Yuan et al., Evaluation of methods for the extraction and purification of DNA from the human microbiome. *PLoS One* 7, e33865 (2012).
Zhang et al., PEAR: a fast and accurate Illumina Paired-End reAd mergeR. *Bioinformatics* 30, 614-620 (2014).
Zhao et al., Effect of sample storage conditions on culture-independent bacterial community measures in cystic fibrosis sputum specimens. *J Clin Microbiol* 49, 3717-3718 (2011).
Zhou et al., BIPES, a cost-effective high-throughput method for assessing microbial diversity. *ISME J* 5, 741-749 (2011).
Papadopoulou et al., The implications of using mutagenic primers in combination with Taq polymerase having proofreading activity, *Biologicals*, 32, pp. 84-87, (2004).

* cited by examiner

FIG. 2

| | |
|---|---|
| V4_515F | GTGCCAGCAGCCGCGGTAA |
| | ********* |
| F_10_A | GTGCCAGCA**A**CCGCGGTAA |
| F_10_T | GTGCCAGCA**T**CCGCGGTAA |
| F_10_C | GTGCCAGCA**C**CCGCGGTAA |
| F_11_A | GTGCCAGCAG**A**CGCGGTAA |
| F_11_T | GTGCCAGCAG**T**CGCGGTAA |
| F_11_G | GTGCCAGCAG**G**CGCGGTAA |
| F_12_A | GTGCCAGCAGC**A**GCGGTAA |
| F_12_T | GTGCCAGCAGC**T**GCGGTAA |
| F_12_G | GTGCCAGCAGC**G**GCGGTAA |
| F_13_A | GTGCCAGCAGCC**A**CGGTAA |
| F_13_T | GTGCCAGCAGCC**T**CGGTAA |
| F_13_C | GTGCCAGCAGCC**C**CGGTAA |
| F_14_A | GTGCCAGCAGCCG**A**GGTAA |
| F_14_T | GTGCCAGCAGCCG**T**GGTAA |
| F_14_G | GTGCCAGCAGCCG**G**GGTAA |
| F_15_A | GTGCCAGCAGCCGC**A**GTAA |
| F_15_T | GTGCCAGCAGCCGC**T**GTAA |
| F_15_C | GTGCCAGCAGCCGC**C**GTAA |
| F_16_A | GTGCCAGCAGCCGCG**A**TAA |
| F_16_T | GTGCCAGCAGCCGCG**T**TAA |
| F_16_C | GTGCCAGCAGCCGCG**C**TAA |
| F_17_A | GTGCCAGCAGCCGCGG**A**AA |
| F_17_G | GTGCCAGCAGCCGCGG**G**AA |
| F_17_C | GTGCCAGCAGCCGCGG**C**AA |
| F_18_T | GTGCCAGCAGCCGCGGT**T**A |
| F_18_G | GTGCCAGCAGCCGCGGT**G**A |
| F_18_C | GTGCCAGCAGCCGCGGT**C**A |
| F_19_T | GTGCCAGCAGCCGCGGTA**T** |
| F_19_G | GTGCCAGCAGCCGCGGTA**G** |
| F_19_C | GTGCCAGCAGCCGCGGTA**C** |

UMGC_233 SGI-DNA pTOPO digest tests

Lane 1 – Ladder
Lane 2 – pTOPO-11_HPy_V4_TCT_A_well_C02, EcoRI digest (*Note: V4 for this standard contains *EcoRI* site)
Lane 3 – pTOPO-11_HPy_V4_TCT_A_well_C02, MlyI digest
Lane 4 – pTOPO-12_LGa_V4_TCT_A_well_D02, EcoRI digest
Lane 5 – pTOPO-12_LGa_V4_TCT_A_well_D02, MlyI digest

*NOTE: *MlyI* Illumina adapter barcode fragment is 148 bp (bottom band)

FIG. 5
% abundance
0
1
2
3
4
6
7
>01_ABa_V4_TCT_A
>02_BCe_V4_TCT_B
>03_BVu_V4_TCT_A
>06_CBe_V4_TCT_A
>08_DRa_V4_TCT_B
>09_EFa_V4_TCT_A
>10_ECo_V4_TCT_C
>11_HPy_V4_TCT_A
>12_LGa_V4_TCT_B
>13_NMe_V4_TCT_A
>14_PAc_V4_TCT_C
>15_PAr_V4_TCT_A
>16_RSp_V4_TCT_A
>17_SAu_V4_TCT_A
>18_SEp_V4_TCT_A
>19_SAg_V4_TCT_A
>20_SMu_V4_TCT_A
>21_SPn_V4_TCT_A
>22_AOd_V4_TCT_A
>23_LMo_V4_TCT_B

FIG. 23

A) An example of five Diversity Standard Sets

| SET ID | TAG IDs | CONCENTRATION IN POOL OF SETS | FREQUENCY OF EACH TAG IN POOL OF ALL SETS |
|---|---|---|---|
| SET A: | Tags #1-#9 | 1 μM | 10% |
| SET B: | Tags #10-#18 | 0.1 μM | 1% |
| SET C: | Tags #19-#26 | 0.01 μM | 0.1% |
| SET D: | Tags #27-#36 | 0.001 μM | 0.01% |
| SET E: | Tags #37-#45 | 0.0001 μM | 0.001% |

B) Constriction of diversity as function of population size of diversity pool

| | EXPECTED # TAGS FROM EACH SET | | | | |
|---|---|---|---|---|---|
| POPULATION SIZE | SET A | SET B | SET C | SET D | SET E |
| 100,000 molecules | 90,000 | 9,000 | 900 | 90 | 9 |
| 10,000 molecules | 9,000 | 900 | 90 | 9 | 1 |
| 1,000 molecules | 900 | 90 | 9 | 1 | 0 |
| 100 molecules | 90 | 9 | 1 | 0 | 0 |
| 10 molecules | 9 | 1 | 0 | 0 | 0 |
| 1 molecule | 1 | 0 | 0 | 0 | 0 |

| | NUMBER OF EACH SET'S TAGS DETECTED | | | | |
|---|---|---|---|---|---|
| POPULATION SIZE | SET A | SET B | SET C | SET D | SET E |
| 100,000 molecules | 9/9 | 9/9 | 9/9 | 9/9 | ≤ 9/9 |
| 10,000 molecules | 9/9 | 9/9 | 9/9 | ≤ 9/9 | 1/9 |
| 1,000 molecules | 9/9 | 9/9 | ≤ 9/9 | 1/9 | 0/9 |
| 100 molecules | 9/9 | < 9/9 | 1/9 | 0/9 | 0/9 |
| 10 molecules | < 9/9 | 1/9 | 0/9 | 0/9 | 0/9 |
| 1 molecule | 1/9 | 0/9 | 0/9 | 0/9 | 0/9 |

ANALYTICAL STANDARDS AND METHODS OF USING SAME

CROSS-REFERENCE TO RELATED APPLICATION

This application is the § 371 U.S. National Stage of International Application No. PCT/US17/31721, filed May 5, 2017, which claims priority to U.S. Provisional Patent Application No. 62/332,879, filed May 6, 2016, each of which is incorporated by reference herein in its entirety.

GOVERNMENT SUPPORT STATEMENT

This invention was made with government support under TR000114 awarded by the National Institutes of Health. The government has certain rights in the invention.

SEQUENCE LISTING

This application contains a Sequence Listing electronically submitted via EFS-Web to the United States Patent and Trademark Office as an ASCII text file entitled "2017-05-05-SequenceListing_ST25.txt" having a size of 313 kilobytes and created on May 5, 2017. The information contained in the Sequence Listing is incorporated by reference herein.

SUMMARY

This disclosure describes, generally, analytical standards that allow one to detect and/or measure sampling, processing, and/or amplification errors in a sample that includes a plurality of polynucleotide molecules.

In one aspect, this disclosure describes a method for measuring and correcting amplification bias in a sample. Generally, the method includes obtaining that includes polynucleotide molecules; spiking the sample with at least one synthetic standard that detects amplification bias between two sample polynucleotides; amplifying polynucleotides in the spiked sample; sequencing a first sample polynucleotide, a second sample polynucleotide, and the standard; measuring the frequency of occurrence of the synthetic standard polynucleotide, the first sample polynucleotide, and the second sample polynucleotide; comparing the measured occurrence of the synthetic standard polynucleotide to an expected frequency of occurrence of the synthetic standard polynucleotide, thereby generating a synthetic standard polynucleotide bias value; and correcting the frequency of occurrence of the first sample polynucleotide and the second sample polynucleotide according to the synthetic standard polynucleotide bias value.

In another aspect, this disclosure describes another method of determining amplification bias among a plurality of polynucleotides. Generally, the method includes amplifying a plurality of polynucleotides in a sample that includes a first sample polynucleotide, a second sample polynucleotide, and a plurality of synthetic standard polynucleotides, wherein the plurality of synthetic standards include a first synthetic standard polynucleotide and a second synthetic standard polynucleotide that differs from the first synthetic standard polynucleotide in G-C content, secondary structure, amplicon size, or degree of mismatch to a primer sequence;

sequencing the first sample polynucleotide, the second sample polynucleotide, and the plurality of synthetic standard polynucleotides; measuring the frequency of occurrence of the first sample polynucleotide, the second sample polynucleotide, the first synthetic standard polynucleotide, and the second synthetic standard polynucleotide; comparing the measured occurrence of the first synthetic standard polynucleotide with an expected frequency of occurrence of the first synthetic standard polynucleotide, thereby generating a first synthetic standard value; comparing the measured occurrence of the second synthetic standard polynucleotide with an expected frequency of occurrence of the second synthetic standard polynucleotide, thereby generating a second synthetic standard value; and detecting amplification bias if the first synthetic standard value differs from the second synthetic standard value.

In another aspect, this disclosure describes another method of determining amplification bias among a plurality of polynucleotides. Generally, the method includes amplifying a plurality of polynucleotides in a sample that includes a first synthetic polynucleotide having a first PCR-free quantitation tag and a second synthetic polynucleotide comprising a second PCR-free quantitation tag; digesting the first synthetic polynucleotide to liberate the first PCR-free quantitation tag; digesting the second synthetic polynucleotide to liberate the second PCR-free quantitation tag; sequencing the first PCR-free quantitation tag and the second PCR-free quantitation tag; and measuring the abundance of the first PCR-free quantitation tag and the second PCR-free quantitation tag.

In another aspect, this disclosure describes a method for detecting sub-sampling error in a sample that includes a plurality of polynucleotides. Generally, the method includes obtaining a sample that includes at least a first sample polynucleotide and a second sample polynucleotide; spiking the sample with at least one synthetic diversity standard designed to detect sub-sampling error; amplifying polynucleotides in the spiked sample; sequencing a first sample polynucleotide, a second sample polynucleotide, and the at least one synthetic diversity standard; measuring the frequency of occurrence of the synthetic diversity standard polynucleotide; comparing the measured occurrence of the synthetic diversity standard polynucleotide to an expected frequency of occurrence of the synthetic diversity standard polynucleotide; and detecting sub-sampling error in the sample if the measured occurrence of the synthetic diversity standard is less than the expected frequency of occurrence of the synthetic diversity standard polynucleotide.

In various embodiments of the various methods summarized above, the synthetic standard polynucleotide can include 16S rRNA gene nucleotides.

In various embodiments of the various methods summarized above, the synthetic standard polynucleotide can include a plurality of different synthetic standard polynucleotides. In some of these embodiments, the different synthetic standard polynucleotides can include differences designed to detect different biases in amplification. For example, a first synthetic standard polynucleotide and a second synthetic standard polynucleotide can differ in G-C content, secondary structure, amplicon size, or degree of mismatch to a primer sequence.

In various embodiments of the various methods summarized above, the synthetic standard polynucleotide can include a primer editing standard.

In various embodiments of the various methods summarized above, the synthetic standard polynucleotide can include a polynucleotide obtained from a biological standard organism that is added to the sample.

In various embodiments of the various methods summarized above, the synthetic standard polynucleotide can include a circular polynucleotide.

In various embodiments of the various methods summarized above, the synthetic standard polynucleotide is spiked into a sample at a defined level in order to measure the absolute or relative abundance of polynucleotides in the sample.

In various embodiments of the various methods summarized above, a plurality of synthetic standard polynucleotides are spiked into a sample at a plurality of defined concentrations in order to measure a limit of detection.

In various embodiments of the various methods summarized above, amplifying the polynucleotides can include using a single set of primers.

In various embodiments of the various methods summarized above, the synthetic standard polynucleotide can include a feature allowing PCR-free quantitation of the synthetic standard. For example, the feature allowing PCR-free quantitation of the synthetic standard can include a barcode.

In various embodiments of the various methods summarized above, the first sample polynucleotide can be from a first microbe and the second sample polynucleotide can be from a second microbe.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 2. Design of the 16S rRNA gene V4 515F region primer editing standards (SEQ ID NOs:288-318). Primer mismatches are shaded.

FIG. 23. The design and use of diversity standard sets. (A) An example of the design of five diversity standard sets, each containing an equimolar pool of nine diversity standards (FIG. 22). Each diversity standard set is combined at a different concentration into a super pool of all five sets, such that the frequency of each tag in each set is known. For example, all tags in Set A are present at 10%, all tags in Set B are present at 1%, and so on. (B). An illustration of the loss of sequence tag diversity experienced as a result of constricting the population size of molecules of the pool of diversity standard sets.

DETAILED DESCRIPTION OF ILLUSTRATIVE EMBODIMENTS

Figure 1:
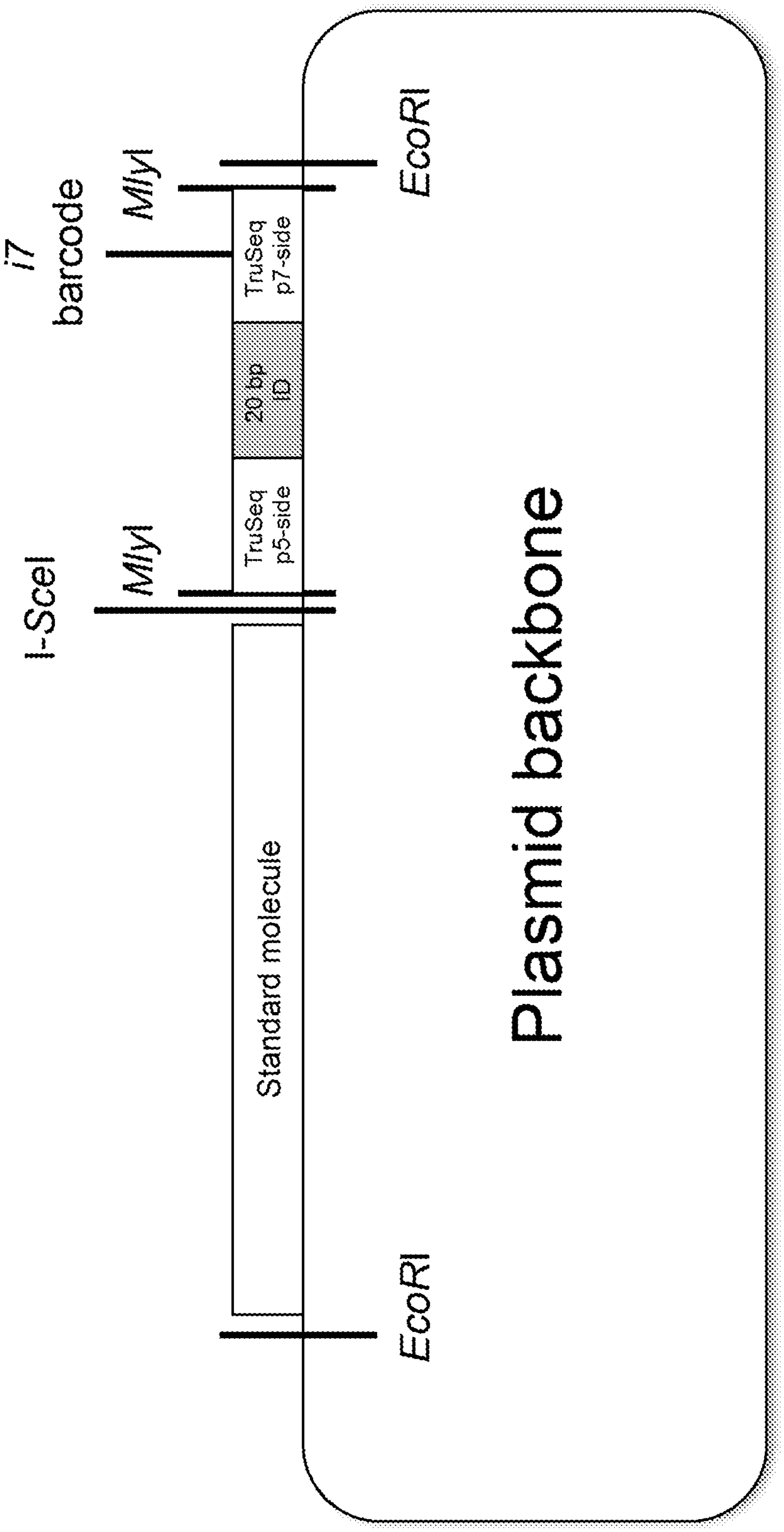
FIG. 1. Design of an exemplary standard construct containing a standard molecule, homing endocuclease I-SceI site for plasmid linearization, and MlyI-flanked PCR-free Illumina sequencing cassette for sequencing-based quantification of standards and standard pools.

This disclosure describes several analytical standards for quantifying and correcting errors and biases in amplicon-based analyses that include an amplification component such as, for example, microbiome experiments and/or quantification experiments that have an amplification component, such as Tn-Seq or pooled RNA interference or CRISPR-Cas9 screens.

The analytical standards used in a particular application can be synthetic nucleic acid standards or biological (recombinant organism-based) standards. The analytical standard can be a synthetic standard or a biological standard. A biological standard can be a recombinant organism that includes any type of synthetic standard sequence. The biological standard can further include an additional synthetic sequence designed specifically to permit one to measure the efficiency of extracting and recovering nucleic acids from the biological standard cells.

A synthetic standard can be a standalone reagent that is amplified in isolation, or it can be a "spike-in" standard that is added to a sample to monitor and/or control errors and biases that occur during the amplification and subsequent processing of the sample. For example, a synthetic spike-in standard can include modified 16S rRNA gene nucleotides that are designed to be spiked into amplification reactions. While discussed below in the context of an exemplary embodiment in which the synthetic standard includes modified 16S rRNA gene nucleotides, the synthetic standard can include nucleotides from any suitable marker gene such as, for example, 18S rRNA or internal transcribed spacer (ITS) for eukaryotes.

In some embodiments when used as a "spike-in" standard, the synthetic standard molecules may be added to a sample to provide ratio of standard polynucleotide to sample polynucleotide (standard polynucleotide:sample polynucleotide ratio) of, for example, from 1:10,000 to 100:1. For example, the synthetic standard can be added to a sample to provide a minimum standard polynucleotide:sample polynucleotide ratio of at least 1:10,000, at least 1:5,000, at least 1:1000, at least 1:500, 1:100, at least 1:50, at least 1:10, at least 1:5, at least 1:1, at least 5:1, at least 10:1, or at least 50:1. The synthetic standard can be added to a sample to provide a maximum standard polynucleotide:sample polynucleotide ratio of no more than 100:1, no more than 50:1, no more than 10:1, no more than 5:1, no more than 1:1, no more than 1:5, no more than 1:10, or no more than 1:50. The synthetic standard can be added to a sample to provide a standard polynucleotide:sample polynucleotide ratio defined by a range having as endpoints any minimum standard polynucleotide:sample polynucleotide ratio set forth above and any maximum standard polynucleotide:sample polynucleotide ratio set forth above that is greater than the minimum standard polynucleotide:sample polynucleotide ratio.

In other embodiments when used as a spike-in standard, the synthetic standard molecule (or molecules) may be added to a sample in an amount of from one molecule to 100,000 molecules. For example, the synthetic standard molecule (or molecules) may be provided in a minimum amount of at least one molecule, at least ten molecules, at least 100 molecules, at least 500 molecules, at least 1000 molecules, at least 5000 molecules, or at least 10,000 molecules. The synthetic standard molecule (or molecules) may be provided in a maximum amount of no more than 100,000 molecules, no more than 50,000 molecules, no more than 10,000 molecules, no more than 5000 molecules, no more than 1000 molecules, no more than 500 molecules, no more than 100 molecules, no more than 50 molecules, or no more than 10 molecules. The synthetic standard can be added to a sample to provide the synthetic standard molecule (or molecules) within a range having as endpoints any minimum amount of standard synthetic molecule (or molecules) set forth above and any maximum amount of synthetic standard molecules set forth above that is greater than the minimum amount of synthetic standard molecule (or molecules).

Regardless of whether a synthetic standard is designed to be a standalone reagent or a spike-in standard, a synthetic standard can be one or more of the following types of sequence-specific standard: a quantitative bias standard, a process standard, a primer editing standard, and/or a diversity standard. As used herein, a quantitation bias standard is designed to measure sequence-specific quantitative amplification errors and biases that can differentially affect the amplification efficiency of sequences from different biological species. As used herein, a process standard is designed to assess the effect of sequence characteristics on amplification bias. As used herein, a primer editing standard is designed to measure the occurrence and extent of primer editing by DNA polymerase during amplification. As used herein, a diversity standard is designed to measure bottlenecks in populations of molecules during laboratory processing.

Process standards can include a collection of molecules that vary systematically in many different sequence properties that can affect amplification. Exemplary properties that can affect amplification include, for example, GC content, secondary structure, amplicon size, and/or the extent of mismatches to primer sequences. Process standards can be designed to be run in parallel to experimental samples in order to detect systematic biases in the amplification process.

Primer editing standards can include 16S rRNA gene nucleotide sequences that are modified to differ systematically in their primer binding sites and report on the efficacy of primer editing in the PCR reaction. Primer editing standards can be spiked into an amplification reaction. Again, while discussed below in the context of an exemplary embodiment in which the synthetic standard includes modified 16S rRNA gene nucleotides, the synthetic standard can include nucleotides from any suitable marker gene such as, for example, 18S rRNA gene or internal transcribed spacer (ITS) for eukaryotes.

Diversity standards can include a population of unique sequence tags at known concentrations in a mixture, such that these standards can be used to report on the absolute size (i.e., number of molecules) of a population of molecules, as well as constrictions ("bottlenecks") that occur in that population during its manipulation. If the population size (number of molecules) is reduced to a number that is below the number of diversity tags, the diversity of tags will be permanently reduced by the stochastic loss of some of the tags from the mixture. The likelihood of "drop-out" of tags will increase as the population size approaches the tag diversity.

Furthermore, diversity tag sets can be designed to permit the measurement of molecular population size across a broad range, by mixing such diversity tag sets across a range of relative concentration (e.g., two-fold dilutions in concentration for each set), such that the loss of diversity is observed first for sets at lower relative concentration.

When diversity standards or diversity standard sets are spiked into a sample that is subjected to serial manipulation, they permit the integrative assessment of population "bottlenecking" during those manipulations by measuring the recovery of the diversity standards or diversity standard sets at a final point following the manipulation, for example, by next-generation sequencing.

Abundance standards can be a collection of molecules that are spiked into a sample to allow for absolute or relative quantification of sample template molecules.

Biological standards can be used to detect biases in extraction and can be spiked into samples prior to extraction to monitor the efficiency of DNA extraction from different types of microbes, including gram negative bacteria, gram positive bacteria, fungi, or other microorganism. A biological standard can include one or more organisms with distinct membrane properties that are designed, for example, to include unique sequence tags that can be amplified and quantified. In these embodiments, the sequence tag can be, for example, an edited 16S rRNA gene polynucleotide or a distinct sequence. In other embodiments, such unique tags could be diversity standards or diversity standard sets designed to measure population sizes and bottlenecks in population size, allow for absolute or relative quantification, or to assess limits of detection. A biological standard may be replication-defective or otherwise inactivated so that they cannot be "re-grown" by a consumer when provided in a commercial analytical kit. In other instances, a biological standard can be replication competent and designed to report on bacterial growth that occurred in transit or storage of samples.

Various embodiments of the standards and methods described herein can provide one or more of the following properties. First, certain standards and methods can correct biases due to differences in amplification efficiency between different primer sets for known targets. The standards and methods can correct for biases due to amplicon properties using a single set of primers. Second, by incorporating more than one type of standard, certain standards and methods described herein allow one to measure and correct biases due to intrinsic biophysical properties of the template molecules and/or additional types of PCR artifact—e.g., such as drop out due to primer mismatches. Third, certain synthetic standards incorporate PCR-free quantification barcodes that allow for, for example, accurate quantification of the standard molecules. Fourth, diversity standards and standard sets allow for the detection and semi-quantitative measurement of artifacts introduced by bottlenecks in the molecular population size during sample processing.

The design of constructs for exemplary nucleotide standards is illustrated in FIG. 1. After synthesis, the standards may be cloned into a plasmid and transformed into a host cell (e.g., *E. coli*) for propagation. The constructs include (1) the standard sequence, (2) a restriction site for optionally linearizing the plasmid prior to amplification, and (3) a barcode. The standard sequence can include any one or more of the nucleotide standards summarized above—i.e., a synthetic amplification bias standard, process standard, primer editing standard, and/or diversity standard. In some embodiments, the restriction site can include the recognition sequence for a homing endonuclease such as, for example, I-SceI. When the restriction site is present, the site can be recognized by any suitable restriction endonuclease, so long as the recognition sequence for the restriction endonuclease is not present between the amplification primers.

In the embodiment illustrated in FIG. 1, the construct includes a 12 bp i7 barcode: AATCAGTCTCGT (SEQ ID NO:7). The particular barcode sequence can be arbitrary.

In addition, for embodiments that allow PCR-free quantification, the construct can include an additional barcode sequence that enables direct PCR-free quantification of the standard molecules. In some embodiments, the PCR-free quantification barcode can be, for example, a MlyI-flanked Illumina adapter-tagged 20 bp barcode so that the standards can be directly quantified, without PCR amplification, using Illumina sequencing. The PCR-free quantification allows one to improve the accuracy of pools of the synthetic standards. Conventional methods for quantifying the standard pools would be to perform quantitative PCR, which can introduce bias into the analysis and, therefore, can result in an inaccurate concentration measurement. The exemplary embodiment illustrated in FIG. 1 includes a 148 bp barcode sequence, which is typically distinct for each synthetic standard, to be liberated by digestion with an appropriate endonuclease—e.g., MlyI as illustrated in FIG. 1. This barcode can, however, be of any suitable length. The liberated molecule can be directly sequenced (e.g., using an Illumina sequencer) with no intervening library preparation or PCR.

Synthetic Spike-in Standards

In some embodiments, a spike-in synthetic standard can include a nucleotide present in all organisms of the sample being subject to the analysis. For example, in some embodiments, the spike-in standard can include a nucleotide that encodes the V4 variable region of the 16S rRNA gene. Synthetic standard molecules were designed for a defined bacterial mock community (made by the Human Microbiome Project) consisting of 20 different organisms present either in equal abundances (an "even mock community") or in varying abundances (a "staggered mock community"). Synthetic standards for each of the unique 16S-V4-encoding regions present in the genomes of the organisms that make up the mock communities were synthesized (see synthetic standards 01-23, below; SEQ ID NO:8 through SEQ ID NO:30). After synthesis, the standards were cloned into a plasmid and transformed into *E. coli*. The 16S V4 region (+20 bp on either side outside of primer sites) was modified to have "TCT" tag at an analogous position for each molecule present in HMP mock community. The modification was made at a highly-conserved position that was identified by aligning 500 16S genes from the Greengenes database using ClustalW. A highly-conserved site within a predicted stem-loop region was chosen to minimize any effects that the "TCT" insertion might have on secondary structure of the synthetic standard molecule. In addition, several molecules were designed to test whether the sequence composition or length of the tag added to the 16S V4 region affects amplification kinetics (testing the following 3 bp tag sequences "TTT", "TCA", "CCC", "GGG", and tags of 1, 2, 5, 7, and 10 bp; see synthetic standards 24-32, below; SEQ ID NO:31 through SEQ ID NO:39).

In other embodiments, the spike-in synthetic standard can include a full-length nucleotide present in all organisms being subject to analysis. Thus, in one embodiment, the synthetic spike-in standard can include a full-length 16S rRNA nucleotide sequence from each of the organisms present in the sample being analyzed. One can assess how closely related the molecules are within a species by, for example, calculating the pair-wise Hamming distances of both the full-length 16S rRNA coding sequence, as well as the V3-V6 variable coding regions. In the exemplary case of 16S rRNA, the Hamming distances indicated that within a single species, the 16S rRNA genes varied by less than 1%, which is typically used as a stringent cut-off for a sequence similarity in defining Operational Taxonomic Units (OTUs). Thus, standards can be designed based on one representative sequence per organism (e.g., a sequence with the lowest cumulative Hamming distance from all other 16S rRNA sequences from a given organism) as the basis for the full-length standards.

To use these full-length standards to assess the effect of the primary sequence or position of the 3 bp exogenous sequence tag on the ability of the standards to model the template-specific PCR biases, three different 3 bp tags, "TAG", "TCT", and "CAT", were inserted into highly-conserved segments of the V3, V4, and V5 regions, respectively (Synthetic standards 78-97, below; SEQ ID NO:85 through SEQ ID NO:104). In addition to the tagged full-length synthetic standards targeting the HMP mock community organisms, another 25 tagged full-length synthetic standards for common human gut microbes were made (Synthetic standards 208-232, below, SEQ ID NO:215 through SEQ ID NO:239).

To test the efficacy of using synthetic standards to correct for amplification biases, even mock community DNA and staggered mock community DNA were amplified using a range of template concentrations and two different enzymes (KAPA HiFi and 5 PRIME Taq). Different amounts and different relative abundances of synthetic standard DNA were spiked into mock community samples (0, 25, 250, and 2500 standard molecules per organism). Samples were amplified using primers that amplify the 16S rRNA gene V4 region and also contain adapter tails. Following the primary amplification, the amplicons were diluted 1:100 in nuclease free water and amplified for an additional 10 cycles using indexing primers that target the adapter tails and add the flow cell adapters and indices required for Illumina sequencing. After the indexing PCR, the reactions were normalized using SequalPrep plates, pooled, and cleaned up and concentrated with 1.8×AmPure XP beads. The pool was then quantified with PicoGreen, diluted to 8 pM, and sequenced on a portion of a MiSeq 2×300 bp run.

After sequencing, the reads for each sample were split into two files using a custom script. One file contained the synthetic standard reads which were identified by the "TCT" tag that was added, and was mapped to a reference file containing the standard sequences. The other file contained the remaining reads and was mapped to a reference file containing the mock community sequences.

Figure 6:
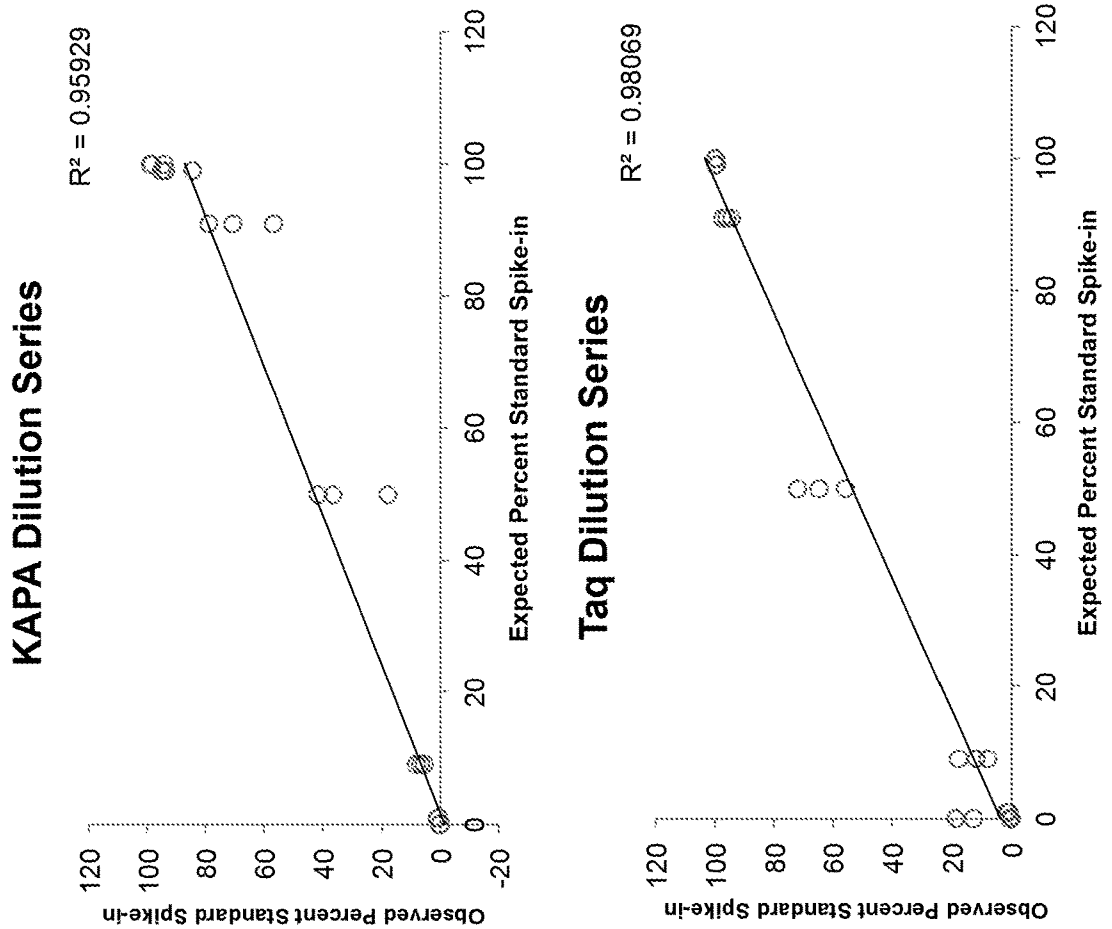
FIG. 6. Percentages of reads corresponding to the spike-in synthetic standards in mock community sequencing datasets correlate well with expected (targeted) percentages.

Based on the relative number of reads assigned to the standard file and mock community file, the relative concentration of spike-in molecules to mock community molecules was well targeted (FIG. 6). The ability to target this ratio correctly allows one to sequence the standard molecules deeply enough to accurately quantify the abundances of the standard molecules, but not so deeply that the standard reads swamp the sample being investigated.

Figure 7:
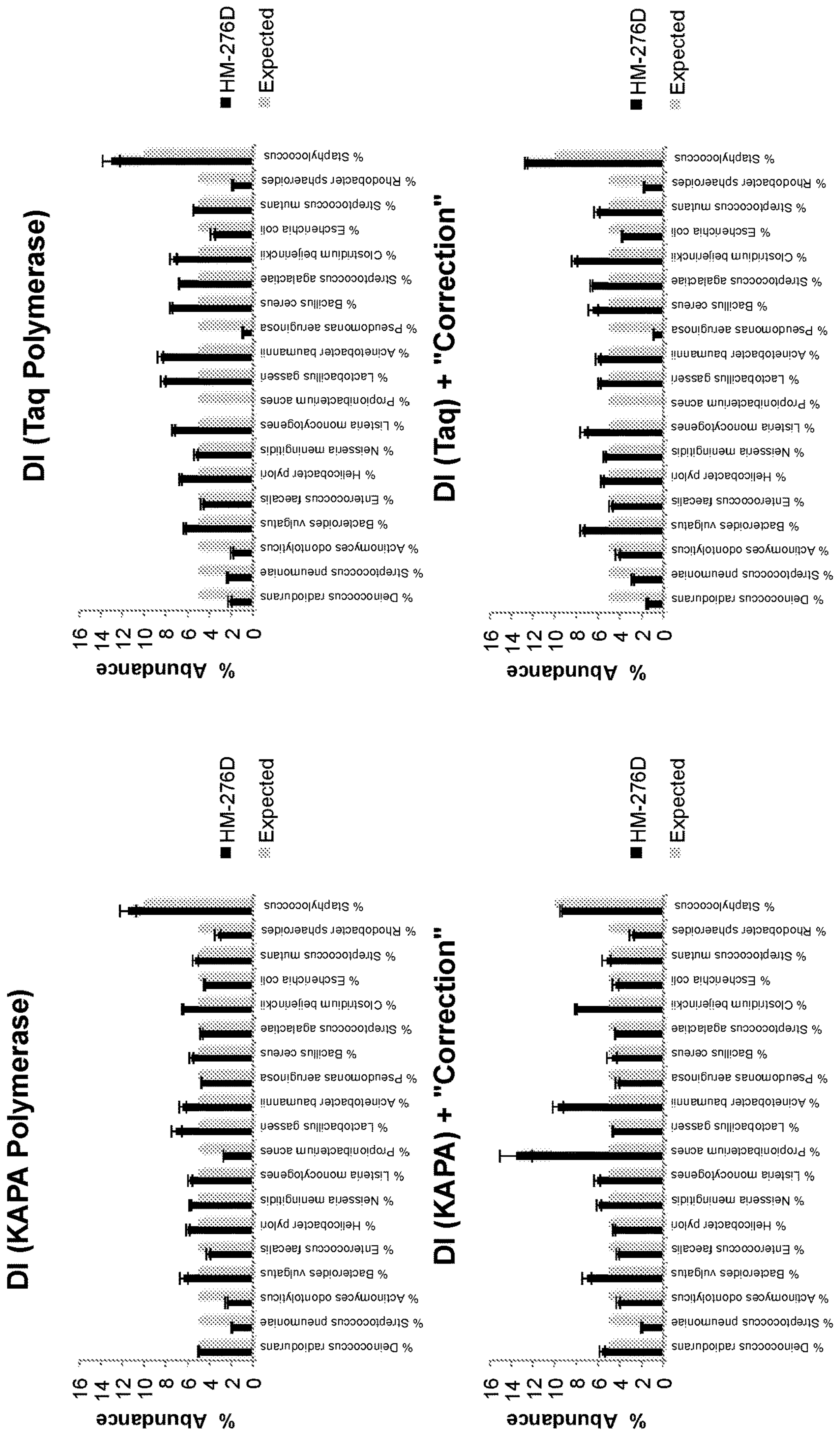
FIG. 7. Abundance analyses of an exemplary mock community. Top: Uncorrected (raw) abundance measurements for the HMP even mock community (HM-276D) amplified using either KAPA HiFi (left) or Taq (right). Bottom: Abundance measurements with linearized V4 synthetic standard-based correction factors applied.

In some applications, the standard molecules can be used to correct for amplification biases in the mock community data. Species-specific correction factors were generated based on the ratio of observed to expected standard molecules (expected values were measured above using the PCR-free quantification barcodes, described in more detail, below). These correction factors were then applied to the mock community data and the accuracy of the data, relative to the known starting abundances, was compared before and after the correction is applied (FIG. 7). For some species (e.g., *Actinomyces odontolyticus* and *Lactobacillus gasseri*), the use of the synthetic standard-based correction factor improved the accuracy of quantification. However, for other species (most prominently *Proprionibacterium acnes* (*P. acnes*)), the use of a synthetic standard-based correction factor decreased the accuracy of quantification.

Figure 8:
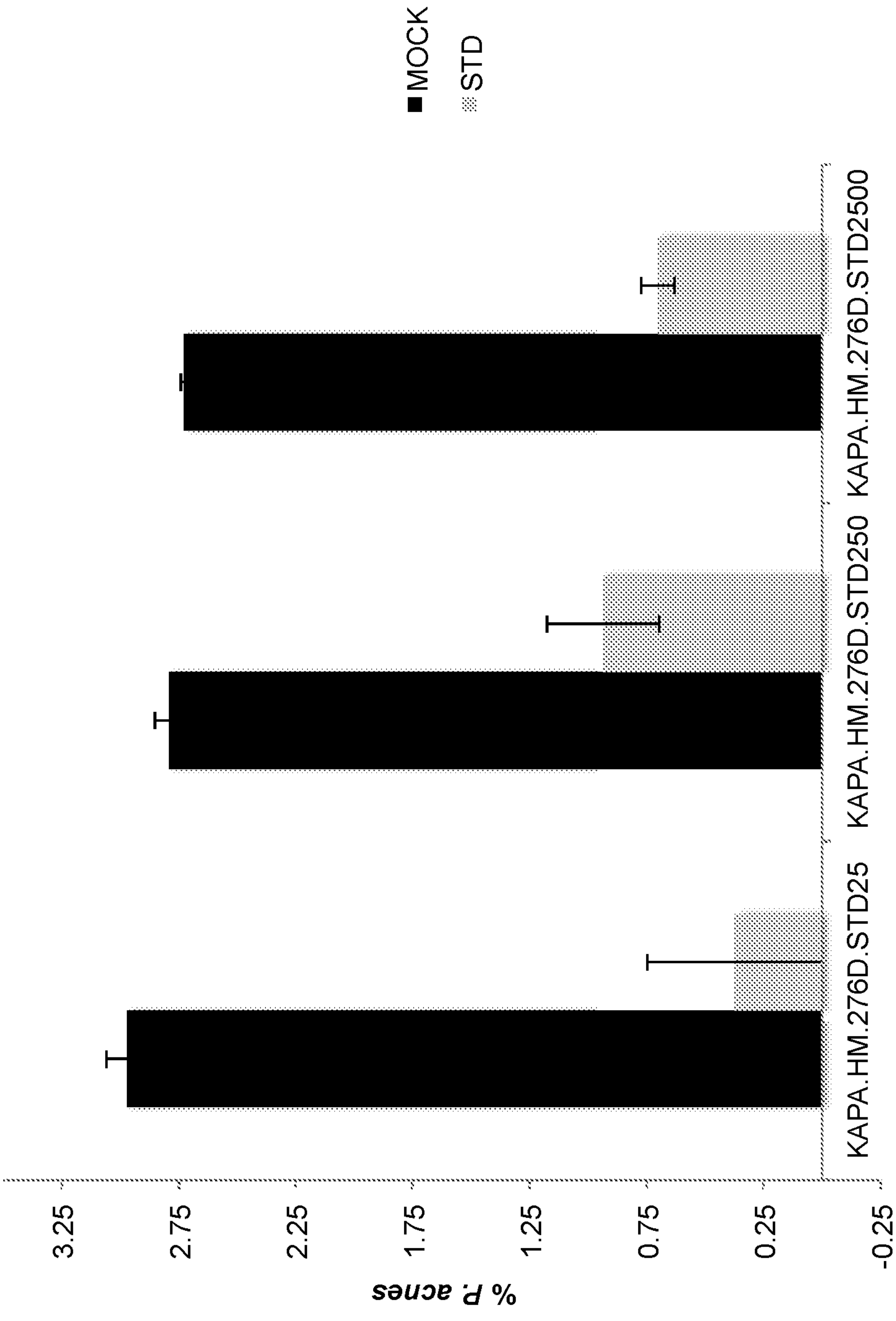
FIG. 8. Amount of *P. acnes* reads observed in the mock community data (left bar) or the linearized V4 synthetic standard data (right bar) for three different concentrations of synthetic standard spike-ins.
Figure 16:
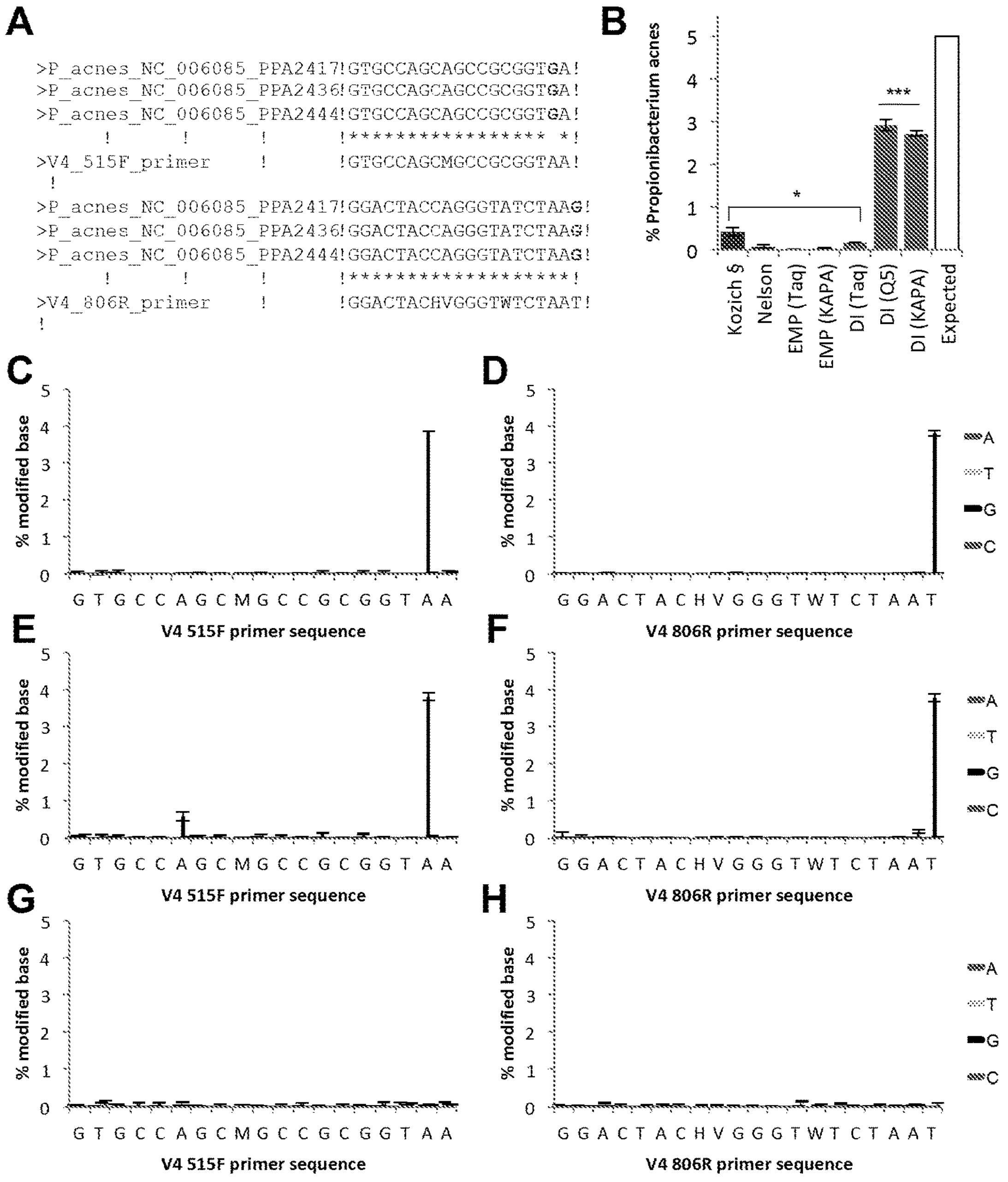
FIG. 16. Primer editing by error-correcting polymerases allow recovery of organisms with mismatches to the amplification primers. (A) Alignment of the 16S rRNA gene V4 primer region of the *Propionibacterium acnes* 16S rRNA gene (SEQ ID NO:319 and SEQ ID NO:321) to the V4 515F (SEQ ID NO:320) and V4 806R primer (SEQ ID NO:322) sequences. Positions with mismatches to the V4 515F and V4 806R primers are shaded. (B) Percentage of reads mapped to *Propionibacterium acnes* in the indicated methods. Error bars are +/−SEM. *** p<0.01, * p<0.05 determined by ANOVA with Tukey HSD post-hoc test. (C) Mean percentage of edited bases in the V4 515F primer (SEQ ID NO:320) region in HM-276D even mock community data measured with the DI protocol with Q5 polymerase. Error bars are +/−SEM, n=4. (D) Mean percentage of edited bases in the V4 806R primer (SEQ ID NO:322) region in HM-276D even mock community data measured with the DI protocol with Q5 polymerase. Error bars are +/−SEM, n=4. (E) Mean percentage of edited bases in the V4 515F primer (SEQ ID NO:320) region in HM-276D even mock community data measured with the DI protocol with KAPA HiFi polymerase. Error bars are +/−SEM, n=4. (F) Mean percentage of edited bases in the V4 806R primer (SEQ ID NO:322) region in HM-276D even mock community data measured with the DI protocol with KAPA HiFi polymerase. Error bars are +/−SEM, n=4. (G) Mean percentage of edited bases in the V4 515F primer (SEQ ID NO:320) region in HM-276D even mock community data measured with the DI protocol with Taq polymerase. Error bars are +/−SEM, n=4. (H) Mean percentage of edited bases in the V4 806R primer (SEQ ID NO:322) region in HM-276D even mock community data measured with the DI protocol with Taq polymerase. Error bars are +/−SEM, n=4.

*P. acnes* is the only organism in the HMP mock community that has a mismatch in its 16S rRNA gene to the V4 amplification primers. Reads from this organism are only seen in the sequencing data when a proofreading polymerase is used, allowing editing of the primer sequences to match the *P. acnes* template (FIG. 16). When the extent of recovery of *P. acnes* sequences from either the mock community or the synthetic standards were evaluated, the standard-based correction factors were inflating the abundance of *P. acnes* was that the standard molecules were not accurately reporting on the primer editing that was occurring with the *P. acnes* template (FIG. 8).

To troubleshoot the misestimation of several species when using the synthetic standard-based correction factors, the effect of linearizing the plasmid on (a) amplification of the standard sequences and (b) the extent of primer correction was evaluated. Again, both the even mock community DNA and the staggered mock community DNA were amplified using a range of template concentrations and two different enzymes (KAPA HiFi and 5 PRIME Taq). Different amounts and different relative abundances of synthetic standard DNA were spiked into the mock community DNA samples (0, 25, 250, and 2500 standard molecules per organism).

Figure 9:
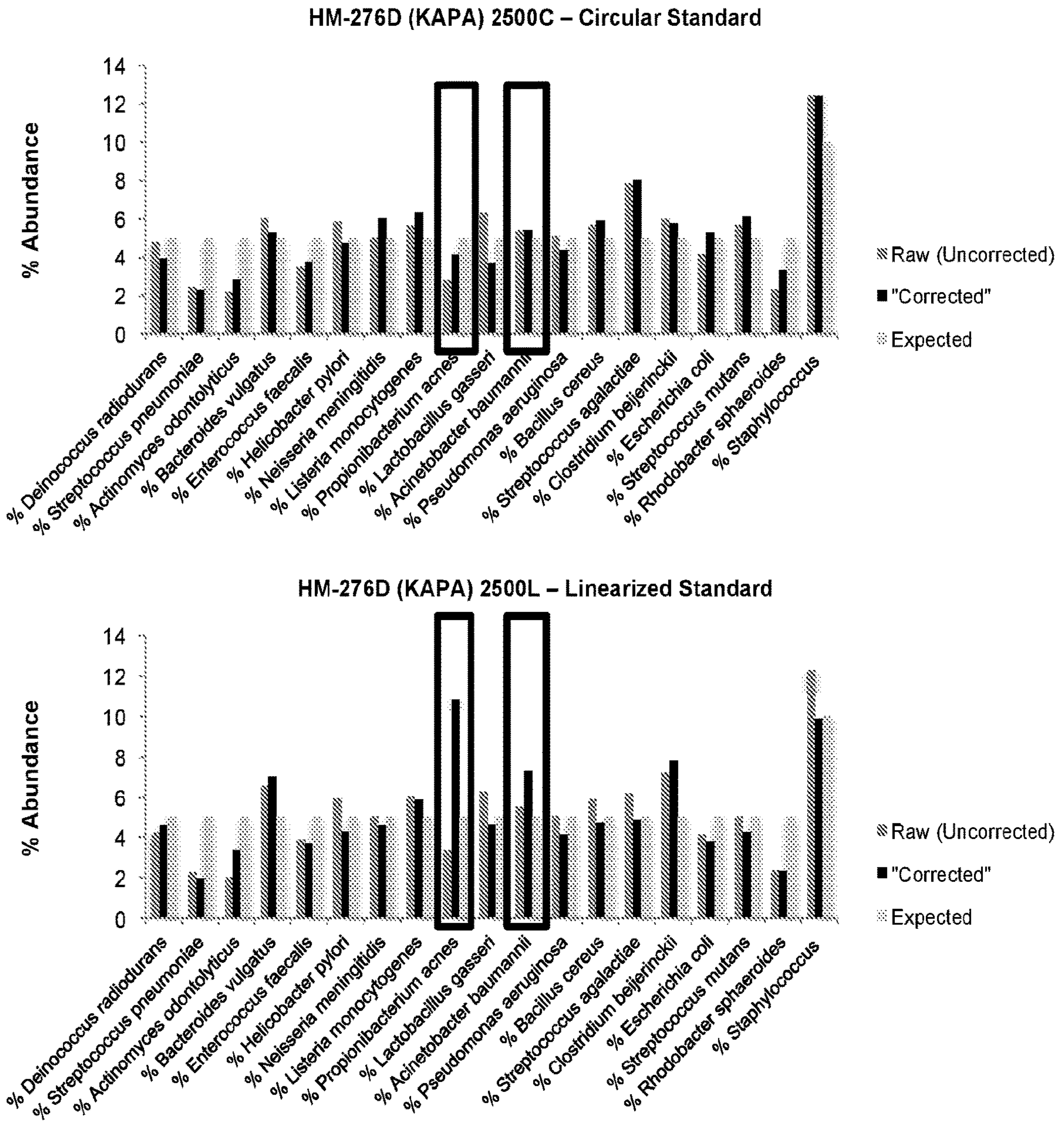
FIG. 9. Comparison of uncorrected and corrected data for the HMP even mock community (HM-276D) using either circular (uncut) or linearized V4 synthetic standard-based correction factors. Black boxes indicate cases where linearized standards "overcorrect" samples.
Figure 10:
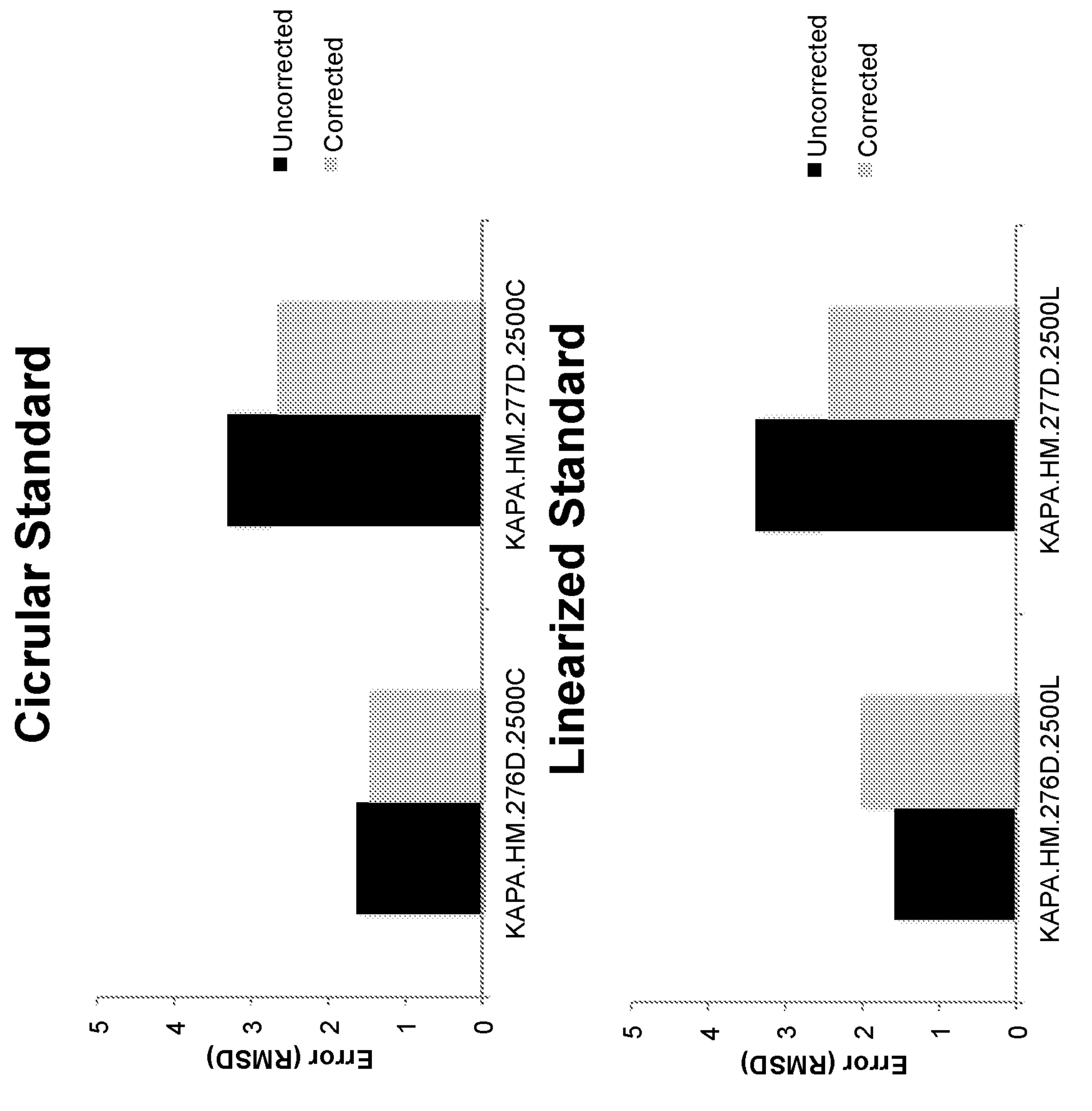
FIG. 10. Aggregate error (RMSD) measurements for the HMP even (HM-276D, left) or staggered (HM-277D, right) mock community with or without V4 synthetic standard-based correction using circularized (top) or linearized (bottom) standards.

Using a circular (uncut) plasmid improved the accuracy of standard-based correction, including for *P. acnes* (FIG. 9). In addition, the overall accuracy across the whole even mock community (as measured by the root mean squared deviation (RMSD) from expected values) was improved with the circular standard based correction relative to both the uncorrected data and to the linear standard corrected data (which was less accurate than uncorrected data). Both the linear and circular standards improved the accuracy of quantification for the staggered mock community, though this effect is likely driven by several of the high abundance organisms in the community (FIG. 10).

Figure 11:
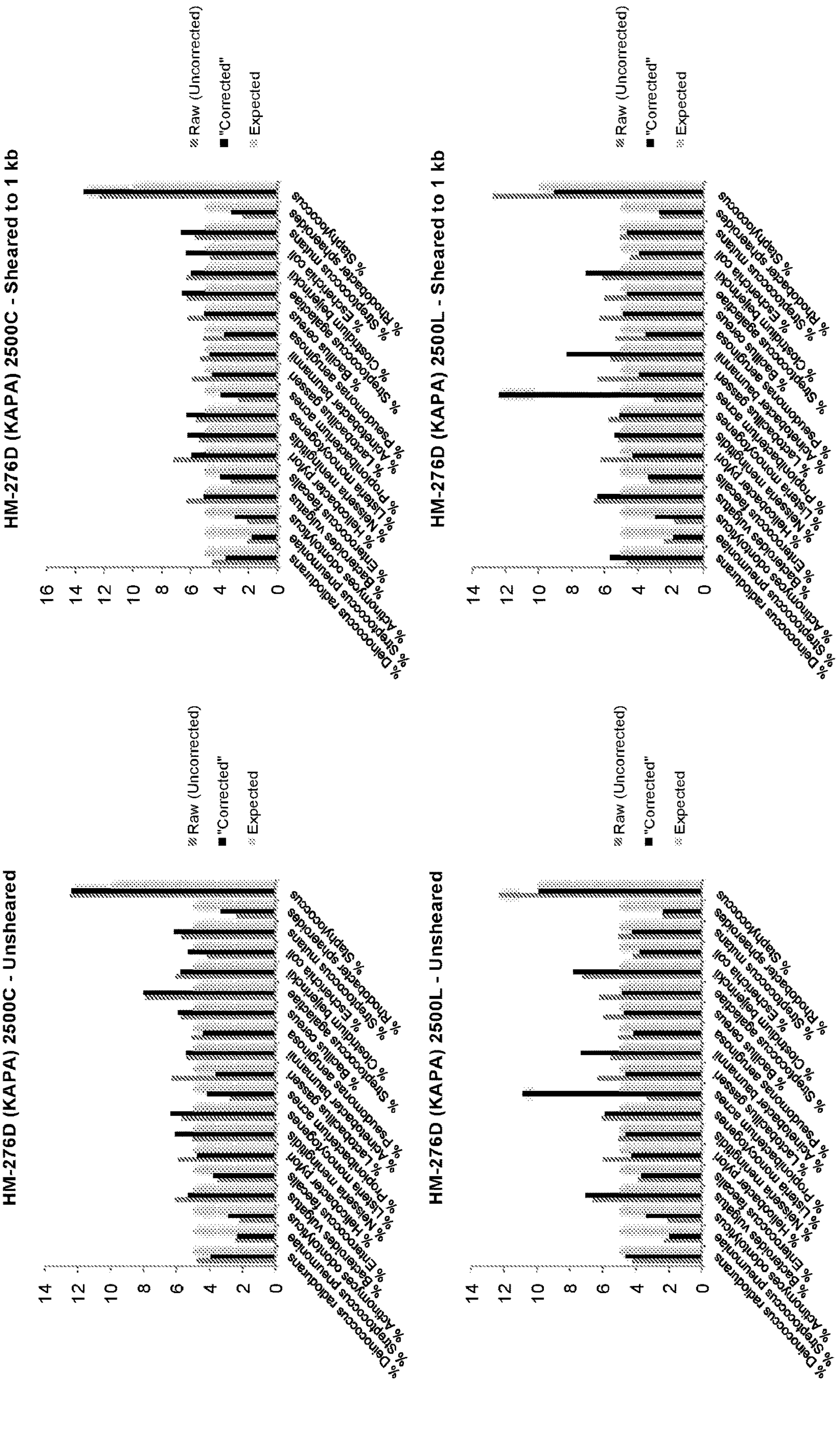
FIG. 11. Comparison of uncorrected and corrected data using circular (top) or linear V4 synthetic standards (bottom), with (right) or without (left) shearing the template DNA.

Also, the effect of shearing the template DNA (to make it more closely resemble the linear standard molecules) on accuracy was tested. There was not a substantial difference in the measurements or corrections with either circular or linear standards between unsheared template and templates sheared to average sizes of 300 bp, 1 kb, or 5 kb (FIG. 11).

Figure 12:
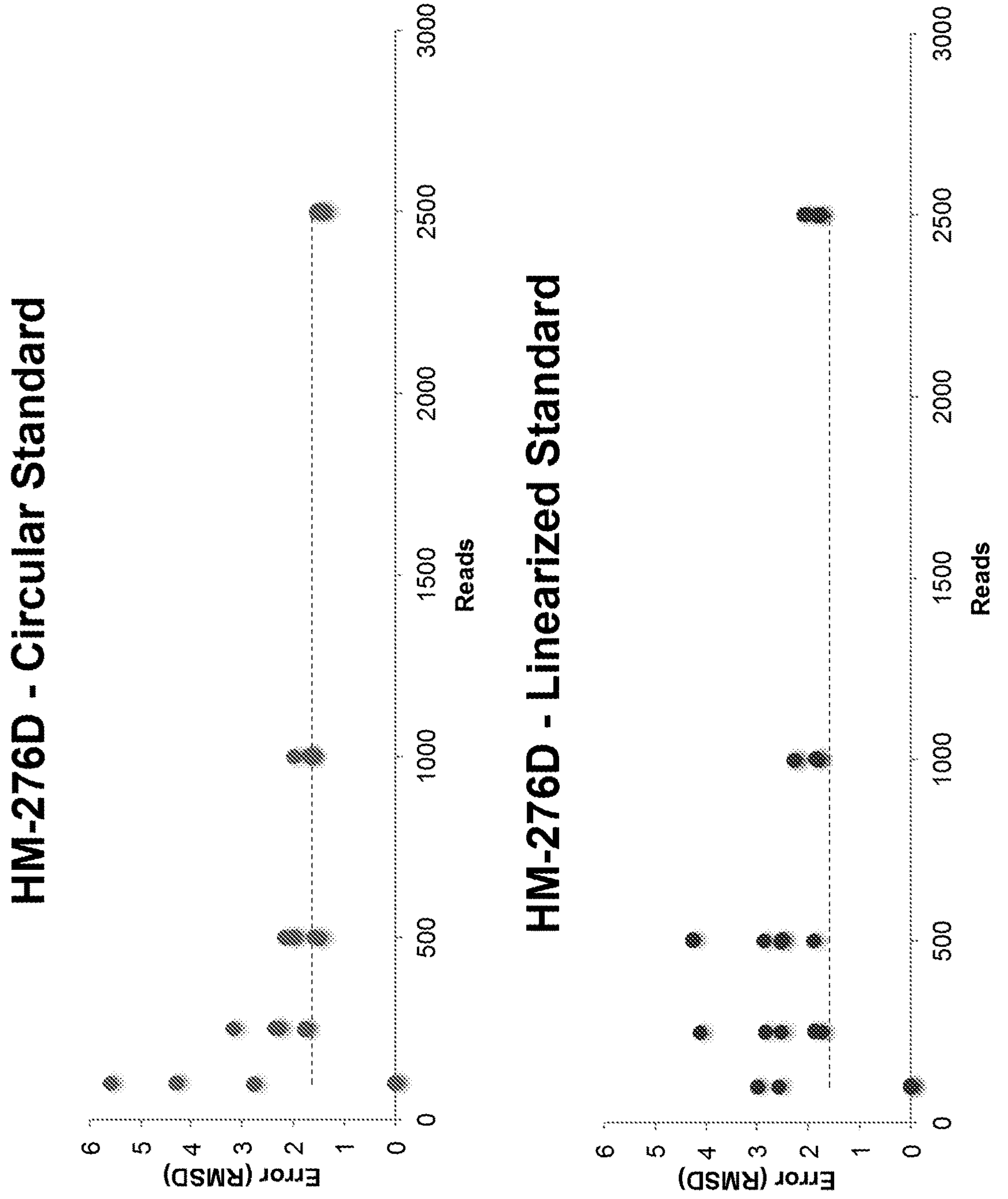
FIG. 12. Plots showing the variance in accuracy of quantification of the HMP mock community when correction factors have been applied using circular (top) or linear (bottom) V4 synthetic standard reads subsampled down to various read depths.

In addition, the depth to which the standard pool needs to be sequenced to get an accurate measurement of the relative abundances of the standard molecules was assessed. The standard reads were subsampled to different levels, correction factors were calculated, the correction factors were applied to the mock community data, and the variance in overall accuracy of quantification was examined. At low subsampling depths (<1,000 reads), the variance of the calculated RMSD values was high. 2,500 reads, however, produced a robust quantification (FIG. 12). This demonstrates that the standards should be able to be spiked in at a small fraction of the sample concentration and still be accurately quantified.

Figure 13:
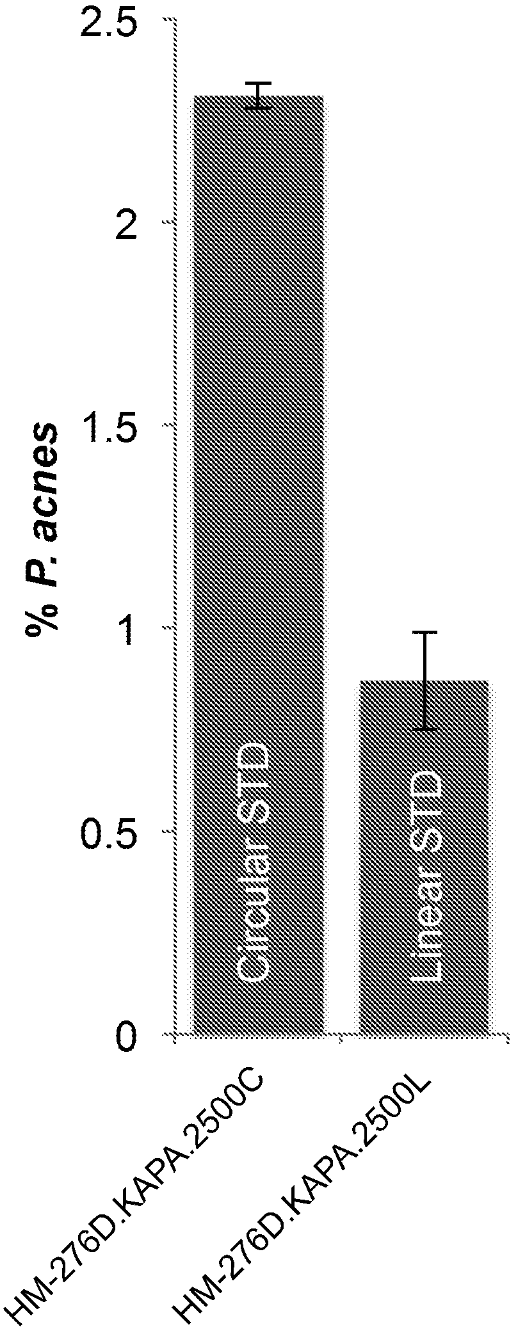
FIG. 13. The circular standard molecules exhibit increased primer editing, detected here as the proportion of reads corresponding to *P. acnes*, a species whose detection depends upon primer editing.
Figure 14:
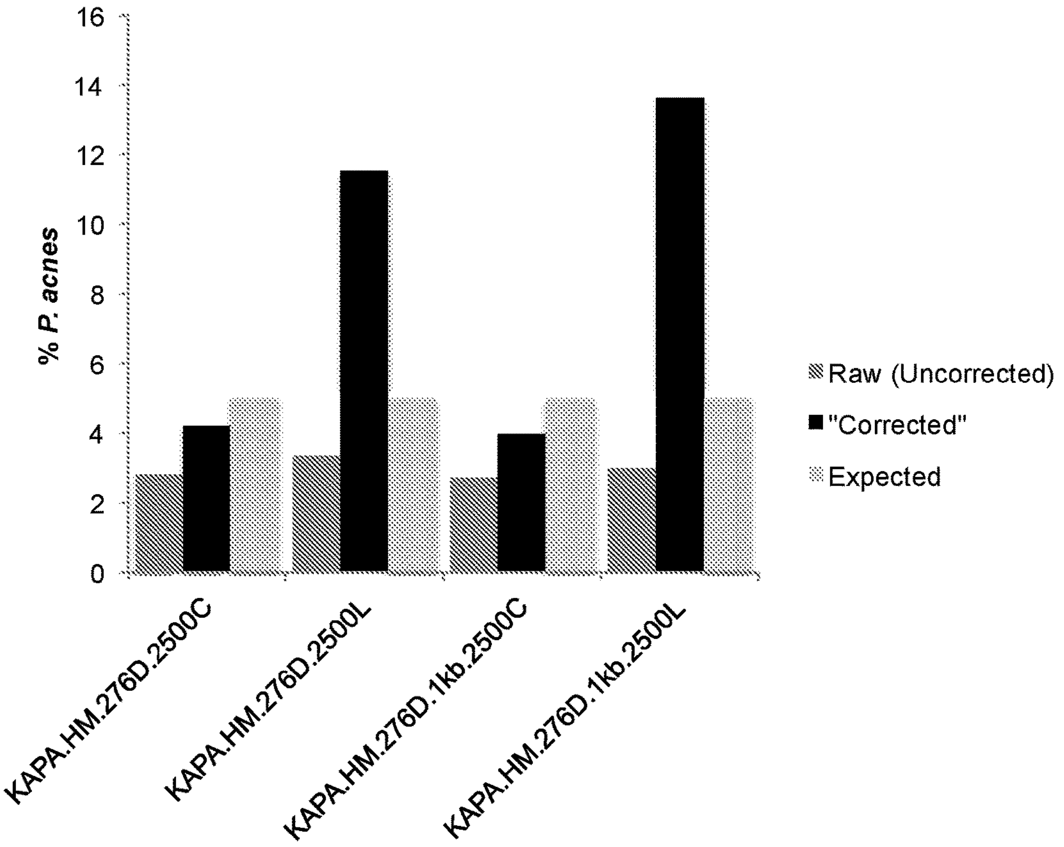
FIG. 14. Linearized V4 synthetic standard-based correction factors (KAPA.HM.276D.2500L and KAPA.HM.276D.1kb.2500L) inflate the estimation of the abundance of *P. acnes* (poor primer editing of the standards leads to a spuriously high correction factor), while circular V4 synthetic standard-based correction factors (KAPA.HM.276D.2500C and KAPA.HM.276D.1kb.2500C) improve quantitative accuracy for *P. acnes*.

The improvement in accuracy seen with the circular standards may be due, at least in part, to the circular standards more effectively reporting on primer editing. The circular standards recovered a much larger amount of standard reads corresponding to *P. acnes* (FIG. 13), which led to an improved standard-based correction for this organism (FIG. 14). The mechanism for this difference in primer editing between the circular and linearized standard templates is currently unknown and under investigation.

Process Standards

Figure 19:
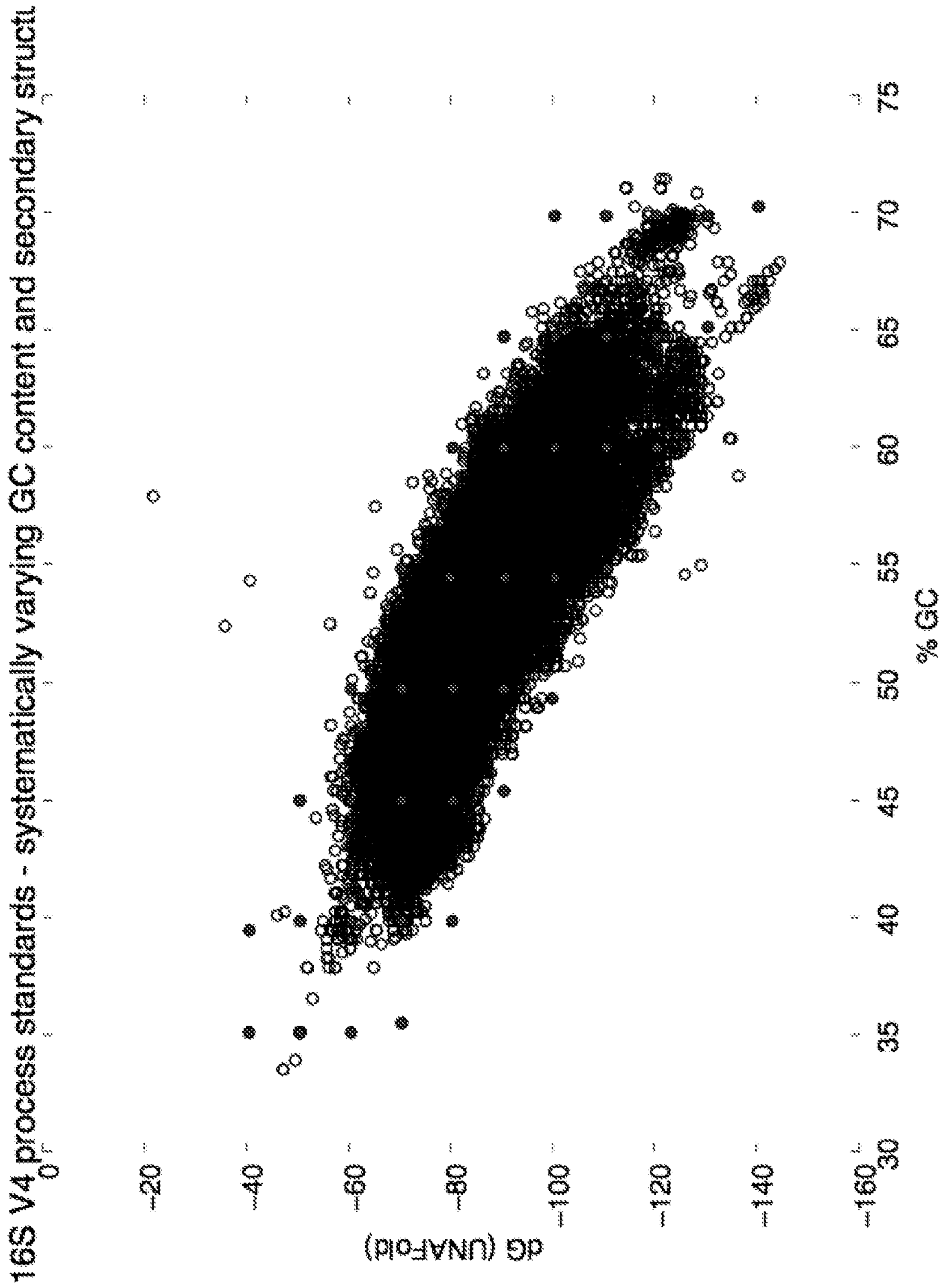
FIG. 19. Distribution of 16S rRNA gene V4 region % GC and predicted secondary structure (dG), black open circles, and designed process control standards, light filled circles. The black smear is the result of densely overlapping black open circles.
Figure 20:
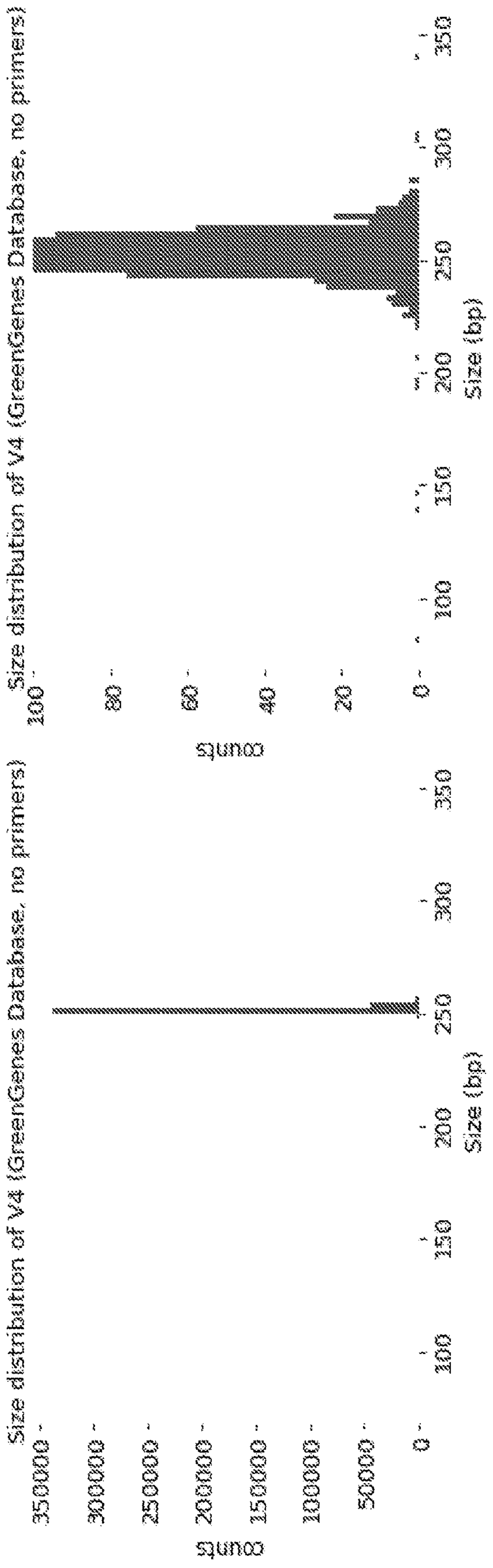
FIG. 20. Natural distribution of 16S rRNA gene V4 region sizes. Process control standards range from 193 bp to 313 bp.

Exemplary process control standards were designed to report on amplification biases that can arise through the interaction of amplification conditions and reagents with the biophysical properties of the template molecules—e.g., GC content, amplicon size, and/or secondary structure. The parameter space encompassed by the natural genetic variation in the V4 region of the 16S rRNA gene was evaluated by assessing the GC content and predicted secondary structure of all of the identifiable V4 regions in the Greengenes database. Next, the sequence of the *E. coli* 16 rRNA gene was varied in silco, adding different amounts of GC or AT bias and generating an in silico library of millions of variant sequences. Then, secondary structure predictions were generated for these sequences, sequences that were >97% identical to a sequence in the Greengenes database were filtered out, a set of molecules that tiled the extent of natural GC content and secondary structure variation were chosen (FIG. 19). The naturally-occurring distribution of V4 region sizes were characterized and a set of standards to cover this size distribution were made, which could be used to detect biases in amplicon size due to size selection or amplification (FIG. 20). (See process control standards 33-96, below, SEQ ID NO:40 through SEQ ID NO:103). An additional set of process control standards was made for the eukaryotic ITS2 region, using similar design considerations (Synthetic standards 160-207, below, SEQ ID NO:167 through SEQ ID NO:214).

Primer Editing Standards

The generation of primer editing standards resulted from an unexpected phenomenon. An error correcting polymerase can edit primer sequences during amplification to correct mismatches between the primer sequence and a template molecule (FIG. 16). The V4 515F and V4 806R primers typically perform poorly for detecting *P. acnes* due to mismatches with the *P. acnes* 16S rRNA gene (FIG. 16). Low levels of *P. acnes* are detected using the EMP protocol, or with the DI (Taq) protocol; the species was also effectively absent in a published mock community EMP dataset (FIG. 16; Nelson et al., 2014, *PLoS One* 9:e94249). Surprisingly, relatively high levels of *P. acnes* were observed with the DI (Q5) and DI (KAPA) protocols (FIG. 16). When we the portion of reads corresponding to the amplification primers for the DI (Q5) and DI (KAPA) datasets were examined, approximately 4% of the V4 515F primer sequences had been edited from A>G at position 18 and approximately 4% of the V4 806R primer sequences had been edited from T>G at position 20, modifications matching the *P. acnes* template sequence (FIG. 16). No such modifications were observed in the DI (Taq) dataset (FIG. 16). These results demonstrate that proofreading polymerases can edit amplification primers in a PCR reaction, permitting the amplification of sequences from organisms whose templates contain primer mismatches. The efficiency of primer editing is noteworthy since the editing must occur in essentially every PCR cycle in order to be observed in the final sequencing reads.

Figure 17:
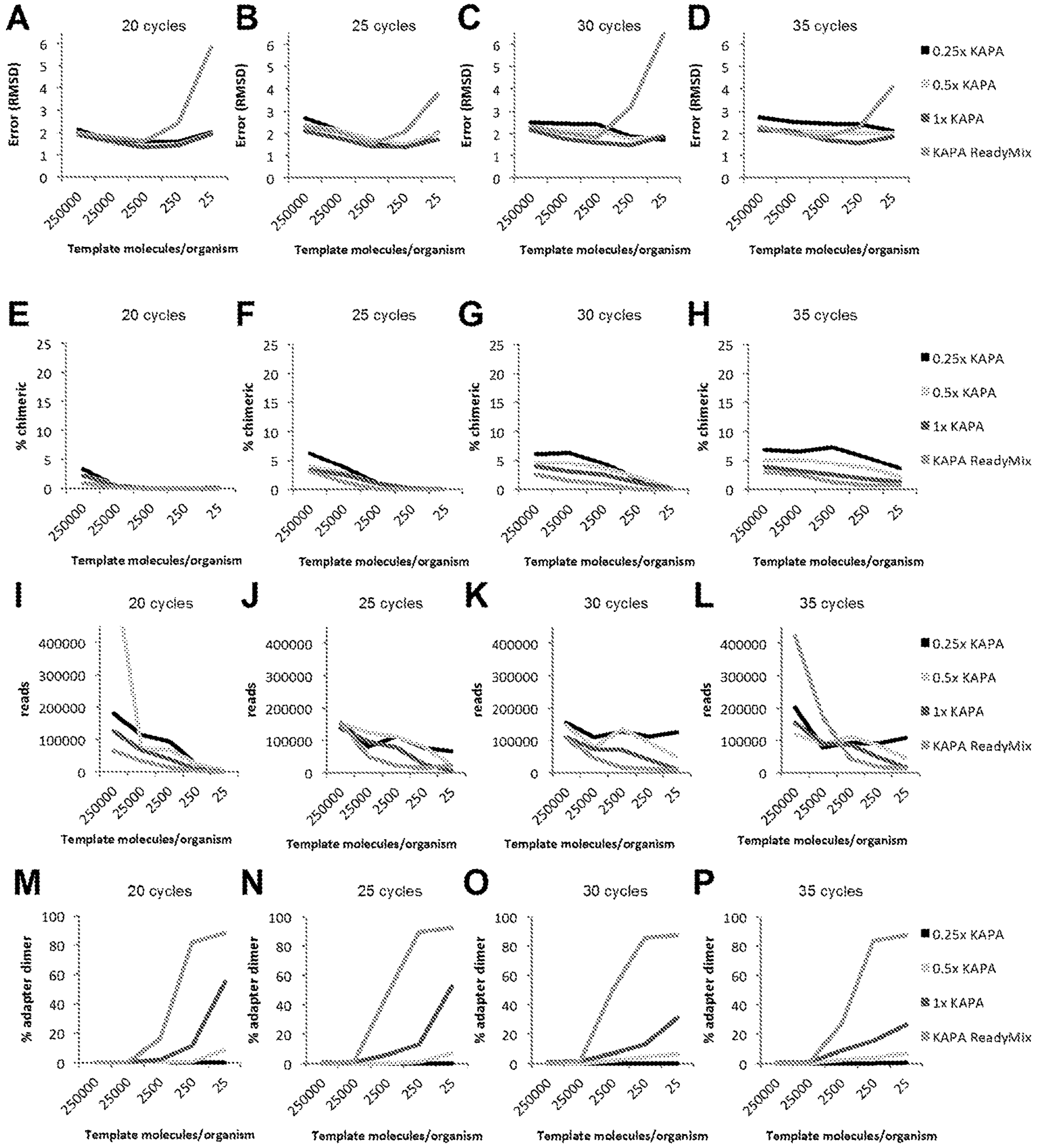
FIG. 17. The effect of KAPA HiFi enzyme concentration on accuracy, chimera formation, sample balance, and adapter dimer formation. Plots for the HM-276D even mock community at 5 different starting template concentrations amplified for 20, 25, 30, or 35 cycles using 0.25×, 0.5×, 1×KAPA HiFi polymerase, or KAPA ReadyMix showing: (A-D) RMSD; (E-H) Percentage of chimeric reads; (I-J) Total number of reads; (M-P) Percentage of adapter dimers.
Figure 18:
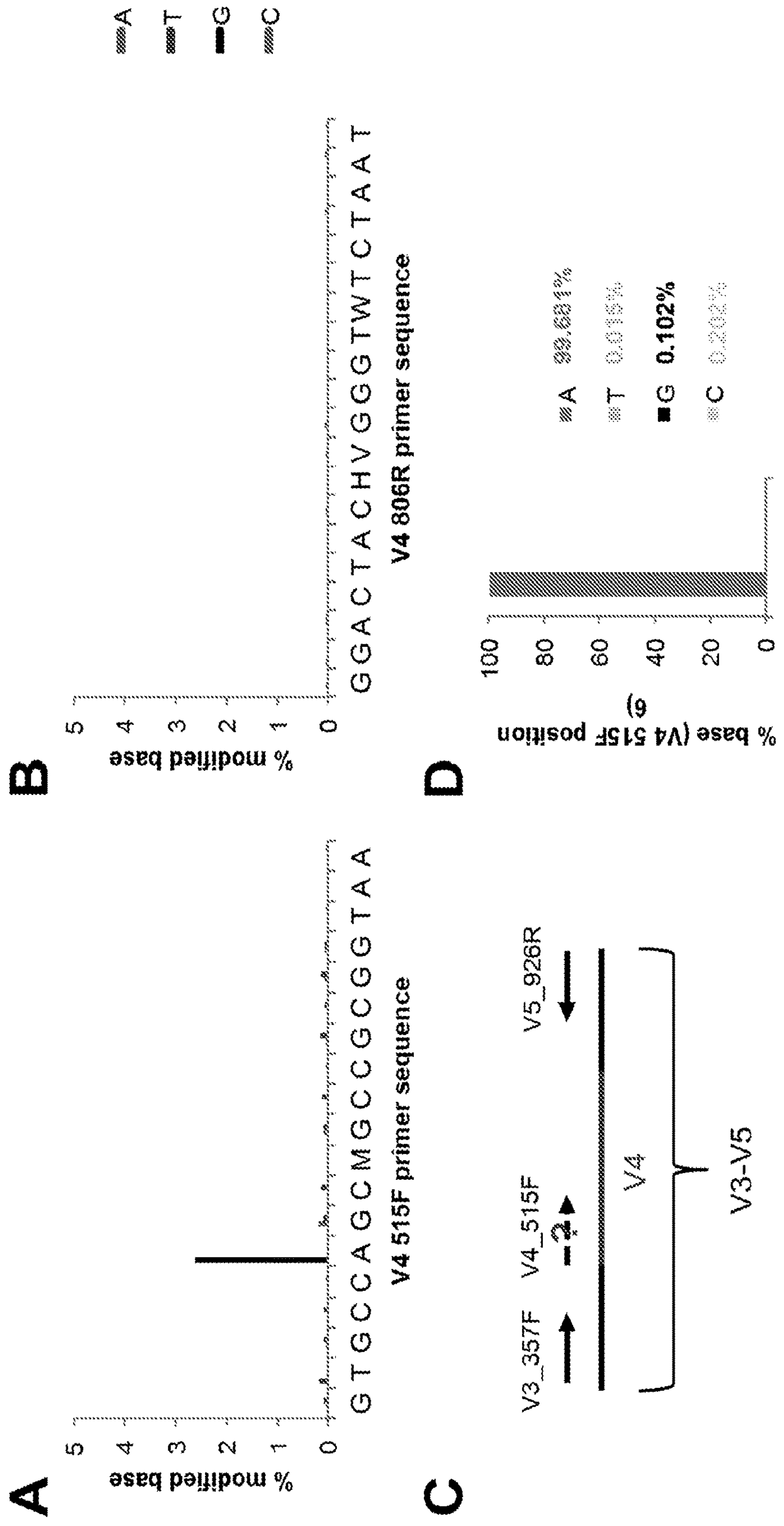
FIG. 18. The effect of KAPA HiFi enzyme concentration primer editing efficiency and the occurrence of primer editing artifacts. (A) Distribution of edited bases in the V4 515F primer (SEQ ID NO:320) region in data from a pure isolate of *Campylobacter jejuni* measured with the DI protocol with KAPA ReadyMix. (B) Distribution of edited bases in the V4 806R primer (SEQ ID NO:322) region in data from a pure isolate of *Campylobacter jejuni* measured with the DI protocol with KAPA ReadyMix. (C) Schematic of 16S V3-V5 amplification from a pure isolate of *Campylobacter jejuni*. This amplicon contains the V4 515F primer sequence, allowing assessment of the endogenous sequence. (D) Percentage of each base observed at position 6 of the sequence corresponding to the V4 515F primer sequence in a V3-V5 amplicon from a pure isolate of *Campylobacter jejuni.*
Figure 21:
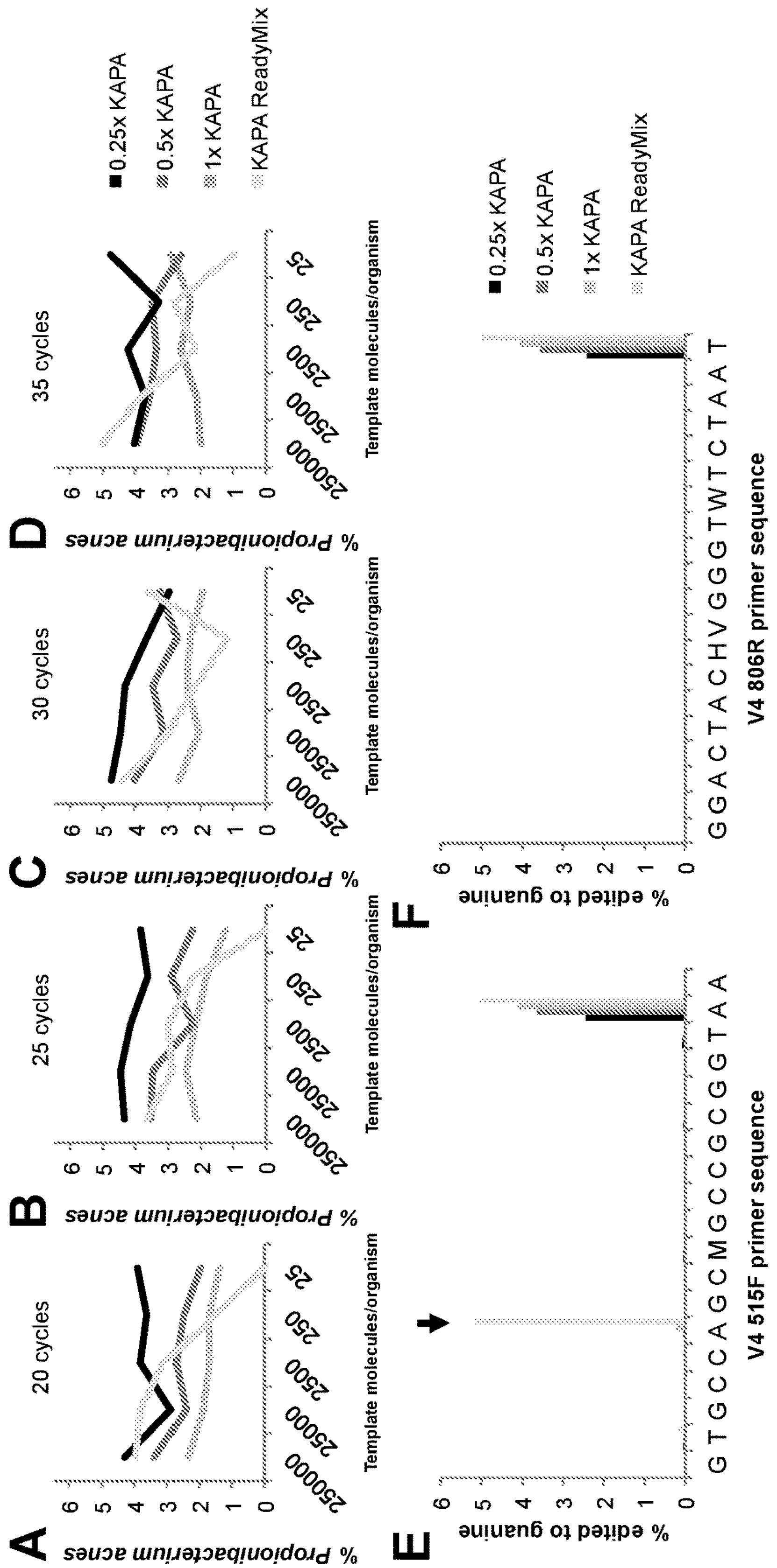
FIG. 21. Analysis of reads using KAPA HiFi polymerase. (A-D) Proportion of *P. acnes* reads recovered with different concentrations of KAPA HiFi polymerase across a range of PCR cycle numbers and starting template concentrations. (E) Proportion of V4 515F primer (SEQ ID NO:320) bases that have been edited to guanine. (F) Proportion of V4 806R primer (SEQ ID NO:320) bases that have been edited to guanine. (SEQ ID NO:322)
Figure 22:
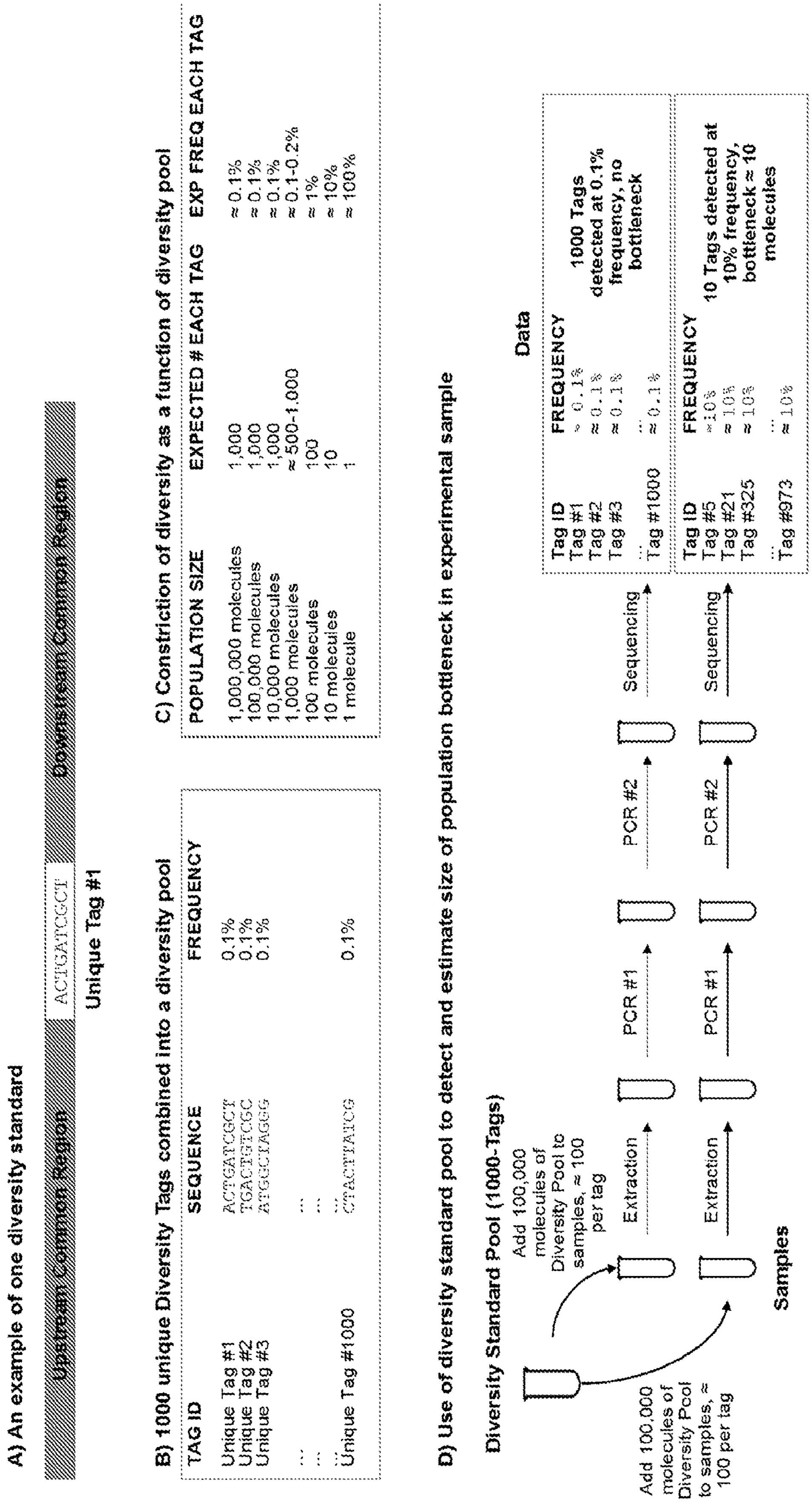
FIG. 22. The design and use of diversity standards. (A) An example of the design of one diversity standard, in which a 10-bp sequence tag (SEQ ID NO:323) that is unique to the standard is flanked by a sequence region common to other diversity standards, to be used to recover the tag from a sample by, for example, PCR amplification). (B) The construction of a pool of diversity standards of complexity equal to 1000 tags, with each tag present at 0.1% of the total population. Tag sequences are shown for tags 1-3 and tag 1000 (SEQ ID NOs:323-326 illustrated) for purposes of illustration, but the entire pool contains 1000 unique tag sequences. (C) An illustration of the loss of sequence tag diversity experienced as a result of constricting the population size of molecules of the pool of diversity standards. (D) An illustration of the use of a diversity standard pool to detect and estimate a population bottleneck of a sample carried through several molecular steps. All that is required for such an estimation is a reliable measurement of the frequency of each tag in the final data.

The extent of adapter dimer formation, and therefore the overall sensitivity of the assay, can also be modulated by adjusting polymerase concentration (FIG. 21). Samples from this dilution series were amplified with KAPA HiFi polymerase either at the manufacturer's recommended enzyme concentration (1×), at 0.5×, or at 0.25× the recommended enzyme concentration. In addition, these datasets were compared to samples amplified with KAPA ReadyMix (a pre-made 2× master mix). There was a strong correlation between the enzyme concentration used and the extent of adapter dimer formation. Samples amplified with the KAPA ReadyMix had by far the largest extent of adapter dimer formation, while samples amplified with 0.25×KAPA HiFi had negligible amounts of adapter dimer formation, even at very low template concentrations (FIG. 17). Except for the KAPA ReadyMix samples, which had very few reads for the samples with lowest template concentrations, accuracy was only moderately reduced with decreased concentrations of KAPA HiFi, particularly at lower PCR cycle numbers (FIG. 17). Decreasing KAPA HiFi concentration and thus the levels of adapter dimer contamination greatly improved sample balance (FIG. 17). Excessive enzyme concentration may mediate adapter dimer formation through, for example, chew-back and extension of primer heterodimers. Thus, optimizing the enzyme concentration can involve a tradeoff between on-target/off-target editing (FIG. 18), sensitivity, and overall accuracy. The extent of primer editing also varies as a function of polymerase concentration (FIG. 21).

Figure 3:
FIG. 3. Introducing a phosphorothiol bond (ITS* primer set) can reduce the formation of adapter dimers (an undesired side-effect of the primer editing process), indicating that the extent of primer editing can be modulated using phosphorothiol modifications.

Since drop-out of a template molecule due to non-amplification represents the most severe form of PCR bias—i.e., it is a qualitative error as opposed to a quantitative misestimation—it be desirable to have standard molecules that can report on the efficacy of primer editing. A set of standards were designed in which the V4_515F primer site from an *E. coli* 16S rRNA gene template has been modified with every possible single base mismatch in the most 3' 10 bp of the primer binding site (FIG. 2). These standards can be used to assess the extent of editing and any base preferences associated with primer editing (see primer editing standards 97-128, below; SEQ ID NO:104 through SEQ ID NO:135). An additional set of primer editing standards was made for the eukaryotic ITS2 region, using similar design considerations (Synthetic standards 129-159, below, SEQ ID NO:136 through SEQ ID NO:166). In addition, FIG. 3 presents data suggesting that the extent of primer editing can be controlled using exonuclease-protecting phosphorothiol modifications in the amplification primers.

Figure 15:
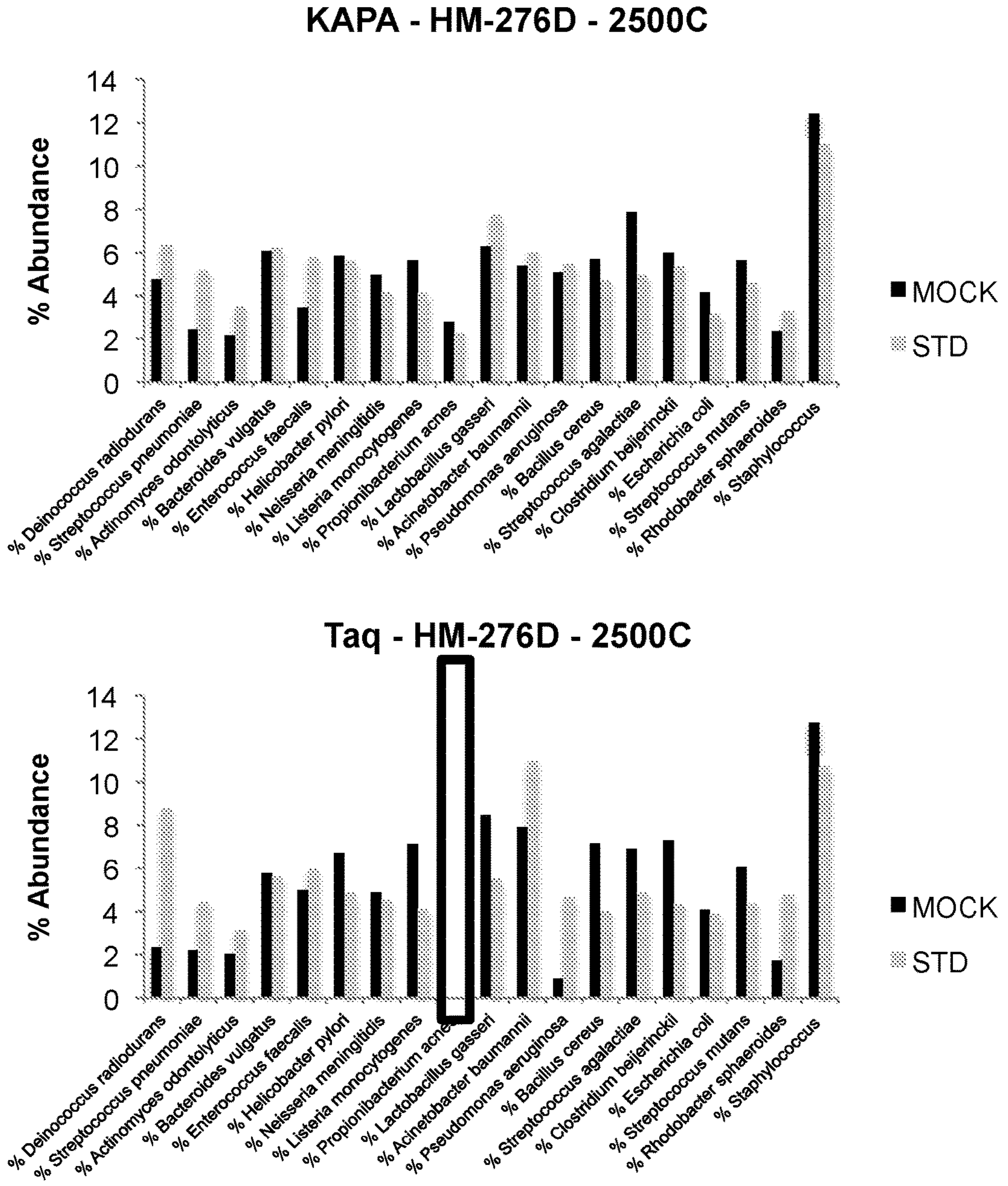
FIG. 15. The absence of reads for a synthetic standard molecule can be used to flag drop out of taxa due to amplification artifacts (in this case, the failure of Taq polymerase to amplify *P. acnes* template).

Organisms with primer mismatches, such as *P. acnes*, are only amplified and present in the sequencing data at appreciable levels when a proofreading polymerase is used. Thus, synthetic standards that can report on the efficacy of primer editing and flag the potential drop out of taxa due to primer mismatches will help to identify qualitative errors in amplicon-based microbiome sequencing. A synthetic standard molecule can be used to identify such a taxon drop out. When the HMP mock community is amplified with standard Taq polymerase prior to sequencing, primer editing does not occur and *P. acnes* is not detected. Similarly, a drop out of the *P. acnes* standard molecule containing the corresponding primer mismatches is also observed (FIG. 15). This demonstrates that in addition to correcting for quantitative errors, synthetic standards can be used to flag qualitative errors (taxa drop out).

PCR-Free Quantification Barcodes

Figure 4:
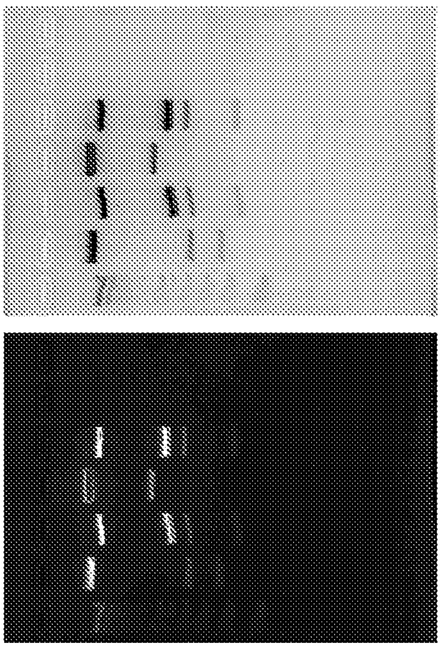
FIG. 4. Digestion with MlyI can liberate a 148 bp molecule containing the quantification barcodes.
Figure 5:
FIG. 5. Illumina-adapter flanked MlyI-liberated quantification barcodes can be directly sequenced and used to quantify the abundance of the standard molecules in a complex pool.

As mentioned above, in some embodiments, the synthetic standard can include a barcode that allows PCR-free quantitation. PCR-free quantitation eliminated bias PCR-mediated amplification bias. A collection of 20 16S rRNA gene V4 synthetic standards were synthesized, cloned into a pTOPO vector, transformed into *E. coli* (DH5alpha), and individual clones were sequence verified by Sanger sequencing. Plasmids were purified from each of the 20 sequence-verified clones using a Qiagen MiniPrep kit, and the plasmid DNA was quantified using a PicoGreen assay. Plasmid DNA from the 20 clones was pooled at an equimolar ratio, such that each plasmid was expected to make up 5% of the standard pool. Next, the plasmid pool was cut with MlyI to liberate the quantification barcodes (FIG. 4; see also FIG. 1). The MlyI digested plasmid material was then directly sequenced using a fraction of a 100 bp single-read Illumina HiSeq lane, generating 592,728 reads. The Illumina adapters were trimmed from the resulting reads, and the reads were mapped to a reference file containing the known barcode sequences using a custom script. Using these counts, one can measure the actual abundances of the standard molecules in the standard pool, which must be accurately assessed for the standards to provide quantitative corrections. The actual abundances for the standard molecules were mostly close to, but not exactly 5%, with a range between 3.4% and 6.3% (FIG. 5).

The PCR-free barcode quantification technology described herein has numerous practical applications and can be used to make reliable measurements of essentially any mixture of engineered DNA constructs where PCR-free barcodes could be inserted. Exemplary applications include, for example, quantifying plasmid pools; quantifying pools of shRNA, CRISPR sgRNA plasmids, or viral vectors (such as would be used on large-scale genetic screening); quantifying transposon or other insertion libraries—e.g., Tn-Seq and related methods.

Figure 30:
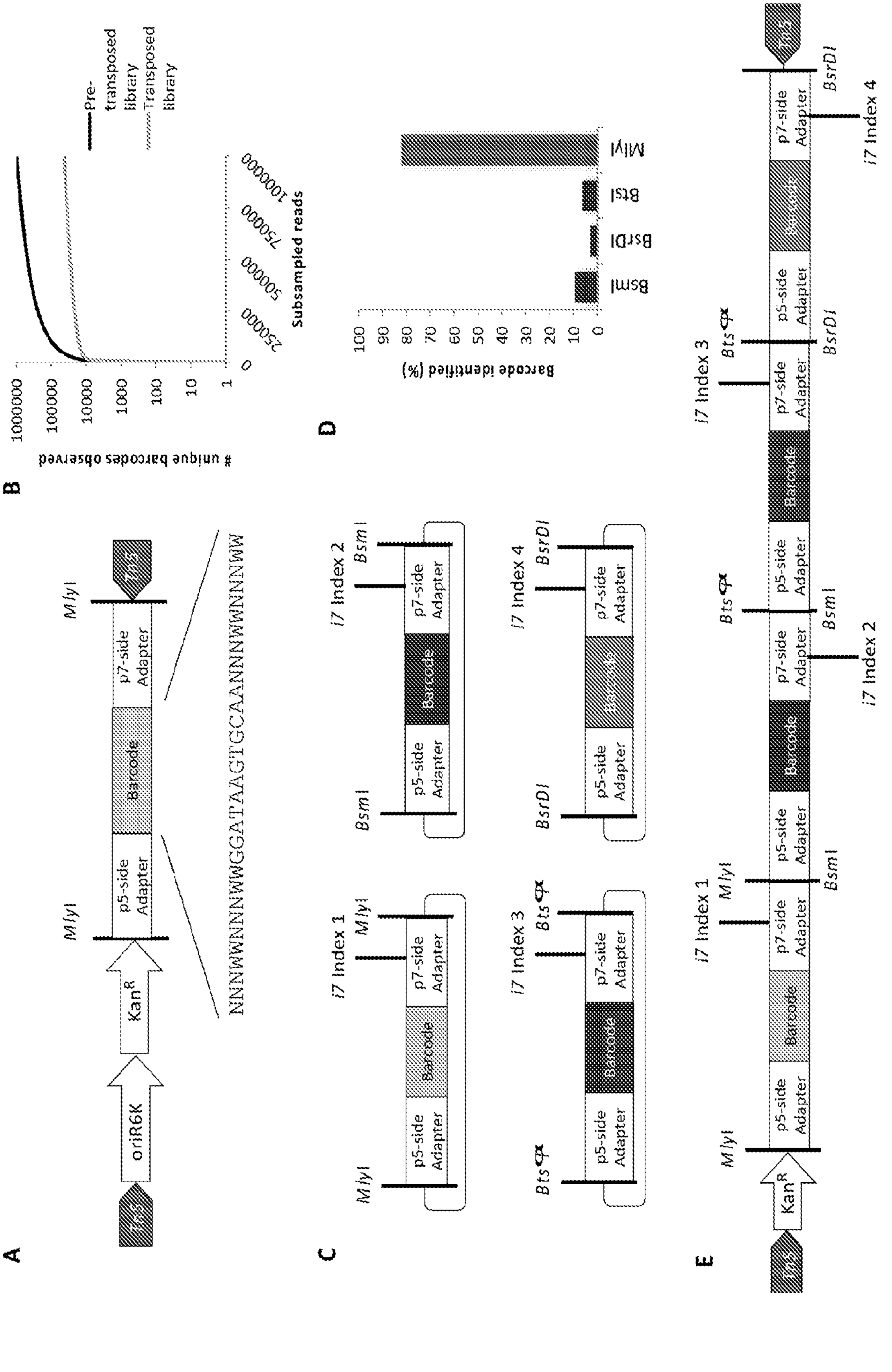
FIG. 30. PCR-free barcode constructs. (A) Tn5 transposon construct containing PCR-free barcode construct (SEQ ID NO:328) that has been used to generate a library of more than 13,000 insertion transposons in *E. coli*. (B) Testing the barcode diversity of the library by liberating the PCR-free barcode construct with MlyI prior to transforming into *E. coli* (Pre-transposed library, black curve), and demonstrating that the PCR-free barcode construct can be liberated from the *E. coli* genome and sequenced directly (Transposed library, gray curve). (C) A strategy for using multiple enzymes to allow multiplexing of PCR-free quantification barcode constructs. (D) Test of specificity of clustering of an evenly pooled mixture of these four plasmids, cut with MlyI. The fact that there is bleed-through of the other barcodes suggests that size selection may be required to improve specificity. (E) Concatamerized PCR-free barcode constructs can be cloned into a transposon or plasmid vector backbone to potentially allow multiplexing of PCR-free barcode measurements.

To demonstrate an exemplary application of this technology, a Tn5 transposon library was constructed containing random barcode-containing PCR-free barcode constructs within the transposon. This Tn5 element was cloned and transformed into *E. coli* together with the Tn5 transposase by electroporation to generate a library of >13,000 insertion strains (FIG. 30A). Prior to transformation, the barcode composition of the Tn5 library was confirmed to be highly diverse by digesting with MlyI, purifying, and sequencing the PCR-free barcode construct (FIG. 30B). In order to use the PCR-free barcodes in the transposon to quantify Tn-Seq libraries, the barcodes are mapped to transposon junctions by fragmenting the library DNA, ligating on adapters, and enriching for the Tn5:genome junction by amplifying with a primer in the transposon and one in the adapter. Once barcode/genome associations have been made, then the library can be quantified in the absence of PCR by simply liberating the PCR-free barcodes using MlyI and sequencing them.

It is possible to sequence the PCR-free quantification barcode cassette in the transposon construct from purified *E. coli* genomic DNA. Because the barcode cassette on the integrated transposon accounts for only a small fraction of the *E. coli* genome (around 1/40,000$^{th}$), it was unclear whether Illumina sequencing of the digested material would be possible in the context of the large amount of non-functional background DNA. Moreover, since the PCR-free quantification barcode molecules are sequenced directly, without any intervening amplification, the quantity of material that can be recovered will in most cases be below the recommended concentrations for loading an Illumina sequencer. Thus, to sequence the PCR-free quantification barcode cassette in the transposon construct from purified *E. coli* genomic DNA, after digestion of the genomic DNA with MlyI, the amount of transposon in the digested sample was quantified. Starting with more than 2 μg of genomic DNA, the PCR-free quantification barcode construct was recovered at a concentration of 112 pM as assessed by qPCR, roughly 1/20$^{th}$ of the recommended concentration for loading an Illumina MiSeq. Sequencing these libraries required a modified denaturation protocol in which the NaOH used to denature the DNA prior to sequencing was neutralized with an equal amount of HCl so that excess NaOH in the sample did not interfere with clustering and sequencing. More than three million reads corresponding to the PCR-free quantification barcode construct from the transposon were obtained, which represented approximately 15,000 unique abundant barcodes, consistent with our estimates of transposon library complexity based on colony counts (FIG. 30B).

In some applications, such as, for example, those in which one would like to assess the same library across many experimental perturbations, it may be desirable to multiplex these measurements in a single sequencing lane. Constructs can be designed to test whether enzymes that leave small single strand overhangs can be used to liberate PCR-free barcode constructs so that multiple tags could be placed into a single concatamerized construct (FIG. 30C-E). The specificity of multiplexed PCR-free barcode constructs was tested by making an even pool of the four plasmids in FIG. 30C and cutting with MlyI to liberate one of the four barcodes. FIG. 30D shows the successful liberation of barcodes by MlyI.

To demonstrate another exemplary application of this technology, size standards were made to characterize the clustering efficiency of molecules of various sizes on different sequencing platforms. These standard molecules contain two PCR-free quantification barcode constructs on the same plasmid, ensuring that each pair is present in a truly equal molar ratio. Each plasmid contains a 164 bp MlyI-liberatable PCR-free barcode construct and a second MlyI-liberatable PCR-free barcode construct of variable size ranging from 150 bp to 1500 bp in 150 bp increments. The ratio of the variably sized construct to the 164 bp normalization control can be used to quantify and compare the number of reads resulting from each standard molecule, allowing direct measurement of sequencing platform-specific size biases (Synthetic standards 233-262, below, SEQ ID NO:240 through SEQ ID NO:269).

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Samples and Standards

The mock community DNA was obtained through BEI Resources, NIAID, NIH, as part of the Human Microbiome Project: Genomic Mock Community B (HM-276D, Even, High Concentration, v5.1H, and HM-277D, Staggered, High Concentration, v5.2H).

16S V4 synthetic standards were synthesized using an SGI-DNA BioXP 3200. These constructs were 3' adenylated by incubating with Taq polymerase and dATP at 72° C. for 10 minutes. Next, the synthetic DNA was cloned into a pTOPO vector (Invitrogen) according to the manufacturer's protocol, transformed into *E. coli* (DH5alpha), and individual clones were sequence verified by Sanger sequencing. Plasmids were purified from each of the 20 sequence-verified clones using a Qiagen MiniPrep kit, and the plasmid DNA was quantified using a PicoGreen assay and pooled as described above.

Full-length 16S rRNA standards, process control standards, and primer editing standards were synthesized as full plasmids (in the pUCGA backbone) using an SGI-DNA BioXP 3200.

DI Method

The V4 region of the 16S rRNA was amplified using a two-step PCR protocol. The primary amplification was done in a qPCR reaction, using the ABI7900 so that the dynamics of the PCR reactions could be monitored. The following recipe was used: 3 μl template DNA, 0.48 μl nuclease-free water, 1.2 μl×KAPA HiFi buffer (Kapa Biosystems, Woburn, Mass.), 0.18 μl 10 mM dNTPs (Kapa Biosystems, Woburn, Mass.), 0.3 μl DMSO (Fisher Scientific, Waltham, Mass.), 0.12 μl ROX (25 μM) (Life Technologies, Carlsbad, Calif.), 0.003 μl 1000×SYBR Green, 0.12 μl KAPA HiFi Polymerase (Kapa Biosystems, Woburn, Mass.), 0.3 μl forward primer (10 μM), 0.3 μl reverse primer (10 μM). Cycling conditions were: 95° C. for 5 minutes, followed by 20 cycles of 98° C. for 20 seconds, 55° C. for 15 seconds, and 72° C. for 1 minute. The primers for the primary amplification contained both 16S-specific primers (V4 515F and V4 806R), as well as adapter tails for adding indices and Illumina flow cell adapters in a secondary amplification. The following primers were used (16S-specific sequences in bold):

V4_515F_Nextera: (SEQ ID NO: 1)
TCGTCGGCAGCGTCAGATGTGTATAAGAGACAGGTGCCAGCMGCCGCGGT
AA

V4_806R_Nextera: (SEQ ID NO: 2)
GTCTCGTGGGCTCGGAGATGTGTATAAGAGACAGGGACTACHVGGGTWTC
TAAT

The amplicons from the primary PCR were diluted 1:100 in sterile, nuclease-free water, and a second PCR reaction was set up to add the Illumina flow cell adapters and indices. The secondary amplification was done using the following recipe: 5 μl template DNA, 1 μl nuclease-free water, 2 μl 5×KAPA HiFi buffer (Kapa Biosystems, Woburn, Mass.), 0.3 μl 10 mM dNTPs (Kapa Biosystems, Woburn, Mass.), 0.5 μl DMSO (Fisher Scientific, Waltham, Mass.) 0.2 μl KAPA HiFi Polymerase (Kapa Biosystems, Woburn, Mass.), 0.5 μl forward primer (10 μM), 0.5 μl reverse primer (10 μM). Cycling conditions were: 95° C. for 5 minutes, followed by 10 cycles of 98° C. for 20 seconds, 55° C. for 15 seconds, 72° C. for 1 minute, followed by a final extension at 72° C. for 10 minutes. The following indexing primers were used (X indicates the positions of the 8 bp indices):

Forward indexing primer: (SEQ ID NO: 3)
AATGATACGGCGACCACCGAGATCTACACXXXXXXXXTCGTCGGCAGCGT
C Reverse indexing primer: (SEQ ID NO: 4)
CAAGCAGAAGACGGCATACGAGATXXXXXXXXGTCTCGTGGGCTCGG Dilution Series Experiments For the dilution series experiments, the DI method primers (V4_515F_Nextera and V4_806R_Nextera, see above) were used for all of the comparisons. A ten-fold dilution series of the HM-276D mock community DNA was amplified for 20, 25, 30, or 35 cycles, using one of two different polymerases: Kapa HiFi HotStart (Kapa Biosystems, Woburn, Mass.), or 5 PRIME HotMasterMix (5 PRIME, Gaithersberg, Md.). PCR recipes and cycling conditions for the primary amplifications were as follows:

KAPA HiFi primary PCR recipe: 2.5 μl DNA template, 0.48 μl nuclease-free water, 2 μl 5×KAPA HiFi buffer (Kapa Biosystems, Woburn, Mass.), 0.3 μl 10 mM dNTPs (Kapa Biosystems, Woburn, Mass.), 0.5 μl DMSO (Fisher Scientific, Waltham, Mass.), 0.2 μl KAPA HiFi Polymerase (Kapa Biosystems, Woburn, Mass.), 0.5 μl forward primer (10 μM), 0.5 μl reverse primer (10 μM).

KAPA HiFi cycling conditions: 95° C. for 5 minutes, followed by 20, 25, 30, or 35 cycles of 98° C. for 20 seconds, 55° C. for 15 seconds, 72° C. for 1 minute, followed by 72° C. for 5 minutes.

5 PRIME Taq cycling conditions: 94° C. for 3 minutes, followed by 20, 25, 30, or 35 cycles of 94° C. for 20 seconds, 55° C. for 15 seconds, 72° C. for 1 minute, followed by 72° C. for 5 minutes.

Primary PCRs were then diluted 1:100 in sterile, nuclease-free water, and a second PCR reaction was set up to add the Illumina flow cell adapters and indices. For these reactions the following recipes were used (polymerase-specific cycling conditions were the same as above, but using 10 cycles in the indexing step):

KAPA HiFi indexing PCR recipe: 5 μl 1:100 DNA template, 5 μl template DNA, 1 μl nuclease-free water, 2 μl 5×KAPA HiFi buffer (Kapa Biosystems, Woburn, Mass.), 0.3 μl 10 mM dNTPs (Kapa Biosystems, Woburn, Mass.), 0.5 μl DMSO (Fisher Scientific, Waltham, Mass.) 0.1 μl KAPA HiFi Polymerase (Kapa Biosystems, Woburn, Mass.), 0.5 μl forward primer (10 μM), 0.5 μl reverse primer (10 μM).

5 PRIME Taq indexing PCR recipe: 5 μl 1:100 DNA template, 4 μl 2×5 PRIME Hot Start High-Fidelity Master Mix, 1 μl sterile, nuclease-free water, dried-down indexing primers (final concentration of 0.5 μM for each primer).

KAPA HiFi Concentration Tests

For the KAPA HiFi concentration tests, amplifications were performed using the KAPA HiFi primary PCR recipe and cycling conditions described in the dilution series experiment section above, but the amount of KAPA HiFi Polymerase added to the 0.5× reactions was cut in half (0.1 μl per 10 μl reaction) and the amount added to the 0.25× reactions was one fourth the 1× concentration (0.05 μl per 10 μl reaction); nuclease-free water was added to compensate for the missing volume. The indexing reactions for each of these conditions was carried out with the 0.5× concentration of KAPA HiFi polymerase, so the differences observed between these conditions are a result of the differing KAPA HiFi polymerase concentrations in the primary PCR reaction.

KAPA HiFi Readymix Amplifications

KAPA HiFi ReadyMix PCRs were carried out as described above, using the DI primers (V4_515F_Nextera and V4_806R_Nextera, see above) using the following recipes: KAPA HiFi Readymix PCR recipe: 2.5 μl DNA template, 5 μl 2×Kapa HiFi HotStart Readymix, 0.5 μl forward primer (10 μM), 0.5 μl reverse primer (10 μM), 1.5 μl sterile, nuclease-free water.

KAPA HiFi ReadyMix indexing PCR recipe: 5 μl 1:100 DNA template, 5 μl 2×Kapa HiFi HotStart Readymix, dried-down indexing primers (final concentration of 0.5 μM for each primer).

Amplifying *C. jejuni* V4 and V3-V5 Variable Regions

DNA from a pure isolate of *C. jejuni* (81-176) was amplified using the V4 515F and V4 806R primers and the KAPA ReadyMix protocol described above, or using the KAPA HiFi (1×) protocol with primers for the V3-V5 variable region. The primer sequences for the primary amplification for the V3-V5 variable region were as follows (16S-specific sequences in bold):

V3F_Nextera:
(SEQ ID NO: 5)
TCGTCGGCAGCGTCAGATGTGTATAAGAGACAGCCTACGGGAGGCAGCAG

V5R_Nextera:
(SEQ ID NO: 6)
GTCTCGTGGGCTCGGAGATGTGTATAAGAGACAGCCGTCAATTCMTTTRA
GT

Normalization and Pooling of Sequencing Libraries

For sample normalization prior to sequencing, for experiments not including the synthetic standard molecules, PCR products were quantified using a PicoGreen dsDNA assay (Life Technologies, Carlsbad, Calif.), and the samples were normalized, pooled, and approximately 1 μg of material was concentrated to 10 μl using 1.8×AMPureXP beads (Beckman Coulter, Inc., Brea, Calif.). The pooled sample was then size selected at 427 bp+/−20% for the DI pools, or at 368 bp+/−20% for the EMP pools, on a Caliper XT DNA 750 chip (Caliper Life Science, Hopkinton, Mass.). The size-selected material was cleaned up using AMPureXP beads, and eluted in 20 μl of EB buffer (10 mM Tris-HCl, pH 8.5). The final pooled sample was quantified using the PicoGreen dsDNA assay.

For experiments containing the synthetic standards, samples were normalized prior to sequencing using a SequalPrep normalization plate kit (ThermoFisher) according to manufacturer's instructions.

The libraries containing the PCR-free quantification barcodes were prepared by treating the standard plasmid pools with MlyI (New England Biolabs, Inc., Ipswich, Mass.), following manufacturer's recommendations for the digest. The resulting digest was purified using AmPureXP beads, and quantified with the PicoGreen assay.

Sequencing

The sample pools were diluted to 2 nM based on the PicoGreen measurements, and 10 μl of the 2 nM pool was denatured with 10 μl of 0.2 N NaOH, diluted to 8 pM in Illumina's HT1 buffer, spiked with 15% PhiX, heat denatured at 96° C. for 2 minutes, and sequenced using a MiSeq 600 cycle v3 kit (Illumina, San Diego, Calif.).

Analysis

The mock community samples were sub sampled to a depth of 10,000 reads per sample. Sequencing adapter sequences were then trimmed using Trimmomatic (Bolger et al., 2014, *Bioinformatics* btu170) and PANDAseq (Masella et al., 2012, *BMC Bioinformatics* 13:31) was used to remove primer sequences (where applicable) and join paired end reads. Fastq files were converted to QIIME (Caporaso et al., 2010, *Nat. Methods* 7:335-336) fastq format using a custom script. Next, individual sample fasta files were concatenated into one fasta file and chimera detection and removal was run using ChimeraSlayer's usearch61 method (Haas et al., 2011, *Genome Res.* 21:494-504). The resulting reads were mapped to an HMP mock community reference file (Salipante et al., 2014, *Appl. Environ. Microbiol.* AEM.02206-14-; doi:10.1128/AEM.02206-14) for the calculation of the percent abundance, RMSD, and MAPE values. The distribution of primer corrections was analyzed by cataloging mismatches to the V4 primer sequences using custom Python scripts and BioPython (Cock et al., 2009, *Bioinformatics* 25:1422-1423). Illumina adapters were trimmed using cutadapt (Martin, M., 2011, *EMBnet.journal* 17:10-12) and paired reads were merged using PANDAseq (Masella et al., 2012, *BMC Bioinformatics* 13:31). In order to filter out noise from indels in the primer regions, a threshold of a maximum of three mismatches per primer sequence was used for this analysis. The primer sequences associated with the differentially abundant OTUs in the NHP and human datasets were analyzed by searching for exact matches to the rep_set sequences from these OTUs in the untrimmed sub-sampled fastq files. The analysis of the PCR-free quantification barcodes and synthetic standard experiments were carried out using custom Python scripts.

Example 2

Primer Editing Standards

Figure 27:
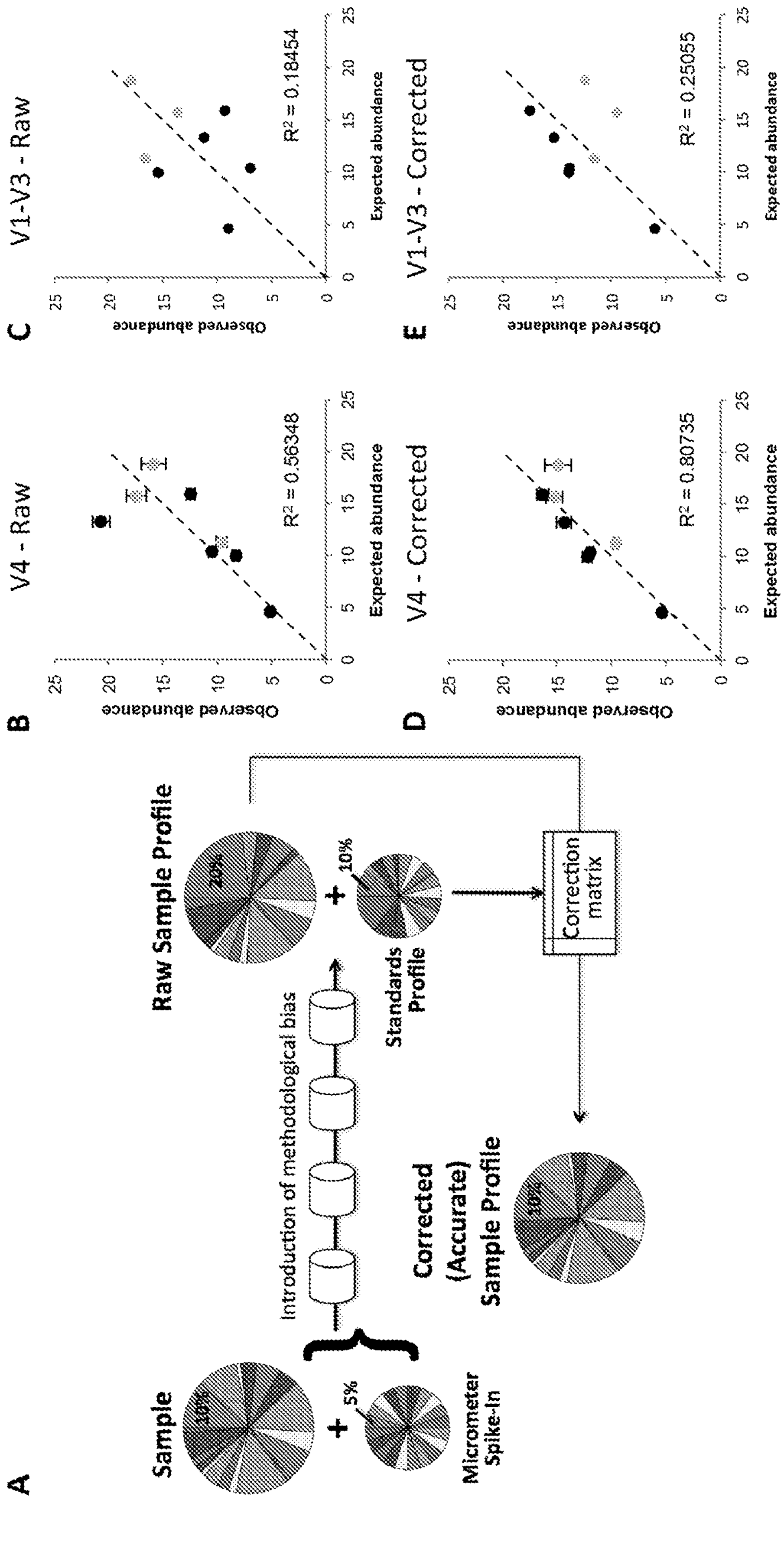
FIG. 27. Analysis of PCR bias using a spike-in control. (A) A synthetic spike-in control is amplified together with a sample of unknown composition. The spike-in control is used to measure the PCR biases specific to different template molecules and used to generate a correction matrix, which is used to infer the starting abundances of different species in the sample. (B) Measured abundance of a mock community comprised of eight bacterial species (five of which, dark dots, are targeted by synthetic standards and three of which, light dots, are not) using the 16S V4 region. (C) Measured abundance the same mock community using the 16S V1-V3 regions. (D-E) Abundance measurements when correction factors from the synthetic spike-in standards are used to correct for amplification bias. Abundances for corrected taxa (dark dots) are closer to expected values (diagonal dashed line).

Synthetic standards were designed that allow primer editing to be studied in greater detail and monitored for the purposes of process quality control/quality assurance. These standards are based on the V4 515F primer region of *E. coli* and include 30 plasmids containing the *E. coli* 16S rRNA gene V4 (variable region 4) with every possible single base mismatch in the last 10 bp of the primer sequence and one wild-type plasmid (FIG. 27A). Similar standards could be designed for any primer region of interest, such as the additional set of standards developed for ITS2. The synthetic primer editing standards were synthesized, cloned into the pUCGA1.0 cloning vector, and transformed into NEB 5Alpha *E. coli* competent cells. Multiple clones were picked for each construct, DNA was extracted and the constructs were sequenced by Sanger sequencing to verify that the sequence of the synthetic DNA was correct. The following primers were used for Sanger verification of these constructs:

```
                              (SEQ ID NO: 270)
pUCGA1.0_Sanger_For: CGACTCTAGAGGATCGAGCACA

                              (SEQ ID NO: 271)
pUCGA1.0_Sanger_Rev: TTCGAGCTCGGTACCCGCAT
```

DNA from the 31 standard plasmids was quantified using the Quant-iT PicoGreen dsDNA quantitation assay (Thermo Fisher Scientific, Inc., Waltham, Mass.) and the plasmids were pooled at equal masses. The PCR-free quantification barcode constructs in the plasmids were used to verify that each construct was present in the pool and to determine the exact ratios of construct abundances. The following restriction digest was used to liberate PCR-free quantification barcodes: 17 μl primer editing standard pool DNA (10 ng/μl), 2 μl Cutsmart buffer (New England Biolabs Inc., Ipswich, Mass.), 1 μl MlyI (New England Biolabs Inc., Ipswich, Mass.). The digests were incubated at 37° C. for one hour, then 30 μl of water was added to the digest (to bring volume up to 50 μl), then 30 μl of magnetic beads (0.6×AMPure XP, Beckman Coulter, Inc., Brea, Calif.) were added and the supernatant added transferred to new tube (discarded beads). The restriction digest (supernatant from 0.6× binding) was purified using magnetic beads (1.8× AmpureXP beads, Beckman Coulter, Inc., Brea, Calif.) and eluted in 25 μl of elution buffer.

The eluted DNA was quantified using both Quant-iT PicoGreen dsDNA quantitation assay (Thermo Fisher Scientific, Inc., Waltham, Mass.) and Bioanalyzer HS analysis (Agilent Technologies, Santa Clara, Calif.). The pool was diluted to 2 nM and sequenced on a fraction of an MISEQ 2×300 bp lane (Illumina, Inc., San Diego, Calif.) following the manufacturer's instructions (8 pM clustering concentration). Composition of the plasmid pool (barcode counts and percentages) was determined using a custom python script.

In order to assess the ability of these standards to report on primer editing, and to compare the editing abilities of different enzymes, the primer editing standard pool was amplified using eight different polymerases: KAPA HiFi (KAPA Biosystems, Woburn, Mass.), Qiagen Taq (Qiagen USA, Germantown, Md.), Q5 (New England Biolabs, Inc., Ipswich, Mass.), PHUSION (Thermo Fisher Scientific, Inc., Waltham, Mass.), VENT (New England Biolabs, Inc., Ipswich, Mass.), Pfu DNA polymerase (Promega Corp., Madison, Wis.), ACCUPRIME Taq (Invitrogen, Thermo Fisher Scientific, Carlsbad, Calif.), and Taq (New England Biolabs, Inc., Ipswich, Mass.) at four different concentrations (0.25×, 0.5×, 1×, or 2× manufacturer's recommended concentration) and the primer editing standard pool at four different template concentrations (250,000 template molecules, 25,000 template molecules, 2,500 template molecules, or 250 template molecules per standard). *E. coli* specific primers (non-degenerate V4 515F/V4 806R) were used for these amplifications:

```
E_coli_V4_515F:
                              (SEQ ID NO: 272)
TCGTCGGCAGCGTCAGATGTGTATAAGAGACAGGTGCCAGCAGCCGCGGT

AA

E_coli_V4_806R:
                              (SEQ ID NO: 273)
GTCTCGTGGGCTCGGAGATGTGTATAAGAGACAGGGACTACCAGGGTATC

TAAT
```

PCR recipes and conditions are listed in Table 1, below (volumes are in microliters, temperatures are in degrees Celsius, all amplifications were done for 30 PCR cycles).

TABLE 1

| Enzyme | KAPA HiFi | Q5 | Phusion | NEB Vent | PfuUltra II | AccuPrime Taq | NEB Taq | Qiagen Taq |
|---|---|---|---|---|---|---|---|---|
| Template DNA | 2.5 | 2.5 | 2.5 | 2.5 | 2.5 | 2.5 | 2.5 | 2.5 |
| Reaction buffer | 2 | 2 | 2 | 1 | 1 | 1 | 1 | 1 |
| dNTP mix | 0.3 | 0.2 | 0.2 | 0.2 | 0.1 | 0.2 | 0.2 | 0.08 |
| Primer 1 | 0.5 | 0.5 | 0.5 | 0.5 | 0.5 | 0.5 | 0.5 | 0.5 |
| Primer 2 | 0.5 | 0.5 | 0.5 | 0.5 | 0.5 | 0.5 | 0.5 | 0.5 |
| MgCl2 | | | | | | | | 0.4 |
| DMSO | 0.5 | 0.5 | 0.5 | 0.5 | 0.5 | 0.5 | 0.5 | 0.5 |
| Enzyme 0.25x condition | 0.05 | 0.025 | 0.025 | 0.025 | 0.05 | 0.0625 | 0.0125 | 0.0125 |
| Water 0.25x condition | 3.65 | 3.775 | 3.775 | 4.775 | 4.85 | 4.7375 | 4.7875 | 4.5075 |
| Enzyme 0.5x condition | 0.1 | 0.05 | 0.05 | 0.05 | 0.1 | 0.125 | 0.025 | 0.025 |
| Water 0.5x condition | 3.6 | 3.75 | 3.75 | 4.75 | 4.8 | 4.675 | 4.775 | 4.495 |
| Enzyme 1x condition | 0.2 | 0.1 | 0.1 | 0.1 | 0.2 | 0.25 | 0.05 | 0.05 |
| Water 1x condition | 3.5 | 3.7 | 3.7 | 4.7 | 4.7 | 4.55 | 4.75 | 4.47 |
| Enzyme 2x condition | 0.4 | 0.2 | 0.2 | 0.2 | 0.4 | 0.5 | 0.1 | 0.1 |
| Water 2x condition | 3.3 | 3.6 | 3.6 | 4.6 | 4.5 | 4.3 | 4.7 | 4.42 |
| Hot start temp | 95 | 98 | 98 | 95 | 95 | 95 | 95 | 95 |

TABLE 1-continued

| Enzyme | KAPA HiFi | Q5 | Phusion | NEB Vent | PfuUltra II | AccuPrime Taq | NEB Taq | Qiagen Taq |
|---|---|---|---|---|---|---|---|---|
| Hot start time | 5 min | 30 sec | 30 sec | 2 min | 2 min | 2 min | 2 min | 5 min |
| Denaturation temp | 98 | 98 | 98 | 95 | 95 | 95 | 95 | 94 |
| Denaturation time | 20 sec | 20 sec | 20 sec | 20 sec | 20 sec | 20 sec | 20 sec | 30 sec |
| Annealing temp | 55 | 55 | 55 | 55 | 55 | 55 | 55 | 55 |
| Annealing time | 15 sec | 15 sec | 15 sec | 15 sec | 15 sec | 15 sec | 15 sec | 30 sec |
| Extension temp | 72 | 72 | 72 | 72 | 72 | 68 | 68 | 72 |
| Extension time | 1 min | 1 min | 1 min | 1 min | 1 min | 1 min | 1 min | 1 min |
| Final extension temp | 72 | 72 | 72 | 72 | 72 | 68 | 68 | 72 |
| Final extension time | 10 min | 5 min | 5 min | 5 min | 5 min | 5 min | 5 min | 10 min |

These amplicons were then diluted 1:100, and amplified with 10 cycles of PCR (using KAPA HiFi 0.5× conditions) with indexing primers to add sample specific indices and Illumina flow cell adapters. Indexing primers had the following sequence ([i5] and [i7] refer to the index sequence codes used by Illumina, the p5 and p7 flow cell adapters are in bold):

Forward indexing primer:
(SEQ ID NO: 274)
AATGATACGGCGACCACCGAGATCTACAC[i5]TCGTCGGCAGCGTC Reverse indexing primer:
(SEQ ID NO: 275)
CAAGCAGAAGACGGCATACGAGAT[i7]GTCTCGTGGGCTCGG Indexed samples were normalized using normalization plates (SEQUALPREP, Thermo Fisher Scientific, Waltham, Mass.), an equal volume of each sample was pooled, and the sample pool was purified and concentrated using magnetic beads (1× AmPureXP, Beckman Coulter, Inc., Brea, Calif.), and eluted in 25 µl of elution buffer. The eluted DNA was quantified using both Quant-iT PicoGreen dsDNA quantitation assay (Thermo Fisher Scientific, Inc., Waltham, Mass.) and Bioanalyzer HS analysis (Agilent Technologies, Santa Clara, Calif.). The pool was diluted to 2 nM and sequenced on a fraction of an MISEQ 2×300 bp lane (Illumina, Inc., San Diego, Calif.) following the manufacturer's instructions (8 pM clustering concentration). Composition of the plasmid pool (barcode counts and percentages) was determined using a custom python script.

Figure 24:
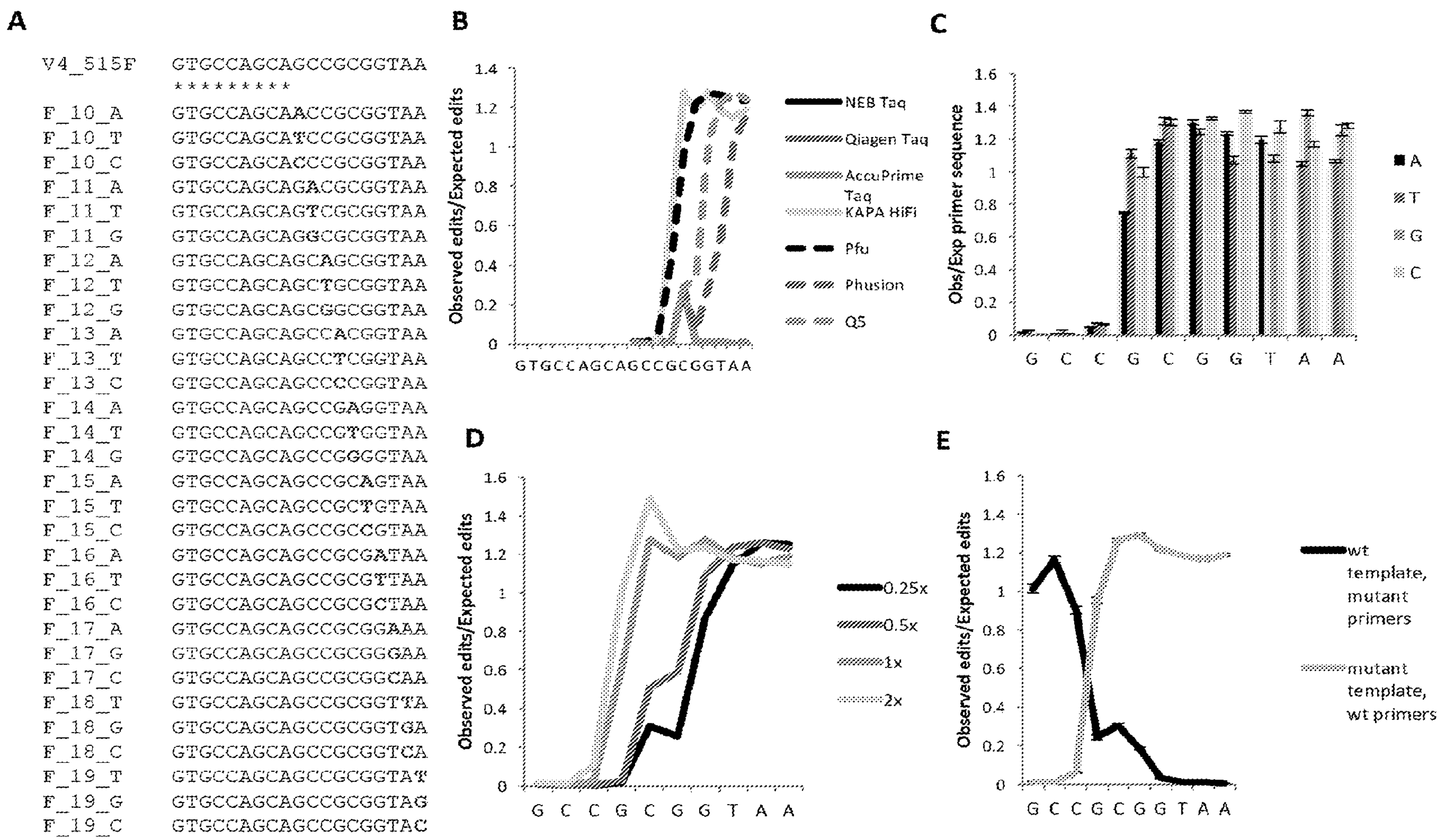
FIG. 24. Design and analysis of primer editing standards. (A) Design of V4 515F region of primer editing standards (SEQ ID NOs:288-318). Primer mismatches are shaded. (B) Primer editing standard (SEQ ID NO:288) used to demonstrate that many proofreading polymerases can support primer editing, though to varying extents. (C) Primer editing standard used to demonstrate that there is little apparent sequence specificity to primer editing of template sequence (SEQ ID NO:327). (D) Primer editing standards used to demonstrate that primer editing of template sequence (SEQ ID NO:327) by KAPA HiFi polymerase is concentration dependent. (E) Primer editing can result in edits that change a wildtype *E. coli* primer (SEQ ID NO:327) to match a mutant template (light curve) or a mutant primer to match a wildtype *E. coli* template (dark curve) with similar efficiency at a given primer position.

Primer editing was not observed with non-proofreading polymerases (e.g., NEB Taq, Qiagen Taq, or Accuprime Taq). The proofreading polymerases tested were all able to edit the amplification primers to match the primer editing standard templates, though the extent to which the editing took place was variable between the different enzymes at the manufacturer's recommended enzyme concentration, 1× (FIG. 24B). There was little apparent sequence specificity to the editing observed by proofreading polymerases, with the possibly exception of a slight bias towards G/C edits in the two 3' terminal positions (FIG. 24C). The extent of primer editing observed was dependent on the concentration of enzyme used (FIG. 24D), though the magnitude of concentration dependence also varied among the different enzymes studied (data not shown). These data provide direct evidence of enzyme concentration dependent primer editing. Template concentration had little discernable effect on primer editing at the concentrations that could be reliably examined. These results demonstrate that the primer editing standards can be used to assess the amount of primer editing that occurs under various reaction conditions.

Next, the wildtype *E. coli* plasmid standard was amplified with a mixed pool of primers containing the 31 possible sequences encoded in the primer editing plasmid pool using KAPA HiFi polymerase (1× reaction condition). The mutant primers were edited to match the wildtype template sequence with a similar extent and frequency as the edits seen in the previous experiments with the primer editing standards. This demonstrates that the primer editing standards accurately report on the extent and frequency of primer editing.

Figure 25:
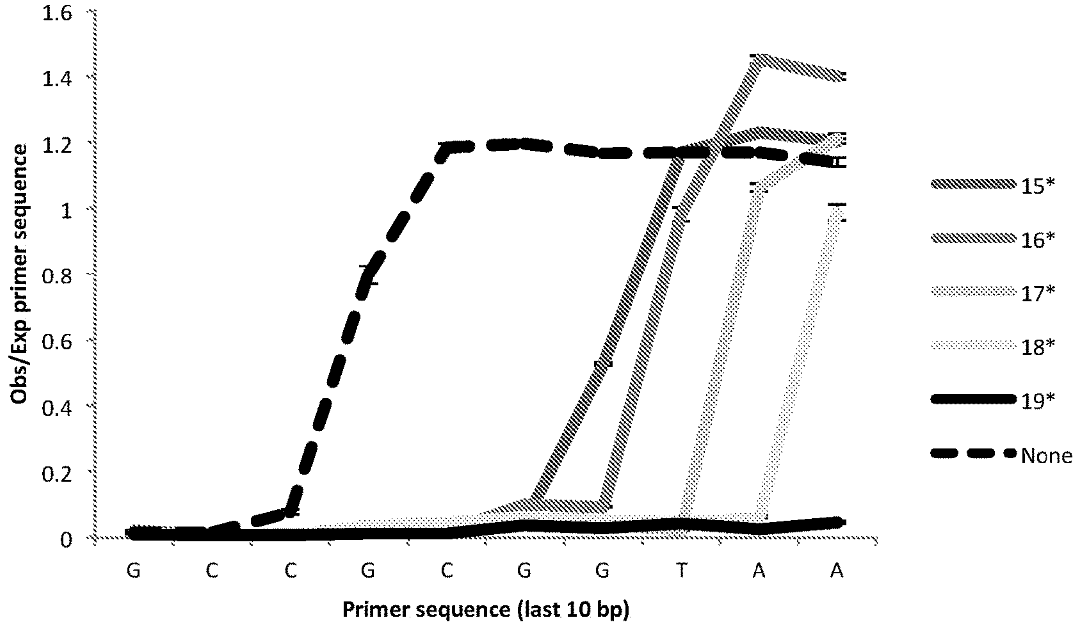
FIG. 25. Primer editing standards used to demonstrate that editing of a primer sequence (SEQ ID NO:327) by KAPA HiFi polymerase can be blocked at a specified position by a single phosphorothiol linkage.

In order to determine whether introduction of a phosphorothiol bond at a specific position in the primer sequence could limit the extent of primer editing, the primer editing standard pool was amplified with KAPA HiFi polymerase (1× reaction condition) using *E_coli*_V4_515F derivatives containing a single phosphorothiol bond at position 15, 16, 17, 18, or 19, together with the *E._coli*_V4_806R primer. These amplicons were indexed and sequenced as described above. Introduction of the phosphorothiol bond at a specific position caused a truncation of any primer editing activity 5' of the position of the phosphorothiol bond (FIG. 25). These results demonstrate that primer editing is tunable by using phosphorothiol modified primers.

Example 3

Biophysical Standards

Figure 26:
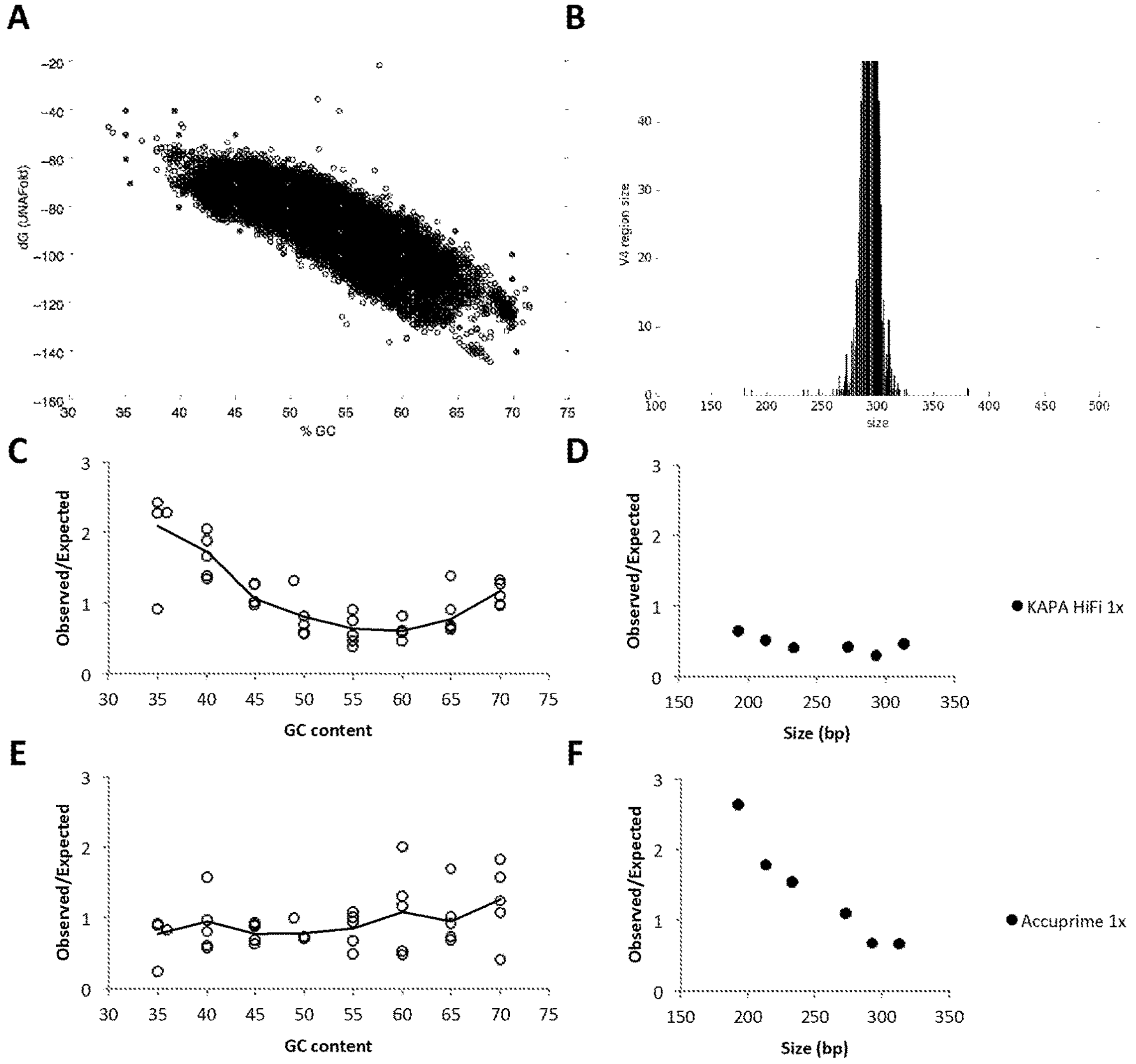
FIG. 26. Analysis of bias using biophysical standards and size standards. (A) Distribution of 16S rRNA gene V4 region % GC and predicted secondary structure (dG) based on sequences in the Greengenes database, black open circles, and designed biophysical standards, light filled circles. As in FIG. 19, the black smear is the result of densely overlapping black open circles. (B) Distribution of 16S rRNA gene V4 region sizes based on sequences in the Greengenes database. V4 size standards range from 193 bp to 313 bp. (C-D) Biophysical standards and size standards used to report on bias due to sequence properties when amplified with KAPA HiFi polymerase. (E-F) Biophysical standards and size standards used to report on bias due to sequence properties when amplified with Accuprime Taq polymerase.

A set of biophysical process control standards were designed to report on amplification biases that arise through the interaction of amplification conditions and reagents with the biophysical properties of the template molecules such as, for example, GC content, amplicon size, and/or secondary structure). These controls were designed to tile the parameter space encompassed by the natural genetic variation in the V4 region of the 16S rRNA gene, as assessed by the GC content and predicted secondary structure of all of the identifiable V4 regions in the Greengenes database (DeSantis et al., 2006. *Appl Environ Microbiol* 72:5069-72). (FIG. 26A). Next, the sequence of the *E. coli* 16 rRNA molecule was varied in silico, adding different amounts of GC or AT bias and generating an in silico library of millions of variant sequences. Then, secondary structure predictions were generated for these sequences, sequences that were >97% identical to a sequence in the Greengenes database were filtered out, and a set of molecules that tiled the extent of natural GC content and secondary structure variation (FIG. 26A) were selected. The naturally occurring distribution of V4 region sizes also were characterized and a set of standards was made to cover this size distribution, which could be used to detect biases in amplicon size due to size selection or amplification bias (FIG. 26B).

The biophysical process control standards were synthesized, cloned, transformed, and sequence verified as described for the primer editing standards in EXAMPLE 2. They were normalized, pooled, and the PCR-free quantification barcodes were used to determine exact pool composition as described for the primer editing standards in EXAMPLE 2.

In order to assess the ability of these standards to report on amplification bias, and to compare the biases of different enzymes, the biophysical standard pool was amplified using eight different polymerases: KAPA HiFi (KAPA Biosystems, Woburn, Mass.), Qiagen Taq (Qiagen USA, Germantown, Md.), Q5 (New England Biolabs, Inc., Ipswich, Mass.), PHUSION (Thermo Fisher Scientific, Inc., Waltham, Mass.), VENT (New England Biolabs, Inc., Ipswich, Mass.), Pfu DNA polymerase (Promega Corp., Madison, Wis.), ACCUPRIME Taq (Invitrogen, Thermo Fisher Scientific, Carlsbad, Calif.), and Taq (New England Biolabs, Inc., Ipswich, Mass.) at four different concentrations (0.25×, 0.5×, 1×, or 2× manufacturer's recommended concentration) and the biophysical standard pool at four different template concentrations (250,000 template molecules, 25,000 template molecules, 2,500 template molecules, or 250 template molecules per standard).

Standard degenerate V4 515F/V4 806R were used for these amplifications:

V4_515F_Nextera:
(SEQ ID NO: 276)
TCGTCGGCAGCGTCAGATGTGTATAAGAGACAGGTGCCAGCMGCCGCGGT
AA V4_806R_Nextera:
(SEQ ID NO: 277)
GTCTCGTGGGCTCGGAGATGTGTATAAGAGACAGGGACTACHVGGGTWTC
TAAT PCR recipes and conditions are listed in Table 1, above, in EXAMPLE 2. These amplicons were indexed and sequenced as described above. Sequence data was trimmed of adapters and primer sequences using cutadapt (Martin, M. 2011. *EMBnet.journal* 17(1):10-12) paired end reads were merged using pandaseq (Masella et al., 2012. *BMC Bioinformatics* 13:31) or PEAR (Zhang et al., 2014. *Bioinformatics* 30(5):614-620) and reads were mapped to a biophysical standards reference file using bowtie2 (Langmead et al., 2012. 9(4):357-359). Size standards were analyzed by counting sequences of various sizes after read merging using a custom python script. Different polymerases produced data that had distinctive patterns with respect to GC content and amplicon size (FIG. 26C-F). These results demonstrate that the biophysical standards can be used to report on bias due to amplicon biophysical properties in an amplification reaction.

Example 4

Full-Length 16S rRNA Gene Synthetic Spike-in Standards

After seeing inconsistent results with synthetic standards targeting just the 16S rRNA gene variable region V4, a set of 20 full-length 16S rRNA gene standards were designed with three independent 3 bp tags in variable regions V3, V4, and V5.

The tagged spike-in standards were synthesized, cloned, transformed, and sequence verified as described above in EXAMPLE 2. They were normalized, pooled, and the PCR-free quantification barcodes were used to determine exact pool composition as described above in EXAMPLE 2.

In order to test the ability of these full-length 16S rRNA gene synthetic standards to correct for amplification bias, a commercially available mock community reference standard was amplified with or without the pool of tagged synthetic spike-in standards. The pool of tagged synthetic spike-in standards contained plasmids corresponding to five of eight bacterial strains in the mock microbial community. These samples were amplified with primers targeting the bacterial 16S rRNA gene variable regions V1-V3, V3-V4, V4, and V5-V6, using either the KAPA HiFi 1×, or Qiagen Taq 1× reaction conditions described above, and the primer sets shown in Table 2.

TABLE 2

| Region | Forward Primer | SEQ ID NO |
|---|---|---|
| V1-V3 | TCGTCGGCAGCGTCAGATGTGTATAAGAGACAGAGAGTTTGATCMTGGCTCAG | 278 |
| V3-V4 | TCGTCGGCAGCGTCAGATGTGTATAAGAGACAGCCTACGGGAGGCAGCAG | 279 |
| V4 | TCGTCGGCAGCGTCAGATGTGTATAAGAGACAGGTGCCAGCMGCCGCGGTAA | 280 |
| V5-V6 | TCGTCGGCAGCGTCAGATGTGTATAAGAGACAGRGGATTAGATACCC | 281 |
| Region | Reverse Primer | |
| V1-V3 | GTCTCGTGGGCTCGGAGATGTGTATAAGAGACAGATTACCGCGGCTGCTGG | 282 |
| V3-V4 | GTCTCGTGGGCTCGGAGATGTGTATAAGAGACAGGGACTACHVGGGTWTCTAAT | 283 |
| V4 | GTCTCGTGGGCTCGGAGATGTGTATAAGAGACAGGGACTACHVGGGTWTCTAAT | 284 |
| V5-V6 | GTCTCGTGGGCTCGGAGATGTGTATAAGAGACAGCGACRRCCATGCANCACCT | 285 |

These amplicons were indexed and sequenced as described above. A custom python script was used to identify reads containing the 3 bp sequence tag that marks a read as corresponding to a spike-in standard, and spike-in standard and non-spike-in standard reads were split into separate fastq files. These reads were then trimmed, merged, and mapped to their respective reference files as described above in EXAMPLE 3. The abundance values for the reads corresponding to the tagged synthetic spike-in standards were then compared to their expected values, determined using the PCR-free barcode counts from the standard pool, in order to determine the extent of amplification bias observed for each construct. The ratio of observed to expected abundance for each construct was used to calculate a correction factor, and applied this correction factor to the mock community data for each sample (for the 5 strains targeted by a tagged spike-in standard), while normalizing the data to keep the total percentage for all organisms at 100% (FIG. 27A). As can be seen in FIG. 27B-E, measurements for strains targeted by a tagged spike-in standard (dark dots) were in general considerably more accurate when the calculated correction factor was applied to the data. In addition, the aggregate accuracy of the measurements for the whole mock community (including the data points for the non-targeted strains, light dots) was also improved when the correction factors were applied (FIG. 27D-E).

Example 5

The precision and accuracy of the PCR-free barcode quantification technology was tested using a standard pool described above in EXAMPLE 1 consisting of 20 tagged synthetic spike-in constructs targeting 16S rRNA gene variable region V4 and each containing a distinct 20 bp PCR-free quantification barcode construct.

Precision of PCR-Free Quantification Barcode Measurements

The 20-construct standard pool was cut with MlyI as follows:

10 μl plasmid DNA (from pooled sample—50 ng/μl)
2 μl Cutsmart buffer (New England Biolabs Inc., Ipswich, Mass.)
7 μl water
1 μl MlyI restriction enzyme (New England Biolabs Inc., Ipswich, Mass.)

Figure 28:
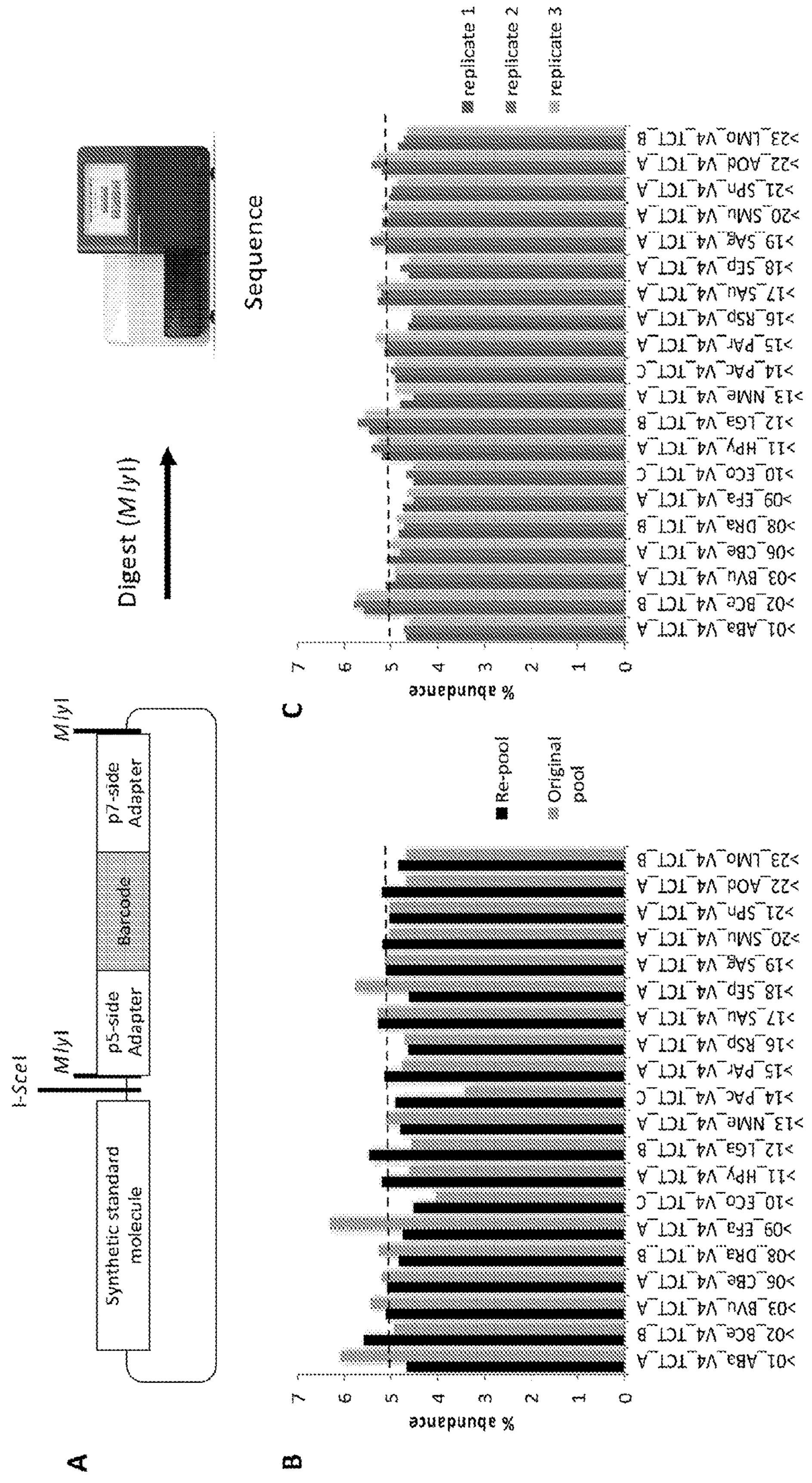
FIG. 28. Design and analysis of PCR-free barcodes. (A) Design of a synthetic DNA standard plasmid incorporating a PCR-free quantification barcode construct. (B) Quantification of a plasmid standard pool using the PCR-free quantification barcodes. This same set of standards was re-pooled using this abundance information and the second pool was quantified using the PCR-free barcode quantification method. (C) Three independent technical replicates of the even re-pooled mixture measured with the PCR-free barcode quantification method, demonstrating that the measurements obtained with this technique are highly precise.

The reaction was incubated at 37° C. for one hour. Next, 14 μl of solid phase reversible immobilization beads (SPRI 0.7×, Beckman Coulter, Inc., Brea, Calif.) were added. The supernatant (35 μl) was transferred to a tube with 70 μl of SPRI beads (2×), washed twice with 80% ethanol, air-dried for 10 minutes, then eluted in 20 μl elution buffer. The eluted DNA was quantified using both Quant-iT PicoGreen dsDNA quantitation assay (Thermo Fisher Scientific, Inc., Waltham, Mass.) and Bioanalyzer HS analysis (Agilent Technologies, Santa Clara, Calif.). The pool was diluted to 2 nM and sequenced on a fraction of an MISEQ 2×300 bp lane (Illumina, Inc., San Diego, Calif.) following the manufacturer's instructions (8 pM clustering concentration). Barcode counts were determined using a custom python script (FIG. 28A).

Based on this initial sequencing data, two additional pools of these standards were made: a re-pooled even pool (targeting 5% abundance for each construct) and a staggered pool (with a range of targeted abundances for each construct spanning roughly four logs). The even re-pooled sample was processed and sequenced as above and yielded data that showed that construct balance was improved in the pool (FIG. 28B).

To test the precision of the PCR-free barcode quantification technique, three independent digests of the re-pooled even standard pool were performed, purified, and sequenced as above. The three technical replicates yielded nearly identical data, demonstrating that this PCR-free barcode quantification technique is highly precise (FIG. 28C).

Accuracy of PCR-Free Quantification Barcode Measurements

Next, the accuracy of the PCR-free barcode quantification method was assessed by first comparing these measurements to those obtained by using PCR to amplify the barcode cassette, followed by comparison of the PCR-free and PCR measurements to droplet digital PCR measurements.

PCR-free barcode measurements of the initial re-pooled even mixture and the staggered pool were made as described above, with the exception that in the case of the staggered mixture 197.2 ng, as opposed to 500 ng of DNA was digested with MlyI. To set up the PCR reactions, pooled DNA was diluted to 1 ng/μl, to which 1 ng of DNA (1 μl diluted in 24 μl of water) per 50 μl PCR reaction was added. 1× Qiagen Taq conditions were used to amplify for 10 cycles, 20 cycles, 30 cycles, or 40 cycles, with the following primers (that target the ends of the PCR-free barcode construct):

```
                                        (SEQ ID NO: 286)
p5: AATGATACGGCGACCACCGA

                                        (SEQ ID NO: 287)
p7: CAAGCAGAAGACGGCATACGA
```

The mixtures were amplified as follows:
95° C.—5 minutes
X cycles
94° C.—30 seconds
60° C.—30 seconds
72° C.—30 seconds
72° C.—10 minutes
4° C.—hold The PCR reactions were purified using magnetic beads (0.8× AmpureXP beads, Beckman Coulter, Inc., Brea, Calif.) and eluted purified DNA in 25 μl of elution buffer. The eluted DNA was quantified using both Quant-iT PicoGreen dsDNA quantitation assay (Thermo Fisher Scientific, Inc., Waltham, Mass.) and Bioanalyzer HS analysis (Agilent Technologies, Santa Clara, Calif.). The pool was diluted to 2 nM and sequenced on a fraction of an MISEQ 2×300 bp lane (Illumina, Inc., San Diego, Calif.) following the manufacturer's instructions (8 pM clustering concentration). Barcode counts were determined using a custom python script.

Increasing the number of PCR cycles led to increased quantitative deviation from the expected values as well as the values measured with the PCR free barcode quantification method for both the even and staggered plasmid pool (FIG. 29A-D).

To further confirm the accuracy of the PCR free barcode quantification method, these measurements we compared to droplet digital PCR (ddPCR) measurements, a gold standard for accurate quantification. To measure the relative amount of each barcode in the even and staggered pools by ddPCR, a collection of 40 primer sets were designed that amplified between the plasmid backbone and each of the unique 20 bp barcode sequences in both the forward and reverse orientations. The specificity of these primer sets was determined by amplifying each individual plasmid construct with all 40 possible primer sets by qPCR. ddPCR reactions were carried out using a QX200 droplet digital PCR system (Bio-Rad Laboratories, Inc., Hercules, Calif.) following the manufacturer's instructions. The following reaction recipe was used:

5 μl—template (1:10,000 dilution of 1 ng/μl plasmid pool template. Note: for staggered template, different dilutions were made for different assays in order to make sure that all measurements were in the quantitative range of the instrument)
0.44 μl primer 1
0.44 μl primer 2
5.12 μl water
11 μl dye (EVAGREEN, Biotium, Fremont, Calif.)

2 µl of I-SceI (New England Biolabs, Inc., Ipswich, Mass.) to linearize the plasmids was added to the reaction master mix.

The reactions were partitioned into emulsions and then cycled using the following PCR conditions (lid temp=105° C.):

95° C.—10 minutes
40 cycles of:
95° C. 30 seconds
55° C. 1 minute
72° C. 5 minutes
12° C. hold Results were analyzed using QuantaSoft software (Bio-Rad Laboratories, Inc., Hercules, Calif.). In cases where there was clear separation of positive and negative droplet signals, a threshold was drawn that separated these populations of droplets in order to generate a molecule count for each assay. Assays that did not show a clear separation of positive and negative droplet signals were not analyzed. Data was averaged for any replicates and for the forward and reverse orientation assays for each construct to produce one measurement for each barcode construct.

Figure 29:
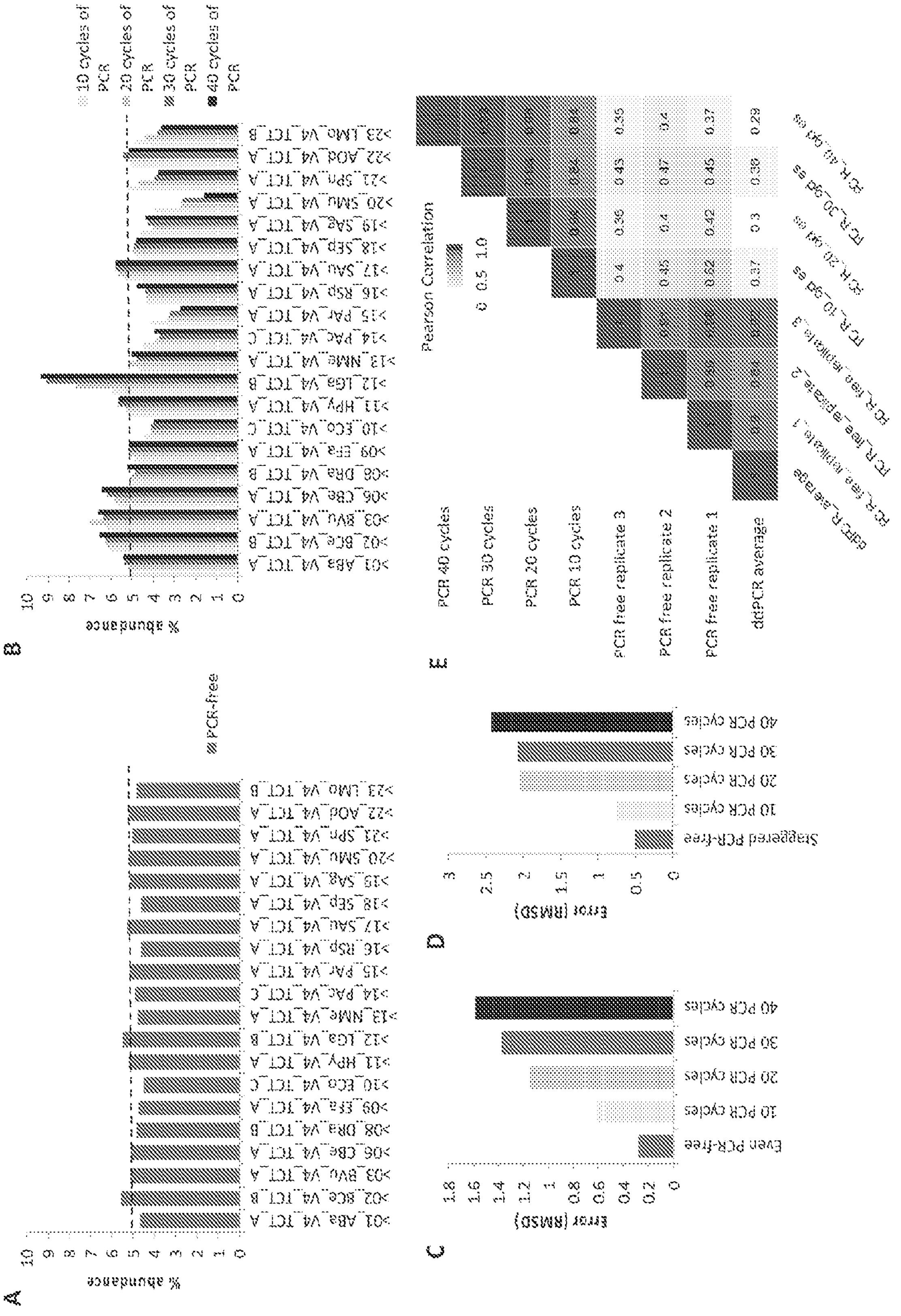
FIG. 29. Abundance analysis using PCR-free barcodes. (A-B) Comparison of quantification of an evenly mixed plasmid standard pool using either the PCR-free barcode quantification method or different amounts of PCR cycles to prepare libraries for Illumina sequencing (dashed line indicated expected values). (C) Root mean squared deviation from expected values for the evenly mixed plasmid pool measured with PCR-free barcodes or with different numbers of PCR cycles. (D) Root mean squared deviation from expected values for the staggered mixture of plasmids measured with PCR-free barcodes or with different numbers of PCR cycles. (E) PCR-free barcode measurements correlate very well with droplet digital PCR data. Increased cycles of PCR result in decreased correlation of the measured abundances with droplet digital PCR data.

The ddPCR measurements of the even plasmid pool correlated very well with the PCR-free barcode measurements, but did not correlate well with the measurements of the barcode constructs made with 10-40 PCR cycles (FIG. 29E). Similar results were obtained for the staggered plasmid pool. The strong correlation of ddPCR measurements with the PCR-free barcode measurements demonstrates that the PCR-free barcode quantitation method is highly accurate.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

| Sequence Listing Free Text |
| --- |
| Synthetic standard sequences - initial 16S rRNA gene V4 region tests (HMP mock community) |

Sequence tag in bold
Illumina adapters in lower case
>01_ABa_V4_TCT (SEQ ID NO: 8)
AATAAGCACCGGCTAACTCTGTGCCAGCAGCCGCGGTAATACAGAGGGTGCGAGCGTTAATCGGATTTAC
TGGGCGTAAATCTGCGTGCGTAGGCGGCTTATTAAGTCGGATGTGAAATCCCCGAGCTTAACTTGGGAAT
TGCATTCGATACTGGTGAGCTAGAGTATGGGAGAGGATGGTAGAATTCCAGGTGTAGCGGTGAAATGCGT
AGAGATCTGGAGGAATACCGATGGCGAAGGCAGCCATCTGGCCTAATACTGACGCTGAGGTACGAAAGCA
TGGGGAGCAAACAGGATTAGATACCCTGGTAGTCCATGCCGTAAACGATGTCTACTAGGGATAACAGGGT
AATGAGTCGACAAaatgatacggcgaccaccgagatctacactctttccctacacgacgctcttccgatc
tGCACATTGTAGCGTTGATAAagatcggaagagcacacgtctgaactccagtcacAATCAGTCTCGTatc
tcgtatgccgtcttctgcttgTTGTCGACTC >02_BCe_V4_TCT (SEQ ID NO: 9)
AGAAAGCCACGGCTAACTACGTGCCAGCAGCCGCGGTAATACGTAGGTGGCAAGCGTTATCCGGAATTAT
TGGGCGTAAATCTGCGCGCGCAGGTGGTTTCTTAAGTCTGATGTGAAAGCCCACGGCTCAACCGTGGAGG
GTCATTGGAAACTGGGAGACTTGAGTGCAGAAGAGGAAAGTGGAATTCCATGTGTAGCGGTGAAATGCGT
AGAGATATGGAGGAACACCAGTGGCGAAGGCGACTTTCTGGTCTGTAACTGACACTGAGGCGCGAAAGCG
TGGGGAGCAAACAGGATTAGATACCCTGGTAGTCCACGCCGTAAACGATGAGTGCTAGGGATAACAGGGT
AATGAGTCGACAAaatgatacggcgaccaccgagatctacactctttccctacacgacgctcttccgatc
tCGGAGGAGCTATAAATGACCagatcggaagagcacacgtctgaactccagtcacAATCAGTCTCGTatc
tcgtatgccgtcttctgcttgTTGTCGACTC >03_BVu_V4_TCT (SEQ ID NO: 10)
AATAAGGATCGGCTAACTCCGTGCCAGCAGCCGCGGTAATACGGAGGATCCGAGCGTTATCCGGATTTAT
TGGGTTTAAATCTGGGAGCGTAGATGGATGTTTAAGTCAGTTGTGAAAGTTTGCGGCTCAACCGTAAAAT
TGCAGTTGATACTGGATATCTTGAGTGCAGTTGAGGCAGGCGGAATTCGTGGTGTAGCGGTGAAATGCTT
AGATATCACGAAGAACTCCGATTGCGAAGGCAGCCTGCTAAGCTGCAACTGACATTGAGGCTCGAAAGTG
TGGGTATCAAACAGGATTAGATACCCTGGTAGTCCACACGGTAAACGATGAATACTAGGGATAACAGGGT
AATGAGTCGACAAaatgatacggcgaccaccgagatctacactctttccctacacgacgctcttccgatc
tTAATCGTACAAATTTCGAAAagatcggaagagcacacgtctgaactccagtcacAATCAGTCTCGTatc
tcgtatgccgtcttctgcttgTTGTCGACTC -continued

| Sequence Listing Free Text |
|---|

>04_BVu_V4_TCT (SEQ ID NO: 11)
AATAAGGATCGGCTAACTCCGTGCCAGCAGCCGCGGTAATACGGAGGATCCGAGCGTTATCCGGATTTAT
TGGGTTTAAATCTGGGAGCGTAGATGGATATTTAAGTCAGTTGTGAAAGTTTGCGGCTCAACCGTAAAAT
TGCAGTTGATACTGGATATCTTGAGTGCAGTTGAGGCAGGCGGAATTCGTGGTGTAGCGGTGAAATGCTT
AGATATCACGAAGAACTCCGATTGCGAAGGCAGCCTGCTAAGCTGCAACTGACATTGAGGCTCGAAAGTG
TGGGTATCAAACAGGATTAGATACCCTGGTAGTCCACACGGTAAACGATGAATACTAGGGATAACAGGGT
AATGAGTCGACAAaatgatacggcgaccaccgagatctacactctttccctacacgacgctcttccgatc
tAACATTCAGGCGCACCTACAagatcggaagagcacacgtctgaactccagtcacAATCAGTCTCGTatc
tcgtatgccgtcttctgcttgTTGTCGACTC >05_BVu_V4_TCT (SEQ ID NO: 12)
AATAAGGATCGGCTAACTCCGTGCCAGCAGCCGCGGTAATACGGAGGATCCGAGCGTTATCCGGATTTAT
TGGGTTTAAATCTGGGAGCGTAGATGGATGTTTAAGTCAGTTGTGAAAGTTTGCGGCTCAACCGTAAAAT
TGCAGTTGATACTGGATATCTTGAGTGCAGTTGAGGCAGGCGGAATTCGTGGTGTAGCGGTGAAATGCTT
AGATATCACGAGGAACTCCGATTGCGAAGGCAGCCTGCTAAGCTGCAACTGACATTGAGGCTCGAAAGTG
TGGGTATCAAACAGGATTAGATACCCTGGTAGTCCACACGGTAAACGATGAATACTAGGGATAACAGGGT
AATGAGTCGACAAaatgatacggcgaccaccgagatctacactctttccctacacgacgctcttccgatc
tTATGCCGCTCGAGACCCATTagatcggaagagcacacgtctgaactccagtcacAATCAGTCTCGTatc
tcgtatgccgtcttctgcttgTTGTCGACTC >06_CBe_V4_TCT (SEQ ID NO: 13)
AGGAAGCCACGGCTAACTACGTGCCAGCAGCCGCGGTAATACGTAGGTGGCAAGCGTTGTCCGGATTTAC
TGGGCGTAAATCTGGGAGCGTAGGTGGATATTTAAGTGGGATGTGAAATACTCGGGCTTAACCTGGGTGC
TGCATTCCAAACTGGATATCTAGAGTGCAGGAGAGGAAAGTAGAATTCCTAGTGTAGCGGTGAAATGCGT
AGAGATTAGGAAGAATACCAGTGGCGAAGGCGACTTTCTGGACTGTAACTGACACTGAGGCTCGAAAGCG
TGGGGAGCAAACAGGATTAGATACCCTGGTAGTCCACGCCGTAAACGATGAATACTAGGGATAACAGGGT
AATGAGTCGACAAaatgatacggcgaccaccgagatctacactctttccctacacgacgctcttccgatc
tTTGGATCACTACGCCAGGACagatcggaagagcacacgtctgaactccagtcacAATCAGTCTCGTatc
tcgtatgccgtcttctgcttgTTGTCGACTC >07_CBe_V4_TCT (SEQ ID NO: 14)
AGGAAGCCACGGCTAACTACGTGCCAGCAGCCGCGGTAATACGTAGGTGGCAAGCGTTGTCCGGATTTAC
TGGGCGTAAATCTGGGAGCGTAGGTGGATATTTAAGTGGGATGTGAAATACTCGGGCTTAACCTGGGTGC
TGCATTCCAAACTGGATATCTAGAGTGCAGGAGAGGAAAGTAGAATTCTTAGTGTAGCGGTGAAATGCGT
AGAGATTAGGAAGAATACCAGTGGCGAAGGCGACTTTCTGGACTGTAACTGACACTGAGGCTCGAAAGCG
TGGGGAGCAAACAGGATTAGATACCCTGGTAGTCCACGCCGTAAACGATGAATACTAGGGATAACAGGGT
AATGAGTCGACAAaatgatacggcgaccaccgagatctacactctttccctacacgacgctcttccgatc
tCATCCTACAGGCTTGTAGCGagatcggaagagcacacgtctgaactccagtcacAATCAGTCTCGTatc
tcgtatgccgtcttctgcttgTTGTCGACTC >08_DRa_V4_TCT (SEQ ID NO: 15)
TAATAGCACCGGCTAACTCCGTGCCAGCAGCCGCGGTAATACGGAGGGTGCAAGCGTTACCCGGAATCAC
TGGGCGTAAATCTGGGCGTGTAGGCGGAAATTTAAGTCTGGTTTTAAAGACCGGGGCTCAACCTCGGGGA
TGGACTGGATACTGGATTTCTTGACCTCTGGAGAGGTAACTGGAATTCCTGGTGTAGCGGTGGAATGCGT
AGATACCAGGAGGAACACCAATGGCGAAGGCAAGTTACTGGACAGAAGGTGACGCTGAGGCGCGAAAGTG
TGGGGAGCAAACCGGATTAGATACCCGGGTAGTCCACACCCTAAACGATGTACGTTAGGGATAACAGGGT
AATGAGTCGACAAaatgatacggcgaccaccgagatctacactctttccctacacgacgctcttccgatc
tAGGCGTTTAGGTACCTGTTCagatcggaagagcacacgtctgaactccagtcacAATCAGTCTCGTatc
tcgtatgccgtcttctgcttgTTGTCGACTC >09_EFa_V4_TCT (SEQ ID NO: 16)
AGAAAGCCACGGCTAACTACGTGCCAGCAGCCGCGGTAATACGTAGGTGGCAAGCGTTGTCCGGATTTAT
TGGGCGTAAATCTGCGAGCGCAGGCGGTTTCTTAAGTCTGATGTGAAAGCCCCCGGCTCAACCGGGGAGG
GTCATTGGAAACTGGGAGACTTGAGTGCAGAAGAGGAGAGTGGAATTCCATGTGTAGCGGTGAAATGCGT
AGATATATGGAGGAACACCAGTGGCGAAGGCGGCTCTCTGGTCTGTAACTGACGCTGAGGCTCGAAAGCG
TGGGGAGCAAACAGGATTAGATACCCTGGTAGTCCACGCCGTAAACGATGAGTGCTAGGGATAACAGGGT
AATGAGTCGACAAaatgatacggcgaccaccgagatctacactctttccctacacgacgctcttccgatc
tTCACAAGTTTCGCAATCGAGagatcggaagagcacacgtctgaactccagtcacAATCAGTCTCGTatc
tcgtatgccgtcttctgcttgTTGTCGACTC >10_ECo_V4_TCT (SEQ ID NO: 17)
AAGAAGCACCGGCTAACTCCGTGCCAGCAGCCGCGGTAATACGGAGGGTGCAAGCGTTAATCGGAATTAC
TGGGCGTAAATCTGCGCACGCAGGCGGTTTGTTAAGTCAGATGTGAAATCCCCGGGCTCAACCTGGGAAC
TGCATCTGATACTGGCAAGCTTGAGTCTCGTAGAGGGGGGTAGAATTCCAGGTGTAGCGGTGAAATGCGT
AGAGATCTGGAGGAATACCGGTGGCGAAGGCGGCCCCCTGGACGAAGACTGACGCTCAGGTGCGAAAGCG
TGGGGAGCAAACAGGATTAGATACCCTGGTAGTCCACGCCGTAAACGATGTCGACTAGGGATAACAGGGT
AATGAGTCGACAAaatgatacggcgaccaccgagatctacactctttccctacacgacgctcttccgatc
tTATTGCTAAGGCTATGGAGAagatcggaagagcacacgtctgaactccagtcacAATCAGTCTCGTatc
tcgtatgccgtcttctgcttgTTGTCGACTC >11_HPy_V4_TCT (SEQ ID NO: 18)
AATAAGCACCGGCTAACTCCGTGCCAGCAGCCGCGGTAATACGGAGGGTGCAAGCGTTACTCGGAATCAC
TGGGCGTAAATCTGAGCGCGTAGGCGGGATAGTCAGTCAGGTGTGAAATCCTATGGCTTAACCATAGAAC
TGCATTTGAAACTACTATTCTAGAGTGTGGGAGAGGTAGGTGGAATTCTTGGTGTAGGGGTAAAATCCGT
AGAGATCAAGAGGAATACTCATTGCGAAGGCGACCTGCTGGAACATTACTGACGCTGATTGCGCGAAAGC
GTGGGGAGCAAACAGGATTAGATACCCTGGTAGTCCACGCCCTAAACGATGGATGCTAGGGATAACAGGG -continued Sequence Listing Free Text TAATGAGTCGACAAaatgatacggcgaccaccgagatctacactctttccctacacgacgctcttccgat
ctCTGACGGGACAAACGGATCTagatcggaagagcacacgtctgaactccagtcacAATCAGTCTCGTat
ctcgtatgccgtcttctgcttgTTGTCGACTC >12_LGa_V4_TCT (SEQ ID NO: 19)
AGAAAGTCACGGCTAACTACGTGCCAGCAGCCGCGGTAATACGTAGGTGGCAAGCGTTGTCCGGATTTAT
TGGGCGTAAATCTGCGAGTGCAGGCGGTTCAATAAGTCTGATGTGAAAGCCTTCGGCTCAACCGGAGAAT
TGCATCAGAAACTGTTGAACTTGAGTGCAGAAGAGGAGAGTGGAACTCCATGTGTAGCGGTGGAATGCGT
AGATATATGGAAGAACACCAGTGGCGAAGGCGGCTCTCTGGTCTGCAACTGACGCTGAGGCTCGAAAGCA
TGGGTAGCGAACAGGATTAGATACCCTGGTAGTCCATGCCGTAAACGATGAGTGCTAGGGATAACAGGGT
AATGAGTCGACAAaatgatacggcgaccaccgagatctacactctttccctacacgacgctcttccgatc
tCATCGCGGACAACGCCAACCagatcggaagagcacacgtctgaactccagtcacAATCAGTCTCGTatc
tcgtatgccgtcttctgcttgTTGTCGACTC >13_NMe_V4_TCT (SEQ ID NO: 20)
AATAAGCACCGGCTAACTACGTGCCAGCAGCCGCGGTAATACGTAGGGTGCGAGCGTTAATCGGAATTAC
TGGGCGTAAATCTGCGGGCGCAGACGGTTACTTAAGCAGGATGTGAAATCCCCGGGCTCAACCCGGGAAC
TGCGTTCTGAACTGGGTGACTCGAGTGTGTCAGAGGGAGGTAGAATTCCACGTGTAGCAGTGAAATGCGT
AGAGATGTGGAGGAATACCGATGGCGAAGGCAGCCTCCTGGGACAACACTGACGTTCATGCCCGAAAGCG
TGGGTAGCAAACAGGATTAGATACCCTGGTAGTCCACGCCCTAAACGATGTCAATTAGGGATAACAGGGT
AATGAGTCGACAAaatgatacggcgaccaccgagatctacactctttccctacacgacgctcttccgatc
tAAGGGTCACACAGTATCATCagatcggaagagcacacgtctgaactccagtcacAATCAGTCTCGTatc
tcgtatgccgtcttctgcttgTTGTCGACTC >14_PAc_V4_TCT (SEQ ID NO: 21)
AAGAAGCACCGGCTAACTACGTGCCAGCAGCCGCGGTGATACGTAGGGTGCGAGCGTTGTCCGGATTTAT
TGGGCGTAAATCTGGGCTCGTAGGTGGTTGATCGCGTCGGAAGTGTAATCTTGGGGCTTAACCCTGAGCG
TGCTTTCGATACGGGTTGACTTGAGGAAGGTAGGGGAGAATGGAATTCCTGGTGGAGCGGTGGAATGCGC
AGATATCAGGAGGAACACCAGTGGCGAAGGCGGTTCTCTGGGCCTTTCCTGACGCTGAGGAGCGAAAGCG
TGGGGAGCGAACAGGCTTAGATACCCTGGTAGTCCACGCTGTAAACGGTGGGTACTAGGGATAACAGGGT
AATGAGTCGACAAaatgatacggcgaccaccgagatctacactctttccctacacgacgctcttccgatc
tGAAGTAGAGAGCCGGCTAACagatcggaagagcacacgtctgaactccagtcacAATCAGTCTCGTatc
tcgtatgccgtcttctgcttgTTGTCGACTC >15_PAr_V4_TCT (SEQ ID NO: 22)
AATAAGCACCGGCTAACTTCGTGCCAGCAGCCGCGGTAATACGAAGGGTGCAAGCGTTAATCGGAATTAC
TGGGCGTAAATCTGCGCGCGTAGGTGGTTCAGCAAGTTGGATGTGAAATCCCCGGGCTCAACCTGGGAAC
TGCATCCAAAACTACTGAGCTAGAGTACGGTAGAGGGTGGTGGAATTTCCTGTGTAGCGGTGAAATGCGT
AGATATAGGAAGGAACACCAGTGGCGAAGGCGACCACCTGGACTGATACTGACACTGAGGTGCGAAAGCG
TGGGGAGCAAACAGGATTAGATACCCTGGTAGTCCACGCCGTAAACGATGTCGACTAGGGATAACAGGGT
AATGAGTCGACAAaatgatacggcgaccaccgagatctacactctttccctacacgacgctcttccgatc
tCCCGGCGGTATACGTTCAAGagatcggaagagcacacgtctgaactccagtcacAATCAGTCTCGTatc
tcgtatgccgtcttctgcttgTTGTCGACTC >16_RSp_V4_TCT (SEQ ID NO: 23)
AAGAAGCCCCGGCTAACTCCGTGCCAGCAGCCGCGGTAATACGGAGGGGGCTAGCGTTATTCGGAATTAC
TGGGCGTAAATCTGCGCACGTAGGCGGATCGGAAAGTCAGAGGTGAAATCCCAGGGCTCAACCCTGGAAC
TGCCTTTGAAACTCCCGATCTTGAGGTCGAGAGAGGTGAGTGGAATTCCGAGTGTAGAGGTGAAATTCGT
AGATATTCGGAGGAACACCAGTGGCGAAGGCGGCTCACTGGCTCGATACTGACGCTGAGGTGCGAAAGCG
TGGGGAGCAAACAGGATTAGATACCCTGGTAGTCCACGCCGTAAACGATGAATGCTAGGGATAACAGGGT
AATGAGTCGACAAaatgatacggcgaccaccgagatctacactctttccctacacgacgctcttccgatc
tGGATGATGCGTTCGTACACAagatcggaagagcacacgtctgaactccagtcacAATCAGTCTCGTatc
tcgtatgccgtcttctgcttgTTGTCGACTC >17_SAu_V4_TCT (SEQ ID NO: 24)
AGAAAGCCACGGCTAACTACGTGCCAGCAGCCGCGGTAATACGTAGGTGGCAAGCGTTATCCGGAATTAT
TGGGCGTAAATCTGCGCGCGTAGGCGGTTTTTTAAGTCTGATGTGAAAGCCCACGGCTCAACCGTGGAGG
GTCATTGGAAACTGGAAAACTTGAGTGCAGAAGAGGAAAGTGGAATTCCATGTGTAGCGGTGAAATGCGC
AGAGATATGGAGGAACACCAGTGGCGAAGGCGACTTTCTGGTCTGTAACTGACGCTGATGTGCGAAAGCG
TGGGGATCAAACAGGATTAGATACCCTGGTAGTCCACGCCGTAAACGATGAGTGCTAGGGATAACAGGGT
AATGAGTCGACAAaatgatacggcgaccaccgagatctacactctttccctacacgacgctcttccgatc
tCGCCACGAGGATTAGAAATTagatcggaagagcacacgtctgaactccagtcacAATCAGTCTCGTatc
tcgtatgccgtcttctgcttgTTGTCGACTC >18_SEp_V4_TCT (SEQ ID NO: 25)
AGAAAGCCACGGCTAACTACGTGCCAGCAGCCGCGGTAATACGTAGGTGGCAAGCGTTGTCCGGAATCAT
TGGGCGTAAATCTGCGCGCGTAGGCGGTTTCTTAAGTCTGATGTGAAAGCCCACGGCTCAACCGTGGAGG
GTCATTGGAAACTGGAGGACTTGAGTGCAGAAGAGGAAAGTGGAATTCCATGTGTAGCGGTGAAATGCGC
AGAGATATGGAGGAACACCAGTGGCGAAGGCGACTTTCTGGTCTGTAACTGACGCTGATGTGCGAAAGCG
TGGGGATCAAACAGGATTAGATACCCTGGTAGTCCACGCCGTAAACGATGAGTGCTAGGGATAACAGGGT
AATGAGTCGACAAaatgatacggcgaccaccgagatctacactctttccctacacgacgctcttccgatc
tTTTCGGTGCTAAATCACACTagatcggaagagcacacgtctgaactccagtcacAATCAGTCTCGTatc
tcgtatgccgtcttctgcttgTTGTCGACTC >19_SAg_V4_TCT (SEQ ID NO: 26)
AGAAAGGGACGGCTAACTACGTGCCAGCAGCCGCGGTAATACGTAGGTCCCGAGCGTTGTCCGGATTTAT
TGGGCGTAAATCTGCGAGCGCAGGCGGTTCTTTAAGTCTGAAGTTAAAGGCAGTGGCTTAACCATTGTAC -continued Sequence Listing Free Text GCTTTGGAAACTGGAGGACTTGAGTGCAGAAGGGGAGAGTGGAATTCCATGTGTAGCGGTGAAATGCGTA
GATATATGGAGGAACACCGGTGGCGAAAGCGGCTCTCTGGTCTGTAACTGACGCTGAGGCTCGAAAGCGT
GGGGAGCAAACAGGATTAGATACCCTGGTAGTCCACGCCGTAAACGATGAGTGCTAGGGATAACAGGGTA
ATGAGTCGACAAaatgatacggcgaccaccgagatctacactctttccctacacgacgctcttccgatct
CCTGCGCATTGCAATGGCGTagatcggaagagcacacgtctgaactccagtcacAATCAGTCTCGTatct
cgtatgccgtcttctgcttgTTGTCGACTC >20_SMu_V4_TCT (SEQ ID NO: 27)
AGAAAGGGACGGCTAACTACGTGCCAGCAGCCGCGGTAATACGTAGGTCCCGAGCGTTGTCCGGATTTAT
TGGGCGTAAATCTGGGAGCGCAGGCGGTCAGGAAAGTCTGGAGTAAAAGGCTATGGCTCAACCATAGTGT
GCTCTGGAAACTGTCTGACTTGAGTGCAGAAGGGGAGAGTGGAATTCCATGTGTAGCGGTGAAATGCGTA
GATATATGGAGGAACACCAGTGGCGAAAGCGGCTCTCTGGTCTGTCACTGACGCTGAGGCTCGAAAGCGT
GGGTAGCGAACAGGATTAGATACCCTGGTAGTCCACGCCGTAAACGATGAGTGCTAGGGATAACAGGGTA
ATGAGTCGACAAaatgatacggcgaccaccgagatctacactctttccctacacgacgctcttccgatct
TCTGGCGGGCGTATCGGAGAagatcggaagagcacacgtctgaactccagtcacAATCAGTCTCGTatct
cgtatgccgtcttctgcttgTTGTCGACTC >21_SPn_V4_TCT (SEQ ID NO: 28)
AGAAAGGGACGGCTAACTACGTGCCAGCAGCCGCGGTAATACGTAGGTCCCGAGCGTTGTCCGGATTTAT
TGGGCGTAAATCTGCGAGCGCAGGCGGTTAGATAAGTCTGAAGTTAAAGGCTGTGGCTTAACCATAGTAG
GCTTTGGAAACTGTTTAACTTGAGTGCAAGAGGGGAGAGTGGAATTCCATGTGTAGCGGTGAAATGCGTA
GATATATGGAGGAACACCGGTGGCGAAAGCGGCTCTCTGGCTTGTAACTGACGCTGAGGCTCGAAAGCGT
GGGGAGCAAACAGGATTAGATACCCTGGTAGTCCACGCTGTAAACGATGAGTGCTAGGGATAACAGGGTA
ATGAGTCGACAAaatgatacggcgaccaccgagatctacactctttccctacacgacgctcttccgatct
ATAGTTAAATAAAGAGCCAAagatcggaagagcacacgtctgaactccagtcacAATCAGTCTCGTatct
cgtatgccgtcttctgcttgTTGTCGACTC >22_AOd_V4_TCT (SEQ ID NO: 29)
AAGAAGCGCCGGCTAACTACGTGCCAGCAGCCGCGGTAATACGTAGGGCGCGAGCGTTGTCCGGAATTAT
TGGGCGTAAATCTGGGCTTGTAGGCGGTTGGTCGCGTCTGCCGTGAAATCCTCTGGCTTAACTGGGGGCG
TGCGGTGGGTACGGGCTGACTTGAGTGCGGTAGGGGAGACTGGAACTCCTGGTGTAGCGGTGGAATGCGC
AGATATCAGGAAGAACACCGGTGGCGAAGGCGGGTCTCTGGGCCGTTACTGACGCTGAGGAGCGAAAGCG
TGGGGAGCGAACAGGATTAGATACCCTGGTAGTCCACGCTGTAAACGTTGGGCACTAGGGATAACAGGGT
AATGAGTCGACAAaatgatacggcgaccaccgagatctacactctttccctacacgacgctcttccgatc
tCTTCCTGGCTCCTAAATTACagatcggaagagcacacgtctgaactccagtcacAATCAGTCTCGTatc
tcgtatgccgtcttctgcttgTTGTCGACTC >23_LMo_V4_TCT (SEQ ID NO: 30)
AGAAAGCCACGGCTAACTACGTGCCAGCAGCCGCGGTAATACGTAGGTGGCAAGCGTTGTCCGGATTTAT
TGGGCGTAAATCTGCGCGCGCAGGCGGTCTTTTAAGTCTGATGTGAAAGCCCCCGGCTTAACCGGGGAGG
GTCATTGGAAACTGGAAGACTGGAGTGCAGAAGAGGAGAGTGGAATTCCACGTGTAGCGGTGAAATGCGT
AGATATGTGGAGGAACACCAGTGGCGAAGGCGACTCTCTGGTCTGTAACTGACGCTGAGGCGCGAAAGCG
TGGGGAGCAAACAGGATTAGATACCCTGGTAGTCCACGCCGTAAACGATGAGTGCTAGGGATAACAGGGT
AATGAGTCGACAAaatgatacggcgaccaccgagatctacactctttccctacacgacgctcttccgatc
tTGTGTTGGCATATTTAAGTAagatcggaagagcacacgtctgaactccagtcacAATCAGTCTCGTatc
tcgtatgccgt0ttctgcttgTTGTCGACTC >24_PAr_V4_TTT (SEQ ID NO: 31)
AATAAGCACCGGCTAACTTCGTGCCAGCAGCCGCGGTAATACGAAGGGTGCAAGCGTTAATCGGAATTAC
TGGGCGTAAATTTGCGCGCGTAGGTGGTTCAGCAAGTTGGATGTGAAATCCCCGGGCTCAACCTGGGAAC
TGCATCCAAAACTACTGAGCTAGAGTACGGTAGAGGGTGGTGGAATTTCCTGTGTAGCGGTGAAATGCGT
AGATATAGGAAGGAACACCAGTGGCGAAGGCGACCACCTGGACTGATACTGACACTGAGGTGCGAAAGCG
TGGGGAGCAAACAGGATTAGATACCCTGGTAGTCCACGCCGTAAACGATGTCGACTAGGGATAACAGGGT
AATGAGTCGACAAaatgatacggcgaccaccgagatctacactctttccctacacgacgctcttccgatc
tCCGAATGAAAGTACCCGAAAagatcggaagagcacacgtctgaactccagtcacAATCAGTCTCGTatc
tcgtatgccgtcttctgcttgTTGTCGACTC >25_PAr_V4_TCA (SEQ ID NO: 32)
AATAAGCACCGGCTAACTTCGTGCCAGCAGCCGCGGTAATACGAAGGGTGCAAGCGTTAATCGGAATTAC
TGGGCGTAAATCAGCGCGCGTAGGTGGTTCAGCAAGTTGGATGTGAAATCCCCGGGCTCAACCTGGGAAC
TGCATCCAAAACTACTGAGCTAGAGTACGGTAGAGGGTGGTGGAATTTCCTGTGTAGCGGTGAAATGCGT
AGATATAGGAAGGAACACCAGTGGCGAAGGCGACCACCTGGACTGATACTGACACTGAGGTGCGAAAGCG
TGGGGAGCAAACAGGATTAGATACCCTGGTAGTCCACGCCGTAAACGATGTCGACTAGGGATAACAGGGT
AATGAGTCGACAAaatgatacggcgaccaccgagatctacactctttccctacacgacgctcttccgatc
tGGTCGTGCTATCAATCCAACagatcggaagagcacacgtctgaactccagtcacAATCAGTCTCGTatc
tcgtatgccgtcttctgcttgTTGTCGACTC >26_PAr_V4_CCC(SEQ ID NO: 33)
AATAAGCACCGGCTAACTTCGTGCCAGCAGCCGCGGTAATACGAAGGGTGCAAGCGTTAATCGGAATTAC
TGGGCGTAAACCCGCGCGCGTAGGTGGTTCAGCAAGTTGGATGTGAAATCCCCGGGCTCAACCTGGGAAC
TGCATCCAAAACTACTGAGCTAGAGTACGGTAGAGGGTGGTGGAATTTCCTGTGTAGCGGTGAAATGCGT
AGATATAGGAAGGAACACCAGTGGCGAAGGCGACCACCTGGACTGATACTGACACTGAGGTGCGAAAGCG
TGGGGAGCAAACAGGATTAGATACCCTGGTAGTCCACGCCGTAAACGATGTCGACTAGGGATAACAGGGT
AATGAGTCGACAAaatgatacggcgaccaccgagatctacactctttccctacacgacgctcttccgatc
tCAGTTACTCGAAGGTATAGGagatcggaagagcacacgtctgaactccagtcacAATCAGTCTCGTatc
tcgtatgccgt0ttctgcttgTTGTCGACTC -continued

| Sequence Listing Free Text |
| --- |

>27_PAr_V4_GGG(SEQ ID NO: 34)
AATAAGCACCGGCTAACTTCGTGCCAGCAGCCGCGGTAATACGAAGGGTGCAAGCGTTAATCGGAATTAC
TGGGCGTAAAGGGGCGCGCGTAGGTGGTTCAGCAAGTTGGATGTGAAATCCCCGGGCTCAACCTGGGAAC
TGCATCCAAAACTACTGAGCTAGAGTACGGTAGAGGGTGGTGGAATTTCCTGTGTAGCGGTGAAATGCGT
AGATATAGGAAGGAACACCAGTGGCGAAGGCGACCACCTGGACTGATACTGACACTGAGGTGCGAAAGCG
TGGGGAGCAAACAGGATTAGATACCCTGGTAGTCCACGCCGTAAACGATGTCGACTAGGGATAACAGGGT
AATGAGTCGACAAaatgatacggcgaccaccgagatctacactctttccctacacgacgctcttccgatc
tGTGATAGCCGGGCGTTACATagatcggaagagcacacgtctgaactccagtcacAATCAGTCTCGTatc
tcgtatgccgtcttctgcttgTTGTCGACTC >28_PAr_V4_1 (SEQ ID NO: 35)
AATAAGCACCGGCTAACTTCGTGCCAGCAGCCGCGGTAATACGAAGGGTGCAAGCGTTAATCGGAATTAC
TGGGCGTAAATGCGCGCGTAGGTGGTTCAGCAAGTTGGATGTGAAATCCCCGGGCTCAACCTGGGAACTG
CATCCAAAACTACTGAGCTAGAGTACGGTAGAGGGTGGTGGAATTTCCTGTGTAGCGGTGAAATGCGTAG
ATATAGGAAGGAACACCAGTGGCGAAGGCGACCACCTGGACTGATACTGACACTGAGGTGCGAAAGCGTG
GGGAGCAAACAGGATTAGATACCCTGGTAGTCCACGCCGTAAACGATGTCGACTAGGGATAACAGGGTAA
TGAGTCGACAAaatgatacggcgaccaccgagatctacactctttccctacacgacgctcttccgatctT
TTGATAGTGCGCGCATAGCagatcggaagagcacacgtctgaactccagtcacAATCAGTCTCGTatctc
gtatgccgtcttctgcttgTTGTCGACTC >29_PAr_V4_2 (SEQ ID NO: 36)
AATAAGCACCGGCTAACTTCGTGCCAGCAGCCGCGGTAATACGAAGGGTGCAAGCGTTAATCGGAATTAC
TGGGCGTAAATCGCGCGCGTAGGTGGTTCAGCAAGTTGGATGTGAAATCCCCGGGCTCAACCTGGGAACT
GCATCCAAAACTACTGAGCTAGAGTACGGTAGAGGGTGGTGGAATTTCCTGTGTAGCGGTGAAATGCGTA
GATATAGGAAGGAACACCAGTGGCGAAGGCGACCACCTGGACTGATACTGACACTGAGGTGCGAAAGCGT
GGGGAGCAAACAGGATTAGATACCCTGGTAGTCCACGCCGTAAACGATGTCGACTAGGGATAACAGGGTA
ATGAGTCGACAAaatgatacggcgaccaccgagatctacactctttccctacacgacgctcttccgatct
GTTCTATGCCTTACCTAAAGagatcggaagagcacacgtctgaactccagtcacAATCAGTCTCGTatct
cgtatgccgtcttctgcttgTTGTCGACTC >30_PAr_V4_5 (SEQ ID NO: 37)
AATAAGCACCGGCTAACTTCGTGCCAGCAGCCGCGGTAATACGAAGGGTGCAAGCGTTAATCGGAATTAC
TGGGCGTAAATCTGAGCGCGCGTAGGTGGTTCAGCAAGTTGGATGTGAAATCCCCGGGCTCAACCTGGGA
ACTGCATCCAAAACTACTGAGCTAGAGTACGGTAGAGGGTGGTGGAATTTCCTGTGTAGCGGTGAAATGC
GTAGATATAGGAAGGAACACCAGTGGCGAAGGCGACCACCTGGACTGATACTGACACTGAGGTGCGAAAG
CGTGGGGAGCAAACAGGATTAGATACCCTGGTAGTCCACGCCGTAAACGATGTCGACTAGGGATAACAGG
GTAATGAGTCGACAAaatgatacggcgaccaccgagatctacactctttccctacacgacgctcttccga
tctGCAGCTTCTTGATGAGGCTTagatcggaagagcacacgtctgaactccagtcacAATCAGTCTCGTa
tctcgtatgccgtcttctgcttgTTGTCGACTC >31_PAr_V4_7 (SEQ ID NO: 38)
AATAAGCACCGGCTAACTTCGTGCCAGCAGCCGCGGTAATACGAAGGGTGCAAGCGTTAATCGGAATTAC
TGGGCGTAAATCTGACTGCGCGCGTAGGTGGTTCAGCAAGTTGGATGTGAAATCCCCGGGCTCAACCTGG
GAACTGCATCCAAAACTACTGAGCTAGAGTACGGTAGAGGGTGGTGGAATTTCCTGTGTAGCGGTGAAAT
GCGTAGATATAGGAAGGAACACCAGTGGCGAAGGCGACCACCTGGACTGATACTGACACTGAGGTGCGAA
AGCGTGGGGAGCAAACAGGATTAGATACCCTGGTAGTCCACGCCGTAAACGATGTCGACTAGGGATAACA
GGGTAATGAGTCGACAAaatgatacggcgaccaccgagatctacactctttccctacacgacgctcttcc
gatctTTTCATTACGCTCCACTTCTagatcggaagagcacacgtctgaactccagtcacAATCAGTCTCG
TatctcgtatgccgtcttctgcttgTTGTCGACTC >32_PAr_V4_10 (SEQ ID NO: 39)
AATAAGCACCGGCTAACTTCGTGCCAGCAGCCGCGGTAATACGAAGGGTGCAAGCGTTAATCGGAATTAC
TGGGCGTAAATCTGACTAAGGCGCGCGTAGGTGGTTCAGCAAGTTGGATGTGAAATCCCCGGGCTCAACC
TGGGAACTGCATCCAAAACTACTGAGCTAGAGTACGGTAGAGGGTGGTGGAATTTCCTGTGTAGCGGTGA
AATGCGTAGATATAGGAAGGAACACCAGTGGCGAAGGCGACCACCTGGACTGATACTGACACTGAGGTGC
GAAAGCGTGGGGAGCAAACAGGATTAGATACCCTGGTAGTCCACGCCGTAAACGATGTCGACTAGGGATA
ACAGGGTAATGAGTCGACAAaatgatacggcgaccaccgagatctacactctttccctacacgacgctct
tccgatctGCTCCTATTTAACCTGGACCagatcggaagagcacacgtctgaactccagtcacAATCAGTC
TCGTatctcgtatgccgtcttctgcttgTTGTCGACTC

| 16S rRNA Gene V4 process standard sequences |
| --- |

Illumina adapters in lower case
>33_GC_dG_35-40_V4 (SEQ ID NO: 40)
AAGAAGCACCGGCTAACTCCGTGCCAGCAGCCGCGGTAATATGAAGGTTGAAAGCGTAATTAGGAATTAT
TGATAGTAAAGTGCACACTAGCGTTTTGTTAAATCTTAAGTGTAATCCCCGAGCTAAAACAAGGAATAAC
ATCTGATAATTACAAGATTGAAAATCGTATTTGGAGGTAGAATTCCAGGAGTAAAGGAGAAATTAATAGT
GTTCTGTAATAATACAAGTATCGTATGCAGCAACTAGGTCGAAGACTGATGATCAGGTGAGAAAGTGTTG
GGAGCTAACTGAATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctGA
TTTGGCACTGTAGGTACTagatcggaagagcacacgtctgaactccagtcacAATCAGTCTCGTatctcg
tatgccgtcttctgcttgTTGTCGACTC >34_GC_dG_35-50_V4 (SEQ ID NO: 41)
AAGAAGCACCGGCTAACTCCGTGCCAGCAGCCGCGGTAATATGGAGGATTCAAACATAAATCAGAATTAC
TGGGCTTAAAATAATCGCATTCTGTTTGTTAAGTAATATGTGTAATCCCCGGGCTAATCCTGGGAAATGC
ATTTAATACTGGCAATCTAGAGTATAATAAAGGAGAATAGTATTTTAGTAGAAACAGAGAATTGTTTAGA -continued

| Sequence Listing Free Text |
|---|

TATTTGGAGGAATAAAGTTAGCATTTGCTGCCCCATGGACGAAAAATGATGCTCATATGCAAAAGCGTGG
TGTACAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctGG
TGCTATAGGCCCTCTTTGagatcggaagagcacacgtctgaactccagtcacAATCAGTCTCGTatctcg
tatgccgtcttctgcttgTTGTCGACTC >35_GC_dG_35-60_V4 (SEQ ID NO: 42)
AAGAAGCACCGGCTAACTCCGTGCCAGCAGCCGCGGTAAAATGAAGAATGAATGCTTTAATCGGTATTAT
TGGTCGTAAAACGCACGCAGGAGGATTGTTAAATTAGATGTGAAATCCACTGGCTTAACATTAGATAAGC
ATCTGATACAGGATAGCTTGATTTTCATATAAGAGGTTTGAAATCCAGATATAGCTTTGTAATTCGTAGA
AATCTGGATGATTACCGGTTATGAAGGCGGTCTCATGGATGAAATCTGATGCTAAAATACGAATGCGTGG
TTATCAAATAATATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctAT
CACATGCTGCTGCGTCCAagatcggaagagcacacgtctgaactccagtcacAATCAGTCTCGTatctcg
tatgccgtcttctgcttgTTGTCGACTC >36_GC_dG_36-70_V4 (SEQ ID NO: 43)
AAGAAGCACCGGCTAACTCCGTGCCAGCAGCCGCGGTAAAACTGATGGTGTAAACGTTTTTCGGTTTAAC
TGAACATAATGTTCACGAAAGATAAATGTTATTACATTTGATATTTATCTTGACTCAACATGGGAACAGC
ATATGATACAGGAAAACTTGAGTCTCGTAGAAGGGAGTTTAATTCCAGGTTAAGCTATTATATGATAATA
GAACTGGAGAAAATCCGGTGTTGATGGCGGTTACTTGGATTTAGACTTACGTTCAGGAACAAAATCTTGT
GGTGCTAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctAG
GCATGGGATCATGTCAGAagatcggaagagcacacgtctgaactccagtcacAATCAGTCTCGTatctcg
tatgccgtcttctgcttgTTGTCGACTC >37_GC_dG_40-40_V4 (SEQ ID NO: 44)
AAGAAGCACCGGCTAACTCCGTGCCAGCAGCCGCGGTAATACGGAGGGTGATAGTGTTAATCGTAATTAC
TAGGCGTTAAGCACAAACAGGTGGATTGTTAAGACAGATATGATATCCCAGGGCTTAAACAGGAAACTGC
AAATGATACTAGCTAGCTTGAGACTCGAATATGGGGGTAGAATACCAGGATTAAAGATGATTTACGTAGA
GATAAGGAGTATTACCGTTGTTAAAGGCGGCAACCTGAATTAATACTAACTAACAGGAAAGAAAGCGTGG
TAAGAAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctCA
GGACCAGATCATGTGATCagatcggaagagcacacgtctgaactccagtcacAATCAGTCTCGTatctcg
tatgccgtcttctgcttgTTGTCGACTC >38_GC_dG_40-50_V4 (SEQ ID NO: 45)
AAGAAGCACCGGCTAACTCCGTGCCAGCAGCCGCGGTAATACGGAGGGTGCAAATTTTAATCGGAATTAC
TGGTAATAAAGCGCACGTAGTCGGTTTGTTAATTCATATTTGAATTCCTAAGTCTAAACCTAGTAACTAC
ATCTGATACTGGTAAACTTGAGTCTCTTAGAGGGGGATAGAATTATAGTTGTAGCGGTGAAATTCGAAGA
GTTCTGGAGTAATACCGGTAGCAAAGACGACCAACTGGACGAAGTCTGACGTTAAGATAAGAAAGTATGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctCA
TGCATGTAAGACGCTCCGagatcggaagagcacacgtctgaactccagtcacAATCAGTCTCGTatctcg
tatgccgtcttctgcttgTTGTCGACTC >39_GC_dG_40-60_V4 (SEQ ID NO: 46)
AAGAAGCACCGGCTAACTCCGTGCCAGCAGCCGCGGTAATACAGAGGGTGTAAGCGTTAATAGAAATTAC
TGGGCGTAAAAAGCACGCAGGCGGTTTGTAAAGTTAGATATAAATTCATTGGACTCTAACTGAGAACTGC
ATTTGATACTTTCAAGCTTTTGTCTCGTTGAGGAGGGTAGAAATTCAGGAGTTGCGATGATATGCTTAGA
GATCTTGAGGAATTCCGGTGTCGAATGCAAACTCCTGGACGAAGACTAACGTTCAGTTGCAAAAGAGTGG
AAATTAAACATTATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctCG
GACAGTCGCTTATCTGCAagatcggaagagcacacgtctgaactccagtcacAATCAGTCTCGTatctcg
tatgccgtcttctgcttgTTGTCGACTC >40_GC_dG_40-70_V4 (SEQ ID NO: 47)
AAGAAGCACCGGCTAACTCCGTGCCAGCAGCCGCGGTAATAAGGAATGAGCTAGCGTTAATCGAAATTAC
TGGGTGTTTTGCTCATGCAGGAGATTAGTTTATTCAGATGTAAAAAACCCGGGTACAACCTGGGAATTGC
ATCTGATACTTATAAGCTAAATACTCGTAGAGGGAGGTAGTATTCCTGGTGTTGTGGTGAAATGTGTAGA
GATCTATATAATTACATGTTGCGAAGGCGGACCCAAGGACGAAGACTGATGCTCAGAAATTAAAACGTGG
AAATCAAACTTGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctGA
TCGTAATTGCCTATGAGTagatcggaagagcacacgtctgaactccagtcacAATCAGTCTCGTatctcg
tatgccgtcttctgcttgTTGTCGACTC >41_GC_dG_40-80_V4 (SEQ ID NO: 48)
AAGAAGCACCGGCTAACTCCGTGCCAGCAGCCGCGGTAATTCAGAATGTGTAAGCGTAATTCGAAATTTC
TGAGAGTAAAGCGAATGCAGATGGTTTATTTTGTTAGAAGTGAAATCCCCGGGCTATACCTGGTTACTGC
ATCTGTTACTGGTAAACTTGAAACTCGAAGAGGGTGATAATATTCCAGGTATTTAGGTTAAATGTGTAGA
TATCTGGATGAATACTAGTGTCTAAGGCAGTCCACTGGACGTAGACTTACTCTCAGGTTCGAAAGCGTGG
GGAACATTCATAATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctCG
AAGGTCGCGGCGGATATGagatcggaagagcacacgtctgaactccagtcacAATCAGTCTCGTatctcg
tatgccgtcttctgcttgTTGTCGACTC -continued

| Sequence Listing Free Text |
|---|

>42_GC_dG_45-50_V4 (SEQ ID NO: 49)
AAGAAGCACCGGCTAACTCCGTGCCAGCAGCCGCGGTAATAAGGAGGGTGCTTGCGTTAAACAGAAATAC
TGGGTGTAAAACGTACGTAGACGGTTTATTAAGTAAGATGTGAAATCCCCGTGCTCAACCTAGGAACTGC
ATATGATATTGGAAAACTTGAGACATATAGAGGGAGATAGAATACTTGGAGTAGCGTTGTAATGCGTATA
GATTTGGAGGAATACCGGTGGCGAAGGCGGCCCCCTGGACGAAGACAGACGCTCAGGTGCGAAATCGTTG
TGATCAAATAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctGC
CCGCAGCTTCGCTCTAAGagatcggaagagcacacgtctgaactccagtcacAATCAGTCTCGTatctcg
tatgccgtcttctgcttgTTGTCGACTC >43_GC_dG_45-60_V4 (SEQ ID NO: 50)
AAGAAGCACCGGCTAACTCCGTGCCAGCAGCCGCGGTAATACGAAGTGTGAAAACGTTATTAAGAATTAC
TGGGCGTAAAGCGTTCGCAGGCGGTTTGTTAAGTCATAAGTGAAATCCCCGGGCACAAACTGGGAACTGA
ATCTGTAACTGACAAGCTTGAGTATCTTATAATGGGATAGAATTTAATGTGTAGCTGTGAAATGCGTAGA
GATCTGGAGATATACCGGTGACTAAGGCGGCCCCCTGGACGAAGACTGACGCTCAGGTGCTAAATCGTGG
GGAACAAAAAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctAA
TGATTTAAAGTCAAGAGAagatcggaagagcacacgtctgaactccagtcacAATCAGTCTCGTatctcg
tatgccgtcttctgcttgTTGTCGACTC >44_GC_dG_45-70_V4 (SEQ ID NO: 51)
AAGAAGCACCGGCTAACTCCGTGCCAGCAGCCGCGGTAAAACTGAGGGTGCAAGCGTTAATCGGAATTAC
TGTGCATAAAGCTCACGCATTCGTTTTGTTAAGTCAGATAATAAATCCTCGAGTTAAACCTGGGAAATGC
ATCTGATACTGAAAAGCTTGATTCTCGTAGAGGGGTGTAGAATTCCAGGTGTAGCAGTAAAATACGTAGA
GATCAGAATGAATTCCGGTGGTGAAGTCGGCCTACTGGACGAAGACTGACGCTAAGGTGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctAC
GTAGGTGATCGGTACCACagatcggaagagcacacgtctgaactccagtcacAATCAGTCTCGTatctcg
tatgccgtcttctgcttgTTGTCGACTC >45_GC_dG_45-80_V4 (SEQ ID NO: 52)
AAGAAGCACCGGCTAACTCCGTGCCAGCAGCCGCGGTAATACGGAGTGTTAAATCGTTAATAGGAATTAC
TGGGCGAAAAGTGCTAGCAGGCGGTTTGTTAAATCAGTTGTGAAATCCCTGGGCACAACCTGGGATCTGC
ATCTGATTTTGGCAAGCTTTAGTCTATTAGAGGGGGGTAAATTTCCATGTGTAGATTTGAAATGCGTTTA
GATCTGGAGGAATACCGGAGGTGAAGGCGATCCCCTGGACGTAGACTGAAGCTCAAGTGAGAAAGCTTGG
AGTGCAAACTAGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctAG
AACACCACTGGTGACCCAagatcggaagagcacacgtctgaactccagtcacAATCAGTCTCGTatctcg
tatgccgtcttctgcttgTTGTCGACTC >46_GC_dG_45-90_V4 (SEQ ID NO: 53)
AAGAAGCACCGGCTAACTCCGTGCCAGCAGCCGCGGTAATACGGAGGGTGCAAGCGATAATAGTATTTAC
TGTGCGAAAAGCATACTTAGGAAGATTTTTATGTCAGATGTGAAATCCCCGGGCTTAACCTGGGAACTGC
ATCTGATACTGACAAGTTTGAGACTCGTATAGGGGGGTAGAATTCCAGGTGTTGCAGTGAAAAGTGTAGA
GATCTGGAAGAATACCGGTGGCGAAGGTTGCCCCCTGTACGAATAATGACGCTATGGTGCGAAAGCATTG
TGTGCAAACAAGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctAC
AGAGGGCAATGACGTACAagatcggaagagcacacgtctgaactccagtcacAATCAGTCTCGTatctcg
tatgccgtcttctgcttgTTGTCGACTC >47_GC_dG_50-60_V4 (SEQ ID NO: 54)
AAGAAGCACCGGCTAACTCCGTGCCAGCAGCCGCGGTAATACGGAAGGTGCAAGTGTTAATCGGAATTAC
TGGGCATAAAGCGCACGAAGGCGGTATGTTAAGTTAGATGTGAAATCCCCGGGCTCAATCTGTGAACTGC
ATCTGATACTGGCAAGCTTGAGTCTCGTAGAGGGGGGTAGAATTCAAGGTGTAGCGGTGAAATGCGTAGA
GATCTAGATGAATACCGGTGGCGAAGGAGGTCCCCTGGACGAAGACTGACACTCTGGTGCGAAATAGTGG
GGAGCAAACAGAATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctTC
ATTGACAGGTTGGGTTAGagatcggaagagcacacgtctgaactccagtcacAATCAGTCTCGTatctcg
tatgccgtcttctgcttgTTGTCGACTC >48_GC_dG_50-70_V4 (SEQ ID NO: 55)
AAGAAGCACCGGCTAACTCCGTGCCAGCAGCCGCGGTAATACGGAGGGTGCAATCGTTAATCGGATTTAC
TGGGCTTAAATCGCACGCAGGCGGTTTGTTAAGTCATATGTGAAAACCCCGGGCTCAACCTGGGAACTGC
ATCTGATACTTGCAAGCTTGAGTCTCGTATAGGGAGGTAGAATTCCAGGTGTAGCGGTGAAATGCGTAGA
GATCTGAAGTAATACCGGTAGCTAATACGGCCCACTGGACGAAGACTGACGCACAGGTGCTAAAGCGTGT
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctAC
ACTGTATGGACCGGTCACagatcggaagagcacacgtctgaactccagtcacAATCAGTCTCGTatctcg
tatgccgtcttctgcttgTTGTCGACTC >49_GC_dG_50-80_V4 (SEQ ID NO: 56)
AAGAAGCACCGGCTAACTCCGTGCCAGCAGCCGCGGTAATACGGAGTGTGCAAGCGTTAATCGGAATTAC
TGGTCGTAAAGCGCACGTAGACGGTTTGTTAATTCAGATGTTAAATTCCAGGGCAAAACCTGGGAACTGC
ATCTTATACTGGCAAGCTTGAGTCTCGTAGAGGGGGTTAGAATTCCAGGTGTAGCGGTGAAATGTGTAAA
GATCTGGAGGAATACCGGTGTTGAAGGCGGCCTCCTGGACGAAGACTGACGCTCAGGTGCGAAAGCGTGG
GGAGCAAACAGGATTAGATACCCTGGTAGTCCACGCCGTAAACGATGTCGACTAGGGATAACAGGGTAAT -continued

| Sequence Listing Free Text |
|---|

GAGTCGACAAaatgatacggcgaccaccgagatctacactctttccctacacgacgctcttccgatctCG
GCCTGGCTCTTATGTAGAagatcggaagagcacacgtctgaactccagtcacAATCAGTCTCGTatctcg
tatgccgtcttctgcttgTTGTCGACTC >50_GC_dG_50-90_V4 (SEQ ID NO: 57)
AAGAAGCACCGGCTAACTCCGTGCCAGCAGCCGCGGTAATACGGAGGGAACAAGCGTTAATCGAAATAAC
TGGGCGTAAAGCGCTCGTAGGTTGTTTGTTAAGTCAGATGTGAAATCCCCGGGTTCAACCTGGGAACTGC
ATCTGATTATGGCAAGCTTGAGTCTCGTAGAGGGGGGTATAATTCCAGTTGAAGCGGTAAAATGCGTTGA
GATCTGGAGGTATACCGGTGGCGAAAGCGGCCCCATGGACGAAGACTGACGCTCATTTGCGAAATCGTTG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctAA
TAGGCCCGCTCATCCCGGagatcggaagagcacacgtctgaactccagtcacAATCAGTCTCGTatctcg
tatgccgtcttctgcttgTTGTCGACTC >51_GC_dG_49-100_V4 (SEQ ID NO: 58)
AAGAAGCACCGGCTAACTCCGTGCCAGCAGCCGCGGTAATTCTTCGGGTACTAGCGTTAATTAGGATTTC
TGCGCGTAAAGTGAACGCAGGCTTGTTGGTCAGTGAGATGTGTATTACAGGTACTTAACCTGTGAACCGC
ATCTGATACTCGCAAGCCTGAGGCTCCTAGTGGGGGGTAGAAATCTATGTGTATCGTTGGAACCCGTAAA
CATCTGTAGGATGGCATGTGTCCAAGGCAGCCCCCTGGTCTGAGACTGACAATCAGTTTCGAAAGCGTGG
GGAGCAAACAGCATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctCT
TAGAGACACTCTTACCGGagatcggaagagcacacgtctgaactccagtcacAATCAGTCTCGTatctcg
tatgccgtcttctgcttgTTGTCGACTC >52_GC_dG_55-70_V4 (SEQ ID NO: 59)
AAGAAGCACCGGCTAACTCCGTGCCAGCAGCCGCGGTAAGACGGAGGGTGCAAGCGTTAATCGGAATAAC
TGGGCGTAAAGCGGTCGCAGGCGGTTTGTTAAGTCAGATGTGAATTCCCCGGGCTCAACGTGGGAACTTC
ACCTAATACGGGCAAGCTTTAGAATCGTAGAGGGGGGTAGAATTATAGGTATAGCGGTGCAATGCGAAGA
GAGCTGGAGGAATCCCGGTGGAGAAGGCAGCCCCCTGGACGAAGACAGAAGCTCAGGGGCGAAACCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctTA
TCGGGCGCTCTCCGGTACagatcggaagagcacacgtctgaactccagtcacAATCAGTCTCGTatctcg
tatgccgtcttctgcttgTTGTCGACTC >53_GC_dG_55-80_V4 (SEQ ID NO: 60)
AAGAAGCACCGGCTAACTCCGTGCCAGCAGCCGCGGTAATACGGAGGGTGCAAGCGTTTATCGGAATTAC
TGGGCGTAAAGCGCACGTAGGCGGTTTGTTAAGTCAGAAGTGAAATCCCCGGGCTCAACCTGGGAACTGC
ATCTGATACTGGCTAGCATGAGTATCGTAGAGGGGGGTAGAATTCCAGGTGTAGCGGTGTAATGCGTAGA
GATCTAGAGGAATACCGGTGGCGAAGGCGGCCCCCTGGACGAAGACTGACGCTCAGGTGTGAAAGCGAGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctTA
CCTATCGCAGCGCGTATAagatcggaagagcacacgtctgaactccagtcacAATCAGTCTCGTatctcg
tatgccgtcttctgcttgTTGTCGACTC >54_GC_dG_55-90_V4 (SEQ ID NO: 61)
AAGAAGCACCGGCTAACTCCGTGCCAGCAGCCGCGGTAATACTGAGGGTGCAAGCGTAAATCGGAATTAC
TGGGCGTAAAGCGCAAGCAGGCAGTTTGTTAAGTCAGATGTGAAATCCCCGGGCTCAACCTGGGAACTGC
ATCAGATACTGGCAAGCTTGAGTCTCGTTGAGGGGGGTAGAATTCCATGTGTAGCGGTGAATTGCGTAGA
GAACTGGAGGAATACCGGTGGCGAAGGCGGCCCCCTGGACGAAGACTGACGCTCAGGTGCGAAAGCGTGG
GGTGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctCC
CGCGTACAGGATTGTTCGagatcggaagagcacacgtctgaactccagtcacAATCAGTCTCGTatctcg
tatgccgtcttctgcttgTTGTCGACTC >55_GC_dG_55-100_V4 (SEQ ID NO: 62)
AAGAAGCACCGGCTAACTCCGTGCCAGCAGCCGCGGTAATACTGAGGGTGCAAGCGTTAGTCGGAATTAC
TGGGCGTAAAGCGCACTCAGGCGGTTTGTTAAGTCAGATGTGAAATCCCCGGGCTCAACCTGGGGACTGC
ATCTGATACTGGCAAGCCTGAGTCTCGTAGTGGGGGGTATAATTCCAGGTGTAGCGGTGAAATGCGTAGA
GATCAGGAAGAAGTCCAGTTGTGAAGGCGGCCCCCTGGACGAAGACTGAGGCTCAGGTGCGAAAGCGTGG
GGAGCAAACAAGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctGA
AGCAAAGGGAGAGCGCGGagatcggaagagcacacgtctgaactccagtcacAATCAGTCTCGTatctcg
tatgccgtcttctgcttgTTGTCGACTC >56_GC_dG_55-110_V4 (SEQ ID NO: 63)
AAGAAGCACCGGCTAACTCCGTGCCAGCAGCCGCGGTAATACCGAGGGTGCAAGAGTTAAGCGGAATTGC
TGGCCGTAAAGCGCACACAGGCGCTTTGTCAAGTTAGATGCGAAATCCCCAGGTTCAACCTGGGAACTGC
ATCTGATACTGGCAAGCTTAACTCTCGTAGAGGGGGTTACAATTCCAGGTGGAGCGCTGAAATGCGTAGA
CATCTGGAGGAATACCGGTGGCGAAGGCGACCCCCTGGACGAAGACTCCCGCTTAGGTTCGCAAGCGGGG
GGAGCAAACAGAATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctAT
AGTCGTTTGCGCACCCGCagatcggaagagcacacgtctgaactccagtcacAATCAGTCTCGTatctcg
tatgccgtcttctgcttgTTGTCGACTC >57_GC_dG_60-80_V4 (SEQ ID NO: 64)
AAGAAGCACCGGCTAACTCCGTGCCAGCAGCCGCGGTAATACGGAGGGGGCAAGCGTTGATCGGAATTAC
CCGGCGTGAAGCGCACGCAGGCGGTTTGTTAAGTCAGATGTGAAATCCCCGGGCTCAACGTGGGAACTGC -continued

| Sequence Listing Free Text |
|---|

ATGTGATACTGGCACGCTTGAGTCTCGCAGAGGGGGGGAGAATTGCAGGGGTAGCGGTGAAAGGCGTAGA
GATCTGGAGGAATACCGGTGGCGAGGGCGGCCCCCTGGAGGAAGACTGACGCTCAGGTGCGAAAGCGTGG
CGAGCAAACACGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctCC
TTTCCTGCTCCCGCCTGGagatcggaagagcacacgtctgaactccagtcacAATCAGTCTCGTatctcg
tatgccgtcttctgcttgTTGTCGACTC >58_GC_dG_60-90_V4 (SEQ ID NO: 65)
AAGAAGCACCGGCTAACTCCGTGCCAGCAGCCGCGGTAATACGGAGGGTGCAAGCGTTAATCGGAATGAC
TGGGCGTAAAGCGCACGCAGGCGCTGTGTTAAGTCAGATGTGGAATCCCCGGGCTCAACCTGGGAACTGC
ATCTGATACTGGCAAGGTTGAGTCTGGTGGAGGGGGGGAGAATCCCAGGTGTGGCGGTGAAATGCGGAGA
GAGCTGGAGGAATACCGGTGGCGAAGGCGGCCCCCTGGACGGAGACTGACGCTCAGGTGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctCA
GATTCGTGTCCTCCACATagatcggaagagcacacgtctgaactccagtcacAATCAGTCTCGTatctcg
tatgccgtcttctgcttgTTGTCGACTC >59_GC_dG_60-100_V4 (SEQ ID NO: 66)
AAGAAGCACCGGCTAACTCCGTGCCAGCAGCCGCGGTAATACGGAGGGTGCAAGCGGTAATCGGAATTAC
TGGGCGTAAACCGCACGCAGGCGGTCTGTTAAGTCAGATGTGAAATCCCCGGGCTCAACCGGGGAACTGC
ATCTGATACTGGCAAGCTTGAGCCTCGTAGAGGGGGGTAGAAGTCCGGGTGTAGCGGTGAACTGCGTAGA
CATCTGGAGGAATACCGGGGGCGAAGGCGGCCCCCTGGACGAAGACTGACGGGCAGGTGCGACAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctAC
CTTCTAAACGTGCGAAGCagatcggaagagcacacgtctgaactccagtcacAATCAGTCTCGTatctcg
tatgccgtcttctgcttgTTGTCGACTC >60_GC_dG_60-110_V4 (SEQ ID NO: 67)
AAGAAGCACCGGCTAACTCCGTGCCAGCAGCCGCGGTAATCCGGAGGGTGCGAGCGTTAATCGGAATTAC
TGCGCGTAAAGCGCACGCAGGCGGTTTCTTAAGTCAGCTGTGAAATCCCCGGGCTCACCCCGGGAACTGC
ATCTGATACTCGCAACCTTGAGTCTCGTAGAGGGGGCCAGAATTCCAGGTGTAGCGGTGAAATGCGTAGA
GATCCGGAGGAATACCGGGGGCGAAGGCGGCCCCCTGGACGAAGACTGACGCTCAGGTGCGAAAGCGCGG
GGAGCAAACCGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctGG
CTTCGCTGTGCCTATGACagatcggaagagcacacgtctgaactccagtcacAATCAGTCTCGTatctcg
tatgccgtcttctgcttgTTGTCGACTC >61_GC_dG_60-120_V4 (SEQ ID NO: 68)
AAGAAGCACCGGCTAACTCCGTGCCAGCAGCCGCGGTAATCCGGAGCGTGCAAGCGTCAATCCGCATTAG
TGGGCGTAAAGCGCACGCAGGCGGGTTGTTAAGTCAGATGTGAAATCCCGGGGCTCAACCTGGGAACTGC
ATCTGAGACTGGCAAGCTTGAGTCTCGTACAGGGGGGTAGAATTCCAGGTCTGGCGCTGAAATGCGTAGA
GATCTGGAGGCAGACCGGTCGCGAAGGCGGCCCCCTGCACGACGAGTGACCCTCAGGCGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctAA
ATAAGACCGCATAGTTATagatcggaagagcacacgtctgaactccagtcacAATCAGTCTCGTatctcg
tatgccgtcttctgcttgTTGTCGACTC >62_GC_dG_65-90_V4 (SEQ ID NO: 69)
AAGAAGCACCGGCTAACTCCGTGCCAGCAGCCGCGGTAATACGCAGGGTGCAAGCGTTAATCGGAATTAC
TGGGCGGAAGGCGCACGCACGCGGCCTGTCAAGTGAGATGTGACATCCCCGGGCTCAACCTCGGAACTGC
GTCTGATACTGGCACGCTTGCGTCGCGTACAGGGGGCGAGAATTCCAGGGGGAGGGGTGAAATGCGTGGC
GATCCGGAGGAATACCGGTGGCGAAGGCGGCCCCCGGGACGAAGACGGCCGCTCAGGGGCCAAAGCGTGG
GGGGCAGACACGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctCG
AACTACAGGGACGAGAGTagatcggaagagcacacgtctgaactccagtcacAATCAGTCTCGTatctcg
tatgccgtcttctgcttgTTGTCGACTC >63_GC_dG_65-100_V4 (SEQ ID NO: 70)
AAGAAGCACCGGCTAACTCCGTGCCAGCAGCCGCGGTAATACGGGGGGTGCAAGCGTGGATCGGAATTGC
TGGGCGTCAAGGGCACGCAGGCGGTTTGTGAAGTCAGACGCGAGAGCCCCGGGCTCCACCGGGGAACTGC
ATCTGATACTGGCAAGCTTGAGTCTCGTAGACGGGGGCAGAATCCCGGGTGTGGCGGGGAAATGCGTAGA
GATCTGGAGGGATCCCGGTGGCGAAGGCGGCCCCCTGGACGGAGACTGACGCTCAGGTGCGGAAGCGGGG
GGACCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctAT
CGGTTCTTGGTCCGCTTAagatcggaagagcacacgtctgaactccagtcacAATCAGTCTCGTatctcg
tatgccgtcttctgcttgTTGTCGACTC >64_GC_dG_65-110_V4 (SEQ ID NO: 71)
AAGAAGCACCGGCTAACTCCGTGCCAGCAGCCGCGGTAATACGCAGGGTGCCAGCGTTAATCGGAATTAC
TGGGCGTGAAGCGCACGCGGGCGGTTTGTTAAGTCAGACGTGAAATCCCCGCGCTCAACCTGGGAGCCGC
ACCTGAGAGTGGCGAGCTTGGGTGTCGTAGAGGGGGGTAGACTTCCAGGTGTAGCGGTGAAATGCGCAGC
GCTCTGGCGGGATACCGCTGGCGAAGGCGGCCCCCCGGGCGAAGCCTGCCGCTCAGGGGCGAAAGCGTGG
GGAGCACACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctCC
GCCTGATGTCACGGCCTTagatcggaagagcacacgtctgaactccagtcacAATCAGTCTCGTatctcg
tatgccgtcttctgcttgTTGTCGACTC -continued Sequence Listing Free Text >65_GC_dG_65-120_V4 (SEQ ID NO: 72)
AAGAAGCACCGGCTAACTCCGTGCCAGCAGCCGCGGTAATACGGAGCGTGCAAGCGCTAACCGGAATTAC
TGCGCGTCAAGCGGACGCAGGCGGTTCGTTAAGTCAGGTGTGAGATCCCCGGGGTCAACCGGGGACCTGC
ATCTGACACCGGCACGCTTGAGTCCCGTAGGGGCGGGTAGAATCCCCGGTGTAGCGGTGCGAGCCGTAGC
GATCCGGAGGAATACCGGTGGCGACGGCCGCCCCCTGGACGAAGGCTGACGCTGAGGTGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctCG
TCACTTAAACACTTCAATagatcggaagagcacacgtctgaactccagtcacAATCAGTCTCGTatctcg
tatgccgtcttctgcttgTTGTCGACTC >66_GC_dG_65-130_V4 (SEQ ID NO: 73)
AAGAAGCACCGGCTAACTCCGTGCCAGCAGCCGCGGTAATACCGCCGGTGCACGCGTTAATCGGAATTAC
TGGGGGTACAGCGCGCGCGGGCGGTTTGTTAGCTCCGGTGTGAAGTCCCGGGGCTCAACCTGGGAACTCC
AGCGGACACTGGCAAGCCTGAGTCTCGTCCCGGGGGGGAGAGTTCCAGCTGTAGCGGTGACGTCCCTGGA
GATCTCGGGGAATACGGGTGGCCAAGGCCGCCCCCTCGAGGAGGAGTCACGCTGAGGCGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctTC
CTGCCAGCGTCGGCAGACagatcggaagagcacacgtctgaactccagtcacAATCAGTCTCGTatctcg
tatgccgtcttctgcttgTTGTCGACTC >67_GC_dG_70-100_V4 (SEQ ID NO: 74)
AAGAAGCACCGGCTAACTCCGTGCCAGCAGCCGCGGTAATGCGGGGGGTGGAAGCGGCGAGCGGACTGGC
GGGGCGCCAAGCGCGCGCCGGCGGCTTGCTAGGTCAGATGTGAGGTGCCCGGCCTCAACCTGGGAACTGC
AGGTGATACTGGGCAGCCGGAGTCGGGTAGACGGGGGTACAATGCCAGGTGTAGCGGGGCAACGGGTAGC
GATGTGGGGGAATACCGGTGGCGAACGGGGCCCCCCGGACGAAGGCTGGCGCTCGGGTGCCACAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctTC
GAAGGATTTATAACGATGagatcggaagagcacacgtctgaactccagtcacAATCAGTCTCGTatctcg
tatgccgtcttctgcttgTTGTCGACTC >68_GC_dG_70-110_V4 (SEQ ID NO: 75)
AAGAAGCACCGGCTAACTCCGTGCCAGCAGCCGCGGTAATGCGGAGGGTGCACGGGGTAACGGGAATGCC
TGGGCGCCCAGCCGACGGAGCCGGTTCGGTAAGTCAGAGGTGAACGCGCCGGGCTCAACCCGCGAACTGC
CGCTGATACCGGGGCGCTTCCGTCTCGTAGAGGGGGGTCGAATTCCAGGTGTGGCGCTGAAGTCCCGAGA
GCTCTGGAGGAAGCGCGGTGGCGAGGGCGCCCGCCCGGACCAAGACTGGCGGCCAGGTGCGAAAGCGCGG
GGAGCGAACGGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctTG
CTGTCTGCGATCCGGAACagatcggaagagcacacgtctgaactccagtcacAATCAGTCTCGTatctcg
tatgccgtcttctgcttgTTGTCGACTC >69_GC_dG_70-120_V4 (SEQ ID NO: 76)
AAGAAGCACCGGCTAACTCCGTGCCAGCAGCCGCGGTAACACGGAGGGCGCAAGCGTTAATCGGAACCAC
TGGCCCTAAAGCGGCCCCAGGCGGGTCGTGAGGTCAGATGTGAAACCGCCGGGGTCAACCGGGGGGGGGC
GGCTGACACTGGCGAGCCTGGGTCTCGTACACGGGGGCAGACCTCCAGGTGTCCCGCTGAGGCGCGTGGA
GATCCGGAGGAGTACCGGTGGGGACGCCGGCCCCCTCGAGGCAGACTGACGCGCAGGTGCGAAAGCGCGG
GGAGCAAACGGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctGT
CTGATCGTTATATGCCGTagatcggaagagcacacgtctgaactccagtcacAATCAGTCTCGTatctcg
tatgccgtcttctgcttgTTGTCGACTC >70_GC_dG_70-130_V4 (SEQ ID NO: 77)
AAGAAGCACCGGCTAACTCCGTGCCAGCAGCCGCGGTAATACGGCGGGTGCCAGCCTTAATCGGAATGCC
CGGGCGCACAGCGGACGCGGGCGGTTCGTTAAGCCGCAGGCGAGATCCCCGGGCCCAACCTCGGCACGGC
GTCTGACACTGGCGAGGTTGAGTCTCGGAGAGGGGGGTAGGATTCCAGGTCCACCGGTGGAACCCCTAGA
GCTCTGGGGGACTACCGGTGGCCCAGGCCGCGGCCTGGACGAACGCTGGCGCTCAGGTCCGCAAGCCTGC
GGCGCACACGGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctCA
TATCGCATCCGCAGAAATagatcggaagagcacacgtctgaactccagtcacAATCAGTCTCGTatctcg
tatgccgtcttctgcttgTTGTCGACTC >71_GC_dG_70-140_V4 (SEQ ID NO: 78)
AAGAAGCACCGGCTAACTCCGTGCCAGCAGCCGCGGTAATACCGCGGGTGCAAGCGTTAATGCGGCTTAC
TGGGCGTAAAGCGGACCCCGGCGGTTTGTGAGGTCACATGTGAAGCCCCCGCCCTCCGCCTGGGAACTGC
GTCTGATACTGGCGGGCTCGGGGCCCGTACAGGGGGGTAGAATCCCAGGTGGAGGGCGGAACCGGGTGCC
GAGCTGCAGGAAGGCCGGCGGCGAAGCCGGCCCCCCGGGCGGAGACTGACGCCCAGGGGCGCGACCGTGG
GGAGCAAGCAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctAT
TCCCTTCTACATGAGTGGagatcggaagagcacacgtctgaactccagtcacAATCAGTCTCGTatctcg
tatgccgtcttctgcttgTTGTCGACTC >72_Size_233_V4 (SEQ ID NO: 79)
AAGAAGCACCGGCTAACTCCGTGCCAGCAGCCGCGGTAATACTGAGGGTGCAAGCGTAAAGCGCAAGCAG
GCAGTTTGTTAAGTCAGATGTGAAATCCCCGGGCTCAACCTGGGAACTGCATCAGATACTGGCAAGCTTG
AGTCTCGTTGAGGGGGGTAGAATTCCATGTGTAGCGGTGAATTGCGTAGAGAACTGGAGGAATACCGGTG
GCGAAGGCGGCCCCCTGGACGAAGACTGACGCTCAGGTGCGAAAGCGTGGGGTGCAAACAGGATTAGATA
CCCTGGTAGTCCACGCCGTAAACGATGTCGACTAGGGATAACAGGGTAATGAGTCGACAAaatgatacgg -continued

| Sequence Listing Free Text |
|---|

cgaccaccgagatctacactctttccctacacgacgctcttccgatctCAAAGACTAACGAATCCGCAag
atcggaagagcacacgtctgaactccagtcacAATCAGTCTCGTatctcgtatgccgtcttctgcttgTT
GTCGACTC >73_Size_213_V4 (SEQ ID NO: 80)
AAGAAGCACCGGCTAACTCCGTGCCAGCAGCCGCGGTAATACTGAGGGTGCAAGCGTAAAAAGTCAGATG
TGAAATCCCCGGGCTCAACCTGGGAACTGCATCAGATACTGGCAAGCTTGAGTCTCGTTGAGGGGGGTAG
AATTCCATGTGTAGCGGTGAATTGCGTAGAGAACTGGAGGAATACCGGTGGCGAAGGCGGCCCCCTGGAC
GAAGACTGACGCTCAGGTGCGAAAGCGTGGGGTGCAAACAGGATTAGATACCCTGGTAGTCCACGCCGTA
AACGATGTCGACTAGGGATAACAGGGTAATGAGTCGACAAaatgatacggcgaccaccgagatctacact
ctttccctacacgacgctcttccgatctGTCTGAGGTGATAAGGGCATagatcggaagagcacacgtctg
aactccagtcacAATCAGTCTCGTatctcgtatgccgtcttctgcttgTTGTCGACTC >74_Size_193_V4 (SEQ ID NO: 81)
AAGAAGCACCGGCTAACTCCGTGCCAGCAGCCGCGGTAATAAGTCAGATGTGAAATCCCCGGGCTCAACC
TGGGAACTGCATCAGATACTGGCAAGCTTGAGTCTCGTTGAGGGGGGTAGAATTCCATGTGTAGCGGTGA
ATTGCGTAGAGAACTGGAGGAATACCGGTGGCGAAGGCGGCCCCCTGGACGAAGACTGACGCTCAGGTGC
GAAAGCGTGGGGTGCAAACAGGATTAGATACCCTGGTAGTCCACGCCGTAAACGATGTCGACTAGGGATA
ACAGGGTAATGAGTCGACAAaatgatacggcgaccaccgagatctacactctttccctacacgacgctct
tccgatctTTGATGGTGAGTGGTGAATGagatcggaagagcacacgtctgaactccagtcacAATCAGTC
TCGTatctcgtatgccgtcttctgcttgTTGTCGACTC >75_Size_273_V4 (SEQ ID NO: 82)
AAGAAGCACCGGCTAACTCCGTGCCAGCAGCCGCGGTAATACTGAGGGTGCAAGCGTAAATCGGAATTAC
TGGGCGTAAAGTAGGGATGGCGATGCATTGGCGCAAGCAGGCAGTTTGTTAAGTCAGATGTGAAATCCCC
GGGCTCAACCTGGGAACTGCATCAGATACTGGCAAGCTTGAGTCTCGTTGAGGGGGGTAGAATTCCATGT
GTAGCGGTGAATTGCGTAGAGAACTGGAGGAATACCGGTGGCGAAGGCGGCCCCCTGGACGAAGACTGAC
GCTCAGGTGCGAAAGCGTGGGGTGCAAACAGGATTAGATACCCTGGTAGTCCACGCCGTAAACGATGTCG
ACTAGGGATAACAGGGTAATGAGTCGACAAaatgatacggcgaccaccgagatctacactctttccctac
acgacgctcttccgatctCGGTATACTACCTTACCAGAagatcggaagagcacacgtctgaactccagtc
acAATCAGTCTCGTatctcgtatgccgtcttctgcttgTTGTCGACTC >76_Size_293_V4 (SEQ ID NO: 83)
AAGAAGCACCGGCTAACTCCGTGCCAGCAGCCGCGGTAATACTGAGGGTGCAAGCGTAAATCGGAATTAC
TGGGCGTAAAGTAGGGATGGCGATGCATTGTCCTGTGTCGCCAACCTTGAGCGCAAGCAGGCAGTTTGTT
AAGTCAGATGTGAAATCCCCGGGCTCAACCTGGGAACTGCATCAGATACTGGCAAGCTTGAGTCTCGTTG
AGGGGGGTAGAATTCCATGTGTAGCGGTGAATTGCGTAGAGAACTGGAGGAATACCGGTGGCGAAGGCGG
CCCCCTGGACGAAGACTGACGCTCAGGTGCGAAAGCGTGGGGTGCAAACAGGATTAGATACCCTGGTAGT
CCACGCCGTAAACGATGTCGACTAGGGATAACAGGGTAATGAGTCGACAAaatgatacggcgaccaccga
gatctacactctttccctacacgacgctcttccgatctACATATCACAACCAGGCCTCagatcggaagag
cacacgtctgaactccagtcacAATCAGTCTCGTatctcgtatgccgtcttctgcttgTTGTCGACTC >77_Size_313_V4 (SEQ ID NO: 84)
AAGAAGCACCGGCTAACTCCGTGCCAGCAGCCGCGGTAATACTGAGGGTGCAAGCGTAAATCGGAATTAC
TGGGCGTAAAGTAGGGATGGCGATGCATTGTCCTGTGTCGCCAACCTTGACTGTACCGCTGTGATAACGC
GCGCAAGCAGGCAGTTTGTTAAGTCAGATGTGAAATCCCCGGGCTCAACCTGGGAACTGCATCAGATACT
GGCAAGCTTGAGTCTCGTTGAGGGGGGTAGAATTCCATGTGTAGCGGTGAATTGCGTAGAGAACTGGAGG
AATACCGGTGGCGAAGGCGGCCCCCTGGACGAAGACTGACGCTCAGGTGCGAAAGCGTGGGGTGCAAACA
GGATTAGATACCCTGGTAGTCCACGCCGTAAACGATGTCGACTAGGGATAACAGGGTAATGAGTCGACAA
aatgatacggcgaccaccgagatctacactctttccctacacgacgctcttccgatctCCCGTAGACTGG
GTCGACGTagatcggaagagcacacgtctgaactccagtcacAATCAGTCTCGTatctcgtatgccgtct
tctgcttgTTGTCGACTC

| Synthetic standard sequences - Full-length 16S rRNA gene tests (HMP mock community) |
|---|

Sequence tags in bold
Illumina adapters in lower case
>78_ABa_Full_TAG_TCT_CAT (SEQ ID NO: 85)
AGAGTTTGATCATGGCTCAGATTGAACGCTGGCGGCAGGCTTAACACATGCAAGTCGAGCGGGGGAAGGT
AGCTTGCTACTGGACCTAGCGGCGGACGGGTGAGTAATGCTTAGGAATCTGCCTATTAGTGGGGGACAAC
ATCTCGAAAGGGATGCTAATACCGCATACGTCCTACGGGAGAAAGCAGGGGATCTTCGGACCTTGCGCTA
ATAGATGAGCCTAAGTCGGATTAGCTAGTTGGTGGGGTAAAGGCCTACCAAGGCGACGATCTGTAGCGGG
TCTGAGAGGATGATCCGCCACACTGGGACTGAGACACGGCCCAGACTCCTACGGGAGGCAGCAGTGGGGA
ATATTGGACAATTAGGGGGGGAACCCTGATCCAGCCATGCCGCGTGTGTGAAGAAGGCCTTATGGTTGTA
AAGCACTTTAAGCGAGGAGGAGGCTACTTTAGTTAATACCTAGAGATAGTGGACGTTACTCGCAGAATAA
GCACCGGCTAACTCTGTGCCAGCAGCCGCGGTAATACAGAGGGTGCGAGCGTTAATCGGATTTACTGGGC
GTAAATCTGCGTGCGTAGGCGGCTTATTAAGTCGGATGTGAAATCCCCGAGCTTAACTTGGGAATTGCAT
TCGATACTGGTGAGCTAGAGTATGGGAGAGGATGGTAGAATTCCAGGTGTAGCGGTGAAATGCGTAGAGA
TCTGGAGGAATACCGATGGCGAAGGCAGCCATCTGGCCTAATACTGACGCTGAGGTACGAAAGCATGGGG
AGCAAACAGGATTAGATACCCTGGTAGTCCATGCCGTAAACGATGTCTACTAGCCGTTGGGGCCTTTGAG
GCTTTAGTGGCGCAGCTAACGCGATAAGTAGACCGCCTGGCATGGAGTACGGTCGCAAGACTAAAACTCA
AATGAATTGACGGGGGCCCGCACAAGCGGTGGAGCATGTGGTTTAATTCGATGCAACGCGAAGAACCTTA
CCTGGCCTTGACATACTAGAAACTTTCCAGAGATGGATTGGTGCCTTCGGGAATCTAGATACAGGTGCTG
CATGGCTGTCGTCAGCTCGTGTCGTGAGATGTTGGGTTAAGTCCCGCAACGAGCGCAACCCTTTTCCTTA
CTTGCCAGCATTTCGGATGGGAACTTTAAGGATACTGCCAGTGACAAACTGGAGGAAGGCGGGGACGACG
TCAAGTCATCATGGCCCTTACGGCCAGGGCTACACACGTGCTACAATGGTCGGTACAAAGGGTTGCTACA -continued Sequence Listing Free Text CAGCGATGTGATGCTAATCTCAAAAAGCCGATCGTAGTCCGGATTGGAGTCTGCAACTCGACTCCATGAA
GTCGGAATCGCTAGTAATCGCGGATCAGAATGCCGCGGTGAATACGTTCCCGGGCCTTGTACACACCGCC
CGTCACACCATGGGAGTTTGTTGCACCAGAAGTAGCTAGCCTAACTGCAAAGAGGGCGGTTACCACGGTG
TGGCCGATGACTGGGGTGAAGTCGTAACAAGGTAGCCGTAGGGGAACCTGCGGCTGGATCACCTCCTTTA
GGGATAACAGGGTAATGAGTCGACAAaatgatacggcgaccaccgagatctacactctttccctacacga
cgctcttccgatctGCTTGTCTGTTCAAGCATCCagatcggaagagcacacgtctgaactccagtcacAA
TCAGTCTCGTatctcgtatgccgtcttctgcttgTTGTCGACTC >79_BCe_Full_TAG_TCT_CAT (SEQ ID NO: 86)
GATGAACGCTGGCGGCGTGCCTAATACATGCAAGTCGAGCGAATGGATTAAGAGCTTGCTCTTATGAAGT
TAGCGGCGGACGGGTGAGTAACACGTGGGTAACCTGCCCATAAGACTGGGATAACTCCGGGAAACCGGGG
CTAATACCGGATAACATTTTGAACCGCATGGTTCGAAATTGAAAGGCGGCTTCGGCTGTCACTTATGGAT
GGACCCGCGTCGCATTAGCTAGTTGGTGAGGTAACGGCTCACCAAGGCAACGATGCGTAGCCGACCTGAG
AGGGTGATCGGCCACACTGGGACTGAGACACGGCCCAGACTCCTACGGGAGGCAGCAGTAGGGAATCTTC
CGCAATTAGGGACGAAAGTCTGACGGAGCAACGCCGCGTGAGTGATGAAGGCTTTCGGGTCGTAAAACTC
TGTTGTTAGGGAAGAACAAGTGCTAGTTGAATAAGCTGGCACCTTGACGGTACCTAACCAGAAAGCCACG
GCTAACTACGTGCCAGCAGCCGCGGTAATACGTAGGTGGCAAGCGTTATCCGGAATTATTGGGCGTAAAT
CTGCGCGCGCAGGTGGTTTCTTAAGTCTGATGTGAAAGCCCACGGCTCAACCGTGGAGGGTCATTGGAAA
CTGGGAGACTTGAGTGCAGAAGAGGAAAGTGGAATTCCATGTGTAGCGGTGAAATGCGTAGAGATATGGA
GGAACACCAGTGGCGAAGGCGACTTTCTGGTCTGTAACTGACACTGAGGCGCGAAAGCGTGGGGAGCAAA
CAGGATTAGATACCCTGGTAGTCCACGCCGTAAACGATGAGTGCTAAGTGTTAGAGGGTTTCCGCCCTTT
AGTGCTGAAGTTAACGCATTAAGCACTCCGCCTGGCATGGAGTACGGCCGCAAGGCTGAAACTCAAAGGA
ATTGACGGGGGCCCGCACAAGCGGTGGAGCATGTGGTTTAATTCGAAGCAACGCGAAGAACCTTACCAGG
TCTTGACATCCTCTGACAACCCTAGAGATAGGGCTTCTCCTTCGGGAGCAGAGTGACAGGTGGTGCATGG
TTGTCGTCAGCTCGTGTCGTGAGATGTTGGGTTAAGTCCCGCAACGAGCGCAACCCTTGATCTTAGTTGC
CATCATTCAGTTGGGCACTCTAAGGTGACTGCCGGTGACAAACCGGAGGAAGGTGGGGATGACGTCAAAT
CATCATGCCCCTTATGACCTGGGCTACACACGTGCTACAATGGACGGTACAAAGAGCTGCAAGACCGCGA
GGTGGAGCTAATCTCATAAAACCGTTCTCAGTTCGGATTGTAGGCTGCAACTCGCCTACATGAAGCTGGA
ATCGCTAGTAATCGCGGATCAGCATGCCGCGGTGAATACGTTCCCGGGCCTTGTACACACCGCCCGTCAC
ACCACGAGAGTTTGTAACACCCGAAGTCGGTGGGGTAACCTTTTGGAGCCAGCCGCCTAAGGTGGGACAG
ATGATTGGGGTGAAGTCGTAACAAGGTAGCCGTATCGGAAGGTGCGGTAGGGATAACAGGGTAATGAGTC
GACAAaatgatacggcgaccaccgagatctacactctttccctacacgacgctcttccgatctTCTCCCT
GTGATTAATGAACagatcggaagagcacacgtctgaactccagtcacAATCAGTCTCGTatctcgtatgc
cgtcttctgcttgTTGTCGACTC >80_BVu_Full_TAG_TCT_CAT (SEQ ID NO: 87)
TATTACAATGAAGAGTTTGATCCTGGCTCAGGATGAACGCTAGCTACAGGCTTAACACATGCAAGTCGAG
GGGCAGCATGGTCTTAGCTTGCTAAGGCCGATGGCGACCGGCGCACGGGTGAGTAACACGTATCCAACCT
GCCGTCTACTCTTGGACAGCCTTCTGAAAGGAAGATTAATACAAGATGGCATCATGAGTCCGCATGTTCA
CATGATTAAAGGTATTCCGGTAGACGATGGGGATGCGTTCCATTAGATAGTAGGCGGGGTAACGGCCCAC
CTAGTCTTCGATGGATAGGGGTTCTGAGAGGAAGGTCCCCCACATTGGAACTGAGACACGGTCCAAACTC
CTACGGGAGGCAGCAGTGAGGAATATTGGTCAATTAGGGGCGAGAGCCTGAACCAGCCAAGTAGCGTGAA
GGATGACTGCCCTATGGGTTGTAAACTTCTTTTATAAAGGAATAAAGTCGGGTATGGATACCCGTTTGCA
TGTACTTTATGAATAAGGATCGGCTAACTCCGTGCCAGCAGCCGCGGTAATACGGAGGATCCGAGCGTTA
TCCGGATTTATTGGGTTTAAATCTGGGAGCGTAGATGGATGTTTAAGTCAGTTGTGAAAGTTTGCGGCTC
AACCGTAAAATTGCAGTTGATACTGGATATCTTGAGTGCAGTTGAGGCAGGCGGAATTCGTGGTGTAGCG
GTGAAATGCTTAGATATCACGAAGAACTCCGATTGCGAAGGCAGCCTGCTAAGCTGCAACTGACATTGAG
GCTCGAAAGTGTGGGTATCAAACAGGATTAGATACCCTGGTAGTCCACACGGTAAACGATGAATACTCGC
TGTTTGCGATATACGGCAAGCGGCCAAGCGAAAGCGTTAAGTATTCCACCTGGCATGGAGTACGCCGGCA
ACGGTGAAACTCAAAGGAATTGACGGGGGCCCGCACAAGCGGAGGAACATGTGGTTTAATTCGATGATAC
GCGAGGAACCTTACCCGGGCTTAAATTGCAGATGAATTACGGTGAAAGCCGTAAGCCGCAAGGCATCTGT
GAAGGTGCTGCATGGTTGTCGTCAGCTCGTGCCGTGAGGTGTCGGCTTAAGTGCCATAACGAGCGCAACC
CTTGTTGTCAGTTACTAACAGGTCATGCTGAGGACTCTGACAAGACTGCCATCGTAAGATGTGAGGAAGG
TGGGGATGACGTCAAATCAGCACGGCCCTTACGTCCGGGGCTACACACGTGTTACAATGGGGGGTACAGA
GGGCCGCTACCACGCGAGTGGATGCCAATCCCCAAAACCTCTCTCAGTTCGGACTGGAGTCTGCAACCCG
ACTCCACGAAGCTGGATTCGCTAGTAATCGCGCATCAGCCACGGCGCGGTGAATACGTTCCCGGGCCTTG
TACACACCGCCCGTCAAGCCATGGGAGCCGGGGGTACCTGAAGTGCGTAACCGCGAGGAGCGCCCTAGGG
TAAAACTGGTGACTGGGGCTAAGTCGTAACAAGGTAGCCGTACCGGAAGTAGGGATAACAGGGTAATGAG
TCGACAAaatgatacggcgaccaccgagatctacactctttccctacacgacgctcttccgatctTAGAG
CCATAGACTGCTGTCagatcggaagagcacacgtctgaactccagtcacAATCAGTCTCGTatctcgtat
gccgtcttctgcttgTTGTCGACTC >81_CBe_Full_TAG_TCT_CAT (SEQ ID NO: 88)
AGAGTTTGATCCTGGCTCAGGACGAACGCTGGCGGCGTGCTTAACACATGCAAGTCGAGCGATGAAGCTC
CTTCGGGAGTGGATTAGCGGCGGACGGGTGAGTAACACGTGGGTAACCTGCCTCATAGAGGGGAATAGCC
TTTCGAAAGGAAGATTAATACCGCATAAGATTGTAGTGCCGCATGGCATAGCAATTAAAGGAGTAATCCG
CTATGAGATGGACCCGCGTCGCATTAGCTAGTTGGTGAGGTAACGGCTCACCAAGGCGACGATGCGTAGC
CGACCTGAGAGGGTGATCGGCCACATTGGGACTGAGACACGGCCCAGACTCCTACGGGAGGCAGCAGTGG
GGAATATTGCACAATTAGGGGGGAAACCCTGATGCAGCAACGCCGCGTGAGTGATGACGGTCTTCGGATT
GTAAAGCTCTGTCTTCAGGGACGATAATGACGGTACCTGAGGAGGAAGCCACGGCTAACTACGTGCCAGC
AGCCGCGGTAATACGTAGGTGGCAAGCGTTGTCCGGATTTACTGGGCGTAAATCTGGGAGCGTAGGTGGA
TATTTAAGTGGGATGTGAAATACTCGGGCTTAACCTGGGTGCTGCATTCCAAACTGGATATCTAGAGTGC
AGGAGAGGAAAGTAGAATTCCTAGTGTAGCGGTGAAATGCGTAGAGATTAGGAAGAATACCAGTGGCGAA
GGCGACTTTCTGGACTGTAACTGACACTGAGGCTCGAAAGCGTGGGGAGCAAACAGGATTAGATACCCTG
GTAGTCCACGCCGTAAACGATGAATACTAGGTGTAGGGGTTGTCATGACCTCTGTGCCGCCGCTAACGCA
TTAAGTATTCCGCCTGGCATGGAGTACGGTCGCAAGATTAAAACTCAAAGGAATTGACGGGGGCCCGCAC
AAGCAGCGGAGCATGTGGTTTAATTCGAAGCAACGCGAAGAACCTTACCTAGACTTGACATCTCCTGAAT -continued

| Sequence Listing Free Text |
| --- |

TACCCTTAATCGGGGAAGCCCTTCGGGGCAGGAAGACAGGTGGTGCATGGTTGTCGTCAGCTCGTGTCGT
GAGATGTTGGGTTAAGTCCCGCAACGAGCGCAACCCTTATTGTTAGTTGCTACCATTTAGTTGAGCACTC
TAGCGAGACTGCCCGGGTTAACCGGGAGGAAGGTGGGGATGACGTCAAATCATCATGCCCCTTATGTCTA
GGGCTACACACGTGCTACAATGGCTGGTACAGAGAGATGCTAAACCGCGAGGTGGAGCCAAACTTTAAAA
CCAGTCTCAGTTCGGATTGTAGGCTGAAACTCGCCTACATGAAGCTGGAGTTGCTAGTAATCGCGAATCA
GAATGTCGCGGTGAATACGTTCCCGGGCCTTGTACACACCGCCCGTCACACCATGAGAGTTGGCAATACC
CAAAGTTCGTGAGCTAACGCGTAAGCGGGGCAGCGACCTAAGGTAGGGTCAGCGATTGGGGTGAAGTCGT
AACAAGGTAGCCGTAGGAGAACCTGCGGCTGGATCACCTCCTTTTAGGGATAACAGGGTAATGAGTCGAC
AAaatgatacggcgaccaccgagatctacactctttccctacacgacgctcttccgatctTAAAGATTAT
TTGCAGCCACagatcggaagagcacacgtctgaactccagtcacAATCAGTCTCGTatctcgtatgccgt
cttctgcttgTTGTCGACTC >82_DRa_Full_TAG_TCT_CAT (SEQ ID NO: 89)
TTTATGGAGAGTTTGATCCTGGCTCAGGGTGAACGCTGGCGGCGTGCTTAAGACATGCAAGTCGAACGCG
GTCTTCGGACCGAGTGGCGCACGGGTGAGTAACACGTAACTGACCTACCCAGAAGTCACGAATAACTGGC
CGAAAGGTCCGCTAATACGTGATGTGGTGATGCACCGTGGTGCATCACTAAAGATTTATCGCTTCTGGAT
GGGGTTGCGTTCCATCAGCTGGTTGGTGGGGTAAAGGCCTACCAAGGCGACGACGGATAGCCGGCCTGAG
AGGGTGGCCGGCCACAGGGGCACTGAGACACGGGTCCCACTCCTACGGGAGGCAGCAGTTAGGAATCTTC
CACAATTAGGGGCGCAAGCCTGATGGAGCGACGCCGCGTGAGGGATGAAGGTTTTCGGATCGTAAACCTC
TGAATCTGGGACGAAAGAGCCTTAGGGCAGATGACGGTACCAGAGTAATAGCACCGGCTAACTCCGTGCC
AGCAGCCGCGGTAATACGGAGGGTGCAAGCGTTACCCGGAATCACTGGGCGTAAATCTGGGCGTGTAGGC
GGAAATTTAAGTCTGGTTTTAAAGACCGGGGCTCAACCTCGGGGATGGACTGGATACTGGATTTCTTGAC
CTCTGGAGAGGTAACTGGAATTCCTGGTGTAGCGGTGGAATGCGTAGATACCAGGAGGAACACCAATGGC
GAAGGCAAGTTACTGGACAGAAGGTGACGCTGAGGCGCGAAAGTGTGGGGAGCAAACCGGATTAGATACC
CGGGTAGTCCACACCCTAAACGATGTACGTTGGCTAAGCGCAGGATGCTGTGCTTGGCGAAGCTAACGCG
ATAAACGTACCGCCTGGCATGAAGTACGGCCGCAAGGTTGAAACTCAAAGGAATTGACGGGGGCCCGCAC
AAGCGGTGGAGCATGTGGTTTAATTCGAAGCAACGCGAAGAACCTTACCAGGTCTTGACATGCTAGGAAC
TTTGCAGAGATGCAGAGGTGCCCTTCGGGGAACCTAGACACAGGTGCTGCATGGCTGTCGTCAGCTCGTG
TCGTGAGATGTTGGGTTAAGTCCCGCAACGAGCGCAACCCTTGCCTTTAGTTGTCAGCATTCAGTTGGAC
ACTCTAGAGGGACTGCCTATGAAAGTAGGAGGAAGGCGGGGATGACGTCTAGTCAGCATGGTCCTTACGT
CCTGGGCGACACACGTGCTACAATGGGTAGGACAACGCGCAGCAAACCCGCGAGGGTAAGCGAATCGCTA
AAACCTATCCCCAGTTCAGATCGGAGTCTGCAACTCGACTCCGTGAAGTTGGAATCGCTAGTAATCGCGG
GTCAGCATACCGCGGTGAATACGTTCCCGGGCCTTGTACACACCGCCCGTCACACCATGGGAGTAGATTG
CAGTTGAAACCGCCGGGAGCTTAACGGCAGGCGTCTAGACTGTGGTTTATGACTGGGGTGAAGTCGTAAC
AAGGTAACTGTACCGGAAGGTGCGGTTGGATCACCTCCTTTTAGGGATAACAGGGTAATGAGTCGACAAa
atgatacggcgaccaccgagatctacactctttccctacacgacgctcttccgatctGTATTCAGCCGTC
AACTTATagatcggaagagcacacgtctgaactccagtcacAATCAGTCTCGTatctcgtatgccgtctt
ctgcttgTTGTCGACTC >83_EFa_Full_TAG_TCT_CAT (SEQ ID NO: 90)
AGAGTTTGATCCTGGCTCAGGACGAACGCTGGCGGCGTGCCTAATACATGCAAGTCGAACGCTTCTTTCC
TCCCGAGTGCTTGCACTCAATTGGAAAGAGGAGTGGCGGACGGGTGAGTAACACGTGGGTAACCTACCCA
TCAGAGGGGGATAACACTTGGAAACAGGTGCTAATACCGCATAACAGTTTATGCCGCATGGCATAAGAGT
GAAAGGCGCTTTCGGGTGTCGCTGATGGATGGACCCGCGGTGCATTAGCTAGTTGGTGAGGTAACGGCTC
ACCAAGGCCACGATGCATAGCCGACCTGAGAGGGTGATCGGCCACACTGGGACTGAGACACGGCCCAGAC
TCCTACGGGAGGCAGCAGTAGGGAATCTTCGGCAATTAGGGACGAAAGTCTGACCGAGCAACGCCGCGTG
AGTGAAGAAGGTTTTCGGATCGTAAAACTCTGTTGTTAGAGAAGAACAAGGACGTTAGTAACTGAACGTC
CCCTGACGGTATCTAACCAGAAAGCCACGGCTAACTACGTGCCAGCAGCCGCGGTAATACGTAGGTGGCA
AGCGTTGTCCGGATTTATTGGGCGTAAATCTGCGAGCGCAGGCGGTTTCTTAAGTCTGATGTGAAAGCCC
CCGGCTCAACCGGGGAGGGTCATTGGAAACTGGGAGACTTGAGTGCAGAAGAGGAGAGTGGAATTCCATG
TGTAGCGGTGAAATGCGTAGATATATGGAGGAACACCAGTGGCGAAGGCGGCTCTCTGGTCTGTAACTGA
CGCTGAGGCTCGAAAGCGTGGGGAGCAAACAGGATTAGATACCCTGGTAGTCCACGCCGTAAACGATGAG
TGCTAAGTGTTGGAGGGTTTCCGCCCTTCAGTGCTGCAGCAAACGCATTAAGCACTCCGCCTGGCATGGA
GTACGACCGCAAGGTTGAAACTCAAAGGAATTGACGGGGGCCCGCACAAGCGGTGGAGCATGTGGTTTAA
TTCGAAGCAACGCGAAGAACCTTACCAGGTCTTGACATCCTTTGACCACTCTAGAGATAGAGCTTTCCCT
TCGGGGACAAAGTGACAGGTGGTGCATGGTTGTCGTCAGCTCGTGTCGTGAGATGTTGGGTTAAGTCCCG
CAACGAGCGCAACCCTTATTGTTAGTTGCCATCATTTAGTTGGGCACTCTAGCGAGACTGCCGGTGACAA
ACCGGAGGAAGGTGGGGATGACGTCAAATCATCATGCCCCTTATGACCTGGGCTACACACGTGCTACAAT
GGGAAGTACAACGAGTCGCTAGACCGCGAGGTCATGCAAATCTCTTAAAGCTTCTCTCAGTTCGGATTGC
AGGCTGCAACTCGCCTGCATGAAGCCGGAATCGCTAGTAATCGCGGATCAGCACGCCGCGGTGAATACGT
TCCCGGGCCTTGTACACACCGCCCGTCACACCACGAGAGTTTGTAACACCCGAAGTCGGTGAGGTAACCT
TTTTGGAGCCAGCCGCCTAAGGTGGGATAGATGATTGGGGTGAAGTCGTAACAAGGTAGCCGTATCGGAA
GGTGCGGCTGGATCACCTTAGGGATAACAGGGTAATGAGTCGACAAaatgatacggcgaccaccgagatc
tacactctttccctacacgacgctcttccgatctTGCTGGGCTCAGAGGTGAATagatcggaagagcaca
cgtctgaactccagtcacAATCAGTCTCGTatctcgtatgccgtcttctgcttgTTGTCGACTC >84_ECc_Full_TAG_TCT_CAT (SEQ ID NO: 91)
AAATTGAAGAGTTTGATCATGGCTCAGATTGAACGCTGGCGGCAGGCCTAACACATGCAAGTCGAACGGT
AACAGGAAGAAGCTTGCTTCTTTGCTGACGAGTGGCGGACGGGTGAGTAATGTCTGGGAAACTGCCTGAT
GGAGGGGGATAACTACTGGAAACGGTAGCTAATACCGCATAACGTCGCAAGACCAAAGAGGGGGACCTTC
GGGCCTCTTGCCATCGGATGTGCCCAGATGGGATTAGCTAGTAGGTGGGGTAACGGCTCACCTAGGCGAC
GATCCCTAGCTGGTCTGAGAGGATGACCAGCCACACTGGAACTGAGACACGGTCCAGACTCCTACGGGAG
GCAGCAGTGGGGAATATTGCACAATTAGGGGCGCAAGCCTGATGCAGCCATGCCGCGTGTATGAAGAAGG
CCTTCGGGTTGTAAAGTACTTTCAGCGGGGAGGAAGGGAGTAAAGTTAATACCTTTGCTCATTGACGTTA
CCCGCAGAAGAAGCACCGGCTAACTCCGTGCCAGCAGCCGCGGTAATACGGAGGGTGCAAGCGTTAATCG
GAATTACTGGGCGTAAATCTGCGCACGCAGGCGGTTTGTTAAGTCAGATGTGAAATCCCCGGGCTCAACC
TGGGAACTGCATCTGATACTGGCAAGCTTGAGTCTCGTAGAGGGGGGTAGAATTCCAGGTGTAGCGGTGA -continued

| Sequence Listing Free Text |
|---|

AATGCGTAGAGATCTGGAGGAATACCGGTGGCGAAGGCGGCCCCCTGGACGAAGACTGACGCTCAGGTGC
GAAAGCGTGGGGAGCAAACAGGATTAGATACCCTGGTAGTCCACGCCGTAAACGATGTCGACTTGGAGGT
TGTGCCCTTGAGGCGTGGCTTCCGGAGCTAACGCGTTAAGTCGACCGCCTGGCATGGAGTACGGCCGCAA
GGTTAAAACTCAAATGAATTGACGGGGGCCCGCACAAGCGGTGGAGCATGTGGTTTAATTCGATGCAACG
CGAAGAACCTTACCTGGTCTTGACATCCACAGAACTTTCCAGAGATGGATTGGTGCCTTCGGGAACTGTG
AGACAGGTGCTGCATGGCTGTCGTCAGCTCGTGTTGTGAAATGTTGGGTTAAGTCCCGCAACGAGCGCAA
CCCTTATCTTTTGTTGCCAGCGGTCCGGCCGGGAACTCAAAGGAGACTGCCAGTGATAAACTGGAGGAAG
GTGGGGATGACGTCAAGTCATCATGGCCCTTACGACCAGGGCTACACACGTGCTACAATGGCGCATACAA
AGAGAAGCGACCTCGCGAGAGCAAGCGGACCTCATAAAGTGCGTCGTAGTCCGGATTGGAGTCTGCAACT
CGACTCCATGAAGTCGGAATCGCTAGTAATCGTGGATCAGAATGCCACGGTGAATACGTTCCCGGGCCTT
GTACACACCGCCCGTCACACCATGGGAGTGGGTTGCAAAAGAAGTAGGTAGCTTAACCTTCGGGAGGGCG
CTTACCACTTTGTGATTCATGACTGGGGTGAAGTCGTAACAAGGTAACCGTAGGGGAACCTGCGGTTGGA
TCACCTCCTTATAGGGATAACAGGGTAATGAGTCGACAAaatgatacggcgaccaccgagatctacactc
tttccctacacgacgctcttccgatctAACAGCACTGTCGCACGGCTagatcggaagagcacacgtctga
actccagtcacAATCAGTCTCGTatctcgtatgccgtcttctgcttgTTGTCGACTC >85_HPy_Full_TAG_TCT_CAT (SEQ ID NO: 92)
TTTATGGAGAGTTTGATCCTGGCTCAGAGTGAACGCTGGCGGCGTGCCTAATACATGCAAGTCGAACGAT
GAAGCTTCTAGCTTGCTAGAGTGCTGATTAGTGGCGCACGGGTGAGTAACGCATAGGTTATGTGCCTCTT
AGTTTGGGATAGCCATTGGAAACGATGATTAATACCAGATACTCCTACGGGGGAAAGATTTATCGCTAAG
AGATCAGCCTATGTCCTATCAGCTTGTTGGTAAGGTAATGGCTTACCAAGGCTATGACGGGTATCCGGCC
TGAGAGGGTGAACGGACACACTGGAACTGAGACACGGTCCAGACTCCTACGGGAGGCAGCAGTAGGGAAT
ATTGCTCAATTAGGGGGAAACCCTGAAGCAGCAACGCCGCGTGGAGGATGAAGGTTTTAGGATTGTAAA
CTCCTTTTGTTAGAGAAGATAATGACGGTATCTAACGAATAAGCACCGGCTAACTCCGTGCCAGCAGCCG
CGGTAATACGGAGGGTGCAAGCGTTACTCGGAATCACTGGGCGTAAATCTGAGCGCGTAGGCGGGATAGT
CAGTCAGGTGTGAAATCCTATGGCTTAACCATAGAACTGCATTTGAAACTACTATTCTAGAGTGTGGGAG
AGGTAGGTGGAATTCTTGGTGTAGGGGTAAAATCCGTAGAGATCAAGAGGAATACTCATTGCGAAGGCGA
CCTGCTGGAACATTACTGACGCTGATTGCGCGAAAGCGTGGGGAGCAAACAGGATTAGATACCCTGGTAG
TCCACGCCCTAAACGATGGATGCTAGTTGTTGGAGGGCTTAGTCTCTCCAGTAATGCAGCTAACGCATTA
AGCATCCCGCCTGGCATGGAGTACGGTCGCAAGATTAAAACTCAAAGGAATAGACGGGGACCCGCACAAG
CGGTGGAGCATGTGGTTTAATTCGAAGATACACGAAGAACCTTACCTAGGCTTGACATTGAGAGAATCCG
CTAGAAATAGTGGAGTGTCTGGCTTGCCAGACCTTGAAAACAGGTGCTGCACGGCTGTCGTCAGCTCGTG
TCGTGAGATGTTGGGTTAAGTCCCGCAACGAGCGCAACCCCTTTTCTTAGTTGCTAACAGGTTATGCTGA
GAACTCTAAGGATACTGCCTCCGTAAGGGGAGGAAGGTGGGGACGACGTCAAGTCATCATGGCCCTTACG
CCTAGGGCTACACACGTGCTACAATGGGGTGCACAAAGAGAAGCAATACTGCGAATGGAGCCAATCTTCA
AAACACCTCTCAGTTCGGATTGTAGGCTGCAACTCGCCTGCATGAAGCTGGAATCGCTAGTAATCGCAAA
TCAGCCATGTTGCGGTGAATACGTTCCCGGGTCTTGTACTCACCGCCCGTCACACCATGGGAGTTGTGTT
TGCCTTAAGTCAGGATGCTAAATTGGCTACTGCCCACGGCACACACAGCGACTGGGGTGAAGTCGTAACA
AGGTAACCGTAGTGAACCTGCGGTTGGATCACCTCCTTAGGGATAACAGGGTAATGAGTCGACAAaatga
tacggcgaccaccgagatctacactctttccctacacgacgctcttccgatctCACGTACTAGTGGTCAG
CGGagatcggaagagcacacgtctgaactccagtcacAATCAGTCTCGTatctcgtatgccgtcttctgc
ttgTTGTCGACTC >86_LGa_Full_TAG_TCT_CAT (SEQ ID NO: 93)
GAAGGAAAATGAGAGTTTGATCCTGGCTCAGGACGAACGCTGGCGGCGTGCCTAATACATGCAAGTCGAG
CGAGCTTGCCTAGATGAATTTGGTGCTTGCACCAGATGAAACTAGATACAAGCGAGCGGCGGACGGGTGA
GTAACACGTGGGTAACCTGCCCAAGAGACTGGGATAACACCTGGAAACAGATGCTAATACCGGATAACAA
CACTAGACGCATGTCTAGAGTTTAAAAGATGGTTCTGCTATCACTCTTGGATGGACCTGCGGTGCATTAG
CTAGTTGGTAAGGTAACGGCTTACCAAGGCAATGATGCATAGCCGAGTTGAGAGACTGATCGGCCACATT
GGGACTGAGACACGGCCCAAACTCCTACGGGAGGCAGCAGTAGGGAATCTTCCACAATTAGGGACGCAAG
TCTGATGGAGCAACGCCGCGTGAGTGAAGAAGGGTTTCGGCTCGTAAAGCTCTGTTGGTAGTGAAGAAAG
ATAGAGGTAGTAACTGGCCTTTATTTGACGGTAATTACTTAGAAAGTCACGGCTAACTACGTGCCAGCAG
CCGCGGTAATACGTAGGTGGCAAGCGTTGTCCGGATTTATTGGGCGTAAATCTGCGAGTGCAGGCGGTTC
AATAAGTCTGATGTGAAAGCCTTCGGCTCAACCGGAGAATTGCATCAGAAACTGTTGAACTTGAGTGCAG
AAGAGGAGAGTGGAACTCCATGTGTAGCGGTGGAATGCGTAGATATATGGAAGAACACCAGTGGCGAAGG
CGGCTCTCTGGTCTGCAACTGACGCTGAGGCTCGAAAGCATGGGTAGCGAACAGGATTAGATACCCTGGT
AGTCCATGCCGTAAACGATGAGTGCTAAGTGTTGGGAGGTTTCCGCCTCTCAGTGCTGCAGCTAACGCAT
TAAGCACTCCGCCTGGCATGGAGTACGACCGCAAGGTTGAAACTCAAAGGAATTGACGGGGGCCCGCACA
AGCGGTGGAGCATGTGGTTTAATTCGAAGCAACGCGAAGAACCTTACCAGGTCTTGACATCCAGTGCAAA
CCTAAGAGATTAGGTGTTCCCTTCGGGGACGCTGAGACAGGTGGTGCATGGCTGTCGTCAGCTCGTGTCG
TGAGATGTTGGGTTAAGTCCCGCAACGAGCGCAACCCTTGTCATTAGTTGCCATCATTAAGTTGGGCACT
CTAATGAGACTGCCGGTGACAAACCGGAGGAAGGTGGGGATGACGTCAAGTCATCATGCCCCTTATGACC
TGGGCTACACACGTGCTACAATGGACGGTACAACGAGAAGCGAACCTGCGAAGGCAAGCGGATCTCTGAA
AGCCGTTCTCAGTTCGGACTGTAGGCTGCAACTCGCCTACACGAAGCTGGAATCGCTAGTAATCGCGGAT
CAGCACGCCGCGGTGAATACGTTCCCGGGCCTTGTACACACCGCCCGTCACACCATGAGAGTCTGTAACA
CCCAAAGCCGGTGGGATAACCTTTATAGGAGTCAGCCGTCTAAGGTAGGACAGATGATTAGGGTGAAGTC
GTAACAAGGTAGCCGTAGGAGAACCTGCGGCTGGATCACCTCCTTTCTTAGGGATAACAGGGTAATGAGT
CGACAAaatgatacggcgaccaccgagatctacactctttccctacacgacgctcttccgatctACGTAA
AGGGTTATTGCATTagatcggaagagcacacgtctgaactccagtcacAATCAGTCTCGTatctcgtatg
ccgtcttctgcttgTTGTCGACTC >87_NMe_Full_TAG_TCT_CAT (SEQ ID NO: 94)
TGAACATAAGAGTTTGATCCTGGCTCAGATTGAACGCTGGCGGCATGCTTTACACATGCAAGTCGGACGG
CAGCACAGAGAAGCTTGCTTCTCGGGTGGCGAGTGGCGAACGGGTGAGTAACATATCGGAACGTACCGAG
TAGTGGGGGATAACTGATCGAAAGATCAGCTAATACCGCATACGTCTTGAGAGAGAAAGCAGGGGACCTT
CGGGCCTTGCGCTATTCGAGCGGCCGATATCTGATTAGCTAGTTGGTGGGGTAAAGGCCTACCAAGGCGA
CGATCAGTAGCGGGTCTGAGAGGATGATCCGCCACACTGGGACTGAGACACGGCCCAGACTCCTACGGGA -continued

| Sequence Listing Free Text |
| --- |

GGCAGCAGTGGGGAATTTTGGACAATTAGGGGCGCAAGCCTGATCCAGCCATGCCGCGTGTCTGAAGAAG
GCCTTCGGGTTGTAAAGGACTTTTGTCAGGGAAGAAAAGGCTGTTGCTAATATCAGCGGCTGATGACGGT
ACCTGAAGAATAAGCACCGGCTAACTACGTGCCAGCAGCCGCGGTAATACGTAGGGTGCGAGCGTTAATC
GGAATTACTGGGCGTAAATCTGCGGGCGCAGACGGTTACTTAAGCAGGATGTGAAATCCCCGGGCTCAAC
CCGGGAACTGCGTTCTGAACTGGGTGACTCGAGTGTGTCAGAGGGAGGTAGAATTCCACGTGTAGCAGTG
AAATGCGTAGAGATGTGGAGGAATACCGATGGCGAAGGCAGCCTCCTGGGACAACACTGACGTTCATGCC
CGAAAGCGTGGGTAGCAAACAGGATTAGATACCCTGGTAGTCCACGCCCTAAACGATGTCAATTAGCTGT
TGGGCAACCTGATTGCTTGGTAGCGTAGCTAACGCGTGAAATTGACCGCCTGGCATGGAGTACGGTCGCA
AGATTAAAACTCAAAGGAATTGACGGGGACCCGCACAAGCGGTGGATGATGTGGATTAATTCGATGCAAC
GCGAAGAACCTTACCTGGTCTTGACATGTACGGAATCCTCCGGAGACGGAGGAGTGCCTTCGGGAGCCGT
AACACAGGTGCTGCATGGCTGTCGTCAGCTCGTGTCGTGAGATGTTGGGTTAAGTCCCGCAACGAGCGCA
ACCCTTGTCATTAGTTGCCATCATTCAGTTGGGCACTCTAATGAGACTGCCGGTGACAAGCCGGAGGAAG
GTGGGGATGACGTCAAGTCCTCATGGCCCTTATGACCAGGGCTTCACACGTCATACAATGGTCGGTACAG
AGGGTAGCCAAGCCGCGAGGCGGAGCCAATCTCACAAAACCGATCGTAGTCCGGATTGCACTCTGCAACT
CGAGTGCATGAAGTCGGAATCGCTAGTAATCGCAGGTCAGCATACTGCGGTGAATACGTTCCCGGGTCTT
GTACACACCGCCCGTCACACCATGGGAGTGGGGGATACCAGAAGTAGGTAGGATAACCACAAGGAGTCCG
CTTACCACGGTATGCTTCATGACTGGGGTGAAGTCGTAACAAGGTAGCCGTAGGGGAACCTGCGGCTGGA
TCACCTCCTTTCTTAGGGATAACAGGGTAATGAGTCGACAAaatgatacggcgaccaccgagatctacac
tctttccctacacgacgctcttccgatctAGTCCCAGGATTGCTGAAATagatcggaagagcacacgtct
gaactccagtcacAATCAGTCTCGTatctcgtatgccgtcttctgcttgTTGTCGACTC >88_PAcFull_TAG_TCT_CAT (SEQ ID NO: 95)
AGAGTTTGATCCTGGCTCAGGACGAACGCTGGCGGCGTGCTTAACACATGCAAGTCGAACGGAAAGGCCC
TGCTTTTGTGGGGTGCTCGAGTGGCGAACGGGTGAGTAACACGTGAGTAACCTGCCCTTGACTTTGGGAT
AACTTCAGGAAACTGGGGCTAATACCGGATAGGAGCTCCTGCTGCATGGTGGGGGTTGGAAAGTTTCGGC
GGTTGGGGATGGACTCGCGGCTTATCAGCTTGTTGGTGGGGTAGTGGCTTACCAAGGCTTTGACGGGTAG
CCGGCCTGAGAGGGTGACCGGCCACATTGGGACTGAGATACGGCCCAGACTCCTACGGGAGGCAGCAGTG
GGGAATATTGCACAATTAGGGGCGGAAGCCTGATGCAGCAACGCCGCGTGCGGGATGACGGCCTTCGGGT
TGTAAACCGCTTTCGCCTGTGACGAAGCGTGAGTGACGGTAATGGGTAAAGAAGCACCGGCTAACTACGT
GCCAGCAGCCGCGGTGATACGTAGGGTGCGAGCGTTGTCCGGATTTATTGGGCGTAAATCTGGGCTCGTA
GGTGGTTGATCGCGTCGGAAGTGTAATCTTGGGGCTTAACCCTGAGCGTGCTTTCGATACGGGTTGACTT
GAGGAAGGTAGGGGAGAATGGAATTCCTGGTGGAGCGGTGGAATGCGCAGATATCAGGAGGAACACCAGT
GGCGAAGGCGGTTCTCTGGGCCTTTCCTGACGCTGAGGAGCGAAAGCGTGGGGAGCGAACAGGCTTAGAT
ACCCTGGTAGTCCACGCTGTAAACGGTGGGTACTAGGTGTGGGGTCCATTCCACGGGTTCCGTGCCGTAG
CTAACGCTTTAAGTACCCCGCCTGGCATGGAGTACGGCCGCAAGGCTAAAACTCAAAGGAATTGACGGGG
CCCCGCACAAGCGGCGGAGCATGCGGATTAATTCGATGCAACGCGTAGAACCTTACCTGGGTTTGACATG
GATCGGGAGTGCTCAGAGATGGGTGTGCCTCTTTTGGGGTCGGTTCACAGGTGGTGCATGGCTGTCGTCA
GCTCGTGTCGTGAGATGTTGGGTTAAGTCCCGCAACGAGCGCAACCCTTGTTCACTGTTGCCAGCACGTT
ATGGTGGGGACTCAGTGGAGACCGCCGGGGTCAACTCGGAGGAAGGTGGGGATGACGTCAAGTCATCATG
CCCCTTATGTCCAGGGCTTCACGCATGCTACAATGGCTGGTACAGAGAGTGGCGAGCCTGTGAGGGTGAG
CGAATCTCGGAAAGCCGGTCTCAGTTCGGATTGGGGTCTGCAACTCGACCTCATGAAGTCGGAGTCGCTA
GTAATCGCAGATCAGCAACGCTGCGGTGAATACGTTCCCGGGGCTTGTACACACCGCCCGTCAAGTCATG
AAAGTTGGTAACACCCGAAGCCGGTGGCCTAACCGTTGTGGGGGAGCCGTCGAAGGTGGGACTGGTGATT
AGGACTAAGTCGTAACAAGGTAGCCGTACCGGAAGGTGCGGCTGGATCACCTCCTTTCTAAGGATAGGGA
TAACAGGGTAATGAGTCGACAAaatgatacggcgaccaccgagatctacactctttccctacacgacgct
cttccgatctGATCACCCTGCATGTACACAagatcggaagagcacacgtctgaactccagtcacAATCAG
TCTCGTatctcgtatgccgtcttctgcttgTTGTCGACTC >89_PAr_Full_TAG_TCT_CAT (SEQ ID NO: 96)
AACTGAAGAGTTTGATCATGGCTCAGATTGAACGCTGGCGGCAGGCCTAACACATGCAAGTCGAGCGGAT
GAAGGGAGCTTGCTCCTGGATTCAGCGGCGGACGGGTGAGTAATGCCTAGGAATCTGCCTGGTAGTGGGG
GATAACGTCCGGAAACGGGCGCTAATACCGCATACGTCCTGAGGGAGAAAGTGGGGGATCTTCGGACCTC
ACGCTATCAGATGAGCCTAGGTCGGATTAGCTAGTTGGTGGGGTAAAGGCCTACCAAGGCGACGATCCGT
AACTGGTCTGAGAGGATGATCAGTCACACTGGAACTGAGACACGGTCCAGACTCCTACGGGAGGCAGCAG
TGGGGAATATTGGACAATTAGGGGCGAAAGCCTGATCCAGCCATGCCGCGTGTGTGAAGAAGGTCTTCGG
ATTGTAAAGCACTTTAAGTTGGGAGGAAGGGCAGTAAGTTAATACCTTGCTGTTTTGACGTTACCAACAG
AATAAGCACCGGCTAACTTCGTGCCAGCAGCCGCGGTAATACGAAGGGTGCAAGCGTTAATCGGAATTAC
TGGGCGTAAATCTGCGCGCGTAGGTGGTTCAGCAAGTTGGATGTGAAATCCCCGGGCTCAACCTGGGAAC
TGCATCCAAAACTACTGAGCTAGAGTACGGTAGAGGGTGGTGGAATTTCCTGTGTAGCGGTGAAATGCGT
AGATATAGGAAGGAACACCAGTGGCGAAGGCGACCACCTGGACTGATACTGACACTGAGGTGCGAAAGCG
TGGGGAGCAAACAGGATTAGATACCCTGGTAGTCCACGCCGTAAACGATGTCGACTAGCCGTTGGGATCC
TTGAGATCTTAGTGGCGCAGCTAACGCGATAAGTCGACCGCCTGGCATGGAGTACGGCCGCAAGGTTAAA
ACTCAAATGAATTGACGGGGGCCCGCACAAGCGGTGGAGCATGTGGTTTAATTCGAAGCAACGCGAAGAA
CCTTACCTGGCCTTGACATGCTGAGAACTTTCCAGAGATGGATTGGTGCCTTCGGGAACTCAGACACAGG
TGCTGCATGGCTGTCGTCAGCTCGTGTCGTGAGATGTTGGGTTAAGTCCCGTAACGAGCGCAACCCTTGT
CCTTAGTTACCAGCACCTCGGGTGGGCACTCTAAGGAGACTGCCGGTGACAAACCGGAGGAAGGTGGGGA
TGACGTCAAGTCATCATGGCCCTTACGGCCAGGGCTACACACGTGCTACAATGGTCGGTACAAAGGGTTG
CCAAGCCGCGAGGTGGAGCTAATCCCATAAAACCGATCGTAGTCCGGATCGCAGTCTGCAACTCGACTGC
GTGAAGTCGGAATCGCTAGTAATCGTGAATCAGAATGTCACGGTGAATACGTTCCCGGGCCTTGTACACA
CCGCCCGTCACACCATGGGAGTGGGTTGCTCCAGAAGTAGCTAGTCTAACCGCAAGGGGGACGGTTACCA
CGGAGTGATTCATGACTGGGGTGAAGTCGTAACAAGGTAGCCGTAGGGGAACCTGCGGCTGGATCACCTC
CTTAATAGGGATAACAGGGTAATGAGTCGACAAaatgatacggcgaccaccgagatctacactctttccc
tacacgacgctcttccgatctGGTAACATATAAGCTTCTCGagatcggaagagcacacgtctgaactcca
gtcacAATCAGTCTCGTatctcgtatgccgtcttctgcttgTTGTCGACTC -continued

| Sequence Listing Free Text |
|---|

>90_RSp_Full_TAG_TCT_CAT (SEQ ID NO: 97)
CAACTTGAGAGTTTGATCCTGGCTCAGAATGAACGCTGGCGGCAGGCCTAACACATGCAAGTCGAGCGAA
GTCTTCGGACTTAGCGGCGGACGGGTGAGTAACGCGTGGGAACGTGCCCTTTGCTTCGGAATAGCCCCGG
GAAACTGGGAGTAATACCGAATGTGCCCTTTGGGGGAAAGATTTATCGGCAAAGGATCGGCCCGCGTTGG
ATTAGGTAGTTGGTGGGGTAATGGCCTACCAAGCCGACGATCCATAGCTGGTTTGAGAGGATGATCAGCC
ACACTGGGACTGAGACACGGCCCAGACTCCTACGGGAGGCAGCAGTGGGGAATCTTAGACAATTAGGGGC
GCAAGCCTGATCTAGCCATGCCGCGTGATCGATGAAGGCCTTAGGGTTGTAAAGATCTTTCAGGTGGGAA
GATAATGACGGTACCACCAGAAGAAGCCCCGGCTAACTCCGTGCCAGCAGCCGCGGTAATACGGAGGGGG
CTAGCGTTATTCGGAATTACTGGGCGTAAATCTGCGCACGTAGGCGGATCGGAAAGTCAGAGGTGAAATC
CCAGGGCTCAACCCTGGAACTGCCTTTGAAACTCCCGATCTTGAGGTCGAGAGAGGTGAGTGGAATTCCG
AGTGTAGAGGTGAAATTCGTAGATATTCGGAGGAACACCAGTGGCGAAGGCGGCTCACTGGCTCGATACT
GACGCTGAGGTGCGAAAGCGTGGGGAGCAAACAGGATTAGATACCCTGGTAGTCCACGCCGTAAACGATG
AATGCCAGTCGTCGGGCAGCATGCTGTTCGGTGACACACCTAACGGATTAAGCATTCCGCCTGGCATGGA
GTACGGCCGCAAGGTTAAAACTCAAAGGAATTGACGGGGGCCCGCACAAGCGGTGGAGCATGTGGTTTAA
TTCGAAGCAACGCGCAGAACCTTACCAACCCTTGACATGGCGATCGCGGTTCCAGAGATGGTTCCTTCAG
TTCGGCTGGATCGCACACAGGTGCTGCATGGCTGTCGTCAGCTCGTGTCGTGAGATGTTCGGTTAAGTCC
GGCAACGAGCGCAACCCACGTCCTTAGTTGCCAGCATTCAGTTGGGCACTCTAGGGAAACTGCCGGTGAT
AAGCCGGAGGAAGGTGTGGATGACGTCAAGTCCTCATGGCCCTTACGGGTTGGGCTACACACGTGCTACA
ATGGCAGTGACAATGGGTTAATCCCAAAAAGCTGTCTCAGTTCGGATTGGGGTCTGCAACTCGACCCCAT
GAAGTCGGAATCGCTAGTAATCGCGTAACAGCATGACGCGGTGAATACGTTCCCGGGCCTTGTACACACC
GCCCGTCACACCATGGGAATTGGTTCTACCCGAAGGCGGTGCGCCAACCTCGCAAGAGGAGGCAGCCGAC
CACGGTAGGATCAGTGACTGGGGTGAAGTCGTAACAAGGTAGCCGTAGGGGAACCTGCGGCTGGATCACC
TCCTTTAGGGATAACAGGGTAATGAGTCGACAAaatgatacggcgaccaccgagatctacactctttccc
tacacgacgctcttccgatctGTAGAAATAATCGGATTCGAagatcggaagagcacacgtctgaactcca
gtcacAATCAGTCTCGTatctcgtatgccgtcttctgcttgTTGTCGACTC >91_SAr_Full_TAG_TCT_CAT (SEQ ID NO: 98)
AGAGTTTGATCCTGGCTCAGGATGAACGCTGGCGGCGTGCCTAATACATGCAAGTCGAGCGAACGGACGA
GAAGCTTGCTTCTCTGATGTTAGCGGCGGACGGGTGAGTAACACGTGGATAACCTACCTATAAGACTGGG
ATAACTTCGGGAAACCGGAGCTAATACCGGATAATATTTTGAACCGCATGGTTCAAAAGTGAAAGACGGT
CTTGCTGTCACTTATAGATGGATCCGCGCTGCATTAGCTAGTTGGTAAGGTAACGGCTTACCAAGGCAAC
GATGCATAGCCGACCTGAGAGGGTGATCGGCCACACTGGAACTGAGACACGGTCCAGACTCCTACGGGAG
GCAGCAGTAGGGAATCTTCCGCAATTAGGGGCGAAAGCCTGACGGAGCAACGCCGCGTGAGTGATGAAGG
TCTTCGGATCGTAAAACTCTGTTATTAGGGAAGAACATATGTGTAAGTAACTGTGCACATCTTGACGGTA
CCTAATCAGAAAGCCACGGCTAACTACGTGCCAGCAGCCGCGGTAATACGTAGGTGGCAAGCGTTATCCG
GAATTATTGGGCGTAAATCTGCGCGCGTAGGCGGTTTTTTAAGTCTGATGTGAAAGCCCACGGCTCAACC
GTGGAGGGTCATTGGAAACTGGAAAACTTGAGTGCAGAAGAGGAAAGTGGAATTCCATGTGTAGCGGTGA
AATGCGCAGAGATATGGAGGAACACCAGTGGCGAAGGCGACTTTCTGGTCTGTAACTGACGCTGATGTGC
GAAAGCGTGGGGATCAAACAGGATTAGATACCCTGGTAGTCCACGCCGTAAACGATGAGTGCTAAGTGTT
AGGGGGTTTCCGCCCCTTAGTGCTGCAGCTAACGCATTAAGCACTCCGCCTGGCATGGAGTACGACCGCA
AGGTTGAAACTCAAAGGAATTGACGGGGACCCGCACAAGCGGTGGAGCATGTGGTTTAATTCGAAGCAAC
GCGAAGAACCTTACCAAATCTTGACATCCTTTGACAACTCTAGAGATAGAGCCTTCCCCTTCGGGGGACA
AAGTGACAGGTGGTGCATGGTTGTCGTCAGCTCGTGTCGTGAGATGTTGGGTTAAGTCCCGCAACGAGCG
CAACCCTTAAGCTTAGTTGCCATCATTAAGTTGGGCACTCTAAGTTGACTGCCGGTGACAAACCGGAGGA
AGGTGGGGATGACGTCAAATCATCATGCCCCTTATGATTTGGGCTACACACGTGCTACAATGGACAATAC
AAAGGGCAGCGAAACCGCGAGGTCAAGCAAATCCCATAAAGTTGTTCTCAGTTCGGATTGTAGTCTGCAA
CTCGACTACATGAAGCTGGAATCGCTAGTAATCGTAGATCAGCATGCTACGGTGAATACGTTCCCGGGTC
TTGTACACACCGCCCGTCACACCACGAGAGTTTGTAACACCCGAAGCCGGTGGAGTAACCTTTTAGGAGC
TAGCCGTCGAAGGTGGGACAAATGATTGGGGTGAAGTCGTAACAAGGTAGCCGTATCGGAAGGTGCGGCT
GGATCACCTTAGGGATAACAGGGTAATGAGTCGACAAaatgatacggcgaccaccgagatctacactctt
tccctacacgacgctcttccgatctTCACCTGCCGGGCGGGCGCGagatcggaagagcacacgtctgaac
tccagtcacAATCAGTCTCGTatctcgtatgccgtcttctgcttgTTGTCGACTC >92_SEp_Full_TAG_TCT_CAT (SEQ ID NO: 99)
TTTTATGGAGAGTTTGATCCTGGCTCAGGATGAACGCTGGCGGCGTGCCTAATACATGCAAGTCGAGCGA
ACAGACGAGGAGCTTGCTCCTCTGACGTTAGCGGCGGACGGGTGAGTAACACGTGGATAACCTACCTATA
AGACTGGGATAACTTCGGGAAACCGGAGCTAATACCGGATAATATATTGAACCGCATGGTTCAATAGTGA
AAGACGGTTTTGCTGTCACTTATAGATGGATCCGCGCCGCATTAGCTAGTTGGTAAGGTAACGGCTTACC
AAGGCAACGATGCGTAGCCGACCTGAGAGGGTGATCGGCCACACTGGAACTGAGACACGGTCCAGACTCC
TACGGGAGGCAGCAGTAGGGAATCTTCCGCAATTAGGGGCGAAAGCCTGACGGAGCAACGCCGCGTGAGT
GATGAAGGTCTTCGGATCGTAAAACTCTGTTATTAGGGAAGAACAAATGTGTAAGTAACTATGCACGTCT
TGACGGTACCTAATCAGAAAGCCACGGCTAACTACGTGCCAGCAGCCGCGGTAATACGTAGGTGGCAAGC
GTTATCCGGAATTATTGGGCGTAAATCTGCGCGCGTAGGCGGTTTTTTAAGTCTGATGTGAAAGCCCACG
GCTCAACCGTGGAGGGTCATTGGAAACTGGAAAACTTGAGTGCAGAAGAGGAAAGTGGAATTCCATGTGT
AGCGGTGAAATGCGCAGAGATATGGAGGAACACCAGTGGCGAAGGCGACTTTCTGGTCTGTAACTGACGC
TGATGTGCGAAAGCGTGGGGATCAAACAGGATTAGATACCCTGGTAGTCCACGCCGTAAACGATGAGTGC
TAAGTGTTAGGGGGTTTCCGCCCCTTAGTGCTGCAGCTAACGCATTAAGCACTCCGCCTGGCATGGAGTA
CGACCGCAAGGTTGAAACTCAAAGGAATTGACGGGGACCCGCACAAGCGGTGGAGCATGTGGTTTAATTC
GAAGCAACGCGAAGAACCTTACCAAATCTTGACATCCTCTGACCCCTCTAGAGATAGAGTTTTCCCCTTC
GGGGGACAGAGTGACAGGTGGTGCATGGTTGTCGTCAGCTCGTGTCGTGAGATGTTGGGTTAAGTCCCGC
AACGAGCGCAACCCTTAAGCTTAGTTGCCATCATTAAGTTGGGCACTCTAAGTTGACTGCCGGTGACAAA
CCGGAGGAAGGTGGGGATGACGTCAAATCATCATGCCCCTTATGATTTGGGCTACACACGTGCTACAATG
GACAATACAAAGGGCAGCGAAACCGCGAGGTCAAGCAAATCCCATAAAGTTGTTCTCAGTTCGGATTGTA
GTCTGCAACTCGACTATATGAAGCTGGAATCGCTAGTAATCGTAGATCAGCATGCTACGGTGAATACGTT
CCCGGGTCTTGTACACACCGCCCGTCACACCACGAGAGTTTGTAACACCCGAAGCCGGTGGAGTAACCAT
TTGGAGCTAGCCGTCGAAGGTGGAACAAATGATTGGGGTGAAGTCGTAACAAGGTAGCCGTATCGGAAGG -continued

| Sequence Listing Free Text |
| --- |

TGCGGCTGGATCACCTCCTTTCTTAGGGATAACAGGGTAATGAGTCGACAAaatgatacggcgaccaccg
agatctacactctttccctacacgacgctcttccgatctCGATAATTTCGGATCGGGATagatcggaaga
gcacacgtctgaactccagtcacAATCAGTCTCGTatctcgtatgccgtcttctgcttgTTGTCGACTC >93_SAg_Full_TAG_TCT_CAT (SEQ ID NO: 100)
TTTAATGAGAGTTTGATCCTGGCTCAGGACGAACGCTGGCGGCGTGCCTAATACATGCAAGTAGAACGCT
GAGGTTTGGTGTTTACACTAGACTGATGAGTTGCGAACGGGTGAGTAACGCGTAGGTAACCTGCCTCATA
GCGGGGGATAACTATTGGAAACGATAGCTAATACCGCATAAGAGTAATTAACACATGTTAGTTATTTAAA
AGGAGCAATTGCTTCACTGTGAGATGGACCTGCGTTGTATTAGCTAGTTGGTGAGGTAAAGGCTCACCAA
GGCGACGATACATAGCCGACCTGAGAGGGTGATCGGCCACACTGGGACTGAGACACGGCCCAGACTCCTA
CGGGAGGCAGCAGTAGGGAATCTTCGGCAATTAGGGACGGAAGTCTGACCGAGCAACGCCGCGTGAGTGA
AGAAGGTTTTCGGATCGTAAAGCTCTGTTGTTAGAGAAGAACGTTGGTAGGAGTGGAAAATCTACCAAGT
GACGGTAACTAACCAGAAAGGGACGGCTAACTACGTGCCAGCAGCCGCGGTAATACGTAGGTCCCGAGCG
TTGTCCGGATTTATTGGGCGTAAATCTGCGAGCGCAGGCGGTTCTTTAAGTCTGAAGTTAAAGGCAGTGG
CTTAACCATTGTACGCTTTGGAAACTGGAGGACTTGAGTGCAGAAGGGGAGAGTGGAATTCCATGTGTAG
CGGTGAAATGCGTAGATATATGGAGGAACACCGGTGGCGAAAGCGGCTCTCTGGTCTGTAACTGACGCTG
AGGCTCGAAAGCGTGGGGAGCAAACAGGATTAGATACCCTGGTAGTCCACGCCGTAAACGATGAGTGCTA
GGTGTTAGGCCCTTTCCGGGGCTTAGTGCCGCAGCTAACGCATTAAGCACTCCGCCTGGCATGGAGTACG
ACCGCAAGGTTGAAACTCAAAGGAATTGACGGGGGCCCGCACAAGCGGTGGAGCATGTGGTTTAATTCGA
AGCAACGCGAAGAACCTTACCAGGTCTTGACATCCTTCTGACCGGCCTAGAGATAGGCTTTCTCTTCGGA
GCAGAAGTGACAGGTGGTGCATGGTTGTCGTCAGCTCGTGTCGTGAGATGTTGGGTTAAGTCCCGCAACG
AGCGCAACCCCTATTGTTAGTTGCCATCATTAAGTTGGGCACTCTAGCGAGACTGCCGGTAATAAACCGG
AGGAAGGTGGGGATGACGTCAAATCATCATGCCCCTTATGACCTGGGCTACACACGTGCTACAATGGTTG
GTACAACGAGTCGCAAGCCGGTGACGGCAAGCTAATCTCTTAAAGCCAATCTCAGTTCGGATTGTAGGCT
GCAACTCGCCTACATGAAGTCGGAATCGCTAGTAATCGCGGATCAGCACGCCGCGGTGAATACGTTCCCG
GGCCTTGTACACACCGCCCGTCACACCACGAGAGTTTGTAACACCCGAAGTCGGTGAGGTAACCTTTTAG
GAGCCAGCCGCCTAAGGTGGGATAGATGATTGGGGTGAAGTCGTAACAAGGTAGCCGTATCGGAAGGTGC
GGCTGGATCACCTCCTTTCTTAGGGATAACAGGGTAATGAGTCGACAAaatgatacggcgaccaccgaga
tctacactctttccctacacgacgctcttccgatctTCATGTCGCCGTTTGGCAAAagatcggaagagca
cacgtctgaactccagtcacAATCAGTCTCGTatctcgtatgccgtcttctgcttgTTGTCGACTC >94_SMu_Full_TAG_TCT_CAT (SEQ ID NO: 101)
AGAGTTTGATCCTGGCTCAGGACGAACGCTGGCGGCGTGCCTAATACATGCAAGTGGACGCAAGAGGAC
ACACTGTGCTTGCACACCGTGTTTTCTTGAGTCGCGAACGGGTGAGTAACGCGTAGGTAACCTGCCTATT
AGCGGGGGATAACTATTGGAAACGATAGCTAATACCGCATAATATTAATTATTGCATGATAATTGATTGA
AAGATGCAAGCGCATCACTAGTAGATGGACCTGCGTTGTATTAGCTAGTTGGTAAGGTAAGAGCTTACCA
AGGCGACGATACATAGCCGACCTGAGAGGGTGATCGGCCACACTGGGACTGAGACACGGCCCAGACTCCT
ACGGGAGGCAGCAGTAGGGAATCTTCGGCAATTAGGGACGAAAGTCTGACCGAGCAACGCCGCGTGAGTG
AAGAAGGTTTTCGGATCGTAAAGCTCTGTTGTAAGTCAAGAACGTGTGTGAGAGTGGAAAGTTCACACAG
TGACGGTAGCTTACCAGAAAGGGACGGCTAACTACGTGCCAGCAGCCGCGGTAATACGTAGGTCCCGAGC
GTTGTCCGGATTTATTGGGCGTAAATCTGGGAGCGCAGGCGGTCAGGAAAGTCTGGAGTAAAAGGCTATG
GCTCAACCATAGTGTGCTCTGGAAACTGTCTGACTTGAGTGCAGAAGGGGAGAGTGGAATTCCATGTGTA
GCGGTGAAATGCGTAGATATATGGAGGAACACCAGTGGCGAAAGCGGCTCTCTGGTCTGTCACTGACGCT
GAGGCTCGAAAGCGTGGGTAGCGAACAGGATTAGATACCCTGGTAGTCCACGCCGTAAACGATGAGTGCT
AGGTGTTAGGCCCTTTCCGGGGCTTAGTGCCGGAGCTAACGCAATAAGCACTCCGCCTGGCATGGAGTAC
GACCGCAAGGTTGAAACTCAAAGGAATTGACGGGGGCCCGCACAAGCGGTGGAGCATGTGGTTTAATTCG
AAGCAACGCGAAGAACCTTACCAGGTCTTGACATCCCGATGCTATTCTTAGAGATAGGAAGTTACTTCGG
TACATCGGAGACAGGTGGTGCATGGTTGTCGTCAGCTCGTGTCGTGAGATGTTGGGTTAAGTCCCGCAAC
GAGCGCAACCCTTATTGTTAGTTGCCATCATTAAGTTGGGCACTCTAGCGAGACTGCCGGTAATAAACCG
GAGGAAGGTGGGGATGACGTCAAATCATCATGCCCCTTATGACCTGGGCTACACACGTGCTACAATGGTC
GGTACAACGAGTTGCGAGCCGGTGACGGCAAGCTAATCTCTGAAAGCCGATCTCAGTTCGGATTGGAGGC
TGCAACTCGCCTCCATGAAGTCGGAATCGCTAGTAATCGCGGATCAGCACGCCGCGGTGAATACGTTCCC
GGGCCTTGTACACACCGCCCGTCACACCACGAGAGTTTGTAACACCCGAAGTCGGTGAGGTAACCTTTTA
GGGGCCAGCCGCCTAAGGTGGGATGGATGATTGGGGTGAAGTCGTAACAAGGTAGCCGTATCGGAAGGTG
CGGCTGGATCACCTCCTTTCTTAGGGATAACAGGGTAATGAGTCGACAAaatgatacggcgaccaccgag
atctacactctttccctacacgacgctcttccgatctTTCTAGCACTGTAAGACACCagatcggaagagc
acacgtctgaactccagtcacAATCAGTCTCGTatctcgtatgccgtcttctgcttgTTGTCGACTC >95_SPn_Full_TAG_TCT_CAT (SEQ ID NO: 102)
AAACTTTTTAATGAGAGTTTGATCCTGGCTCAGGACGAACGCTGGCGGCGTGCCTAATACATGCAAGTAG
AACGCTGAAGGAGGAGCTTGCTTCTCTGGATGAGTTGCGAACGGGTGAGTAACGCGTAGGTAACCTGCCT
GGTAGCGGGGGATAACTATTGGAAACGATAGCTAATACCGCATAAGAGTAGATGTTGCATGACATTTGCT
TAAAAGGTGCACTTGCATCACTACCAGATGGACCTGCGTTGTATTAGCTAGTTGGTGGGGTAACGGCTCA
CCAAGGCGACGATACATAGCCGACCTGAGAGGGTGATCGGCCACACTGGGACTGAGACACGGCCCAGACT
CCTACGGGAGGCAGCAGTAGGGAATCTTCGGCAATTAGGGACGGAAGTCTGACCGAGCAACGCCGCGTGA
GTGAAGAAGGTTTTCGGATCGTAAAGCTCTGTTGTAAGAGAAGAACGAGTGTGAGAGTGGAAAGTTCACA
CTGTGACGGTATCTTACCAGAAAGGGACGGCTAACTACGTGCCAGCAGCCGCGGTAATACGTAGGTCCCG
AGCGTTGTCCGGATTTATTGGGCGTAAATCTGCGAGCGCAGGCGGTTAGATAAGTCTGAAGTTAAAGGCT
GTGGCTTAACCATAGTAGGCTTTGGAAACTGTTTAACTTGAGTGCAAGAGGGGAGAGTGGAATTCCATGT
GTAGCGGTGAAATGCGTAGATATATGGAGGAACACCGGTGGCGAAAGCGGCTCTCTGGCTTGTAACTGAC
GCTGAGGCTCGAAAGCGTGGGGAGCAAACAGGATTAGATACCCTGGTAGTCCACGCTGTAAACGATGAGT
GCTAGGTGTTAGACCCTTTCCGGGGTTTAGTGCCGTAGCTAACGCATTAAGCACTCCGCCTGGCATGGAG
TACGACCGCAAGGTTGAAACTCAAAGGAATTGACGGGGGCCCGCACAAGCGGTGGAGCATGTGGTTTAAT
TCGAAGCAACGCGAAGAACCTTACCAGGTCTTGACATCCCTCTGACCGCTCTAGAGATAGAGCTTTCCTT
CGGGACAGAGGTGACAGGTGGTGCATGGTTGTCGTCAGCTCGTGTCGTGAGATGTTGGGTTAAGTCCCGC
AACGAGCGCAACCCCTATTGTTAGTTGCCATCATTTAGTTGGGCACTCTAGCGAGACTGCCGGTAATAAA
CCGGAGGAAGGTGGGGATGACGTCAAATCATCATGCCCCTTATGACCTGGGCTACACACGTGCTACAATG -continued Sequence Listing Free Text GCTGGTACAACGAGTCGCAAGCCGGTGACGGCAAGCTAATCTCTTAAAGCCAGTCTCAGTTCGGATTGTA
GGCTGCAACTCGCCTACATGAAGTCGGAATCGCTAGTAATCGCGGATCAGCACGCCGCGGTGAATACGTT
CCCGGGCCTTGTACACACCGCCCGTCACACCACGAGAGTTTGTAACACCCGAAGTCGGTGAGGTAACCGT
AAGGAGCCAGCCGCCTAAGGTGGGATAGATGATTGGGGTGAAGTCGTAACAAGGTAGCCGTATCGGAAGG
TGCGGCTGGATCACCTCCTTTCTAAGGATTAGGGATAACAGGGTAATGAGTCGACAAaatgatacggcga
ccaccgagatctacactctttccctacacgacgctcttccgatctGACCTACGGATTAGACTATTagatc
ggaagagcacacgtctgaactccagtcacAATCAGTCTCGTatctcgtatgccgtcttctgcttgTTGTC
GACTC >96_AOd_Full_TAG_TCT_CAT (SEQ ID NO: 103)
AGAGTTTGATCCTGGCTCAGGACGAACGCTGGCGGCGTGCTTAACACATGCAAGTCGAACGCTGAAGCCC
AGCTTGCTGGGTGGATGAGTGGCGAACGGGTGAGTAACACGTGAGTAACCTGCCCCCTTCTTTGGGATAA
CGCCCGGAAACGGGTGCTAATACTGGATATTCACTGATCTTCGCATGGGGGTTGGTGGAAAGGTTTTTTC
TGGTGGGGGATGGGCTCGCGGCCTATCAGCTTGTTGGTGGGGTGATGGCCTACCAAGGCTTTGACGGGTA
GCCGGCCTGAGAGGGTGACCGGTCACATTGGGACTGAGATACGGCCCAGACTCCTACGGGAGGCAGCAGT
GGGGAATATTGCACAATTAGGGGCGAAAGCCTGATGCAGCGACGCCGCGTGAGGGATGGAGGCCTTCGGG
TTGTAAACCTCTTTCGCTCATGGTCAAGCCGCAACTCAAGGTTGTGGTGAGGGTAGTGGGTAAAGAAGCG
CCGGCTAACTACGTGCCAGCAGCCGCGGTAATACGTAGGGCGCGAGCGTTGTCCGGAATTATTGGGCGTA
AATCTGGGCTTGTAGGCGGTTGGTCGCGTCTGCCGTGAAATCCTCTGGCTTAACTGGGGGCGTGCGGTGG
GTACGGGCTGACTTGAGTGCGGTAGGGGAGACTGGAACTCCTGGTGTAGCGGTGGAATGCGCAGATATCA
GGAAGAACACCGGTGGCGAAGGCGGGTCTCTGGGCCGTTACTGACGCTGAGGAGCGAAAGCGTGGGGAGC
GAACAGGATTAGATACCCTGGTAGTCCACGCTGTAAACGTTGGGCACTAGGTGTGGGGGCCACCCGTGGT
TTCTGCGCCGTAGCTAACGCTTTAAGTGCCCCGCCTGGCATGGAGTACGGCCGCAAGGCTAAAACTCAAA
GGAATTGACGGGGGCCCGCACAAGCGGCGGAGCATGCGGATTAATTCGATGCAACGCGAAGAACCTTACC
AAGGCTTGACATGCACGGCGGCACTGCAGAGATGTGGTGGCATTTAGTTGGTCGTGTGCAGGTGGTGCAT
GGTTGTCGTCAGCTCGTGTCGTGAGATGTTGGGTTAAGTCCCGCAACGAGCGCAACCCTTGCCCTATGTT
GCCAGCACGTGATGGTGGGGACTCGTGGGGGACTGCCGGGGTTAACTCGGAGGAAGGTGGGGATGACGTC
AAATCATCATGCCCCTTATGTCTTGGGCTTCACGCATGCTACAATGGCTGGTACAGAGGGTTGCGATACT
GTGAGGTGGAGCGAATCCCTTAAAGCCAGTCTCAGTTCGGATTGGGGTCTGCAACTCGACCCCATGAAGG
TGGAGTCGCTAGTAATCGCAGATCAGCAACGCTGCGGTGAATACGTTCTCGGGCCTTGTACACACCGCCC
GTCACGTCACGAAAGTTGGTAACACCCGAAGCCCATGGCCTAACCGCTTTGTGCTAGGGATAACAGGGTA
ATGAGTCGACAAaatgatacggcgaccaccgagatctacactctttccctacacgacgctcttccgatct
TTTAAACTCTATCCATCCCAagatcggaagagcacacgtctgaactccagtcacAATCAGTCTCGTatct
cgtatgccgtcttctgcttgTTGTCGACTC >97_LMo_Full_TAG_TCT_CAT (SEQ ID NO: 104)
GAGAGTTTGATCCTGGCTCAGGACGAACGCTGGCGGCGTGCCTAATACATGCAAGTCGAACGAACGGAGG
AAGAGCTTGCTCTTCCAATGTTAGTGGCGGACGGGTGAGTAACACGTGGGCAACCTGCCTGTAAGTTGGG
GATAACTCCGGGAAACCGGGGCTAATACCGAATGATAAGATGTGGCGCATGCCACGCCTTTGAAAGATGG
TTTCGGCTATCGCTTACAGATGGGCCCGCGGTGCATTAGCTAGTTGGTAGGGTAATGGCCTACCAAGGCA
ACGATGCATAGCCGACCTGAGAGGGTGATCGGCCACACTGGGACTGAGACACGGCCCAGACTCCTACGGG
AGGCAGCAGTAGGGAATCTTCCGCAATTAGGGACGAAAGTCTGACGGAGCAACGCCGCGTGTATGAAGAA
GGTTTTCGGATCGTAAAGTACTGTTGTTAGAGAAGAACAAGGATAAGAGTAACTGCTTGTCCCTTGACGG
TATCTAACCAGAAAGCCACGGCTAACTACGTGCCAGCAGCCGCGGTAATACGTAGGTGGCAAGCGTTGTC
CGGATTTATTGGGCGTAAATCTGCGCGCGCAGGCGGTCTTTTAAGTCTGATGTGAAAGCCCCCGGCTTAA
CCGGGGAGGGTCATTGGAAACTGGAAGACTGGAGTGCAGAAGAGGAGAGTGGAATTCCACGTGTAGCGGT
GAAATGCGTAGATATGTGGAGGAACACCAGTGGCGAAGGCGACTCTCTGGTCTGTAACTGACGCTGAGGC
GCGAAAGCGTGGGGAGCAAACAGGATTAGATACCCTGGTAGTCCACGCCGTAAACGATGAGTGCTAAGTG
TTAGGGGGTTTCCGCCCCTTAGTGCTGCAGCTAACGCATTAAGCACTCCGCCTGGCATGGAGTACGACCG
CAAGGTTGAAACTCAAAGGAATTGACGGGGGCCCGCACAAGCGGTGGAGCATGTGGTTTAATTCGAAGCA
ACGCGAAGAACCTTACCAGGTCTTGACATCCTTTGACCACTCTGGAGACAGAGCTTTCCCTTCGGGGACA
AAGTGACAGGTGGTGCATGGTTGTCGTCAGCTCGTGTCGTGAGATGTTGGGTTAAGTCCCGCAACGAGCG
CAACCCTTGATTTTAGTTGCCAGCATTTAGTTGGGCACTCTAAAGTGACTGCCGGTGCAAGCCGGAGGAA
GGTGGGGATGACGTCAAATCATCATGCCCCTTATGACCTGGGCTACACACGTGCTACAATGGATAGTACA
AAGGGTCGCGAAGCCGCGAGGTGGAGCTAATCCCATAAAACTATTCTCAGTTCGGATTGTAGGCTGCAAC
TCGCCTACATGAAGCCGGAATCGCTAGTAATCGTGGATCAGCATGCCACGGTGAATACGTTCCCGGGCCT
TGTACACACCGCCCGTCACACCACGAGAGTTTGTAACACCCGAAGTCGGTAGGGTAACCTTTATGGAGCC
AGCCGCCGAAGGTGGGACAGATAATTGGGGTGAAGTCGTAACAAGGTAGCCGTATCGGAAGGTGCGGCTG
GATCACCTCCTTTCTTAGGGATAACAGGGTAATGAGTCGACAAaatgatacggcgaccaccgagatctac
actctttccctacacgacgctcttccgatctCTAACTTATGTGTCGTCGGTagatcggaagagcacacgt
ctgaactccagtcacAATCAGTCTCGTatctcgtatgccgtcttctgcttgTTGTCGACTC 16S rRNA Gene V4 Primer editing standard sequences Illumina adapters in lower case
>98_Eco_V4_WT (SEQ ID NO: 105)
AAGAAGCACCGGCTAACTCCGTGCCAGCAGCCGCGGTAATACGGAGGGTGCAAGCGTTAATCGGAATTAC
TGGGCGTAAAGCGCACGCAGGCGGTTTGTTAAGTCAGATGTGAAATCCCCGGGCTCAACCTGGGAACTGC
ATCTGATACTGGCAAGCTTGAGTCTCGTAGAGGGGGGTAGAATTCCAGGTGTAGCGGTGAAATGCGTAGA
GATCTGGAGGAATACCGGTGGCGAAGGCGGCCCCCTGGACGAAGACTGACGCTCAGGTGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctAT
GACATCAGAATTGAGTGCagatcggaagagcacacgtctgaactccagtcacAATCAGTCTCGTatctcg
tatgccgtcttctgcttgTTGTCGACTC -continued

| Sequence Listing Free Text |
| --- |

>99_Eco_V4_10_A (SEQ ID NO: 106)
AAGAAGCACCGGCTAACTCCGTGCCAGCAACCGCGGTAATACGGAGGGTGCAAGCGTTAATCGGAATTAC
TGGGCGTAAAGCGCACGCAGGCGGTTTGTTAAGTCAGATGTGAAATCCCCGGGCTCAACCTGGGAACTGC
ATCTGATACTGGCAAGCTTGAGTCTCGTAGAGGGGGGTAGAATTCCAGGTGTAGCGGTGAAATGCGTAGA
GATCTGGAGGAATACCGGTGGCGAAGGCGGCCCCCTGGACGAAGACTGACGCTCAGGTGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctCG
ACACTGCCAGTGTCACTCagatcggaagagcacacgtctgaactccagtcacAATCAGTCTCGTatctcg
tatgccgtcttctgcttgTTGTCGACTC >100_Eco_V4_10_T (SEQ ID NO: 107)
AAGAAGCACCGGCTAACTCCGTGCCAGCATCCGCGGTAATACGGAGGGTGCAAGCGTTAATCGGAATTAC
TGGGCGTAAAGCGCACGCAGGCGGTTTGTTAAGTCAGATGTGAAATCCCCGGGCTCAACCTGGGAACTGC
ATCTGATACTGGCAAGCTTGAGTCTCGTAGAGGGGGGTAGAATTCCAGGTGTAGCGGTGAAATGCGTAGA
GATCTGGAGGAATACCGGTGGCGAAGGCGGCCCCCTGGACGAAGACTGACGCTCAGGTGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctGA
AGTGGACTTGCTTATACGagatcggaagagcacacgtctgaactccagtcacAATCAGTCTCGTatctcg
tatgccgtcttctgcttgTTGTCGACTC >101_Eco_V4_10_C (SEQ ID NO: 108)
AAGAAGCACCGGCTAACTCCGTGCCAGCACCCGCGGTAATACGGAGGGTGCAAGCGTTAATCGGAATTAC
TGGGCGTAAAGCGCACGCAGGCGGTTTGTTAAGTCAGATGTGAAATCCCCGGGCTCAACCTGGGAACTGC
ATCTGATACTGGCAAGCTTGAGTCTCGTAGAGGGGGGTAGAATTCCAGGTGTAGCGGTGAAATGCGTAGA
GATCTGGAGGAATACCGGTGGCGAAGGCGGCCCCCTGGACGAAGACTGACGCTCAGGTGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctGG
AGGCGTTGATTGGCGGCTagatcggaagagcacacgtctgaactccagtcacAATCAGTCTCGTatctcg
tatgccgtcttctgcttgTTGTCGACTC >102_Eco_V4_11_A (SEQ ID NO: 109)
AAGAAGCACCGGCTAACTCCGTGCCAGCAGACGCGGTAATACGGAGGGTGCAAGCGTTAATCGGAATTAC
TGGGCGTAAAGCGCACGCAGGCGGTTTGTTAAGTCAGATGTGAAATCCCCGGGCTCAACCTGGGAACTGC
ATCTGATACTGGCAAGCTTGAGTCTCGTAGAGGGGGGTAGAATTCCAGGTGTAGCGGTGAAATGCGTAGA
GATCTGGAGGAATACCGGTGGCGAAGGCGGCCCCCTGGACGAAGACTGACGCTCAGGTGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctGA
CGACCAATAATGAACTTGagatcggaagagcacacgtctgaactccagtcacAATCAGTCTCGTatctcg
tatgccgtcttctgcttgTTGTCGACTC >103_Eco_V4_11_T (SEQ ID NO: 110)
AAGAAGCACCGGCTAACTCCGTGCCAGCAGTCGCGGTAATACGGAGGGTGCAAGCGTTAATCGGAATTAC
TGGGCGTAAAGCGCACGCAGGCGGTTTGTTAAGTCAGATGTGAAATCCCCGGGCTCAACCTGGGAACTGC
ATCTGATACTGGCAAGCTTGAGTCTCGTAGAGGGGGGTAGAATTCCAGGTGTAGCGGTGAAATGCGTAGA
GATCTGGAGGAATACCGGTGGCGAAGGCGGCCCCCTGGACGAAGACTGACGCTCAGGTGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctCC
CGGAAACAAATCCGGGCTagatcggaagagcacacgtctgaactccagtcacAATCAGTCTCGTatctcg
tatgccgtcttctgcttgTTGTCGACTC >104_Eco_V4_11_G (SEQ ID NO: 111)
AAGAAGCACCGGCTAACTCCGTGCCAGCAGGCGCGGTAATACGGAGGGTGCAAGCGTTAATCGGAATTAC
TGGGCGTAAAGCGCACGCAGGCGGTTTGTTAAGTCAGATGTGAAATCCCCGGGCTCAACCTGGGAACTGC
ATCTGATACTGGCAAGCTTGAGTCTCGTAGAGGGGGGTAGAATTCCAGGTGTAGCGGTGAAATGCGTAGA
GATCTGGAGGAATACCGGTGGCGAAGGCGGCCCCCTGGACGAAGACTGACGCTCAGGTGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctAC
TTAAAGACCATTTGATGAagatcggaagagcacacgtctgaactccagtcacAATCAGTCTCGTatctcg
tatgccgtcttctgcttgTTGTCGACTC >105_Eco_V4_12_A (SEQ ID NO: 112)
AAGAAGCACCGGCTAACTCCGTGCCAGCAGCAGCGGTAATACGGAGGGTGCAAGCGTTAATCGGAATTAC
TGGGCGTAAAGCGCACGCAGGCGGTTTGTTAAGTCAGATGTGAAATCCCCGGGCTCAACCTGGGAACTGC
ATCTGATACTGGCAAGCTTGAGTCTCGTAGAGGGGGGTAGAATTCCAGGTGTAGCGGTGAAATGCGTAGA
GATCTGGAGGAATACCGGTGGCGAAGGCGGCCCCCTGGACGAAGACTGACGCTCAGGTGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctCG
GTGCCAGACTTAAGTTTGagatcggaagagcacacgtctgaactccagtcacAATCAGTCTCGTatctcg
tatgccgtcttctgcttgTTGTCGACTC >106_Eco_V4_12_T (SEQ ID NO: 113)
AAGAAGCACCGGCTAACTCCGTGCCAGCAGCTGCGGTAATACGGAGGGTGCAAGCGTTAATCGGAATTAC
TGGGCGTAAAGCGCACGCAGGCGGTTTGTTAAGTCAGATGTGAAATCCCCGGGCTCAACCTGGGAACTGC
ATCTGATACTGGCAAGCTTGAGTCTCGTAGAGGGGGGTAGAATTCCAGGTGTAGCGGTGAAATGCGTAGA
GATCTGGAGGAATACCGGTGGCGAAGGCGGCCCCCTGGACGAAGACTGACGCTCAGGTGCGAAAGCGTGG
GGAGCAAACAGGATTAGATACCCTGGTAGTCCACGCCGTAAACGATGTCGACTAGGGATAACAGGGTAAT

```
GAGTCGACAAaatgatacggcgaccaccgagatctacactctttccctacacgacgctcttccgatctAG
CTCTCTGCTTAGATGACGagatcggaagagcacacgtctgaactccagtcacAATCAGTCTCGTatctcg
tatgccgtcttctgcttgTTGTCGACTC

>107_Eco_V4_12_G (SEQ ID NO: 114)
AAGAAGCACCGGCTAACTCCGTGCCAGCAGCGGCGGTAATACGGAGGGTGCAAGCGTTAATCGGAATTAC
TGGGCGTAAAGCGCACGCAGGCGGTTTGTTAAGTCAGATGTGAAATCCCCGGGCTCAACCTGGGAACTGC
ATCTGATACTGGCAAGCTTGAGTCTCGTAGAGGGGGGTAGAATTCCAGGTGTAGCGGTGAAATGCGTAGA
GATCTGGAGGAATACCGGTGGCGAAGGCGGCCCCCTGGACGAAGACTGACGCTCAGGTGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctGG
TTATTAGGATATGCCGTTagatcggaagagcacacgtctgaactccagtcacAATCAGTCTCGTatctcg
tatgccgtcttctgcttgTTGTCGACTC

>108_Eco_V4_13_A (SEQ ID NO: 115)
AAGAAGCACCGGCTAACTCCGTGCCAGCAGCCACGGTAATACGGAGGGTGCAAGCGTTAATCGGAATTAC
TGGGCGTAAAGCGCACGCAGGCGGTTTGTTAAGTCAGATGTGAAATCCCCGGGCTCAACCTGGGAACTGC
ATCTGATACTGGCAAGCTTGAGTCTCGTAGAGGGGGGTAGAATTCCAGGTGTAGCGGTGAAATGCGTAGA
GATCTGGAGGAATACCGGTGGCGAAGGCGGCCCCCTGGACGAAGACTGACGCTCAGGTGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctAC
CAAATGCCGAGGTTTGACagatcggaagagcacacgtctgaactccagtcacAATCAGTCTCGTatctcg
tatgccgtcttctgcttgTTGTCGACTC

>109_Eco_V4_13_T (SEQ ID NO: 116)
AAGAAGCACCGGCTAACTCCGTGCCAGCAGCCTCGGTAATACGGAGGGTGCAAGCGTTAATCGGAATTAC
TGGGCGTAAAGCGCACGCAGGCGGTTTGTTAAGTCAGATGTGAAATCCCCGGGCTCAACCTGGGAACTGC
ATCTGATACTGGCAAGCTTGAGTCTCGTAGAGGGGGGTAGAATTCCAGGTGTAGCGGTGAAATGCGTAGA
GATCTGGAGGAATACCGGTGGCGAAGGCGGCCCCCTGGACGAAGACTGACGCTCAGGTGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctCG
ATATATAAAGGTAACCAAagatcggaagagcacacgtctgaactccagtcacAATCAGTCTCGTatctcg
tatgccgtcttctgcttgTTGTCGACTC

>110_Eco_V4_13_C (SEQ ID NO: 117)
AAGAAGCACCGGCTAACTCCGTGCCAGCAGCCCCGGTAATACGGAGGGTGCAAGCGTTAATCGGAATTAC
TGGGCGTAAAGCGCACGCAGGCGGTTTGTTAAGTCAGATGTGAAATCCCCGGGCTCAACCTGGGAACTGC
ATCTGATACTGGCAAGCTTGAGTCTCGTAGAGGGGGGTAGAATTCCAGGTGTAGCGGTGAAATGCGTAGA
GATCTGGAGGAATACCGGTGGCGAAGGCGGCCCCCTGGACGAAGACTGACGCTCAGGTGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctGC
TGTGGTCAGCTTATCATAagatcggaagagcacacgtctgaactccagtcacAATCAGTCTCGTatctcg
tatgccgtcttctgcttgTTGTCGACTC

>111_Eco_V4_14_A (SEQ ID NO: 118)
AAGAAGCACCGGCTAACTCCGTGCCAGCAGCCGAGGTAATACGGAGGGTGCAAGCGTTAATCGGAATTAC
TGGGCGTAAAGCGCACGCAGGCGGTTTGTTAAGTCAGATGTGAAATCCCCGGGCTCAACCTGGGAACTGC
ATCTGATACTGGCAAGCTTGAGTCTCGTAGAGGGGGGTAGAATTCCAGGTGTAGCGGTGAAATGCGTAGA
GATCTGGAGGAATACCGGTGGCGAAGGCGGCCCCCTGGACGAAGACTGACGCTCAGGTGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctCA
GTGGTTACTCCAGCCCGAagatcggaagagcacacgtctgaactccagtcacAATCAGTCTCGTatctcg
tatgccgtcttctgcttgTTGTCGACTC

>112_Eco_V4_14_T (SEQ ID NO: 119)
AAGAAGCACCGGCTAACTCCGTGCCAGCAGCCGTGGTAATACGGAGGGTGCAAGCGTTAATCGGAATTAC
TGGGCGTAAAGCGCACGCAGGCGGTTTGTTAAGTCAGATGTGAAATCCCCGGGCTCAACCTGGGAACTGC
ATCTGATACTGGCAAGCTTGAGTCTCGTAGAGGGGGGTAGAATTCCAGGTGTAGCGGTGAAATGCGTAGA
GATCTGGAGGAATACCGGTGGCGAAGGCGGCCCCCTGGACGAAGACTGACGCTCAGGTGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctAG
TAATTGCACTAGAGGCGGagatcggaagagcacacgtctgaactccagtcacAATCAGTCTCGTatctcg
tatgccgtcttctgcttgTTGTCGACTC

>113_Eco_V4_14_G (SEQ ID NO: 120)
AAGAAGCACCGGCTAACTCCGTGCCAGCAGCCGGGGTAATACGGAGGGTGCAAGCGTTAATCGGAATTAC
TGGGCGTAAAGCGCACGCAGGCGGTTTGTTAAGTCAGATGTGAAATCCCCGGGCTCAACCTGGGAACTGC
ATCTGATACTGGCAAGCTTGAGTCTCGTAGAGGGGGGTAGAATTCCAGGTGTAGCGGTGAAATGCGTAGA
GATCTGGAGGAATACCGGTGGCGAAGGCGGCCCCCTGGACGAAGACTGACGCTCAGGTGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctTG
CGCGGGTAAGCCCATAGAagatcggaagagcacacgtctgaactccagtcacAATCAGTCTCGTatctcg
tatgccgtcttctgcttgTTGTCGACTC

>114_Eco_V4_15_A (SEQ ID NO: 121)
AAGAAGCACCGGCTAACTCCGTGCCAGCAGCCGCAGTAATACGGAGGGTGCAAGCGTTAATCGGAATTAC
TGGGCGTAAAGCGCACGCAGGCGGTTTGTTAAGTCAGATGTGAAATCCCCGGGCTCAACCTGGGAACTGC
```

-continued

Sequence Listing Free Text

ATCTGATACTGGCAAGCTTGAGTCTCGTAGAGGGGGGTAGAATTCCAGGTGTAGCGGTGAAATGCGTAGA
GATCTGGAGGAATACCGGTGGCGAAGGCGGCCCCCTGGACGAAGACTGACGCTCAGGTGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctTC
ACACGGAGCGTGTTATACagatcggaagagcacacgtctgaactccagtcacAATCAGTCTCGTatctcg
tatgccgtcttctgcttgTTGTCGACTC >115_Eco_V4_15_T (SEQ ID NO: 122)
AAGAAGCACCGGCTAACTCCGTGCCAGCAGCCGCTGTAATACGGAGGGTGCAAGCGTTAATCGGAATTAC
TGGGCGTAAAGCGCACGCAGGCGGTTTGTTAAGTCAGATGTGAAATCCCCGGGCTCAACCTGGGAACTGC
ATCTGATACTGGCAAGCTTGAGTCTCGTAGAGGGGGGTAGAATTCCAGGTGTAGCGGTGAAATGCGTAGA
GATCTGGAGGAATACCGGTGGCGAAGGCGGCCCCCTGGACGAAGACTGACGCTCAGGTGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctTG
ATGATGATCACACTACCTagatcggaagagcacacgtctgaactccagtcacAATCAGTCTCGTatctcg
tatgccgtcttctgcttgTTGTCGACTC >116_Eco_V4_15_C (SEQ ID NO: 123)
AAGAAGCACCGGCTAACTCCGTGCCAGCAGCCGCCGTAATACGGAGGGTGCAAGCGTTAATCGGAATTAC
TGGGCGTAAAGCGCACGCAGGCGGTTTGTTAAGTCAGATGTGAAATCCCCGGGCTCAACCTGGGAACTGC
ATCTGATACTGGCAAGCTTGAGTCTCGTAGAGGGGGGTAGAATTCCAGGTGTAGCGGTGAAATGCGTAGA
GATCTGGAGGAATACCGGTGGCGAAGGCGGCCCCCTGGACGAAGACTGACGCTCAGGTGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctCG
GTTCCAGGCTAAATGTCCagatcggaagagcacacgtctgaactccagtcacAATCAGTCTCGTatctcg
tatgccgtcttctgcttgTTGTCGACTC >117_Eco_V4_16_A (SEQ ID NO: 124)
AAGAAGCACCGGCTAACTCCGTGCCAGCAGCCGCGATAATACGGAGGGTGCAAGCGTTAATCGGAATTAC
TGGGCGTAAAGCGCACGCAGGCGGTTTGTTAAGTCAGATGTGAAATCCCCGGGCTCAACCTGGGAACTGC
ATCTGATACTGGCAAGCTTGAGTCTCGTAGAGGGGGGTAGAATTCCAGGTGTAGCGGTGAAATGCGTAGA
GATCTGGAGGAATACCGGTGGCGAAGGCGGCCCCCTGGACGAAGACTGACGCTCAGGTGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctGG
AGCAGGAAGGATGGCGAGagatcggaagagcacacgtctgaactccagtcacAATCAGTCTCGTatctcg
tatgccgtcttctgcttgTTGTCGACTC >118_Eco_V4_16_T (SEQ ID NO: 125)
AAGAAGCACCGGCTAACTCCGTGCCAGCAGCCGCGTTAATACGGAGGGTGCAAGCGTTAATCGGAATTAC
TGGGCGTAAAGCGCACGCAGGCGGTTTGTTAAGTCAGATGTGAAATCCCCGGGCTCAACCTGGGAACTGC
ATCTGATACTGGCAAGCTTGAGTCTCGTAGAGGGGGGTAGAATTCCAGGTGTAGCGGTGAAATGCGTAGA
GATCTGGAGGAATACCGGTGGCGAAGGCGGCCCCCTGGACGAAGACTGACGCTCAGGTGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctAC
GTCCCTGAGCTACGTGTGagatcggaagagcacacgtctgaactccagtcacAATCAGTCTCGTatctcg
tatgccgtcttctgcttgTTGTCGACTC >119_Eco_V4_16_C (SEQ ID NO: 126)
AAGAAGCACCGGCTAACTCCGTGCCAGCAGCCGCGCTAATACGGAGGGTGCAAGCGTTAATCGGAATTAC
TGGGCGTAAAGCGCACGCAGGCGGTTTGTTAAGTCAGATGTGAAATCCCCGGGCTCAACCTGGGAACTGC
ATCTGATACTGGCAAGCTTGAGTCTCGTAGAGGGGGGTAGAATTCCAGGTGTAGCGGTGAAATGCGTAGA
GATCTGGAGGAATACCGGTGGCGAAGGCGGCCCCCTGGACGAAGACTGACGCTCAGGTGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctCA
TTCCCTCACGGACCGGTAagatcggaagagcacacgtctgaactccagtcacAATCAGTCTCGTatctcg
tatgccgtcttctgcttgTTGTCGACTC >120_Eco_V4_17_A (SEQ ID NO: 127)
AAGAAGCACCGGCTAACTCCGTGCCAGCAGCCGCGGAAATACGGAGGGTGCAAGCGTTAATCGGAATTAC
TGGGCGTAAAGCGCACGCAGGCGGTTTGTTAAGTCAGATGTGAAATCCCCGGGCTCAACCTGGGAACTGC
ATCTGATACTGGCAAGCTTGAGTCTCGTAGAGGGGGGTAGAATTCCAGGTGTAGCGGTGAAATGCGTAGA
GATCTGGAGGAATACCGGTGGCGAAGGCGGCCCCCTGGACGAAGACTGACGCTCAGGTGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctTA
CTCTCAGACGAGCGGCCCagatcggaagagcacacgtctgaactccagtcacAATCAGTCTCGTatctcg
tatgccgtcttctgcttgTTGTCGACTC >121_Eco_V4_17_G (SEQ ID NO: 128)
AAGAAGCACCGGCTAACTCCGTGCCAGCAGCCGCGGGAATACGGAGGGTGCAAGCGTTAATCGGAATTAC
TGGGCGTAAAGCGCACGCAGGCGGTTTGTTAAGTCAGATGTGAAATCCCCGGGCTCAACCTGGGAACTGC
ATCTGATACTGGCAAGCTTGAGTCTCGTAGAGGGGGGTAGAATTCCAGGTGTAGCGGTGAAATGCGTAGA
GATCTGGAGGAATACCGGTGGCGAAGGCGGCCCCCTGGACGAAGACTGACGCTCAGGTGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctAG
GCAGGTCACATCGCTGACagatcggaagagcacacgtctgaactccagtcacAATCAGTCTCGTatctcg
tatgccgtcttctgcttgTTGTCGACTC -continued

| Sequence Listing Free Text |
| --- |

>122_Eco_V4_17_C (SEQ ID NO: 129)
AAGAAGCACCGGCTAACTCCGTGCCAGCAGCCGCGGCAATACGGAGGGTGCAAGCGTTAATCGGAATTAC
TGGGCGTAAAGCGCACGCAGGCGGTTTGTTAAGTCAGATGTGAAATCCCCGGGCTCAACCTGGGAACTGC
ATCTGATACTGGCAAGCTTGAGTCTCGTAGAGGGGGGTAGAATTCCAGGTGTAGCGGTGAAATGCGTAGA
GATCTGGAGGAATACCGGTGGCGAAGGCGGCCCCCTGGACGAAGACTGACGCTCAGGTGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctGA
AACCTAGCTGTTGCAGGCagatcggaagagcacacgtctgaactccagtcacAATCAGTCTCGTatctcg
tatgccgtcttctgcttgTTGTCGACTC >123_Eco_V4_18_T (SEQ ID NO: 130)
AAGAAGCACCGGCTAACTCCGTGCCAGCAGCCGCGGTTATACGGAGGGTGCAAGCGTTAATCGGAATTAC
TGGGCGTAAAGCGCACGCAGGCGGTTTGTTAAGTCAGATGTGAAATCCCCGGGCTCAACCTGGGAACTGC
ATCTGATACTGGCAAGCTTGAGTCTCGTAGAGGGGGGTAGAATTCCAGGTGTAGCGGTGAAATGCGTAGA
GATCTGGAGGAATACCGGTGGCGAAGGCGGCCCCCTGGACGAAGACTGACGCTCAGGTGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctTT
AGCACTACGGTTCCGAACagatcggaagagcacacgtctgaactccagtcacAATCAGTCTCGTatctcg
tatgccgtcttctgcttgTTGTCGACTC >124_Eco_V4_18_G (SEQ ID NO: 131)
AAGAAGCACCGGCTAACTCCGTGCCAGCAGCCGCGGTGATACGGAGGGTGCAAGCGTTAATCGGAATTAC
TGGGCGTAAAGCGCACGCAGGCGGTTTGTTAAGTCAGATGTGAAATCCCCGGGCTCAACCTGGGAACTGC
ATCTGATACTGGCAAGCTTGAGTCTCGTAGAGGGGGGTAGAATTCCAGGTGTAGCGGTGAAATGCGTAGA
GATCTGGAGGAATACCGGTGGCGAAGGCGGCCCCCTGGACGAAGACTGACGCTCAGGTGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctCT
GCTCTCTGGTTTACAGGTagatcggaagagcacacgtctgaactccagtcacAATCAGTCTCGTatctcg
tatgccgtcttctgcttgTTGTCGACTC >125_Eco_V4_18_C (SEQ ID NO: 132)
AAGAAGCACCGGCTAACTCCGTGCCAGCAGCCGCGGTCATACGGAGGGTGCAAGCGTTAATCGGAATTAC
TGGGCGTAAAGCGCACGCAGGCGGTTTGTTAAGTCAGATGTGAAATCCCCGGGCTCAACCTGGGAACTGC
ATCTGATACTGGCAAGCTTGAGTCTCGTAGAGGGGGGTAGAATTCCAGGTGTAGCGGTGAAATGCGTAGA
GATCTGGAGGAATACCGGTGGCGAAGGCGGCCCCCTGGACGAAGACTGACGCTCAGGTGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctCC
CGTACACTACATCGGGTTagatcggaagagcacacgtctgaactccagtcacAATCAGTCTCGTatctcg
tatgccgtcttctgcttgTTGTCGACTC >126_Eco_V4_19_T (SEQ ID NO: 133)
AAGAAGCACCGGCTAACTCCGTGCCAGCAGCCGCGGTATTACGGAGGGTGCAAGCGTTAATCGGAATTAC
TGGGCGTAAAGCGCACGCAGGCGGTTTGTTAAGTCAGATGTGAAATCCCCGGGCTCAACCTGGGAACTGC
ATCTGATACTGGCAAGCTTGAGTCTCGTAGAGGGGGGTAGAATTCCAGGTGTAGCGGTGAAATGCGTAGA
GATCTGGAGGAATACCGGTGGCGAAGGCGGCCCCCTGGACGAAGACTGACGCTCAGGTGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctTT
CGCTCGACTTCCATTCGCagatcggaagagcacacgtctgaactccagtcacAATCAGTCTCGTatctcg
tatgccgtcttctgcttgTTGTCGACTC >127_Eco_V4_19_G (SEQ ID NO: 134)
AAGAAGCACCGGCTAACTCCGTGCCAGCAGCCGCGGTAGTACGGAGGGTGCAAGCGTTAATCGGAATTAC
TGGGCGTAAAGCGCACGCAGGCGGTTTGTTAAGTCAGATGTGAAATCCCCGGGCTCAACCTGGGAACTGC
ATCTGATACTGGCAAGCTTGAGTCTCGTAGAGGGGGGTAGAATTCCAGGTGTAGCGGTGAAATGCGTAGA
GATCTGGAGGAATACCGGTGGCGAAGGCGGCCCCCTGGACGAAGACTGACGCTCAGGTGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctGT
ATGCCTTGAGGCCCATAGagatcggaagagcacacgtctgaactccagtcacAATCAGTCTCGTatctcg
tatgccgtcttctgcttgTTGTCGACTC >128_Eco_V4_19_C (SEQ ID NO: 135)
AAGAAGCACCGGCTAACTCCGTGCCAGCAGCCGCGGTACTACGGAGGGTGCAAGCGTTAATCGGAATTAC
TGGGCGTAAAGCGCACGCAGGCGGTTTGTTAAGTCAGATGTGAAATCCCCGGGCTCAACCTGGGAACTGC
ATCTGATACTGGCAAGCTTGAGTCTCGTAGAGGGGGGTAGAATTCCAGGTGTAGCGGTGAAATGCGTAGA
GATCTGGAGGAATACCGGTGGCGAAGGCGGCCCCCTGGACGAAGACTGACGCTCAGGTGCGAAAGCGTGG
GGAGCAAACAGGATTAGATACCCTGGTAGTCCACGCCGTAAACGATGTCGACTAGGGATAACAGGGTAAT
GAGTCGACAAaatgatacggcgaccaccgagatctacactctttccctacacgacgctcttccgatctGT
ACTTTCAAGTAGATTGAGagatcggaagagcacacgtctgaactccagtcacAATCAGTCTCGTatctcg
tatgccgtcttctgcttgTTGTCGACTC

| ITS2 Primer editing standard sequences |
| --- |

Illumina adapters in lower case
>129_Sce_ITS2_WT
CGGATCTCTTGGTTCTCGCATCGATGAAGAACGCAGCGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG -continued

| Sequence Listing Free Text |
| --- |

CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA
GAGAGCGTCTAGGCGAACAATGTTCTTAAAGTTTGACCTCAAATCAGGTAGGAGTACCCGCTGAACTTAA
GCATATCAATAAGCGGAGGAAAAGAAACCAACCGGGATTGTAGGGATAACAGGGTAATGAGTCGACAAaa
tgatacggcgaccaccgagatctacactctttccctacacgacgctcttccgatctTATATCATCACTAT
GGTAACagatcggaagagcacacgtctgaactccagtcacAATCAGTCTCGTatctcgtatgccgtcttc
tgcttgTTGTCGACTC >130_Sce_ITS2_09_A
CGGATCTCTTGGTTCTCGCATCGATGAAAAACGCAGCGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA
GAGAGCGTCTAGGCGAACAATGTTCTTAAAGTTTGACCTCAAATCAGGTAGGAGTACCCGCTGAACTTAA
GCATATCAATAAGCGGAGGAAAAGAAACCAACCGGGATTGTAGGGATAACAGGGTAATGAGTCGACAAaa
tgatacggcgaccaccgagatctacactctttccctacacgacgctcttccgatctGGTTCATAATCGGA
TACGAGagatcggaagagcacacgtctgaactccagtcacAATCAGTCTCGTatctcgtatgccgtcttc
tgcttgTTGTCGACTC >131_Sce_ITS2_09_T
CGGATCTCTTGGTTCTCGCATCGATGAATAACGCAGCGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA
GAGAGCGTCTAGGCGAACAATGTTCTTAAAGTTTGACCTCAAATCAGGTAGGAGTACCCGCTGAACTTAA
GCATATCAATAAGCGGAGGAAAAGAAACCAACCGGGATTGTAGGGATAACAGGGTAATGAGTCGACAAaa
tgatacggcgaccaccgagatctacactctttccctacacgacgctcttccgatctACTCATGGTAAACC
AGGCTGagatcggaagagcacacgtctgaactccagtcacAATCAGTCTCGTatctcgtatgccgtcttc
tgcttgTTGTCGACTC >132_Sce_ITS2_09_C
CGGATCTCTTGGTTCTCGCATCGATGAACAACGCAGCGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA
GAGAGCGTCTAGGCGAACAATGTTCTTAAAGTTTGACCTCAAATCAGGTAGGAGTACCCGCTGAACTTAA
GCATATCAATAAGCGGAGGAAAAGAAACCAACCGGGATTGTAGGGATAACAGGGTAATGAGTCGACAAaa
tgatacggcgaccaccgagatctacactctttccctacacgacgctcttccgatctCTGAAACCTTTCAC
TGGCCCagatcggaagagcacacgtctgaactccagtcacAATCAGTCTCGTatctcgtatgccgtcttc
tgcttgTTGTCGACTC >133_Sce_ITS2_10_T
CGGATCTCTTGGTTCTCGCATCGATGAAGTACGCAGCGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA
GAGAGCGTCTAGGCGAACAATGTTCTTAAAGTTTGACCTCAAATCAGGTAGGAGTACCCGCTGAACTTAA
GCATATCAATAAGCGGAGGAAAAGAAACCAACCGGGATTGTAGGGATAACAGGGTAATGAGTCGACAAaa
tgatacggcgaccaccgagatctacactctttccctacacgacgctcttccgatctTTCCGAGCCCTGCA
CTCTTGagatcggaagagcacacgtctgaactccagtcacAATCAGTCTCGTatctcgtatgccgtcttc
tgcttgTTGTCGACTC >134_Sce_ITS2_10_G
CGGATCTCTTGGTTCTCGCATCGATGAAGGACGCAGCGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA
GAGAGCGTCTAGGCGAACAATGTTCTTAAAGTTTGACCTCAAATCAGGTAGGAGTACCCGCTGAACTTAA
GCATATCAATAAGCGGAGGAAAAGAAACCAACCGGGATTGTAGGGATAACAGGGTAATGAGTCGACAAaa
tgatacggcgaccaccgagatctacactctttccctacacgacgctcttccgatctTTCATTCCTGGTGA
GAAGATagatcggaagagcacacgtctgaactccagtcacAATCAGTCTCGTatctcgtatgccgtcttc
tgcttgTTGTCGACTC >135_Sce_ITS2_10_C
CGGATCTCTTGGTTCTCGCATCGATGAAGCACGCAGCGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA
GAGAGCGTCTAGGCGAACAATGTTCTTAAAGTTTGACCTCAAATCAGGTAGGAGTACCCGCTGAACTTAA

```
GCATATCAATAAGCGGAGGAAAAGAAACCAACCGGGATTGTAGGGATAACAGGGTAATGAGTCGACAAaa
tgatacggcgaccaccgagatctacactctttccctacacgacgctcttccgatctGGTACTGATTCGAA
ACCAGTagatcggaagagcacacgtctgaactccagtcacAATCAGTCTCGTatctcgtatgccgtcttc
tgcttgTTGTCGACTC

>136_Sce_ITS2_11_T
CGGATCTCTTGGTTCTCGCATCGATGAAGATCGCAGCGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA
GAGAGCGTCTAGGCGAACAATGTTCTTAAAGTTTGACCTCAAATCAGGTAGGAGTACCCGCTGAACTTAA
GCATATCAATAAGCGGAGGAAAAGAAACCAACCGGGATTGTAGGGATAACAGGGTAATGAGTCGACAAaa
tgatacggcgaccaccgagatctacactctttccctacacgacgctcttccgatctAAGCATAGCCGGCC
CGAAGAagatcggaagagcacacgtctgaactccagtcacAATCAGTCTCGTatctcgtatgccgtcttc
tgcttgTTGTCGACTC

>137_Sce_ITS2_11_G
CGGATCTCTTGGTTCTCGCATCGATGAAGAGCGCAGCGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA
GAGAGCGTCTAGGCGAACAATGTTCTTAAAGTTTGACCTCAAATCAGGTAGGAGTACCCGCTGAACTTAA
GCATATCAATAAGCGGAGGAAAAGAAACCAACCGGGATTGTAGGGATAACAGGGTAATGAGTCGACAAaa
tgatacggcgaccaccgagatctacactctttccctacacgacgctcttccgatctGTGCATTAGTGGCT
TCGACAagatcggaagagcacacgtctgaactccagtcacAATCAGTCTCGTatctcgtatgccgtcttc
tgcttgTTGTCGACTC

>138_Sce_ITS2_11_C
CGGATCTCTTGGTTCTCGCATCGATGAAGACCGCAGCGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA
GAGAGCGTCTAGGCGAACAATGTTCTTAAAGTTTGACCTCAAATCAGGTAGGAGTACCCGCTGAACTTAA
GCATATCAATAAGCGGAGGAAAAGAAACCAACCGGGATTGTAGGGATAACAGGGTAATGAGTCGACAAaa
tgatacggcgaccaccgagatctacactctttccctacacgacgctcttccgatctATACAGTCCTGCTC
CCGTGCagatcggaagagcacacgtctgaactccagtcacAATCAGTCTCGTatctcgtatgccgtcttc
tgcttgTTGTCGACTC

>139_Sce_ITS2_12_A
CGGATCTCTTGGTTCTCGCATCGATGAAGAAAGCAGCGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA
GAGAGCGTCTAGGCGAACAATGTTCTTAAAGTTTGACCTCAAATCAGGTAGGAGTACCCGCTGAACTTAA
GCATATCAATAAGCGGAGGAAAAGAAACCAACCGGGATTGTAGGGATAACAGGGTAATGAGTCGACAAaa
tgatacggcgaccaccgagatctacactctttccctacacgacgctcttccgatctTCCCAAGTGGGATC
AGTTTAagatcggaagagcacacgtctgaactccagtcacAATCAGTCTCGTatctcgtatgccgtcttc
tgcttgTTGTCGACTC

>140_Sce_ITS2_12_T
CGGATCTCTTGGTTCTCGCATCGATGAAGAATGCAGCGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA
GAGAGCGTCTAGGCGAACAATGTTCTTAAAGTTTGACCTCAAATCAGGTAGGAGTACCCGCTGAACTTAA
GCATATCAATAAGCGGAGGAAAAGAAACCAACCGGGATTGTAGGGATAACAGGGTAATGAGTCGACAAaa
tgatacggcgaccaccgagatctacactctttccctacacgacgctcttccgatctTCAACACCCAGTGG
ACGCATagatcggaagagcacacgtctgaactccagtcacAATCAGTCTCGTatctcgtatgccgtcttc
tgcttgTTGTCGACTC

>141_Sce_ITS2_12_G
CGGATCTCTTGGTTCTCGCATCGATGAAGAAGGCAGCGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA
GAGAGCGTCTAGGCGAACAATGTTCTTAAAGTTTGACCTCAAATCAGGTAGGAGTACCCGCTGAACTTAA
GCATATCAATAAGCGGAGGAAAAGAAACCAACCGGGATTGTAGGGATAACAGGGTAATGAGTCGACAAaa
tgatacggcgaccaccgagatctacactctttccctacacgacgctcttccgatctACTAGGAAGTCCGG
ACCTATagatcggaagagcacacgtctgaactccagtcacAATCAGTCTCGTatctcgtatgccgtcttc
tgcttgTTGTCGACTC
```

-continued

| Sequence Listing Free Text |
|---|

>142_Sce_ITS2_13_A
CGGATCTCTTGGTTCTCGCATCGATGAAGAACACAGCGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA
GAGAGCGTCTAGGCGAACAATGTTCTTAAAGTTTGACCTCAAATCAGGTAGGAGTACCCGCTGAACTTAA
GCATATCAATAAGCGGAGGAAAAGAAACCAACCGGGATTGTAGGGATAACAGGGTAATGAGTCGACAAaa
tgatacggcgaccaccgagatctacactctttccctacacgacgctcttccgatctTCCTGGGAGGGAGG
TCTCGTagatcggaagagcacacgtctgaactccagtcacAATCAGTCTCGTatctcgtatgccgtcttc
tgcttgTTGTCGACTC >143_Sce_ITS2_13_T
CGGATCTCTTGGTTCTCGCATCGATGAAGAACTCAGCGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA
GAGAGCGTCTAGGCGAACAATGTTCTTAAAGTTTGACCTCAAATCAGGTAGGAGTACCCGCTGAACTTAA
GCATATCAATAAGCGGAGGAAAAGAAACCAACCGGGATTGTAGGGATAACAGGGTAATGAGTCGACAAaa
tgatacggcgaccaccgagatctacactctttccctacacgacgctcttccgatctGAAGAATATACCTA
CCGGAAagatcggaagagcacacgtctgaactccagtcacAATCAGTCTCGTatctcgtatgccgtcttc
tgcttgTTGTCGACTC >144_Sce_ITS2_13_C
CGGATCTCTTGGTTCTCGCATCGATGAAGAACCCAGCGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA
GAGAGCGTCTAGGCGAACAATGTTCTTAAAGTTTGACCTCAAATCAGGTAGGAGTACCCGCTGAACTTAA
GCATATCAATAAGCGGAGGAAAAGAAACCAACCGGGATTGTAGGGATAACAGGGTAATGAGTCGACAAaa
tgatacggcgaccaccgagatctacactctttccctacacgacgctcttccgatctCGGGCAGAGCGCTT
ACGTACagatcggaagagcacacgtctgaactccagtcacAATCAGTCTCGTatctcgtatgccgtcttc
tgcttgTTGTCGACTC >145_Sce_ITS2_14_A
CGGATCTCTTGGTTCTCGCATCGATGAAGAACGAAGCGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA
GAGAGCGTCTAGGCGAACAATGTTCTTAAAGTTTGACCTCAAATCAGGTAGGAGTACCCGCTGAACTTAA
GCATATCAATAAGCGGAGGAAAAGAAACCAACCGGGATTGTAGGGATAACAGGGTAATGAGTCGACAAaa
tgatacggcgaccaccgagatctacactctttccctacacgacgctcttccgatctCGTGGAATATTTGG
GTTCGGagatcggaagagcacacgtctgaactccagtcacAATCAGTCTCGTatctcgtatgccgtcttc
tgcttgTTGTCGACTC >146_Sce_ITS2_14_T
CGGATCTCTTGGTTCTCGCATCGATGAAGAACGTAGCGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA
GAGAGCGTCTAGGCGAACAATGTTCTTAAAGTTTGACCTCAAATCAGGTAGGAGTACCCGCTGAACTTAA
GCATATCAATAAGCGGAGGAAAAGAAACCAACCGGGATTGTAGGGATAACAGGGTAATGAGTCGACAAaa
tgatacggcgaccaccgagatctacactctttccctacacgacgctcttccgatctGCACCCGACAAGGG
TTCGGGagatcggaagagcacacgtctgaactccagtcacAATCAGTCTCGTatctcgtatgccgtcttc
tgcttgTTGTCGACTC >147_Sce_ITS2_14_G
CGGATCTCTTGGTTCTCGCATCGATGAAGAACGGAGCGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA
GAGAGCGTCTAGGCGAACAATGTTCTTAAAGTTTGACCTCAAATCAGGTAGGAGTACCCGCTGAACTTAA
GCATATCAATAAGCGGAGGAAAAGAAACCAACCGGGATTGTAGGGATAACAGGGTAATGAGTCGACAAaa
tgatacggcgaccaccgagatctacactctttccctacacgacgctcttccgatctAGAGCGTTCGTAAT
ACCGGAagatcggaagagcacacgtctgaactccagtcacAATCAGTCTCGTatctcgtatgccgtcttc
tgcttgTTGTCGACTC >148_Sce_ITS2_15_T
CGGATCTCTTGGTTCTCGCATCGATGAAGAACGCTGCGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT -continued

| Sequence Listing Free Text |
| --- |

CGTTTTAGGTTTTACCAACTGCGGCTAATCTTTTTTTATACTGAGCGTATTGGAACGTTATCGATAAGAA
GAGAGCGTCTAGGCGAACAATGTTCTTAAAGTTTGACCTCAAATCAGGTAGGAGTACCCGCTGAACTTAA
GCATATCAATAAGCGGAGGAAAAGAAACCAACCGGGATTGTAGGGATAACAGGGTAATGAGTCGACAAaa
tgatacggcgaccaccgagatctacactctttccctacacgacgctcttccgatctTACGCCTGTCATCA
TGACTAagatcggaagagcacacgtctgaactccagtcacAATCAGTCTCGTatctcgtatgccgtcttc
tgcttgTTGTCGACTC >149_Sce_ITS2_15_G
CGGATCTCTTGGTTCTCGCATCGATGAAGAACGCGGCGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA
GAGAGCGTCTAGGCGAACAATGTTCTTAAAGTTTGACCTCAAATCAGGTAGGAGTACCCGCTGAACTTAA
GCATATCAATAAGCGGAGGAAAAGAAACCAACCGGGATTGTAGGGATAACAGGGTAATGAGTCGACAAaa
tgatacggcgaccaccgagatctacactctttccctacacgacgctcttccgatctACGCATCACGCCTA
CGACGGagatcggaagagcacacgtctgaactccagtcacAATCAGTCTCGTatctcgtatgccgtcttc
tgcttgTTGTCGACTC >150_Sce_ITS2_15_C
CGGATCTCTTGGTTCTCGCATCGATGAAGAACGCCGCGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA
GAGAGCGTCTAGGCGAACAATGTTCTTAAAGTTTGACCTCAAATCAGGTAGGAGTACCCGCTGAACTTAA
GCATATCAATAAGCGGAGGAAAAGAAACCAACCGGGATTGTAGGGATAACAGGGTAATGAGTCGACAAaa
tgatacggcgaccaccgagatctacactctttccctacacgacgctcttccgatctGAGGGAGGATGACC
GTAGGTagatcggaagagcacacgtctgaactccagtcacAATCAGTCTCGTatctcgtatgccgtcttc
tgcttgTTGTCGACTC >151_Sce_ITS2_16_A
CGGATCTCTTGGTTCTCGCATCGATGAAGAACGCAACGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA
GAGAGCGTCTAGGCGAACAATGTTCTTAAAGTTTGACCTCAAATCAGGTAGGAGTACCCGCTGAACTTAA
GCATATCAATAAGCGGAGGAAAAGAAACCAACCGGGATTGTAGGGATAACAGGGTAATGAGTCGACAAaa
tgatacggcgaccaccgagatctacactctttccctacacgacgctcttccgatctCGATAATATCATCC
CGGACTagatcggaagagcacacgtctgaactccagtcacAATCAGTCTCGTatctcgtatgccgtcttc
tgcttgTTGTCGACTC >152_Sce_ITS2_16_T
CGGATCTCTTGGTTCTCGCATCGATGAAGAACGCATCGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA
GAGAGCGTCTAGGCGAACAATGTTCTTAAAGTTTGACCTCAAATCAGGTAGGAGTACCCGCTGAACTTAA
GCATATCAATAAGCGGAGGAAAAGAAACCAACCGGGATTGTAGGGATAACAGGGTAATGAGTCGACAAaa
tgatacggcgaccaccgagatctacactctttccctacacgacgctcttccgatctATGACGATCACTTT
CTAGCTagatcggaagagcacacgtctgaactccagtcacAATCAGTCTCGTatctcgtatgccgtcttc
tgcttgTTGTCGACTC >153_Sce_ITS2_16_C
CGGATCTCTTGGTTCTCGCATCGATGAAGAACGCACCGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA
GAGAGCGTCTAGGCGAACAATGTTCTTAAAGTTTGACCTCAAATCAGGTAGGAGTACCCGCTGAACTTAA
GCATATCAATAAGCGGAGGAAAAGAAACCAACCGGGATTGTAGGGATAACAGGGTAATGAGTCGACAAaa
tgatacggcgaccaccgagatctacactctttccctacacgacgctcttccgatctAGTACTCGGTCCCT
TCCTAGagatcggaagagcacacgtctgaactccagtcacAATCAGTCTCGTatctcgtatgccgtcttc
tgcttgTTGTCGACTC >154_Sce_ITS2_17_A
CGGATCTCTTGGTTCTCGCATCGATGAAGAACGCAGAGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA
GAGAGCGTCTAGGCGAACAATGTTCTTAAAGTTTGACCTCAAATCAGGTAGGAGTACCCGCTGAACTTAA
GCATATCAATAAGCGGAGGAAAAGAAACCAACCGGGATTGTAGGGATAACAGGGTAATGAGTCGACAAaa -continued

| Sequence Listing Free Text |
|---|

tgatacggcgaccaccgagatctacactctttccctacacgacgctcttccgatctATTCATACCAGATA
TCCCTCagatcggaagagcacacgtctgaactccagtcacAATCAGTCTCGTatctcgtatgccgtcttc
tgcttgTTGTCGACTC >155_Sce_ITS2_17_T
CGGATCTCTTGGTTCTCGCATCGATGAAGAACGCAGTGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA
GAGAGCGTCTAGGCGAACAATGTTCTTAAAGTTTGACCTCAAATCAGGTAGGAGTACCCGCTGAACTTAA
GCATATCAATAAGCGGAGGAAAAGAAACCAACCGGGATTGTAGGGATAACAGGGTAATGAGTCGACAAaa
tgatacggcgaccaccgagatctacactctttccctacacgacgctcttccgatctGACTGTGTGTTACT
GCTGACagatcggaagagcacacgtctgaactccagtcacAATCAGTCTCGTatctcgtatgccgtcttc
tgcttgTTGTCGACTC >156_Sce_ITS2_17_G
CGGATCTCTTGGTTCTCGCATCGATGAAGAACGCAGGGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA
GAGAGCGTCTAGGCGAACAATGTTCTTAAAGTTTGACCTCAAATCAGGTAGGAGTACCCGCTGAACTTAA
GCATATCAATAAGCGGAGGAAAAGAAACCAACCGGGATTGTAGGGATAACAGGGTAATGAGTCGACAAaa
tgatacggcgaccaccgagatctacactctttccctacacgacgctcttccgatctAAATACTGTTTATA
CGGTTGagatcggaagagcacacgtctgaactccagtcacAATCAGTCTCGTatctcgtatgccgtcttc
tgcttgTTGTCGACTC >157_Sce_ITS2_18_A
CGGATCTCTTGGTTCTCGCATCGATGAAGAACGCAGCAAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA
GAGAGCGTCTAGGCGAACAATGTTCTTAAAGTTTGACCTCAAATCAGGTAGGAGTACCCGCTGAACTTAA
GCATATCAATAAGCGGAGGAAAAGAAACCAACCGGGATTGTAGGGATAACAGGGTAATGAGTCGACAAaa
tgatacggcgaccaccgagatctacactctttccctacacgacgctcttccgatctGTAAACAGTAAGGA
GGCATCagatcggaagagcacacgtctgaactccagtcacAATCAGTCTCGTatctcgtatgccgtcttc
tgcttgTTGTCGACTC >158_Sce_ITS2_18_T
CGGATCTCTTGGTTCTCGCATCGATGAAGAACGCAGCTAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA
GAGAGCGTCTAGGCGAACAATGTTCTTAAAGTTTGACCTCAAATCAGGTAGGAGTACCCGCTGAACTTAA
GCATATCAATAAGCGGAGGAAAAGAAACCAACCGGGATTGTAGGGATAACAGGGTAATGAGTCGACAAaa
tgatacggcgaccaccgagatctacactctttccctacacgacgctcttccgatctTTGCAGACAGGTGC
GGGATGagatcggaagagcacacgtctgaactccagtcacAATCAGTCTCGTatctcgtatgccgtcttc
tgcttgTTGTCGACTC >159_Sce_ITS2_18_C
CGGATCTCTTGGTTCTCGCATCGATGAAGAACGCAGCCAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA
GAGAGCGTCTAGGCGAACAATGTTCTTAAAGTTTGACCTCAAATCAGGTAGGAGTACCCGCTGAACTTAA
GCATATCAATAAGCGGAGGAAAAGAAACCAACCGGGATTGTAGGGATAACAGGGTAATGAGTCGACAAaa
tgatacggcgaccaccgagatctacactctttccctacacgacgctcttccgatctCTCATTCAGCTTTG
TTAAAGagatcggaagagcacacgtctgaactccagtcacAATCAGTCTCGTatctcgtatgccgtcttc
tgcttgTTGTCGACTC

| ITS2 process standard sequences |
|---|

Illumina adapters in lower case
>160_GC_dG_35-40_ITS2
CGGATCTCTTGGTTCTCGCATCGATGAAGAACGCAGCGTATGAAGGTTGAAAGCGTAATTAGGAATTATT
GATAGTAAAGTGCACACTAGCGTTTTGTTAAATCTTAAGTGTAATCCCCGAGCTAAAACAAGGAATAACA
TCTGATAATTACAAGATTGAAAATCGTATTTGGAGGTAGAATTCCAGGAGTAAAGGAGAAATTAATAGTG
TTCTGTAATAATACAAGTATCGTATGCAGCAACTAGGTCGAAGACTGATGATCAGGTGAGAAAGTGTTGG
GAGCTAACTGAGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctGGC
CATACTCGCAGTGGCTCagatcggaagagcacacgtctgaactccagtcacAATCAGTCTCGTatctcgt
atgccgtcttctgcttgTTGTCGACTC -continued

| Sequence Listing Free Text |
| --- |

>161_GC_dG_35-50_ITS2
CGGATCTCTTGGTTCTCGCATCGATGAAGAACGCAGCGTATGGAGGATTCAAACATAAATCAGAATTACT
GGGCTTAAAATAATCGCATTCTGTTTGTTAAGTAATATGTGTAATCCCCGGGCTAATCCTGGGAAATGCA
TTTAATACTGGCAATCTAGAGTATAATAAAGGAGAATAGTATTTTAGTAGAAACAGAGAATTGTTTAGAT
ATTTGGAGGAATAAAGTTAGCATTTGCTGCCCCATGGACGAAAAATGATGCTCATATGCAAAAGCGTGGT
GTACAAACAGGGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctGTG
TCCTACCGCTATACCGCagatcggaagagcacacgtctgaactccagtcacAATCAGTCTCGTatctcgt
atgccgtcttctgcttgTTGTCGACTC >162_GC_dG_35-60_ITS2
CGGATCTCTTGGTTCTCGCATCGATGAAGAACGCAGCGAATGAAGAATGAATGCTTTAATCGGTATTATT
GGTCGTAAAACGCACGCAGGAGGATTGTTAAATTAGATGTGAAATCCACTGGCTTAACATTAGATAAGCA
TCTGATACAGGATAGCTTGATTTTCATATAAGAGGTTTGAAATCCAGATATAGCTTTGTAATTCGTAGAA
ATCTGGATGATTACCGGTTATGAAGGCGGTCTCATGGATGAAATCTGATGCTAAAATACGAATGCGTGGT
TATCAAATAATGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctGCT
CGAACACACAGCCGGTAagatcggaagagcacacgtctgaactccagtcacAATCAGTCTCGTatctcgt
atgccgtcttctgcttgTTGTCGACTC >163_GC_dG_36-70_ITS2
CGGATCTCTTGGTTCTCGCATCGATGAAGAACGCAGCGAACTGATGGTGTAAACGTTTTTCGGTTTAACT
GAACATAATGTTCACGAAAGATAAATGTTATTACATTTGATATTTATCTTGACTCAACATGGGAACAGCA
TATGATACAGGAAAACTTGAGTCTCGTAGAAGGGAGTTTAATTCCAGGTTAAGCTATTATATGATAATAG
AACTGGAGAAAATCCGGTGTTGATGGCGGTTACTTGGATTTAGACTTACGTTCAGGAACAAAATCTTGTG
GTGCTAACAGGGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctCCA
GGTGGGTAGGTCTTTGGagatcggaagagcacacgtctgaactccagtcacAATCAGTCTCGTatctcgt
atgccgtcttctgcttgTTGTCGACTC >164_GC_dG_40-40_ITS2
CGGATCTCTTGGTTCTCGCATCGATGAAGAACGCAGCGTACGGAGGGTGATAGTGTTAATCGTAATTACT
AGGCGTTAAGCACAAACAGGTGGATTGTTAAGACAGATATGATATCCCAGGGCTTAAACAGGAAACTGCA
AATGATACTAGCTAGCTTGAGACTCGAATATGGGGGTAGAATACCAGGATTAAAGATGATTTACGTAGAG
ATAAGGAGTATTACCGTTGTTAAAGGCGGCAACCTGAATTAATACTAACTAACAGGAAAGAAAGCGTGGT
AAGAAAACAGGGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctGTC
TCACTCAGTCAGTACGAagatcggaagagcacacgtctgaactccagtcacAATCAGTCTCGTatctcgt
atgccgtcttctgcttgTTGTCGACTC >165_GC_dG_40-50_ITS2
CGGATCTCTTGGTTCTCGCATCGATGAAGAACGCAGCGTACGGAGGGTGCAAATTTTAATCGGAATTACT
GGTAATAAAGCGCACGTAGTCGGTTTGTTAATTCATATTTGAATTCCTAAGTCTAAACCTAGTAACTACA
TCTGATACTGGTAAACTTGAGTCTCTTAGAGGGGGATAGAATTATAGTTGTAGCGGTGAAATTCGAAGAG
TTCTGGAGTAATACCGGTAGCAAAGACGACCAACTGGACGAAGTCTGACGTTAAGATAAGAAAGTATGGG
GAGCAAACAGGGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctTGA
TCTCGAGTGTCGTCACAagatcggaagagcacacgtctgaactccagtcacAATCAGTCTCGTatctcgt
atgccgtcttctgcttgTTGTCGACTC >166_GC_dG_40-60_ITS2
CGGATCTCTTGGTTCTCGCATCGATGAAGAACGCAGCGTACAGAGGGTGTAAGCGTTAATAGAAATTACT
GGGCGTAAAAAGCACGCAGGCGGTTTGTAAAGTTAGATATAAATTCATTGGACTCTAACTGAGAACTGCA
TTTGATACTTTCAAGCTTTTGTCTCGTTGAGGAGGGTAGAAATTCAGGAGTTGCGATGATATGCTTAGAG
ATCTTGAGGAATTCCGGTGTCGAATGCAAACTCCTGGACGAAGACTAACGTTCAGTTGCAAAAGAGTGGA
AATTAAACATTGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctGTG
TAGCTAACTTAAGGTGGagatcggaagagcacacgtctgaactccagtcacAATCAGTCTCGTatctcgt
atgccgtcttctgcttgTTGTCGACTC >167_GC_dG_40-70_ITS2
CGGATCTCTTGGTTCTCGCATCGATGAAGAACGCAGCGTAAGGAATGAGCTAGCGTTAATCGAAATTACT
GGGTGTTTTGCTCATGCAGGAGATTAGTTTATTCAGATGTAAAAAACCCGGGTACAACCTGGGAATTGCA
TCTGATACTTATAAGCTAAATACTCGTAGAGGGAGGTAGTATTCCTGGTGTTGTGGTGAAATGTGTAGAG
ATCTATATAATTACATGTTGCGAAGGCGGACCCAAGGACGAAGACTGATGCTCAGAAATTAAAACGTGGA
AATCAAACTTGGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctAAC
GTTGTCCAGCCGTATGTagatcggaagagcacacgtctgaactccagtcacAATCAGTCTCGTatctcgt
atgccgtcttctgcttgTTGTCGACTC >168_GC_dG_40-80_ITS2
CGGATCTCTTGGTTCTCGCATCGATGAAGAACGCAGCGTTCAGAATGTGTAAGCGTAATTCGAAATTTCT
GAGAGTAAAGCGAATGCAGATGGTTTATTTTGTTAGAAGTGAAATCCCCGGGCTATACCTGGTTACTGCA
TCTGTTACTGGTAAACTTGAAACTCGAAGAGGGTGATAATATTCCAGGTATTTAGGTTAAATGTGTAGAT
ATCTGGATGAATACTAGTGTCTAAGGCAGTCCACTGGACGTAGACTTACTCTCAGGTTCGAAAGCGTGGG
GAACATTCATAGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctACC -continued

| Sequence Listing Free Text |
| --- |

CGGACGGCGGTCAATAAagatcggaagagcacacgtctgaactccagtcacAATCAGTCTCGTatctcgt
atgccgtcttctgcttgTTGTCGACTC >169_GC_dG_45-50_ITS2
CGGATCTCTTGGTTCTCGCATCGATGAAGAACGCAGCGTAAGGAGGGTGCTTGCGTTAAACAGAAATACT
GGGTGTAAAACGTACGTAGACGGTTTATTAAGTAAGATGTGAAATCCCCGTGCTCAACCTAGGAACTGCA
TATGATATTGGAAAACTTGAGACATATAGAGGGAGATAGAATACTTGGAGTAGCGTTGTAATGCGTATAG
ATTTGGAGGAATACCGGTGGCGAAGGCGGCCCCCTGGACGAAGACAGACGCTCAGGTGCGAAATCGTTGT
GATCAAATAGGGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctTCA
CTCGGGTTCTCGGCACGagatcggaagagcacacgtctgaactccagtcacAATCAGTCTCGTatctcgt
atgccgtcttctgcttgTTGTCGACTC >170_GC_dG_45-60_ITS2
CGGATCTCTTGGTTCTCGCATCGATGAAGAACGCAGCGTACGAAGTGTGAAAACGTTATTAAGAATTACT
GGGCGTAAAGCGTTCGCAGGCGGTTTGTTAAGTCATAAGTGAAATCCCCGGGCACAAACTGGGAACTGAA
TCTGTAACTGACAAGCTTGAGTATCTTATAATGGGATAGAATTTAATGTGTAGCTGTGAAATGCGTAGAG
ATCTGGAGATATACCGGTGACTAAGGCGGCCCCCTGGACGAAGACTGACGCTCAGGTGCTAAATCGTGGG
GAACAAAAAGGGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctAAA
CAACTCTGGCTCGATAAagatcggaagagcacacgtctgaactccagtcacAATCAGTCTCGTatctcgt
atgccgtcttctgcttgTTGTCGACTC >171_GC_dG_45-70_ITS2
CGGATCTCTTGGTTCTCGCATCGATGAAGAACGCAGCGAACTGAGGGTGCAAGCGTTAATCGGAATTACT
GTGCATAAAGCTCACGCATTCGTTTTGTTAAGTCAGATAATAAATCCTCGAGTTAAACCTGGGAAATGCA
TCTGATACTGAAAAGCTTGATTCTCGTAGAGGGGTGTAGAATTCCAGGTGTAGCAGTAAAATACGTAGAG
ATCAGAATGAATTCCGGTGGTGAAGTCGGCCTACTGGACGAAGACTGACGCTAAGGTGCGAAAGCGTGGG
GAGCAAACAGGGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctCGA
CAGTCCGACCGCAACAGagatcggaagagcacacgtctgaactccagtcacAATCAGTCTCGTatctcgt
atgccgtcttctgcttgTTGTCGACTC >172_GC_dG_45-80_ITS2
CGGATCTCTTGGTTCTCGCATCGATGAAGAACGCAGCGTACGGAGTGTTAAATCGTTAATAGGAATTACT
GGGCGAAAAGTGCTAGCAGGCGGTTTGTTAAATCAGTTGTGAAATCCCTGGGCACAACCTGGGATCTGCA
TCTGATTTTGGCAAGCTTTAGTCTATTAGAGGGGGGTAAATTTCCATGTGTAGATTTGAAATGCGTTTAG
ATCTGGAGGAATACCGGAGGTGAAGGCGATCCCCTGGACGTAGACTGAAGCTCAAGTGAGAAAGCTTGGA
GTGCAAACTAGGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctACA
GATACGAGGGAGCAGGTagatcggaagagcacacgtctgaactccagtcacAATCAGTCTCGTatctcgt
atgccgtcttctgcttgTTGTCGACTC >173_GC_dG_45-90_ITS2
CGGATCTCTTGGTTCTCGCATCGATGAAGAACGCAGCGTACGGAGGGTGCAAGCGATAATAGTATTTACT
GTGCGAAAAGCATACTTAGGAAGATTTTTATGTCAGATGTGAAATCCCCGGGCTTAACCTGGGAACTGCA
TCTGATACTGACAAGTTTGAGACTCGTATAGGGGGGTAGAATTCCAGGTGTTGCAGTGAAAAGTGTAGAG
ATCTGGAAGAATACCGGTGGCGAAGGTTGCCCCCTGTACGAATAATGACGCTATGGTGCGAAAGCATTGT
GTGCAAACAAGGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctAGT
TTCCAGTCGGTTCTCACagatcggaagagcacacgtctgaactccagtcacAATCAGTCTCGTatctcgt
atgccgtcttctgcttgTTGTCGACTC >174_GC_dG_50-60_ITS2
CGGATCTCTTGGTTCTCGCATCGATGAAGAACGCAGCGTACGGAAGGTGCAAGTGTTAATCGGAATTACT
GGGCATAAAGCGCACGAAGGCGGTATGTTAAGTTAGATGTGAAATCCCCGGGCTCAATCTGTGAACTGCA
TCTGATACTGGCAAGCTTGAGTCTCGTAGAGGGGGGTAGAATTCAAGGTGTAGCGGTGAAATGCGTAGAG
ATCTAGATGAATACCGGTGGCGAAGGAGGTCCCCTGGACGAAGACTGACACTCTGGTGCGAAATAGTGGG
GAGCAAACAGAGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctCAC
GTTTACTGACACGAAGCagatcggaagagcacacgtctgaactccagtcacAATCAGTCTCGTatctcgt
atgccgtcttctgcttgTTGTCGACTC >175_GC_dG_50-70_ITS2
CGGATCTCTTGGTTCTCGCATCGATGAAGAACGCAGCGTACGGAGGGTGCAATCGTTAATCGGATTTACT
GGGCTTAAATCGCACGCAGGCGGTTTGTTAAGTCATATGTGAAAACCCCGGGCTCAACCTGGGAACTGCA
TCTGATACTTGCAAGCTTGAGTCTCGTATAGGGAGGTAGAATTCCAGGTGTAGCGGTGAAATGCGTAGAG
ATCTGAAGTAATACCGGTAGCTAATACGGCCCACTGGACGAAGACTGACGCACAGGTGCTAAAGCGTGTG
GAGCAAACAGGGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctGAT
ATAAGCAGCCTCCGCAAagatcggaagagcacacgtctgaactccagtcacAATCAGTCTCGTatctcgt
atgccgtcttctgcttgTTGTCGACTC >176_GC_dG_50-80_ITS2
CGGATCTCTTGGTTCTCGCATCGATGAAGAACGCAGCGTACGGAGTGTGCAAGCGTTAATCGGAATTACT
GGTCGTAAAGCGCACGTAGACGGTTTGTTAATTCAGATGTTAAATTCCAGGGCAAAACCTGGGAACTGCA
TCTTATACTGGCAAGCTTGAGTCTCGTAGAGGGGGTTAGAATTCCAGGTGTAGCGGTGAAATGTGTAAAG -continued

| Sequence Listing Free Text |
|---|

ATCTGGAGGAATACCGGTGTTGAAGGCGGCCTCCTGGACGAAGACTGACGCTCAGGTGCGAAAGCGTGGG
GAGCAAACAGGGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctGAA
TTTAGTGAGCACGAAGGagatcggaagagcacacgtctgaactccagtcacAATCAGTCTCGTatctcgt
atgccgtcttctgcttgTTGTCGACTC >177_GC_dG_50-90_ITS2
CGGATCTCTTGGTTCTCGCATCGATGAAGAACGCAGCGTACGGAGGGAACAAGCGTTAATCGAAATAACT
GGGCGTAAAGCGCTCGTAGGTTGTTTGTTAAGTCAGATGTGAAATCCCCGGGTTCAACCTGGGAACTGCA
TCTGATTATGGCAAGCTTGAGTCTCGTAGAGGGGGGTATAATTCCAGTTGAAGCGGTAAAATGCGTTGAG
ATCTGGAGGTATACCGGTGGCGAAAGCGGCCCCATGGACGAAGACTGACGCTCATTTGCGAAATCGTTGG
GAGCAAACAGGGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctATT
TAAGTGCAGCTATGTCCagatcggaagagcacacgtctgaactccagtcacAATCAGTCTCGTatctcgt
atgccgtcttctgcttgTTGTCGACTC >178_GC_dG_49-100_ITS2
CGGATCTCTTGGTTCTCGCATCGATGAAGAACGCAGCGTTCTTCGGGTACTAGCGTTAATTAGGATTTCT
GCGCGTAAAGTGAACGCAGGCTTGTTGGTCAGTGAGATGTGTATTACAGGTACTTAACCTGTGAACCGCA
TCTGATACTCGCAAGCCTGAGGCTCCTAGTGGGGGGTAGAAATCTATGTGTATCGTTGGAACCCGTAAAC
ATCTGTAGGATGGCATGTGTCCAAGGCAGCCCCCTGGTCTGAGACTGACAATCAGTTTCGAAAGCGTGGG
GAGCAAACAGCGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctAAG
AGGATAACTCCAGTCTGagatcggaagagcacacgtctgaactccagtcacAATCAGTCTCGTatctcgt
atgccgtcttctgcttgTTGTCGACTC >179_GC_dG_55-70_ITS2
CGGATCTCTTGGTTCTCGCATCGATGAAGAACGCAGCGGACGGAGGGTGCAAGCGTTAATCGGAATAACT
GGGCGTAAAGCGGTCGCAGGCGGTTTGTTAAGTCAGATGTGAATTCCCCGGGCTCAACGTGGGAACTTCA
CCTAATACGGGCAAGCTTTAGAATCGTAGAGGGGGGTAGAATTATAGGTATAGCGGTGCAATGCGAAGAG
AGCTGGAGGAATCCCGGTGGAGAAGGCAGCCCCCTGGACGAAGACAGAAGCTCAGGGGCGAAACCGTGGG
GAGCAAACAGGGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctTGG
GCAAGGTAATCCGTGCAagatcggaagagcacacgtctgaactccagtcacAATCAGTCTCGTatctcgt
atgccgtcttctgcttgTTGTCGACTC >180_GC_dG_55-80_ITS2
CGGATCTCTTGGTTCTCGCATCGATGAAGAACGCAGCGTACGGAGGGTGCAAGCGTTTATCGGAATTACT
GGGCGTAAAGCGCACGTAGGCGGTTTGTTAAGTCAGAAGTGAAATCCCCGGGCTCAACCTGGGAACTGCA
TCTGATACTGGCTAGCATGAGTATCGTAGAGGGGGGTAGAATTCCAGGTGTAGCGGTGTAATGCGTAGAG
ATCTAGAGGAATACCGGTGGCGAAGGCGGCCCCCTGGACGAAGACTGACGCTCAGGTGTGAAAGCGAGGG
GAGCAAACAGGGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctCTT
CCGTCTTTATCTAACTAagatcggaagagcacacgtctgaactccagtcacAATCAGTCTCGTatctcgt
atgccgtcttctgcttgTTGTCGACTC >181_GC_dG_55-90_ITS2
CGGATCTCTTGGTTCTCGCATCGATGAAGAACGCAGCGTACTGAGGGTGCAAGCGTAAATCGGAATTACT
GGGCGTAAAGCGCAAGCAGGCAGTTTGTTAAGTCAGATGTGAAATCCCCGGGCTCAACCTGGGAACTGCA
TCAGATACTGGCAAGCTTGAGTCTCGTTGAGGGGGGTAGAATTCCATGTGTAGCGGTGAATTGCGTAGAG
AACTGGAGGAATACCGGTGGCGAAGGCGGCCCCCTGGACGAAGACTGACGCTCAGGTGCGAAAGCGTGGG
GTGCAAACAGGGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctATG
TAGGTGGAATACCCAAAagatcggaagagcacacgtctgaactccagtcacAATCAGTCTCGTatctcgt
atgccgtcttctgcttgTTGTCGACTC >182_GC_dG_55-100_ITS2
CGGATCTCTTGGTTCTCGCATCGATGAAGAACGCAGCGTACTGAGGGTGCAAGCGTTAGTCGGAATTACT
GGGCGTAAAGCGCACTCAGGCGGTTTGTTAAGTCAGATGTGAAATCCCCGGGCTCAACCTGGGGACTGCA
TCTGATACTGGCAAGCCTGAGTCTCGTAGTGGGGGGTATAATTCCAGGTGTAGCGGTGAAATGCGTAGAG
ATCAGGAAGAAGTCCAGTTGTGAAGGCGGCCCCCTGGACGAAGACTGAGGCTCAGGTGCGAAAGCGTGGG
GAGCAAACAAGGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctTGG
ATACCTAGACCCGAGGAagatcggaagagcacacgtctgaactccagtcacAATCAGTCTCGTatctcgt
atgccgtcttctgcttgTTGTCGACTC >183_GC_dG_55-110_ITS2
CGGATCTCTTGGTTCTCGCATCGATGAAGAACGCAGCGTACCGAGGGTGCAAGAGTTAAGCGGAATTGCT
GGCCGTAAAGCGCACACAGGCGCTTTGTCAAGTTAGATGCGAAATCCCCAGGTTCAACCTGGGAACTGCA
TCTGATACTGGCAAGCTTAACTCTCGTAGAGGGGGTTACAATTCCAGGTGGAGCGCTGAAATGCGTAGAC
ATCTGGAGGAATACCGGTGGCGAAGGCGACCCCCTGGACGAAGACTCCCGCTTAGGTTCGCAAGCGGGGG
GAGCAAACAGAGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctTTG
TGCTAACAAGCCGCGGAagatcggaagagcacacgtctgaactccagtcacAATCAGTCTCGTatctcgt
atgccgtcttctgcttgTTGTCGACTC -continued

| Sequence Listing Free Text |
| --- |

>184_GC_dG_60-80_ITS2
CGGATCTCTTGGTTCTCGCATCGATGAAGAACGCAGCGTACGGAGGGGGCAAGCGTTGATCGGAATTACC
CGGCGTGAAGCGCACGCAGGCGGTTTGTTAAGTCAGATGTGAAATCCCCGGGCTCAACGTGGGAACTGCA
TGTGATACTGGCACGCTTGAGTCTCGCAGAGGGGGGGAGAATTGCAGGGGTAGCGGTGAAAGGCGTAGAG
ATCTGGAGGAATACCGGTGGCGAGGGCGGCCCCCTGGAGGAAGACTGACGCTCAGGTGCGAAAGCGTGGC
GAGCAAACACGGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctGAA
TTTGTCCAGTCACGCATagatcggaagagcacacgtctgaactccagtcacAATCAGTCTCGTatctcgt
atgccgtcttctgcttgTTGTCGACTC >185_GC_dG_60-90_ITS2
CGGATCTCTTGGTTCTCGCATCGATGAAGAACGCAGCGTACGGAGGGTGCAAGCGTTAATCGGAATGACT
GGGCGTAAAGCGCACGCAGGCGCTGTGTTAAGTCAGATGTGGAATCCCCGGGCTCAACCTGGGAACTGCA
TCTGATACTGGCAAGGTTGAGTCTGGTGGAGGGGGGGAGAATCCCAGGTGTGGCGGTGAAATGCGGAGAG
AGCTGGAGGAATACCGGTGGCGAAGGCGGCCCCCTGGACGGAGACTGACGCTCAGGTGCGAAAGCGTGGG
GAGCAAACAGGGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctAGG
GAAGATAGGAGGCTCCCagatcggaagagcacacgtctgaactccagtcacAATCAGTCTCGTatctcgt
atgccgtcttctgcttgTTGTCGACTC >186_GC_dG_60-100_ITS2
CGGATCTCTTGGTTCTCGCATCGATGAAGAACGCAGCGTACGGAGGGTGCAAGCGGTAATCGGAATTACT
GGGCGTAAACCGCACGCAGGCGGTCTGTTAAGTCAGATGTGAAATCCCCGGGCTCAACCGGGGAACTGCA
TCTGATACTGGCAAGCTTGAGCCTCGTAGAGGGGGGTAGAAGTCCGGGTGTAGCGGTGAACTGCGTAGAC
ATCTGGAGGAATACCGGGGGCGAAGGCGGCCCCCTGGACGAAGACTGACGGGCAGGTGCGACAGCGTGGG
GAGCAAACAGGGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctTAT
TGTACGGTACAGGTTCAagatcggaagagcacacgtctgaactccagtcacAATCAGTCTCGTatctcgt
atgccgtcttctgcttgTTGTCGACTC >187_GC_dG_60-110_ITS2
CGGATCTCTTGGTTCTCGCATCGATGAAGAACGCAGCGTCCGGAGGGTGCGAGCGTTAATCGGAATTACT
GCGCGTAAAGCGCACGCAGGCGGTTTCTTAAGTCAGCTGTGAAATCCCCGGGCTCACCCCGGGAACTGCA
TCTGATACTCGCAACCTTGAGTCTCGTAGAGGGGGCCAGAATTCCAGGTGTAGCGGTGAAATGCGTAGAG
ATCCGGAGGAATACCGGGGGCGAAGGCGGCCCCCTGGACGAAGACTGACGCTCAGGTGCGAAAGCGCGGG
GAGCAAACCGGGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctAAG
AAGGCACCTGAAGCTCAagatcggaagagcacacgtctgaactccagtcacAATCAGTCTCGTatctcgt
atgccgtcttctgcttgTTGTCGACTC >188_GC_dG_60-120_ITS2
CGGATCTCTTGGTTCTCGCATCGATGAAGAACGCAGCGTCCGGAGCGTGCAAGCGTCAATCCGCATTAGT
GGGCGTAAAGCGCACGCAGGCGGGTTGTTAAGTCAGATGTGAAATCCCGGGGCTCAACCTGGGAACTGCA
TCTGAGACTGGCAAGCTTGAGTCTCGTACAGGGGGGTAGAATTCCAGGTCTGGCGCTGAAATGCGTAGAG
ATCTGGAGGCAGACCGGTCGCGAAGGCGGCCCCCTGCACGACGAGTGACCCTCAGGCGCGAAAGCGTGGG
GAGCAAACAGGGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctTGC
CGACGTTCGACCCGTTAagatcggaagagcacacgtctgaactccagtcacAATCAGTCTCGTatctcgt
atgccgtcttctgcttgTTGTCGACTC >189_GC_dG_65-90_ITS2
CGGATCTCTTGGTTCTCGCATCGATGAAGAACGCAGCGTACGCAGGGTGCAAGCGTTAATCGGAATTACT
GGGCGGAAGGCGCACGCACGCGGCCTGTCAAGTGAGATGTGACATCCCCGGGCTCAACCTCGGAACTGCG
TCTGATACTGGCACGCTTGCGTCGCGTACAGGGGGCGAGAATTCCAGGGGGAGGGGTGAAATGCGTGGCG
ATCCGGAGGAATACCGGTGGCGAAGGCGGCCCCCGGGACGAAGACGGCCGCTCAGGGGCCAAAGCGTGGG
GGGCAGACACGGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctTAA
ATGATCCGCCTGGTCAGagatcggaagagcacacgtctgaactccagtcacAATCAGTCTCGTatctcgt
atgccgtcttctgcttgTTGTCGACTC >190_GC_dG_65-100_ITS2
CGGATCTCTTGGTTCTCGCATCGATGAAGAACGCAGCGTACGGGGGGTGCAAGCGTGGATCGGAATTGCT
GGGCGTCAAGGGCACGCAGGCGGTTTGTGAAGTCAGACGCGAGAGCCCCGGGCTCCACCGGGGAACTGCA
TCTGATACTGGCAAGCTTGAGTCTCGTAGACGGGGGCAGAATCCCGGGTGTGGCGGGGAAATGCGTAGAG
ATCTGGAGGGATCCCGGTGGCGAAGGCGGCCCCCTGGACGGAGACTGACGCTCAGGTGCGGAAGCGGGGG
GACCAAACAGGGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctGCA
GCTCCGCACTAAGCGACagatcggaagagcacacgtctgaactccagtcacAATCAGTCTCGTatctcgt
atgccgtcttctgcttgTTGTCGACTC >191_GC_dG_65-110_ITS2
CGGATCTCTTGGTTCTCGCATCGATGAAGAACGCAGCGTACGCAGGGTGCCAGCGTTAATCGGAATTACT
GGGCGTGAAGCGCACGCGGGCGGTTTGTTAAGTCAGACGTGAAATCCCCGCGCTCAACCTGGGAGCCGCA
CCTGAGAGTGGCGAGCTTGGGTGTCGTAGAGGGGGGTAGACTTCCAGGTGTAGCGGTGAAATGCGCAGCG
CTCTGGCGGGATACCGCTGGCGAAGGCGGCCCCCCGGGCGAAGCCTGCCGCTCAGGGGCGAAAGCGTGGG
GAGCACACAGGGCATATCAATAAGCGGAGGAAAAGAAACCAACCGGGATTGTAGGGATAACAGGGTAATG -continued

| Sequence Listing Free Text |
|---|

AGTCGACAAaatgatacggcgaccaccgagatctacactctttccctacacgacgctcttccgatctTAC
TTGGGTCCTAGGGACCAagatcggaagagcacacgtctgaactccagtcacAATCAGTCTCGTatctcgt
atgccgtcttctgcttgTTGTCGACTC >192_GC_dG_65-120_ITS2
CGGATCTCTTGGTTCTCGCATCGATGAAGAACGCAGCGTACGGAGCGTGCAAGCGCTAACCGGAATTACT
GCGCGTCAAGCGGACGCAGGCGGTTCGTTAAGTCAGGTGTGAGATCCCCGGGGTCAACCGGGGACCTGCA
TCTGACACCGGCACGCTTGAGTCCCGTAGGGGCGGGTAGAATCCCCGGTGTAGCGGTGCGAGCCGTAGCG
ATCCGGAGGAATACCGGTGGCGACGGCCGCCCCCTGGACGAAGGCTGACGCTGAGGTGCGAAAGCGTGGG
GAGCAAACAGGGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctCGG
ATTTACGATAGTAGGACagatcggaagagcacacgtctgaactccagtcacAATCAGTCTCGTatctcgt
atgccgtcttctgcttgTTGTCGACTC >193_GC_dG_65-130_ITS2
CGGATCTCTTGGTTCTCGCATCGATGAAGAACGCAGCGTACCGCCGGTGCACGCGTTAATCGGAATTACT
GGGGGTACAGCGCGCGCGGGCGGTTTGTTAGCTCCGGTGTGAAGTCCCGGGGCTCAACCTGGGAACTCCA
GCGGACACTGGCAAGCCTGAGTCTCGTCCCGGGGGGGAGAGTTCCAGCTGTAGCGGTGACGTCCCTGGAG
ATCTCGGGGAATACGGGTGGCCAAGGCCGCCCCCTCGAGGAGGAGTCACGCTGAGGCGCGAAAGCGTGGG
GAGCAAACAGGGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctTTA
TCACTGTAGACGGGAATagatcggaagagcacacgtctgaactccagtcacAATCAGTCTCGTatctcgt
atgccgtcttctgcttgTTGTCGACTC >194_GC_dG_70-100_ITS2
CGGATCTCTTGGTTCTCGCATCGATGAAGAACGCAGCGTGCGGGGGGTGGAAGCGGCGAGCGGACTGGCG
GGGCGCCAAGCGCGCGCCGGCGGCTTGCTAGGTCAGATGTGAGGTGCCCGGCCTCAACCTGGGAACTGCA
GGTGATACTGGGCAGCCGGAGTCGGGTAGACGGGGGTACAATGCCAGGTGTAGCGGGGCAACGGGTAGCG
ATGTGGGGGAATACCGGTGGCGAACGGGGCCCCCCGGACGAAGGCTGGCGCTCGGGTGCCACAGCGTGGG
GAGCAAACAGGGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctTAA
GTTCTTATGCAGCTATTagatcggaagagcacacgtctgaactccagtcacAATCAGTCTCGTatctcgt
atgccgtcttctgcttgTTGTCGACTC >195_GC_dG_70-110_ITS2
CGGATCTCTTGGTTCTCGCATCGATGAAGAACGCAGCGTGCGGAGGGTGCACGGGGTAACGGGAATGCCT
GGGCGCCCAGCCGACGGAGCCGGTTCGGTAAGTCAGAGGTGAACGCGCCGGGCTCAACCCGCGAACTGCC
GCTGATACCGGGGCGCTTCCGTCTCGTAGAGGGGGGTCGAATTCCAGGTGTGGCGCTGAAGTCCCGAGAG
CTCTGGAGGAAGCGCGGTGGCGAGGGCGCCCGCCCGGACCAAGACTGGCGGCCAGGTGCGAAAGCGCGGG
GAGCGAACGGGGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctTGA
CAGAGAGACCTCCCTACagatcggaagagcacacgtctgaactccagtcacAATCAGTCTCGTatctcgt
atgccgtcttctgcttgTTGTCGACTC >196_GC_dG_70-120_ITS2
CGGATCTCTTGGTTCTCGCATCGATGAAGAACGCAGCGCACGGAGGGCGCAAGCGTTAATCGGAACCACT
GGCCCTAAAGCGGCCCCAGGCGGGTCGTGAGGTCAGATGTGAAACCGCCGGGGTCAACCGGGGGGGGGCG
GCTGACACTGGCGAGCCTGGGTCTCGTACACGGGGGCAGACCTCCAGGTGTCCCGCTGAGGCGCGTGGAG
ATCCGGAGGAGTACCGGTGGGGACGCCGGCCCCCTCGAGGCAGACTGACGCGCAGGTGCGAAAGCGCGGG
GAGCAAACGGGGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctCCT
ACGTTAATGCGCAAATTagatcggaagagcacacgtctgaactccagtcacAATCAGTCTCGTatctcgt
atgccgtcttctgcttgTTGTCGACTC >197_GC_dG_70-130_ITS2
CGGATCTCTTGGTTCTCGCATCGATGAAGAACGCAGCGTACGGCGGGTGCCAGCCTTAATCGGAATGCCC
GGGCGCACAGCGGACGCGGGCGGTTCGTTAAGCCGCAGGCGAGATCCCCGGGCCCAACCTCGGCACGGCG
TCTGACACTGGCGAGGTTGAGTCTCGGAGAGGGGGGTAGGATTCCAGGTCCACCGGTGGAACCCCTAGAG
CTCTGGGGGACTACCGGTGGCCCAGGCCGCGGCCTGGACGAACGCTGGCGCTCAGGTCCGCAAGCCTGCG
GCGCACACGGGGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctAAC
CCATGTAAAGAGTTATCagatcggaagagcacacgtctgaactccagtcacAATCAGTCTCGTatctcgt
atgccgtcttctgcttgTTGTCGACTC >198_GC_dG_70-140_ITS2
CGGATCTCTTGGTTCTCGCATCGATGAAGAACGCAGCGTACCGCGGGTGCAAGCGTTAATGCGGCTTACT
GGGCGTAAAGCGGACCCCGGCGGTTTGTGAGGTCACATGTGAAGCCCCCGCCCTCCGCCTGGGAACTGCG
TCTGATACTGGCGGGCTCGGGGCCCGTACAGGGGGGTAGAATCCCAGGTGGAGGGCGGAACCGGGTGCCG
AGCTGCAGGAAGGCCGGCGGCGAAGCCGGCCCCCCGGGCGGAGACTGACGCCCAGGGGCGCGACCGTGGG
GAGCAAGCAGGGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctCGT
GTGTATCTCTAGCCTTCagatcggaagagcacacgtctgaactccagtcacAATCAGTCTCGTatctcgt
atgccgtcttctgcttgTTGTCGACTC >199_Size_213_ITS2
CGGATCTCTTGGTTCTCGCATCGATGAAGAACGCAGCGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG -continued

| Sequence Listing Free Text |
| --- |

CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCATATCAATAAGCGGAGGAAAAGAAACC
AACCGGGATTGTAGGGATAACAGGGTAATGAGTCGACAAaatgatacggcgaccaccgagatctacactc
tttccctacacgacgctcttccgatctGTTGTCTCTTAGGCCCTCAGagatcggaagagcacacgtctga
actccagtcacAATCAGTCTCGTatctcgtatgccgtcttctgcttgTTGTCGACTC >200_Size_243_ITS2
CGGATCTCTTGGTTCTCGCATCGATGAAGAACGCAGCGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGCATATCAATAAGCGGAGGAAAAGAAACCAACCGGGATTGTAGGGATAACAGGGTAATGAGTCGACAAa
atgatacggcgaccaccgagatctacactctttccctacacgacgctcttccgatctACGCAATGTTTCG
ATGAGCTagatcggaagagcacacgtctgaactccagtcacAATCAGTCTCGTatctcgtatgccgtctt
ctgcttgTTGTCGACTC >201_Size_273_ITS2
CGGATCTCTTGGTTCTCGCATCGATGAAGAACGCAGCGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTGCATATCAATAAGCGGAGGAAAAGAAACCAACCGGGATT
GTAGGGATAACAGGGTAATGAGTCGACAAaatgatacggcgaccaccgagatctacactctttccctaca
cgacgctcttccgatctCACCTTTGGAGAATGTCACCagatcggaagagcacacgtctgaactccagtca
cAATCAGTCTCGTatctcgtatgccgtcttctgcttgTTGTCGACTC >202_Size_303_ITS2
CGGATCTCTTGGTTCTCGCATCGATGAAGAACGCAGCGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATGCATATCAA
TAAGCGGAGGAAAAGAAACCAACCGGGATTGTAGGGATAACAGGGTAATGAGTCGACAAaatgatacggc
gaccaccgagatctacactctttccctacacgacgctcttccgatctAGGACCCGACAAGCACACGTaga
tcggaagagcacacgtctgaactccagtcacAATCAGTCTCGTatctcgtatgccgtcttctgcttgTTG
TCGACTC >203_Size_333_ITS2
CGGATCTCTTGGTTCTCGCATCGATGAAGAACGCAGCGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA
GAGAGCGTCTAGGCGAACAATGCATATCAATAAGCGGAGGAAAAGAAACCAACCGGGATTGTAGGGATAA
CAGGGTAATGAGTCGACAAaatgatacggcgaccaccgagatctacactctttccctacacgacgctctt
ccgatctTTTAGCGGTGCGAGTGATCAagatcggaagagcacacgtctgaactccagtcacAATCAGTCT
CGTatctcgtatgccgtcttctgcttgTTGTCGACTC >204_Size_363_ITS2
CGGATCTCTTGGTTCTCGCATCGATGAAGAACGCAGCGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA
GAGAGCGTCTAGGCGAACAATGTTCTTAAAGTTTGACCTCAAATCAGGTAGGCATATCAATAAGCGGAGG
AAAAGAAACCAACCGGGATTGTAGGGATAACAGGGTAATGAGTCGACAAaatgatacggcgaccaccgag
atctacactctttccctacacgacgctcttccgatctTCTCGCAATCGACATGACCGagatcggaagagc
acacgtctgaactccagtcacAATCAGTCTCGTatctcgtatgccgtcttctgcttgTTGTCGACTC >205_Size_403_ITS2
CGGATCTCTTGGTTCTCGCATCGATGAAGAACGCAGCGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA
GAGAGCGTCTAGGCGAACAATGTTCTTAAAGTTTGACCTCAAATCAGGTAGCCTTAGTAACGGCGAGTGA
AGCGGCAAAAGCTCAAATTTGGCATATCAATAAGCGGAGGAAAAGAAACCAACCGGGATTGTAGGGATAA
CAGGGTAATGAGTCGACAAaatgatacggcgaccaccgagatctacactctttccctacacgacgctctt
ccgatctAGTGACAGTGTTGAGAGGATagatcggaagagcacacgtctgaactccagtcacAATCAGTCT
CGTatctcgtatgccgtcttctgcttgTTGTCGACTC >206_Size_433_ITS2
CGGATCTCTTGGTTCTCGCATCGATGAAGAACGCAGCGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA -continued

| Sequence Listing Free Text |
| --- |

GAGAGCGTCTAGGCGAACAATGTTCTTAAAGTTTGACCTCAAATCAGGTAGCCTTAGTAACGGCGAGTGA
AGCGGCAAAAGCTCAAATTTGAAATCTGGTACCTTCGGTGCCCGAGTTGTAGCATATCAATAAGCGGAGG
AAAAGAAACCAACCGGGATTGTAGGGATAACAGGTAATGAGTCGACAAaatgatacggcgaccaccgag
atctacactctttccctacacgacgctcttccgatctCCAAAGCACGTACGGGAAGTagatcggaagagc
acacgtctgaactccagtcacAATCAGTCTCGTatctcgtatgccgtcttctgcttgTTGTCGACTC >207_Size_463_ITS2
CGGATCTCTTGGTTCTCGCATCGATGAAGAACGCAGCGAAATGCGATACGTAATGTGAATTGCAGAATTC
CGTGAATCATCGAATCGCCTTTGAACGCACATTGCGCCCCTTGGTATTCCAGGGGGCATGCCTGTTTGAG
CGTCATTTCCTTCTCAAACATTCTGTTTGGTAGTGAGTGATACTCTTTGGAGTTAACTTGAAATTGCTGG
CCTTTTCATTGGATGTTTTTTTTCCAAAGAGAGGTTTCTCTGCGTGCTTGAGGTATAATGCAAGTACGGT
CGTTTTAGGTTTTACCAACTGCGGCTAATCTTTTTTTATACTGAGCGTATTGGAACGTTATCGATAAGAA
GAGAGCGTCTAGGCGAACAATGTTCTTAAAGTTTGACCTCAAATCAGGTAGCCTTAGTAACGGCGAGTGA
AGCGGCAAAAGCTCAAATTTGAAATCTGGTACCTTCGGTGCCCGAGTTGTAATTTGGAGAGGGCAACTTT
GGGGCCGTTCCGCATATCAATAAGCGGAGGAAAAGAAACCAACCGGGATTGTAGGGATAACAGGGTAATG
AGTCGACAAaatgatacggcgaccaccgagatctacactctttccctacacgacgctcttccgatctGTA
CCCGAGGTTCCATACTCagatcggaagagcacacgtctgaactccagtcacAATCAGTCTCGTatctcgt
atgccgtcttctgcttgTTGTCGACTC

| Synthetic standard sequences - Full-length 16S rRNA gene tests (select human gut microbes) |
| --- |

Illumina adapters in lower case
>208_Bov_Full_TAG_TCT_CAT
TTACAATGAAGAGTTTGATCCTGGCTCAGGATGAACGCTAGCTACAGGCTTAACACATGCAAGTCGAGGG
GCAGCATTTTAGTTTGCTTGCAAACTGAAGATGGCGACCGGCGCACGGGTGAGTAACACGTATCCAACCT
GCCGATAACTCCGGAATAGCCTTTCGAAAGAAAGATTAATACCGGATAGCATACGAATATCGCATGATAT
TTTTATTAAAGAATTTCGGTTATCGATGGGGATGCGTTCCATTAGTTTGTTGGCGGGGTAACGGCCCACC
AAGACTACGATGGATAGGGGTTCTGAGAGGAAGGTCCCCCACATTGGAACTGAGACACGGTCCAAACTCC
TACGGGAGGCAGCAGTGAGGAATATTGGTACAATAGTGGGCGAGAGCCTGAACCAGCCAAGTAGCGTGAA
GGATGAAGGCTCTATGGGTCGTAAACTTCTTTTATATGGGAATAAAGTTTTCCACGTGTGGAATTTTGTA
TGTACCATATGAATAAGGATCGGCTAACTCCGTGCCAGCAGCCGCGGTAATACGGAGGATCCGAGCGTTA
TCCGGATTTATTGGGTTTAAATCTGGGAGCGTAGGTGGATTGTTAAGTCAGTTGTGAAAGTTTGCGGCTC
AACCGTAAAATTGCAGTTGAAACTGGCAGTCTTGAGTACAGTAGAGGTGGGCGGAATTCGTGGTGTAGCG
GTGAAATGCTTAGATATCACGAAGAACTCCGATTGCGAAGGCAGCTCACTAGACTGTTACTGACACTGAT
GCTCGAAAGTGTAGGTATCAAACAGGATTAGATACCCTGGTAGTCCACACAGTAAACGATGAATACTCGC
TGTTTGCGATATACAGTAAGCGGCCAAGCGAAAGCATTAAGTATTCCACCTGGCATGGTACGCCGGCAAC
GGTGAAACTCAAAGGAATTGACGGGGGCCCGCACAAGCGGAGGAACATGTGGTTTAATTCGATGATACGC
GAGGAACCTTACCCGGGCTTAAATTGCAACAGAATATATTGGAAACAGTATAGCCGTAAGGCTGTTGTGA
AGGTGCTGCATGGTTGTCGTCAGCTCGTGCCGTGAGGTGTCGGCTTAAGTGCCATAACGAGCGCAACCCT
TATCTTTAGTTACTAACAGGTTATGCTGAGGACTCTAGAGAGACTGCCGTCGTAAGATGTGAGGAAGGTG
GGGATGACGTCAAATCAGCACGGCCCTTACGTCCGGGGCTACACACGTGTTACAATGGGGGGTACAGAAG
GCAGCTACACGGCGACGTGATGCTAATCCCAAAAACCTCTCTCAGTTCGGATCGAAGTCTGCAACCCGAC
TTCGTGAAGCTGGATTCGCTAGTAATCGCGCATCAGCCATGGCGCGGTGAATACGTTCCCGGGCCTTGTA
CACACCGCCCGTCAAGCCATGAAAGCCGGGGGTACCTGAAGTACGTAACCGCAAGGAGCGTCCTAGGGTA
AAACTGGTAATTGGGGCTAAGTCGTAACAAGGTAGCCGTACCGGAAGGTGCGGCTGGAACACCTCCTTTC
TTAGGGATAACAGGGTAATGAGTCGACAAaatgatacggcgaccaccgagatctacactctttccctaca
cgacgctcttccgatctCTCAGCCAATGAGAAGGAGCagatcggaagagcacacgtctgaactccagtca
cAATCAGTCTCGTatctcgtatgccgtcttctgcttgTTGTCGACTC >209_Pdi_Full_TAG_TCT_CAT
ACAACGAAGAGTTTGATCCTGGCTCAGGATGAACGCTAGCGACAGGCTTAACACATGCAAGTCGAGGGGC
AGCGGGGTGTAGCAATACACCGCCGGCGACCGGCGCACGGGTGAGTAACGCGTATGCAACTTGCCTATCA
GAGGGGGATAACCCGGCGAAAGTCGGACTAATACCGCATGAAGCAGGGATCCCGCATGGGAATATTTGCT
AAAGATTCATCGCTGATAGATAGGCATGCGTTCCATTAGGCAGTTGGCGGGGTAACGGCCCACCAAACCG
ACGATGGATAGGGGTTCTGAGAGGAAGGTCCCCCACATTGGTACTGAGACACGGACCAAACTCCTACGGG
AGGCAGCAGTGAGGAATATTGGTACAATAGTGGGCGTAAGCCTGAACCAGCCAAGTCGCGTGAGGGATGA
AGGTTCTATGGATCGTAAACCTCTTTTATAAGGGAATAAAGTGCGGGACGTGTCCCGTTTTGTATGTACC
TTATGAATAAGGATCGGCTAACTCCGTGCCAGCAGCCGCGGTAATACGGAGGATCCGAGCGTTATCCGGA
TTTATTGGGTTTAAATCTGGGTGCGTAGGCGGCCTTTTAAGTCAGCGGTGAAAGTCTGTGGCTCAACCAT
AGAATTGCCGTTGAAACTGGGGGGCTTGAGTATGTTTGAGGCAGGCGGAATGCGTGGTGTAGCGGTGAAA
TGCATAGATATCACGCAGAACCCCGATTGCGAAGGCAGCCTGCCAAGCCATTACTGACGCTGATGCACGA
AAGCGTGGGGATCAAACAGGATTAGATACCCTGGTAGTCCACGCAGTAAACGATGATCACTAGCTGTTTG
CGATACACTGTAAGCGGCACAGCGAAAGCGTTAAGTGATCCACCTGGCATGGTACGCCGGCAACGGTGAA
ACTCAAAGGAATTGACGGGGGCCCGCACAAGCGGAGGAACATGTGGTTTAATTCGATGATACGCGAGGAA
CCTTACCCGGGTTTGAACGCATTCGGACCGAGGTGGAAACACCTTTTCTAGCAATAGCCGTTTGCGAGGT
GCTGCATGGTTGTCGTCAGCTCGTGCCGTGAGGTGTCGGCTTAAGTGCCATAACGAGCGCAACCCTTGCC
ACTAGTTACTAACAGGTTAGGCTGAGGACTCTGGTGGGACTGCCAGCGTAAGCTGCGAGGAAGGCGGGGA
TGACGTCAAATCAGCACGGCCCTTACATCCGGGGCGACACACGTGTTACAATGGCGTGGACAAAGGGAGG
CCACCTGGCGACAGGGAGCGAATCCCCAAACCACGTCTCAGTTCGGATCGGAGTCTGCAACCCGACTCCG
TGAAGCTGGATTCGCTAGTAATCGCGCATCAGCCATGGCGCGGTGAATACGTTCCCGGGCCTTGTACACA
CCGCCCGTCAAGCCATGGGAGCCGGGGGTACCTGAAGTCCGTAACCGCGAGGATCGGCCTAGGGTAAAAC
TGGTGACTGGGGCTAAGTCGTAACAAGGTAGCCGTACCGGAAGGTGCGGCTGGAACACCTCCTTTAGGGA
TAACAGGGTAATGAGTCGACAAaatgatacggcgaccaccgagatctacactctttccctacacgacgct
cttccgatctCCCACAAAGATCGCGCCGGCagatcggaagagcacacgtctgaactccagtcacAATCAG
TCTCGTatctcgtatgccgtcttctgcttgTTGTCGACTC -continued

| Sequence Listing Free Text |
|---|

>210_Fpr_Full_TAG_TCT_CAT
GAGAGTTTGATTCTGGCTCAGGACGAACGCTGGCGGCGCGCCTAACACATGCAAGTCGAACGAGCGAGAG
AGGAGCTTGCTTTCTCAAGCGAGTGGCGAACGGGTGAGTAACGCGTGAGGAACCTGCCTCAAAGAGGGGG
ACAACAGTTGGAAACGACTGCTAATACCGCATAAGCCCACGACCTGGCATCGGGTAGAGGGAAAAGGAGC
AATCCGCTTTGAGATGGCCTCGCGTCCGATTAGCTAGTTGGTGAGGTAACGGCCCACCAAGGCGACGATC
GGTAGCCGGACTGAGAGGTTGAACGGCCACATTGGGACTGAGACACGGCCCAGACTCCTACGGGAGGCAG
CAGTGGGGAATATTGCACAATAGTGGGGAAACCCTGATGCAGCGACGCCGCGTGGAGGAAGAAGGTCT
TCGGATTGTAAACTCCTGTTGTTGAGGAAGATAATGACGGTACTCAACAAGGAAGTGACGGCTAACTACG
TGCCAGCAGCCGCGGTAAAACGTAGGTCACAAGCGTTGTCCGGAATTACTGGGTGTAAATCTGGGAGCGC
AGGCGGGAAGGCAAGTTGGAAGTGAAATCCATGGGCTCAACCCATGAACTGCTTTCAAAACTGTTTTTCT
TGAGTAGTGCAGAGGTAGGCGGAATTCCCGGTGTAGCGGTGGAATGCGTAGATATCGGGAGGAACACCAG
TGGCGAAGGCGGCCTACTGGGCACCAACTGACGCTGAGGCTCGAAAGTGTGGGTAGCAAACAGGATTAGA
TACCCTGGTAGTCCACACTGTAAACGATGATTACTAGGTGTTGGAGGATTGACCCCTTCAGTGCCGCAGT
TAACACAATAAGTAATCCACCTGGCATGGTACGACCGCAAGGTTGAAACTCAAAGGAATTGACGGGGGCC
CGCACAAGCAGTGGAGTATGTGGTTTAATTCGACGCAACGCGAAGAACCTTACCAAGTCTTGACATCCTG
CGACGCGCATAGAAATATGTGTTTCTTCGGGACCAGAGACAGGTGGTGCATGGTTGTCGTCAGCTCGTGT
CGTGAGATGTTGGGTTAAGTCCCGCAACGAGCGCAACCCTTATGGTCAGTTACTACGCAAGAGGACTCTG
GCCAGACTGCCGTTGACAAAACGGAGGAAGGTGGGGATGACGTCAAATCATCATGCCCTTTATGACTTGG
GCTACACACGTACTACAATGGCGTTAAACAAAGAGAAGCAAGACCGCGAGGCGAGCAAAACTCAGAAACT
TCGTCCCAGTTCGGACTGCAGGCTGCAACTCGCCTGCACGAAGTCGGAATTGCTAGTAATCGCAGATCAG
CATGCTGCGGTGAATACGTTCCCGGGCCTGTACACACCGCCCGTCACACCATGAGAGCCGGGGGGACCCG
AAGTCGGTAGTCTAACCGCAAGGAGGACGCCGCCGAAGTAAAACTGGTGATTGGGGTGAAGTCGTAACAA
GGTAGCCGTAGAGAACCTGCGGCTGGATCACCTCCTTTAGGGATAACAGGGTAATGAGTCGACAAaatga
tacggcgaccaccgagatctacactctttccctacacgacgctcttccgatctCAAGTCAATGAAAGCGC
ATGagatcggaagagcacacgtctgaactccagtcacAATCAGTCTCGTatctcgtatgccgtcttctgc
ttgTTGTCGACTC >211_Rin_Full_TAG_TCT_CAT
TTGATCCTGGCTCAGGATGAACGCTGGCGGCGTGCTTAACACATGCAAGTCGAACGAAGCACTTTTACAG
ATTTCTTCGGAATGAAGTTTTAGTGACTGAGTGGCGGACGGGTGAGTAACGCGTGGGTAACCTGCCTCAC
ACAGGGGGATAACAGTTGGAAACGGCTGCTAATACCGCATAAGCGCACAGTACCGCATGGTACAGTGTGA
AAAACTCCGGTGGTGTGAGATGGACCCGCGTCTGATTAGCTAGTTGGCAGGGCAACGGCCTACCAAGGCG
ACGATCAGTAGCCGACCTGAGAGGGTGACCGGCCACATTGGGACTGAGACACGGCCCAAACTCCTACGGG
AGGCAGCAGTGGGGAATATTGCACAATAGTGGGGGAAACCCTGATGCAGCGACGCCGCGTGAGCGAAGA
AGTATTTCGGTATGTAAAGCTCTATCAGCAGGGAAGAAGAAATGACGGTACCTGACTAAGAAGCACCGGC
TAAATACGTGCCAGCAGCCGCGGTAATACGTATGGTGCAAGCGTTATCCGGATTTACTGGGTGTAAATCT
GGGAGCGCAGGCGGAAGGCTAAGTCTGATGTGAAAGCCCGGGGCTCAACCCCGGTACTGCATTGGAAACT
GGTCATCTAGAGTGTCGGAGGGGTAAGTGGAATTCCTAGTGTAGCGGTGAAATGCGTAGATATTAGGAGG
AACACCAGTGGCGAAGGCGGCTTACTGGACGATAACTGACGCTGAGGCTCGAAAGCGTGGGGAGCAAACA
GGATTAGATACCCTGGTAGTCCACGCCGTAAACGATGAATACTAGGTGTCGGAAAGCACAGCTTTTCGGT
GCCGCCGCAAACGCATTAAGTATTCCACCTGGCATGGTACGTTCGCAAGAATGAAACTCAAAGGAATTGA
CGGGGACCCGCACAAGCGGTGGAGCATGTGGTTTAATTCGAAGCAACGCGAAGAACCTTACCAAGTCTTG
ACATCCTTCTGACCGGACAGTAATGTGTCCTTTCCTTCGGGACAGAAGTGACAGGTGGTGCATGGTTGTC
GTCAGCTCGTGTCGTGAGATGTTGGGTTAAGTCCCGCAACGAGCGCAACCCTTATCCCCAGTAGCCAGCG
GTTCGGACGGGCACTCTGAGGAGACTGCCAGGGATAACCTGGAGGAAGGTGGGGATGACGTCAAATCATC
ATGCCCCTTATGACTTGGGCTACACACGTGCTACAATGGCGTAAACAAAGGGAAGCGAGACCGTGAGGTG
GAGCAAATCCCAAAAATAACGTCTCAGTTCGGACTGTAGTCTGCAACCCGACTACACGAAGCTGGAATCG
CTAGTAATCGCAGATCAGAATGCTGCGGTGAATACGTTCCCGGGTCTTGTACACACCGCCCGTCACACCA
TGGGAGTTGGAAATGCCCGAAGTCAGTGACCCAACCGCAAGGAGGGAGCTGCGAAGGCAGGTTAGGGATA
ACAGGGTAATGAGTCGACAAaatgatacggcgaccaccgagatctacactctttccctacacgacgctct
tccgatctGTTAGGGAGCTAGTTTAGGCagatcggaagagcacacgtctgaactccagtcacAATCAGTC
TCGTatctcgtatgccgtcttctgcttgTTGTCGACTC >212_Bbi_Full_TAG_TCT_CAT
TTTTGTGGAGGGTTCGATTCTGGCTCAGGATGAACGCTGGCGGCGTGCTTAACACATGCAAGTCGAACG
GGATCCATCAAGCTTGCTTGGTGGTGAGAGTGGCGAACGGGTGAGTAATGCGTGACCGACCTGCCCCATG
CTCCGGAATAGCTCCTGGAAACGGGTGGTAATGCCGGATGTTCCACATGATCGCATGTGATTGTGGGAAA
GATTCTATCGGCGTGGGATGGGGTCGCGTCCTATCAGCTTGTTGGTGAGGTAACGGCTCACCAAGGCTTC
GACGGGTAGCCGGCCTGAGAGGGCGACCGGCCACATTGGGACTGAGATACGGCCCAGACTCCTACGGGAG
GCAGCAGTGGGGAATATTGCACAATAGTGGGCGCAAGCCTGATGCAGCGACGCCGCGTGAGGGATGGAG
GCCTTCGGGTTGTAAACCTCTTTTGTTTGGGAGCAAGCCTTCGGGTGAGTGTACCTTTCGAATAAGCGCC
GGCTAACTACGTGCCAGCAGCCGCGGTAATACGTAGGGCGCAAGCGTTATCCGGATTTATTGGGCGTAAA
TCTGGGCTCGTAGGCGGCTCGTCGCGTCCGGTGTGAAAGTCCATCGCTTAACGGTGGATCTGCGCCGGGT
ACGGGCGGGCTGGAGTGCGGTAGGGGAGACTGGAATTCCCGGTGTAACGGTGGAATGTGTAGATATCGGG
AAGAACACCGATGGCGAAGGCAGGTCTCTGGGCCGTCACTGACGCTGAGGAGCGAAAGCGTGGGGAGCGA
ACAGGATTAGATACCCTGGTAGTCCACGCCGTAAACGGTGGACGCTGGATGTGGGGCACGTTCCACGTGT
TCCGTGTCGGAGCTAACGCGTTAAGCGTCCCGCCTGGCATGGTACGGCCGCAAGGCTAAAACTCAAAGAA
ATTGACGGGGGCCCGCACAAGCGGCGGAGCATGCGGATTAATTCGATGCAACGCGAAGAACCTTACCTGG
GCTTGACATGTTCCCGACGACGCCAGAGATGGCGTTTCCCTTCGGGGCGGGTTCACAGGTGGTGCATGGT
CGTCGTCAGCTCGTGTCGTGAGATGTTGGGTTAAGTCCCGCAACGAGCGCAACCCTCGCCCCGTGTTGCC
AGCACGTTATGGTGGGAACTCACGGGGGACCGCCGGGGTTAACTCGGAGGAAGGTGGGGATGACGTCAGA
TCATCATGCCCCTTACGTCCAGGGCTTCACGCATGCTACAATGGCCGGTACAGCGGGATGCGACATGGCG
ACATGGAGCGGATCCCTGAAAACCGGTCTCAGTTCGGATCGGAGCCTGCAACCCGGCTCCGTGAAGGCGG
AGTCGCTAGTAATCGCGGATCAGCAACGCCGCGGTGAATGCGTTCCCGGGCCTTGTACACACCGCCCGTC
AAGTCATGAAAGTGGGCAGCACCCGAAGCCGGTGGCCTAACCCCTTGTGGGATGGAGCCGTCTAAGGTGA
GGCTCGTGATTGGGACTAAGTCGTAACAAGGTAGCCGTACCGGAAGGTGCGGCTGGATCACCTCCTTTCT
ACGGAGTAGGGATAACAGGGTAATGAGTCGACAAaatgatacggcgaccaccgagatctacactctttcc -continued

| Sequence Listing Free Text |
| --- |

ctacacgacgctcttccgatctGAGCACGGGAATTACTCCGAagatcggaagagcacacgtctgaactcc
agtcacAATCAGTCTCGTatctcgtatgccgtcttctgcttgTTGTCGACTC >213_Hpa_Full_TAG_TCT_CAT
CAGATTGAACGCTGGCGGCAGGCTTAACACATGCAAGTCGAACGGTAACAGGAAGAAGCTTGCTTCTTTG
CTGACGAGTGGCGGACGGGTGAGTAATGCTTGGGTATCTGGCTTATGGAGGGGGATAACTACGGGAAACT
GTAGCTAATACCGCGTAGTATCGGAAGATGAAAGTGTGGGACCGCAAGGCCACATGCCATAGGATGAGCC
CAAGTGGGATTAGGTAGTTGGTGAGGTAATGGCTCACCAAGCCGACGATCTCTAGCTGGTCTGAGAGGAT
GACCAGCCACACCGGGACTGAGACACGGCCCGGACTCCTACGGGAGGCAGCAGTGGGGAATATTGCGACA
ATAGTGGGGGCAACCCTGACGCAGCCATGCCGCGTGAATGAAGAAGGCCTTCGGGTTGTAAAGTTCTTTC
GGTAGCGAGGAAGGCATTTAGTTTAATAGACTAGATGATTGACGTTAACTACAGAAGAAGCACCGGCTAA
CTCCGTGCCAGCAGCCGCGGTAATACGGAGGGTGCGAGCGTTAATCGGAATAACTGGGCGTAAATCTGGG
CACGCAGGCGGACTTTTAAGTGAGGTGTGAAAGCCCCGGGCTTAACCTGGGAATTGCATTTCAGACTGGG
AGTCTAGAGTACTTTAGGGAGGGGTAGAATTCCACGTGTAGCGGTGAAATGCGTAGAGATGTGGAGGAAT
ACCGAAGGCGAAGGCAGCCCCTTGGGAATGTACTGACGCTCATGTGCGAAAGCGTGGGGAGCAAACAGGA
TTAGATACCCTGGTAGTCCACGCTGTAAACGCTGTCGATTTGGGGATTGGGCTTAATGCTTGGTGCCCGT
AGCTAACGTGATAAATCGACCGCCTGGCATGGTACGGCCGCAAGGTTAAAACTCAAATGAATTGACGGGG
GCCCGCACAAGCGGTGGAGCATGTGGTTTAATTCGATGCAACGCGAAGAACCTTACCTACTCTTGACATC
CAGAGAACTTTCCAGAGATGGATTGGTGCCTTCGGGAGCTCTGAGACAGGTGCTGCATGGCTGTCGTCAG
CTCGTGTTGTGAAATGTTGGGTTAAGTCCCGCAACGAGCGCAACCCTTATCCTTTGTTGCCAGCGATTTG
GTCGGGAACTCAAAGGAGACTGCCGGTGATAAACCGGAGGAAGGTGGGGATGACGTCAAGTCATCATGGC
CCTTACGAGTAGGGCTACACACGTGCTACAATGGCGTATACAGAGGGAGGCGAAGCAGCGATGTGGAGCG
AATCCCAGAAAGTGCGTCTAAGTCCGGATTGGAGTCTGCAACTCGACTCCATGAAGTCGGAATCGCTAGT
AATCGCGAATCAGAATGTCGCGGTGAATACGTTCCCGGGCCTTGTACACACCGCCCGTCACACCATGGGA
GTGGGTTGTACCAGAAGTAGATAGCTTAACCTTCGGGAGGGCGTTTACCACGGTATGATTCATGACTGGG
GTGATAGGGATAACAGGGTAATGAGTCGACAAaatgatacggcgaccaccgagatctacactctttccct
acacgacgctcttccgatctGAGCCATAAACCAGCTCGGAagatcggaagagcacacgtctgaactccag
tcacAATCAGTCTCGTatctcgtatgccgtcttctgcttgTTGTCGACTC >214_Ssa_Full_TAG_TCT_CAT
TGATCCTGGCTCAGGACGAACGCTGGCGGCGTGCCTAATACATGCAAGTAGAACGCTGAAGAGAGGAGCT
TGCTCTTCTTGGATGAGTTGCGAACGGGTGAGTAACGCGTAGGTAACCTGCCTGGTAGCGGGGGATAACT
ATTGGAAACGATAGCTAATACCGCATAAAATTGATTATTGCATGATAATTAATTGAAAGATGCAATTGCA
TCACTACCAGATGGACCTGCGTTGTATTAGCTAGTTGGTGAGGTAACGGCTCACCAAGGCGACGATACAT
AGCCGACCTGAGAGGGTGATCGGCCACACTGGGACTGAGACACGGCCCAGACTCCTACGGGAGGCAGCAG
TAGGGAATCTTCGGACAATAGTGGGGGGAACCCTGACCGAGCAACGCCGCGTGAGTGAAGAAGGTTTTCG
GATCGTAAAGCTCTGTTGTAAGAGAAGAACGGGTGTGAGAGTGGAAAGTTCACACTGTGACGGTATCTTA
CCAGAAAGGGACGGCTAACTACGTGCCAGCAGCCGCGGTAATACGTAGGTCCCGAGCGTTGTCCGGATTT
ATTGGGCGTAAATCTGCGAGCGCAGGCGGTTAGATAAGTCTGAAGTTAAAGGCTGTGGCTTAACCATAGT
ATGCTTTGGAAACTGTTTAACTTGAGTGCAGAAGGGGAGAGTGGAATTCCATGTGTAGCGGTGAAATGCG
TAGATATATGGAGGAACACCGGTGGCGAAAGCGGCTCTCTGGTCTGTAACTGACGCTGAGGCTCGAAAGC
GTGGGGAGCAAACAGGATTAGATACCCTGGTAGTCCACGCCGTAAACGATGAGTGCTAGGTGTTAGGCCC
TTTCCGGGGCTTAGTGCCGCAGCTAACGCATTAAGCACTCCGCCTGGCATGGTACGACCGCAAGGTTGAA
ACTCAAAGGAATTGACGGGGGCCCGCACAAGCGGTGGAGCATGTGGTTTAATTCGAAGCAACGCGAAGAA
CCTTACCAGGTCTTGACATCCCTCTGACCGCTCTAGAGATAGAGTTTTCCTTCGGGACAGAGGTGACAGG
TGGTGCATGGTTGTCGTCAGCTCGTGTCGTGAGATGTTGGGTTAAGTCCCGCAACGAGCGCAACCCCTAT
TGTTAGTTGCCATCATTCAGTTGGGCACTCTAGCGAGACTGCCGGTAATAAACCGGAGGAAGGTGGGGAT
GACGTCAAATCATCATGCCCCTTATGACCTGGGCTACACACGTGCTACAATGGCTGGTACAACGAGTCGC
AAGCCGGTGACGGCAAGCTAATCTCTGAAAGCCAGTCTCAGTTCGGATTGTAGGCTGCAACTCGCCTACA
TGAAGTCGGAATCGCTAGTAATCGCGGATCAGCACGCCGCGGTGAATACGTTCCCGGGCCTTGTACACAC
CGCCCGTCACACCACGAGAGTTTGTAACACCCGAAGTCGGTGAGGTAACCGTAAGGAGCCAGCCGCCTTA
GGGATAACAGGGTAATGAGTCGACAAaatgatacggcgaccaccgagatctacactctttccctacacga
cgctcttccgatctTTGGCCGGAGTACAGTATCAagatcggaagagcacacgtctgaactccagtcacAA
TCAGTCTCGTatctcgtatgccgtcttctgcttgTTGTCGACTC >215_Vpa_Full_TAG_TCT_CAT
GCTGGCGGCGTGCTTAACACATGCAAGTCGAACGAAGAGCGATGGAAGCTTGCTTCTATCAATCTTAGTG
GCGAACGGGTGAGTAACGCGTAATCAACCTGCCCTTCAGAGGGGGACAACAGTTGGAAACGACTGCTAAT
ACCGCATACGATCTAACCTCGGCATCGAGGAAAGATGAAAGGTGGCCTCTATTTATAAGCTATCACTGAA
GGAGGGGATTGCGTCTGATTAGCTAGTTGGAGGGGTAACGGCCCACCAAGGCGATGATCAGTAGCCGGTC
TGAGAGGATGAACGGCCACATTGGGACTGAGACACGGCCCAGACTCCTACGGGAGGCAGCAGTGGGGAAT
CTTCCGACAATAGTGGACGAAAGTCTGACGGAGCAACGCCGCGTGAGTGATGACGGCCTTCGGGTTGTAA
AGCTCTGTTAATCGGGACGAAAGGCCTTCTTGCGAACAGTTAGAAGGATTGACGGTACCGGAATAGAAAG
CCACGGCTAACTACGTGCCAGCAGCCGCGGTAATACGTAGGTGGCAAGCGTTGTCCGGAATTATTGGGCG
TAAATCTGCGCGCGCAGGCGGATCAGTCAGTCTGTCTTAAAAGTTCGGGGCTTAACCCCGTGATGGGATG
GAAACTGCTGATCTAGAGTATCGGAGAGGAAAGTGGAATTCCTAGTGTAGCGGTGAAATGCGTAGATATT
AGGAAGAACACCAGTGGCGAAGGCGACTTTCTGGACGAAAACTGACGCTGAGGCGCGAAAGCCAGGGGAG
CGAACGGGATTAGATACCCCGGTAGTCCTGGCCGTAAACGATGGGTACTAGGTGTAGGAGGTATCGACCC
CTTCTGTGCCGGAGTTAACGCAATAAGTACCCCGCCTGGCATGGTACGACCGCAAGGTTGAAACTCAAAG
GAATTGACGGGGGCCCGCACAAGCGGTGGAGTATGTGGTTTAATTCGACGCAACGCGAAGAACCTTACCA
GGTCTTGACATTGATGGACAGAACCAGAGATGGTTCCTCTTCTTCGGAAGCCAGAAAACAGGTGGTGCAC
GGTTGTCGTCAGCTCGTGTCGTGAGATGTTGGGTTAAGTCCCGCAACGAGCGCAACCCCTATCTTATGTT
GCCAGCACTTTGGGTGGGAACTCATGAGAGACTGCCGCAGACAATGCGGAGGAAGGCGGGGATGACGTCA
AATCATCATGCCCCTTATGACCTGGGCTACACACGTACTACAATGGGAGTTAATAGACGGAAGCGAGATC
GCGAGATGGAGCAAACCCGAGAAACACTCTCTCAGTTCGGATCGTAGGCTGCAACTCGCCTACGTGAAGT
CGGAATCGCTAGTAATCGCAGGTCAGCATACTGCGGTGAATACGTTCCCGGGCCTTGTACACACCGCCCG
TCACACCACGAAAGTCGGAAGTGCCCAAAGCCGGTGGGGTAACCTTCGGGAGCCAGCCGTCTAAGGTAAA -continued

| Sequence Listing Free Text |
| --- |

GTCGATGATTGGGGTGAAGTCGTAACAAGGTAGCCTAGGGATAACAGGGTAATGAGTCGACAAaatgata
cggcgaccaccgagatctacactctttccctacacgacgctcttccgatctGTCCCGCTATTCGGCTTGT
CagatcggaagagcacacgtctgaactccagtcacAATCAGTCTCGTatctcgtatgccgtcttctgctt
gTTGTCGACTC >216_Ele_Full_TAG_TCT_CAT
AGAGTTTGATCCTGGCTCAGGATGAACGCTGGCGGCGTGCCTAACACATGCAAGTCGAACGATGAAACCG
CCCTCGGGCGGACATGAAGTGGCGAACGGGTGAGTAACACGTGACCAACCTGCCCCTTGCTCCGGGACAA
CCTTGGGAAACCGAGGCTAATACCGGATACTCCTCGCCCCCCTCCTGGGGGGCCCGGGAAAGCCCAGACG
GCAAGGGATGGGGTCGCGGCCCATTAGGTAGTAGGCGGGGTAACGGCCCACCTAGCCCGCGATGGGTAGC
CGGGTTGAGAGACCGACCGGCCACATTGGGACTGAGATACGGCCCAGACTCCTACGGGAGGCAGCAGTGG
GGAATTTTGCGACAATAGTGGGGAAACCCTGACGCAGCAACGCCGCGTGCGGGACGACGGCCTTCGGGT
TGTAAACCGCTTTCAGCAGGGAAGAAATTCGACGGTACCTGCAGAAGAAGCTCCGGCTAACTACGTGCCA
GCAGCCGCGGTAATACGTAGGGAGCGAGCGTTATCCGGATTCATTGGGCGTAAATCTGAGCGCGTAGGCG
GCCTCTCAAGCGGGATCTCTAATCCGAGGGCTCAACCCCCGGCCGGATCCCGAACTGGGAGGCTCGAGTT
CGGTAGAGGCAGGCGGAATTCCCGGTGTAGCGGTGGAATGCGCAGATATCGGGAAGAACACCGATGGCGA
AGGCAGCCTGCTGGGCCGCAACTGACGCTGAGGCGCGAAAGCTAGGGGAGCGAACAGGATTAGATACCCT
GGTAGTCCTAGCCGTAAACGATGGATACTAGGTGTGGGGCTCCGCCCTCCGTGCCGCAGCCAACGCATTA
AGTATCCCGCCTGGCATGGTACGGCCGCAAGGCTAAAACTCAAAGGAATTGACGGGGGCCCGCACAAGCA
GCGGAGCATGTGGCTTAATTCGAAGCAACGCGAAGAACCTTACCAGGGCTTGACATGGACGTGAAGCCGG
GGAAACCCGGTGGCCGAGAGGAGCGTCCGCAGGTGGTGCATGGCTGTCGTCAGCTCGTGTCGTGAGATGT
TGGGTTAAGTCCCGCAACGAGCGCAACCCCTGCCCCATGTTGCCAGCATTAGGTTGGGGACTCATGGGGG
ACTGCCGGCGTCAAGCCGGAGGAAGGTGGGGACGACGTCAAGTCATCATGCCCTTTATGCCCTGGGCTGC
ACACGTGCTACAATGGCCGGTACAACGGGCTGCGAGACCGCGAGGTCGAGCGAATCCCTCAAAGCCGGCC
CCAGTTCGGATCGGAGGCTGCAACCCGCCTCCGTGAAGTCGGAGTTGCTAGTAATCGCGGATCAGCATGC
CGCGGTGAATACGTTCCCGGGCCTTGTACACACCGCCCGTCACACCACCCGAGTCGTATGCACCCGAAGC
CGCCGGCCGAACCCGCAAGGGGCGGAGGCGTCGAAGGTGTGGAGGGTAAGGGGGGTGAAGTCGTAACAAG
GTAGCCGTACCGGAAGGTGCGGCTGGATCACCTCCTTTTAGGGATAACAGGGTAATGAGTCGACAAaatg
atacggcgaccaccgagatctacactctttccctacacgacgctcttccgatctCTTCGTGTTGGTGCCG
GTCTagatcggaagagcacacgtctgaactccagtcacAATCAGTCTCGTatctcgtatgccgtcttctg
cttgTTGTCGACTC >217_Dde_Full_TAG_TCT_CAT
TGAACTGGAGAGTTTGATTCTGGCTCAGATTGAACGCTGGCGGCGTGCTTAACACATGCAAGTCGAACGC
GAAAGGGACTTCGGTCCTGAGTAAAGTGGCGCACGGGTGAGTAACGCGTGGATAATCTGCCCTTATGATC
GGGATAACAGTTGGAAACGGCTGCTAATACCGGATACGCTCAAAATGAACTTTTTGAGGAAAGATGGCCT
CTGCTTGCATGCTATCACGTAAGGATGAGTCCGCGTCCCATTAGCTTGTTGGCGGGGTAACGGCCCACCA
AGGCATCGATGGGTAGCCGATTTGAGAGGATGATCGGCCACACTGGAACTGAAACACGGTCCAGACTCCT
ACGGGAGGCAGCAGTGGGGAATATTGCGACAATAGTGGGCGAAAGCCTGACGCAGCGACGCCGCGTGAGG
GATGAAGGTTTTCGGATCGTAAACCTCTGTCAGAAGGGAAGAAACTACGTTGTGCTAATCAGCAGCGTAC
TGACGGTACCTTCAAAGGAAGCACCGGCTAACTCCGTGCCAGCAGCCGCGGTAATACGGAGGGTGCAAGC
GTTAATCGGAATTACTGGGCGTAAATCTGCGCACGTAGGCTGTAGTGTAAGTCAGGGGTGAAATCCCACG
GCTCAACCGTGGAACTGCCTTTGATACTGCACAACTTGAATCCGGGAGAGGGTGGCGGAATTCCAGGTGT
AGGAGTGAAATCCGTAGATATCTGGAGGAACATCAGTGGCGAAGGCGGCCACCTGGACCGGTATTGACGC
TGAGGTGCGAAAGCGTGGGGAGCAAACAGGATTAGATACCCTGGTAGTCCACGCTGTAAACGATGGATGC
TAGATGTCGGGGAGTATTCTTCGGTGTCGTAGTTAACGCGTTAAGCATCCCGCCTGGCATGGTACGGTCG
CAAGGCTGAAACTCAAAGAAATTGACGGGGGCCCGCACAAGCGGTGGAGTATGTGGTTTAATTCGATGCA
ACGCGAAGAACCTTACCTAGGTTTGACATCCACGGAACCCTCCCGAAAAGGAGGGGTGCCCTTCGGGGAG
CCGTGAGACAGGTGCTGCATGGCTGTCGTCAGCTCGTGTCGTGAGATGTTGGGTTAAGTCCCGCAACGAG
CGCAACCCCTATGGATAGTTGCCAGCAAGTAATGTTGGGCACTCTATTCAGACTGCCCGGGTTAACCGGG
AGGAAGGTGGGGACGACGTCAAGTCATCATGGCCCTTACGCCTAGGGCTACACACGTACTACAATGGCGC
GCACAAAGGGGAGCGAGACCGCGAGGTGGAGCCAATCCCAAAAAACGCGTCCCAGTCCGGATTGCAGTCT
GCAACTCGACTGCATGAAGTTGGAATCGCTAGTAATTCGAGATCAGCATGCTCGGGTGAATGCGTTCCCG
GGCCTTGTACACACCGCCCGTCACACCACGAAAGTCGGTTTTACCCGAAGCCGGTGAGCCAACCAGCAAT
GGAGGCAGCCGTCTACGGTAGGGCCGATGATTGGGGTGAAGTCGTAACAAGGTAGCCGTAGGGGAACCTG
CGGCTGGATCACCTCCTTTAGGGATAACAGGGTAATGAGTCGACAAaatgatacggcgaccaccgagatc
tacactctttccctacacgacgctcttccgatctGTCCGATCAGTCGCGTGCACagatcggaagagcaca
cgtctgaactccagtcacAATCAGTCTCGTatctcgtatgccgtcttctgcttgTTGTCGACTC >218_Apa_Full_TAG_TCT_CAT
ATGGAGAGTTCGATCCTGGCTCAGGATGAACGCTGGCGGCGCGCCTAACACATGCAAGTCGAACGATTAA
AGCACCTTCGGGTGTGTATAAAGTGGCGAACGGCTGAGTAACACGTGGGCAACCTGCCCCTTTCATTGGG
ATAGCCACGGGAAACCGTGGATAATACCGAATACTTCGAGACTTCCGCATGGAAGACTCGAGAAAGCTCC
GGCGGAGAGGGATGGCCCGCGGCCTGTTAGCTTGTTGGTGGGGTAACGGCCTACCAAGGCAATGATGGG
TAGCTGGGTTGAGAGACCGACCAGCCAGATTGGGACTGAGACACGGCCCAGACTCCTACGGGAGGCAGCA
GTGGGGAATCTTGCAACAATAGTGGGCGAAAGCCTGATGCAGCGACGCCGCGTGCGGGATGAAGGCCTTC
GGGTTGTAAACCGCTTTCAGCAGGGACGAAAGTGACGGTACCTGCAGAAGAAGCCCCGGCTAACT
ACGTGCCAGCAGCCGCGGTAATACGTAGGGGGCAAGCGTTATCCGGATTCATTGGGCGTAAATCTGCGCT
CGTAGGCGGTCTGTTAGGTCGGGAGTTAAATCCGGGGGCTCAACCCCCGCTCGCTCTCGATACCGGCAGA
CTTGAGTTTGGTAGGGGAAGGTGGAATTCCTAGTGTAGCGGTGGAATGCGCAGATATTAGGAAGAACACC
AGTGGCGAAGGCGGCCTTCTGGGCCATAACTGACGCTGAGGAGCGAAAGCTAGGGGAGCAAACAGGATTA
GATACCCTGGTAGTCCTAGCCGTAAACGATGGACACTAGGTGTGGGGGAGTATTTCTTCCGTGCCGCAGC
TAACGCATTAAGTGTCCCGCCTGGCATGGTACGGCCGCAAGGCTAAAACTCAAAGGAATTGACGGGGGCC
CGCACAAGCAGCGGAGCATGTGGTTTAATTCGAAGCAACGCGAAGAACCTTACCAGGGCTTGACATTTAG
GTGAAGCGGCGGAAACGTCGTGGCCGAAAGGAGCCTAAACAGGTGGTGCATGGCTGTCGTCAGCTCGTGT
CGTGAGATGTTAGGTTAAGTCCTGCAACGAGCGCAACCCTCGTCGTATGTTGCCAGCGGTTAGGCCGGGC
ACCCATACGAGACCGCCGGCGTCAAGCCGGAGGAAGGTGGGGACGACGTCAAGTCATCATGCCCCTTATG -continued

| Sequence Listing Free Text |
| --- |

TCCTGGGCTACACACGTGCTACAATGGCCGGCACAATGGGCTGCCAACCCGCGAGGGTGAGCGAATCCCT
AAAGCCGGTCCCAGTTCGGATTGGAGGCTGCAACCCGCCTCCATGAAGTCGGAGTTGCTAGTAATCGCGG
ATCAGCACGCCGCGGTGAATGCGTTCCCGGGCCTTGTACACACCGCCCGTCACACCACCCGAGTCGATTG
CACCCGAAGTCGTCGGCCTAACCTTTTAGGAGGGAGACGCCGAAGGTGTGGTTGGTAAGGGGGGTGAAGT
CGTAACAAGGTAGCCGTACCGGAAGGTGCGGCTGGATCACCTCCTTTCTAGGGAGTAGGGATAACAGGGT
AATGAGTCGACAAatgatacggcgaccaccgagatctacactctttccctacacgacgctcttccgatc
tACACGTCAAGCAGCAGTGGAagatcggaagagcacacgtctgaactccagtcacAATCAGTCTCGTatc
tcgtatgccgtcttctgcttgTTGTCGACTC >219_Gad_Full_TAG_TCT_CAT
AGTTTGATCATGGCTCAGGACGAACGCTGGCGGCGTGCCTAATACATGCAAGTCGAACGAGAGCGACCGG
TGCTTGCACTGGTCAATCTAGTGGCGAACGGGTGAGTAACACGTGGGTAACCTGCCCATCAGAGGGGGAT
AACATCCGGAAACGGATGCTAAAACCGCATAGGTCTTCGAGCCGCATGGCTTGAAGAGGAAAAGAGGCGC
AAGCTTCTGCTGATGGATGGACCCGCGGTGCATTAGCTAGTTGGTGAGGTAACGGCTCACCAAGGCCGTG
ATGCATAGCCGACCTGAGAGGGTGATCGGCCACATTGGGACTGAGACACGGCCCAAACTCCTACGGGAGG
CAGCAGTAGGGAATCTTCCGACAATAGTGGACGCAAGTCTGACGGAGCAACGCCGCGTGAGTGAAGAAGG
TTTTCGGATCGTAAAACTCTGTTGTTAGAGAAGAACAAGTGCTAGAGTAACTGTTAGCGCCTTGACGGTA
TCTAACCAGAAAGCCACGGCTAACTACGTGCCAGCAGCCGCGGTAATACGTAGGTGGCAAGCGTTGTCCG
GATTTATTGGGCGTAAATCTGCGAGCGCAGGCGGTTCCTTAAGTCTGATGTGAAAGCCCCCGGCTCAACC
GGGGAGGGTCATTGGAAACTGGGGAACTTGAGTGCAGAAGAGGAGAGTGGAATTCCATGTGTAGCGGTGA
AATGCGTAGATATATGGAGGAACACCAGTGGCGAAGGCGACTCTCTGGTCTGTAACTGACGCTGAGGCTC
GAAAGCGTGGGTAGCAAACAGGATTAGATACCCTGGTAGTCCACGCCGTAAACGATGAGTGCTAAGTGTT
GGAGGGTTTCCGCCCTTCAGTGCTGCAGTTAACGCATTAAGCACTCCGCCTGGCATGGTACGACCGCAAG
GTTGAAACTCAAAGGAATTGACGGGGACCCGCACAAGCGGTGGAGCATGTGGTTTAATTCGAAGCAACGC
GAAGAACCTTACCAAGTCTTGACATCCTTTGACCACTCTAGAGATAGAGCTTTCCCTTCGGGGACAAAGT
GACAGGTGGTGCATGGTTGTCGTCAGCTCGTGTCGTGAGATGTTGGGTTAAGTCCCGCAACGAGCGCAAC
CCTTATTACTAGTTGCCAGCATTCAGTTGGGCACTCTAGTGAGACTGCCGGTGACAAACCGGAGGAAGGT
GGGGATGACGTCAAATCATCATGCCCCTTATGACTTGGGCTACACACGTGCTACAATGGATGGTACAACG
AGCAGCGAACTCGCGAGGGTAAGCGAATCTCTTAAAGCCATTCTCAGTTCGGATTGTAGGCTGCAACTCG
CCTACATGAAGCCGGAATCGCTAGTAATCGCGGATCAGCACGCCGCGGTGAATACGTTCCCGGGTCTTGT
ACACACCGCCCGTCACACCACGAGAGTTTGTAACACCCAAAGTCGGTGAGGTAACCATTTGGAGCCAGCC
GCCTAAGGTGGGATAGATGATTGGGGTGAAGTCGTAACAAGGTAGCCGTATAGGGATAACAGGGTAATGA
GTCGACAAaatgatacggcgaccaccgagatctacactctttccctacacgacgctcttccgatctATCC
TTGCGCAGGTCACCTGagatcggaagagcacacgtctgaactccagtcacAATCAGTCTCGTatctcgta
tgccgtcttctgcttgTTGTCGACTC >220_Aca_Full_TAG_TCT_CAT
AGAGTTTGATCCATGGCTCAGGATGAACGCTGGCGGCGTGCTTAACACATGCAAGTCGAACGAAGCATTT
AGGATTGAAGTTTTCGGATGGATTTCCTATATGACTGAGTGGCGGACGGGTGAGTAACGCGTGGGGAACC
TGCCCTATACAGGGGGATAACAGCTGGAAACGGCTGCTAATACCGCATAAGCGCACAGAATCGCATGATT
CAGTGTGAAAAGCCCTGGCAGTATAGGATGGTCCCGCGTCTGATTAGCTGGTTGGTGAGGTAACGGCTCA
CCAAGGCGACGATCAGTAGCCGGCTTGAGAGAGTGAACGGCCACATTGGGACTGAGACACGGCCCAAACT
CCTACGGGAGGCAGCAGTGGGGAATATTGCACAATAGTGGGGGAAACCCTGATGCAGCGACGCCGCGTG
AGTGAAGAAGTATTTCGGTATGTAAAGCTCTATCAGCAGGGAAGAAAACAGACGGTACCTGACTAAGAAG
CCCCGGCTAACTACGTGCCAGCAGCCGCGGTAATACGTAGGGGGCAAGCGTTATCCGGAATTACTGGGTG
TAAATCTGGGTGCGTAGGTGGCATGGTAAGTCAGAAGTGAAAGCCCGGGGCTTAACCCCGGGACTGCTTT
TGAAACTGTCATGCTGGAGTGCAGGAGAGGTAAGCGGAATTCCTAGTGTAGCGGTGAAATGCGTAGATAT
TAGGAGGAACACCAGTGGCGAAGGCGGCTTACTGGACTGTCACTGACACTGATGCACGAAAGCGTGGGGA
GCAAACAGGATTAGATACCCTGGTAGTCCACGCCGTAAACGATGAATACTAGGTGTCGGGGCCGTAGAGG
CTTCGGTGCCGCAGCAAACGCAGTAAGTATTCCACCTGGCATGGTACGTTCGCAAGAATGAAACTCAAAG
GAATTGACGGGGACCCGCACAAGCGGTGGAGCATGTGGTTTAATTCGAAGCAACGCGAAGAACCTTACCT
GGTCTTGACATCCCAATGACCGAACCTTAACCGGTTTTTTCTTTCGAGACATTGGAGACAGGTGGTGCAT
GGTTGTCGTCAGCTCGTGTCGTGAGATGTTGGGTTAAGTCCCGCAACGAGCGCAACCCCTATCTTTAGTA
GCCAGCATTTGAGGTGGGCACTCTAGAGAGACTGCCAGGGATAACCTGGAGGAAGGTGGGGACGACGTCA
AATCATCATGCCCCTTATGGCCAGGGCTACACACGTGCTACAATGGCGTAAACAAAGGGAAGCGAAGTCG
TGAGGCGAAGCAAATCCCAGAAATAACGTCTCAGTTCGGATTGTAGTCTGCAACTCGACTACATGAAGCT
GGAATCGCTAGTAATCGTGAATCAGAATGTCACGGTGAATACGTTCCCGGGTCTTGTACACACCGCCCGT
CACACCATGGGAGTCAGTAACGCCCGAAGTCAGTGACCCAACCGCAAGGAGGGAGCTGCCGAAGGTGGGA
CCGATAACTGGGGTGAAGTCGTAACAAGGTAGCCGTATCGGTAGGGATAACAGGGTAATGAGTCGACAAa
atgatacggcgaccaccgagatctacactctttccctacacgacgctcttccgatctGGCACCTAGAATA
GCCGTTGagatcggaagagcacacgtctgaactccagtcacAATCAGTCTCGTatctcgtatgccgtctt
ctgcttgTTGTCGACTC >221_Rmu_Full_TAG_TCT_CAT
AGAGTTTGATCATGGCTCAGGACGAACGCTGGCGGCGTGCTTAACACATGCAAGTCGAACGATGAAGCCT
AGCTTGCTAGGTGGATTAGTGGCGAACGGGTGAGTAATACGTGAGTAACCTACCTTTAACTCTGGGATAA
GCCTGGGAAACTGGGTCTAATACCGGATACGACCAATCTCCGCATGGGGTGTTGGTGGAAAGCGTTATGT
AGTGGTTATAGATGGGCTCACGGCCTATCAGCTCGTTGGTGAGGTAACGGCTCACCAAGGCGACGACGGG
TAGCCGGCCTGAGAGGGTGACCGGCCACACTGGGACTGAGACACGGCCCAGACTCCTACGGGAGGCAGCA
GTGGGGAATATTGCAACAATAGTGGGCGCAAGCCTGATGCAGCGACGCCGCGTGAGGGATGACGGCCTTC
GGGTTGTAAACCTCTGTTAGCAGGGAAGAAGAGAGATTGACGGTACCTGCAGAGAAAGCGCCGGCTAACT
ACGTGCCAGCAGCCGCGGTAATACGTAGGGCGCGAGCGTTGTCCGGAATTATTGGGCGTAAATCTGAGCT
TGTAGGCGGTTTGTCGCGTCTGCTGTGAAAGGCCGGGGCTTAACTCCGTGTATTGCAGTGGGTACGGGCA
GACTAGAGTGCAGTAGGGGAGACTGGAATTCCTGGTGTAGCGGTGGAATGCGCAGATATCAGGAGGAACA
CCGATGGCGAAGGCAGGTCTCTGGGCTGTAACTGACGCTGAGAAGCGAAAGCATGGGGAGCGAACAGGAT
TAGATACCCTGGTAGTCCATGCCGTAAACGTTGGGCACTAGGTGTGGGGGACATTCCACGTTTTCCGCGC
CGTAGCTAACGCATTAAGTGCCCCGCCTGGCATGGTACGGCCGCAAGGCTAAAACTCAAAGAAATTGACG -continued

| Sequence Listing Free Text |
|---|

GGGGCCCGCACAAGCGGCGGAGCATGCGGATTAATTCGATGCAACGCGAAGAACCTTACCAAGGCTTGAC
ATATACTGGACCGCATCAGAGATGGTGTTTCCCTTCGGGGCTGGTATACAGGTGGTGCATGGTTGTCGTC
AGCTCGTGTCGTGAGATGTTGGGTTAAGTCCCGCAACGAGCGCAACCCTCGTTCTATGTTGCCAGCACGT
TATGGTGGGGACTCATAGGAGACTGCCGGGGTCAACTCGGAGGAAGGTGGGGATGACGTCAAATCATCAT
GCCCCTTATGTCTTGGGCTTCACGCATGCTACAATGGCCGGTACAGAGGGTTGCGATACTGTGAGGTGGA
GCTAATCCCTAAAAGCCGGTCTCAGTTCGGATTGGGGTCTGCAACTCGACCCCATGAAGTCGGAGTCGCT
AGTAATCGCAGATCAGCAACGCTGCGGTGAATACGTTCCCGGGCCTTGTACACACCGCCCGTCAAGTCAC
GAAAGTTGGTAACACCCAAAGCCGGTGGCCTAACCCTTTTGGGAGGGAGCCGTCTAAGGTGGGATTGGCG
ATTGGGACTAAGTCGTAACAAGGTAGCCTAGGGATAACAGGGTAATGAGTCGACAAaatgatacggcgac
caccgagatctacactctttccctacacgacgctcttccgatctACACCTATTAGAGGTCAGACagatcg
gaagagcacacgtctgaactccagtcacAATCAGTCTCGTatctcgtatgccgtcttctgcttgTTGTCG
ACTC >222_Kpn_Full_TAG_TCT_CAT
TGAACGCTGGCGGCAGGCCTAACACATGCAAGTCGAGCGGTAGCACAGAGAGCTTGCTCTCGGGTGACGA
GCGGCGGACGGGTGAGTAATGTCTGGGAAACTGCCTGATGGAGGGGGATAACTACTGGAAACGGTAGCTA
ATACCGCATAACGTCGCAAGACCAAAGTGGGGGACCTTCGGGCCTCATGCCATCAGATGTGCCCAGATGG
GATTAGCTAGTAGGTGGGGTAACGGCTCACCTAGGCGACGATCCCTAGCTGGTCTGAGAGGATGACCAGC
CACACTGGAACTGAGACACGGTCCAGACTCCTACGGGAGGCAGCAGTGGGGAATATTGCAACAATAGTGG
GCGCAAGCCTGATGCAGCCATGCCGCGTGTGTGAAGAAGGCCTTCGGGTTGTAAAGCACTTTCAGCGGGG
AGGAAGGCGATAAGGTTAATAACCTTGTCGATTGACGTTACCCGCAGAAGAAGCACCGGCTAACTCCGTG
CCAGCAGCCGCGGTAATACGGAGGGTGCAAGCGTTAATCGGAATTACTGGGCGTAAATCTGCGCACGCAG
GCGGTCTGTCAAGTCGGATGTGAAATCCCCGGGCTCAACCTGGGAACTGCATTCGAAACTGGCAGGCTAG
AGTCTTGTAGAGGGGGGTAGAATTCCAGGTGTAGCGGTGAAATGCGTAGAGATCTGGAGGAATACCGGTG
GCGAAGGCGGCCCCCTGGACAAAGACTGACGCTCAGGTGCGAAAGCGTGGGGAGCAAACAGGATTAGATA
CCCTGGTAGTCCACGCCGTAAACGATGTCGATTTGGAGGTTGTGCCCTTGAGGCGTGGCTTCCGGAGCTA
ACGCGTTAAATCGACCGCCTGGCATGGTACGGCCGCAAGGTTAAAACTCAAATGAATTGACGGGGGCCCG
CACAAGCGGTGGAGCATGTGGTTTAATTCGATGCAACGCGAAGAACCTTACCTGGTCTTGACATCCACAG
AACTTAGCAGAGATGCTTTGGTGCCTTCGGGAACTGTGAGACAGGTGCTGCATGGCTGTCGTCAGCTCGT
GTTGTGAAATGTTGGGTTAAGTCCCGCAACGAGCGCAACCCTTATCCTTTGTTGCCAGCGGTTAGGCCGG
GAACTCAAAGGAGACTGCCAGTGATAAACTGGAGGAAGGTGGGGATGACGTCAAGTCATCATGGCCCTTA
CGACCAGGGCTACACACGTGCTACAATGGCATATACAAAGAGAAGCGACCTCGCGAGAGCAAGCGGACCT
CATAAAGTATGTCGTAGTCCGGATTGGAGTCTGCAACTCGACTCCATGAAGTCGGAATCGCTAGTAATCG
TAGATCAGAATGCTACGGTGAATACGTTCCCGGGCCTTGTACACACCGCCCGTCACACCATGGGAGTGGG
TTGCAAAAGAAGTAGGTAGCTTAACCTTCGGGAGGGCGCTTACCACTTTGTGATTCATGATAGGGATAAC
AGGGTAATGAGTCGACAAaatgatacggcgaccaccgagatctacactctttccctacacgacgctcttc
cgatctTTTGTATGCACCTTGTAAATagatcggaagagcacacgtctgaactccagtcacAATCAGTCTC
GTatctcgtatgccgtcttctgcttgTTGTCGACTC >223_Pco_Full_TAG_TCT_CAT
TACAATGGAGAGTTTGATCCTGGCTCAGGATGAACGCTAGCTACAGGCTTAACACATGCAAGTCGAGGGG
AAACGACATCGAAAGCTTGCTTTTGATGGGCGTCGACCGGCGCACGGGTGAGTAACGCGTATCCAACCTG
CCCACCACTTGGGGATAACCTTGCGAAAGTAAGACTAATACCCAATGATATCTCTAGAAGACATCTGAAA
GAGATTAAAGATTTATCGGTGATGGATGGGGATGCGTCTGATTAGCTTGTTGGCGGGGTAACGGCCCACC
AAGGCGACGATCAGTAGGGGTTCTGAGAGGAAGGTCCCCCACATTGGAACTGAGACACGGTCCAAACTCC
TACGGGAGGCAGCAGTGAGGAATATTGGTACAATAGTGGGCGAGAGCCTGAACCAGCCAAGTAGCGTGCA
GGATGACGGCCCTATGGGTTGTAAACTGCTTTTATAAGGGAATAAAGTTAGTCTCGTGAGACTTTTTGCA
TGTACCTTATGAATAAGGACCGGCTAATTCCGTGCCAGCAGCCGCGGTAATACGGAAGGTCCGGGCGTTA
TCCGGATTTATTGGGTTTAAATCTGGGAGCGTAGGCCGGAGATTAAGCGTGTTGTGAAATGTAGGCGCTC
AACGTCTGCACTGCAGCGCGAACTGGTTTCCTTGAGTACGCACAAAGTGGGTGGAATTCGTGGTGTAGCG
GTGAAATGCTTAGATATCACGAAGAACTCCGATTGCGAAGGCAGCTCACTGGAGCGCAACTGACGCTGAA
GCTCGAAAGTGCGGGTATCGAACAGGATTAGATACCCTGGTAGTCCGCACGGTAAACGATGGATGCCCGC
TGTTGGTCTGAACAGGTCAGCGGCCAAGCGAAAGCATTAAGCATCCCACCTGGCATGGTACGCCGGCAAC
GGTGAAACTCAAAGGAATTGACGGGGGCCCGCACAAGCGGAGGAACATGTGGTTTAATTCGATGATACGC
GAGGAACCTTACCCGGGCTTGAATTGCAGAGGAAGGATTTGGAGACAATGACGCCCTTCGGGGCCTCTGT
GAAGGTGCTGCATGGTTGTCGTCAGCTCGTGCCGTGAGGTGTCGGCTTAAGTGCCATAACGAGCGCAACC
CCTCTCCTTAGTTGCCATCAGGTTATGCTGGGCACTCTGGGGACACTGCCACCGTAAGGTGTGAGGAAGG
TGGGGATGACGTCAAATCAGCACGGCCCTTACGTCCGGGGCTACACACGTGTTACAATGGCAGGTACAGA
GAGACGGTTGTACGTAAGTACGATCAAATCCTTAAAGCCTGTCTCAGTTCGGATTGGGGTCTGCAACCCG
ACCCCACGAAGCTGGATTCGCTAGTAATCGCGCATCAGCCATGGCGCGGTGAATACGTTCCCGGGCCTTG
TACACACCGCCCGTCAAGCCATGAAAGCCGGGGGCGCCTAAAGTCCGTGACCGTAAGGAGCGGCCTAGGG
CGAAACTGGTAATTGGGGCTAAGTCGTAACAAGGTAGCCGTACCGGAAGGTGCGGCTGGAACACCTCCTT
TAGGGATAACAGGGTAATGAGTCGACAAaatgatacggcgaccaccgagatctacactctttccctacac
gacgctcttccgatctGGAACGGGTGTTGCCCAGATagatcggaagagcacacgtctgaactccagtcac
AATCAGTCTCGTatctcgtatgccgtcttctgcttgTTGTCGACTC >224_Apu_Full_TAG_TCT_CAT
GAGAGTTTGATCCTGGCTCAGGATGAACGCTAGCGGCAGGCTTAACACATGCAAGTCGAGGGGCAGCATA
ATGGATAGCAATATCTATGGTGGCGACCGGCGCACGGGTGCGTAACGCGTATGCAACCTACCTTTAACAG
GGGGATAACACTGAGAAATTGGTACTAATACCCCATAATATCATAGAAGGCATCTTTTATGGTTGAAAAT
TCCGATGGTTAGAGATGGGCATGCGTTGTATTAGCTAGTTGGTGGGGTAACGGCTCACCAAGGCGACGAT
ACATAGGGGGACTGAGAGGTTAACCCCCCACACTGGTACTGAGACACGGACCAGACTCCTACGGGAGGCA
GCAGTGAGGAATATTGGTACAATAGTGGACGCAAGTCTGAACCAGCCATGCCGCGTGCAGGATGACGGCT
CTATGAGTTGTAAACTGCTTTTGTACGAGGGTAAACGCAGATACGTGTATCTGTCTGAAAGTATCGTACG
AATAAGGATCGGCTAACTCCGTGCCAGCAGCCGCGGTAATACGGAGGATTCAAGCGTTATCCGGATTTAT
TGGGTTTAAATCTGGGTGCGTAGGCGGTTTGATAAGTTAGAGGTGAAATTTCGGGGCTCAACCCTGAACG
TGCCTCTAATACTGTTGAGCTAGAGAGTAGTTGCGGTAGGCGGAATGTATGGTGTAGCGGTGAAATGCTT -continued

| Sequence Listing Free Text |
|---|

AGAGATCATACAGAACACCGATTGCGAAGGCAGCTTACCAAACTATATCTGACGTTGAGGCACGAAAGCG
TGGGGAGCAAACAGGATTAGATACCCTGGTAGTCCACGCAGTAAACGATGATAACTCGTTGTCGGCGATA
CACAGTCGGTGACTAAGCGAAAGCGATAAGTTATCCACCTGGCATGGTACGTTCGCAAGAATGAAACTCA
AAGGAATTGACGGGGGCCCGCACAAGCGGAGGAACATGTGGTTTAATTCGATGATACGCGAGGAACCTTA
CCCGGGCTTGAAAGTTAGCGACGATTCTTGAAAGAGGATTTCCCTTCGGGGCGCGAAACTAGGTGCTGCA
TGGTTGTCGTCAGCTCGTGCCGTGAGGTGTCGGGTTAAGTCCCATAACGAGCGCAACCCCTACCGTTAGT
TGCCATCAGGTGAAGCTGGGCACTCTGGCGGGACTGCCGGTGTAAGCCGAGAGGAAGGTGGGGATGACGT
CAAATCAGCACGGCCCTTACGTCCGGGGCTACACACGTGTTACAATGGTAGGTACAGAGGGCAGCTACCC
AGCGATGGGATGCGAATCTCGAAAGCCTATCTCAGTTCGGATTGGAGGCTGAAACCCGCCTCCATGAAGT
TGGATTCGCTAGTAATCGCGCATCAGCCATGGCGCGGTGAATACGTTCCCGGGCCTTGTACACACCGCCC
GTCAAGCCATGGGAGCCGGGGGTGCCTGAAGTTCGTGACCGCAAGGAGCGACCTAGGGCAAAACTGGTGA
CTGGGGCTAAGTCGTAACAAGGTAGCCGTACCGGAAGGTGCGGCTGGAACACCTCCTTTCTTAGGGATAA
CAGGGTAATGAGTCGACAAaatgatacggcgaccaccgagatctacactctttccctacacgacgctctt
ccgatctCAGTGCTCGACCCGACACCCagatcggaagagcacacgtctgaactccagtcacAATCAGTCT
CGTatctcgtatgccgtcttctgcttgTTGTCGACTC >225_Ere_Full_TAG_TCT_CAT
AGAGTTTGATCCTGGCTCAGGATGAACGCTGGCGGCGTGCTTAACACATGCAAGTCGAACGAAGCACTTT
ATTTGATTTCCTTCGGGACTGATTATTTTGTGACTGAGTGGCGGACGGGTGAGTAACGCGTGGGTAACCT
GCCTTGTACAGGGGGATAACAGTTGGAAACGACTGCTAATACCGCATAAGCGCACAGTATCGCATGATGC
AGTGTGAAAAACTCCGGTGGTATAAGATGGACCCGCGTTGGATTAGCTAGTTGGTGAGGTGACGGCCCAC
CAAGGCGACGATCCATAGCCGACCTGAGAGGGTGACCGGCCACATTGGGACTGAGACACGGCCCAAACTC
CTACGGGAGGCAGCAGTGGGGAATATTGCAACAATAGTGGGCGAAAGCCTGATGCAGCGACGCCGCGTGA
GCGAAGAAGTATTTCGGTATGTAAAGCTCTATCAGCAGGGAAGATAATGACGGTACCTGACTAAGAAGCA
CCGGCTAAATACGTGCCAGCAGCCGCGGTAATACGTATGGTGCAAGCGTTATCCGGATTTACTGGGTGTA
AATCTGGGAGCGCAGGCGGTGCGGCAAGTCTGATGTGAAAGCCCGGGGCTCAACCCCGGTACTGCATTGG
AAACTGTCGTACTAGAGTGTCGGAGGGGTAAGCGGAATTCCTAGTGTAGCGGTGAAATGCGTAGATATTA
GGAGGAACACCAGTGGCGAAGGCGGCTTACTGGACGATAACTGACGCTGAGGCTCGAAAGCGTGGGGAGC
AAACAGGATTAGATACCCTGGTAGTCCACGCCGTAAACGATGAATACTAGGTGTTGGGAAGCATTGCTTC
TCGGTGCCGTCGCAAACGCAGTAAGTATTCCACCTGGCATGGTACGTTCGCAAGAATGAAACTCAAAGGA
ATTGACGGGGACCCGCACAAGCGGTGGAGCATGTGGTTTAATTCGAAGCAACGCGAAGAACCTTACCAAG
TCTTGACATCCTTCTGACCGGTACTTAACCGTACCTTCTCTTCGGAGCAGGAGTGACAGGTGGTGCATGG
TTGTCGTCAGCTCGTGTCGTGAGATGTTGGGTTAAGTCCCGCAACGAGCGCAACCCTTATCTTTAGTAGC
CAGCGGTTCGGCCGGGCACTCTAGAGAGACTGCCAGGGATAACCTGGAGGAAGGCGGGGATGACGTCAAA
TCATCATGCCCCTTATGACTTGGGCTACACACGTGCTACAATGGCGTAAACAAAGGGAAGCAAAGCTGTG
AAGCCGAGCAAATCTCAAAAATAACGTCTCAGTTCGGACTGTAGTCTGCAACCCGACTACACGAAGCTGG
AATCGCTAGTAATCGCAGATCAGAATGCTGCGGTGAATACGTTCCCGGGTCTTGTACACACCGCCCGTCA
CACCATGGGAGTTGGGAATGCCCGAACCAGTGACCTAACCGTAAGGAAGGAGCTGTCGAAGGCAGGCTCG
ATAACTGGGGTGAAGTCTAACAAGGTAACCTAGGGATAACAGGGTAATGAGTCGACAAaatgatacggcg
accaccgagatctacactctttccctacacgacgctcttccgatctGAGTTTACCTGCGCCCAGTTagat
cggaagagcacacgtctgaactccagtcacAATCAGTCTCGTatctcgtatgccgtcttctgcttgTTGT
CGACTC >226_Rbr_Full_TAG_TCT_CAT
GACGAACGCTGGCGGCGTGCCTAACACATGCAAGTCGAACGGAACTGTTTTGAAAGATTTCTTCGGAATG
AATTTGATTTAGTTTAGTGGCGGACGGGTGAGTAACGCGTGAGTAACCTGCCTTCAAGAGGGGGATAACA
TTCTGAAAAGAATGCTAATACCGCATGACATATCGGAACCACATGGTTTTGATATCAAAGATTTATCGC
TTGAAGATGGACTCGCGTCCGATTAGTTAGTTGGTGAGGTAACGGCTCACCAAGACCGCGATCGGTAGCC
GGACTGAGAGGTTGAACGGCCACATTGGGACTGAGACACGGCCCAGACTCCTACGGGAGGCAGCAGTGGG
GGATATTGCGACAATAGTGGGGGCAACCCTGACGCAGCAACGCCGCGTGAAGGATGAAGGTTTTCGGATT
GTAAACTTCTTTTATTAAGGACGAAACTTGACGGTACTTAATGAATAAGCTCCGGCTAACTACGTGCCAG
CAGCCGCGGTAATACGTAGGGAGCAAGCGTTGTCCGGATTTACTGGGTGTAAATCTGGGTGCGTAGGCGG
CTTTGCAAGTCAGATGTGAAATCTATGGGCTCAACCCATAAACTGCATTTGAAACTGTAGAGCTTGAGTG
AAGTAGAGGCAGGCGGAATTCCCCGTGTAGCGGTGAAATGCGTAGAGATGGGGAGGAACACCAGTGGCGA
AGGCGGCCTGCTGGGCTTTAACTGACGCTGAGGCACGAAAGCGTGGGTAGCAAACAGGATTAGATACCCT
GGTAGTCCACGCTGTAAACGATGATTACTAGGTGTGGGGGGTCTGACCCCTTCCGTGCCGGAGTTAACAC
AATAAGTAATCCACCTGGCATGGTACGGCCGCAAGGTTGAAACTCAAAGGAATTGACGGGGGCCCGCACA
AGCAGTGGAGTATGTGGTTTAATTCGAAGCAACGCGAAGAACCTTACCAGGTCTTGACATCCAACTAACG
AAGTAGAGATACATTAGGTGCCCTTCGGGGAAAGTTGAGACAGGTGGTGCATGGTTGTCGTCAGCTCGTG
TCGTGAGATGTTGGGTTAAGTCCCGCAACGAGCGCAACCCTTGCTATTAGTTGCTACGCAAGAGCACTCT
AATAGGACTGCCGTTGACAAAACGGAGGAAGGTGGGGACGACGTCAAATCATCATGCCCCTTATGACCTG
GGCTACACACGTACTACAATGGATGTTAACAGAGGGAAGCAAGACAGCGATGTGGAGCAAACCCCTAAAA
ACATTCTCAGTTCAGATTGCAGGCTGCAACCCGCCTGCATGAAGATGGAATTGCTAGTAATCGCGGATCA
GCATGCCGCGGTGAATACGTTCCCGGGCCTTGTACACACCGCCCGTCACACCATGGGAGCCGGTAATACC
CGAAGTCAGTAGTCCAACCTCGTGAGGACGCTGCCGAAGGTAGGATTGGCGACTGGGGTGTAGGGATAAC
AGGGTAATGAGTCGACAAaatgatacggcgaccaccgagatctacactctttccctacacgacgctcttc
cgatctAAGATGCATACGAGGAGCAAagatcggaagagcacacgtctgaactccagtcacAATCAGTCTC
GTatctcgtatgccgtcttctgcttgTTGTCGACTC >227_Osp_Full_TAG_TCT_CAT
AGAGTTTGATCCTGGCTCAGGATAACGCTAGCGACAGGCTTAACACATGCAAGTCGAGGGGCATCATGAG
GTAGCAATACCTTGATGGCGACCGGCGCACGGGTGAGTAACGCGTATGCAACCTGCCTGATACCGGGGTA
TAGCCCATGGAAACGTGGATTAACACCCCATAGTACTTTTATCCTGCATGGGATGTGAGTTAAATGTTCA
AGGTATCGGATGGGCATGCGTCCTATTAGTTAGTTGGCGGGGTAACAGCCCACCAAGACGATGATAGGTA
GGGGTTCTGAGAGGAAGGTCCCCCACATTGGAACTGAGACACGGTCCAAACTCCTACGGGAGGCAGCAGT
GAGGAATATTGGTACAATAGTGGACGTAAGTCTGAACCAGCCAAGTCGCGTGAGGGAAGACTGCCCTATG
GGTTGTAAACCTCTTTTATAAGGGAAGAATAAGTTCTACGTGTAGAATGATGCCTGTACCTTATGAATAA -continued

| Sequence Listing Free Text |
| --- |

GCATCGGCTAACTCCGTGCCAGCAGCCGCGGTAATACGGAGGATGCGAGCGTTATCCGGATTTATTGGGT
TTAAATCTGGGTGCGTAGGCGGTTTATTAAGTTAGTGGTTAAATATTTGAGCTAAACTCAATTGTGCCAT
TAATACTGGTAAACTGGAGTACAGACGAGGTAGGCGGAATAAGTTAAGTAGCGGTGAAATGCATAGATAT
AACTTAGAACTCCGATAGCGAAGGCAGCTTACCAGACTGTAACTGACGCTGAAGCACGAGAGCGTGGGTA
GCGAACAGGATTAGATACCCTGGTAGTCCACGCCGTAAACGATGCTCACTGGTTCTGTGCGATATATTGT
ACGGGATTAAGCGAAAGTATTAAGTGAGCCACCTGGCATGGTACGTCGGCAACGATGAAACTCAAAGGAA
TTGACGGGGGCCCGCACAAGCGGAGGAACATGTGGTTTAATTCGATGATACGCGAGGAACCTTACCTGGG
TTTAAATGGAAATGTCGTATTTGGAAACAGATATTCTCTTCGGAGCGTTTTTCAAGGTGCTGCATGGTT
GTCGTCAGCTCGTGCCGTGAGGTGTCGGGTTAAGTCCCATAACGAGCGCAACCCTTACCGTTAGTTGCTA
GCATGTAATGATGAGCACTCTAACGGGACTGCCACCGTAAGGTGAGAGGAAGGCGGGGATGACGTCAAAT
CAGCACGGCCCTTACACCCAGGGCTACACACGTGTTACAATGGCCGGTACAGAGGGCCGCTACCAGGTGA
CTGGATGCCAATCTCAAAAGCCGGTCGTAGTTCGGATTGGAGTCTGTAACCCGACTCCATGAAGTTGGAT
TCGCTAGTAATCGCGCATCAGCCATGGCGCGGTGAATACGTTCCCGGGCCTTGTACACACCGCCCGTCAA
GCCATGGAAGCCGGGGGTGCCTGAAGTCCGTAACCGCGAGGATCGGCCTAGGGCAAAACTGGTAACTGGG
GCTAAGTCGTAACATAGGGATAACAGGGTAATGAGTCGACAAaatgatacggcgaccaccgagatctaca
ctctttccctacacgacgctcttccgatctATCATGATACTGCCGTTTCGagatcggaagagcacacgtc
tgaactccagtcacAATCAGTCTCGTatctcgtatgccgtcttctgcttgTTGTCGACTC >228_Amu_Full_TAG_TCT_CAT
AACGAACGCTGGCGGCGTGGATAAGACATGCAAGTCGAACGAGAGAATTGCTAGCTTGCTAATAATTCTC
TAGTGGCGCACGGGTGAGTAACACGTGAGTAACCTGCCCCCGAGAGCGGGATAGCCCTGGGAAACTGGGA
TTAATACCGCATAGTATCGAAAGATTAAAGCAGCAATGCGCTTGGGGATGGGCTCGCGGCCTATTAGTTA
GTTGGTGAGGTAACGGCTCACCAAGGCGATGACGGGTAGCCGGTCTGAGAGGATGTCCGGCCACACTGGA
ACTGAGACACGGTCCAGACACCTACGGGTGGCAGCAGTCGAGAATCATTCAACAATAGTGGGGGAAACCC
TGATGGTGCGACGCCGCGTGGGGGAATGAAGGTCTTCGGATTGTAAACCCCTGTCATGTGGGAGCAAATT
AAAAAGATAGTACCACAAGAGGAAGAGACGGCTAACTCTGTGCCAGCAGCCGCGGTAATACAGAGGTCTC
AAGCGTTGTTCGGAATCACTGGGCGTAAATCTGCGTGCGTAGGCTGTTTCGTAAGTCGTGTGTGAAAGGC
GCGGGCTCAACCCGCGGACGGCACATGATACTGCGAGACTAGAGTAATGGAGGGGGAACCGGAATTCTCG
GTGTAGCAGTGAAATGCGTAGATATCGAGAGGAACACTCGTGGCGAAGGCGGGTTCCTGGACATTAACTG
ACGCTGAGGCACGAAGGCCAGGGGAGCGAAAGGGATTAGATACCCCTGTAGTCCTGGCAGTAAACGGTGC
ACGCTTGGTGTGCGGGGAATCGACCCCCTGCGTGCCGGAGTAACGCGTTAAGCGTGCCGCCTGGCATGGT
ACGGTCGCAAGATTAAAACTCAAAGAAATTGACGGGGACCCGCACAAGCGGTGGAGTATGTGGCTTAATT
CGATGCAACGCGAAGAACCTTACCTGGGCTTGACATGTAATGAACAACATGTGAAAGCATGCGACTCTTC
GGAGGCGTTACACAGGTGCTGCATGGCCGTCGTCAGCTCGTGTCGTGAGATGTTTGGTTAAGTCCAGCAA
CGAGCGCAACCCCTGTTGCCAGTTACCAGCACGTGAAGGTGGGGACTCTGGCGAGACTGCCCAGATCAAC
TGGGAGGAAGGTGGGGACGACGTCAGGTCAGTATGGCCCTTATGCCCAGGGCTGCACACGTACTACAATG
CCCAGTACAGAGGGGGCCGAAGCCGCGAGGCGGAGGAAATCCTAAAAACTGGGCCCAGTTCGGACTGTAG
GCTGCAACCCGCCTACACGAAGCCGGAATCGCTAGTAATGGCGCATCAGCTACGGCGCCGTGAATACGTT
CCCGGGTCTTGTACACACCGCCCGTCACATCATGGAAGCTGGTCGCACCCGAAGTATCTGAAGCCAACCG
CAAGGAGGCAGGGTCCTAAGGTGAGACTGGTAACTGGGATGTAGGGATAACAGGGTAATGAGTCGACAAa
atgatacggcgaccaccgagatctacactctttccctacacgacgctcttccgatctTGTCTTATCTGAA
TACAGAGagatcggaagagcacacgtctgaactccagtcacAATCAGTCTCGTatctcgtatgccgtctt
ctgcttgTTGTCGACTC >229_Din_Full_TAG_TCT_CAT
GACGAACGCTGGCGGCGTGCTTAACACATGCAAGTCGAACGAAAAGACGGAAAGAGCTTGCTCTTTTCAG
AATTGAGTGGCAAACGGGTGAGTAACACGTAAACAACCTGCCTTCAGGATGGGGACAACAGACGGAAACG
ACTGCTAATACCGAATAAGTTCCAAGAGCCGCATGGCCCATGGAAGAAAAGGTGGCCTCTACCTGTAAGC
TATCGCCTGAAGAGGGGTTTGCGTCTGATTAGCTGGTTGGAGGGGTAACGGCCCACCAAGGCGACGATCA
GTAGCCGGTCTGAGAGGATGAACGGCCACACTGGAACTGAGACACGGTCCAGACTCCTACGGGAGGCAGC
AGTGGGGAATCTTCCGACAATAGTGGGCGAAAGCCTGACGGAGCAACGCCGCGTGAGTGATGACGGCCTT
CGGGTTGTAAAACTCTGTGATCCGGGACGAAAAGGCAGAGTGCGAAGAACAAACTGCATTGACGGTACCG
GAAAAGCAAGCCACGGCTAACTACGTGCCAGCAGCCGCGGTAATACGTAGGTGGCAAGCGTTGTCCGGAA
TTATTGGGCGTAAATCTGCGCGCGCAGGCGGCTTCCCAAGTCCCTCTTAAAAGTGCGGGGCTTAACCCCG
TGATGGGAAGGAAACTGGGAAGCTGGAGTATCGGAGAGGAAAGTGGAATTCCTAGTGTAGCGGTGAAATG
CGTAGAGATTAGGAAGAACACCGGTGGCGAAGGCGACTTTCTGGACGAAAACTGACGCTGAGGCGCGAAA
GCGTGGGGCAAACAGGATTAGATACCCTGGTAGTCCACGCCGTAAACGATGGATACTAGGTGTAGGAGGT
ATCGACCCCTCCTGTGCCGGAGTTAACGCAATAAGTATCCCGCCTCATGGGAAGTACGATCGCAAGATTA
AAACTCAAAGGAATTGACGGGGGCCCGCACAAGCGGTGGAGTATGTGGTTTAATTCGACGCAACGCGAAG
AACCTTACCAGGTCTTGACATTGATCGCGATCTGCAGAAATGCGGAGTTCTTCTTCGGAAGACGAGAAAA
CAGGTGGTGCACGGCTGTCGTCAGCTCGTGTCGTGAGATGTTGGGTTAAGTCCCGCAACGAGCGCAACCC
CTATCATTTGTTACCAGCACGTAAAGGTGGGGACTCAAATGAGACCGCCGCGGACAACGCGGAGGAAGGC
GGGGACGACGTCAAGTCATCATGCCCCTTATGACCTGGGCTACACACGTACTACAATGGGTGTCAACAAA
GAGAAGCGAACCCGCGAGGAAGAGCAAACCTCAAAAACACACCCCCAGTTCAGATCGCAGGCTGCAACCC
GCCTGCGTGAAGTAGGAATCGCTAGTAATCGCGGGTCAGCATACCGCGGTGAATACGTTCCCGGGCCTTG
TACACACCGCCCGTCACACTATGAGAGTCAGAAACACCCGAAGCCGGTGAGGTAACCGCAAGGAGCCAGC
CGTCGAAGGCGGAGCTGATGATTGGAGTGAAGTCGTAACAAGGTAGCCGTATCGGAAGGTGCTAGGGATA
ACAGGGTAATGAGTCGACAAatgatacggcgaccaccgagatctacactctttccctacacgacgctct
tccgatctTGGCAGCCATAACATAGTCCagatcggaagagcacacgtctgaactccagtcacAATCAGTC
TCGTatctcgtatgccgtcttctgcttgTTGTCGACTC >230_Bun_Full_TAG_TCT_CAT
TTTGATCATGGCTCAGGATGAACGCTAGCTACAGGCTTAACACATGCAAGTCGAGGGGCAGCATGAACTT
AGCTTGCTAAGTTTGATGGCGACCGGCGCACGGGTGAGTAACACGTATCCAACCTGCCGATGACTCGGGG
ATAGCCTTTCGAAAGAAAGATTAATACCCGATGGCATAGTTCTTCCGCATGGTGGAACTATTAAAGAATT
TCGGTCATCGATGGGGATGCGTTCCATTAGGTTGTTGGCGGGGTAACGGCCCACCAAGCCTTCGATGGAT
AGGGGTTCTGAGAGGAAGGTCCCCCACATTGGAACTGAGACACGGTCCAAACTCCTACGGGAGGCAGCAG -continued

| Sequence Listing Free Text |
| --- |

TGAGGAATATTGGTACAATAGTGGACGAGAGTCTGAACCAGCCAAGTAGCGTGAAGGATGACTGCCCTAT
GGGTTGTAAACTTCTTTTATACGGGAATAAAGTGAGGCACGTGTGCCTTTTTGTATGTACCGTATGAATA
AGGATCGGCTAACTCCGTGCCAGCAGCCGCGGTAATACGGAGGATCCGAGCGTTATCCGGATTTATTGGG
TTTAAATCTGGGAGCGTAGGCGGACGCTTAAGTCAGTTGTGAAAGTTTGCGGCTCAACCGTAAAATTGCA
GTTGATACTGGGTGTCTTGAGTACAGTAGAGGCAGGCGGAATTCGTGGTGTAGCGGTGAAATGCTTAGAT
ATCACGAAGAACTCCGATTGCGAAGGCAGCTTGCTGGACTGTAACTGACGCTGATGCTCGAAAGTGTGGG
TATCAAACAGGATTAGATACCCTGGTAGTCCACACAGTAAACGATGAATACTCGCTGTTTGCGATATACA
GTAAGCGGCCAAGCGAAAGCGTTAAGTATTCCACCTGGCATGGTACGCCGGCAACGGTGAAACTCAAAGG
AATTGACGGGGGCCCGCACAAGCGGAGGAACATGTGGTTTAATTCGATGATACGCGAGGAACTTACCCGG
GCTTGAATTGCAACTGAATGATGTGGAGACATGTCAGCCGCAAGGCAGTTGTGAAGGTGCTGCATGGTTG
TCGTCAGCTCGTGCCGTGAGGTGTCGGCTTAAGTGCCATAACGAGCGCAACCCTTATCGATAGTTACCAT
CAGGTGATGCTGGGGACTCTGTCGAGACTGCCGTCGTAAGATGTGAGGAAGGTGGGGATGACGTCAAATC
AGCACGGCCCTTACGTCCGGGGCTACACACGTGTTACAATGGGGGGTACAGAAGGCAGCTACACGGCGAC
GTGATGCTAATCCCTAAAGCCTCTCTCAGTTCGGATTGGAGTCTGCAACCCGACTCCATGAAGCTGGATT
CGCTAGTAATCGCGCATCAGCCACGGCGCGGTGAATACGTTCCCGGGCCTTGTACACACCGCCCGTCAAG
CCATGAAAGCCGGGGGTACCTGAAGTGCGTAACCGCAAGGAGCGCCCTAGGGTAAAACTGGTGATTGGGG
CTAATAGGGATAACAGGGTAATGAGTCGACAAaatgatacggcgaccaccgagatctacactctttccct
acacgacgctcttccgatctGGCACGCGGGTCCGACAGCCagatcggaagagcacacgtctgaactccag
tcacAATCAGTCTCGTatctcgtatgccgtcttctgcttgTTGTCGACTC >231_Bth_Full_TAG_TCT_CAT
TTACAATGAAGAGTTTGATCCTGGCTCAGGATGAACGCTAGCTACAGGCTTAACACATGCAAGTCGAGGG
GCAGCATTTCAGTTTGCTTGCAAACTGGAGATGGCGACCGGCGCACGGGTGAGTAACACGTATCCAACCT
GCCGATAACTCGGGGATAGCCTTTCGAAAGAAAGATTAATACCCGATGGTATAATCAGACCGCATGGTCT
TGTTATTAAAGAATTTCGGTTATCGATGGGGATGCGTTCCATTAGGCAGTTGGTGAGGTAACGGCTCACC
AAACCTTCGATGGATAGGGGTTCTGAGAGGAAGGTCCCCCACATTGGAACTGAGACACGGTCCAAACTCC
TACGGGAGGCAGCAGTGAGGAATATTGGTACAATAGTGGGCGCAGGCCTGAACCAGCCAAGTAGCGTGAA
GGATGACTGCCCTATGGGTTGTAAACTTCTTTTATATGGGAATAAAGTTTTCCACGTGTGGAATTTTGTA
TGTACCATATGAATAAGGATCGGCTAACTCCGTGCCAGCAGCCGCGGTAATACGGAGGATCCGAGCGTTA
TCCGGATTTATTGGGTTTAAATCTGGGAGCGTAGGTGGACAGTTAAGTCAGTTGTGAAAGTTTGCGGCTC
AACCGTAAAATTGCAGTTGATACTGGCTGTCTTGAGTACAGTAGAGGTGGGCGGAATTCGTGGTGTAGCG
GTGAAATGCTTAGATATCACGAAGAACTCCGATTGCGAAGGCAGCTCACTGGACTGCAACTGACACTGAT
GCTCGAAAGTGTGGGTATCAAACAGGATTAGATACCCTGGTAGTCCACACAGTAAACGATGAATACTCGC
TGTTTGCGATATACAGTAAGCGGCCAAGCGAAAGCATTAAGTATTCCACCTGGCATGGTACGCCGGCAAC
GGGTGAAACTCAAAGGAATTGACGGGGGCCCGTACAAGCGGAGGAACATGTGGTTTAATTCGATGATACG
CGAGGAACCTTACCCGGGCTTAAATTGCATTTGAATATATTGGAAACAGTATAGCCGTAAGGCAAATGTG
AAGGTGCTGCATGGTTGTCGTCAGCTCGTGCCGTGAGGTGTCGGCTTAAGTGCCATAACGAGCGCAACCC
TTATCTTTAGTTACTAACAGGTCATGCTGAGGACTCTAGAGAGACTGCCGTCGTAAGATGTGAGGAAGGT
GGGGATGACGTCAAATCAGCACGGCCCTTACGTCCGGGGCTACACACGTGTTACAATGGGGGGTACAGAA
GGCAGCTACCTGGTGACAGGATGCTAATCCCAAAAGCCTCTCTCAGTTCGGATCGAAGTCTGCAACCCGA
CTTCGTCAAGCTGGATTCGCTAGTAATCGCGCATCAGCCATGGCGCGGTGAATACGTTCCCGGGCCTTGT
ACACACCGCCCGTCAAGCCATGAAAGCCGGGGGTACCTGAAGTACGTAACCGCAAGGAGCGTCCTAGGGT
AAAACTGGTAATTGGGGCTAAGTCGTAACAAGGTAGCCGTACCGGAAGGTGCGGCTGGAACACCTCCTTT
CTTAGGGATAACAGGGTAATGAGTCGACAAaatgatacggcgaccaccgagatctacactctttccctac
acgacgctcttccgatctCAAGTCGCATCCGAATATTAagatcggaagagcacacgtctgaactccagtc
acAATCAGTCTCGTatctcgtatgccgtcttctgcttgTTGTCGACTC >232_Bfr_Full_TAG_TCT_CAT
ATGAACGCTAGCTACAGGCTTAACACATGCAAGTCGAGGGGCATCAGGAAGAAAGCTTGCTTTCTTTGCT
GGCGACCGGCGCACGGGTGAGTAACACGTATCCAACCTGCCCTTTACTCGGGGATAGCCTTTCGAAAGAA
AGATTAATACCCGATAGCATAATGATTCCGCATGGTTTCATTATTAAAGGATTCCGGTAAAGGATGGGGA
TGCGTTCCATTAGGTTGTTGGTGAGGTAACGGCTCACCAAGCCTTCGATGGATAGGGGTTCTGAGAGGAA
GGTCCCCCACATTGGAACTGAGACACGGTCCAAACTCCTACGGGAGGCAGCAGTGAGGAATATTGGTACA
ATAGTGGGCGCTAGCCTGAACCAGCCAAGTAGCGTGAAGGATGAAGGCTCTATGGGTCGTAAACTTCTTT
TATATAAGAATAAAGTGCAGTATGTATACTGTTTTGTATGTATTATATGAATAAGGATCGGCTAACTCCG
TGCCAGCAGCCGCGGTAATACGGAGGATCCGAGCGTTATCCGGATTTATTGGGTTTAAATCTGGGAGCGT
AGGTGGACTGGTAAGTCAGTTGTGAAAGTTTGCGGCTCAACCGTAAAATTGCAGTTGATACTGTCAGTCT
TGAGTACAGTAGAGGTGGGCGGAATTCGTGGTGTAGCGGTGAAATGCTTAGATATCACGAAGAACTCCGA
TTGCGAAGGCAGCTCACTGGACTGCAACTGACACTGATGCTCGAAAGTGTGGGTATCAAACAGGATTAGA
TACCCTGGTAGTCCACACAGTAAACGATGAATACTCGCTGTTTGCGATATACAGTAAGCGGCCAAGCGAA
AGCATTAAGTATTCCACCTGGCATGGTACGCCGGCAACGGTGAAACTCAAAGGAATTGACGGGGGCCCGC
ACAAGCGGAGGAACATGTGGTTTAATTCGATGATACGCGAGGAACCTTACCCGGGCTTAAATTGCAGTGG
AATGATGTGGAAACATGTCAGTGAGCAATCACCGCTGTGAAGGTGCTGCATGGTTGTCGTCAGCTCGTGC
CGTGAGGTGTCGGCTTAAGTGCCATAACGAGCGCAACCCTTATCTTTAGTTACTAACAGGTTATGCTGAG
GACTCTAGAGAGACTGCCGTCGTAAGATGTGAGGAAGGTGGGGATGACGTCAAATCAGCACGGCCCTTAC
GTCCGGGGCTACACACGTGTTACAATGGGGGGTACAGAAGGCAGCTAGCGGGTGACCGTATGCTAATCCC
AAAATCCTCTCTCAGTTCGGATCGAAGTCTGCAACCCGACTTCGTGAAGCTGGATTCGCTAGTAATCGCG
CATCAGCCACGGCGCGGTGAATACGTTCCCGGGCCTTGTACACACCGCCCGTCAAGCCATGGGAGCCGGG
GGTACCTGAAGTACGTAACCGCAAGGATCGTCCTAGGGTAAAACTAGGGATAACAGGGTAATGAGTCGAC
AAaatgatacggcgaccaccgagatctacactctttccctacacgacgctcttccgatctCGCGCCGCGG
CAGCAATCCAagatcggaagagcacacgtctgaactccagtcacAATCAGTCTCGTatctcgtatgccgt
cttctgcttgTTGTCGACTC -continued

| Sequence Listing Free Text |
|---|

Size standard sequences

Illumina adapters in lower case
>233_ILL_size_150_ECO_16S
GAGTCGACAAaatgatacggcgaccaccgagatctacactctttccctacacgacgctcttccgatctGA
GCATGCCGATGGTTTGTTAAagatcggaagagcacacgtctgaactccagtcacAATCAGTCTCGTatct
cgtatgccgtcttctgcttgTTGTCGACTCTAGGGATAACAGGGTAATGAGTCGACAAcaagcagaagac
ggcatacgagatTGGTCAACGATAgtctcgtgggctcggagatgtgtataagagacagGCCGCCCGTCAC
AGCACGTActgtctcttatacacatctgacgctgccgacgaATCACCAGGTGTgtgtagatctcggtggt
cgccgtatcattTTGTCGACTC >234_ILL_size_300_ECO_16S
GAGTCGACAAaatgatacggcgaccaccgagatctacactctttccctacacgacgctcttccgatctAG
ACTATCGCCTTTAGCCTCAAATTGAAGAGTTTGATCATGGCTCAGATTGAACGCTGGCGGCAGGCCTAAC
ACATGCAAGTCGAACGGTAACAGGAAGAAGCTTGCTCTTTGCTGACGAGTGGCGGACGGGTGAGTAATGT
CTGGGAAACTGCCTGATGGAGGGGGATAACagatcggaagagcacacgtctgaactccagtcacAATCAG
TCTCGTatctcgtatgccgtcttctgcttgTTGTCGACTCTAGGGATAACAGGGTAATGAGTCGACAAca
agcagaagacggcatacgagatTGGTCAACGATAgtctcgtgggctcggagatgtgtataagagacagGC
AGCTGTTAGAGACGAATCctgtctcttatacacatctgacgctgccgacgaATCACCAGGTGTgtgtaga
tctcggtggtcgccgtatcattTTGTCGACTC >235_ILL_size_450_ECO_16S
GAGTCGACAAaatgatacggcgaccaccgagatctacactctttccctacacgacgctcttccgatctTG
ATGTATATAGCCGGCGGCAAATTGAAGAGTTTGATCATGGCTCAGATTGAACGCTGGCGGCAGGCCTAAC
ACATGCAAGTCGAACGGTAACAGGAAGAAGCTTGCTCTTTGCTGACGAGTGGCGGACGGGTGAGTAATGT
CTGGGAAACTGCCTGATGGAGGGGGATAACTACTGGAAACGGTAGCTAATACCGCATAACGTCGCAAGAC
CAAAGAGGGGGACCTTCGGGCCTCTTGCCATCGGATGTGCCCAGATGGGATTAGCTAGTAGGTGGGGTAA
CGGCTCACCTAGGCGACGATCCCTAGCTGGTCTGAGAGGAagatcggaagagcacacgtctgaactccag
tcacAATCAGTCTCGTatctcgtatgccgtcttctgcttgTTGTCGACTCTAGGGATAACAGGGTAATGA
GTCGACAAcaagcagaagacggcatacgagatTGGTCAACGATAgtctcgtgggctcggagatgtgtata
agagacagGGACAAACAGAAATATCACGctgtctcttatacacatctgacgctgccgacgaATCACCAGG
TGTgtgtagatctcggtggtcgccgtatcattTTGTCGACTC >236_ILL_size_600_ECO_16S
GAGTCGACAAaatgatacggcgaccaccgagatctacactctttccctacacgacgctcttccgatctCA
ACGGAACGTGCACTGCAGAAATTGAAGAGTTTGATCATGGCTCAGATTGAACGCTGGCGGCAGGCCTAAC
ACATGCAAGTCGAACGGTAACAGGAAGAAGCTTGCTCTTTGCTGACGAGTGGCGGACGGGTGAGTAATGT
CTGGGAAACTGCCTGATGGAGGGGGATAACTACTGGAAACGGTAGCTAATACCGCATAACGTCGCAAGAC
CAAAGAGGGGGACCTTCGGGCCTCTTGCCATCGGATGTGCCCAGATGGGATTAGCTAGTAGGTGGGGTAA
CGGCTCACCTAGGCGACGATCCCTAGCTGGTCTGAGAGGATGACCAGCCACACTGGAACTGAGACACGGT
CCAGACTCCTACGGGAGGCAGCAGTGGGGAATATTGCACAATGGGCGCAAGCCTGATGCAGCCATGCCGC
GTGTATGAAGAAGGCCTTCGGGTTGTAAAGTACTTTCAGCGGGGAGGAAGagatcggaagagcacacgtc
tgaactccagtcacAATCAGTCTCGTatctcgtatgccgtcttctgcttgTTGTCGACTCTAGGGATAAC
AGGGTAATGAGTCGACAAcaagcagaagacggcatacgagatTGGTCAACGATAgtctcgtgggctcgga
gatgtgtataagagacagGGCCACCGTAAACAGTGCGActgtctcttatacacatctgacgctgccgacg
aATCACCAGGTGTgtgtagatctcggtggtcgccgtatcattTTGTCGACTC >237_ILL_size_750_ECO_16S
GAGTCGACAAaatgatacggcgaccaccgagatctacactctttccctacacgacgctcttccgatctAA
TGTGAGCGTATCAGGAGAAAATTGAAGAGTTTGATCATGGCTCAGATTGAACGCTGGCGGCAGGCCTAAC
ACATGCAAGTCGAACGGTAACAGGAAGAAGCTTGCTCTTTGCTGACGAGTGGCGGACGGGTGAGTAATGT
CTGGGAAACTGCCTGATGGAGGGGGATAACTACTGGAAACGGTAGCTAATACCGCATAACGTCGCAAGAC
CAAAGAGGGGGACCTTCGGGCCTCTTGCCATCGGATGTGCCCAGATGGGATTAGCTAGTAGGTGGGGTAA
CGGCTCACCTAGGCGACGATCCCTAGCTGGTCTGAGAGGATGACCAGCCACACTGGAACTGAGACACGGT
CCAGACTCCTACGGGAGGCAGCAGTGGGGAATATTGCACAATGGGCGCAAGCCTGATGCAGCCATGCCGC
GTGTATGAAGAAGGCCTTCGGGTTGTAAAGTACTTTCAGCGGGGAGGAAGGGAGTAAAGTTAATACCTTT
GCTCATTGACGTTACCCGCAGAAGAAGCACCGGCTAACTCCGTGCCAGCAGCCGCGGTAATACGGAGGGT
GCAAGCGTTAATCGGAATTACTGGGCGTAAAGCGCACGCAGGCGGTTTGTTAAGTCAGATagatcggaag
agcacacgtctgaactccagtcacAATCAGTCTCGTatctcgtatgccgtcttctgcttgTTGTCGACTC
TAGGGATAACAGGGTAATGAGTCGACAAcaagcagaagacggcatacgagatTGGTCAACGATAgtctcg
tgggctcggagatgtgtataagagacagTAGCGCCCACAGCAAGTGATctgtctcttatacacatctgac
gctgccgacgaATCACCAGGTGTgtgtagatctcggtggtcgccgtatcattTTGTCGACTC >238_ILL_size_900_ECO_16S
GAGTCGACAAaatgatacggcgaccaccgagatctacactctttccctacacgacgctcttccgatctCG
GCGGGTAGTACCTGTACCAAATTGAAGAGTTTGATCATGGCTCAGATTGAACGCTGGCGGCAGGCCTAAC
ACATGCAAGTCGAACGGTAACAGGAAGAAGCTTGCTCTTTGCTGACGAGTGGCGGACGGGTGAGTAATGT
CTGGGAAACTGCCTGATGGAGGGGGATAACTACTGGAAACGGTAGCTAATACCGCATAACGTCGCAAGAC
CAAAGAGGGGGACCTTCGGGCCTCTTGCCATCGGATGTGCCCAGATGGGATTAGCTAGTAGGTGGGGTAA
CGGCTCACCTAGGCGACGATCCCTAGCTGGTCTGAGAGGATGACCAGCCACACTGGAACTGAGACACGGT
CCAGACTCCTACGGGAGGCAGCAGTGGGGAATATTGCACAATGGGCGCAAGCCTGATGCAGCCATGCCGC
GTGTATGAAGAAGGCCTTCGGGTTGTAAAGTACTTTCAGCGGGGAGGAAGGGAGTAAAGTTAATACCTTT
GCTCATTGACGTTACCCGCAGAAGAAGCACCGGCTAACTCCGTGCCAGCAGCCGCGGTAATACGGAGGGT
GCAAGCGTTAATCGGAATTACTGGGCGTAAAGCGCACGCAGGCGGTTTGTTAAGTCAGATGTGAAATCCC
CGGGCTCAACCTGGGAACTGCATCTGATACTGGCAAGCTTGAGTCTCGTAGAGGGGGGTAGAATTCCAGG
TGTAGCGGTGAAATGCGTAGAGATCTGGAGGAATACCGGTGGCGAAGGCGGCCCCCTGGACGAAGACTGA -continued

| Sequence Listing Free Text |
| --- |

agatcggaagagcacacgtctgaactccagtcacAATCAGTCTCGTatctcgtatgccgtcttctgcttg
TTGTCGACTCTAGGGATAACAGGGTAATGAGTCGACAAcaagcagaagacggcatacgagatTGGTCAAC
GATAgtctcgtgggctcggagatgtgtataagagacagACAAGCCCTAATGATGATAGctgtctcttata
cacatctgacgctgccgacgaATCACCAGGTGTgtgtagatctcggtggtcgccgtatcattTTGTCGAC
TC >239_ILL_size_1050_ECO_16S
GAGTCGACAAaatgatacggcgaccaccgagatctacactctttccctacacgacgctcttccgatctGT
TCTCCTGCTACAGAGGTTAAATTGAAGAGTTTGATCATGGCTCAGATTGAACGCTGGCGGCAGGCCTAAC
ACATGCAAGTCGAACGGTAACAGGAAGAAGCTTGCTCTTTGCTGACGAGTGGCGGACGGGTGAGTAATGT
CTGGGAAACTGCCTGATGGAGGGGGATAACTACTGGAAACGGTAGCTAATACCGCATAACGTCGCAAGAC
CAAAGAGGGGGACCTTCGGGCCTCTTGCCATCGGATGTGCCCAGATGGGATTAGCTAGTAGGTGGGGTAA
CGGCTCACCTAGGCGACGATCCCTAGCTGGTCTGAGAGGATGACCAGCCACACTGGAACTGAGACACGGT
CCAGACTCCTACGGGAGGCAGCAGTGGGGAATATTGCACAATGGGCGCAAGCCTGATGCAGCCATGCCGC
GTGTATGAAGAAGGCCTTCGGGTTGTAAAGTACTTTCAGCGGGGAGGAAGGGAGTAAAGTTAATACCTTT
GCTCATTGACGTTACCCGCAGAAGAAGCACCGGCTAACTCCGTGCCAGCAGCCGCGGTAATACGGAGGGT
GCAAGCGTTAATCGGAATTACTGGGCGTAAAGCGCACGCAGGCGGTTTGTTAAGTCAGATGTGAAATCCC
CGGGCTCAACCTGGGAACTGCATCTGATACTGGCAAGCTTGAGTCTCGTAGAGGGGGGTAGAATTCCAGG
TGTAGCGGTGAAATGCGTAGAGATCTGGAGGAATACCGGTGGCGAAGGCGGCCCCCTGGACGAAGACTGA
CGCTCAGGTGCGAAAGCGTGGGGAGCAAACAGGATTAGATACCCTGGTAGTCCACGCCGTAAACGATGTC
GACTTGGAGGTTGTGCCCTTGAGGCGTGGCTTCCGGAGCTAACGCGTTAAGTCGACCGCCTGGGGAGTAC
GGCCGCAAGGagatcggaagagcacacgtctgaactccagtcacAATCAGTCTCGTatctcgtatgccgt
cttctgcttgTTGTCGACTCTAGGGATAACAGGGTAATGAGTCGACAAcaagcagaagacggcatacgag
atTGGTCAACGATAgtctcgtgggctcggagatgtgtataagagacagACGCTGATAAATATCGAGTTct
gtctcttatacacatctgacgctgccgacgaATCACCAGGTGTgtgtagatctcggtggtcgccgtatca
ttTTGTCGACTC >240_ILL_size_1200_ECO_16S
GAGTCGACAAaatgatacggcgaccaccgagatctacactctttccctacacgacgctcttccgatctCC
CACATGCCGGAACGCACCAAATTGAAGAGTTTGATCATGGCTCAGATTGAACGCTGGCGGCAGGCCTAAC
ACATGCAAGTCGAACGGTAACAGGAAGAAGCTTGCTCTTTGCTGACGAGTGGCGGACGGGTGAGTAATGT
CTGGGAAACTGCCTGATGGAGGGGGATAACTACTGGAAACGGTAGCTAATACCGCATAACGTCGCAAGAC
CAAAGAGGGGGACCTTCGGGCCTCTTGCCATCGGATGTGCCCAGATGGGATTAGCTAGTAGGTGGGGTAA
CGGCTCACCTAGGCGACGATCCCTAGCTGGTCTGAGAGGATGACCAGCCACACTGGAACTGAGACACGGT
CCAGACTCCTACGGGAGGCAGCAGTGGGGAATATTGCACAATGGGCGCAAGCCTGATGCAGCCATGCCGC
GTGTATGAAGAAGGCCTTCGGGTTGTAAAGTACTTTCAGCGGGGAGGAAGGGAGTAAAGTTAATACCTTT
GCTCATTGACGTTACCCGCAGAAGAAGCACCGGCTAACTCCGTGCCAGCAGCCGCGGTAATACGGAGGGT
GCAAGCGTTAATCGGAATTACTGGGCGTAAAGCGCACGCAGGCGGTTTGTTAAGTCAGATGTGAAATCCC
CGGGCTCAACCTGGGAACTGCATCTGATACTGGCAAGCTTGAGTCTCGTAGAGGGGGGTAGAATTCCAGG
TGTAGCGGTGAAATGCGTAGAGATCTGGAGGAATACCGGTGGCGAAGGCGGCCCCCTGGACGAAGACTGA
CGCTCAGGTGCGAAAGCGTGGGGAGCAAACAGGATTAGATACCCTGGTAGTCCACGCCGTAAACGATGTC
GACTTGGAGGTTGTGCCCTTGAGGCGTGGCTTCCGGAGCTAACGCGTTAAGTCGACCGCCTGGGGAGTAC
GGCCGCAAGGTTAAAACTCAAATGAATTGACGGGGGCCCGCACAAGCGGTGGAGCATGTGGTTTAATTCG
ATGCAACGCGAAGAACCTTACCTGGTCTTGACATCCACGGAAGTTTTCAGAGATGAGAATGTGCCTTCGG
GAACCGTGAGACAGGTGCTGagatcggaagagcacacgtctgaactccagtcacAATCAGTCTCGTatct
cgtatgccgtcttctgcttgTTGTCGACTCTAGGGATAACAGGGTAATGAGTCGACAAcaagcagaagac
ggcatacgagatTGGTCAACGATAgtctcgtgggctcggagatgtgtataagagacagTCGTTCTAAGAG
GGTGCCAGctgtctcttatacacatctgacgctgccgacgaATCACCAGGTGTgtgtagatctcggtggt
cgccgtatcattTTGTCGACTC >241_ILL_size_1350_ECO_16S
GAGTCGACAAaatgatacggcgaccaccgagatctacactctttccctacacgacgctcttccgatctCC
CAAACGTCGGAAAGGTCTAAATTGAAGAGTTTGATCATGGCTCAGATTGAACGCTGGCGGCAGGCCTAAC
ACATGCAAGTCGAACGGTAACAGGAAGAAGCTTGCTCTTTGCTGACGAGTGGCGGACGGGTGAGTAATGT
CTGGGAAACTGCCTGATGGAGGGGGATAACTACTGGAAACGGTAGCTAATACCGCATAACGTCGCAAGAC
CAAAGAGGGGGACCTTCGGGCCTCTTGCCATCGGATGTGCCCAGATGGGATTAGCTAGTAGGTGGGGTAA
CGGCTCACCTAGGCGACGATCCCTAGCTGGTCTGAGAGGATGACCAGCCACACTGGAACTGAGACACGGT
CCAGACTCCTACGGGAGGCAGCAGTGGGGAATATTGCACAATGGGCGCAAGCCTGATGCAGCCATGCCGC
GTGTATGAAGAAGGCCTTCGGGTTGTAAAGTACTTTCAGCGGGGAGGAAGGGAGTAAAGTTAATACCTTT
GCTCATTGACGTTACCCGCAGAAGAAGCACCGGCTAACTCCGTGCCAGCAGCCGCGGTAATACGGAGGGT
GCAAGCGTTAATCGGAATTACTGGGCGTAAAGCGCACGCAGGCGGTTTGTTAAGTCAGATGTGAAATCCC
CGGGCTCAACCTGGGAACTGCATCTGATACTGGCAAGCTTGAGTCTCGTAGAGGGGGGTAGAATTCCAGG
TGTAGCGGTGAAATGCGTAGAGATCTGGAGGAATACCGGTGGCGAAGGCGGCCCCCTGGACGAAGACTGA
CGCTCAGGTGCGAAAGCGTGGGGAGCAAACAGGATTAGATACCCTGGTAGTCCACGCCGTAAACGATGTC
GACTTGGAGGTTGTGCCCTTGAGGCGTGGCTTCCGGAGCTAACGCGTTAAGTCGACCGCCTGGGGAGTAC
GGCCGCAAGGTTAAAACTCAAATGAATTGACGGGGGCCCGCACAAGCGGTGGAGCATGTGGTTTAATTCG
ATGCAACGCGAAGAACCTTACCTGGTCTTGACATCCACGGAAGTTTTCAGAGATGAGAATGTGCCTTCGG
GAACCGTGAGACAGGTGCTGCATGGCTGTCGTCAGCTCGTGTTGTGAAATGTTGGGTTAAGTCCCGCAAC
GAGCGCAACCCTTATCCTTTGTTGCCAGCGGTCCGGCCGGGAACTCAAAGGAGACTGCCAGTGATAAACT
GGAGGAAGGTGGGGATGACGTCAAGTCATCagatcggaagagcacacgtctgaactccagtcacAATCAG
TCTCGTatctcgtatgccgtcttctgcttgTTGTCGACTCTAGGGATAACAGGGTAATGAGTCGACAAca
agcagaagacggcatacgagatTGGTCAACGATAgtctcgtgggctcggagatgtgtataagagacagTG
CAACTCAACGGTCCCAGGctgtctcttatacacatctgacgctgccgacgaATCACCAGGTGTgtgtaga
tctcggtggtcgccgtatcattTTGTCGACTC -continued

| Sequence Listing Free Text |
| --- |

>242_ILL_size_1500_ECO_16S
GAGTCGACAAaatgatacggcgaccaccgagatctacactctttccctacacgacgctcttccgatctAA
CCAGAGGATGAGACACGTAAATTGAAGAGTTTGATCATGGCTCAGATTGAACGCTGGCGGCAGGCCTAAC
ACATGCAAGTCGAACGGTAACAGGAAGAAGCTTGCTCTTTGCTGACGAGTGGCGGACGGGTGAGTAATGT
CTGGGAAACTGCCTGATGGAGGGGGATAACTACTGGAAACGGTAGCTAATACCGCATAACGTCGCAAGAC
CAAAGAGGGGGACCTTCGGGCCTCTTGCCATCGGATGTGCCCAGATGGGATTAGCTAGTAGGTGGGGTAA
CGGCTCACCTAGGCGACGATCCCTAGCTGGTCTGAGAGGATGACCAGCCACACTGGAACTGAGACACGGT
CCAGACTCCTACGGGAGGCAGCAGTGGGGAATATTGCACAATGGGCGCAAGCCTGATGCAGCCATGCCGC
GTGTATGAAGAAGGCCTTCGGGTTGTAAAGTACTTTCAGCGGGGAGGAAGGGAGTAAAGTTAATACCTTT
GCTCATTGACGTTACCCGCAGAAGAAGCACCGGCTAACTCCGTGCCAGCAGCCGCGGTAATACGGAGGGT
GCAAGCGTTAATCGGAATTACTGGGCGTAAAGCGCACGCAGGCGGTTTGTTAAGTCAGATGTGAAATCCC
CGGGCTCAACCTGGGAACTGCATCTGATACTGGCAAGCTTGAGTCTCGTAGAGGGGGGTAGAATTCCAGG
TGTAGCGGTGAAATGCGTAGAGATCTGGAGGAATACCGGTGGCGAAGGCGGCCCCCTGGACGAAGACTGA
CGCTCAGGTGCGAAAGCGTGGGGAGCAAACAGGATTAGATACCCTGGTAGTCCACGCCGTAAACGATGTC
GACTTGGAGGTTGTGCCCTTGAGGCGTGGCTTCCGGAGCTAACGCGTTAAGTCGACCGCCTGGGGAGTAC
GGCCGCAAGGTTAAAACTCAAATGAATTGACGGGGGCCCGCACAAGCGGTGGAGCATGTGGTTTAATTCG
ATGCAACGCGAAGAACCTTACCTGGTCTTGACATCCACGGAAGTTTTCAGAGATGAGAATGTGCCTTCGG
GAACCGTGAGACAGGTGCTGCATGGCTGTCGTCAGCTCGTGTTGTGAAATGTTGGGTTAAGTCCCGCAAC
GAGCGCAACCCTTATCCTTTGTTGCCAGCGGTCCGGCCGGGAACTCAAAGGAGACTGCCAGTGATAAACT
GGAGGAAGGTGGGGATGACGTCAAGTCATCATGGCCCTTACGACCAGGGCTACACACGTGCTACAATGGC
GCATACAAAGAGAAGCGACCTCGCGAGAGCAAGCGGACCTCATAAAGTGCGTCGTAGTCCGGATTGGAGT
CTGCAACTCGACTCCATGAAGTCGGAATCGCTAGTAATCGagatcggaagagcacacgtctgaactccag
tcacAATCAGTCTCGTatctcgtatgccgtcttctgcttgTTGTCGACTCTAGGGATAACAGGGTAATGA
GTCGACAAcaagcagaagacggcatacgagatTGGTCAACGATAgtctcgtgggctcggagatgtgtata
agagacagTGGCTCCTTCTGTTAAGGCActgtctcttatacacatctgacgctgccgacgaATCACCAGG
TGTgtgtagatctcggtggtcgccgtatcattTTGTCGACTC >243_ILL_size_150_GAPDH
GAGTCGACAAaatgatacggcgaccaccgagatctacactctttccctacacgacgctcttccgatctCC
ACCTAACAGACACTTGTTAGagatcggaagagcacacgtctgaactccagtcacAATCAGTCTCGTatct
cgtatgccgtcttctgcttgTTGTCGACTCTAGGGATAACAGGGTAATGAGTCGACAAcaagcagaagac
ggcatacgagatTGGTCAACGATAgtctcgtgggctcggagatgtgtataagagacagGGTAAGTAGTGC
GTGAGGGTctgtctcttatacacatctgacgctgccgacgaATCACCAGGTGTgtgtagatctcggtggt
cgccgtatcattTTGTCGACTC >244_ILL_size_300_GAPDH
GAGTCGACAAaatgatacggcgaccaccgagatctacactctttccctacacgacgctcttccgatctGC
GCCCTGGCGCCGGCCAGGTTTTTAAGGCGCTTATATAATCAAACCCTTTGTAAAAATTAAAGTTTTAAAT
GGAATTCTAATCGATTTATTTCACATTAGCTTTATTTAAGTGTGACCTACGCAGAAAGCTAGCGAAATAC
TCATCAACCCTCCCCCGCCATCGCAGCGCCagatcggaagagcacacgtctgaactccagtcacAATCAG
TCTCGTatctcgtatgccgtcttctgcttgTTGTCGACTCTAGGGATAACAGGGTAATGAGTCGACAAca
agcagaagacggcatacgagatTGGTCAACGATAgtctcgtgggctcggagatgtgtataagagacagAC
GGAGTAGTACGGTCAAATctgtctcttatacacatctgacgctgccgacgaATCACCAGGTGTgtgtaga
tctcggtggtcgccgtatcattTTGTCGACTC >245_ILL_size_450_GAPDH
GAGTCGACAAaatgatacggcgaccaccgagatctacactctttccctacacgacgctcttccgatctCT
ACTAAACAATAATGGGAATTTTTAAGGCGCTTATATAATCAAACCCTTTGTAAAAATTAAAGTTTTAAAT
GGAATTCTAATCGATTTATTTCACATTAGCTTTATTTAAGTGTGACCTACGCAGAAAGCTAGCGAAATAC
TCATCAACCCTCCCCCGCCATCGCAGCGCCATTCTCCTAATTTGCGAAAAAAGCTCCGGGAAAAGGAAAA
AGCGGCAGTCGTAATAGCGAACTGAAACTGAACGAGAGTAAAAGTGAAAAGACAGCAGGAACTCAGCCAT
GTCGAAGATCGGAATTAACGGATTTGGCCGCATCGGCCGCagatcggaagagcacacgtctgaactccag
tcacAATCAGTCTCGTatctcgtatgccgtcttctgcttgTTGTCGACTCTAGGGATAACAGGGTAATGA
GTCGACAAcaagcagaagacggcatacgagatTGGTCAACGATAgtctcgtgggctcggagatgtgtata
agagacagGGATTGCCACACGCGATAGActgtctcttatacacatctgacgctgccgacgaATCACCAGG
TGTgtgtagatctcggtggtcgccgtatcattTTGTCGACTC >246_ILL_size_600_GAPDH
GAGTCGACAAaatgatacggcgaccaccgagatctacactctttccctacacgacgctcttccgatctCT
GTGTTCGGCCTTCGAGATTTTTAAGGCGCTTATATAATCAAACCCTTTGTAAAAATTAAAGTTTTAAAT
GGAATTCTAATCGATTTATTTCACATTAGCTTTATTTAAGTGTGACCTACGCAGAAAGCTAGCGAAATAC
TCATCAACCCTCCCCCGCCATCGCAGCGCCATTCTCCTAATTTGCGAAAAAAGCTCCGGGAAAAGGAAAA
AGCGGCAGTCGTAATAGCGAACTGAAACTGAACGAGAGTAAAAGTGAAAAGACAGCAGGAACTCAGCCAT
GTCGAAGATCGGAATTAACGGATTTGGCCGCATCGGCCGCTTGGTGCTCCGCGCCGCCATCGATAAGGGC
GCCTCCGTGGTGGCCGTCAACGATCCCTTCATCGATGTCAACTACATGGTTTACCTGTTTAAATTCGACT
CGACTCACGGTCGTTTCAAGGGCACCGTTGCGGCTGAGGGCGGATTCCTGagatcggaagagcacacgtc
tgaactccagtcacAATCAGTCTCGTatctcgtatgccgtcttctgcttgTTGTCGACTCTAGGGATAAC
AGGGTAATGAGTCGACAAcaagcagaagacggcatacgagatTGGTCAACGATAgtctcgtgggctcgga
gatgtgtataagagacagTAGTGTTTAAGTGCGAACCTctgtctcttatacacatctgacgctgccgacg
aATCACCAGGTGTgtgtagatctcggtggtcgccgtatcattTTGTCGACTC >247_ILL_size_750_GAPDH
GAGTCGACAAaatgatacggcgaccaccgagatctacactctttccctacacgacgctcttccgatctTA
TGAAATCGGAGTATCAGTTTTTTAAGGCGCTTATATAATCAAACCCTTTGTAAAAATTAAAGTTTTAAAT
GGAATTCTAATCGATTTATTTCACATTAGCTTTATTTAAGTGTGACCTACGCAGAAAGCTAGCGAAATAC
TCATCAACCCTCCCCCGCCATCGCAGCGCCATTCTCCTAATTTGCGAAAAAAGCTCCGGGAAAAGGAAAA -continued

| Sequence Listing Free Text |
| --- |

AGCGGCAGTCGTAATAGCGAACTGAAACTGAACGAGAGTAAAAGTGAAAAGACAGCAGGAACTCAGCCAT
GTCGAAGATCGGAATTAACGGATTTGGCCGCATCGGCCGCTTGGTGCTCCGCGCCGCCATCGATAAGGGC
GCCTCCGTGGTGGCCGTCAACGATCCCTTCATCGATGTCAACTACATGGTTTACCTGTTTAAATTCGACT
CGACTCACGGTCGTTTCAAGGGCACCGTTGCGGCTGAGGGCGGATTCCTGGTGGTGAACGGCCAGAAGAT
CACCGTGTTCAGCGAGCGCGACCCGGCCAACATCAACTGGGCCAGTGCTGGAGCCGAGTATGTGGTGGAG
TCCACCGGAGTGTTCACCACCATTGACAAGGCGTCCACCCACTTGAAGGGCGGCGCCAAGagatcggaag
agcacacgtctgaactccagtcacAATCAGTCTCGTatctcgtatgccgtcttctgcttgTTGTCGACTC
TAGGGATAACAGGGTAATGAGTCGACAAcaagcagaagacggcatacgagatTGGTCAACGATAgtctcg
tgggctcggagatgtgtataagagacagAAGAGCCCTGCCTCAAGTCCctgtctcttatacacatctgac
gctgccgacgaATCACCAGGTGTgtgtagatctcggtggtcgccgtatcattTTGTCGACTC >248_ILL_size_900_GAPDH
GAGTCGACAAaatgatacggcgaccaccgagatctacactctttccctacacgacgctcttccgatctAG
CCAAACGTCTGAACAGATTTTTTAAGGCGCTTATATAATCAAACCCTTTGTAAAAATTAAAGTTTTAAAT
GGAATTCTAATCGATTTATTTCACATTAGCTTTATTTAAGTGTGACCTACGCAGAAAGCTAGCGAAATAC
TCATCAACCCTCCCCCGCCATCGCAGCGCCATTCTCCTAATTTGCGAAAAAAGCTCCGGGAAAAGGAAAA
AGCGGCAGTCGTAATAGCGAACTGAAACTGAACGAGAGTAAAAGTGAAAAGACAGCAGGAACTCAGCCAT
GTCGAAGATCGGAATTAACGGATTTGGCCGCATCGGCCGCTTGGTGCTCCGCGCCGCCATCGATAAGGGC
GCCTCCGTGGTGGCCGTCAACGATCCCTTCATCGATGTCAACTACATGGTTTACCTGTTTAAATTCGACT
CGACTCACGGTCGTTTCAAGGGCACCGTTGCGGCTGAGGGCGGATTCCTGGTGGTGAACGGCCAGAAGAT
CACCGTGTTCAGCGAGCGCGACCCGGCCAACATCAACTGGGCCAGTGCTGGAGCCGAGTATGTGGTGGAG
TCCACCGGAGTGTTCACCACCATTGACAAGGCGTCCACCCACTTGAAGGGCGGCGCCAAGAAGGTCATCA
TCTCGGCCCCATCCGCCGATGCGCCCATGTTCGTGTGCGGCGTTAACCTGGACGCCTACAGCCCCGACAT
GAAGGTGGTCTCCAACGCCTCGTGCACCACCAACTGCCTGGCTCCCCTGGCCAAGGTCATCAATGACAAC
agatcggaagagcacacgtctgaactccagtcacAATCAGTCTCGTatctcgtatgccgtcttctgcttg
TTGTCGACTCTAGGGATAACAGGGTAATGAGTCGACAAcaagcagaagacggcatacgagatTGGTCAAC
GATAgtctcgtgggctcggagatgtgtataagagacagCCGTGTCGAACGCCACTCGActgtctcttata
cacatctgacgctgccgacgaATCACCAGGTGTgtgtagatctcggtggtcgccgtatcattTTGTCGAC
TC >249_ILL_size_1050_GAPDH
GAGTCGACAAaatgatacggcgaccaccgagatctacactctttccctacacgacgctcttccgatctCA
AGTCCAGGGCACTCGCCTTTTTTAAGGCGCTTATATAATCAAACCCTTTGTAAAAATTAAAGTTTTAAAT
GGAATTCTAATCGATTTATTTCACATTAGCTTTATTTAAGTGTGACCTACGCAGAAAGCTAGCGAAATAC
TCATCAACCCTCCCCCGCCATCGCAGCGCCATTCTCCTAATTTGCGAAAAAAGCTCCGGGAAAAGGAAAA
AGCGGCAGTCGTAATAGCGAACTGAAACTGAACGAGAGTAAAAGTGAAAAGACAGCAGGAACTCAGCCAT
GTCGAAGATCGGAATTAACGGATTTGGCCGCATCGGCCGCTTGGTGCTCCGCGCCGCCATCGATAAGGGC
GCCTCCGTGGTGGCCGTCAACGATCCCTTCATCGATGTCAACTACATGGTTTACCTGTTTAAATTCGACT
CGACTCACGGTCGTTTCAAGGGCACCGTTGCGGCTGAGGGCGGATTCCTGGTGGTGAACGGCCAGAAGAT
CACCGTGTTCAGCGAGCGCGACCCGGCCAACATCAACTGGGCCAGTGCTGGAGCCGAGTATGTGGTGGAG
TCCACCGGAGTGTTCACCACCATTGACAAGGCGTCCACCCACTTGAAGGGCGGCGCCAAGAAGGTCATCA
TCTCGGCCCCATCCGCCGATGCGCCCATGTTCGTGTGCGGCGTTAACCTGGACGCCTACAGCCCCGACAT
GAAGGTGGTCTCCAACGCCTCGTGCACCACCAACTGCCTGGCTCCCCTGGCCAAGGTCATCAATGACAAC
TTCGAGATCGTCGAGGGTCTGATGACCACCGTGCACGCCACCACTGCCACCCAGAAGACCGTCGACGGTC
CCTCTGGCAAACTGTGGCGCGATGGACGTGGCGCCGCCCAGAACATCATCCCGGCCGCCACCGGAGCCGC
CAAGGCTGTGagatcggaagagcacacgtctgaactccagtcacAATCAGTCTCGTatctcgtatgccgt
cttctgcttgTTGTCGACTCTAGGGATAACAGGGTAATGAGTCGACAAcaagcagaagacggcatacgag
atTGGTCAACGATAgtctcgtgggctcggagatgtgtataagagacagTATGCCATGGGCTTTCGAACct
gtctcttatacacatctgacgctgccgacgaATCACCAGGTGTgtgtagatctcggtggtcgccgtatca
ttTTGTCGACTC >250_ILL_size_1200_GAPDH
GAGTCGACAAaatgatacggcgaccaccgagatctacactctttccctacacgacgctcttccgatctAT
TTCTACTCATAGGTTCATTTTTTAAGGCGCTTATATAATCAAACCCTTTGTAAAAATTAAAGTTTTAAAT
GGAATTCTAATCGATTTATTTCACATTAGCTTTATTTAAGTGTGACCTACGCAGAAAGCTAGCGAAATAC
TCATCAACCCTCCCCCGCCATCGCAGCGCCATTCTCCTAATTTGCGAAAAAAGCTCCGGGAAAAGGAAAA
AGCGGCAGTCGTAATAGCGAACTGAAACTGAACGAGAGTAAAAGTGAAAAGACAGCAGGAACTCAGCCAT
GTCGAAGATCGGAATTAACGGATTTGGCCGCATCGGCCGCTTGGTGCTCCGCGCCGCCATCGATAAGGGC
GCCTCCGTGGTGGCCGTCAACGATCCCTTCATCGATGTCAACTACATGGTTTACCTGTTTAAATTCGACT
CGACTCACGGTCGTTTCAAGGGCACCGTTGCGGCTGAGGGCGGATTCCTGGTGGTGAACGGCCAGAAGAT
CACCGTGTTCAGCGAGCGCGACCCGGCCAACATCAACTGGGCCAGTGCTGGAGCCGAGTATGTGGTGGAG
TCCACCGGAGTGTTCACCACCATTGACAAGGCGTCCACCCACTTGAAGGGCGGCGCCAAGAAGGTCATCA
TCTCGGCCCCATCCGCCGATGCGCCCATGTTCGTGTGCGGCGTTAACCTGGACGCCTACAGCCCCGACAT
GAAGGTGGTCTCCAACGCCTCGTGCACCACCAACTGCCTGGCTCCCCTGGCCAAGGTCATCAATGACAAC
TTCGAGATCGTCGAGGGTCTGATGACCACCGTGCACGCCACCACTGCCACCCAGAAGACCGTCGACGGTC
CCTCTGGCAAACTGTGGCGCGATGGACGTGGCGCCGCCCAGAACATCATCCCGGCCGCCACCGGAGCCGC
CAAGGCTGTGGGCAAGGTCATCCCCGCCCTGAACGGCAAGCTGACCGGCATGGCTTTCCGCGTGCCCACG
CCCAATGTCTCCGTTGTGGATCTTACCGTCCGCTTGGGCAAGGGAGCCACCTATGACGAAATCAAGGCTA
AGGTCGAGGAGGCCTCCAAGagatcggaagagcacacgtctgaactccagtcacAATCAGTCTCGTatct
cgtatgccgtcttctgcttgTTGTCGACTCTAGGGATAACAGGGTAATGAGTCGACAAcaagcagaagac
ggcatacgagatTGGTCAACGATAgtctcgtgggctcggagatgtgtataagagacagTTAGATCAGATA
GAAGGTACctgtctcttatacacatctgacgctgccgacgaATCACCAGGTGTgtgtagatctcggtggt
cgccgtatcattTTGTCGACTC >251_ILL_size_1350_GAPDH
GAGTCGACAAaatgatacggcgaccaccgagatctacactctttccctacacgacgctcttccgatctTT
AAGACTGTTAGTTCGAGGTTTTTAAGGCGCTTATATAATCAAACCCTTTGTAAAAATTAAAGTTTTAAAT -continued Sequence Listing Free Text GGAATTCTAATCGATTTATTTCACATTAGCTTTATTTAAGTGTGACCTACGCAGAAAGCTAGCGAAATAC
TCATCAACCCTCCCCCGCCATCGCAGCGCCATTCTCCTAATTTGCGAAAAAAGCTCCGGGAAAAGGAAAA
AGCGGCAGTCGTAATAGCGAACTGAAACTGAACGAGAGTAAAAGTGAAAAGACAGCAGGAACTCAGCCAT
GTCGAAGATCGGAATTAACGGATTTGGCCGCATCGGCCGCTTGGTGCTCCGCGCCGCCATCGATAAGGGC
GCCTCCGTGGTGGCCGTCAACGATCCCTTCATCGATGTCAACTACATGGTTTACCTGTTTAAATTCGACT
CGACTCACGGTCGTTTCAAGGGCACCGTTGCGGCTGAGGGCGGATTCCTGGTGGTGAACGGCCAGAAGAT
CACCGTGTTCAGCGAGCGCGACCCGGCCAACATCAACTGGGCCAGTGCTGGAGCCGAGTATGTGGTGGAG
TCCACCGGAGTGTTCACCACCATTGACAAGGCGTCCACCCACTTGAAGGGCGGCGCCAAGAAGGTCATCA
TCTCGGCCCCATCCGCCGATGCGCCCATGTTCGTGTGCGGCGTTAACCTGGACGCCTACAGCCCCGACAT
GAAGGTGGTCTCCAACGCCTCGTGCACCACCAACTGCCTGGCTCCCCTGGCCAAGGTCATCAATGACAAC
TTCGAGATCGTCGAGGGTCTGATGACCACCGTGCACGCCACCACTGCCACCCAGAAGACCGTCGACGGTC
CCTCTGGCAAACTGTGGCGCGATGGACGTGGCGCCGCCCAGAACATCATCCCGGCCGCCACCGGAGCCGC
CAAGGCTGTGGGCAAGGTCATCCCCGCCCTGAACGGCAAGCTGACCGGCATGGCTTTCCGCGTGCCCACG
CCCAATGTCTCCGTTGTGGATCTTACCGTCCGCTTGGGCAAGGGAGCCACCTATGACGAAATCAAGGCTA
AGGTCGAGGAGGCCTCCAAGGGACCCCTGAAGGGAATCCTGGGCTACACCGATGAGGAGGTGGTCTCCAC
CGACTTCTTCAGCGACACCCATTCGTCTGTGTTCGACGCCAAGGCTGGCATTTCGCTGAACGATAAGTTC
GTCAAGCTAATCTCGTGGTACGACAACGAGagatcggaagagcacacgtctgaactccagtcacAATCAG
TCTCGTatctcgtatgccgtcttctgcttgTTGTCGACTCTAGGGATAACAGGGTAATGAGTCGACAAca
agcagaagacggcatacgagatTGGTCAACGATAgtctcgtgggctcggagatgtgtataagagacagTT
TATATTGTTCTGCCTCACctgtctcttatacacatctgacgctgccgacgaATCACCAGGTGTgtgtaga
tctcggtggtcgccgtatcattTTGTCGACTC >252_ILL_size_1500_GAPDH
GAGTCGACAAaatgatacggcgaccaccgagatctacactctttccctacacgacgctcttccgatctAG
TTACTGGCTTTGTAGGATTTTTTAAGGCGCTTATATAATCAAACCCTTTGTAAAAATTAAAGTTTTAAAT
GGAATTCTAATCGATTTATTTCACATTAGCTTTATTTAAGTGTGACCTACGCAGAAAGCTAGCGAAATAC
TCATCAACCCTCCCCCGCCATCGCAGCGCCATTCTCCTAATTTGCGAAAAAAGCTCCGGGAAAAGGAAAA
AGCGGCAGTCGTAATAGCGAACTGAAACTGAACGAGAGTAAAAGTGAAAAGACAGCAGGAACTCAGCCAT
GTCGAAGATCGGAATTAACGGATTTGGCCGCATCGGCCGCTTGGTGCTCCGCGCCGCCATCGATAAGGGC
GCCTCCGTGGTGGCCGTCAACGATCCCTTCATCGATGTCAACTACATGGTTTACCTGTTTAAATTCGACT
CGACTCACGGTCGTTTCAAGGGCACCGTTGCGGCTGAGGGCGGATTCCTGGTGGTGAACGGCCAGAAGAT
CACCGTGTTCAGCGAGCGCGACCCGGCCAACATCAACTGGGCCAGTGCTGGAGCCGAGTATGTGGTGGAG
TCCACCGGAGTGTTCACCACCATTGACAAGGCGTCCACCCACTTGAAGGGCGGCGCCAAGAAGGTCATCA
TCTCGGCCCCATCCGCCGATGCGCCCATGTTCGTGTGCGGCGTTAACCTGGACGCCTACAGCCCCGACAT
GAAGGTGGTCTCCAACGCCTCGTGCACCACCAACTGCCTGGCTCCCCTGGCCAAGGTCATCAATGACAAC
TTCGAGATCGTCGAGGGTCTGATGACCACCGTGCACGCCACCACTGCCACCCAGAAGACCGTCGACGGTC
CCTCTGGCAAACTGTGGCGCGATGGACGTGGCGCCGCCCAGAACATCATCCCGGCCGCCACCGGAGCCGC
CAAGGCTGTGGGCAAGGTCATCCCCGCCCTGAACGGCAAGCTGACCGGCATGGCTTTCCGCGTGCCCACG
CCCAATGTCTCCGTTGTGGATCTTACCGTCCGCTTGGGCAAGGGAGCCACCTATGACGAAATCAAGGCTA
AGGTCGAGGAGGCCTCCAAGGGACCCCTGAAGGGAATCCTGGGCTACACCGATGAGGAGGTGGTCTCCAC
CGACTTCTTCAGCGACACCCATTCGTCTGTGTTCGACGCCAAGGCTGGCATTTCGCTGAACGATAAGTTC
GTCAAGCTAATCTCGTGGTACGACAACGAGTTCGGTTACTCCAACCGCGTCATCGACCTGATCAAGTATA
TGCAGAGCAAGGACTAAACTAGCCAAAACTATCGTACAAACCCGGCGCCCAGCAGCTGGTCGGGAATCAC
TGTTGCATAATCCGCAAGGGGCGCAATTGAGGATGCTTTTagatcggaagagcacacgtctgaactccag
tcacAATCAGTCTCGTatctcgtatgccgtcttctgcttgTTGTCGACTCTAGGGATAACAGGGTAATGA
GTCGACAAcaagcagaagacggcatacgagatTGGTCAACGATAgtctcgtgggctcggagatgtgtata
agagacagTGTGGCTCCAATTGCTGCAActgtctcttatacacatctgacgctgccgacgaATCACCAGG
TGTgtgtagatctcggtggtcgccgtatcattTTGTCGACTC >253_ILL_size_150_TUB
GAGTCGACAAaatgatacggcgaccaccgagatctacactctttccctacacgacgctcttccgatctAA
CGGTTGATGGGCCTGGTATCagatcggaagagcacacgtctgaactccagtcacAATCAGTCTCGTatct
cgtatgccgtcttctgcttgTTGTCGACTCTAGGGATAACAGGGTAATGAGTCGACAAcaagcagaagac
ggcatacgagatTGGTCAACGATAgtctcgtgggctcggagatgtgtataagagacagCACGCGTACGTG
CTATCTTCctgtctcttatacacatctgacgctgccgacgaATCACCAGGTGTgtgtagatctcggtggt
cgccgtatcattTTGTCGACTC >254_ILL_size_300_TUB
GAGTCGACAAaatgatacggcgaccaccgagatctacactctttccctacacgacgctcttccgatctCG
TTGTGTTTGCTGGCGCAATCATATTCGTTTTACGTTTGTCAAGCCTCATAGCCGGCAGTTCGAACGTATA
CGCTCTCTGAGTCAGACCTCGAAATCGTAGCTCTACACAATTCTGTGAATTTTCCTTGTCGCGTGTGAAA
CACTTCCAATAAAAACTCAATATGCGTGAAagatcggaagagcacacgtctgaactccagtcacAATCAG
TCTCGTatctcgtatgccgtcttctgcttgTTGTCGACTCTAGGGATAACAGGGTAATGAGTCGACAAca
agcagaagacggcatacgagatTGGTCAACGATAgtctcgtgggctcggagatgtgtataagagacagTC
GCGACCAAATGGTCAGTCctgtctcttatacacatctgacgctgccgacgaATCACCAGGTGTgtgtaga
tctcggtggtcgccgtatcattTTGTCGACTC >255_ILL_size_450_TUB
GAGTCGACAAaatgatacggcgaccaccgagatctacactctttccctacacgacgctcttccgatctGG
CTGACGGTTGAGAGGGATTCATATTCGTTTTACGTTTGTCAAGCCTCATAGCCGGCAGTTCGAACGTATA
CGCTCTCTGAGTCAGACCTCGAAATCGTAGCTCTACACAATTCTGTGAATTTTCCTTGTCGCGTGTGAAA
CACTTCCAATAAAAACTCAATATGCGTGAATGTATCTCTATCCATGTTGGTCAGGCTGGTGTCCAGATTG
GAAACGCCTGCTGGGAGCTCTACTGCTTGGAGCACGGCATCCAGCCCGATGGCCAGATGCCGTCTGACAA
GACCGTGGGCGGAGGTGATGACTCGTTCAACACCTTCTTCagatcggaagagcacacgtctgaactccag
tcacAATCAGTCTCGTatctcgtatgccgtcttctgcttgTTGTCGACTCTAGGGATAACAGGGTAATGA
GTCGACAAcaagcagaagacggcatacgagatTGGTCAACGATAgtctcgtgggctcggagatgtgtata -continued

| Sequence Listing Free Text |
|---|

agagacagTTCGGCAATCAGAAAGGGTActgtctcttatacacatctgacgctgccgacgaATCACCAGG
TGTgtgtagatctcggtggtcgccgtatcattTTGTCGACTC >256_ILL_size_600_TUB
GAGTCGACAAaatgatacggcgaccaccgagatctacactctttccctacacgacgctcttccgatctTT
CACATCGCCTTGACCTTATCATATTCGTTTTACGTTTGTCAAGCCTCATAGCCGGCAGTTCGAACGTATA
CGCTCTCTGAGTCAGACCTCGAAATCGTAGCTCTACACAATTCTGTGAATTTTCCTTGTCGCGTGTGAAA
CACTTCCAATAAAAACTCAATATGCGTGAATGTATCTCTATCCATGTTGGTCAGGCTGGTGTCCAGATTG
GAAACGCCTGCTGGGAGCTCTACTGCTTGGAGCACGGCATCCAGCCCGATGGCCAGATGCCGTCTGACAA
GACCGTGGGCGGAGGTGATGACTCGTTCAACACCTTCTTCAGCGAGACTGGAGCTGGCAAGCACGTGCCC
CGCGCCGTGTTTGTGGATCTGGAACCCACTGTGGTCGATGAGGTCCGTACCGGAACCTACCGTCAGCTGT
TCCACCCCGAGCAGCTGATCACTGGTAAGGAGGATGCGGCCAACAACTACagatcggaagagcacacgtc
tgaactccagtcacAATCAGTCTCGTatctcgtatgccgtcttctgcttgTTGTCGACTCTAGGGATAAC
AGGGTAATGAGTCGACAAcaagcagaagacggcatacgagatTGGTCAACGATAgtctcgtgggctcgga
gatgtgtataagagacagTTAGGACCGGATTAGGTTCActgtctcttatacacatctgacgctgccgacg
aATCACCAGGTGTgtgtagatctcggtggtcgccgtatcattTTGTCGACTC >257_ILL_size_750_TUB
GAGTCGACAAaatgatacggcgaccaccgagatctacactctttccctacacgacgctcttccgatctTG
GTACTGCCTCCTGGCCTCTCATATTCGTTTTACGTTTGTCAAGCCTCATAGCCGGCAGTTCGAACGTATA
CGCTCTCTGAGTCAGACCTCGAAATCGTAGCTCTACACAATTCTGTGAATTTTCCTTGTCGCGTGTGAAA
CACTTCCAATAAAAACTCAATATGCGTGAATGTATCTCTATCCATGTTGGTCAGGCTGGTGTCCAGATTG
GAAACGCCTGCTGGGAGCTCTACTGCTTGGAGCACGGCATCCAGCCCGATGGCCAGATGCCGTCTGACAA
GACCGTGGGCGGAGGTGATGACTCGTTCAACACCTTCTTCAGCGAGACTGGAGCTGGCAAGCACGTGCCC
CGCGCCGTGTTTGTGGATCTGGAACCCACTGTGGTCGATGAGGTCCGTACCGGAACCTACCGTCAGCTGT
TCCACCCCGAGCAGCTGATCACTGGTAAGGAGGATGCGGCCAACAACTACGCCCGTGGCCACTACACCAT
CGGCAAGGAGATCGTCGATCTGGTTCTGGACAGGATCCGCAAGCTGGCCGATCAGTGCACCGGTCTGCAG
GGCTTCCTCATCTTCCACTCGTTCGGTGGAGGTACCGGCTCCGGCTTCACCTCGCTGCTGagatcggaag
agcacacgtctgaactccagtcacAATCAGTCTCGTatctcgtatgccgtcttctgcttgTTGTCGACTC
TAGGGATAACAGGGTAATGAGTCGACAAcaagcagaagacggcatacgagatTGGTCAACGATAgtctcg
tgggctcggagatgtgtataagagacagAGACCTCGGACGAGGCTCACctgtctcttatacacatctgac
gctgccgacgaATCACCAGGTGTgtgtagatctcggtggtcgccgtatcattTTGTCGACTC >258_ILL_size_900_TUB
GAGTCGACAAaatgatacggcgaccaccgagatctacactctttccctacacgacgctcttccgatctCG
ACCGTCATTGACGGCCCTTCATATTCGTTTTACGTTTGTCAAGCCTCATAGCCGGCAGTTCGAACGTATA
CGCTCTCTGAGTCAGACCTCGAAATCGTAGCTCTACACAATTCTGTGAATTTTCCTTGTCGCGTGTGAAA
CACTTCCAATAAAAACTCAATATGCGTGAATGTATCTCTATCCATGTTGGTCAGGCTGGTGTCCAGATTG
GAAACGCCTGCTGGGAGCTCTACTGCTTGGAGCACGGCATCCAGCCCGATGGCCAGATGCCGTCTGACAA
GACCGTGGGCGGAGGTGATGACTCGTTCAACACCTTCTTCAGCGAGACTGGAGCTGGCAAGCACGTGCCC
CGCGCCGTGTTTGTGGATCTGGAACCCACTGTGGTCGATGAGGTCCGTACCGGAACCTACCGTCAGCTGT
TCCACCCCGAGCAGCTGATCACTGGTAAGGAGGATGCGGCCAACAACTACGCCCGTGGCCACTACACCAT
CGGCAAGGAGATCGTCGATCTGGTTCTGGACAGGATCCGCAAGCTGGCCGATCAGTGCACCGGTCTGCAG
GGCTTCCTCATCTTCCACTCGTTCGGTGGAGGTACCGGCTCCGGCTTCACCTCGCTGCTGATGGAGCGTC
TCTCCGTGGACTACGGCAAGAAGTCCAAGCTGGAGTTCGCCATCTACCCAGCCCCCCAGGTGTCCACTGC
CGTGGTCGAGCCCTACAACTCCATCCTGACCACCCACACCACCCTGGAGCATTCCGACTGCGCCTTCATG
agatcggaagagcacacgtctgaactccagtcacAATCAGTCTCGTatctcgtatgccgtcttctgcttg
TTGTCGACTCTAGGGATAACAGGGTAATGAGTCGACAAcaagcagaagacggcatacgagatTGGTCAAC
GATAgtctcgtgggctcggagatgtgtataagagacagACCTGAAATACACAGTAACCctgtctcttata
cacatctgacgctgccgacgaATCACCAGGTGTgtgtagatctcggtggtcgccgtatcattTTGTCGAC
TC >259_ILL_size_1050_TUB
GAGTCGACAAaatgatacggcgaccaccgagatctacactctttccctacacgacgctcttccgatctTA
TCACCAGGGATGCATTGATCATATTCGTTTTACGTTTGTCAAGCCTCATAGCCGGCAGTTCGAACGTATA
CGCTCTCTGAGTCAGACCTCGAAATCGTAGCTCTACACAATTCTGTGAATTTTCCTTGTCGCGTGTGAAA
CACTTCCAATAAAAACTCAATATGCGTGAATGTATCTCTATCCATGTTGGTCAGGCTGGTGTCCAGATTG
GAAACGCCTGCTGGGAGCTCTACTGCTTGGAGCACGGCATCCAGCCCGATGGCCAGATGCCGTCTGACAA
GACCGTGGGCGGAGGTGATGACTCGTTCAACACCTTCTTCAGCGAGACTGGAGCTGGCAAGCACGTGCCC
CGCGCCGTGTTTGTGGATCTGGAACCCACTGTGGTCGATGAGGTCCGTACCGGAACCTACCGTCAGCTGT
TCCACCCCGAGCAGCTGATCACTGGTAAGGAGGATGCGGCCAACAACTACGCCCGTGGCCACTACACCAT
CGGCAAGGAGATCGTCGATCTGGTTCTGGACAGGATCCGCAAGCTGGCCGATCAGTGCACCGGTCTGCAG
GGCTTCCTCATCTTCCACTCGTTCGGTGGAGGTACCGGCTCCGGCTTCACCTCGCTGCTGATGGAGCGTC
TCTCCGTGGACTACGGCAAGAAGTCCAAGCTGGAGTTCGCCATCTACCCAGCCCCCCAGGTGTCCACTGC
CGTGGTCGAGCCCTACAACTCCATCCTGACCACCCACACCACCCTGGAGCATTCCGACTGCGCCTTCATG
GTCGACAACGAGGCTATCTACGACATCTGCCGCCGCAATCTGGACATTGAGCGCCCCACGTACACCAACC
TGAACCGTCTGATTGGCCAGATCGTGTCCTCGATTACCGCCTCTCTGCGATTCGATGGTGCCCTTAACGT
GGATCTGACTagatcggaagagcacacgtctgaactccagtcacAATCAGTCTCGTatctcgtatgccgt
cttctgcttgTTGTCGACTCTAGGGATAACAGGGTAATGAGTCGACAAcaagcagaagacggcatacgag
atTGGTCAACGATAgtctcgtgggctcggagatgtgtataagagacagTATTGTGTAAGACATTACCGct
gtctcttatacacatctgacgctgccgacgaATCACCAGGTGTgtgtagatctcggtggtcgccgtatca
ttTTGTCGACTC >260_ILL_size_1200_TUB
GAGTCGACAAaatgatacggcgaccaccgagatctacactctttccctacacgacgctcttccgatctGG
ACCATATTTAGTTATGACTCATATTCGTTTTACGTTTGTCAAGCCTCATAGCCGGCAGTTCGAACGTATA
CGCTCTCTGAGTCAGACCTCGAAATCGTAGCTCTACACAATTCTGTGAATTTTCCTTGTCGCGTGTGAAA -continued Sequence Listing Free Text CACTTCCAATAAAAACTCAATATGCGTGAATGTATCTCTATCCATGTTGGTCAGGCTGGTGTCCAGATTG
GAAACGCCTGCTGGGAGCTCTACTGCTTGGAGCACGGCATCCAGCCCGATGGCCAGATGCCGTCTGACAA
GACCGTGGGCGGAGGTGATGACTCGTTCAACACCTTCTTCAGCGAGACTGGAGCTGGCAAGCACGTGCCC
CGCGCCGTGTTTGTGGATCTGGAACCCACTGTGGTCGATGAGGTCCGTACCGGAACCTACCGTCAGCTGT
TCCACCCCGAGCAGCTGATCACTGGTAAGGAGGATGCGGCCAACAACTACGCCCGTGGCCACTACACCAT
CGGCAAGGAGATCGTCGATCTGGTTCTGGACAGGATCCGCAAGCTGGCCGATCAGTGCACCGGTCTGCAG
GGCTTCCTCATCTTCCACTCGTTCGGTGGAGGTACCGGCTCCGGCTTCACCTCGCTGCTGATGGAGCGTC
TCTCCGTGGACTACGGCAAGAAGTCCAAGCTGGAGTTCGCCATCTACCCAGCCCCCCAGGTGTCCACTGC
CGTGGTCGAGCCCTACAACTCCATCCTGACCACCCACACCACCCTGGAGCATTCCGACTGCGCCTTCATG
GTCGACAACGAGGCTATCTACGACATCTGCCGCCGCAATCTGGACATTGAGCGCCCCACGTACACCAACC
TGAACCGTCTGATTGGCCAGATCGTGTCCTCGATTACCGCCTCTCTGCGATTCGATGGTGCCCTTAACGT
GGATCTGACTGAGTTCCAGACCAACTTGGTGCCCTACCCACGTATTCACTTCCCTCTGGTGACCTACGCC
CCCGTTATCTCCGCCGAGAAGGCCTACCACGAGCAGCTGTCGGTGGCTGAGATCACCAACGCCTGCTTCG
AGCCGGCCAACCAGATGGTCagatcggaagagcacacgtctgaactccagtcacAATCAGTCTCGTatct
cgtatgccgtcttctgcttgTTGTCGACTCTAGGGATAACAGGGTAATGAGTCGACAAcaagcagaagac
ggcatacgagatTGGTCAACGATAgtctcgtgggctcggagatgtgtataagagacagTGGAGGTATTGC
TAATAATGctgtctcttatacacatctgacgctgccgacgaATCACCAGGTGTgtgtagatctcggtggt
cgccgtatcattTTGTCGACTC >261_ILL_size_1350_TUB
GAGTCGACAAaatgatacggcgaccaccgagatctacactctttccctacacgacgctcttccgatctCG
ATTTCTAGGTGTTACTTGTCATATTCGTTTTACGTTTGTCAAGCCTCATAGCCGGCAGTTCGAACGTATA
CGCTCTCTGAGTCAGACCTCGAAATCGTAGCTCTACACAATTCTGTGAATTTTCCTTGTCGCGTGTGAAA
CACTTCCAATAAAAACTCAATATGCGTGAATGTATCTCTATCCATGTTGGTCAGGCTGGTGTCCAGATTG
GAAACGCCTGCTGGGAGCTCTACTGCTTGGAGCACGGCATCCAGCCCGATGGCCAGATGCCGTCTGACAA
GACCGTGGGCGGAGGTGATGACTCGTTCAACACCTTCTTCAGCGAGACTGGAGCTGGCAAGCACGTGCCC
CGCGCCGTGTTTGTGGATCTGGAACCCACTGTGGTCGATGAGGTCCGTACCGGAACCTACCGTCAGCTGT
TCCACCCCGAGCAGCTGATCACTGGTAAGGAGGATGCGGCCAACAACTACGCCCGTGGCCACTACACCAT
CGGCAAGGAGATCGTCGATCTGGTTCTGGACAGGATCCGCAAGCTGGCCGATCAGTGCACCGGTCTGCAG
GGCTTCCTCATCTTCCACTCGTTCGGTGGAGGTACCGGCTCCGGCTTCACCTCGCTGCTGATGGAGCGTC
TCTCCGTGGACTACGGCAAGAAGTCCAAGCTGGAGTTCGCCATCTACCCAGCCCCCCAGGTGTCCACTGC
CGTGGTCGAGCCCTACAACTCCATCCTGACCACCCACACCACCCTGGAGCATTCCGACTGCGCCTTCATG
GTCGACAACGAGGCTATCTACGACATCTGCCGCCGCAATCTGGACATTGAGCGCCCCACGTACACCAACC
TGAACCGTCTGATTGGCCAGATCGTGTCCTCGATTACCGCCTCTCTGCGATTCGATGGTGCCCTTAACGT
GGATCTGACTGAGTTCCAGACCAACTTGGTGCCCTACCCACGTATTCACTTCCCTCTGGTGACCTACGCC
CCCGTTATCTCCGCCGAGAAGGCCTACCACGAGCAGCTGTCGGTGGCTGAGATCACCAACGCCTGCTTCG
AGCCGGCCAACCAGATGGTCAAGTGCGATCCCCGTCACGGCAAGTACATGGCCTGCTGCATGCTGTACCG
CGGTGATGTTGTGCCCAAGGACGTCAACGCCGCTATTGCCACCATCAAGACCAAGCGCACCATTCAATTC
GTCGACTGGTGCCCCACTGGCTTCAAGGTTagatcggaagagcacacgtctgaactccagtcacAATCAG
TCTCGTatctcgtatgccgtcttctgcttgTTGTCGACTCTAGGGATAACAGGGTAATGAGTCGACAAca
agcagaagacggcatacgagatTGGTCAACGATAgtctcgtgggctcggagatgtgtataagagacagCC
TGCGTGTGCCGTGTAGGActgtctcttatacacatctgacgctgccgacgaATCACCAGGTGTgtgtaga
tctcggtggtcgccgtatcattTTGTCGACTC >262_ILL_size_1500_TUB
GAGTCGACAAaatgatacggcgaccaccgagatctacactctttccctacacgacgctcttccgatctTT
TGAGGGTCGCTACAGAATTCATATTCGTTTTACGTTTGTCAAGCCTCATAGCCGGCAGTTCGAACGTATA
CGCTCTCTGAGTCAGACCTCGAAATCGTAGCTCTACACAATTCTGTGAATTTTCCTTGTCGCGTGTGAAA
CACTTCCAATAAAAACTCAATATGCGTGAATGTATCTCTATCCATGTTGGTCAGGCTGGTGTCCAGATTG
GAAACGCCTGCTGGGAGCTCTACTGCTTGGAGCACGGCATCCAGCCCGATGGCCAGATGCCGTCTGACAA
GACCGTGGGCGGAGGTGATGACTCGTTCAACACCTTCTTCAGCGAGACTGGAGCTGGCAAGCACGTGCCC
CGCGCCGTGTTTGTGGATCTGGAACCCACTGTGGTCGATGAGGTCCGTACCGGAACCTACCGTCAGCTGT
TCCACCCCGAGCAGCTGATCACTGGTAAGGAGGATGCGGCCAACAACTACGCCCGTGGCCACTACACCAT
CGGCAAGGAGATCGTCGATCTGGTTCTGGACAGGATCCGCAAGCTGGCCGATCAGTGCACCGGTCTGCAG
GGCTTCCTCATCTTCCACTCGTTCGGTGGAGGTACCGGCTCCGGCTTCACCTCGCTGCTGATGGAGCGTC
TCTCCGTGGACTACGGCAAGAAGTCCAAGCTGGAGTTCGCCATCTACCCAGCCCCCCAGGTGTCCACTGC
CGTGGTCGAGCCCTACAACTCCATCCTGACCACCCACACCACCCTGGAGCATTCCGACTGCGCCTTCATG
GTCGACAACGAGGCTATCTACGACATCTGCCGCCGCAATCTGGACATTGAGCGCCCCACGTACACCAACC
TGAACCGTCTGATTGGCCAGATCGTGTCCTCGATTACCGCCTCTCTGCGATTCGATGGTGCCCTTAACGT
GGATCTGACTGAGTTCCAGACCAACTTGGTGCCCTACCCACGTATTCACTTCCCTCTGGTGACCTACGCC
CCCGTTATCTCCGCCGAGAAGGCCTACCACGAGCAGCTGTCGGTGGCTGAGATCACCAACGCCTGCTTCG
AGCCGGCCAACCAGATGGTCAAGTGCGATCCCCGTCACGGCAAGTACATGGCCTGCTGCATGCTGTACCG
CGGTGATGTTGTGCCCAAGGACGTCAACGCCGCTATTGCCACCATCAAGACCAAGCGCACCATTCAATTC
GTCGACTGGTGCCCCACTGGCTTCAAGGTTGGCATCAACTACCAGCCACCCACCGTGGTGCCTGGAGGTG
ATTTGGCCAAGGTGCAGCGTGCCGTGTGCATGTTGTCCAACACCACGGCCATCGCCGAGGCCTGGGCCCG
TCTGGACCACAAGTTCGATCTGATGTACGCCAAGCGTGCCagatcggaagagcacacgtctgaactccag
tcacAATCAGTCTCGTatctcgtatgccgtcttctgcttgTTGTCGACTCTAGGGATAACAGGGTAATGA
GTCGACAAcaagcagaagacggcatacgagatTGGTCAACGATAgtctcgtgggctcggagatgtgtata
agagacagTGGTTTCACCTCACGACAAGctgtctcttatacacatctgacgctgccgacgaATCACCAGG
TGTgtgtagatctcggtggtcgccgtatcattTTGTCGACTC

What is claimed is:

1. A method for measuring and correcting amplification bias in a sample comprising a plurality of polynucleotides, the method comprising:

obtaining a sample comprising at least a first sample polynucleotide and a second sample polynucleotide;

spiking the sample with at least one synthetic standard polynucleotide comprising a primer editing sequence designed to detect amplification bias between two sample polynucleotides;

amplifying polynucleotides in the spiked sample;

sequencing a first sample polynucleotide, a second sample polynucleotide, and the standard;

measuring the frequency of occurrence of the synthetic standard polynucleotide, the first sample polynucleotide, and the second sample polynucleotide;

comparing the measured occurrence of the synthetic standard polynucleotide to an expected frequency of occurrence of the synthetic standard polynucleotide, thereby generating a synthetic standard polynucleotide bias value; and correcting the frequency of occurrence of the first sample polynucleotide and the second sample polynucleotide according to the synthetic standard polynucleotide bias value.

2. The method of claim 1 wherein the synthetic standard polynucleotide comprises 16S rRNA gene nucleotides.

3. The method of claim 1 wherein the synthetic standard polynucleotide comprises a plurality of different synthetic standard polynucleotides.

4. The method of claim 3 wherein the different synthetic standard polynucleotides comprise differences designed to detect different biases in amplification.

5. The method of claim 3 wherein a first synthetic standard polynucleotide and a second synthetic standard polynucleotide differ in G-C content, secondary structure, amplicon size, or degree of mismatch to a primer sequence.

6. The method of claim 1 wherein the synthetic standard polynucleotide comprises a polynucleotide obtained from a biological standard organism that is added to the sample.

7. The method of claim 1 wherein the synthetic standard polynucleotide comprises a circular polynucleotide.

8. The method of claim 1 wherein the synthetic standard polynucleotide is spiked into a sample at a defined level in order to measure the absolute or relative abundance of polynucleotides in the sample.

9. The method of claim 1 wherein a plurality of synthetic standard polynucleotides are spiked into a sample at a plurality of defined concentrations in order to measure a limit of detection.

10. The method of claim 8 wherein the synthetic standard polynucleotide is spiked into the sample at a standard polynucleotide:sample polynucleotide ratio of at least 1:10, 000 and no more than 100:1.

11. The method of claim 10 wherein the synthetic standard polynucleotide is spiked into the sample at a standard polynucleotide: sample polynucleotide ratio of at least 1:3 and no more than 3:1.

12. The method of claim 8 wherein the synthetic standard polynucleotide is spiked into the sample in an amount of from one molecule to 100,000 molecules.

13. The method of claim 1 wherein amplifying the polynucleotides comprises using a single set of primers.

14. The method of claim 1 wherein the synthetic standard polynucleotide comprises a feature allowing PCR-free quantitation of the synthetic standard.

15. The method of claim 14 wherein the feature allowing PCR-free quantitation of the synthetic standard comprises a barcode.

16. The method of claim 1 wherein:

the first sample polynucleotide comprises a polynucleotide from a first microbe; and the second sample polynucleotide comprises a polynucleotide from a second microbe.

17. The method of claim 16 wherein the first microbe and the second microbe are members of a microbiome sample.

18. A method of determining amplification bias among a plurality of polynucleotides, the method comprising:

amplifying a plurality of polynucleotides in a sample, the sample comprising:

a first sample polynucleotide;

a second sample polynucleotide; and a plurality of synthetic standard polynucleotides comprising:

a first synthetic standard polynucleotide; and a second synthetic standard polynucleotide that differs from the first synthetic standard polynucleotide in G-C content, secondary structure, amplicon size, or degree of mismatch to a primer sequence, wherein at least one of the plurality of synthetic standard polynucleotides is a primer editing standard;

sequencing the first sample polynucleotide, the second sample polynucleotide, and the plurality of synthetic standard polynucleotides;

measuring the frequency of occurrence of the first sample polynucleotide, the second sample polynucleotide, the first synthetic standard polynucleotide, and the second synthetic standard polynucleotide;

comparing the measured occurrence of the first synthetic standard polynucleotide with an expected frequency of occurrence of the first synthetic standard polynucleotide, thereby generating a first synthetic standard value;

comparing the measured occurrence of the second synthetic standard polynucleotide with an expected frequency of occurrence of the second synthetic standard polynucleotide, thereby generating a second synthetic standard value; and detecting amplification bias if the first synthetic standard value differs from the second synthetic standard value.

19. The method of claim 18 wherein the plurality of synthetic standard polynucleotides are provided at a plurality of concentrations; and failing to detect a synthetic standard defines a limit of detection.

* * * * *

SEQUENCE LISTING

<160> NUMBER OF SEQ ID NOS: 328

<210> SEQ ID NO 1
<211> LENGTH: 52
<212> TYPE: DNA
<213> ORGANISM: Artificial
<220> FEATURE:
<223> OTHER INFORMATION: Polynucleotide

<400> SEQUENCE: 1
tcgtcggcag cgtcagatgt gtataagaga caggtgccag cmgccgcggt aa 52

<210> SEQ ID NO 2
<211> LENGTH: 54
<212> TYPE: DNA
<213> ORGANISM: Artificial
<220> FEATURE:
<223> OTHER INFORMATION: Polynucleotide

<400> SEQUENCE: 2
gtctcgtggg ctcggagatg tgtataagag acagggacta chvgggtwtc taat 54

<210> SEQ ID NO 3
<211> LENGTH: 51
<212> TYPE: DNA
<213> ORGANISM: Artificial
<220> FEATURE:
<223> OTHER INFORMATION: Polynucleotide
<220> FEATURE:
<221> NAME/KEY: misc_feature
<222> LOCATION: (30)..(37)
<223> OTHER INFORMATION: n is a, c, g, or t

<400> SEQUENCE: 3
aatgatacgg cgaccaccga gatctacacn nnnnnnntcg tcggcagcgt c 51

<210> SEQ ID NO 4
<211> LENGTH: 47
<212> TYPE: DNA
<213> ORGANISM: Artificial
<220> FEATURE:
<223> OTHER INFORMATION: Polynucleotide
<220> FEATURE:
<221> NAME/KEY: misc_feature
<222> LOCATION: (25)..(32)
<223> OTHER INFORMATION: n is a, c, g, or t

<400> SEQUENCE: 4
caagcagaag acggcatacg agatnnnnnn nngtctcgtg ggctcgg 47

<210> SEQ ID NO 5
<211> LENGTH: 50
<212> TYPE: DNA
<213> ORGANISM: Artificial
<220> FEATURE:
<223> OTHER INFORMATION: Polynucleotide

<400> SEQUENCE: 5
tcgtcggcag cgtcagatgt gtataagaga cagcctacgg gaggcagcag 50

<210> SEQ ID NO 6
<211> LENGTH: 52
<212> TYPE: DNA
<213> ORGANISM: Artificial
<220> FEATURE:
<223> OTHER INFORMATION: Polynucleotide

<400> SEQUENCE: 6
gtctcgtggg ctcggagatg tgtataagag acagccgtca attcmtttra gt 52

<210> SEQ ID NO 7
<211> LENGTH: 12
<212> TYPE: DNA
<213> ORGANISM: Artificial
<220> FEATURE:
<223> OTHER INFORMATION: Polynucleotide

<400> SEQUENCE: 7
aatcagtctc gt 12

<210> SEQ ID NO 8
<211> LENGTH: 521
<212> TYPE: DNA
<213> ORGANISM: Artificial
<220> FEATURE:
<223> OTHER INFORMATION: Polynucleotide

<400> SEQUENCE: 8
aataagcacc ggctaactct gtgccagcag ccgcggtaat acagagggtg cgagcgttaa 60
tcggatttac tgggcgtaaa tctgcgtgcg taggcggctt attaagtcgg atgtgaaatc 120
cccgagctta acttgggaat tgcattcgat actggtgagc tagagtatgg gagaggatgg 180
tagaattcca ggtgtagcgg tgaaatgcgt agagatctgg aggaataccg atggcgaagg 240
cagccatctg gcctaatact gacgctgagg tacgaaagca tggggagcaa acaggattag 300
ataccctggt agtccatgcc gtaaacgatg tctactaggg ataacagggt aatgagtcga 360
caaaatgata cggcgaccac cgagatctac actctttccc tacacgacgc tcttccgatc 420
tgcacattgt agcgttgata aagatcggaa gagcacacgt ctgaactcca gtcacaatca 480
gtctcgtatc tcgtatgccg tcttctgctt gttgtcgact c 521

<210> SEQ ID NO 9
<211> LENGTH: 521
<212> TYPE: DNA
<213> ORGANISM: Artificial
<220> FEATURE:
<223> OTHER INFORMATION: Polynucleotide

<400> SEQUENCE: 9
agaaagccac ggctaactac gtgccagcag ccgcggtaat acgtaggtgg caagcgttat 60
ccggaattat tgggcgtaaa tctgcgcgcg caggtggttt cttaagtctg atgtgaaagc 120
ccacggctca accgtggagg gtcattggaa actgggagac ttgagtgcag aagaggaaag 180
tggaattcca tgtgtagcgg tgaaatgcgt agagatatgg aggaacacca gtggcgaagg 240
cgactttctg gtctgtaact gacactgagg cgcgaaagcg tggggagcaa acaggattag 300
ataccctggt agtccacgcc gtaaacgatg agtgctaggg ataacagggt aatgagtcga 360
caaaatgata cggcgaccac cgagatctac actctttccc tacacgacgc tcttccgatc 420
tcggaggagc tataaatgac cagatcggaa gagcacacgt ctgaactcca gtcacaatca 480
gtctcgtatc tcgtatgccg tcttctgctt gttgtcgact c 521

<210> SEQ ID NO 10
<211> LENGTH: 521
<212> TYPE: DNA
<213> ORGANISM: Artificial
<220> FEATURE:
<223> OTHER INFORMATION: Polynucleotide

<400> SEQUENCE: 10
aataaggatc ggctaactcc gtgccagcag ccgcggtaat acggaggatc cgagcgttat 60
ccggatttat tgggtttaaa tctgggagcg tagatggatg tttaagtcag ttgtgaaagt 120
ttgcggctca accgtaaaat tgcagttgat actggatatc ttgagtgcag ttgaggcagg 180
cggaattcgt ggtgtagcgg tgaaatgctt agatatcacg aagaactccg attgcgaagg 240
cagcctgcta agctgcaact gacattgagg ctcgaaagtg tgggtatcaa acaggattag 300
ataccctggt agtccacacg gtaaacgatg aatactaggg ataacagggt aatgagtcga 360
caaaatgata cggcgaccac cgagatctac actctttccc tacacgacgc tcttccgatc 420
ttaatcgtac aaatttcgaa aagatcggaa gagcacacgt ctgaactcca gtcacaatca 480
gtctcgtatc tcgtatgccg tcttctgctt gttgtcgact c 521

<210> SEQ ID NO 11
<211> LENGTH: 521
<212> TYPE: DNA
<213> ORGANISM: Artificial
<220> FEATURE:
<223> OTHER INFORMATION: Polynucleotide

<400> SEQUENCE: 11
aataaggatc ggctaactcc gtgccagcag ccgcggtaat acggaggatc cgagcgttat 60
ccggatttat tgggtttaaa tctgggagcg tagatggata tttaagtcag ttgtgaaagt 120
ttgcggctca accgtaaaat tgcagttgat actggatatc ttgagtgcag ttgaggcagg 180
cggaattcgt ggtgtagcgg tgaaatgctt agatatcacg aagaactccg attgcgaagg 240
cagcctgcta agctgcaact gacattgagg ctcgaaagtg tgggtatcaa acaggattag 300
ataccctggt agtccacacg gtaaacgatg aatactaggg ataacagggt aatgagtcga 360
caaaatgata cggcgaccac cgagatctac actctttccc tacacgacgc tcttccgatc 420
taacattcag gcgcacctac aagatcggaa gagcacacgt ctgaactcca gtcacaatca 480
gtctcgtatc tcgtatgccg tcttctgctt gttgtcgact c 521

<210> SEQ ID NO 12
<211> LENGTH: 521
<212> TYPE: DNA
<213> ORGANISM: Artificial
<220> FEATURE:
<223> OTHER INFORMATION: Polynucleotide

<400> SEQUENCE: 12
aataaggatc ggctaactcc gtgccagcag ccgcggtaat acggaggatc cgagcgttat 60
ccggatttat tgggtttaaa tctgggagcg tagatggatg tttaagtcag ttgtgaaagt 120
ttgcggctca accgtaaaat tgcagttgat actggatatc ttgagtgcag ttgaggcagg 180
cggaattcgt ggtgtagcgg tgaaatgctt agatatcacg aggaactccg attgcgaagg 240
cagcctgcta agctgcaact gacattgagg ctcgaaagtg tgggtatcaa acaggattag 300
ataccctggt agtccacacg gtaaacgatg aatactaggg ataacagggt aatgagtcga 360
caaaatgata cggcgaccac cgagatctac actctttccc tacacgacgc tcttccgatc 420
ttatgccgct cgagacccat tagatcggaa gagcacacgt ctgaactcca gtcacaatca 480
gtctcgtatc tcgtatgccg tcttctgctt gttgtcgact c 521

<210> SEQ ID NO 13
<211> LENGTH: 521

<212> TYPE: DNA
<213> ORGANISM: Artificial
<220> FEATURE:
<223> OTHER INFORMATION: Polynucleotide

<400> SEQUENCE: 13
aggaagccac ggctaactac gtgccagcag ccgcggtaat acgtaggtgg caagcgttgt 60
ccggatttac tgggcgtaaa tctgggagcg taggtggata tttaagtggg atgtgaaata 120
ctcgggctta acctgggtgc tgcattccaa actggatatc tagagtgcag gagaggaaag 180
tagaattcct agtgtagcgg tgaaatgcgt agagattagg aagaatacca gtggcgaagg 240
cgactttctg gactgtaact gacactgagg ctcgaaagcg tggggagcaa acaggattag 300
ataccctggt agtccacgcc gtaaacgatg aatactaggg ataacagggt aatgagtcga 360
caaaatgata cggcgaccac cgagatctac actctttccc tacacgacgc tcttccgatc 420
tttggatcac tacgccagga cagatcggaa gagcacacgt ctgaactcca gtcacaatca 480
gtctcgtatc tcgtatgccg tcttctgctt gttgtcgact c 521

<210> SEQ ID NO 14
<211> LENGTH: 521
<212> TYPE: DNA
<213> ORGANISM: Artificial
<220> FEATURE:
<223> OTHER INFORMATION: Polynucleotide

<400> SEQUENCE: 14
aggaagccac ggctaactac gtgccagcag ccgcggtaat acgtaggtgg caagcgttgt 60
ccggatttac tgggcgtaaa tctgggagcg taggtggata tttaagtggg atgtgaaata 120
ctcgggctta acctgggtgc tgcattccaa actggatatc tagagtgcag gagaggaaag 180
tagaattctt agtgtagcgg tgaaatgcgt agagattagg aagaatacca gtggcgaagg 240
cgactttctg gactgtaact gacactgagg ctcgaaagcg tggggagcaa acaggattag 300
ataccctggt agtccacgcc gtaaacgatg aatactaggg ataacagggt aatgagtcga 360
caaaatgata cggcgaccac cgagatctac actctttccc tacacgacgc tcttccgatc 420
tcatcctaca ggcttgtagc gagatcggaa gagcacacgt ctgaactcca gtcacaatca 480
gtctcgtatc tcgtatgccg tcttctgctt gttgtcgact c 521

<210> SEQ ID NO 15
<211> LENGTH: 521
<212> TYPE: DNA
<213> ORGANISM: Artificial
<220> FEATURE:
<223> OTHER INFORMATION: Polynucleotide

<400> SEQUENCE: 15
taatagcacc ggctaactcc gtgccagcag ccgcggtaat acggagggtg caagcgttac 60
ccggaatcac tgggcgtaaa tctgggcgtg taggcggaaa tttaagtctg gttttaaaga 120
ccggggctca acctcgggga tggactggat actggatttc ttgacctctg gagaggtaac 180
tggaattcct ggtgtagcgg tggaatgcgt agataccagg aggaacacca atggcgaagg 240
caagttactg gacagaaggt gacgctgagg cgcgaaagtg tggggagcaa accggattag 300
atacccgggt agtccacacc ctaaacgatg tacgttaggg ataacagggt aatgagtcga 360
caaaatgata cggcgaccac cgagatctac actctttccc tacacgacgc tcttccgatc 420
taggcgttta ggtacctgtt cagatcggaa gagcacacgt ctgaactcca gtcacaatca 480

-continued

```
gtctcgtatc tcgtatgccg tcttctgctt gttgtcgact c                   521


<210> SEQ ID NO 16
<211> LENGTH: 521
<212> TYPE: DNA
<213> ORGANISM: Artificial
<220> FEATURE:
<223> OTHER INFORMATION: Polynucleotide

<400> SEQUENCE: 16

agaaagccac ggctaactac gtgccagcag ccgcggtaat acgtaggtgg caagcgttgt    60

ccggatttat tgggcgtaaa tctgcgagcg caggcggttt cttaagtctg atgtgaaagc   120

ccccggctca accggggagg gtcattggaa actgggagac ttgagtgcag aagaggagag   180

tggaattcca tgtgtagcgg tgaaatgcgt agatatatgg aggaacacca gtggcgaagg   240

cggctctctg gtctgtaact gacgctgagg ctcgaaagcg tggggagcaa acaggattag   300

ataccctggt agtccacgcc gtaaacgatg agtgctaggg ataacagggt aatgagtcga   360

caaaatgata cggcgaccac cgagatctac actctttccc tacacgacgc tcttccgatc   420

ttcacaagtt tcgcaatcga gagatcggaa gagcacacgt ctgaactcca gtcacaatca   480

gtctcgtatc tcgtatgccg tcttctgctt gttgtcgact c                       521


<210> SEQ ID NO 17
<211> LENGTH: 521
<212> TYPE: DNA
<213> ORGANISM: Artificial
<220> FEATURE:
<223> OTHER INFORMATION: Polynucleotide

<400> SEQUENCE: 17

aagaagcacc ggctaactcc gtgccagcag ccgcggtaat acggagggtg caagcgttaa    60

tcggaattac tgggcgtaaa tctgcgcacg caggcggttt gttaagtcag atgtgaaatc   120

cccgggctca acctgggaac tgcatctgat actggcaagc ttgagtctcg tagagggggg   180

tagaattcca ggtgtagcgg tgaaatgcgt agagatctgg aggaataccg gtggcgaagg   240

cggccccctg gacgaagact gacgctcagg tgcgaaagcg tggggagcaa acaggattag   300

ataccctggt agtccacgcc gtaaacgatg tcgactaggg ataacagggt aatgagtcga   360

caaaatgata cggcgaccac cgagatctac actctttccc tacacgacgc tcttccgatc   420

ttattgctaa ggctatggag aagatcggaa gagcacacgt ctgaactcca gtcacaatca   480

gtctcgtatc tcgtatgccg tcttctgctt gttgtcgact c                       521


<210> SEQ ID NO 18
<211> LENGTH: 522
<212> TYPE: DNA
<213> ORGANISM: Artificial
<220> FEATURE:
<223> OTHER INFORMATION: Polynucleotide

<400> SEQUENCE: 18

aataagcacc ggctaactcc gtgccagcag ccgcggtaat acggagggtg caagcgttac    60

tcggaatcac tgggcgtaaa tctgagcgcg taggcgggat agtcagtcag gtgtgaaatc   120

ctatggctta accatagaac tgcatttgaa actactattc tagagtgtgg gagaggtagg   180

tggaattctt ggtgtagggg taaaatccgt agagatcaag aggaatactc attgcgaagg   240

cgacctgctg gaacattact gacgctgatt gcgcgaaagc gtggggagca aacaggatta   300

gataccctgg tagtccacgc cctaaacgat ggatgctagg gataacaggg taatgagtcg   360
```

acaaaatgat acggcgacca ccgagatcta cactctttcc ctacacgacg ctcttccgat 420
ctctgacggg acaaacggat ctagatcgga agagcacacg tctgaactcc agtcacaatc 480
agtctcgtat ctcgtatgcc gtcttctgct tgttgtcgac tc 522

<210> SEQ ID NO 19
<211> LENGTH: 521
<212> TYPE: DNA
<213> ORGANISM: Artificial
<220> FEATURE:
<223> OTHER INFORMATION: Polynucleotide

<400> SEQUENCE: 19
agaaagtcac ggctaactac gtgccagcag ccgcggtaat acgtaggtgg caagcgttgt 60
ccggatttat tgggcgtaaa tctgcgagtg caggcggttc aataagtctg atgtgaaagc 120
cttcggctca accggagaat tgcatcagaa actgttgaac ttgagtgcag aagaggagag 180
tggaactcca tgtgtagcgg tggaatgcgt agatatatgg aagaacacca gtggcgaagg 240
cggctctctg gtctgcaact gacgctgagg ctcgaaagca tgggtagcga acaggattag 300
ataccctggt agtccatgcc gtaaacgatg agtgctaggg ataacagggt aatgagtcga 360
caaaatgata cggcgaccac cgagatctac actctttccc tacacgacgc tcttccgatc 420
tcatcgcgga caacgccaac cagatcggaa gagcacacgt ctgaactcca gtcacaatca 480
gtctcgtatc tcgtatgccg tcttctgctt gttgtcgact c 521

<210> SEQ ID NO 20
<211> LENGTH: 521
<212> TYPE: DNA
<213> ORGANISM: Artificial
<220> FEATURE:
<223> OTHER INFORMATION: Polynucleotide

<400> SEQUENCE: 20
aataagcacc ggctaactac gtgccagcag ccgcggtaat acgtagggtg cgagcgttaa 60
tcggaattac tgggcgtaaa tctgcgggcg cagacggtta cttaagcagg atgtgaaatc 120
cccgggctca acccgggaac tgcgttctga actgggtgac tcgagtgtgt cagagggagg 180
tagaattcca cgtgtagcag tgaaatgcgt agagatgtgg aggaataccg atggcgaagg 240
cagcctcctg ggacaacact gacgttcatg cccgaaagcg tgggtagcaa acaggattag 300
ataccctggt agtccacgcc ctaaacgatg tcaattaggg ataacagggt aatgagtcga 360
caaaatgata cggcgaccac cgagatctac actctttccc tacacgacgc tcttccgatc 420
taagggtcac acagtatcat cagatcggaa gagcacacgt ctgaactcca gtcacaatca 480
gtctcgtatc tcgtatgccg tcttctgctt gttgtcgact c 521

<210> SEQ ID NO 21
<211> LENGTH: 521
<212> TYPE: DNA
<213> ORGANISM: Artificial
<220> FEATURE:
<223> OTHER INFORMATION: Polynucleotide

<400> SEQUENCE: 21
aagaagcacc ggctaactac gtgccagcag ccgcggtgat acgtagggtg cgagcgttgt 60
ccggatttat tgggcgtaaa tctgggctcg taggtggttg atcgcgtcgg aagtgtaatc 120
ttggggctta accctgagcg tgctttcgat acgggttgac ttgaggaagg taggggagaa 180

```
tggaattcct ggtggagcgg tggaatgcgc agatatcagg aggaacacca gtggcgaagg    240

cggttctctg ggcctttcct gacgctgagg agcgaaagcg tggggagcga acaggcttag    300

ataccctggt agtccacgct gtaaacggtg ggtactaggg ataacagggt aatgagtcga    360

caaaatgata cggcgaccac cgagatctac actctttccc tacacgacgc tcttccgatc    420

tgaagtagag agccggctaa cagatcggaa gagcacacgt ctgaactcca gtcacaatca    480

gtctcgtatc tcgtatgccg tcttctgctt gttgtcgact c                        521
```

```
<210> SEQ ID NO 22
<211> LENGTH: 521
<212> TYPE: DNA
<213> ORGANISM: Artificial
<220> FEATURE:
<223> OTHER INFORMATION: Polynucleotide

<400> SEQUENCE: 22

aataagcacc ggctaacttc gtgccagcag ccgcggtaat acgaagggtg caagcgttaa     60

tcggaattac tgggcgtaaa tctgcgcgcg taggtggttc agcaagttgg atgtgaaatc    120

cccgggctca acctgggaac tgcatccaaa actactgagc tagagtacgg tagagggtgg    180

tggaatttcc tgtgtagcgg tgaaatgcgt agatatagga aggaacacca gtggcgaagg    240

cgaccacctg gactgatact gacactgagg tgcgaaagcg tggggagcaa acaggattag    300

ataccctggt agtccacgcc gtaaacgatg tcgactaggg ataacagggt aatgagtcga    360

caaaatgata cggcgaccac cgagatctac actctttccc tacacgacgc tcttccgatc    420

tcccggcggt atacgttcaa gagatcggaa gagcacacgt ctgaactcca gtcacaatca    480

gtctcgtatc tcgtatgccg tcttctgctt gttgtcgact c                        521
```

```
<210> SEQ ID NO 23
<211> LENGTH: 521
<212> TYPE: DNA
<213> ORGANISM: Artificial
<220> FEATURE:
<223> OTHER INFORMATION: Polynucleotide

<400> SEQUENCE: 23

aagaagcccc ggctaactcc gtgccagcag ccgcggtaat acggaggggg ctagcgttat     60

tcggaattac tgggcgtaaa tctgcgcacg taggcggatc ggaaagtcag aggtgaaatc    120

ccagggctca accctggaac tgcctttgaa actcccgatc ttgaggtcga gagaggtgag    180

tggaattccg agtgtagagg tgaaattcgt agatattcgg aggaacacca gtggcgaagg    240

cggctcactg gctcgatact gacgctgagg tgcgaaagcg tggggagcaa acaggattag    300

ataccctggt agtccacgcc gtaaacgatg aatgctaggg ataacagggt aatgagtcga    360

caaaatgata cggcgaccac cgagatctac actctttccc tacacgacgc tcttccgatc    420

tggatgatgc gttcgtacac aagatcggaa gagcacacgt ctgaactcca gtcacaatca    480

gtctcgtatc tcgtatgccg tcttctgctt gttgtcgact c                        521
```

```
<210> SEQ ID NO 24
<211> LENGTH: 521
<212> TYPE: DNA
<213> ORGANISM: Artificial
<220> FEATURE:
<223> OTHER INFORMATION: Polynucleotide

<400> SEQUENCE: 24

agaaagccac ggctaactac gtgccagcag ccgcggtaat acgtaggtgg caagcgttat     60
```

```
ccggaattat tgggcgtaaa tctgcgcgcg taggcggttt tttaagtctg atgtgaaagc    120

ccacggctca accgtggagg gtcattggaa actggaaaac ttgagtgcag aagaggaaag    180

tggaattcca tgtgtagcgg tgaaatgcgc agagatatgg aggaacacca gtggcgaagg    240

cgactttctg gtctgtaact gacgctgatg tgcgaaagcg tggggatcaa acaggattag    300

ataccctggt agtccacgcc gtaaacgatg agtgctaggg ataacagggt aatgagtcga    360

caaaatgata cggcgaccac cgagatctac actctttccc tacacgacgc tcttccgatc    420

tcgccacgag gattagaaat tagatcggaa gagcacacgt ctgaactcca gtcacaatca    480

gtctcgtatc tcgtatgccg tcttctgctt gttgtcgact c                        521


<210> SEQ ID NO 25
<211> LENGTH: 521
<212> TYPE: DNA
<213> ORGANISM: Artificial
<220> FEATURE:
<223> OTHER INFORMATION: Polynucleotide

<400> SEQUENCE: 25

agaaagccac ggctaactac gtgccagcag ccgcggtaat acgtaggtgg caagcgttgt     60

ccggaatcat tgggcgtaaa tctgcgcgcg taggcggttt cttaagtctg atgtgaaagc    120

ccacggctca accgtggagg gtcattggaa actggaggac ttgagtgcag aagaggaaag    180

tggaattcca tgtgtagcgg tgaaatgcgc agagatatgg aggaacacca gtggcgaagg    240

cgactttctg gtctgtaact gacgctgatg tgcgaaagcg tggggatcaa acaggattag    300

ataccctggt agtccacgcc gtaaacgatg agtgctaggg ataacagggt aatgagtcga    360

caaaatgata cggcgaccac cgagatctac actctttccc tacacgacgc tcttccgatc    420

ttttcggtgc taaatcacac tagatcggaa gagcacacgt ctgaactcca gtcacaatca    480

gtctcgtatc tcgtatgccg tcttctgctt gttgtcgact c                        521


<210> SEQ ID NO 26
<211> LENGTH: 520
<212> TYPE: DNA
<213> ORGANISM: Artificial
<220> FEATURE:
<223> OTHER INFORMATION: Polynucleotide

<400> SEQUENCE: 26

agaaagggac ggctaactac gtgccagcag ccgcggtaat acgtaggtcc cgagcgttgt     60

ccggatttat tgggcgtaaa tctgcgagcg caggcggttc tttaagtctg aagttaaagg    120

cagtggctta accattgtac gctttggaaa ctggaggact tgagtgcaga aggggagagt    180

ggaattccat gtgtagcggt gaaatgcgta gatatatgga ggaacaccgg tggcgaaagc    240

ggctctctgg tctgtaactg acgctgaggc tcgaaagcgt ggggagcaaa caggattaga    300

taccctggta gtccacgccg taaacgatga gtgctaggga taacagggta atgagtcgac    360

aaaatgatac ggcgaccacc gagatctaca ctctttccct acacgacgct cttccgatct    420

cctgcgcatt gcaatggcgt agatcggaag agcacacgtc tgaactccag tcacaatcag    480

tctcgtatct cgtatgccgt cttctgcttg ttgtcgactc                         520


<210> SEQ ID NO 27
<211> LENGTH: 520
<212> TYPE: DNA
<213> ORGANISM: Artificial
<220> FEATURE:
```

<223> OTHER INFORMATION: Polynucleotide

<400> SEQUENCE: 27
agaaagggac ggctaactac gtgccagcag ccgcggtaat acgtaggtcc cgagcgttgt 60
ccggatttat tgggcgtaaa tctgggagcg caggcggtca ggaaagtctg gagtaaaagg 120
ctatggctca accatagtgt gctctggaaa ctgtctgact tgagtgcaga aggggagagt 180
ggaattccat gtgtagcggt gaaatgcgta gatatatgga ggaacaccag tggcgaaagc 240
ggctctctgg tctgtcactg acgctgaggc tcgaaagcgt gggtagcgaa caggattaga 300
taccctggta gtccacgccg taaacgatga gtgctaggga taacagggta atgagtcgac 360
aaaatgatac ggcgaccacc gagatctaca ctctttccct acacgacgct cttccgatct 420
tctggcgggc gtatcggaga agatcggaag agcacacgtc tgaactccag tcacaatcag 480
tctcgtatct cgtatgccgt cttctgcttg ttgtcgactc 520

<210> SEQ ID NO 28
<211> LENGTH: 520
<212> TYPE: DNA
<213> ORGANISM: Artificial
<220> FEATURE:
<223> OTHER INFORMATION: Polynucleotide

<400> SEQUENCE: 28
agaaagggac ggctaactac gtgccagcag ccgcggtaat acgtaggtcc cgagcgttgt 60
ccggatttat tgggcgtaaa tctgcgagcg caggcggtta gataagtctg aagttaaagg 120
ctgtggctta accatagtag gctttggaaa ctgtttaact tgagtgcaag aggggagagt 180
ggaattccat gtgtagcggt gaaatgcgta gatatatgga ggaacaccgg tggcgaaagc 240
ggctctctgg cttgtaactg acgctgaggc tcgaaagcgt ggggagcaaa caggattaga 300
taccctggta gtccacgctg taaacgatga gtgctaggga taacagggta atgagtcgac 360
aaaatgatac ggcgaccacc gagatctaca ctctttccct acacgacgct cttccgatct 420
atagttaaat aaagagccaa agatcggaag agcacacgtc tgaactccag tcacaatcag 480
tctcgtatct cgtatgccgt cttctgcttg ttgtcgactc 520

<210> SEQ ID NO 29
<211> LENGTH: 521
<212> TYPE: DNA
<213> ORGANISM: Artificial
<220> FEATURE:
<223> OTHER INFORMATION: Polynucleotide

<400> SEQUENCE: 29
aagaagcgcc ggctaactac gtgccagcag ccgcggtaat acgtagggcg cgagcgttgt 60
ccggaattat tgggcgtaaa tctgggcttg taggcggttg gtcgcgtctg ccgtgaaatc 120
ctctggctta actgggggcg tgcggtgggt acgggctgac ttgagtgcgg taggggagac 180
tggaactcct ggtgtagcgg tggaatgcgc agatatcagg aagaacaccg gtggcgaagg 240
cgggtctctg ggccgttact gacgctgagg agcgaaagcg tggggagcga acaggattag 300
ataccctggt agtccacgct gtaaacgttg ggcactaggg ataacagggt aatgagtcga 360
caaaatgata cggcgaccac cgagatctac actctttccc tacacgacgc tcttccgatc 420
tcttcctggc tcctaaatta cagatcggaa gagcacacgt ctgaactcca gtcacaatca 480
gtctcgtatc tcgtatgccg tcttctgctt gttgtcgact c 521

<210> SEQ ID NO 30
<211> LENGTH: 521
<212> TYPE: DNA
<213> ORGANISM: Artificial
<220> FEATURE:
<223> OTHER INFORMATION: Polynucleotide

<400> SEQUENCE: 30
agaaagccac ggctaactac gtgccagcag ccgcggtaat acgtaggtgg caagcgttgt 60
ccggatttat tgggcgtaaa tctgcgcgcg caggcggtct tttaagtctg atgtgaaagc 120
ccccggctta accggggagg gtcattggaa actggaagac tggagtgcag aagaggagag 180
tggaattcca cgtgtagcgg tgaaatgcgt agatatgtgg aggaacacca gtggcgaagg 240
cgactctctg gtctgtaact gacgctgagg cgcgaaagcg tggggagcaa acaggattag 300
ataccctggt agtccacgcc gtaaacgatg agtgctaggg ataacagggt aatgagtcga 360
caaaatgata cggcgaccac cgagatctac actctttccc tacacgacgc tcttccgatc 420
ttgtgttggc atatttaagt aagatcggaa gagcacacgt ctgaactcca gtcacaatca 480
gtctcgtatc tcgtatgccg tcttctgctt gttgtcgact c 521

<210> SEQ ID NO 31
<211> LENGTH: 521
<212> TYPE: DNA
<213> ORGANISM: Artificial
<220> FEATURE:
<223> OTHER INFORMATION: Polynucleotide

<400> SEQUENCE: 31
aataagcacc ggctaacttc gtgccagcag ccgcggtaat acgaagggtg caagcgttaa 60
tcggaattac tgggcgtaaa tttgcgcgcg taggtggttc agcaagttgg atgtgaaatc 120
cccgggctca acctgggaac tgcatccaaa actactgagc tagagtacgg tagagggtgg 180
tggaatttcc tgtgtagcgg tgaaatgcgt agatatagga aggaacacca gtggcgaagg 240
cgaccacctg gactgatact gacactgagg tgcgaaagcg tggggagcaa acaggattag 300
ataccctggt agtccacgcc gtaaacgatg tcgactaggg ataacagggt aatgagtcga 360
caaaatgata cggcgaccac cgagatctac actctttccc tacacgacgc tcttccgatc 420
tccgaatgaa agtacccgaa aagatcggaa gagcacacgt ctgaactcca gtcacaatca 480
gtctcgtatc tcgtatgccg tcttctgctt gttgtcgact c 521

<210> SEQ ID NO 32
<211> LENGTH: 521
<212> TYPE: DNA
<213> ORGANISM: Artificial
<220> FEATURE:
<223> OTHER INFORMATION: Polynucleotide

<400> SEQUENCE: 32
aataagcacc ggctaacttc gtgccagcag ccgcggtaat acgaagggtg caagcgttaa 60
tcggaattac tgggcgtaaa tcagcgcgcg taggtggttc agcaagttgg atgtgaaatc 120
cccgggctca acctgggaac tgcatccaaa actactgagc tagagtacgg tagagggtgg 180
tggaatttcc tgtgtagcgg tgaaatgcgt agatatagga aggaacacca gtggcgaagg 240
cgaccacctg gactgatact gacactgagg tgcgaaagcg tggggagcaa acaggattag 300
ataccctggt agtccacgcc gtaaacgatg tcgactaggg ataacagggt aatgagtcga 360
caaaatgata cggcgaccac cgagatctac actctttccc tacacgacgc tcttccgatc 420

-continued

```
tggtcgtgct atcaatccaa cagatcggaa gagcacacgt ctgaactcca gtcacaatca    480

gtctcgtatc tcgtatgccg tcttctgctt gttgtcgact c                        521
```

<210> SEQ ID NO 33
<211> LENGTH: 521
<212> TYPE: DNA
<213> ORGANISM: Artificial
<220> FEATURE:
<223> OTHER INFORMATION: Polynucleotide

<400> SEQUENCE: 33

```
aataagcacc ggctaacttc gtgccagcag ccgcggtaat acgaagggtg caagcgttaa     60

tcggaattac tgggcgtaaa cccgcgcgcg taggtggttc agcaagttgg atgtgaaatc    120

cccgggctca acctgggaac tgcatccaaa actactgagc tagagtacgg tagagggtgg    180

tggaatttcc tgtgtagcgg tgaaatgcgt agatatagga aggaacacca gtggcgaagg    240

cgaccacctg gactgatact gacactgagg tgcgaaagcg tggggagcaa acaggattag    300

ataccctggt agtccacgcc gtaaacgatg tcgactaggg ataacagggt aatgagtcga    360

caaaatgata cggcgaccac cgagatctac actctttccc tacacgacgc tcttccgatc    420

tcagttactc gaaggtatag gagatcggaa gagcacacgt ctgaactcca gtcacaatca    480

gtctcgtatc tcgtatgccg tcttctgctt gttgtcgact c                        521
```

<210> SEQ ID NO 34
<211> LENGTH: 521
<212> TYPE: DNA
<213> ORGANISM: Artificial
<220> FEATURE:
<223> OTHER INFORMATION: Polynucleotide

<400> SEQUENCE: 34

```
aataagcacc ggctaacttc gtgccagcag ccgcggtaat acgaagggtg caagcgttaa     60

tcggaattac tgggcgtaaa ggggcgcgcg taggtggttc agcaagttgg atgtgaaatc    120

cccgggctca acctgggaac tgcatccaaa actactgagc tagagtacgg tagagggtgg    180

tggaatttcc tgtgtagcgg tgaaatgcgt agatatagga aggaacacca gtggcgaagg    240

cgaccacctg gactgatact gacactgagg tgcgaaagcg tggggagcaa acaggattag    300

ataccctggt agtccacgcc gtaaacgatg tcgactaggg ataacagggt aatgagtcga    360

caaaatgata cggcgaccac cgagatctac actctttccc tacacgacgc tcttccgatc    420

tgtgatagcc gggcgttaca tagatcggaa gagcacacgt ctgaactcca gtcacaatca    480

gtctcgtatc tcgtatgccg tcttctgctt gttgtcgact c                        521
```

<210> SEQ ID NO 35
<211> LENGTH: 519
<212> TYPE: DNA
<213> ORGANISM: Artificial
<220> FEATURE:
<223> OTHER INFORMATION: Polynucleotide

<400> SEQUENCE: 35

```
aataagcacc ggctaacttc gtgccagcag ccgcggtaat acgaagggtg caagcgttaa     60

tcggaattac tgggcgtaaa tgcgcgcgta ggtggttcag caagttggat gtgaaatccc    120

cgggctcaac ctgggaactg catccaaaac tactgagcta gagtacggta gagggtggtg    180

gaatttcctg tgtagcggtg aaatgcgtag atataggaag gaacaccagt ggcgaaggcg    240

accacctgga ctgatactga cactgaggtg cgaaagcgtg gggagcaaac aggattagat    300
```

accctggtag tccacgccgt aaacgatgtc gactagggat aacagggtaa tgagtcgaca 360
aaatgatacg gcgaccaccg agatctacac tctttcccta cacgacgctc ttccgatctt 420
ttgatagtgc gcgcatagca gatcggaaga gcacacgtct gaactccagt cacaatcagt 480
ctcgtatctc gtatgccgtc ttctgcttgt tgtcgactc 519

<210> SEQ ID NO 36
<211> LENGTH: 520
<212> TYPE: DNA
<213> ORGANISM: Artificial
<220> FEATURE:
<223> OTHER INFORMATION: Polynucleotide

<400> SEQUENCE: 36
aataagcacc ggctaacttc gtgccagcag ccgcggtaat acgaagggtg caagcgttaa 60
tcggaattac tgggcgtaaa tcgcgcgcgt aggtggttca gcaagttgga tgtgaaatcc 120
ccgggctcaa cctgggaact gcatccaaaa ctactgagct agagtacggt agagggtggt 180
ggaatttcct gtgtagcggt gaaatgcgta gatataggaa ggaacaccag tggcgaaggc 240
gaccacctgg actgatactg acactgaggt gcgaaagcgt ggggagcaaa caggattaga 300
taccctggta gtccacgccg taaacgatgt cgactaggga taacagggta atgagtcgac 360
aaaatgatac ggcgaccacc gagatctaca ctctttccct acacgacgct cttccgatct 420
gttctatgcc ttacctaaag agatcggaag agcacacgtc tgaactccag tcacaatcag 480
tctcgtatct cgtatgccgt cttctgcttg ttgtcgactc 520

<210> SEQ ID NO 37
<211> LENGTH: 523
<212> TYPE: DNA
<213> ORGANISM: Artificial
<220> FEATURE:
<223> OTHER INFORMATION: Polynucleotide

<400> SEQUENCE: 37
aataagcacc ggctaacttc gtgccagcag ccgcggtaat acgaagggtg caagcgttaa 60
tcggaattac tgggcgtaaa tctgagcgcg cgtaggtggt tcagcaagtt ggatgtgaaa 120
tccccgggct caacctggga actgcatcca aaactactga gctagagtac ggtagagggt 180
ggtggaattt cctgtgtagc ggtgaaatgc gtagatatag gaaggaacac cagtggcgaa 240
ggcgaccacc tggactgata ctgacactga ggtgcgaaag cgtggggagc aaacaggatt 300
agataccctg gtagtccacg ccgtaaacga tgtcgactag ggataacagg gtaatgagtc 360
gacaaaatga tacggcgacc accgagatct acactctttc cctacacgac gctcttccga 420
tctgcagctt cttgatgagg cttagatcgg aagagcacac gtctgaactc cagtcacaat 480
cagtctcgta tctcgtatgc cgtcttctgc ttgttgtcga ctc 523

<210> SEQ ID NO 38
<211> LENGTH: 525
<212> TYPE: DNA
<213> ORGANISM: Artificial
<220> FEATURE:
<223> OTHER INFORMATION: Polynucleotide

<400> SEQUENCE: 38
aataagcacc ggctaacttc gtgccagcag ccgcggtaat acgaagggtg caagcgttaa 60
tcggaattac tgggcgtaaa tctgactgcg cgcgtaggtg gttcagcaag ttggatgtga 120

-continued

```
aatccccggg ctcaacctgg gaactgcatc caaaactact gagctagagt acggtagagg    180

gtggtggaat ttcctgtgta gcggtgaaat gcgtagatat aggaaggaac accagtggcg    240

aaggcgacca cctggactga tactgacact gaggtgcgaa agcgtgggga gcaaacagga    300

ttagataccc tggtagtcca cgccgtaaac gatgtcgact agggataaca gggtaatgag    360

tcgacaaaat gatacggcga ccaccgagat ctacactctt tccctacacg acgctcttcc    420

gatcttttca ttacgctcca cttctagatc ggaagagcac acgtctgaac tccagtcaca    480

atcagtctcg tatctcgtat gccgtcttct gcttgttgtc gactc                    525
```

<210> SEQ ID NO 39
<211> LENGTH: 528
<212> TYPE: DNA
<213> ORGANISM: Artificial
<220> FEATURE:
<223> OTHER INFORMATION: Polynucleotide

<400> SEQUENCE: 39

```
aataagcacc ggctaacttc gtgccagcag ccgcggtaat acgaagggtg caagcgttaa     60

tcggaattac tgggcgtaaa tctgactaag gcgcgcgtag gtggttcagc aagttggatg    120

tgaaatcccc gggctcaacc tgggaactgc atccaaaact actgagctag agtacggtag    180

agggtggtgg aatttcctgt gtagcggtga aatgcgtaga tataggaagg aacaccagtg    240

gcgaaggcga ccacctggac tgatactgac actgaggtgc gaaagcgtgg ggagcaaaca    300

ggattagata ccctggtagt ccacgccgta aacgatgtcg actagggata acagggtaat    360

gagtcgacaa aatgatacgg cgaccaccga gatctacact ctttccctac acgacgctct    420

tccgatctgc tcctatttaa cctggaccag atcggaagag cacacgtctg aactccagtc    480

acaatcagtc tcgtatctcg tatgccgtct tctgcttgtt gtcgactc                 528
```

<210> SEQ ID NO 40
<211> LENGTH: 518
<212> TYPE: DNA
<213> ORGANISM: Artificial
<220> FEATURE:
<223> OTHER INFORMATION: Polynucleotide

<400> SEQUENCE: 40

```
aagaagcacc ggctaactcc gtgccagcag ccgcggtaat atgaaggttg aaagcgtaat     60

taggaattat tgatagtaaa gtgcacacta gcgttttgtt aaatcttaag tgtaatcccc    120

gagctaaaac aaggaataac atctgataat tacaagattg aaaatcgtat ttggaggtag    180

aattccagga gtaaaggaga aattaatagt gttctgtaat aatacaagta tcgtatgcag    240

caactaggtc gaagactgat gatcaggtga gaaagtgttg ggagctaact gaattagata    300

ccctggtagt ccacgccgta aacgatgtcg actagggata acagggtaat gagtcgacaa    360

aatgatacgg cgaccaccga gatctacact ctttccctac acgacgctct tccgatctga    420

tttggcactg taggtactag atcggaagag cacacgtctg aactccagtc acaatcagtc    480

tcgtatctcg tatgccgtct tctgcttgtt gtcgactc                            518
```

<210> SEQ ID NO 41
<211> LENGTH: 518
<212> TYPE: DNA
<213> ORGANISM: Artificial
<220> FEATURE:
<223> OTHER INFORMATION: Polynucleotide

<400> SEQUENCE: 41
aagaagcacc ggctaactcc gtgccagcag ccgcggtaat atggaggatt caaacataaa 60
tcagaattac tgggcttaaa ataatcgcat tctgtttgtt aagtaatatg tgtaatcccc 120
gggctaatcc tgggaaatgc atttaatact ggcaatctag agtataataa aggagaatag 180
tattttagta gaaacagaga attgtttaga tatttggagg aataaagtta gcatttgctg 240
ccccatggac gaaaaatgat gctcatatgc aaaagcgtgg tgtacaaaca ggattagata 300
ccctggtagt ccacgccgta aacgatgtcg actagggata acagggtaat gagtcgacaa 360
aatgatacgg cgaccaccga gatctacact ctttccctac acgacgctct tccgatctgg 420
tgctataggc cctctttgag atcggaagag cacacgtctg aactccagtc acaatcagtc 480
tcgtatctcg tatgccgtct tctgcttgtt gtcgactc 518

<210> SEQ ID NO 42
<211> LENGTH: 518
<212> TYPE: DNA
<213> ORGANISM: Artificial
<220> FEATURE:
<223> OTHER INFORMATION: Polynucleotide

<400> SEQUENCE: 42
aagaagcacc ggctaactcc gtgccagcag ccgcggtaaa atgaagaatg aatgctttaa 60
tcggtattat tggtcgtaaa acgcacgcag gaggattgtt aaattagatg tgaaatccac 120
tggcttaaca ttagataagc atctgataca ggatagcttg attttcatat aagaggtttg 180
aaatccagat atagctttgt aattcgtaga aatctggatg attaccggtt atgaaggcgg 240
tctcatggat gaaatctgat gctaaaatac gaatgcgtgg ttatcaaata atattagata 300
ccctggtagt ccacgccgta aacgatgtcg actagggata acagggtaat gagtcgacaa 360
aatgatacgg cgaccaccga gatctacact ctttccctac acgacgctct tccgatctat 420
cacatgctgc tgcgtccaag atcggaagag cacacgtctg aactccagtc acaatcagtc 480
tcgtatctcg tatgccgtct tctgcttgtt gtcgactc 518

<210> SEQ ID NO 43
<211> LENGTH: 518
<212> TYPE: DNA
<213> ORGANISM: Artificial
<220> FEATURE:
<223> OTHER INFORMATION: Polynucleotide

<400> SEQUENCE: 43
aagaagcacc ggctaactcc gtgccagcag ccgcggtaaa actgatggtg taaacgtttt 60
tcggtttaac tgaacataat gttcacgaaa gataaatgtt attacatttg atatttatct 120
tgactcaaca tgggaacagc atatgataca ggaaaacttg agtctcgtag aagggagttt 180
aattccaggt taagctatta tatgataata gaactggaga aaatccggtg ttgatggcgg 240
ttacttggat ttagacttac gttcaggaac aaaatcttgt ggtgctaaca ggattagata 300
ccctggtagt ccacgccgta aacgatgtcg actagggata acagggtaat gagtcgacaa 360
aatgatacgg cgaccaccga gatctacact ctttccctac acgacgctct tccgatctag 420
gcatgggatc atgtcagaag atcggaagag cacacgtctg aactccagtc acaatcagtc 480
tcgtatctcg tatgccgtct tctgcttgtt gtcgactc 518

<210> SEQ ID NO 44
<211> LENGTH: 518
<212> TYPE: DNA

<213> ORGANISM: Artificial
<220> FEATURE:
<223> OTHER INFORMATION: Polynucleotide

<400> SEQUENCE: 44
aagaagcacc ggctaactcc gtgccagcag ccgcggtaat acggagggtg atagtgttaa 60
tcgtaattac taggcgttaa gcacaaacag gtggattgtt aagacagata tgatatccca 120
gggcttaaac aggaaactgc aaatgatact agctagcttg agactcgaat atgggggtag 180
aataccagga ttaaagatga tttacgtaga gataaggagt attaccgttg ttaaaggcgg 240
caacctgaat taatactaac taacaggaaa gaaagcgtgg taagaaaaca ggattagata 300
ccctggtagt ccacgccgta aacgatgtcg actagggata acagggtaat gagtcgacaa 360
aatgatacgg cgaccaccga gatctacact ctttccctac acgacgctct tccgatctca 420
ggaccagatc atgtgatcag atcggaagag cacacgtctg aactccagtc acaatcagtc 480
tcgtatctcg tatgccgtct tctgcttgtt gtcgactc 518

<210> SEQ ID NO 45
<211> LENGTH: 518
<212> TYPE: DNA
<213> ORGANISM: Artificial
<220> FEATURE:
<223> OTHER INFORMATION: Polynucleotide

<400> SEQUENCE: 45
aagaagcacc ggctaactcc gtgccagcag ccgcggtaat acggagggtg caaattttaa 60
tcggaattac tggtaataaa gcgcacgtag tcggtttgtt aattcatatt tgaattccta 120
agtctaaacc tagtaactac atctgatact ggtaaacttg agtctcttag agggggatag 180
aattatagtt gtagcggtga aattcgaaga gttctggagt aataccggta gcaaagacga 240
ccaactggac gaagtctgac gttaagataa gaaagtatgg ggagcaaaca ggattagata 300
ccctggtagt ccacgccgta aacgatgtcg actagggata acagggtaat gagtcgacaa 360
aatgatacgg cgaccaccga gatctacact ctttccctac acgacgctct tccgatctca 420
tgcatgtaag acgctccgag atcggaagag cacacgtctg aactccagtc acaatcagtc 480
tcgtatctcg tatgccgtct tctgcttgtt gtcgactc 518

<210> SEQ ID NO 46
<211> LENGTH: 518
<212> TYPE: DNA
<213> ORGANISM: Artificial
<220> FEATURE:
<223> OTHER INFORMATION: Polynucleotide

<400> SEQUENCE: 46
aagaagcacc ggctaactcc gtgccagcag ccgcggtaat acagagggtg taagcgttaa 60
tagaaattac tgggcgtaaa aagcacgcag gcggtttgta aagttagata taaattcatt 120
ggactctaac tgagaactgc atttgatact ttcaagcttt tgtctcgttg aggagggtag 180
aaattcagga gttgcgatga tatgcttaga gatcttgagg aattccggtg tcgaatgcaa 240
actcctggac gaagactaac gttcagttgc aaaagagtgg aaattaaaca ttattagata 300
ccctggtagt ccacgccgta aacgatgtcg actagggata acagggtaat gagtcgacaa 360
aatgatacgg cgaccaccga gatctacact ctttccctac acgacgctct tccgatctcg 420
gacagtcgct tatctgcaag atcggaagag cacacgtctg aactccagtc acaatcagtc 480
tcgtatctcg tatgccgtct tctgcttgtt gtcgactc 518

<210> SEQ ID NO 47
<211> LENGTH: 518
<212> TYPE: DNA
<213> ORGANISM: Artificial
<220> FEATURE:
<223> OTHER INFORMATION: Polynucleotide

<400> SEQUENCE: 47
aagaagcacc ggctaactcc gtgccagcag ccgcggtaat aaggaatgag ctagcgttaa 60
tcgaaattac tgggtgtttt gctcatgcag gagattagtt tattcagatg taaaaaaccc 120
gggtacaacc tgggaattgc atctgatact tataagctaa atactcgtag agggaggtag 180
tattcctggt gttgtggtga aatgtgtaga gatctatata attacatgtt gcgaaggcgg 240
acccaaggac gaagactgat gctcagaaat taaaacgtgg aaatcaaact tgattagata 300
ccctggtagt ccacgccgta aacgatgtcg actagggata acagggtaat gagtcgacaa 360
aatgatacgg cgaccaccga gatctacact ctttccctac acgacgctct tccgatctga 420
tcgtaattgc ctatgagtag atcggaagag cacacgtctg aactccagtc acaatcagtc 480
tcgtatctcg tatgccgtct tctgcttgtt gtcgactc 518

<210> SEQ ID NO 48
<211> LENGTH: 518
<212> TYPE: DNA
<213> ORGANISM: Artificial
<220> FEATURE:
<223> OTHER INFORMATION: Polynucleotide

<400> SEQUENCE: 48
aagaagcacc ggctaactcc gtgccagcag ccgcggtaat tcagaatgtg taagcgtaat 60
tcgaaatttc tgagagtaaa gcgaatgcag atggtttatt ttgttagaag tgaaatcccc 120
gggctatacc tggttactgc atctgttact ggtaaacttg aaactcgaag agggtgataa 180
tattccaggt atttaggtta aatgtgtaga tatctggatg aatactagtg tctaaggcag 240
tccactggac gtagacttac tctcaggttc gaaagcgtgg ggaacattca taattagata 300
ccctggtagt ccacgccgta aacgatgtcg actagggata acagggtaat gagtcgacaa 360
aatgatacgg cgaccaccga gatctacact ctttccctac acgacgctct tccgatctcg 420
aaggtcgcgg cggatatgag atcggaagag cacacgtctg aactccagtc acaatcagtc 480
tcgtatctcg tatgccgtct tctgcttgtt gtcgactc 518

<210> SEQ ID NO 49
<211> LENGTH: 518
<212> TYPE: DNA
<213> ORGANISM: Artificial
<220> FEATURE:
<223> OTHER INFORMATION: Polynucleotide

<400> SEQUENCE: 49
aagaagcacc ggctaactcc gtgccagcag ccgcggtaat aaggagggtg cttgcgttaa 60
acagaaatac tgggtgtaaa acgtacgtag acggtttatt aagtaagatg tgaaatcccc 120
gtgctcaacc taggaactgc atatgatatt ggaaaacttg agacatatag agggagatag 180
aatacttgga gtagcgttgt aatgcgtata gatttggagg aataccggtg gcgaaggcgg 240
ccccctggac gaagacagac gctcaggtgc gaaatcgttg tgatcaaata ggattagata 300
ccctggtagt ccacgccgta aacgatgtcg actagggata acagggtaat gagtcgacaa 360
aatgatacgg cgaccaccga gatctacact ctttccctac acgacgctct tccgatctgc 420
ccgcagcttc gctctaagag atcggaagag cacacgtctg aactccagtc acaatcagtc 480
tcgtatctcg tatgccgtct tctgcttgtt gtcgactc 518

<210> SEQ ID NO 50
<211> LENGTH: 518
<212> TYPE: DNA
<213> ORGANISM: Artificial
<220> FEATURE:
<223> OTHER INFORMATION: Polynucleotide

<400> SEQUENCE: 50
aagaagcacc ggctaactcc gtgccagcag ccgcggtaat acgaagtgtg aaaacgttat 60
taagaattac tgggcgtaaa gcgttcgcag gcggtttgtt aagtcataag tgaaatcccc 120
gggcacaaac tgggaactga atctgtaact gacaagcttg agtatcttat aatgggatag 180
aatttaatgt gtagctgtga aatgcgtaga gatctggaga tataccggtg actaaggcgg 240
ccccctggac gaagactgac gctcaggtgc taaatcgtgg ggaacaaaaa ggattagata 300
ccctggtagt ccacgccgta aacgatgtcg actagggata acagggtaat gagtcgacaa 360
aatgatacgg cgaccaccga gatctacact ctttccctac acgacgctct tccgatctaa 420
tgatttaaag tcaagagaag atcggaagag cacacgtctg aactccagtc acaatcagtc 480
tcgtatctcg tatgccgtct tctgcttgtt gtcgactc 518

<210> SEQ ID NO 51
<211> LENGTH: 518
<212> TYPE: DNA
<213> ORGANISM: Artificial
<220> FEATURE:
<223> OTHER INFORMATION: Polynucleotide

<400> SEQUENCE: 51
aagaagcacc ggctaactcc gtgccagcag ccgcggtaaa actgagggtg caagcgttaa 60
tcggaattac tgtgcataaa gctcacgcat tcgttttgtt aagtcagata ataaatcctc 120
gagttaaacc tgggaaatgc atctgatact gaaaagcttg attctcgtag aggggtgtag 180
aattccaggt gtagcagtaa aatacgtaga gatcagaatg aattccggtg gtgaagtcgg 240
cctactggac gaagactgac gctaaggtgc gaaagcgtgg ggagcaaaca ggattagata 300
ccctggtagt ccacgccgta aacgatgtcg actagggata acagggtaat gagtcgacaa 360
aatgatacgg cgaccaccga gatctacact ctttccctac acgacgctct tccgatctac 420
gtaggtgatc ggtaccacag atcggaagag cacacgtctg aactccagtc acaatcagtc 480
tcgtatctcg tatgccgtct tctgcttgtt gtcgactc 518

<210> SEQ ID NO 52
<211> LENGTH: 518
<212> TYPE: DNA
<213> ORGANISM: Artificial
<220> FEATURE:
<223> OTHER INFORMATION: Polynucleotide

<400> SEQUENCE: 52
aagaagcacc ggctaactcc gtgccagcag ccgcggtaat acggagtgtt aaatcgttaa 60
taggaattac tgggcgaaaa gtgctagcag gcggtttgtt aaatcagttg tgaaatccct 120
gggcacaacc tgggatctgc atctgatttt ggcaagcttt agtctattag agggggggtaa 180 atttccatgt gtagatttga aatgcgttta gatctggagg aataccggag gtgaaggcga 240
tcccctggac gtagactgaa gctcaagtga gaaagcttgg agtgcaaact agattagata 300
ccctggtagt ccacgccgta aacgatgtcg actagggata acagggtaat gagtcgacaa 360
aatgatacgg cgaccaccga gatctacact ctttccctac acgacgctct tccgatctag 420
aacaccactg gtgacccaag atcggaagag cacacgtctg aactccagtc acaatcagtc 480
tcgtatctcg tatgccgtct tctgcttgtt gtcgactc 518

<210> SEQ ID NO 53
<211> LENGTH: 518
<212> TYPE: DNA
<213> ORGANISM: Artificial
<220> FEATURE:
<223> OTHER INFORMATION: Polynucleotide

<400> SEQUENCE: 53
aagaagcacc ggctaactcc gtgccagcag ccgcggtaat acggagggtg caagcgataa 60
tagtatttac tgtgcgaaaa gcatacttag gaagattttt atgtcagatg tgaaatcccc 120
gggcttaacc tgggaactgc atctgatact gacaagtttg agactcgtat agggggggtag 180 aattccaggt gttgcagtga aaagtgtaga gatctggaag aataccggtg gcgaaggttg 240
ccccctgtac gaataatgac gctatggtgc gaaagcattg tgtgcaaaca agattagata 300
ccctggtagt ccacgccgta aacgatgtcg actagggata acagggtaat gagtcgacaa 360
aatgatacgg cgaccaccga gatctacact ctttccctac acgacgctct tccgatctac 420
agagggcaat gacgtacaag atcggaagag cacacgtctg aactccagtc acaatcagtc 480
tcgtatctcg tatgccgtct tctgcttgtt gtcgactc 518

<210> SEQ ID NO 54
<211> LENGTH: 518
<212> TYPE: DNA
<213> ORGANISM: Artificial
<220> FEATURE:
<223> OTHER INFORMATION: Polynucleotide

<400> SEQUENCE: 54
aagaagcacc ggctaactcc gtgccagcag ccgcggtaat acggaaggtg caagtgttaa 60
tcggaattac tgggcataaa gcgcacgaag gcggtatgtt aagttagatg tgaaatcccc 120
gggctcaatc tgtgaactgc atctgatact ggcaagcttg agtctcgtag agggggggtag 180 aattcaaggt gtagcggtga aatgcgtaga gatctagatg aataccggtg gcgaaggagg 240
tcccctggac gaagactgac actctggtgc gaaatagtgg ggagcaaaca gaattagata 300
ccctggtagt ccacgccgta aacgatgtcg actagggata acagggtaat gagtcgacaa 360
aatgatacgg cgaccaccga gatctacact ctttccctac acgacgctct tccgatcttc 420
attgacaggt tgggttagag atcggaagag cacacgtctg aactccagtc acaatcagtc 480
tcgtatctcg tatgccgtct tctgcttgtt gtcgactc 518

<210> SEQ ID NO 55
<211> LENGTH: 518
<212> TYPE: DNA
<213> ORGANISM: Artificial
<220> FEATURE:
<223> OTHER INFORMATION: Polynucleotide

<400> SEQUENCE: 55
aagaagcacc ggctaactcc gtgccagcag ccgcggtaat acggagggtg caatcgttaa 60
tcggatttac tgggcttaaa tcgcacgcag gcggtttgtt aagtcatatg tgaaaacccc 120
gggctcaacc tgggaactgc atctgatact tgcaagcttg agtctcgtat agggaggtag 180
aattccaggt gtagcggtga aatgcgtaga gatctgaagt aataccggta gctaatacgg 240
cccactggac gaagactgac gcacaggtgc taaagcgtgt ggagcaaaca ggattagata 300
ccctggtagt ccacgccgta aacgatgtcg actagggata acagggtaat gagtcgacaa 360
aatgatacgg cgaccaccga gatctacact ctttccctac acgacgctct tccgatctac 420
actgtatgga ccggtcacag atcggaagag cacacgtctg aactccagtc acaatcagtc 480
tcgtatctcg tatgccgtct tctgcttgtt gtcgactc 518

<210> SEQ ID NO 56
<211> LENGTH: 518
<212> TYPE: DNA
<213> ORGANISM: Artificial
<220> FEATURE:
<223> OTHER INFORMATION: Polynucleotide

<400> SEQUENCE: 56
aagaagcacc ggctaactcc gtgccagcag ccgcggtaat acggagtgtg caagcgttaa 60
tcggaattac tggtcgtaaa gcgcacgtag acggtttgtt aattcagatg ttaaattcca 120
gggcaaaacc tgggaactgc atcttatact ggcaagcttg agtctcgtag agggggttag 180
aattccaggt gtagcggtga aatgtgtaaa gatctggagg aataccggtg ttgaaggcgg 240
cctcctggac gaagactgac gctcaggtgc gaaagcgtgg ggagcaaaca ggattagata 300
ccctggtagt ccacgccgta aacgatgtcg actagggata acagggtaat gagtcgacaa 360
aatgatacgg cgaccaccga gatctacact ctttccctac acgacgctct tccgatctcg 420
gcctggctct tatgtagaag atcggaagag cacacgtctg aactccagtc acaatcagtc 480
tcgtatctcg tatgccgtct tctgcttgtt gtcgactc 518

<210> SEQ ID NO 57
<211> LENGTH: 518
<212> TYPE: DNA
<213> ORGANISM: Artificial
<220> FEATURE:
<223> OTHER INFORMATION: Polynucleotide

<400> SEQUENCE: 57
aagaagcacc ggctaactcc gtgccagcag ccgcggtaat acggagggaa caagcgttaa 60
tcgaaataac tgggcgtaaa gcgctcgtag gttgtttgtt aagtcagatg tgaaatcccc 120
gggttcaacc tgggaactgc atctgattat ggcaagcttg agtctcgtag agggggggtat 180 aattccagtt gaagcggtaa aatgcgttga gatctggagg tataccggtg gcgaaagcgg 240
ccccatggac gaagactgac gctcatttgc gaaatcgttg ggagcaaaca ggattagata 300
ccctggtagt ccacgccgta aacgatgtcg actagggata acagggtaat gagtcgacaa 360
aatgatacgg cgaccaccga gatctacact ctttccctac acgacgctct tccgatctaa 420
taggcccgct catcccggag atcggaagag cacacgtctg aactccagtc acaatcagtc 480
tcgtatctcg tatgccgtct tctgcttgtt gtcgactc 518

<210> SEQ ID NO 58
<211> LENGTH: 518
<212> TYPE: DNA
<213> ORGANISM: Artificial
<220> FEATURE:
<223> OTHER INFORMATION: Polynucleotide

<400> SEQUENCE: 58
aagaagcacc ggctaactcc gtgccagcag ccgcggtaat tcttcgggta ctagcgttaa 60
ttaggatttc tgcgcgtaaa gtgaacgcag gcttgttggt cagtgagatg tgtattacag 120
gtacttaacc tgtgaaccgc atctgatact cgcaagcctg aggctcctag tggggggtag 180
aaatctatgt gtatcgttgg aacccgtaaa catctgtagg atggcatgtg tccaaggcag 240
ccccctggtc tgagactgac aatcagtttc gaaagcgtgg ggagcaaaca gcattagata 300
ccctggtagt ccacgccgta aacgatgtcg actagggata acagggtaat gagtcgacaa 360
aatgatacgg cgaccaccga gatctacact ctttccctac acgacgctct tccgatctct 420
tagagacact cttaccggag atcggaagag cacacgtctg aactccagtc acaatcagtc 480
tcgtatctcg tatgccgtct tctgcttgtt gtcgactc 518

<210> SEQ ID NO 59
<211> LENGTH: 518
<212> TYPE: DNA
<213> ORGANISM: Artificial
<220> FEATURE:
<223> OTHER INFORMATION: Polynucleotide

<400> SEQUENCE: 59
aagaagcacc ggctaactcc gtgccagcag ccgcggtaag acggagggtg caagcgttaa 60
tcggaataac tgggcgtaaa gcggtcgcag gcggtttgtt aagtcagatg tgaattcccc 120
gggctcaacg tgggaacttc acctaatacg ggcaagcttt agaatcgtag aggggggtag 180
aattataggt atagcggtgc aatgcgaaga gagctggagg aatcccggtg gagaaggcag 240
ccccctggac gaagacagaa gctcaggggc gaaaccgtgg ggagcaaaca ggattagata 300
ccctggtagt ccacgccgta aacgatgtcg actagggata acagggtaat gagtcgacaa 360
aatgatacgg cgaccaccga gatctacact ctttccctac acgacgctct tccgatctta 420
tcgggcgctc tccggtacag atcggaagag cacacgtctg aactccagtc acaatcagtc 480
tcgtatctcg tatgccgtct tctgcttgtt gtcgactc 518

<210> SEQ ID NO 60
<211> LENGTH: 518
<212> TYPE: DNA
<213> ORGANISM: Artificial
<220> FEATURE:
<223> OTHER INFORMATION: Polynucleotide

<400> SEQUENCE: 60
aagaagcacc ggctaactcc gtgccagcag ccgcggtaat acggagggtg caagcgttta 60
tcggaattac tgggcgtaaa gcgcacgtag gcggtttgtt aagtcagaag tgaaatcccc 120
gggctcaacc tgggaactgc atctgatact ggctagcatg agtatcgtag aggggggtag 180
aattccaggt gtagcggtgt aatgcgtaga gatctagagg aataccggtg gcgaaggcgg 240
ccccctggac gaagactgac gctcaggtgt gaaagcgagg ggagcaaaca ggattagata 300
ccctggtagt ccacgccgta aacgatgtcg actagggata acagggtaat gagtcgacaa 360
aatgatacgg cgaccaccga gatctacact ctttccctac acgacgctct tccgatctta 420
cctatcgcag cgcgtataag atcggaagag cacacgtctg aactccagtc acaatcagtc 480
tcgtatctcg tatgccgtct tctgcttgtt gtcgactc 518

<210> SEQ ID NO 61

<211> LENGTH: 518
<212> TYPE: DNA
<213> ORGANISM: Artificial
<220> FEATURE:
<223> OTHER INFORMATION: Polynucleotide

<400> SEQUENCE: 61
aagaagcacc ggctaactcc gtgccagcag ccgcggtaat actgagggtg caagcgtaaa 60
tcggaattac tgggcgtaaa gcgcaagcag gcagtttgtt aagtcagatg tgaaatcccc 120
gggctcaacc tgggaactgc atcagatact ggcaagcttg agtctcgttg aggggggtag 180
aattccatgt gtagcggtga attgcgtaga gaactggagg aataccggtg gcgaaggcgg 240
ccccctggac gaagactgac gctcaggtgc gaaagcgtgg ggtgcaaaca ggattagata 300
ccctggtagt ccacgccgta aacgatgtcg actagggata acagggtaat gagtcgacaa 360
aatgatacgg cgaccaccga gatctacact ctttccctac acgacgctct tccgatctcc 420
cgcgtacagg attgttcgag atcggaagag cacacgtctg aactccagtc acaatcagtc 480
tcgtatctcg tatgccgtct tctgcttgtt gtcgactc 518

<210> SEQ ID NO 62
<211> LENGTH: 518
<212> TYPE: DNA
<213> ORGANISM: Artificial
<220> FEATURE:
<223> OTHER INFORMATION: Polynucleotide

<400> SEQUENCE: 62
aagaagcacc ggctaactcc gtgccagcag ccgcggtaat actgagggtg caagcgttag 60
tcggaattac tgggcgtaaa gcgcactcag gcggtttgtt aagtcagatg tgaaatcccc 120
gggctcaacc tggggactgc atctgatact ggcaagcctg agtctcgtag tggggggtat 180
aattccaggt gtagcggtga aatgcgtaga gatcaggaag aagtccagtt gtgaaggcgg 240
ccccctggac gaagactgag gctcaggtgc gaaagcgtgg ggagcaaaca agattagata 300
ccctggtagt ccacgccgta aacgatgtcg actagggata acagggtaat gagtcgacaa 360
aatgatacgg cgaccaccga gatctacact ctttccctac acgacgctct tccgatctga 420
agcaaaggga gagcgcggag atcggaagag cacacgtctg aactccagtc acaatcagtc 480
tcgtatctcg tatgccgtct tctgcttgtt gtcgactc 518

<210> SEQ ID NO 63
<211> LENGTH: 518
<212> TYPE: DNA
<213> ORGANISM: Artificial
<220> FEATURE:
<223> OTHER INFORMATION: Polynucleotide

<400> SEQUENCE: 63
aagaagcacc ggctaactcc gtgccagcag ccgcggtaat accgagggtg caagagttaa 60
gcggaattgc tggccgtaaa gcgcacacag gcgctttgtc aagttagatg cgaaatcccc 120
aggttcaacc tgggaactgc atctgatact ggcaagctta actctcgtag agggggttac 180
aattccaggt ggagcgctga aatgcgtaga catctggagg aataccggtg gcgaaggcga 240
ccccctggac gaagactccc gcttaggttc gcaagcgggg ggagcaaaca gaattagata 300
ccctggtagt ccacgccgta aacgatgtcg actagggata acagggtaat gagtcgacaa 360
aatgatacgg cgaccaccga gatctacact ctttccctac acgacgctct tccgatctat 420
agtcgtttgc gcacccgcag atcggaagag cacacgtctg aactccagtc acaatcagtc 480
tcgtatctcg tatgccgtct tctgcttgtt gtcgactc 518

<210> SEQ ID NO 64
<211> LENGTH: 518
<212> TYPE: DNA
<213> ORGANISM: Artificial
<220> FEATURE:
<223> OTHER INFORMATION: Polynucleotide

<400> SEQUENCE: 64
aagaagcacc ggctaactcc gtgccagcag ccgcggtaat acggaggggg caagcgttga 60
tcggaattac ccggcgtgaa gcgcacgcag gcggtttgtt aagtcagatg tgaaatcccc 120
gggctcaacg tgggaactgc atgtgatact ggcacgcttg agtctcgcag agggggggag 180
aattgcaggg gtagcggtga aaggcgtaga gatctggagg aataccggtg gcgagggcgg 240
ccccctggag gaagactgac gctcaggtgc gaaagcgtgg cgagcaaaca cgattagata 300
ccctggtagt ccacgccgta aacgatgtcg actagggata acagggtaat gagtcgacaa 360
aatgatacgg cgaccaccga gatctacact ctttccctac acgacgctct tccgatctcc 420
tttcctgctc ccgcctggag atcggaagag cacacgtctg aactccagtc acaatcagtc 480
tcgtatctcg tatgccgtct tctgcttgtt gtcgactc 518

<210> SEQ ID NO 65
<211> LENGTH: 518
<212> TYPE: DNA
<213> ORGANISM: Artificial
<220> FEATURE:
<223> OTHER INFORMATION: Polynucleotide

<400> SEQUENCE: 65
aagaagcacc ggctaactcc gtgccagcag ccgcggtaat acggagggtg caagcgttaa 60
tcggaatgac tgggcgtaaa gcgcacgcag gcgctgtgtt aagtcagatg tggaatcccc 120
gggctcaacc tgggaactgc atctgatact ggcaaggttg agtctggtgg agggggggag 180
aatcccaggt gtggcggtga aatgcggaga gagctggagg aataccggtg gcgaaggcgg 240
ccccctggac ggagactgac gctcaggtgc gaaagcgtgg ggagcaaaca ggattagata 300
ccctggtagt ccacgccgta aacgatgtcg actagggata acagggtaat gagtcgacaa 360
aatgatacgg cgaccaccga gatctacact ctttccctac acgacgctct tccgatctca 420
gattcgtgtc ctccacatag atcggaagag cacacgtctg aactccagtc acaatcagtc 480
tcgtatctcg tatgccgtct tctgcttgtt gtcgactc 518

<210> SEQ ID NO 66
<211> LENGTH: 518
<212> TYPE: DNA
<213> ORGANISM: Artificial
<220> FEATURE:
<223> OTHER INFORMATION: Polynucleotide

<400> SEQUENCE: 66
aagaagcacc ggctaactcc gtgccagcag ccgcggtaat acggagggtg caagcggtaa 60
tcggaattac tgggcgtaaa ccgcacgcag gcggtctgtt aagtcagatg tgaaatcccc 120
gggctcaacc ggggaactgc atctgatact ggcaagcttg agcctcgtag agggggggtag 180 aagtccgggt gtagcggtga actgcgtaga catctggagg aataccgggg gcgaaggcgg 240
ccccctggac gaagactgac gggcaggtgc gacagcgtgg ggagcaaaca ggattagata 300

-continued ccctggtagt ccacgccgta aacgatgtcg actagggata acagggtaat gagtcgacaa 360
aatgatacgg cgaccaccga gatctacact ctttccctac acgacgctct tccgatctac 420
cttctaaacg tgcgaagcag atcggaagag cacacgtctg aactccagtc acaatcagtc 480
tcgtatctcg tatgccgtct tctgcttgtt gtcgactc 518

<210> SEQ ID NO 67
<211> LENGTH: 518
<212> TYPE: DNA
<213> ORGANISM: Artificial
<220> FEATURE:
<223> OTHER INFORMATION: Polynucleotide

<400> SEQUENCE: 67
aagaagcacc ggctaactcc gtgccagcag ccgcggtaat ccggagggtg cgagcgttaa 60
tcggaattac tgcgcgtaaa gcgcacgcag gcggtttctt aagtcagctg tgaaatcccc 120
gggctcaccc cgggaactgc atctgatact cgcaaccttg agtctcgtag agggggccag 180
aattccaggt gtagcggtga aatgcgtaga gatccggagg aataccgggg gcgaaggcgg 240
ccccctggac gaagactgac gctcaggtgc gaaagcgcgg ggagcaaacc ggattagata 300
ccctggtagt ccacgccgta aacgatgtcg actagggata acagggtaat gagtcgacaa 360
aatgatacgg cgaccaccga gatctacact ctttccctac acgacgctct tccgatctgg 420
cttcgctgtg cctatgacag atcggaagag cacacgtctg aactccagtc acaatcagtc 480
tcgtatctcg tatgccgtct tctgcttgtt gtcgactc 518

<210> SEQ ID NO 68
<211> LENGTH: 518
<212> TYPE: DNA
<213> ORGANISM: Artificial
<220> FEATURE:
<223> OTHER INFORMATION: Polynucleotide

<400> SEQUENCE: 68
aagaagcacc ggctaactcc gtgccagcag ccgcggtaat ccggagcgtg caagcgtcaa 60
tccgcattag tgggcgtaaa gcgcacgcag gcgggttgtt aagtcagatg tgaaatcccg 120
gggctcaacc tgggaactgc atctgagact ggcaagcttg agtctcgtac agggggggtag 180 aattccaggt ctggcgctga aatgcgtaga gatctggagg cagaccggtc gcgaaggcgg 240
ccccctgcac gacgagtgac cctcaggcgc gaaagcgtgg ggagcaaaca ggattagata 300
ccctggtagt ccacgccgta aacgatgtcg actagggata acagggtaat gagtcgacaa 360
aatgatacgg cgaccaccga gatctacact ctttccctac acgacgctct tccgatctaa 420
ataagaccgc atagttatag atcggaagag cacacgtctg aactccagtc acaatcagtc 480
tcgtatctcg tatgccgtct tctgcttgtt gtcgactc 518

<210> SEQ ID NO 69
<211> LENGTH: 518
<212> TYPE: DNA
<213> ORGANISM: Artificial
<220> FEATURE:
<223> OTHER INFORMATION: Polynucleotide

<400> SEQUENCE: 69
aagaagcacc ggctaactcc gtgccagcag ccgcggtaat acgcagggtg caagcgttaa 60
tcggaattac tgggcggaag gcgcacgcac gcggcctgtc aagtgagatg tgacatcccc 120
gggctcaacc tcggaactgc gtctgatact ggcacgcttg cgtcgcgtac agggggcgag 180

```
aattccaggg ggaggggtga aatgcgtggc gatccggagg aataccggtg gcgaaggcgg    240

cccccgggac gaagacggcc gctcaggggc caaagcgtgg ggggcagaca cgattagata    300

ccctggtagt ccacgccgta aacgatgtcg actagggata acagggtaat gagtcgacaa    360

aatgatacgg cgaccaccga gatctacact ctttccctac acgacgctct tccgatctcg    420

aactacaggg acgagagtag atcggaagag cacacgtctg aactccagtc acaatcagtc    480

tcgtatctcg tatgccgtct tctgcttgtt gtcgactc                            518
```

```
<210> SEQ ID NO 70
<211> LENGTH: 518
<212> TYPE: DNA
<213> ORGANISM: Artificial
<220> FEATURE:
<223> OTHER INFORMATION: Polynucleotide

<400> SEQUENCE: 70

aagaagcacc ggctaactcc gtgccagcag ccgcggtaat acggggggtg caagcgtgga     60

tcggaattgc tgggcgtcaa gggcacgcag gcggtttgtg aagtcagacg cgagagcccc    120

gggctccacc ggggaactgc atctgatact ggcaagcttg agtctcgtag acgggggcag    180

aatcccgggt gtggcgggga aatgcgtaga gatctggagg gatcccggtg gcgaaggcgg    240

ccccctggac ggagactgac gctcaggtgc ggaagcgggg ggaccaaaca ggattagata    300

ccctggtagt ccacgccgta aacgatgtcg actagggata acagggtaat gagtcgacaa    360

aatgatacgg cgaccaccga gatctacact ctttccctac acgacgctct tccgatctat    420

cggttcttgg tccgcttaag atcggaagag cacacgtctg aactccagtc acaatcagtc    480

tcgtatctcg tatgccgtct tctgcttgtt gtcgactc                            518
```

```
<210> SEQ ID NO 71
<211> LENGTH: 518
<212> TYPE: DNA
<213> ORGANISM: Artificial
<220> FEATURE:
<223> OTHER INFORMATION: Polynucleotide

<400> SEQUENCE: 71

aagaagcacc ggctaactcc gtgccagcag ccgcggtaat acgcagggtg ccagcgttaa     60

tcggaattac tgggcgtgaa gcgcacgcgg gcggtttgtt aagtcagacg tgaaatcccc    120

gcgctcaacc tgggagccgc acctgagagt ggcgagcttg ggtgtcgtag agggggggtag    180

acttccaggt gtagcggtga aatgcgcagc gctctggcgg gataccgctg gcgaaggcgg    240

ccccccgggc gaagcctgcc gctcaggggc gaaagcgtgg ggagcacaca ggattagata    300

ccctggtagt ccacgccgta aacgatgtcg actagggata acagggtaat gagtcgacaa    360

aatgatacgg cgaccaccga gatctacact ctttccctac acgacgctct tccgatctcc    420

gcctgatgtc acggccttag atcggaagag cacacgtctg aactccagtc acaatcagtc    480

tcgtatctcg tatgccgtct tctgcttgtt gtcgactc                            518
```

```
<210> SEQ ID NO 72
<211> LENGTH: 518
<212> TYPE: DNA
<213> ORGANISM: Artificial
<220> FEATURE:
<223> OTHER INFORMATION: Polynucleotide

<400> SEQUENCE: 72
```

-continued

```
aagaagcacc ggctaactcc gtgccagcag ccgcggtaat acggagcgtg caagcgctaa     60

ccggaattac tgcgcgtcaa gcggacgcag gcggttcgtt aagtcaggtg tgagatcccc    120

ggggtcaacc ggggacctgc atctgacacc ggcacgcttg agtcccgtag gggcgggtag    180

aatccccggt gtagcggtgc gagccgtagc gatccggagg aataccggtg gcgacggccg    240

ccccctggac gaaggctgac gctgaggtgc gaaagcgtgg ggagcaaaca ggattagata    300

ccctggtagt ccacgccgta aacgatgtcg actagggata acagggtaat gagtcgacaa    360

aatgatacgg cgaccaccga gatctacact ctttccctac acgacgctct tccgatctcg    420

tcacttaaac acttcaatag atcggaagag cacacgtctg aactccagtc acaatcagtc    480

tcgtatctcg tatgccgtct tctgcttgtt gtcgactc                            518
```

<210> SEQ ID NO 73
<211> LENGTH: 518
<212> TYPE: DNA
<213> ORGANISM: Artificial
<220> FEATURE:
<223> OTHER INFORMATION: Polynucleotide

<400> SEQUENCE: 73

```
aagaagcacc ggctaactcc gtgccagcag ccgcggtaat accgccggtg cacgcgttaa     60

tcggaattac tgggggtaca gcgcgcgcgg gcggtttgtt agctccggtg tgaagtcccg    120

gggctcaacc tgggaactcc agcggacact ggcaagcctg agtctcgtcc cgggggggag    180

agttccagct gtagcggtga cgtccctgga gatctcgggg aatacgggtg gccaaggccg    240

ccccctcgag gaggagtcac gctgaggcgc gaaagcgtgg ggagcaaaca ggattagata    300

ccctggtagt ccacgccgta aacgatgtcg actagggata acagggtaat gagtcgacaa    360

aatgatacgg cgaccaccga gatctacact ctttccctac acgacgctct tccgatcttc    420

ctgccagcgt cggcagacag atcggaagag cacacgtctg aactccagtc acaatcagtc    480

tcgtatctcg tatgccgtct tctgcttgtt gtcgactc                            518
```

<210> SEQ ID NO 74
<211> LENGTH: 518
<212> TYPE: DNA
<213> ORGANISM: Artificial
<220> FEATURE:
<223> OTHER INFORMATION: Polynucleotide

<400> SEQUENCE: 74

```
aagaagcacc ggctaactcc gtgccagcag ccgcggtaat gcggggggtg gaagcggcga     60

gcggactggc ggggcgccaa gcgcgcgccg gcggcttgct aggtcagatg tgaggtgccc    120

ggcctcaacc tgggaactgc aggtgatact gggcagccgg agtcgggtag acgggggtac    180

aatgccaggt gtagcggggc aacgggtagc gatgtggggg aataccggtg gcgaacgggg    240

ccccccggac gaaggctggc gctcgggtgc cacagcgtgg ggagcaaaca ggattagata    300

ccctggtagt ccacgccgta aacgatgtcg actagggata acagggtaat gagtcgacaa    360

aatgatacgg cgaccaccga gatctacact ctttccctac acgacgctct tccgatcttc    420

gaaggattta taacgatgag atcggaagag cacacgtctg aactccagtc acaatcagtc    480

tcgtatctcg tatgccgtct tctgcttgtt gtcgactc                            518
```

<210> SEQ ID NO 75
<211> LENGTH: 518
<212> TYPE: DNA
<213> ORGANISM: Artificial

<220> FEATURE:
<223> OTHER INFORMATION: Polynucleotide

<400> SEQUENCE: 75
aagaagcacc ggctaactcc gtgccagcag ccgcggtaat gcggagggtg cacggggtaa 60
cgggaatgcc tgggcgccca gccgacggag ccggttcggt aagtcagagg tgaacgcgcc 120
gggctcaacc cgcgaactgc cgctgatacc ggggcgcttc cgtctcgtag aggggggtcg 180
aattccaggt gtggcgctga agtcccgaga gctctggagg aagcgcggtg gcgagggcgc 240
ccgcccggac caagactggc ggccaggtgc gaaagcgcgg ggagcgaacg ggattagata 300
ccctggtagt ccacgccgta aacgatgtcg actagggata acagggtaat gagtcgacaa 360
aatgatacgg cgaccaccga gatctacact ctttccctac acgacgctct tccgatcttg 420
ctgtctgcga tccggaacag atcggaagag cacacgtctg aactccagtc acaatcagtc 480
tcgtatctcg tatgccgtct tctgcttgtt gtcgactc 518

<210> SEQ ID NO 76
<211> LENGTH: 518
<212> TYPE: DNA
<213> ORGANISM: Artificial
<220> FEATURE:
<223> OTHER INFORMATION: Polynucleotide

<400> SEQUENCE: 76
aagaagcacc ggctaactcc gtgccagcag ccgcggtaac acggagggcg caagcgttaa 60
tcggaaccac tggccctaaa gcggccccag gcgggtcgtg aggtcagatg tgaaaccgcc 120
ggggtcaacc ggggggggc ggctgacact ggcgagcctg ggtctcgtac acgggggcag 180
acctccaggt gtcccgctga ggcgcgtgga gatccggagg agtaccggtg gggacgccgg 240
ccccctcgag gcagactgac gcgcaggtgc gaaagcgcgg ggagcaaacg ggattagata 300
ccctggtagt ccacgccgta aacgatgtcg actagggata acagggtaat gagtcgacaa 360
aatgatacgg cgaccaccga gatctacact ctttccctac acgacgctct tccgatctgt 420
ctgatcgtta tatgccgtag atcggaagag cacacgtctg aactccagtc acaatcagtc 480
tcgtatctcg tatgccgtct tctgcttgtt gtcgactc 518

<210> SEQ ID NO 77
<211> LENGTH: 518
<212> TYPE: DNA
<213> ORGANISM: Artificial
<220> FEATURE:
<223> OTHER INFORMATION: Polynucleotide

<400> SEQUENCE: 77
aagaagcacc ggctaactcc gtgccagcag ccgcggtaat acggcgggtg ccagccttaa 60
tcggaatgcc cgggcgcaca gcggacgcgg gcggttcgtt aagccgcagg cgagatcccc 120
gggcccaacc tcggcacggc gtctgacact ggcgaggttg agtctcggag agggggtag 180 gattccaggt ccaccggtgg aacccctaga gctctggggg actaccggtg gcccaggccg 240
cggcctggac gaacgctggc gctcaggtcc gcaagcctgc ggcgcacacg ggattagata 300
ccctggtagt ccacgccgta aacgatgtcg actagggata acagggtaat gagtcgacaa 360
aatgatacgg cgaccaccga gatctacact ctttccctac acgacgctct tccgatctca 420
tatcgcatcc gcagaaatag atcggaagag cacacgtctg aactccagtc acaatcagtc 480
tcgtatctcg tatgccgtct tctgcttgtt gtcgactc 518

<210> SEQ ID NO 78
<211> LENGTH: 518
<212> TYPE: DNA
<213> ORGANISM: Artificial
<220> FEATURE:
<223> OTHER INFORMATION: Polynucleotide

<400> SEQUENCE: 78
aagaagcacc ggctaactcc gtgccagcag ccgcggtaat accgcgggtg caagcgttaa 60
tgcggcttac tgggcgtaaa gcggaccccg gcggtttgtg aggtcacatg tgaagccccc 120
gccctccgcc tgggaactgc gtctgatact ggcgggctcg ggcccgtac agggggtag 180 aatcccaggt ggagggcgga accgggtgcc gagctgcagg aaggccggcg gcgaagccgg 240
ccccccgggc ggagactgac gcccaggggc gcgaccgtgg ggagcaagca ggattagata 300
ccctggtagt ccacgccgta aacgatgtcg actagggata acagggtaat gagtcgacaa 360
aatgatacgg cgaccaccga gatctacact ctttccctac acgacgctct tccgatctat 420
tcccttctac atgagtggag atcggaagag cacacgtctg aactccagtc acaatcagtc 480
tcgtatctcg tatgccgtct tctgcttgtt gtcgactc 518

<210> SEQ ID NO 79
<211> LENGTH: 498
<212> TYPE: DNA
<213> ORGANISM: Artificial
<220> FEATURE:
<223> OTHER INFORMATION: Polynucleotide

<400> SEQUENCE: 79
aagaagcacc ggctaactcc gtgccagcag ccgcggtaat actgagggtg caagcgtaaa 60
gcgcaagcag gcagtttgtt aagtcagatg tgaaatcccc gggctcaacc tgggaactgc 120
atcagatact ggcaagcttg agtctcgttg agggggtag aattccatgt gtagcggtga 180
attgcgtaga gaactggagg aataccggtg gcgaaggcgg ccccctggac gaagactgac 240
gctcaggtgc gaaagcgtgg ggtgcaaaca ggattagata ccctggtagt ccacgccgta 300
aacgatgtcg actagggata acagggtaat gagtcgacaa aatgatacgg cgaccaccga 360
gatctacact ctttccctac acgacgctct tccgatctca aagactaacg aatccgcaag 420
atcggaagag cacacgtctg aactccagtc acaatcagtc tcgtatctcg tatgccgtct 480
tctgcttgtt gtcgactc 498

<210> SEQ ID NO 80
<211> LENGTH: 478
<212> TYPE: DNA
<213> ORGANISM: Artificial
<220> FEATURE:
<223> OTHER INFORMATION: Polynucleotide

<400> SEQUENCE: 80
aagaagcacc ggctaactcc gtgccagcag ccgcggtaat actgagggtg caagcgtaaa 60
aagtcagatg tgaaatcccc gggctcaacc tgggaactgc atcagatact ggcaagcttg 120
agtctcgttg agggggtag aattccatgt gtagcggtga attgcgtaga gaactggagg 180
aataccggtg gcgaaggcgg ccccctggac gaagactgac gctcaggtgc gaaagcgtgg 240
ggtgcaaaca ggattagata ccctggtagt ccacgccgta aacgatgtcg actagggata 300
acagggtaat gagtcgacaa aatgatacgg cgaccaccga gatctacact ctttccctac 360
acgacgctct tccgatctgt ctgaggtgat aagggcatag atcggaagag cacacgtctg 420
aactccagtc acaatcagtc tcgtatctcg tatgccgtct tctgcttgtt gtcgactc 478

<210> SEQ ID NO 81
<211> LENGTH: 458
<212> TYPE: DNA
<213> ORGANISM: Artificial
<220> FEATURE:
<223> OTHER INFORMATION: Polynucleotide

<400> SEQUENCE: 81
aagaagcacc ggctaactcc gtgccagcag ccgcggtaat aagtcagatg tgaaatcccc 60
gggctcaacc tgggaactgc atcagatact ggcaagcttg agtctcgttg aggggggtag 120
aattccatgt gtagcggtga attgcgtaga gaactggagg aataccggtg gcgaaggcgg 180
ccccctggac gaagactgac gctcaggtgc gaaagcgtgg ggtgcaaaca ggattagata 240
ccctggtagt ccacgccgta aacgatgtcg actagggata acagggtaat gagtcgacaa 300
aatgatacgg cgaccaccga gatctacact ctttccctac acgacgctct tccgatcttt 360
gatggtgagt ggtgaatgag atcggaagag cacacgtctg aactccagtc acaatcagtc 420
tcgtatctcg tatgccgtct tctgcttgtt gtcgactc 458

<210> SEQ ID NO 82
<211> LENGTH: 538
<212> TYPE: DNA
<213> ORGANISM: Artificial
<220> FEATURE:
<223> OTHER INFORMATION: Polynucleotide

<400> SEQUENCE: 82
aagaagcacc ggctaactcc gtgccagcag ccgcggtaat actgagggtg caagcgtaaa 60
tcggaattac tgggcgtaaa gtagggatgg cgatgcattg gcgcaagcag gcagtttgtt 120
aagtcagatg tgaaatcccc gggctcaacc tgggaactgc atcagatact ggcaagcttg 180
agtctcgttg aggggggtag aattccatgt gtagcggtga attgcgtaga gaactggagg 240
aataccggtg gcgaaggcgg ccccctggac gaagactgac gctcaggtgc gaaagcgtgg 300
ggtgcaaaca ggattagata ccctggtagt ccacgccgta aacgatgtcg actagggata 360
acagggtaat gagtcgacaa aatgatacgg cgaccaccga gatctacact ctttccctac 420
acgacgctct tccgatctcg gtatactacc ttaccagaag atcggaagag cacacgtctg 480
aactccagtc acaatcagtc tcgtatctcg tatgccgtct tctgcttgtt gtcgactc 538

<210> SEQ ID NO 83
<211> LENGTH: 558
<212> TYPE: DNA
<213> ORGANISM: Artificial
<220> FEATURE:
<223> OTHER INFORMATION: Polynucleotide

<400> SEQUENCE: 83
aagaagcacc ggctaactcc gtgccagcag ccgcggtaat actgagggtg caagcgtaaa 60
tcggaattac tgggcgtaaa gtagggatgg cgatgcattg tcctgtgtcg ccaaccttga 120
gcgcaagcag gcagtttgtt aagtcagatg tgaaatcccc gggctcaacc tgggaactgc 180
atcagatact ggcaagcttg agtctcgttg aggggggtag aattccatgt gtagcggtga 240
attgcgtaga gaactggagg aataccggtg gcgaaggcgg ccccctggac gaagactgac 300
gctcaggtgc gaaagcgtgg ggtgcaaaca ggattagata ccctggtagt ccacgccgta 360
aacgatgtcg actagggata acagggtaat gagtcgacaa aatgatacgg cgaccaccga 420
gatctacact ctttccctac acgacgctct tccgatctac atatcacaac caggcctcag 480
atcggaagag cacacgtctg aactccagtc acaatcagtc tcgtatctcg tatgccgtct 540
tctgcttgtt gtcgactc 558

<210> SEQ ID NO 84
<211> LENGTH: 578
<212> TYPE: DNA
<213> ORGANISM: Artificial
<220> FEATURE:
<223> OTHER INFORMATION: Polynucleotide

<400> SEQUENCE: 84
aagaagcacc ggctaactcc gtgccagcag ccgcggtaat actgagggtg caagcgtaaa 60
tcggaattac tgggcgtaaa gtagggatgg cgatgcattg tcctgtgtcg ccaaccttga 120
ctgtaccgct gtgataacgc gcgcaagcag gcagtttgtt aagtcagatg tgaaatcccc 180
gggctcaacc tgggaactgc atcagatact ggcaagcttg agtctcgttg aggggggtag 240
aattccatgt gtagcggtga attgcgtaga gaactggagg aataccggtg gcgaaggcgg 300
ccccctggac gaagactgac gctcaggtgc gaaagcgtgg ggtgcaaaca ggattagata 360
ccctggtagt ccacgccgta aacgatgtcg actagggata acagggtaat gagtcgacaa 420
aatgatacgg cgaccaccga gatctacact ctttccctac acgacgctct tccgatctcc 480
cgtagactgg gtcgacgtag atcggaagag cacacgtctg aactccagtc acaatcagtc 540
tcgtatctcg tatgccgtct tctgcttgtt gtcgactc 578

<210> SEQ ID NO 85
<211> LENGTH: 1724
<212> TYPE: DNA
<213> ORGANISM: Artificial
<220> FEATURE:
<223> OTHER INFORMATION: Polynucleotide

<400> SEQUENCE: 85
agagtttgat catggctcag attgaacgct ggcggcaggc ttaacacatg caagtcgagc 60
gggggaaggt agcttgctac tggacctagc ggcggacggg tgagtaatgc ttaggaatct 120
gcctattagt gggggacaac atctcgaaag ggatgctaat accgcatacg tcctacggga 180
gaaagcaggg gatcttcgga ccttgcgcta atagatgagc ctaagtcgga ttagctagtt 240
ggtggggtaa aggcctacca aggcgacgat ctgtagcggg tctgagagga tgatccgcca 300
cactgggact gagacacggc ccagactcct acgggaggca gcagtgggga atattggaca 360
attagggggg gaaccctgat ccagccatgc cgcgtgtgtg aagaaggcct tatggttgta 420
aagcacttta agcgaggagg aggctacttt agttaatacc tagagatagt ggacgttact 480
cgcagaataa gcaccggcta actctgtgcc agcagccgcg gtaatacaga gggtgcgagc 540
gttaatcgga tttactgggc gtaaatctgc gtgcgtaggc ggcttattaa gtcggatgtg 600
aaatccccga gcttaacttg ggaattgcat tcgatactgg tgagctagag tatgggagag 660
gatggtagaa ttccaggtgt agcggtgaaa tgcgtagaga tctggaggaa taccgatggc 720
gaaggcagcc atctggccta atactgacgc tgaggtacga aagcatgggg agcaaacagg 780
attagatacc ctggtagtcc atgccgtaaa cgatgtctac tagccgttgg ggcctttgag 840
gctttagtgg cgcagctaac gcgataagta gaccgcctgg catggagtac ggtcgcaaga 900
ctaaaactca aatgaattga cggggcccg cacaagcggt ggagcatgtg gtttaattcg 960
atgcaacgcg aagaacctta cctggccttg acatactaga aactttccag agatggattg 1020
gtgccttcgg gaatctagat acaggtgctg catggctgtc gtcagctcgt gtcgtgagat 1080
gttgggttaa gtcccgcaac gagcgcaacc cttttcctta cttgccagca tttcggatgg 1140
gaactttaag gatactgcca gtgacaaact ggaggaaggc ggggacgacg tcaagtcatc 1200
atggccctta cggccagggc tacacacgtg ctacaatggt cggtacaaag ggttgctaca 1260
cagcgatgtg atgctaatct caaaaagccg atcgtagtcc ggattggagt ctgcaactcg 1320
actccatgaa gtcggaatcg ctagtaatcg cggatcagaa tgccgcggtg aatacgttcc 1380
cgggccttgt acacaccgcc cgtcacacca tgggagtttg ttgcaccaga agtagctagc 1440
ctaactgcaa agagggcggt taccacggtg tggccgatga ctggggtgaa gtcgtaacaa 1500
ggtagccgta ggggaacctg cggctggatc acctccttta gggataacag ggtaatgagt 1560
cgacaaaatg atacggcgac caccgagatc tacactcttt ccctacacga cgctcttccg 1620
atctgcttgt ctgttcaagc atccagatcg gaagagcaca cgtctgaact ccagtcacaa 1680
tcagtctcgt atctcgtatg ccgtcttctg cttgttgtcg actc 1724

<210> SEQ ID NO 86
<211> LENGTH: 1703
<212> TYPE: DNA
<213> ORGANISM: Artificial
<220> FEATURE:
<223> OTHER INFORMATION: Polynucleotide

<400> SEQUENCE: 86
gatgaacgct ggcggcgtgc ctaatacatg caagtcgagc gaatggatta agagcttgct 60
cttatgaagt tagcggcgga cgggtgagta acacgtgggt aacctgccca taagactggg 120
ataactccgg gaaaccgggg ctaataccgg ataacatttt gaaccgcatg gttcgaaatt 180
gaaaggcggc ttcggctgtc acttatggat ggacccgcgt cgcattagct agttggtgag 240
gtaacggctc accaaggcaa cgatgcgtag ccgacctgag agggtgatcg gccacactgg 300
gactgagaca cggcccagac tcctacggga ggcagcagta gggaatcttc cgcaattagg 360
gacgaaagtc tgacggagca acgccgcgtg agtgatgaag gctttcgggt cgtaaaactc 420
tgttgttagg gaagaacaag tgctagttga ataagctggc accttgacgg tacctaacca 480
gaaagccacg gctaactacg tgccagcagc cgcggtaata cgtaggtggc aagcgttatc 540
cggaattatt gggcgtaaat ctgcgcgcgc aggtggtttc ttaagtctga tgtgaaagcc 600
cacggctcaa ccgtggaggg tcattggaaa ctgggagact tgagtgcaga agaggaaagt 660
ggaattccat gtgtagcggt gaaatgcgta gagatatgga ggaacaccag tggcgaaggc 720
gactttctgg tctgtaactg acactgaggc gcgaaagcgt ggggagcaaa caggattaga 780
taccctggta gtccacgccg taaacgatga gtgctaagtg ttagagggtt tccgcccttt 840
agtgctgaag ttaacgcatt aagcactccg cctggcatgg agtacggccg caaggctgaa 900
actcaaagga attgacgggg gcccgcacaa gcggtggagc atgtggttta attcgaagca 960
acgcgaagaa ccttaccagg tcttgacatc ctctgacaac cctagagata gggcttctcc 1020
ttcgggagca gagtgacagg tggtgcatgg ttgtcgtcag ctcgtgtcgt gagatgttgg 1080
gttaagtccc gcaacgagcg caacccttga tcttagttgc catcattcag ttgggcactc 1140
taaggtgact gccggtgaca aaccggagga aggtggggat gacgtcaaat catcatgccc 1200
cttatgacct gggctacaca cgtgctacaa tggacggtac aaagagctgc aagaccgcga 1260

```
ggtggagcta atctcataaa accgttctca gttcggattg taggctgcaa ctcgcctaca   1320

tgaagctgga atcgctagta atcgcggatc agcatgccgc ggtgaatacg ttcccgggcc   1380

ttgtacacac cgcccgtcac accacgagag tttgtaacac ccgaagtcgg tggggtaacc   1440

ttttggagcc agccgcctaa ggtgggacag atgattgggg tgaagtcgta acaaggtagc   1500

cgtatcggaa ggtgcggtag ggataacagg gtaatgagtc gacaaaatga tacggcgacc   1560

accgagatct acactctttc cctacacgac gctcttccga tcttctccct gtgattaatg   1620

aacagatcgg aagagcacac gtctgaactc cagtcacaat cagtctcgta tctcgtatgc   1680

cgtcttctgc ttgttgtcga ctc                                           1703
```

<210> SEQ ID NO 87
<211> LENGTH: 1705
<212> TYPE: DNA
<213> ORGANISM: Artificial
<220> FEATURE:
<223> OTHER INFORMATION: Polynucleotide

<400> SEQUENCE: 87

```
tattacaatg aagagtttga tcctggctca ggatgaacgc tagctacagg cttaacacat     60

gcaagtcgag ggcagcatgg gtcttagctt gctaaggccg atggcgaccg gcgcacgggt    120

gagtaacacg tatccaacct gccgtctact cttggacagc cttctgaaag gaagattaat    180

acaagatggc atcatgagtc cgcatgttca catgattaaa ggtattccgg tagacgatgg    240

ggatgcgttc cattagatag taggcggggt aacggcccac ctagtcttcg atggataggg    300

gttctgagag gaaggtcccc cacattggaa ctgagacacg gtccaaactc ctacgggagg    360

cagcagtgag gaatattggt caattagggg cgagagcctg aaccagccaa gtagcgtgaa    420

ggatgactgc cctatgggtt gtaaacttct tttataaagg aataaagtcg ggtatggata    480

cccgtttgca tgtactttat gaataaggat cggctaactc cgtgccagca gccgcggtaa    540

tacggaggat ccgagcgtta tccggattta ttgggtttaa atctgggagc gtagatggat    600

gtttaagtca gttgtgaaag tttgcggctc aaccgtaaaa ttgcagttga tactggatat    660

cttgagtgca gttgaggcag gcggaattcg tggtgtagcg gtgaaatgct tagatatcac    720

gaagaactcc gattgcgaag gcagcctgct aagctgcaac tgacattgag gctcgaaagt    780

gtgggtatca aacaggatta gataccctgg tagtccacac ggtaaacgat gaatactcgc    840

tgtttgcgat atacggcaag cggccaagcg aaagcgttaa gtattccacc tggcatggag    900

tacgccggca acggtgaaac tcaaaggaat tgacgggggc ccgcacaagc ggaggaacat    960

gtggtttaat tcgatgatac gcgaggaacc ttacccgggc ttaaattgca gatgaattac   1020

ggtgaaagcc gtaagccgca aggcatctgt gaaggtgctg catggttgtc gtcagctcgt   1080

gccgtgaggt gtcggcttaa gtgccataac gagcgcaacc cttgttgtca gttactaaca   1140

ggtcatgctg aggactctga caagactgcc atcgtaagat gtgaggaagg tggggatgac   1200

gtcaaatcag cacggccctt acgtccgggg ctacacacgt gttacaatgg ggggtacaga   1260

gggccgctac cacgcgagtg gatgccaatc cccaaaacct ctctcagttc ggactggagt   1320

ctgcaacccg actccacgaa gctggattcg ctagtaatcg cgcatcagcc acggcgcggt   1380

gaatacgttc ccgggccttg tacacaccgc ccgtcaagcc atgggagccg gggtacctg    1440

aagtgcgtaa ccgcgaggag cgccctaggg taaaactggt gactggggct aagtcgtaac   1500

aaggtagccg taccggaagt agggataaca gggtaatgag tcgacaaaat gatacggcga   1560

ccaccgagat ctacactctt tccctacacg acgctcttcc gatcttagag ccatagactg   1620
```

ctgtcagatc ggaagagcac acgtctgaac tccagtcaca atcagtctcg tatctcgtat 1680
gccgtcttct gcttgttgtc gactc 1705

<210> SEQ ID NO 88
<211> LENGTH: 1700
<212> TYPE: DNA
<213> ORGANISM: Artificial
<220> FEATURE:
<223> OTHER INFORMATION: Polynucleotide

<400> SEQUENCE: 88
agagtttgat cctggctcag gacgaacgct ggcggcgtgc ttaacacatg caagtcgagc 60
gatgaagctc cttcgggagt ggattagcgg cggacgggtg agtaacacgt gggtaacctg 120
cctcatagag gggaatagcc tttcgaaagg aagattaata ccgcataaga ttgtagtgcc 180
gcatggcata gcaattaaag gagtaatccg ctatgagatg gacccgcgtc gcattagcta 240
gttggtgagg taacggctca ccaaggcgac gatgcgtagc cgacctgaga gggtgatcgg 300
ccacattggg actgagacac ggcccagact cctacgggag gcagcagtgg ggaatattgc 360
acaattaggg ggaaaccct gatgcagcaa cgccgcgtga gtgatgacgg tcttcggatt 420
gtaaagctct gtcttcaggg acgataatga cggtacctga ggaggaagcc acggctaact 480
acgtgccagc agccgcggta atacgtaggt ggcaagcgtt gtccggattt actgggcgta 540
aatctgggag cgtaggtgga tatttaagtg ggatgtgaaa tactcgggct taacctgggt 600
gctgcattcc aaactggata tctagagtgc aggagaggaa agtagaattc ctagtgtagc 660
ggtgaaatgc gtagagatta ggaagaatac cagtggcgaa ggcgactttc tggactgtaa 720
ctgacactga ggctcgaaag cgtggggagc aaacaggatt agataccctg gtagtccacg 780
ccgtaaacga tgaatactag gtgtaggggt tgtcatgacc tctgtgccgc cgctaacgca 840
ttaagtattc cgcctggcat ggagtacggt cgcaagatta aaactcaaag gaattgacgg 900
gggcccgcac aagcagcgga gcatgtggtt taattcgaag caacgcgaag aaccttacct 960
agacttgaca tctcctgaat taccettaat cggggaagcc cttcggggca ggaagacagg 1020
tggtgcatgg ttgtcgtcag ctcgtgtcgt gagatgttgg gttaagtccc gcaacgagcg 1080
caacccttat tgttagttgc taccatttag ttgagcactc tagcgagact gcccgggtta 1140
accgggagga aggtggggat gacgtcaaat catcatgccc cttatgtcta gggctacaca 1200
cgtgctacaa tggctggtac agagagatgc taaaccgcga ggtggagcca aactttaaaa 1260
ccagtctcag ttcggattgt aggctgaaac tcgcctacat gaagctggag ttgctagtaa 1320
tcgcgaatca gaatgtcgcg gtgaatacgt tcccgggcct tgtacacacc gcccgtcaca 1380
ccatgagagt tggcaatacc caaagttcgt gagctaacgc gtaagcgggg cagcgaccta 1440
aggtagggtc agcgattggg gtgaagtcgt aacaaggtag ccgtaggaga acctgcggct 1500
ggatcacctc cttttaggga taacagggta atgagtcgac aaaatgatac ggcgaccacc 1560
gagatctaca ctctttccct acacgacgct cttccgatct taaagattat ttgcagccac 1620
agatcggaag agcacacgtc tgaactccag tcacaatcag tctcgtatct cgtatgccgt 1680
cttctgcttg ttgtcgactc 1700

<210> SEQ ID NO 89
<211> LENGTH: 1697
<212> TYPE: DNA
<213> ORGANISM: Artificial
<220> FEATURE:

<223> OTHER INFORMATION: Polynucleotide

<400> SEQUENCE: 89
tttatggaga gtttgatcct ggctcagggt gaacgctggc ggcgtgctta agacatgcaa 60
gtcgaacgcg gtcttcggac cgagtggcgc acgggtgagt aacacgtaac tgacctaccc 120
agaagtcacg aataactggc cgaaaggtcc gctaatacgt gatgtggtga tgcaccgtgg 180
tgcatcacta aagatttatc gcttctggat ggggttgcgt tccatcagct ggttggtggg 240
gtaaaggcct accaaggcga cgacggatag ccggcctgag agggtggccg gccacagggg 300
cactgagaca cgggtcccac tcctacggga ggcagcagtt aggaatcttc cacaattagg 360
ggcgcaagcc tgatggagcg acgccgcgtg agggatgaag gttttcggat cgtaaacctc 420
tgaatctggg acgaaagagc cttagggcag atgacggtac cagagtaata gcaccggcta 480
actccgtgcc agcagccgcg gtaatacgga gggtgcaagc gttacccgga atcactgggc 540
gtaaatctgg gcgtgtaggc ggaaatttaa gtctggtttt aaagaccggg gctcaacctc 600
ggggatggac tggatactgg atttcttgac ctctggagag gtaactggaa ttcctggtgt 660
agcggtggaa tgcgtagata ccaggaggaa caccaatggc gaaggcaagt tactggacag 720
aaggtgacgc tgaggcgcga aagtgtgggg agcaaaccgg attagatacc cgggtagtcc 780
acaccctaaa cgatgtacgt tggctaagcg caggatgctg tgcttggcga agctaacgcg 840
ataaacgtac cgcctggcat gaagtacggc cgcaaggttg aaactcaaag gaattgacgg 900
gggcccgcac aagcggtgga gcatgtggtt taattcgaag caacgcgaag aaccttacca 960
ggtcttgaca tgctaggaac tttgcagaga tgcagaggtg cccttcgggg aacctagaca 1020
caggtgctgc atggctgtcg tcagctcgtg tcgtgagatg ttgggttaag tcccgcaacg 1080
agcgcaaccc ttgcctttag ttgtcagcat tcagttggac actctagagg gactgcctat 1140
gaaagtagga ggaaggcggg gatgacgtct agtcagcatg gtccttacgt cctgggcgac 1200
acacgtgcta caatgggtag gacaacgcgc agcaaacccg cgagggtaag cgaatcgcta 1260
aaacctatcc ccagttcaga tcggagtctg caactcgact ccgtgaagtt ggaatcgcta 1320
gtaatcgcgg gtcagcatac cgcggtgaat acgttcccgg gccttgtaca caccgcccgt 1380
cacaccatgg gagtagattg cagttgaaac cgccgggagc ttaacggcag gcgtctagac 1440
tgtggtttat gactggggtg aagtcgtaac aaggtaactg taccggaagg tgcggttgga 1500
tcacctcctt ttagggataa cagggtaatg agtcgacaaa atgatacggc gaccaccgag 1560
atctacactc tttccctaca cgacgctctt ccgatctgta ttcagccgtc aacttataga 1620
tcggaagagc acacgtctga actccagtca caatcagtct cgtatctcgt atgccgtctt 1680
ctgcttgttg tcgactc 1697

<210> SEQ ID NO 90
<211> LENGTH: 1744
<212> TYPE: DNA
<213> ORGANISM: Artificial
<220> FEATURE:
<223> OTHER INFORMATION: Polynucleotide

<400> SEQUENCE: 90
agagtttgat cctggctcag gacgaacgct ggcggcgtgc ctaatacatg caagtcgaac 60
gcttctttcc tcccgagtgc ttgcactcaa ttggaaagag gagtggcgga cgggtgagta 120
acacgtgggt aacctaccca tcagaggggg ataacacttg gaaacaggtg ctaataccgc 180
ataacagttt atgccgcatg gcataagagt gaaaggcgct ttcgggtgtc gctgatggat 240
ggacccgcgg tgcattagct agttggtgag gtaacggctc accaaggcca cgatgcatag 300
ccgacctgag agggtgatcg gccacactgg gactgagaca cggcccagac tcctacggga 360
ggcagcagta gggaatcttc ggcaattagg gacgaaagtc tgaccgagca acgccgcgtg 420
agtgaagaag gttttcggat cgtaaaactc tgttgttaga gaagaacaag gacgttagta 480
actgaacgtc ccctgacggt atctaaccag aaagccacgg ctaactacgt gccagcagcc 540
gcggtaatac gtaggtggca agcgttgtcc ggatttattg ggcgtaaatc tgcgagcgca 600
ggcggtttct taagtctgat gtgaaagccc ccggctcaac cggggagggt cattggaaac 660
tgggagactt gagtgcagaa gaggagagtg gaattccatg tgtagcggtg aaatgcgtag 720
atatatggag gaacaccagt ggcgaaggcg gctctctggt ctgtaactga cgctgaggct 780
cgaaagcgtg gggagcaaac aggattagat accctggtag tccacgccgt aaacgatgag 840
tgctaagtgt tggagggttt ccgcccttca gtgctgcagc aaacgcatta agcactccgc 900
ctggcatgga gtacgaccgc aaggttgaaa ctcaaaggaa ttgacggggg cccgcacaag 960
cggtggagca tgtggtttaa ttcgaagcaa cgcgaagaac cttaccaggt cttgacatcc 1020
tttgaccact ctagagatag agctttccct tcggggacaa agtgacaggt ggtgcatggt 1080
tgtcgtcagc tcgtgtcgtg agatgttggg ttaagtcccg caacgagcgc aacccttatt 1140
gttagttgcc atcatttagt tgggcactct agcgagactg ccggtgacaa accggaggaa 1200
ggtggggatg acgtcaaatc atcatgcccc ttatgacctg ggctacacac gtgctacaat 1260
gggaagtaca acgagtcgct agaccgcgag gtcatgcaaa tctcttaaag cttctctcag 1320
ttcggattgc aggctgcaac tcgcctgcat gaagccggaa tcgctagtaa tcgcggatca 1380
gcacgccgcg gtgaatacgt tcccgggcct tgtacacacc gcccgtcaca ccacgagagt 1440
ttgtaacacc cgaagtcggt gaggtaacct tttggagcc agccgcctaa ggtgggatag 1500
atgattgggg tgaagtcgta acaaggtagc cgtatcggaa ggtgcggctg gatcacctta 1560
gggataacag ggtaatgagt cgacaaaatg atacggcgac caccgagatc tacactcttt 1620
ccctacacga cgctcttccg atcttgctgg gctcagaggt gaatagatcg gaagagcaca 1680
cgtctgaact ccagtcacaa tcagtctcgt atctcgtatg ccgtcttctg cttgttgtcg 1740
actc 1744

<210> SEQ ID NO 91
<211> LENGTH: 1737
<212> TYPE: DNA
<213> ORGANISM: Artificial
<220> FEATURE:
<223> OTHER INFORMATION: Polynucleotide

<400> SEQUENCE: 91
aaattgaaga gtttgatcat ggctcagatt gaacgctggc ggcaggccta acacatgcaa 60
gtcgaacggt aacaggaaga agcttgcttc tttgctgacg agtggcggac gggtgagtaa 120
tgtctgggaa actgcctgat ggagggggat aactactgga aacggtagct aataccgcat 180
aacgtcgcaa gaccaaagag ggggaccttc gggcctcttg ccatcggatg tgcccagatg 240
ggattagcta gtaggtgggg taacggctca cctaggcgac gatccctagc tggtctgaga 300
ggatgaccag ccacactgga actgagacac ggtccagact cctacgggag gcagcagtgg 360
ggaatattgc acaattaggg gcgcaagcct gatgcagcca tgccgcgtgt atgaagaagg 420
ccttcgggtt gtaaagtact ttcagcgggg aggaagggag taaagttaat acctttgctc 480
attgacgtta cccgcagaag aagcaccggc taactccgtg ccagcagccg cggtaatacg 540
gagggtgcaa gcgttaatcg gaattactgg gcgtaaatct gcgcacgcag gcggtttgtt 600
aagtcagatg tgaaatcccc gggctcaacc tgggaactgc atctgatact ggcaagcttg 660
agtctcgtag agggggtag aattccaggt gtagcggtga aatgcgtaga gatctggagg 720
aataccggtg gcgaaggcgg cccctggac gaagactgac gctcaggtgc gaaagcgtgg 780
ggagcaaaca ggattagata ccctggtagt ccacgccgta aacgatgtcg acttggaggt 840
tgtgcccttg aggcgtggct tccggagcta acgcgttaag tcgaccgcct ggcatggagt 900
acggccgcaa ggttaaaact caaatgaatt gacgggggcc cgcacaagcg gtggagcatg 960
tggtttaatt cgatgcaacg cgaagaacct tacctggtct tgacatccac agaactttcc 1020
agagatggat tggtgccttc gggaactgtg agacaggtgc tgcatggctg tcgtcagctc 1080
gtgttgtgaa atgttgggtt aagtcccgca acgagcgcaa cccttatctt ttgttgccag 1140
cggtccggcc gggaactcaa aggagactgc cagtgataaa ctggaggaag gtggggatga 1200
cgtcaagtca tcatggccct tacgaccagg gctacacacg tgctacaatg gcgcatacaa 1260
agagaagcga cctcgcgaga gcaagcggac ctcataaagt gcgtcgtagt ccggattgga 1320
gtctgcaact cgactccatg aagtcggaat cgctagtaat cgtggatcag aatgccacgg 1380
tgaatacgtt cccgggcctt gtacacaccg cccgtcacac catgggagtg ggttgcaaaa 1440
gaagtaggta gcttaacctt cgggagggcg cttaccactt tgtgattcat gactggggtg 1500
aagtcgtaac aaggtaaccg taggggaacc tgcggttgga tcacctcctt atagggataa 1560
cagggtaatg agtcgacaaa atgatacggc gaccaccgag atctacactc tttccctaca 1620
cgacgctctt ccgatctaac agcactgtcg cacggctaga tcggaagagc acacgtctga 1680
actccagtca caatcagtct cgtatctcgt atgccgtctt ctgcttgttg tcgactc 1737

<210> SEQ ID NO 92
<211> LENGTH: 1693
<212> TYPE: DNA
<213> ORGANISM: Artificial
<220> FEATURE:
<223> OTHER INFORMATION: Polynucleotide

<400> SEQUENCE: 92
tttatggaga gtttgatcct ggctcagagt gaacgctggc ggcgtgccta atacatgcaa 60
gtcgaacgat gaagcttcta gcttgctaga gtgctgatta gtggcgcacg ggtgagtaac 120
gcataggtta tgtgcctctt agtttgggat agccattgga aacgatgatt aataccagat 180
actcctacgg gggaaagatt tatcgctaag agatcagcct atgtcctatc agcttgttgg 240
taaggtaatg gcttaccaag gctatgacgg gtatccggcc tgagagggtg aacggacaca 300
ctggaactga gacacggtcc agactcctac gggaggcagc agtagggaat attgctcaat 360
taggggggaa accctgaagc agcaacgccg cgtggaggat gaaggtttta ggattgtaaa 420
ctccttttgt tagagaagat aatgacggta tctaacgaat aagcaccggc taactccgtg 480
ccagcagccg cggtaatacg gagggtgcaa gcgttactcg gaatcactgg gcgtaaatct 540
gagcgcgtag gcgggatagt cagtcaggtg tgaaatccta tggcttaacc atagaactgc 600
atttgaaact actattctag agtgtgggag aggtaggtgg aattcttggt gtaggggtaa 660
aatccgtaga gatcaagagg aatactcatt gcgaaggcga cctgctggaa cattactgac 720
gctgattgcg cgaaagcgtg gggagcaaac aggattagat accctggtag tccacgccct 780
aaacgatgga tgctagttgt tggagggctt agtctctcca gtaatgcagc taacgcatta 840
agcatcccgc ctggcatgga gtacggtcgc aagattaaaa ctcaaaggaa tagacgggga 900
cccgcacaag cggtggagca tgtggtttaa ttcgaagata cacgaagaac cttacctagg 960
cttgacattg agagaatccg ctagaaatag tggagtgtct ggcttgccag accttgaaaa 1020
caggtgctgc acggctgtcg tcagctcgtg tcgtgagatg ttgggttaag tcccgcaacg 1080
agcgcaaccc cttttcttag ttgctaacag gttatgctga gaactctaag gatactgcct 1140
ccgtaagggg aggaaggtgg ggacgacgtc aagtcatcat ggcccttacg cctagggcta 1200
cacacgtgct acaatggggt gcacaaagag aagcaatact gcgaatggag ccaatcttca 1260
aaacacctct cagttcggat tgtaggctgc aactcgcctg catgaagctg gaatcgctag 1320
taatcgcaaa tcagccatgt tgcggtgaat acgttcccgg gtcttgtact caccgcccgt 1380
cacaccatgg gagttgtgtt tgccttaagt caggatgcta aattggctac tgcccacggc 1440
acacacagcg actggggtga agtcgtaaca aggtaaccgt agtgaacctg cggttggatc 1500
acctccttag ggataacagg gtaatgagtc gacaaaatga tacggcgacc accgagatct 1560
acactctttc cctacacgac gctcttccga tctcacgtac tagtggtcag cggagatcgg 1620
aagagcacac gtctgaactc cagtcacaat cagtctcgta tctcgtatgc cgtcttctgc 1680
ttgttgtcga ctc 1693

<210> SEQ ID NO 93
<211> LENGTH: 1774
<212> TYPE: DNA
<213> ORGANISM: Artificial
<220> FEATURE:
<223> OTHER INFORMATION: Polynucleotide

<400> SEQUENCE: 93
gaaggaaaat gagagtttga tcctggctca ggacgaacgc tggcggcgtg cctaatacat 60
gcaagtcgag cgagcttgcc tagatgaatt tggtgcttgc accagatgaa actagataca 120
agcgagcggc ggacgggtga gtaacacgtg ggtaacctgc ccaagagact gggataacac 180
ctggaaacag atgctaatac cggataacaa cactagacgc atgtctagag tttaaaagat 240
ggttctgcta tcactcttgg atggacctgc ggtgcattag ctagttggta aggtaacggc 300
ttaccaaggc aatgatgcat agccgagttg agagactgat cggccacatt gggactgaga 360
cacggcccaa actcctacgg gaggcagcag tagggaatct tccacaatta gggacgcaag 420
tctgatggag caacgccgcg tgagtgaaga agggtttcgg ctcgtaaagc tctgttggta 480
gtgaagaaag atagaggtag taactggcct ttatttgacg gtaattactt agaaagtcac 540
ggctaactac gtgccagcag ccgcggtaat acgtaggtgg caagcgttgt ccggatttat 600
tgggcgtaaa tctgcgagtg caggcggttc aataagtctg atgtgaaagc cttcggctca 660
accggagaat tgcatcagaa actgttgaac ttgagtgcag aagaggagag tggaactcca 720
tgtgtagcgg tggaatgcgt agatatatgg aagaacacca gtggcgaagg cggctctctg 780
gtctgcaact gacgctgagg ctcgaaagca tgggtagcga acaggattag ataccctggt 840
agtccatgcc gtaaacgatg agtgctaagt gttgggaggt ttccgcctct cagtgctgca 900
gctaacgcat taagcactcc gcctggcatg gagtacgacc gcaaggttga aactcaaagg 960
aattgacggg ggcccgcaca agcggtggag catgtggttt aattcgaagc aacgcgaaga 1020
accttaccag gtcttgacat ccagtgcaaa cctaagagat taggtgttcc cttcggggac 1080
gctgagacag gtggtgcatg gctgtcgtca gctcgtgtcg tgagatgttg ggttaagtcc 1140
cgcaacgagc gcaacccttg tcattagttg ccatcattaa gttgggcact ctaatgagac 1200
tgccggtgac aaaccggagg aaggtgggga tgacgtcaag tcatcatgcc ccttatgacc 1260
tgggctacac acgtgctaca atggacggta caacgagaag cgaacctgcg aaggcaagcg 1320
gatctctgaa agccgttctc agttcggact gtaggctgca actcgcctac acgaagctgg 1380
aatcgctagt aatcgcggat cagcacgccg cggtgaatac gttcccgggc cttgtacaca 1440
ccgcccgtca caccatgaga gtctgtaaca cccaaagccg gtgggataac ctttatagga 1500
gtcagccgtc taaggtagga cagatgatta gggtgaagtc gtaacaaggt agccgtagga 1560
gaacctgcgg ctggatcacc tcctttctta gggataacag ggtaatgagt cgacaaaatg 1620
atacggcgac caccgagatc tacactcttt ccctacacga cgctcttccg atctacgtaa 1680
agggttattg cattagatcg gaagagcaca cgtctgaact ccagtcacaa tcagtctcgt 1740
atctcgtatg ccgtcttctg cttgttgtcg actc 1774

<210> SEQ ID NO 94
<211> LENGTH: 1739
<212> TYPE: DNA
<213> ORGANISM: Artificial
<220> FEATURE:
<223> OTHER INFORMATION: Polynucleotide

<400> SEQUENCE: 94
tgaacataag agtttgatcc tggctcagat tgaacgctgg cggcatgctt tacacatgca 60
agtcggacgg cagcacagag aagcttgctt ctcgggtggc gagtggcgaa cgggtgagta 120
acatatcgga acgtaccgag tagtggggga taactgatcg aaagatcagc taataccgca 180
tacgtcttga gagagaaagc aggggacctt cgggccttgc gctattcgag cggccgatat 240
ctgattagct agttggtggg gtaaaggcct accaaggcga cgatcagtag cgggtctgag 300
aggatgatcc gccacactgg gactgagaca cggcccagac tcctacggga ggcagcagtg 360
gggaattttg gacaattagg ggcgcaagcc tgatccagcc atgccgcgtg tctgaagaag 420
gccttcgggt tgtaaaggac ttttgtcagg gaagaaaagg ctgttgctaa tatcagcggc 480
tgatgacggt acctgaagaa taagcaccgg ctaactacgt gccagcagcc gcggtaatac 540
gtagggtgcg agcgttaatc ggaattactg ggcgtaaatc tgcgggcgca gacggttact 600
taagcaggat gtgaaatccc cgggctcaac ccgggaactg cgttctgaac tgggtgactc 660
gagtgtgtca gagggaggta gaattccacg tgtagcagtg aaatgcgtag agatgtggag 720
gaataccgat ggcgaaggca gcctcctggg acaacactga cgttcatgcc cgaaagcgtg 780
ggtagcaaac aggattagat accctggtag tccacgccct aaacgatgtc aattagctgt 840
tgggcaacct gattgcttgg tagcgtagct aacgcgtgaa attgaccgcc tggcatggag 900
tacggtcgca agattaaaac tcaaaggaat tgacggggac ccgcacaagc ggtggatgat 960
gtggattaat tcgatgcaac gcgaagaacc ttacctggtc ttgacatgta cggaatcctc 1020
cggagacgga ggagtgcctt cgggagccgt aacacaggtg ctgcatggct gtcgtcagct 1080
cgtgtcgtga gatgttgggt taagtcccgc aacgagcgca acccttgtca ttagttgcca 1140
tcattcagtt gggcactcta atgagactgc cggtgacaag ccggaggaag gtggggatga 1200
cgtcaagtcc tcatggccct tatgaccagg gcttcacacg tcatacaatg gtcggtacag 1260
agggtagcca agccgcgagg cggagccaat ctcacaaaac cgatcgtagt ccggattgca 1320
ctctgcaact cgagtgcatg aagtcggaat cgctagtaat cgcaggtcag catactgcgg 1380
tgaatacgtt cccgggtctt gtacacaccg cccgtcacac catgggagtg ggggatacca 1440

```
gaagtaggta ggataaccac aaggagtccg cttaccacgg tatgcttcat gactggggtg   1500

aagtcgtaac aaggtagccg taggggaacc tgcggctgga tcacctcctt tcttagggat   1560

aacagggtaa tgagtcgaca aaatgatacg gcgaccaccg agatctacac tctttcccta   1620

cacgacgctc ttccgatcta gtcccaggat tgctgaaata gatcggaaga gcacacgtct   1680

gaactccagt cacaatcagt ctcgtatctc gtatgccgtc ttctgcttgt tgtcgactc    1739


<210> SEQ ID NO 95
<211> LENGTH: 1720
<212> TYPE: DNA
<213> ORGANISM: Artificial
<220> FEATURE:
<223> OTHER INFORMATION: Polynucleotide

<400> SEQUENCE: 95

agagtttgat cctggctcag gacgaacgct ggcggcgtgc ttaacacatg caagtcgaac     60

ggaaaggccc tgcttttgtg gggtgctcga gtggcgaacg ggtgagtaac acgtgagtaa    120

cctgcccttg actttgggat aacttcagga aactggggct aataccggat aggagctcct    180

gctgcatggt gggggttgga aagtttcggc ggttggggat ggactcgcgg cttatcagct    240

tgttggtggg gtagtggctt accaaggctt tgacgggtag ccggcctgag agggtgaccg    300

gccacattgg gactgagata cggcccagac tcctacggga ggcagcagtg gggaatattg    360

cacaattagg ggcggaagcc tgatgcagca acgccgcgtg cgggatgacg gccttcgggt    420

tgtaaaccgc tttcgcctgt gacgaagcgt gagtgacggt aatgggtaaa gaagcaccgg    480

ctaactacgt gccagcagcc gcggtgatac gtagggtgcg agcgttgtcc ggatttattg    540

ggcgtaaatc tgggctcgta ggtggttgat cgcgtcggaa gtgtaatctt ggggcttaac    600

cctgagcgtg ctttcgatac gggttgactt gaggaaggta ggggagaatg gaattcctgg    660

tggagcggtg gaatgcgcag atatcaggag gaacaccagt ggcgaaggcg gttctctggg    720

cctttcctga cgctgaggag cgaaagcgtg gggagcgaac aggcttagat accctggtag    780

tccacgctgt aaacggtggg tactaggtgt ggggtccatt ccacgggttc cgtgccgtag    840

ctaacgcttt aagtaccccg cctggcatgg agtacggccg caaggctaaa actcaaagga    900

attgacgggg ccccgcacaa gcggcggagc atgcggatta attcgatgca acgcgtagaa    960

ccttacctgg gtttgacatg gatcgggagt gctcagagat gggtgtgcct cttttggggt   1020

cggttcacag gtggtgcatg gctgtcgtca gctcgtgtcg tgagatgttg ggttaagtcc   1080

cgcaacgagc gcaacccttg ttcactgttg ccagcacgtt atggtgggga ctcagtggag   1140

accgccgggg tcaactcgga ggaaggtggg gatgacgtca agtcatcatg ccccttatgt   1200

ccagggcttc acgcatgcta caatggctgg tacagagagt ggcgagcctg tgagggtgag   1260

cgaatctcgg aaagccggtc tcagttcgga ttggggtctg caactcgacc tcatgaagtc   1320

ggagtcgcta gtaatcgcag atcagcaacg ctgcggtgaa tacgttcccg ggcttgtac    1380

acaccgcccg tcaagtcatg aaagttggta acacccgaag ccggtggcct aaccgttgtg   1440

gggggagccgt cgaaggtggg actggtgatt aggactaagt cgtaacaagg tagccgtacc   1500

ggaaggtgcg gctggatcac ctcctttcta aggataggga taacagggta atgagtcgac   1560

aaaatgatac ggcgaccacc gagatctaca ctctttccct acacgacgct cttccgatct   1620

gatcaccctg catgtacaca agatcggaag agcacacgtc tgaactccag tcacaatcag   1680

tctcgtatct cgtatgccgt cttctgcttg ttgtcgactc                          1720
```

<210> SEQ ID NO 96
<211> LENGTH: 1731
<212> TYPE: DNA
<213> ORGANISM: Artificial
<220> FEATURE:
<223> OTHER INFORMATION: Polynucleotide

<400> SEQUENCE: 96
aactgaagag tttgatcatg gctcagattg aacgctggcg gcaggcctaa cacatgcaag 60
tcgagcggat gaagggagct tgctcctgga ttcagcggcg gacgggtgag taatgcctag 120
gaatctgcct ggtagtgggg gataacgtcc ggaaacgggc gctaataccg catacgtcct 180
gagggagaaa gtgggggatc ttcggacctc acgctatcag atgagcctag gtcggattag 240
ctagttggtg gggtaaaggc ctaccaaggc gacgatccgt aactggtctg agaggatgat 300
cagtcacact ggaactgaga cacggtccag actcctacgg gaggcagcag tggggaatat 360
tggacaatta ggggcgaaag cctgatccag ccatgccgcg tgtgtgaaga aggtcttcgg 420
attgtaaagc actttaagtt gggaggaagg gcagtaagtt aataccttgc tgttttgacg 480
ttaccaacag aataagcacc ggctaacttc gtgccagcag ccgcggtaat acgaagggtg 540
caagcgttaa tcggaattac tgggcgtaaa tctgcgcgcg taggtggttc agcaagttgg 600
atgtgaaatc cccgggctca acctgggaac tgcatccaaa actactgagc tagagtacgg 660
tagagggtgg tggaatttcc tgtgtagcgg tgaaatgcgt agatatagga aggaacacca 720
gtggcgaagg cgaccacctg gactgatact gacactgagg tgcgaaagcg tggggagcaa 780
acaggattag ataccctggt agtccacgcc gtaaacgatg tcgactagcc gttgggatcc 840
ttgagatctt agtggcgcag ctaacgcgat aagtcgaccg cctggcatgg agtacggccg 900
caaggttaaa actcaaatga attgacgggg gcccgcacaa gcggtggagc atgtggttta 960
attcgaagca acgcgaagaa ccttacctgg ccttgacatg ctgagaactt tccagagatg 1020
gattggtgcc ttcgggaact cagacacagg tgctgcatgg ctgtcgtcag ctcgtgtcgt 1080
gagatgttgg gttaagtccc gtaacgagcg caacccttgt ccttagttac cagcacctcg 1140
ggtgggcact ctaaggagac tgccggtgac aaaccggagg aaggtgggga tgacgtcaag 1200
tcatcatggc ccttacggcc agggctacac acgtgctaca atggtcggta caaagggttg 1260
ccaagccgcg aggtggagct aatcccataa aaccgatcgt agtccggatc gcagtctgca 1320
actcgactgc gtgaagtcgg aatcgctagt aatcgtgaat cagaatgtca cggtgaatac 1380
gttcccgggc cttgtacaca ccgcccgtca caccatggga gtgggttgct ccagaagtag 1440
ctagtctaac cgcaaggggg acggttacca cggagtgatt catgactggg gtgaagtcgt 1500
aacaaggtag ccgtagggga acctgcggct ggatcacctc cttaataggg ataacagggt 1560
aatgagtcga caaaatgata cggcgaccac cgagatctac actctttccc tacacgacgc 1620
tcttccgatc tggtaacata taagcttctc gagatcggaa gagcacacgt ctgaactcca 1680
gtcacaatca gtctcgtatc tcgtatgccg tcttctgctt gttgtcgact c 1731

<210> SEQ ID NO 97
<211> LENGTH: 1661
<212> TYPE: DNA
<213> ORGANISM: Artificial
<220> FEATURE:
<223> OTHER INFORMATION: Polynucleotide

<400> SEQUENCE: 97
caacttgaga gtttgatcct ggctcagaat gaacgctggc ggcaggccta acacatgcaa 60

```
gtcgagcgaa gtcttcggac ttagcggcgg acgggtgagt aacgcgtggg aacgtgccct    120
ttgcttcgga atagccccgg gaaactggga gtaataccga atgtgccctt tgggggaaag    180
atttatcggc aaaggatcgg cccgcgttgg attaggtagt tggtggggta atggcctacc    240
aagccgacga tccatagctg gtttgagagg atgatcagcc acactgggac tgagacacgg    300
cccagactcc tacgggaggc agcagtgggg aatcttagac aattaggggc gcaagcctga    360
tctagccatg ccgcgtgatc gatgaaggcc ttagggttgt aaagatcttt caggtgggaa    420
gataatgacg gtaccaccag aagaagcccc ggctaactcc gtgccagcag ccgcggtaat    480
acggaggggg ctagcgttat tcggaattac tgggcgtaaa tctgcgcacg taggcggatc    540
ggaaagtcag aggtgaaatc ccagggctca accctggaac tgcctttgaa actcccgatc    600
ttgaggtcga gagaggtgag tggaattccg agtgtagagg tgaaattcgt agatattcgg    660
aggaacacca gtggcgaagg cggctcactg gctcgatact gacgctgagg tgcgaaagcg    720
tggggagcaa acaggattag ataccctggt agtccacgcc gtaaacgatg aatgccagtc    780
gtcgggcagc atgctgttcg gtgacacacc taacggatta agcattccgc ctggcatgga    840
gtacggccgc aaggttaaaa ctcaaaggaa ttgacggggg cccgcacaag cggtggagca    900
tgtggtttaa ttcgaagcaa cgcgcagaac cttaccaacc cttgacatgg cgatcgcggt    960
tccagagatg gttccttcag ttcggctgga tcgcacacag gtgctgcatg gctgtcgtca   1020
gctcgtgtcg tgagatgttc ggttaagtcc ggcaacgagc gcaacccacg tccttagttg   1080
ccagcattca gttgggcact ctagggaaac tgccggtgat aagccggagg aaggtgtgga   1140
tgacgtcaag tcctcatggc ccttacgggt tgggctacac acgtgctaca atggcagtga   1200
caatgggtta atcccaaaaa gctgtctcag ttcggattgg ggtctgcaac tcgaccccat   1260
gaagtcggaa tcgctagtaa tcgcgtaaca gcatgacgcg gtgaatacgt tcccgggcct   1320
tgtacacacc gcccgtcaca ccatgggaat tggttctacc cgaaggcggt gcgccaacct   1380
cgcaagagga ggcagccgac cacggtagga tcagtgactg gggtgaagtc gtaacaaggt   1440
agccgtaggg gaacctgcgg ctggatcacc tcctttaggg ataacagggt aatgagtcga   1500
caaaatgata cggcgaccac cgagatctac actctttccc tacacgacgc tcttccgatc   1560
tgtagaaata atcggattcg aagatcggaa gagcacacgt ctgaactcca gtcacaatca   1620
gtctcgtatc tcgtatgccg tcttctgctt gttgtcgact c                         1661
```

<210> SEQ ID NO 98
<211> LENGTH: 1735
<212> TYPE: DNA
<213> ORGANISM: Artificial
<220> FEATURE:
<223> OTHER INFORMATION: Polynucleotide

<400> SEQUENCE: 98

```
agagtttgat cctggctcag gatgaacgct ggcggcgtgc ctaatacatg caagtcgagc     60
gaacggacga gaagcttgct tctctgatgt tagcggcgga cgggtgagta acacgtggat    120
aacctaccta taagactggg ataacttcgg gaaaccggag ctaataccgg ataatatttt    180
gaaccgcatg gttcaaaagt gaaagacggt cttgctgtca cttatagatg gatccgcgct    240
gcattagcta gttggtaagg taacggctta ccaaggcaac gatgcatagc cgacctgaga    300
gggtgatcgg ccacactgga actgagacac ggtccagact cctacgggag gcagcagtag    360
ggaatcttcc gcaattaggg gcgaaagcct gacggagcaa cgccgcgtga gtgatgaagg    420
```

tcttcggatc gtaaaactct gttattaggg aagaacatat gtgtaagtaa ctgtgcacat 480
cttgacggta cctaatcaga aagccacggc taactacgtg ccagcagccg cggtaatacg 540
taggtggcaa gcgttatccg gaattattgg gcgtaaatct gcgcgcgtag gcggtttttt 600
aagtctgatg tgaaagccca cggctcaacc gtggagggtc attggaaact ggaaaacttg 660
agtgcagaag aggaaagtgg aattccatgt gtagcggtga aatgcgcaga gatatggagg 720
aacaccagtg gcgaaggcga ctttctggtc tgtaactgac gctgatgtgc gaaagcgtgg 780
ggatcaaaca ggattagata ccctggtagt ccacgccgta aacgatgagt gctaagtgtt 840
agggggtttc cgccccttag tgctgcagct aacgcattaa gcactccgcc tggcatggag 900
tacgaccgca aggttgaaac tcaaaggaat tgacggggac ccgcacaagc ggtggagcat 960
gtggtttaat tcgaagcaac gcgaagaacc ttaccaaatc ttgacatcct ttgacaactc 1020
tagagataga gccttcccct tcgggggaca aagtgacagg tggtgcatgg ttgtcgtcag 1080
ctcgtgtcgt gagatgttgg gttaagtccc gcaacgagcg caacccttaa gcttagttgc 1140
catcattaag ttgggcactc taagttgact gccggtgaca aaccggagga aggtggggat 1200
gacgtcaaat catcatgccc cttatgattt gggctacaca cgtgctacaa tggacaatac 1260
aaagggcagc gaaaccgcga ggtcaagcaa atcccataaa gttgttctca gttcggattg 1320
tagtctgcaa ctcgactaca tgaagctgga atcgctagta atcgtagatc agcatgctac 1380
ggtgaatacg ttcccgggtc ttgtacacac cgcccgtcac accacgagag tttgtaacac 1440
ccgaagccgg tggagtaacc ttttaggagc tagccgtcga aggtgggaca aatgattggg 1500
gtgaagtcgt aacaaggtag ccgtatcgga aggtgcggct ggatcacctt agggataaca 1560
gggtaatgag tcgacaaaat gatacggcga ccaccgagat ctacactctt tccctacacg 1620
acgctcttcc gatcttcacc tgccgggcgg gcgcgagatc ggaagagcac acgtctgaac 1680
tccagtcaca atcagtctcg tatctcgtat gccgtcttct gcttgttgtc gactc 1735

<210> SEQ ID NO 99
<211> LENGTH: 1749
<212> TYPE: DNA
<213> ORGANISM: Artificial
<220> FEATURE:
<223> OTHER INFORMATION: Polynucleotide

<400> SEQUENCE: 99
ttttatggag agtttgatcc tggctcagga tgaacgctgg cggcgtgcct aatacatgca 60
agtcgagcga acagacgagg agcttgctcc tctgacgtta gcggcggacg ggtgagtaac 120
acgtggataa cctacctata agactgggat aacttcggga aaccggagct aataccggat 180
aatatattga accgcatggt tcaatagtga aagacggttt tgctgtcact tatagatgga 240
tccgcgccgc attagctagt tggtaaggta acggcttacc aaggcaacga tgcgtagccg 300
acctgagagg gtgatcggcc acactggaac tgagacacgg tccagactcc tacgggaggc 360
agcagtaggg aatcttccgc aattaggggc gaaagcctga cggagcaacg ccgcgtgagt 420
gatgaaggtc ttcggatcgt aaaactctgt tattagggaa gaacaaatgt gtaagtaact 480
atgcacgtct tgacggtacc taatcagaaa gccacggcta actacgtgcc agcagccgcg 540
gtaatacgta ggtggcaagc gttatccgga attattgggc gtaaatctgc gcgcgtaggc 600 ggtttttttaa gtctgatgtg aaagcccacg gctcaaccgt ggagggtcat tggaaactgg 660
aaaacttgag tgcagaagag gaaagtggaa ttccatgtgt agcggtgaaa tgcgcagaga 720
tatggaggaa caccagtggc gaaggcgact ttctggtctg taactgacgc tgatgtgcga 780

```
aagcgtgggg atcaaacagg attagatacc ctggtagtcc acgccgtaaa cgatgagtgc    840

taagtgttag ggggtttccg ccccttagtg ctgcagctaa cgcattaagc actccgcctg    900

gcatggagta cgaccgcaag gttgaaactc aaaggaattg acggggaccc gcacaagcgg    960

tggagcatgt ggtttaattc gaagcaacgc gaagaacctt accaaatctt gacatcctct   1020

gacccctcta gagatagagt tttccccttc gggggacaga gtgacaggtg gtgcatggtt   1080

gtcgtcagct cgtgtcgtga gatgttgggt taagtcccgc aacgagcgca acccttaagc   1140

ttagttgcca tcattaagtt gggcactcta agttgactgc cggtgacaaa ccggaggaag   1200

gtggggatga cgtcaaatca tcatgcccct tatgatttgg gctacacacg tgctacaatg   1260

gacaatacaa agggcagcga aaccgcgagg tcaagcaaat cccataaagt tgttctcagt   1320

tcggattgta gtctgcaact cgactatatg aagctggaat cgctagtaat cgtagatcag   1380

catgctacgg tgaatacgtt cccgggtctt gtacacaccg cccgtcacac cacgagagtt   1440

tgtaacaccc gaagccggtg gagtaaccat ttggagctag ccgtcgaagg tggaacaaat   1500

gattggggtg aagtcgtaac aaggtagccg tatcggaagg tgcggctgga tcacctcctt   1560

tcttagggat aacagggtaa tgagtcgaca aaatgatacg gcgaccaccg agatctacac   1620

tctttcccta cacgacgctc ttccgatctc gataatttcg gatcgggata gatcggaaga   1680

gcacacgtct gaactccagt cacaatcagt ctcgtatctc gtatgccgtc ttctgcttgt   1740

tgtcgactc                                                           1749
```

<210> SEQ ID NO 100
<211> LENGTH: 1746
<212> TYPE: DNA
<213> ORGANISM: Artificial
<220> FEATURE:
<223> OTHER INFORMATION: Polynucleotide

<400> SEQUENCE: 100

```
tttaatgaga gtttgatcct ggctcaggac gaacgctggc ggcgtgccta atacatgcaa     60

gtagaacgct gaggtttggt gtttacacta gactgatgag ttgcgaacgg gtgagtaacg    120

cgtaggtaac ctgcctcata gcgggggata actattggaa acgatagcta ataccgcata    180

agagtaatta acacatgtta gttatttaaa aggagcaatt gcttcactgt gagatggacc    240

tgcgttgtat tagctagttg gtgaggtaaa ggctcaccaa ggcgacgata catagccgac    300

ctgagagggt gatcggccac actgggactg agacacggcc cagactccta cgggaggcag    360

cagtagggaa tcttcggcaa ttagggacgg aagtctgacc gagcaacgcc gcgtgagtga    420

agaaggtttt cggatcgtaa agctctgttg ttagagaaga acgttggtag gagtggaaaa    480

tctaccaagt gacggtaact aaccagaaag ggacggctaa ctacgtgcca gcagccgcgg    540

taatacgtag gtcccgagcg ttgtccggat ttattgggcg taaatctgcg agcgcaggcg    600

gttctttaag tctgaagtta aaggcagtgg cttaaccatt gtacgctttg gaaactggag    660

gacttgagtg cagaagggga gagtggaatt ccatgtgtag cggtgaaatg cgtagatata    720

tggaggaaca ccggtggcga aagcggctct ctggtctgta actgacgctg aggctcgaaa    780

gcgtggggag caaacaggat tagataccct ggtagtccac gccgtaaacg atgagtgcta    840

ggtgttaggc cctttccggg gcttagtgcc gcagctaacg cattaagcac tccgcctggc    900

atggagtacg accgcaaggt tgaaactcaa aggaattgac gggggcccgc acaagcggtg    960

gagcatgtgg tttaattcga agcaacgcga agaaccttac caggtcttga catccttctg   1020
```

-continued

```
accggcctag agataggctt tctcttcgga gcagaagtga caggtggtgc atggttgtcg   1080

tcagctcgtg tcgtgagatg ttgggttaag tcccgcaacg agcgcaaccc ctattgttag   1140

ttgccatcat taagttgggc actctagcga gactgccggt aataaaccgg aggaaggtgg   1200

ggatgacgtc aaatcatcat gccccttatg acctgggcta cacacgtgct acaatggttg   1260

gtacaacgag tcgcaagccg gtgacggcaa gctaatctct taaagccaat ctcagttcgg   1320

attgtaggct gcaactcgcc tacatgaagt cggaatcgct agtaatcgcg gatcagcacg   1380

ccgcggtgaa tacgttcccg ggccttgtac acaccgcccg tcacaccacg agagtttgta   1440

acacccgaag tcggtgaggt aaccttttag gagccagccg cctaaggtgg gatagatgat   1500

tggggtgaag tcgtaacaag gtagccgtat cggaaggtgc ggctggatca cctcctttct   1560

tagggataac agggtaatga gtcgacaaaa tgatacggcg accaccgaga tctacactct   1620

ttccctacac gacgctcttc cgatcttcat gtcgccgttt ggcaaaagat cggaagagca   1680

cacgtctgaa ctccagtcac aatcagtctc gtatctcgta tgccgtcttc tgcttgttgt   1740

cgactc                                                              1746
```

```
<210> SEQ ID NO 101
<211> LENGTH: 1747
<212> TYPE: DNA
<213> ORGANISM: Artificial
<220> FEATURE:
<223> OTHER INFORMATION: Polynucleotide

<400> SEQUENCE: 101
```

```
agagtttgat cctggctcag gacgaacgct ggcggcgtgc ctaatacatg caagtgggac     60

gcaagaggac acactgtgct tgcacaccgt gttttcttga gtcgcgaacg ggtgagtaac    120

gcgtaggtaa cctgcctatt agcgggggat aactattgga aacgatagct aataccgcat    180

aatattaatt attgcatgat aattgattga aagatgcaag cgcatcacta gtagatggac    240

ctgcgttgta ttagctagtt ggtaaggtaa gagcttacca aggcgacgat acatagccga    300

cctgagaggg tgatcggcca cactgggact gagacacggc ccagactcct acgggaggca    360

gcagtaggga atcttcggca attagggacg aaagtctgac cgagcaacgc cgcgtgagtg    420

aagaaggttt tcggatcgta aagctctgtt gtaagtcaag aacgtgtgtg agagtggaaa    480

gttcacacag tgacggtagc ttaccagaaa gggacggcta actacgtgcc agcagccgcg    540

gtaatacgta ggtcccgagc gttgtccgga tttattgggc gtaaatctgg gagcgcaggc    600

ggtcaggaaa gtctggagta aaaggctatg gctcaaccat agtgtgctct ggaaactgtc    660

tgacttgagt gcagaagggg agagtggaat tccatgtgta gcggtgaaat gcgtagatat    720

atggaggaac accagtggcg aaagcggctc tctggtctgt cactgacgct gaggctcgaa    780

agcgtgggta gcgaacagga ttagataccc tggtagtcca cgccgtaaac gatgagtgct    840

aggtgttagg ccctttccgg ggcttagtgc cggagctaac gcaataagca ctccgcctgg    900

catggagtac gaccgcaagg ttgaaactca aaggaattga cgggggcccg cacaagcggt    960

ggagcatgtg gtttaattcg aagcaacgcg aagaacctta ccaggtcttg acatcccgat   1020

gctattctta gagataggaa gttacttcgg tacatcggag acaggtggtg catggttgtc   1080

gtcagctcgt gtcgtgagat gttgggttaa gtcccgcaac gagcgcaacc cttattgtta   1140

gttgccatca ttaagttggg cactctagcg agactgccgg taataaaccg gaggaaggtg   1200

gggatgacgt caaatcatca tgccccttat gacctgggct acacacgtgc tacaatggtc   1260

ggtacaacga gttgcgagcc ggtgacggca agctaatctc tgaaagccga tctcagttcg   1320
```

```
gattggaggc tgcaactcgc ctccatgaag tcggaatcgc tagtaatcgc ggatcagcac   1380

gccgcggtga atacgttccc gggccttgta cacaccgccc gtcacaccac gagagtttgt   1440

aacacccgaa gtcggtgagg taacctttta ggggccagcc gcctaaggtg ggatggatga   1500

ttggggtgaa gtcgtaacaa ggtagccgta tcggaaggtg cggctggatc acctcctttc   1560

ttagggataa cagggtaatg agtcgacaaa atgatacggc gaccaccgag atctacactc   1620

tttccctaca cgacgctctt ccgatctttc tagcactgta agacaccaga tcggaagagc   1680

acacgtctga actccagtca caatcagtct cgtatctcgt atgccgtctt ctgcttgttg   1740

tcgactc                                                             1747
```

<210> SEQ ID NO 102
<211> LENGTH: 1755
<212> TYPE: DNA
<213> ORGANISM: Artificial
<220> FEATURE:
<223> OTHER INFORMATION: Polynucleotide

<400> SEQUENCE: 102

```
aaacttttta atgagagttt gatcctggct caggacgaac gctggcggcg tgcctaatac     60

atgcaagtag aacgctgaag gaggagcttg cttctctgga tgagttgcga acgggtgagt    120

aacgcgtagg taacctgcct ggtagcgggg gataactatt ggaaacgata gctaataccg    180

cataagagta gatgttgcat gacatttgct taaaaggtgc acttgcatca ctaccagatg    240

gacctgcgtt gtattagcta gttggtgggg taacggctca ccaaggcgac gatacatagc    300

cgacctgaga gggtgatcgg ccacactggg actgagacac ggcccagact cctacgggag    360

gcagcagtag ggaatcttcg gcaattaggg acggaagtct gaccgagcaa cgccgcgtga    420

gtgaagaagg ttttcggatc gtaaagctct gttgtaagag aagaacgagt gtgagagtgg    480

aaagttcaca ctgtgacggt atcttaccag aaagggacgg ctaactacgt gccagcagcc    540

gcggtaatac gtaggtcccg agcgttgtcc ggatttattg ggcgtaaatc tgcgagcgca    600

ggcggttaga taagtctgaa gttaaaggct gtggcttaac catagtaggc tttggaaact    660

gtttaacttg agtgcaagag gggagagtgg aattccatgt gtagcggtga aatgcgtaga    720

tatatggagg aacaccggtg gcgaaagcgg ctctctggct tgtaactgac gctgaggctc    780

gaaagcgtgg ggagcaaaca ggattagata ccctggtagt ccacgctgta aacgatgagt    840

gctaggtgtt agaccctttc cggggtttag tgccgtagct aacgcattaa gcactccgcc    900

tggcatggag tacgaccgca aggttgaaac tcaaaggaat tgacgggggc ccgcacaagc    960

ggtggagcat gtggtttaat tcgaagcaac gcgaagaacc ttaccaggtc ttgacatccc   1020

tctgaccgct ctagagatag agctttcctt cgggacagag gtgacaggtg gtgcatggtt   1080

gtcgtcagct cgtgtcgtga gatgttgggt taagtcccgc aacgagcgca acccctattg   1140

ttagttgcca tcatttagtt gggcactcta gcgagactgc cggtaataaa ccggaggaag   1200

gtggggatga cgtcaaatca tcatgcccct tatgacctgg gctacacacg tgctacaatg   1260

gctggtacaa cgagtcgcaa gccggtgacg gcaagctaat ctcttaaagc cagtctcagt   1320

tcggattgta ggctgcaact cgcctacatg aagtcggaat cgctagtaat cgcggatcag   1380

cacgccgcgg tgaatacgtt cccgggcctt gtacacaccg cccgtcacac cacgagagtt   1440

tgtaacaccc gaagtcggtg aggtaaccgt aaggagccag ccgcctaagg tgggatagat   1500

gattggggtg aagtcgtaac aaggtagccg tatcggaagg tgcggctgga tcacctcctt   1560
```

```
tctaaggatt agggataaca gggtaatgag tcgacaaaat gatacggcga ccaccgagat   1620

ctacactctt tccctacacg acgctcttcc gatctgacct acggattaga ctattagatc   1680

ggaagagcac acgtctgaac tccagtcaca atcagtctcg tatctcgtat gccgtcttct   1740

gcttgttgtc gactc                                                    1755
```

<210> SEQ ID NO 103
<211> LENGTH: 1640
<212> TYPE: DNA
<213> ORGANISM: Artificial
<220> FEATURE:
<223> OTHER INFORMATION: Polynucleotide

<400> SEQUENCE: 103

```
agagtttgat cctggctcag gacgaacgct ggcggcgtgc ttaacacatg caagtcgaac     60

gctgaagccc agcttgctgg gtggatgagt ggcgaacggg tgagtaacac gtgagtaacc    120

tgccccccttc tttgggataa cgcccggaaa cgggtgctaa tactggatat tcactgatct   180

tcgcatgggg gttggtggaa aggttttttc tggtggggga tgggctcgcg gcctatcagc    240

ttgttggtgg ggtgatggcc taccaaggct ttgacgggta gccggcctga gagggtgacc    300

ggtcacattg ggactgagat acggcccaga ctcctacggg aggcagcagt ggggaatatt    360

gcacaattag ggcgaaagc ctgatgcagc gacgccgcgt gagggatgga ggccttcggg     420

ttgtaaacct ctttcgctca tggtcaagcc gcaactcaag gttgtggtga gggtagtggg    480

taaagaagcg ccggctaact acgtgccagc agccgcggta atacgtaggg cgcgagcgtt    540

gtccggaatt attgggcgta aatctgggct tgtaggcggt tggtcgcgtc tgccgtgaaa    600

tcctctggct taactggggg cgtgcggtgg gtacgggctg acttgagtgc ggtaggggag    660

actggaactc ctggtgtagc ggtggaatgc gcagatatca ggaagaacac cggtggcgaa    720

ggcgggtctc tgggccgtta ctgacgctga ggagcgaaag cgtggggagc gaacaggatt    780

agataccctg gtagtccacg ctgtaaacgt tgggcactag gtgtgggggc cacccgtggt    840

ttctgcgccg tagctaacgc tttaagtgcc ccgcctggca tggagtacgg ccgcaaggct    900

aaaactcaaa ggaattgacg ggggcccgca caagcggcgg agcatgcgga ttaattcgat    960

gcaacgcgaa gaaccttacc aaggcttgac atgcacggcg gcactgcaga gatgtggtgg   1020

catttagttg gtcgtgtgca ggtggtgcat ggttgtcgtc agctcgtgtc gtgagatgtt   1080

gggttaagtc ccgcaacgag cgcaaccctt gccctatgtt gccagcacgt gatggtgggg   1140

actcgtgggg gactgccggg gttaactcgg aggaaggtgg ggatgacgtc aaatcatcat   1200

gccccttatg tcttgggctt cacgcatgct acaatggctg gtacagaggg ttgcgatact   1260

gtgaggtgga gcgaatccct taaagccagt ctcagttcgg attggggtct gcaactcgac   1320

cccatgaagg tggagtcgct agtaatcgca gatcagcaac gctgcggtga atacgttctc   1380

gggccttgta cacaccgccc gtcacgtcac gaaagttggt aacacccgaa gcccatggcc   1440

taaccgcttt gtgctaggga taacagggta atgagtcgac aaaatgatac ggcgaccacc   1500

gagatctaca ctctttccct acacgacgct cttccgatct tttaaactct atccatccca   1560

agatcggaag agcacacgtc tgaactccag tcacaatcag tctcgtatct cgtatgccgt   1620

cttctgcttg ttgtcgactc                                               1640
```

<210> SEQ ID NO 104
<211> LENGTH: 1741
<212> TYPE: DNA
<213> ORGANISM: Artificial
<220> FEATURE:
<223> OTHER INFORMATION: Polynucleotide

<400> SEQUENCE: 104
gagagtttga tcctggctca ggacgaacgc tggcggcgtg cctaatacat gcaagtcgaa 60
cgaacggagg aagagcttgc tcttccaatg ttagtggcgg acgggtgagt aacacgtggg 120
caacctgcct gtaagttggg gataactccg ggaaaccggg gctaataccg aatgataaga 180
tgtggcgcat gccacgcctt tgaaagatgg tttcggctat cgcttacaga tgggcccgcg 240
gtgcattagc tagttggtag ggtaatggcc taccaaggca acgatgcata gccgacctga 300
gagggtgatc ggccacactg ggactgagac acggcccaga ctcctacggg aggcagcagt 360
agggaatctt ccgcaattag ggacgaaagt ctgacggagc aacgccgcgt gtatgaagaa 420
ggttttcgga tcgtaaagta ctgttgttag agaagaacaa ggataagagt aactgcttgt 480
cccttgacgg tatctaacca gaaagccacg gctaactacg tgccagcagc cgcggtaata 540
cgtaggtggc aagcgttgtc cggatttatt gggcgtaaat ctgcgcgcgc aggcggtctt 600
ttaagtctga tgtgaaagcc cccggcttaa ccggggaggg tcattggaaa ctggaagact 660
ggagtgcaga agaggagagt ggaattccac gtgtagcggt gaaatgcgta gatatgtgga 720
ggaacaccag tggcgaaggc gactctctgg tctgtaactg acgctgaggc gcgaaagcgt 780
ggggagcaaa caggattaga taccctggta gtccacgccg taaacgatga gtgctaagtg 840
ttagggggtt tccgcccctt agtgctgcag ctaacgcatt aagcactccg cctggcatgg 900
agtacgaccg caaggttgaa actcaaagga attgacgggg gcccgcacaa gcggtggagc 960
atgtggttta attcgaagca acgcgaagaa ccttaccagg tcttgacatc ctttgaccac 1020
tctggagaca gagctttccc ttcggggaca aagtgacagg tggtgcatgg ttgtcgtcag 1080
ctcgtgtcgt gagatgttgg gttaagtccc gcaacgagcg caacccttga ttttagttgc 1140
cagcatttag ttgggcactc taaagtgact gccggtgcaa gccggaggaa ggtggggatg 1200
acgtcaaatc atcatgcccc ttatgacctg ggctacacac gtgctacaat ggatagtaca 1260
aagggtcgcg aagccgcgag gtggagctaa tcccataaaa ctattctcag ttcggattgt 1320
aggctgcaac tcgcctacat gaagccggaa tcgctagtaa tcgtggatca gcatgccacg 1380
gtgaatacgt tcccgggcct tgtacacacc gcccgtcaca ccacgagagt ttgtaacacc 1440
cgaagtcggt agggtaacct ttatggagcc agccgccgaa ggtgggacag ataattgggg 1500
tgaagtcgta acaaggtagc cgtatcggaa ggtgcggctg gatcacctcc tttcttaggg 1560
ataacagggt aatgagtcga caaaatgata cggcgaccac cgagatctac actctttccc 1620
tacacgacgc tcttccgatc tctaacttat gtgtcgtcgg tagatcggaa gagcacacgt 1680
ctgaactcca gtcacaatca gtctcgtatc tcgtatgccg tcttctgctt gttgtcgact 1740
c 1741

<210> SEQ ID NO 105
<211> LENGTH: 518
<212> TYPE: DNA
<213> ORGANISM: Artificial
<220> FEATURE:
<223> OTHER INFORMATION: Polynucleotide

<400> SEQUENCE: 105
aagaagcacc ggctaactcc gtgccagcag ccgcggtaat acggagggtg caagcgttaa 60
tcggaattac tgggcgtaaa gcgcacgcag gcggtttgtt aagtcagatg tgaaatcccc 120

-continued

```
gggctcaacc tgggaactgc atctgatact ggcaagcttg agtctcgtag agggggggtag    180

aattccaggt gtagcggtga aatgcgtaga gatctggagg aataccggtg gcgaaggcgg    240

ccccctggac gaagactgac gctcaggtgc gaaagcgtgg ggagcaaaca ggattagata    300

ccctggtagt ccacgccgta aacgatgtcg actagggata acagggtaat gagtcgacaa    360

aatgatacgg cgaccaccga gatctacact ctttccctac acgacgctct tccgatctat    420

gacatcagaa ttgagtgcag atcggaagag cacacgtctg aactccagtc acaatcagtc    480

tcgtatctcg tatgccgtct tctgcttgtt gtcgactc                             518
```

<210> SEQ ID NO 106
<211> LENGTH: 518
<212> TYPE: DNA
<213> ORGANISM: Artificial
<220> FEATURE:
<223> OTHER INFORMATION: Polynucleotide

<400> SEQUENCE: 106

```
aagaagcacc ggctaactcc gtgccagcaa ccgcggtaat acggagggtg caagcgttaa     60

tcggaattac tgggcgtaaa gcgcacgcag gcggtttgtt aagtcagatg tgaaatcccc    120

gggctcaacc tgggaactgc atctgatact ggcaagcttg agtctcgtag agggggggtag    180

aattccaggt gtagcggtga aatgcgtaga gatctggagg aataccggtg gcgaaggcgg    240

ccccctggac gaagactgac gctcaggtgc gaaagcgtgg ggagcaaaca ggattagata    300

ccctggtagt ccacgccgta aacgatgtcg actagggata acagggtaat gagtcgacaa    360

aatgatacgg cgaccaccga gatctacact ctttccctac acgacgctct tccgatctcg    420

acactgccag tgtcactcag atcggaagag cacacgtctg aactccagtc acaatcagtc    480

tcgtatctcg tatgccgtct tctgcttgtt gtcgactc                             518
```

<210> SEQ ID NO 107
<211> LENGTH: 518
<212> TYPE: DNA
<213> ORGANISM: Artificial
<220> FEATURE:
<223> OTHER INFORMATION: Polynucleotide

<400> SEQUENCE: 107

```
aagaagcacc ggctaactcc gtgccagcat ccgcggtaat acggagggtg caagcgttaa     60

tcggaattac tgggcgtaaa gcgcacgcag gcggtttgtt aagtcagatg tgaaatcccc    120

gggctcaacc tgggaactgc atctgatact ggcaagcttg agtctcgtag agggggggtag    180

aattccaggt gtagcggtga aatgcgtaga gatctggagg aataccggtg gcgaaggcgg    240

ccccctggac gaagactgac gctcaggtgc gaaagcgtgg ggagcaaaca ggattagata    300

ccctggtagt ccacgccgta aacgatgtcg actagggata acagggtaat gagtcgacaa    360

aatgatacgg cgaccaccga gatctacact ctttccctac acgacgctct tccgatctga    420

agtggacttg cttatacgag atcggaagag cacacgtctg aactccagtc acaatcagtc    480

tcgtatctcg tatgccgtct tctgcttgtt gtcgactc                             518
```

<210> SEQ ID NO 108
<211> LENGTH: 518
<212> TYPE: DNA
<213> ORGANISM: Artificial
<220> FEATURE:
<223> OTHER INFORMATION: Polynucleotide

<400> SEQUENCE: 108
aagaagcacc ggctaactcc gtgccagcac ccgcggtaat acggagggtg caagcgttaa 60
tcggaattac tgggcgtaaa gcgcacgcag gcggtttgtt aagtcagatg tgaaatcccc 120
gggctcaacc tgggaactgc atctgatact ggcaagcttg agtctcgtag aggggggtag 180
aattccaggt gtagcggtga aatgcgtaga gatctggagg aataccggtg gcgaaggcgg 240
ccccctggac gaagactgac gctcaggtgc gaaagcgtgg ggagcaaaca ggattagata 300
ccctggtagt ccacgccgta aacgatgtcg actagggata acagggtaat gagtcgacaa 360
aatgatacgg cgaccaccga gatctacact ctttccctac acgacgctct tccgatctgg 420
aggcgttgat tggcggctag atcggaagag cacacgtctg aactccagtc acaatcagtc 480
tcgtatctcg tatgccgtct tctgcttgtt gtcgactc 518

<210> SEQ ID NO 109
<211> LENGTH: 518
<212> TYPE: DNA
<213> ORGANISM: Artificial
<220> FEATURE:
<223> OTHER INFORMATION: Polynucleotide

<400> SEQUENCE: 109
aagaagcacc ggctaactcc gtgccagcag acgcggtaat acggagggtg caagcgttaa 60
tcggaattac tgggcgtaaa gcgcacgcag gcggtttgtt aagtcagatg tgaaatcccc 120
gggctcaacc tgggaactgc atctgatact ggcaagcttg agtctcgtag aggggggtag 180
aattccaggt gtagcggtga aatgcgtaga gatctggagg aataccggtg gcgaaggcgg 240
ccccctggac gaagactgac gctcaggtgc gaaagcgtgg ggagcaaaca ggattagata 300
ccctggtagt ccacgccgta aacgatgtcg actagggata acagggtaat gagtcgacaa 360
aatgatacgg cgaccaccga gatctacact ctttccctac acgacgctct tccgatctga 420
cgaccaataa tgaacttgag atcggaagag cacacgtctg aactccagtc acaatcagtc 480
tcgtatctcg tatgccgtct tctgcttgtt gtcgactc 518

<210> SEQ ID NO 110
<211> LENGTH: 518
<212> TYPE: DNA
<213> ORGANISM: Artificial
<220> FEATURE:
<223> OTHER INFORMATION: Polynucleotide

<400> SEQUENCE: 110
aagaagcacc ggctaactcc gtgccagcag tcgcggtaat acggagggtg caagcgttaa 60
tcggaattac tgggcgtaaa gcgcacgcag gcggtttgtt aagtcagatg tgaaatcccc 120
gggctcaacc tgggaactgc atctgatact ggcaagcttg agtctcgtag aggggggtag 180
aattccaggt gtagcggtga aatgcgtaga gatctggagg aataccggtg gcgaaggcgg 240
ccccctggac gaagactgac gctcaggtgc gaaagcgtgg ggagcaaaca ggattagata 300
ccctggtagt ccacgccgta aacgatgtcg actagggata acagggtaat gagtcgacaa 360
aatgatacgg cgaccaccga gatctacact ctttccctac acgacgctct tccgatctcc 420
cggaaacaaa tccgggctag atcggaagag cacacgtctg aactccagtc acaatcagtc 480
tcgtatctcg tatgccgtct tctgcttgtt gtcgactc 518

<210> SEQ ID NO 111
<211> LENGTH: 518
<212> TYPE: DNA

```
<213> ORGANISM: Artificial
<220> FEATURE:
<223> OTHER INFORMATION: Polynucleotide

<400> SEQUENCE: 111

aagaagcacc ggctaactcc gtgccagcag gcgcggtaat acggagggtg caagcgttaa     60

tcggaattac tgggcgtaaa gcgcacgcag gcggtttgtt aagtcagatg tgaaatcccc    120

gggctcaacc tgggaactgc atctgatact ggcaagcttg agtctcgtag aggggggtag    180

aattccaggt gtagcggtga aatgcgtaga gatctggagg aataccggtg gcgaaggcgg    240

ccccctggac gaagactgac gctcaggtgc gaaagcgtgg ggagcaaaca ggattagata    300

ccctggtagt ccacgccgta aacgatgtcg actagggata acagggtaat gagtcgacaa    360

aatgatacgg cgaccaccga gatctacact ctttccctac acgacgctct tccgatctac    420

ttaaagacca tttgatgaag atcggaagag cacacgtctg aactccagtc acaatcagtc    480

tcgtatctcg tatgccgtct tctgcttgtt gtcgactc                            518


<210> SEQ ID NO 112
<211> LENGTH: 518
<212> TYPE: DNA
<213> ORGANISM: Artificial
<220> FEATURE:
<223> OTHER INFORMATION: Polynucleotide

<400> SEQUENCE: 112

aagaagcacc ggctaactcc gtgccagcag cagcggtaat acggagggtg caagcgttaa     60

tcggaattac tgggcgtaaa gcgcacgcag gcggtttgtt aagtcagatg tgaaatcccc    120

gggctcaacc tgggaactgc atctgatact ggcaagcttg agtctcgtag aggggggtag    180

aattccaggt gtagcggtga aatgcgtaga gatctggagg aataccggtg gcgaaggcgg    240

ccccctggac gaagactgac gctcaggtgc gaaagcgtgg ggagcaaaca ggattagata    300

ccctggtagt ccacgccgta aacgatgtcg actagggata acagggtaat gagtcgacaa    360

aatgatacgg cgaccaccga gatctacact ctttccctac acgacgctct tccgatctcg    420

gtgccagact taagtttgag atcggaagag cacacgtctg aactccagtc acaatcagtc    480

tcgtatctcg tatgccgtct tctgcttgtt gtcgactc                            518


<210> SEQ ID NO 113
<211> LENGTH: 518
<212> TYPE: DNA
<213> ORGANISM: Artificial
<220> FEATURE:
<223> OTHER INFORMATION: Polynucleotide

<400> SEQUENCE: 113

aagaagcacc ggctaactcc gtgccagcag ctgcggtaat acggagggtg caagcgttaa     60

tcggaattac tgggcgtaaa gcgcacgcag gcggtttgtt aagtcagatg tgaaatcccc    120

gggctcaacc tgggaactgc atctgatact ggcaagcttg agtctcgtag aggggggtag    180

aattccaggt gtagcggtga aatgcgtaga gatctggagg aataccggtg gcgaaggcgg    240

ccccctggac gaagactgac gctcaggtgc gaaagcgtgg ggagcaaaca ggattagata    300

ccctggtagt ccacgccgta aacgatgtcg actagggata acagggtaat gagtcgacaa    360

aatgatacgg cgaccaccga gatctacact ctttccctac acgacgctct tccgatctag    420

ctctctgctt agatgacgag atcggaagag cacacgtctg aactccagtc acaatcagtc    480

tcgtatctcg tatgccgtct tctgcttgtt gtcgactc                            518
```

<210> SEQ ID NO 114
<211> LENGTH: 518
<212> TYPE: DNA
<213> ORGANISM: Artificial
<220> FEATURE:
<223> OTHER INFORMATION: Polynucleotide

<400> SEQUENCE: 114
aagaagcacc ggctaactcc gtgccagcag cggcggtaat acggagggtg caagcgttaa 60
tcggaattac tgggcgtaaa gcgcacgcag gcggtttgtt aagtcagatg tgaaatcccc 120
gggctcaacc tgggaactgc atctgatact ggcaagcttg agtctcgtag aggggggtag 180
aattccaggt gtagcggtga aatgcgtaga gatctggagg aataccggtg gcgaaggcgg 240
ccccctggac gaagactgac gctcaggtgc gaaagcgtgg ggagcaaaca ggattagata 300
ccctggtagt ccacgccgta aacgatgtcg actagggata acagggtaat gagtcgacaa 360
aatgatacgg cgaccaccga gatctacact ctttccctac acgacgctct tccgatctgg 420
ttattaggat atgccgttag atcggaagag cacacgtctg aactccagtc acaatcagtc 480
tcgtatctcg tatgccgtct tctgcttgtt gtcgactc 518

<210> SEQ ID NO 115
<211> LENGTH: 518
<212> TYPE: DNA
<213> ORGANISM: Artificial
<220> FEATURE:
<223> OTHER INFORMATION: Polynucleotide

<400> SEQUENCE: 115
aagaagcacc ggctaactcc gtgccagcag ccacggtaat acggagggtg caagcgttaa 60
tcggaattac tgggcgtaaa gcgcacgcag gcggtttgtt aagtcagatg tgaaatcccc 120
gggctcaacc tgggaactgc atctgatact ggcaagcttg agtctcgtag aggggggtag 180
aattccaggt gtagcggtga aatgcgtaga gatctggagg aataccggtg gcgaaggcgg 240
ccccctggac gaagactgac gctcaggtgc gaaagcgtgg ggagcaaaca ggattagata 300
ccctggtagt ccacgccgta aacgatgtcg actagggata acagggtaat gagtcgacaa 360
aatgatacgg cgaccaccga gatctacact ctttccctac acgacgctct tccgatctac 420
caaatgccga ggtttgacag atcggaagag cacacgtctg aactccagtc acaatcagtc 480
tcgtatctcg tatgccgtct tctgcttgtt gtcgactc 518

<210> SEQ ID NO 116
<211> LENGTH: 518
<212> TYPE: DNA
<213> ORGANISM: Artificial
<220> FEATURE:
<223> OTHER INFORMATION: Polynucleotide

<400> SEQUENCE: 116
aagaagcacc ggctaactcc gtgccagcag cctcggtaat acggagggtg caagcgttaa 60
tcggaattac tgggcgtaaa gcgcacgcag gcggtttgtt aagtcagatg tgaaatcccc 120
gggctcaacc tgggaactgc atctgatact ggcaagcttg agtctcgtag aggggggtag 180
aattccaggt gtagcggtga aatgcgtaga gatctggagg aataccggtg gcgaaggcgg 240
ccccctggac gaagactgac gctcaggtgc gaaagcgtgg ggagcaaaca ggattagata 300
ccctggtagt ccacgccgta aacgatgtcg actagggata acagggtaat gagtcgacaa 360
aatgatacgg cgaccaccga gatctacact ctttccctac acgacgctct tccgatctcg 420
atatataaag gtaaccaaag atcggaagag cacacgtctg aactccagtc acaatcagtc 480
tcgtatctcg tatgccgtct tctgcttgtt gtcgactc 518

<210> SEQ ID NO 117
<211> LENGTH: 518
<212> TYPE: DNA
<213> ORGANISM: Artificial
<220> FEATURE:
<223> OTHER INFORMATION: Polynucleotide

<400> SEQUENCE: 117
aagaagcacc ggctaactcc gtgccagcag ccccggtaat acggagggtg caagcgttaa 60
tcggaattac tgggcgtaaa gcgcacgcag gcggtttgtt aagtcagatg tgaaatcccc 120
gggctcaacc tgggaactgc atctgatact ggcaagcttg agtctcgtag agggggtag 180 aattccaggt gtagcggtga aatgcgtaga gatctggagg aataccggtg gcgaaggcgg 240
ccccctggac gaagactgac gctcaggtgc gaaagcgtgg ggagcaaaca ggattagata 300
ccctggtagt ccacgccgta aacgatgtcg actagggata acagggtaat gagtcgacaa 360
aatgatacgg cgaccaccga gatctacact ctttccctac acgacgctct tccgatctgc 420
tgtggtcagc ttatcataag atcggaagag cacacgtctg aactccagtc acaatcagtc 480
tcgtatctcg tatgccgtct tctgcttgtt gtcgactc 518

<210> SEQ ID NO 118
<211> LENGTH: 518
<212> TYPE: DNA
<213> ORGANISM: Artificial
<220> FEATURE:
<223> OTHER INFORMATION: Polynucleotide

<400> SEQUENCE: 118
aagaagcacc ggctaactcc gtgccagcag ccgaggtaat acggagggtg caagcgttaa 60
tcggaattac tgggcgtaaa gcgcacgcag gcggtttgtt aagtcagatg tgaaatcccc 120
gggctcaacc tgggaactgc atctgatact ggcaagcttg agtctcgtag agggggtag 180 aattccaggt gtagcggtga aatgcgtaga gatctggagg aataccggtg gcgaaggcgg 240
ccccctggac gaagactgac gctcaggtgc gaaagcgtgg ggagcaaaca ggattagata 300
ccctggtagt ccacgccgta aacgatgtcg actagggata acagggtaat gagtcgacaa 360
aatgatacgg cgaccaccga gatctacact ctttccctac acgacgctct tccgatctca 420
gtggttactc cagcccgaag atcggaagag cacacgtctg aactccagtc acaatcagtc 480
tcgtatctcg tatgccgtct tctgcttgtt gtcgactc 518

<210> SEQ ID NO 119
<211> LENGTH: 518
<212> TYPE: DNA
<213> ORGANISM: Artificial
<220> FEATURE:
<223> OTHER INFORMATION: Polynucleotide

<400> SEQUENCE: 119
aagaagcacc ggctaactcc gtgccagcag ccgtggtaat acggagggtg caagcgttaa 60
tcggaattac tgggcgtaaa gcgcacgcag gcggtttgtt aagtcagatg tgaaatcccc 120
gggctcaacc tgggaactgc atctgatact ggcaagcttg agtctcgtag agggggtag 180 aattccaggt gtagcggtga aatgcgtaga gatctggagg aataccggtg gcgaaggcgg 240

```
ccccctggac gaagactgac gctcaggtgc gaaagcgtgg ggagcaaaca ggattagata    300

ccctggtagt ccacgccgta aacgatgtcg actagggata acagggtaat gagtcgacaa    360

aatgatacgg cgaccaccga gatctacact ctttccctac acgacgctct tccgatctag    420

taattgcact agaggcggag atcggaagag cacacgtctg aactccagtc acaatcagtc    480

tcgtatctcg tatgccgtct tctgcttgtt gtcgactc                            518
```

<210> SEQ ID NO 120
<211> LENGTH: 518
<212> TYPE: DNA
<213> ORGANISM: Artificial
<220> FEATURE:
<223> OTHER INFORMATION: Polynucleotide

<400> SEQUENCE: 120

```
aagaagcacc ggctaactcc gtgccagcag ccggggtaat acggagggtg caagcgttaa     60

tcggaattac tgggcgtaaa gcgcacgcag gcggtttgtt aagtcagatg tgaaatcccc    120

gggctcaacc tgggaactgc atctgatact ggcaagcttg agtctcgtag aggggggtag    180

aattccaggt gtagcggtga aatgcgtaga gatctggagg aataccggtg gcgaaggcgg    240

ccccctggac gaagactgac gctcaggtgc gaaagcgtgg ggagcaaaca ggattagata    300

ccctggtagt ccacgccgta aacgatgtcg actagggata acagggtaat gagtcgacaa    360

aatgatacgg cgaccaccga gatctacact ctttccctac acgacgctct tccgatcttg    420

cgcgggtaag cccatagaag atcggaagag cacacgtctg aactccagtc acaatcagtc    480

tcgtatctcg tatgccgtct tctgcttgtt gtcgactc                            518
```

<210> SEQ ID NO 121
<211> LENGTH: 518
<212> TYPE: DNA
<213> ORGANISM: Artificial
<220> FEATURE:
<223> OTHER INFORMATION: Polynucleotide

<400> SEQUENCE: 121

```
aagaagcacc ggctaactcc gtgccagcag ccgcagtaat acggagggtg caagcgttaa     60

tcggaattac tgggcgtaaa gcgcacgcag gcggtttgtt aagtcagatg tgaaatcccc    120

gggctcaacc tgggaactgc atctgatact ggcaagcttg agtctcgtag aggggggtag    180

aattccaggt gtagcggtga aatgcgtaga gatctggagg aataccggtg gcgaaggcgg    240

ccccctggac gaagactgac gctcaggtgc gaaagcgtgg ggagcaaaca ggattagata    300

ccctggtagt ccacgccgta aacgatgtcg actagggata acagggtaat gagtcgacaa    360

aatgatacgg cgaccaccga gatctacact ctttccctac acgacgctct tccgatcttc    420

acacggagcg tgttatacag atcggaagag cacacgtctg aactccagtc acaatcagtc    480

tcgtatctcg tatgccgtct tctgcttgtt gtcgactc                            518
```

<210> SEQ ID NO 122
<211> LENGTH: 518
<212> TYPE: DNA
<213> ORGANISM: Artificial
<220> FEATURE:
<223> OTHER INFORMATION: Polynucleotide

<400> SEQUENCE: 122

```
aagaagcacc ggctaactcc gtgccagcag ccgctgtaat acggagggtg caagcgttaa     60
```

tcggaattac tgggcgtaaa gcgcacgcag gcggtttgtt aagtcagatg tgaaatcccc 120
gggctcaacc tgggaactgc atctgatact ggcaagcttg agtctcgtag aggggggtag 180
aattccaggt gtagcggtga aatgcgtaga gatctggagg aataccggtg gcgaaggcgg 240 cccccctggac gaagactgac gctcaggtgc gaaagcgtgg ggagcaaaca ggattagata 300
ccctggtagt ccacgccgta aacgatgtcg actagggata acagggtaat gagtcgacaa 360
aatgatacgg cgaccaccga gatctacact ctttccctac acgacgctct tccgatcttg 420
atgatgatca cactacctag atcggaagag cacacgtctg aactccagtc acaatcagtc 480
tcgtatctcg tatgccgtct tctgcttgtt gtcgactc 518

<210> SEQ ID NO 123
<211> LENGTH: 518
<212> TYPE: DNA
<213> ORGANISM: Artificial
<220> FEATURE:
<223> OTHER INFORMATION: Polynucleotide

<400> SEQUENCE: 123
aagaagcacc ggctaactcc gtgccagcag ccgccgtaat acggagggtg caagcgttaa 60
tcggaattac tgggcgtaaa gcgcacgcag gcggtttgtt aagtcagatg tgaaatcccc 120
gggctcaacc tgggaactgc atctgatact ggcaagcttg agtctcgtag aggggggtag 180
aattccaggt gtagcggtga aatgcgtaga gatctggagg aataccggtg gcgaaggcgg 240 cccccctggac gaagactgac gctcaggtgc gaaagcgtgg ggagcaaaca ggattagata 300
ccctggtagt ccacgccgta aacgatgtcg actagggata acagggtaat gagtcgacaa 360
aatgatacgg cgaccaccga gatctacact ctttccctac acgacgctct tccgatctcg 420
gttccaggct aaatgtccag atcggaagag cacacgtctg aactccagtc acaatcagtc 480
tcgtatctcg tatgccgtct tctgcttgtt gtcgactc 518

<210> SEQ ID NO 124
<211> LENGTH: 518
<212> TYPE: DNA
<213> ORGANISM: Artificial
<220> FEATURE:
<223> OTHER INFORMATION: Polynucleotide

<400> SEQUENCE: 124
aagaagcacc ggctaactcc gtgccagcag ccgcgataat acggagggtg caagcgttaa 60
tcggaattac tgggcgtaaa gcgcacgcag gcggtttgtt aagtcagatg tgaaatcccc 120
gggctcaacc tgggaactgc atctgatact ggcaagcttg agtctcgtag aggggggtag 180
aattccaggt gtagcggtga aatgcgtaga gatctggagg aataccggtg gcgaaggcgg 240 cccccctggac gaagactgac gctcaggtgc gaaagcgtgg ggagcaaaca ggattagata 300
ccctggtagt ccacgccgta aacgatgtcg actagggata acagggtaat gagtcgacaa 360
aatgatacgg cgaccaccga gatctacact ctttccctac acgacgctct tccgatctgg 420
agcaggaagg atggcgagag atcggaagag cacacgtctg aactccagtc acaatcagtc 480
tcgtatctcg tatgccgtct tctgcttgtt gtcgactc 518

<210> SEQ ID NO 125
<211> LENGTH: 518
<212> TYPE: DNA
<213> ORGANISM: Artificial
<220> FEATURE:
<223> OTHER INFORMATION: Polynucleotide

<400> SEQUENCE: 125
aagaagcacc ggctaactcc gtgccagcag ccgcgttaat acggagggtg caagcgttaa 60
tcggaattac tgggcgtaaa gcgcacgcag gcggtttgtt aagtcagatg tgaaatcccc 120
gggctcaacc tgggaactgc atctgatact ggcaagcttg agtctcgtag aggggggtag 180
aattccaggt gtagcggtga aatgcgtaga gatctggagg aataccggtg gcgaaggcgg 240
ccccctggac gaagactgac gctcaggtgc gaaagcgtgg ggagcaaaca ggattagata 300
ccctggtagt ccacgccgta aacgatgtcg actagggata acagggtaat gagtcgacaa 360
aatgatacgg cgaccaccga gatctacact ctttccctac acgacgctct tccgatctac 420
gtccctgagc tacgtgtgag atcggaagag cacacgtctg aactccagtc acaatcagtc 480
tcgtatctcg tatgccgtct tctgcttgtt gtcgactc 518

<210> SEQ ID NO 126
<211> LENGTH: 518
<212> TYPE: DNA
<213> ORGANISM: Artificial
<220> FEATURE:
<223> OTHER INFORMATION: Polynucleotide

<400> SEQUENCE: 126
aagaagcacc ggctaactcc gtgccagcag ccgcgctaat acggagggtg caagcgttaa 60
tcggaattac tgggcgtaaa gcgcacgcag gcggtttgtt aagtcagatg tgaaatcccc 120
gggctcaacc tgggaactgc atctgatact ggcaagcttg agtctcgtag aggggggtag 180
aattccaggt gtagcggtga aatgcgtaga gatctggagg aataccggtg gcgaaggcgg 240
ccccctggac gaagactgac gctcaggtgc gaaagcgtgg ggagcaaaca ggattagata 300
ccctggtagt ccacgccgta aacgatgtcg actagggata acagggtaat gagtcgacaa 360
aatgatacgg cgaccaccga gatctacact ctttccctac acgacgctct tccgatctca 420
ttccctcacg gaccggtaag atcggaagag cacacgtctg aactccagtc acaatcagtc 480
tcgtatctcg tatgccgtct tctgcttgtt gtcgactc 518

<210> SEQ ID NO 127
<211> LENGTH: 518
<212> TYPE: DNA
<213> ORGANISM: Artificial
<220> FEATURE:
<223> OTHER INFORMATION: Polynucleotide

<400> SEQUENCE: 127
aagaagcacc ggctaactcc gtgccagcag ccgcggaaat acggagggtg caagcgttaa 60
tcggaattac tgggcgtaaa gcgcacgcag gcggtttgtt aagtcagatg tgaaatcccc 120
gggctcaacc tgggaactgc atctgatact ggcaagcttg agtctcgtag aggggggtag 180
aattccaggt gtagcggtga aatgcgtaga gatctggagg aataccggtg gcgaaggcgg 240
ccccctggac gaagactgac gctcaggtgc gaaagcgtgg ggagcaaaca ggattagata 300
ccctggtagt ccacgccgta aacgatgtcg actagggata acagggtaat gagtcgacaa 360
aatgatacgg cgaccaccga gatctacact ctttccctac acgacgctct tccgatctta 420
ctctcagacg agcggcccag atcggaagag cacacgtctg aactccagtc acaatcagtc 480
tcgtatctcg tatgccgtct tctgcttgtt gtcgactc 518

<210> SEQ ID NO 128

<211> LENGTH: 518
<212> TYPE: DNA
<213> ORGANISM: Artificial
<220> FEATURE:
<223> OTHER INFORMATION: Polynucleotide

<400> SEQUENCE: 128
aagaagcacc ggctaactcc gtgccagcag ccgcgggaat acggagggtg caagcgttaa 60
tcggaattac tgggcgtaaa gcgcacgcag gcggtttgtt aagtcagatg tgaaatcccc 120
gggctcaacc tgggaactgc atctgatact ggcaagcttg agtctcgtag aggggggtag 180
aattccaggt gtagcggtga aatgcgtaga gatctggagg aataccggtg gcgaaggcgg 240
ccccctggac gaagactgac gctcaggtgc gaaagcgtgg ggagcaaaca ggattagata 300
ccctggtagt ccacgccgta aacgatgtcg actagggata acagggtaat gagtcgacaa 360
aatgatacgg cgaccaccga gatctacact ctttccctac acgacgctct tccgatctag 420
gcaggtcaca tcgctgacag atcggaagag cacacgtctg aactccagtc acaatcagtc 480
tcgtatctcg tatgccgtct tctgcttgtt gtcgactc 518

<210> SEQ ID NO 129
<211> LENGTH: 518
<212> TYPE: DNA
<213> ORGANISM: Artificial
<220> FEATURE:
<223> OTHER INFORMATION: Polynucleotide

<400> SEQUENCE: 129
aagaagcacc ggctaactcc gtgccagcag ccgcggcaat acggagggtg caagcgttaa 60
tcggaattac tgggcgtaaa gcgcacgcag gcggtttgtt aagtcagatg tgaaatcccc 120
gggctcaacc tgggaactgc atctgatact ggcaagcttg agtctcgtag aggggggtag 180
aattccaggt gtagcggtga aatgcgtaga gatctggagg aataccggtg gcgaaggcgg 240
ccccctggac gaagactgac gctcaggtgc gaaagcgtgg ggagcaaaca ggattagata 300
ccctggtagt ccacgccgta aacgatgtcg actagggata acagggtaat gagtcgacaa 360
aatgatacgg cgaccaccga gatctacact ctttccctac acgacgctct tccgatctga 420
aacctagctg ttgcaggcag atcggaagag cacacgtctg aactccagtc acaatcagtc 480
tcgtatctcg tatgccgtct tctgcttgtt gtcgactc 518

<210> SEQ ID NO 130
<211> LENGTH: 518
<212> TYPE: DNA
<213> ORGANISM: Artificial
<220> FEATURE:
<223> OTHER INFORMATION: Polynucleotide

<400> SEQUENCE: 130
aagaagcacc ggctaactcc gtgccagcag ccgcggttat acggagggtg caagcgttaa 60
tcggaattac tgggcgtaaa gcgcacgcag gcggtttgtt aagtcagatg tgaaatcccc 120
gggctcaacc tgggaactgc atctgatact ggcaagcttg agtctcgtag aggggggtag 180
aattccaggt gtagcggtga aatgcgtaga gatctggagg aataccggtg gcgaaggcgg 240
ccccctggac gaagactgac gctcaggtgc gaaagcgtgg ggagcaaaca ggattagata 300
ccctggtagt ccacgccgta aacgatgtcg actagggata acagggtaat gagtcgacaa 360
aatgatacgg cgaccaccga gatctacact ctttccctac acgacgctct tccgatcttt 420
agcactacgg ttccgaacag atcggaagag cacacgtctg aactccagtc acaatcagtc 480
tcgtatctcg tatgccgtct tctgcttgtt gtcgactc 518

<210> SEQ ID NO 131
<211> LENGTH: 518
<212> TYPE: DNA
<213> ORGANISM: Artificial
<220> FEATURE:
<223> OTHER INFORMATION: Polynucleotide

<400> SEQUENCE: 131
aagaagcacc ggctaactcc gtgccagcag ccgcggtgat acggagggtg caagcgttaa 60
tcggaattac tgggcgtaaa gcgcacgcag gcggtttgtt aagtcagatg tgaaatcccc 120
gggctcaacc tgggaactgc atctgatact ggcaagcttg agtctcgtag aggggggtag 180
aattccaggt gtagcggtga aatgcgtaga gatctggagg aataccggtg gcgaaggcgg 240
ccccctggac gaagactgac gctcaggtgc gaaagcgtgg ggagcaaaca ggattagata 300
ccctggtagt ccacgccgta aacgatgtcg actagggata acagggtaat gagtcgacaa 360
aatgatacgg cgaccaccga gatctacact ctttccctac acgacgctct tccgatctct 420
gctctctggt ttacaggtag atcggaagag cacacgtctg aactccagtc acaatcagtc 480
tcgtatctcg tatgccgtct tctgcttgtt gtcgactc 518

<210> SEQ ID NO 132
<211> LENGTH: 518
<212> TYPE: DNA
<213> ORGANISM: Artificial
<220> FEATURE:
<223> OTHER INFORMATION: Polynucleotide

<400> SEQUENCE: 132
aagaagcacc ggctaactcc gtgccagcag ccgcggtcat acggagggtg caagcgttaa 60
tcggaattac tgggcgtaaa gcgcacgcag gcggtttgtt aagtcagatg tgaaatcccc 120
gggctcaacc tgggaactgc atctgatact ggcaagcttg agtctcgtag aggggggtag 180
aattccaggt gtagcggtga aatgcgtaga gatctggagg aataccggtg gcgaaggcgg 240
ccccctggac gaagactgac gctcaggtgc gaaagcgtgg ggagcaaaca ggattagata 300
ccctggtagt ccacgccgta aacgatgtcg actagggata acagggtaat gagtcgacaa 360
aatgatacgg cgaccaccga gatctacact ctttccctac acgacgctct tccgatctcc 420
cgtacactac atcgggttag atcggaagag cacacgtctg aactccagtc acaatcagtc 480
tcgtatctcg tatgccgtct tctgcttgtt gtcgactc 518

<210> SEQ ID NO 133
<211> LENGTH: 518
<212> TYPE: DNA
<213> ORGANISM: Artificial
<220> FEATURE:
<223> OTHER INFORMATION: Polynucleotide

<400> SEQUENCE: 133
aagaagcacc ggctaactcc gtgccagcag ccgcggtatt acggagggtg caagcgttaa 60
tcggaattac tgggcgtaaa gcgcacgcag gcggtttgtt aagtcagatg tgaaatcccc 120
gggctcaacc tgggaactgc atctgatact ggcaagcttg agtctcgtag aggggggtag 180
aattccaggt gtagcggtga aatgcgtaga gatctggagg aataccggtg gcgaaggcgg 240
ccccctggac gaagactgac gctcaggtgc gaaagcgtgg ggagcaaaca ggattagata 300
ccctggtagt ccacgccgta aacgatgtcg actagggata acagggtaat gagtcgacaa 360
aatgatacgg cgaccaccga gatctacact ctttccctac acgacgctct tccgatcttt 420
cgctcgactt ccattcgcag atcggaagag cacacgtctg aactccagtc acaatcagtc 480
tcgtatctcg tatgccgtct tctgcttgtt gtcgactc 518

<210> SEQ ID NO 134
<211> LENGTH: 518
<212> TYPE: DNA
<213> ORGANISM: Artificial
<220> FEATURE:
<223> OTHER INFORMATION: Polynucleotide

<400> SEQUENCE: 134
aagaagcacc ggctaactcc gtgccagcag ccgcggtagt acggagggtg caagcgttaa 60
tcggaattac tgggcgtaaa gcgcacgcag gcggtttgtt aagtcagatg tgaaatcccc 120
gggctcaacc tgggaactgc atctgatact ggcaagcttg agtctcgtag agggggggtag 180 aattccaggt gtagcggtga aatgcgtaga gatctggagg aataccggtg gcgaaggcgg 240
ccccctggac gaagactgac gctcaggtgc gaaagcgtgg ggagcaaaca ggattagata 300
ccctggtagt ccacgccgta aacgatgtcg actagggata acagggtaat gagtcgacaa 360
aatgatacgg cgaccaccga gatctacact ctttccctac acgacgctct tccgatctgt 420
atgccttgag gcccatagag atcggaagag cacacgtctg aactccagtc acaatcagtc 480
tcgtatctcg tatgccgtct tctgcttgtt gtcgactc 518

<210> SEQ ID NO 135
<211> LENGTH: 518
<212> TYPE: DNA
<213> ORGANISM: Artificial
<220> FEATURE:
<223> OTHER INFORMATION: Polynucleotide

<400> SEQUENCE: 135
aagaagcacc ggctaactcc gtgccagcag ccgcggtact acggagggtg caagcgttaa 60
tcggaattac tgggcgtaaa gcgcacgcag gcggtttgtt aagtcagatg tgaaatcccc 120
gggctcaacc tgggaactgc atctgatact ggcaagcttg agtctcgtag agggggggtag 180 aattccaggt gtagcggtga aatgcgtaga gatctggagg aataccggtg gcgaaggcgg 240
ccccctggac gaagactgac gctcaggtgc gaaagcgtgg ggagcaaaca ggattagata 300
ccctggtagt ccacgccgta aacgatgtcg actagggata acagggtaat gagtcgacaa 360
aatgatacgg cgaccaccga gatctacact ctttccctac acgacgctct tccgatctgt 420
actttcaagt agattgagag atcggaagag cacacgtctg aactccagtc acaatcagtc 480
tcgtatctcg tatgccgtct tctgcttgtt gtcgactc 518

<210> SEQ ID NO 136
<211> LENGTH: 646
<212> TYPE: DNA
<213> ORGANISM: Artificial
<220> FEATURE:
<223> OTHER INFORMATION: Polynucleotide

<400> SEQUENCE: 136
cggatctctt ggttctcgca tcgatgaaga acgcagcgaa atgcgatacg taatgtgaat 60
tgcagaattc cgtgaatcat cgaatcgcct ttgaacgcac attgcgcccc ttggtattcc 120
agggggcatg cctgtttgag cgtcatttcc ttctcaaaca ttctgtttgg tagtgagtga 180
tactctttgg agttaacttg aaattgctgg ccttttcatt ggatgttttt tttccaaaga 240
gaggtttctc tgcgtgcttg aggtataatg caagtacggt cgttttaggt tttaccaact 300
gcggctaatc ttttttata ctgagcgtat tggaacgtta tcgataagaa gagagcgtct 360
aggcgaacaa tgttcttaaa gtttgacctc aaatcaggta ggagtacccg ctgaacttaa 420
gcatatcaat aagcggagga aaagaaacca accgggattg tagggataac agggtaatga 480
gtcgacaaaa tgatacggcg accaccgaga tctacactct ttccctacac gacgctcttc 540
cgatcttata tcatcactat ggtaacagat cggaagagca cacgtctgaa ctccagtcac 600
aatcagtctc gtatctcgta tgccgtcttc tgcttgttgt cgactc 646

<210> SEQ ID NO 137
<211> LENGTH: 646
<212> TYPE: DNA
<213> ORGANISM: Artificial
<220> FEATURE:
<223> OTHER INFORMATION: Polynucleotide

<400> SEQUENCE: 137
cggatctctt ggttctcgca tcgatgaaaa acgcagcgaa atgcgatacg taatgtgaat 60
tgcagaattc cgtgaatcat cgaatcgcct ttgaacgcac attgcgcccc ttggtattcc 120
agggggcatg cctgtttgag cgtcatttcc ttctcaaaca ttctgtttgg tagtgagtga 180
tactctttgg agttaacttg aaattgctgg ccttttcatt ggatgttttt tttccaaaga 240
gaggtttctc tgcgtgcttg aggtataatg caagtacggt cgttttaggt tttaccaact 300
gcggctaatc ttttttata ctgagcgtat tggaacgtta tcgataagaa gagagcgtct 360
aggcgaacaa tgttcttaaa gtttgacctc aaatcaggta ggagtacccg ctgaacttaa 420
gcatatcaat aagcggagga aaagaaacca accgggattg tagggataac agggtaatga 480
gtcgacaaaa tgatacggcg accaccgaga tctacactct ttccctacac gacgctcttc 540
cgatctggtt cataatcgga tacgagagat cggaagagca cacgtctgaa ctccagtcac 600
aatcagtctc gtatctcgta tgccgtcttc tgcttgttgt cgactc 646

<210> SEQ ID NO 138
<211> LENGTH: 646
<212> TYPE: DNA
<213> ORGANISM: Artificial
<220> FEATURE:
<223> OTHER INFORMATION: Polynucleotide

<400> SEQUENCE: 138
cggatctctt ggttctcgca tcgatgaata acgcagcgaa atgcgatacg taatgtgaat 60
tgcagaattc cgtgaatcat cgaatcgcct ttgaacgcac attgcgcccc ttggtattcc 120
agggggcatg cctgtttgag cgtcatttcc ttctcaaaca ttctgtttgg tagtgagtga 180
tactctttgg agttaacttg aaattgctgg ccttttcatt ggatgttttt tttccaaaga 240
gaggtttctc tgcgtgcttg aggtataatg caagtacggt cgttttaggt tttaccaact 300
gcggctaatc ttttttata ctgagcgtat tggaacgtta tcgataagaa gagagcgtct 360
aggcgaacaa tgttcttaaa gtttgacctc aaatcaggta ggagtacccg ctgaacttaa 420
gcatatcaat aagcggagga aaagaaacca accgggattg tagggataac agggtaatga 480
gtcgacaaaa tgatacggcg accaccgaga tctacactct ttccctacac gacgctcttc 540
cgatctactc atggtaaacc aggctgagat cggaagagca cacgtctgaa ctccagtcac 600
aatcagtctc gtatctcgta tgccgtcttc tgcttgttgt cgactc 646

<210> SEQ ID NO 139
<211> LENGTH: 646
<212> TYPE: DNA
<213> ORGANISM: Artificial
<220> FEATURE:
<223> OTHER INFORMATION: Polynucleotide

<400> SEQUENCE: 139
cggatctctt ggttctcgca tcgatgaaca acgcagcgaa atgcgatacg taatgtgaat 60
tgcagaattc cgtgaatcat cgaatcgcct ttgaacgcac attgcgcccc ttggtattcc 120
agggggcatg cctgtttgag cgtcatttcc ttctcaaaca ttctgtttgg tagtgagtga 180
tactctttgg agttaacttg aaattgctgg ccttttcatt ggatgttttt tttccaaaga 240
gaggtttctc tgcgtgcttg aggtataatg caagtacggt cgttttaggt tttaccaact 300
gcggctaatc ttttttata ctgagcgtat tggaacgtta tcgataagaa gagagcgtct 360
aggcgaacaa tgttcttaaa gtttgacctc aaatcaggta ggagtacccg ctgaacttaa 420
gcatatcaat aagcggagga aaagaaacca accgggattg tagggataac agggtaatga 480
gtcgacaaaa tgatacggcg accaccgaga tctacactct ttccctacac gacgctcttc 540
cgatctctga aacctttcac tggcccagat cggaagagca cacgtctgaa ctccagtcac 600
aatcagtctc gtatctcgta tgccgtcttc tgcttgttgt cgactc 646

<210> SEQ ID NO 140
<211> LENGTH: 646
<212> TYPE: DNA
<213> ORGANISM: Artificial
<220> FEATURE:
<223> OTHER INFORMATION: Polynucleotide

<400> SEQUENCE: 140
cggatctctt ggttctcgca tcgatgaagt acgcagcgaa atgcgatacg taatgtgaat 60
tgcagaattc cgtgaatcat cgaatcgcct ttgaacgcac attgcgcccc ttggtattcc 120
agggggcatg cctgtttgag cgtcatttcc ttctcaaaca ttctgtttgg tagtgagtga 180
tactctttgg agttaacttg aaattgctgg ccttttcatt ggatgttttt tttccaaaga 240
gaggtttctc tgcgtgcttg aggtataatg caagtacggt cgttttaggt tttaccaact 300
gcggctaatc ttttttata ctgagcgtat tggaacgtta tcgataagaa gagagcgtct 360
aggcgaacaa tgttcttaaa gtttgacctc aaatcaggta ggagtacccg ctgaacttaa 420
gcatatcaat aagcggagga aaagaaacca accgggattg tagggataac agggtaatga 480
gtcgacaaaa tgatacggcg accaccgaga tctacactct ttccctacac gacgctcttc 540
cgatctttcc gagccctgca ctcttgagat cggaagagca cacgtctgaa ctccagtcac 600
aatcagtctc gtatctcgta tgccgtcttc tgcttgttgt cgactc 646

<210> SEQ ID NO 141
<211> LENGTH: 646
<212> TYPE: DNA
<213> ORGANISM: Artificial
<220> FEATURE:
<223> OTHER INFORMATION: Polynucleotide

<400> SEQUENCE: 141
cggatctctt ggttctcgca tcgatgaagg acgcagcgaa atgcgatacg taatgtgaat 60
tgcagaattc cgtgaatcat cgaatcgcct ttgaacgcac attgcgcccc ttggtattcc 120

```
agggggcatg cctgtttgag cgtcatttcc ttctcaaaca ttctgtttgg tagtgagtga    180

tactctttgg agttaacttg aaattgctgg ccttttcatt ggatgttttt tttccaaaga    240

gaggtttctc tgcgtgcttg aggtataatg caagtacggt cgttttaggt tttaccaact    300

gcggctaatc ttttttata ctgagcgtat tggaacgtta tcgataagaa gagagcgtct    360

aggcgaacaa tgttcttaaa gtttgacctc aaatcaggta ggagtacccg ctgaacttaa    420

gcatatcaat aagcggagga aaagaaacca accgggattg tagggataac agggtaatga    480

gtcgacaaaa tgatacggcg accaccgaga tctacactct ttccctacac gacgctcttc    540

cgatctttca ttcctggtga gaagatagat cggaagagca cacgtctgaa ctccagtcac    600

aatcagtctc gtatctcgta tgccgtcttc tgcttgttgt cgactc                  646
```

<210> SEQ ID NO 142
<211> LENGTH: 646
<212> TYPE: DNA
<213> ORGANISM: Artificial
<220> FEATURE:
<223> OTHER INFORMATION: Polynucleotide

<400> SEQUENCE: 142

```
cggatctctt ggttctcgca tcgatgaagc acgcagcgaa atgcgatacg taatgtgaat     60

tgcagaattc cgtgaatcat cgaatcgcct ttgaacgcac attgcgcccc ttggtattcc    120

agggggcatg cctgtttgag cgtcatttcc ttctcaaaca ttctgtttgg tagtgagtga    180

tactctttgg agttaacttg aaattgctgg ccttttcatt ggatgttttt tttccaaaga    240

gaggtttctc tgcgtgcttg aggtataatg caagtacggt cgttttaggt tttaccaact    300

gcggctaatc ttttttata ctgagcgtat tggaacgtta tcgataagaa gagagcgtct    360

aggcgaacaa tgttcttaaa gtttgacctc aaatcaggta ggagtacccg ctgaacttaa    420

gcatatcaat aagcggagga aaagaaacca accgggattg tagggataac agggtaatga    480

gtcgacaaaa tgatacggcg accaccgaga tctacactct ttccctacac gacgctcttc    540

cgatctggta ctgattcgaa accagtagat cggaagagca cacgtctgaa ctccagtcac    600

aatcagtctc gtatctcgta tgccgtcttc tgcttgttgt cgactc                  646
```

<210> SEQ ID NO 143
<211> LENGTH: 646
<212> TYPE: DNA
<213> ORGANISM: Artificial
<220> FEATURE:
<223> OTHER INFORMATION: Polynucleotide

<400> SEQUENCE: 143

```
cggatctctt ggttctcgca tcgatgaaga tcgcagcgaa atgcgatacg taatgtgaat     60

tgcagaattc cgtgaatcat cgaatcgcct ttgaacgcac attgcgcccc ttggtattcc    120

agggggcatg cctgtttgag cgtcatttcc ttctcaaaca ttctgtttgg tagtgagtga    180

tactctttgg agttaacttg aaattgctgg ccttttcatt ggatgttttt tttccaaaga    240

gaggtttctc tgcgtgcttg aggtataatg caagtacggt cgttttaggt tttaccaact    300

gcggctaatc ttttttata ctgagcgtat tggaacgtta tcgataagaa gagagcgtct    360

aggcgaacaa tgttcttaaa gtttgacctc aaatcaggta ggagtacccg ctgaacttaa    420

gcatatcaat aagcggagga aaagaaacca accgggattg tagggataac agggtaatga    480

gtcgacaaaa tgatacggcg accaccgaga tctacactct ttccctacac gacgctcttc    540
```

cgatctaagc atagccggcc cgaagaagat cggaagagca cacgtctgaa ctccagtcac 600
aatcagtctc gtatctcgta tgccgtcttc tgcttgttgt cgactc 646

<210> SEQ ID NO 144
<211> LENGTH: 646
<212> TYPE: DNA
<213> ORGANISM: Artificial
<220> FEATURE:
<223> OTHER INFORMATION: Polynucleotide

<400> SEQUENCE: 144
cggatctctt ggttctcgca tcgatgaaga gcgcagcgaa atgcgatacg taatgtgaat 60
tgcagaattc cgtgaatcat cgaatcgcct ttgaacgcac attgcgcccc ttggtattcc 120
agggggcatg cctgtttgag cgtcatttcc ttctcaaaca ttctgtttgg tagtgagtga 180
tactctttgg agttaacttg aaattgctgg ccttttcatt ggatgttttt tttccaaaga 240
gaggtttctc tgcgtgcttg aggtataatg caagtacggt cgttttaggt tttaccaact 300
gcggctaatc ttttttata ctgagcgtat tggaacgtta tcgataagaa gagagcgtct 360
aggcgaacaa tgttcttaaa gtttgacctc aaatcaggta ggagtacccg ctgaacttaa 420
gcatatcaat aagcggagga aaagaaacca accgggattg tagggataac agggtaatga 480
gtcgacaaaa tgatacggcg accaccgaga tctacactct ttccctacac gacgctcttc 540
cgatctgtgc attagtggct tcgacaagat cggaagagca cacgtctgaa ctccagtcac 600
aatcagtctc gtatctcgta tgccgtcttc tgcttgttgt cgactc 646

<210> SEQ ID NO 145
<211> LENGTH: 646
<212> TYPE: DNA
<213> ORGANISM: Artificial
<220> FEATURE:
<223> OTHER INFORMATION: Polynucleotide

<400> SEQUENCE: 145
cggatctctt ggttctcgca tcgatgaaga ccgcagcgaa atgcgatacg taatgtgaat 60
tgcagaattc cgtgaatcat cgaatcgcct ttgaacgcac attgcgcccc ttggtattcc 120
agggggcatg cctgtttgag cgtcatttcc ttctcaaaca ttctgtttgg tagtgagtga 180
tactctttgg agttaacttg aaattgctgg ccttttcatt ggatgttttt tttccaaaga 240
gaggtttctc tgcgtgcttg aggtataatg caagtacggt cgttttaggt tttaccaact 300
gcggctaatc ttttttata ctgagcgtat tggaacgtta tcgataagaa gagagcgtct 360
aggcgaacaa tgttcttaaa gtttgacctc aaatcaggta ggagtacccg ctgaacttaa 420
gcatatcaat aagcggagga aaagaaacca accgggattg tagggataac agggtaatga 480
gtcgacaaaa tgatacggcg accaccgaga tctacactct ttccctacac gacgctcttc 540
cgatctatac agtcctgctc ccgtgcagat cggaagagca cacgtctgaa ctccagtcac 600
aatcagtctc gtatctcgta tgccgtcttc tgcttgttgt cgactc 646

<210> SEQ ID NO 146
<211> LENGTH: 646
<212> TYPE: DNA
<213> ORGANISM: Artificial
<220> FEATURE:
<223> OTHER INFORMATION: Polynucleotide

<400> SEQUENCE: 146
cggatctctt ggttctcgca tcgatgaaga aagcagcgaa atgcgatacg taatgtgaat 60
tgcagaattc cgtgaatcat cgaatcgcct ttgaacgcac attgcgcccc ttggtattcc 120
agggggcatg cctgtttgag cgtcatttcc ttctcaaaca ttctgtttgg tagtgagtga 180
tactctttgg agttaacttg aaattgctgg ccttttcatt ggatgttttt tttccaaaga 240
gaggtttctc tgcgtgcttg aggtataatg caagtacggt cgttttaggt tttaccaact 300
gcggctaatc tttttttata ctgagcgtat tggaacgtta tcgataagaa gagagcgtct 360
aggcgaacaa tgttcttaaa gtttgacctc aaatcaggta ggagtacccg ctgaacttaa 420
gcatatcaat aagcggagga aaagaaacca accgggattg tagggataac agggtaatga 480
gtcgacaaaa tgatacggcg accaccgaga tctacactct ttccctacac gacgctcttc 540
cgatcttccc aagtgggatc agtttaagat cggaagagca cacgtctgaa ctccagtcac 600
aatcagtctc gtatctcgta tgccgtcttc tgcttgttgt cgactc 646

<210> SEQ ID NO 147
<211> LENGTH: 646
<212> TYPE: DNA
<213> ORGANISM: Artificial
<220> FEATURE:
<223> OTHER INFORMATION: Polynucleotide

<400> SEQUENCE: 147
cggatctctt ggttctcgca tcgatgaaga atgcagcgaa atgcgatacg taatgtgaat 60
tgcagaattc cgtgaatcat cgaatcgcct ttgaacgcac attgcgcccc ttggtattcc 120
agggggcatg cctgtttgag cgtcatttcc ttctcaaaca ttctgtttgg tagtgagtga 180
tactctttgg agttaacttg aaattgctgg ccttttcatt ggatgttttt tttccaaaga 240
gaggtttctc tgcgtgcttg aggtataatg caagtacggt cgttttaggt tttaccaact 300
gcggctaatc tttttttata ctgagcgtat tggaacgtta tcgataagaa gagagcgtct 360
aggcgaacaa tgttcttaaa gtttgacctc aaatcaggta ggagtacccg ctgaacttaa 420
gcatatcaat aagcggagga aaagaaacca accgggattg tagggataac agggtaatga 480
gtcgacaaaa tgatacggcg accaccgaga tctacactct ttccctacac gacgctcttc 540
cgatcttcaa cacccagtgg acgcatagat cggaagagca cacgtctgaa ctccagtcac 600
aatcagtctc gtatctcgta tgccgtcttc tgcttgttgt cgactc 646

<210> SEQ ID NO 148
<211> LENGTH: 646
<212> TYPE: DNA
<213> ORGANISM: Artificial
<220> FEATURE:
<223> OTHER INFORMATION: Polynucleotide

<400> SEQUENCE: 148
cggatctctt ggttctcgca tcgatgaaga aggcagcgaa atgcgatacg taatgtgaat 60
tgcagaattc cgtgaatcat cgaatcgcct ttgaacgcac attgcgcccc ttggtattcc 120
agggggcatg cctgtttgag cgtcatttcc ttctcaaaca ttctgtttgg tagtgagtga 180
tactctttgg agttaacttg aaattgctgg ccttttcatt ggatgttttt tttccaaaga 240
gaggtttctc tgcgtgcttg aggtataatg caagtacggt cgttttaggt tttaccaact 300
gcggctaatc tttttttata ctgagcgtat tggaacgtta tcgataagaa gagagcgtct 360
aggcgaacaa tgttcttaaa gtttgacctc aaatcaggta ggagtacccg ctgaacttaa 420
gcatatcaat aagcggagga aaagaaacca accgggattg tagggataac agggtaatga 480

-continued

```
gtcgacaaaa tgatacggcg accaccgaga tctacactct ttccctacac gacgctcttc    540

cgatctacta ggaagtccgg acctatagat cggaagagca cacgtctgaa ctccagtcac    600

aatcagtctc gtatctcgta tgccgtcttc tgcttgttgt cgactc                   646


<210> SEQ ID NO 149
<211> LENGTH: 646
<212> TYPE: DNA
<213> ORGANISM: Artificial
<220> FEATURE:
<223> OTHER INFORMATION: Polynucleotide

<400> SEQUENCE: 149

cggatctctt ggttctcgca tcgatgaaga acacagcgaa atgcgatacg taatgtgaat     60

tgcagaattc cgtgaatcat cgaatcgcct ttgaacgcac attgcgcccc ttggtattcc    120

agggggcatg cctgtttgag cgtcatttcc ttctcaaaca ttctgtttgg tagtgagtga    180

tactctttgg agttaacttg aaattgctgg ccttttcatt ggatgttttt tttccaaaga    240

gaggtttctc tgcgtgcttg aggtataatg caagtacggt cgttttaggt tttaccaact    300

gcggctaatc tttttttata ctgagcgtat tggaacgtta tcgataagaa gagagcgtct    360

aggcgaacaa tgttcttaaa gtttgacctc aaatcaggta ggagtacccg ctgaacttaa    420

gcatatcaat aagcggagga aaagaaacca accgggattg tagggataac agggtaatga    480

gtcgacaaaa tgatacggcg accaccgaga tctacactct ttccctacac gacgctcttc    540

cgatcttcct gggagggagg tctcgtagat cggaagagca cacgtctgaa ctccagtcac    600

aatcagtctc gtatctcgta tgccgtcttc tgcttgttgt cgactc                   646


<210> SEQ ID NO 150
<211> LENGTH: 646
<212> TYPE: DNA
<213> ORGANISM: Artificial
<220> FEATURE:
<223> OTHER INFORMATION: Polynucleotide

<400> SEQUENCE: 150

cggatctctt ggttctcgca tcgatgaaga actcagcgaa atgcgatacg taatgtgaat     60

tgcagaattc cgtgaatcat cgaatcgcct ttgaacgcac attgcgcccc ttggtattcc    120

agggggcatg cctgtttgag cgtcatttcc ttctcaaaca ttctgtttgg tagtgagtga    180

tactctttgg agttaacttg aaattgctgg ccttttcatt ggatgttttt tttccaaaga    240

gaggtttctc tgcgtgcttg aggtataatg caagtacggt cgttttaggt tttaccaact    300

gcggctaatc tttttttata ctgagcgtat tggaacgtta tcgataagaa gagagcgtct    360

aggcgaacaa tgttcttaaa gtttgacctc aaatcaggta ggagtacccg ctgaacttaa    420

gcatatcaat aagcggagga aaagaaacca accgggattg tagggataac agggtaatga    480

gtcgacaaaa tgatacggcg accaccgaga tctacactct ttccctacac gacgctcttc    540

cgatctgaag aatataccta ccggaaagat cggaagagca cacgtctgaa ctccagtcac    600

aatcagtctc gtatctcgta tgccgtcttc tgcttgttgt cgactc                   646


<210> SEQ ID NO 151
<211> LENGTH: 646
<212> TYPE: DNA
<213> ORGANISM: Artificial
<220> FEATURE:
<223> OTHER INFORMATION: Polynucleotide

<400> SEQUENCE: 151
```

```
cggatctctt ggttctcgca tcgatgaaga acccagcgaa atgcgatacg taatgtgaat     60
tgcagaattc cgtgaatcat cgaatcgcct ttgaacgcac attgcgcccc ttggtattcc    120
agggggcatg cctgtttgag cgtcatttcc ttctcaaaca ttctgtttgg tagtgagtga    180
tactctttgg agttaacttg aaattgctgg ccttttcatt ggatgttttt tttccaaaga    240
gaggtttctc tgcgtgcttg aggtataatg caagtacggt cgttttaggt tttaccaact    300
gcggctaatc tttttttata ctgagcgtat tggaacgtta tcgataagaa gagagcgtct    360
aggcgaacaa tgttcttaaa gtttgacctc aaatcaggta ggagtacccg ctgaacttaa    420
gcatatcaat aagcggagga aaagaaacca accgggattg tagggataac agggtaatga    480
gtcgacaaaa tgatacggcg accaccgaga tctacactct ttccctacac gacgctcttc    540
cgatctcggg cagagcgctt acgtacagat cggaagagca cacgtctgaa ctccagtcac    600
aatcagtctc gtatctcgta tgccgtcttc tgcttgttgt cgactc                   646
```

<210> SEQ ID NO 152
<211> LENGTH: 646
<212> TYPE: DNA
<213> ORGANISM: Artificial
<220> FEATURE:
<223> OTHER INFORMATION: Polynucleotide

<400> SEQUENCE: 152

```
cggatctctt ggttctcgca tcgatgaaga acgaagcgaa atgcgatacg taatgtgaat     60
tgcagaattc cgtgaatcat cgaatcgcct ttgaacgcac attgcgcccc ttggtattcc    120
agggggcatg cctgtttgag cgtcatttcc ttctcaaaca ttctgtttgg tagtgagtga    180
tactctttgg agttaacttg aaattgctgg ccttttcatt ggatgttttt tttccaaaga    240
gaggtttctc tgcgtgcttg aggtataatg caagtacggt cgttttaggt tttaccaact    300
gcggctaatc tttttttata ctgagcgtat tggaacgtta tcgataagaa gagagcgtct    360
aggcgaacaa tgttcttaaa gtttgacctc aaatcaggta ggagtacccg ctgaacttaa    420
gcatatcaat aagcggagga aaagaaacca accgggattg tagggataac agggtaatga    480
gtcgacaaaa tgatacggcg accaccgaga tctacactct ttccctacac gacgctcttc    540
cgatctcgtg gaatatttgg gttcggagat cggaagagca cacgtctgaa ctccagtcac    600
aatcagtctc gtatctcgta tgccgtcttc tgcttgttgt cgactc                   646
```

<210> SEQ ID NO 153
<211> LENGTH: 646
<212> TYPE: DNA
<213> ORGANISM: Artificial
<220> FEATURE:
<223> OTHER INFORMATION: Polynucleotide

<400> SEQUENCE: 153

```
cggatctctt ggttctcgca tcgatgaaga acgtagcgaa atgcgatacg taatgtgaat     60
tgcagaattc cgtgaatcat cgaatcgcct ttgaacgcac attgcgcccc ttggtattcc    120
agggggcatg cctgtttgag cgtcatttcc ttctcaaaca ttctgtttgg tagtgagtga    180
tactctttgg agttaacttg aaattgctgg ccttttcatt ggatgttttt tttccaaaga    240
gaggtttctc tgcgtgcttg aggtataatg caagtacggt cgttttaggt tttaccaact    300
gcggctaatc tttttttata ctgagcgtat tggaacgtta tcgataagaa gagagcgtct    360
aggcgaacaa tgttcttaaa gtttgacctc aaatcaggta ggagtacccg ctgaacttaa    420
```

gcatatcaat aagcggagga aaagaaacca accgggattg tagggataac agggtaatga 480
gtcgacaaaa tgatacggcg accaccgaga tctacactct ttccctacac gacgctcttc 540
cgatctgcac ccgacaaggg ttcgggagat cggaagagca cacgtctgaa ctccagtcac 600
aatcagtctc gtatctcgta tgccgtcttc tgcttgttgt cgactc 646

<210> SEQ ID NO 154
<211> LENGTH: 646
<212> TYPE: DNA
<213> ORGANISM: Artificial
<220> FEATURE:
<223> OTHER INFORMATION: Polynucleotide

<400> SEQUENCE: 154
cggatctctt ggttctcgca tcgatgaaga acggagcgaa atgcgatacg taatgtgaat 60
tgcagaattc cgtgaatcat cgaatcgcct ttgaacgcac attgcgcccc ttggtattcc 120
agggggcatg cctgtttgag cgtcatttcc ttctcaaaca ttctgtttgg tagtgagtga 180
tactctttgg agttaacttg aaattgctgg ccttttcatt ggatgttttt tttccaaaga 240
gaggtttctc tgcgtgcttg aggtataatg caagtacggt cgttttaggt tttaccaact 300
gcggctaatc ttttttttata ctgagcgtat tggaacgtta tcgataagaa gagagcgtct 360
aggcgaacaa tgttcttaaa gtttgacctc aaatcaggta ggagtacccg ctgaacttaa 420
gcatatcaat aagcggagga aaagaaacca accgggattg tagggataac agggtaatga 480
gtcgacaaaa tgatacggcg accaccgaga tctacactct ttccctacac gacgctcttc 540
cgatctagag cgttcgtaat accggaagat cggaagagca cacgtctgaa ctccagtcac 600
aatcagtctc gtatctcgta tgccgtcttc tgcttgttgt cgactc 646

<210> SEQ ID NO 155
<211> LENGTH: 646
<212> TYPE: DNA
<213> ORGANISM: Artificial
<220> FEATURE:
<223> OTHER INFORMATION: Polynucleotide

<400> SEQUENCE: 155
cggatctctt ggttctcgca tcgatgaaga acgctgcgaa atgcgatacg taatgtgaat 60
tgcagaattc cgtgaatcat cgaatcgcct ttgaacgcac attgcgcccc ttggtattcc 120
agggggcatg cctgtttgag cgtcatttcc ttctcaaaca ttctgtttgg tagtgagtga 180
tactctttgg agttaacttg aaattgctgg ccttttcatt ggatgttttt tttccaaaga 240
gaggtttctc tgcgtgcttg aggtataatg caagtacggt cgttttaggt tttaccaact 300
gcggctaatc ttttttttata ctgagcgtat tggaacgtta tcgataagaa gagagcgtct 360
aggcgaacaa tgttcttaaa gtttgacctc aaatcaggta ggagtacccg ctgaacttaa 420
gcatatcaat aagcggagga aaagaaacca accgggattg tagggataac agggtaatga 480
gtcgacaaaa tgatacggcg accaccgaga tctacactct ttccctacac gacgctcttc 540
cgatcttacg cctgtcatca tgactaagat cggaagagca cacgtctgaa ctccagtcac 600
aatcagtctc gtatctcgta tgccgtcttc tgcttgttgt cgactc 646

<210> SEQ ID NO 156
<211> LENGTH: 646
<212> TYPE: DNA
<213> ORGANISM: Artificial
<220> FEATURE:
<223> OTHER INFORMATION: Polynucleotide

<400> SEQUENCE: 156
cggatctctt ggttctcgca tcgatgaaga acgcggcgaa atgcgatacg taatgtgaat 60
tgcagaattc cgtgaatcat cgaatcgcct ttgaacgcac attgcgcccc ttggtattcc 120
agggggcatg cctgtttgag cgtcatttcc ttctcaaaca ttctgtttgg tagtgagtga 180
tactctttgg agttaacttg aaattgctgg ccttttcatt ggatgttttt tttccaaaga 240
gaggtttctc tgcgtgcttg aggtataatg caagtacggt cgttttaggt tttaccaact 300
gcggctaatc tttttttata ctgagcgtat tggaacgtta tcgataagaa gagagcgtct 360
aggcgaacaa tgttcttaaa gtttgacctc aaatcaggta ggagtacccg ctgaacttaa 420
gcatatcaat aagcggagga aaagaaacca accgggattg tagggataac agggtaatga 480
gtcgacaaaa tgatacggcg accaccgaga tctacactct ttccctacac gacgctcttc 540
cgatctacgc atcacgccta cgacggagat cggaagagca cacgtctgaa ctccagtcac 600
aatcagtctc gtatctcgta tgccgtcttc tgcttgttgt cgactc 646

<210> SEQ ID NO 157
<211> LENGTH: 646
<212> TYPE: DNA
<213> ORGANISM: Artificial
<220> FEATURE:
<223> OTHER INFORMATION: Polynucleotide

<400> SEQUENCE: 157
cggatctctt ggttctcgca tcgatgaaga acgccgcgaa atgcgatacg taatgtgaat 60
tgcagaattc cgtgaatcat cgaatcgcct ttgaacgcac attgcgcccc ttggtattcc 120
agggggcatg cctgtttgag cgtcatttcc ttctcaaaca ttctgtttgg tagtgagtga 180
tactctttgg agttaacttg aaattgctgg ccttttcatt ggatgttttt tttccaaaga 240
gaggtttctc tgcgtgcttg aggtataatg caagtacggt cgttttaggt tttaccaact 300
gcggctaatc tttttttata ctgagcgtat tggaacgtta tcgataagaa gagagcgtct 360
aggcgaacaa tgttcttaaa gtttgacctc aaatcaggta ggagtacccg ctgaacttaa 420
gcatatcaat aagcggagga aaagaaacca accgggattg tagggataac agggtaatga 480
gtcgacaaaa tgatacggcg accaccgaga tctacactct ttccctacac gacgctcttc 540
cgatctgagg gaggatgacc gtaggtagat cggaagagca cacgtctgaa ctccagtcac 600
aatcagtctc gtatctcgta tgccgtcttc tgcttgttgt cgactc 646

<210> SEQ ID NO 158
<211> LENGTH: 646
<212> TYPE: DNA
<213> ORGANISM: Artificial
<220> FEATURE:
<223> OTHER INFORMATION: Polynucleotide

<400> SEQUENCE: 158
cggatctctt ggttctcgca tcgatgaaga acgcaacgaa atgcgatacg taatgtgaat 60
tgcagaattc cgtgaatcat cgaatcgcct ttgaacgcac attgcgcccc ttggtattcc 120
agggggcatg cctgtttgag cgtcatttcc ttctcaaaca ttctgtttgg tagtgagtga 180
tactctttgg agttaacttg aaattgctgg ccttttcatt ggatgttttt tttccaaaga 240
gaggtttctc tgcgtgcttg aggtataatg caagtacggt cgttttaggt tttaccaact 300
gcggctaatc tttttttata ctgagcgtat tggaacgtta tcgataagaa gagagcgtct 360

```
aggcgaacaa tgttcttaaa gtttgacctc aaatcaggta ggagtacccg ctgaacttaa    420

gcatatcaat aagcggagga aaagaaacca accgggattg tagggataac agggtaatga    480

gtcgacaaaa tgatacggcg accaccgaga tctacactct ttccctacac gacgctcttc    540

cgatctcgat aatatcatcc cggactagat cggaagagca cacgtctgaa ctccagtcac    600

aatcagtctc gtatctcgta tgccgtcttc tgcttgttgt cgactc                  646
```

```
<210> SEQ ID NO 159
<211> LENGTH: 646
<212> TYPE: DNA
<213> ORGANISM: Artificial
<220> FEATURE:
<223> OTHER INFORMATION: Polynucleotide

<400> SEQUENCE: 159

cggatctctt ggttctcgca tcgatgaaga acgcatcgaa atgcgatacg taatgtgaat     60

tgcagaattc cgtgaatcat cgaatcgcct ttgaacgcac attgcgcccc ttggtattcc    120

agggggcatg cctgtttgag cgtcatttcc ttctcaaaca ttctgtttgg tagtgagtga    180

tactctttgg agttaacttg aaattgctgg ccttttcatt ggatgttttt tttccaaaga    240

gaggtttctc tgcgtgcttg aggtataatg caagtacggt cgttttaggt tttaccaact    300

gcggctaatc tttttttata ctgagcgtat tggaacgtta tcgataagaa gagagcgtct    360

aggcgaacaa tgttcttaaa gtttgacctc aaatcaggta ggagtacccg ctgaacttaa    420

gcatatcaat aagcggagga aaagaaacca accgggattg tagggataac agggtaatga    480

gtcgacaaaa tgatacggcg accaccgaga tctacactct ttccctacac gacgctcttc    540

cgatctatga cgatcacttt ctagctagat cggaagagca cacgtctgaa ctccagtcac    600

aatcagtctc gtatctcgta tgccgtcttc tgcttgttgt cgactc                  646
```

```
<210> SEQ ID NO 160
<211> LENGTH: 646
<212> TYPE: DNA
<213> ORGANISM: Artificial
<220> FEATURE:
<223> OTHER INFORMATION: Polynucleotide

<400> SEQUENCE: 160

cggatctctt ggttctcgca tcgatgaaga acgcaccgaa atgcgatacg taatgtgaat     60

tgcagaattc cgtgaatcat cgaatcgcct ttgaacgcac attgcgcccc ttggtattcc    120

agggggcatg cctgtttgag cgtcatttcc ttctcaaaca ttctgtttgg tagtgagtga    180

tactctttgg agttaacttg aaattgctgg ccttttcatt ggatgttttt tttccaaaga    240

gaggtttctc tgcgtgcttg aggtataatg caagtacggt cgttttaggt tttaccaact    300

gcggctaatc tttttttata ctgagcgtat tggaacgtta tcgataagaa gagagcgtct    360

aggcgaacaa tgttcttaaa gtttgacctc aaatcaggta ggagtacccg ctgaacttaa    420

gcatatcaat aagcggagga aaagaaacca accgggattg tagggataac agggtaatga    480

gtcgacaaaa tgatacggcg accaccgaga tctacactct ttccctacac gacgctcttc    540

cgatctagta ctcggtccct tcctagagat cggaagagca cacgtctgaa ctccagtcac    600

aatcagtctc gtatctcgta tgccgtcttc tgcttgttgt cgactc                  646
```

```
<210> SEQ ID NO 161
<211> LENGTH: 646
<212> TYPE: DNA
<213> ORGANISM: Artificial
```

<220> FEATURE:
<223> OTHER INFORMATION: Polynucleotide

<400> SEQUENCE: 161
cggatctctt ggttctcgca tcgatgaaga acgcagagaa atgcgatacg taatgtgaat 60
tgcagaattc cgtgaatcat cgaatcgcct ttgaacgcac attgcgcccc ttggtattcc 120
agggggcatg cctgtttgag cgtcatttcc ttctcaaaca ttctgtttgg tagtgagtga 180
tactctttgg agttaacttg aaattgctgg ccttttcatt ggatgttttt tttccaaaga 240
gaggtttctc tgcgtgcttg aggtataatg caagtacggt cgttttaggt tttaccaact 300
gcggctaatc tttttttata ctgagcgtat tggaacgtta tcgataagaa gagagcgtct 360
aggcgaacaa tgttcttaaa gtttgacctc aaatcaggta ggagtacccg ctgaacttaa 420
gcatatcaat aagcggagga aaagaaacca accgggattg tagggataac agggtaatga 480
gtcgacaaaa tgatacggcg accaccgaga tctacactct ttccctacac gacgctcttc 540
cgatctattc ataccagata tccctcagat cggaagagca cacgtctgaa ctccagtcac 600
aatcagtctc gtatctcgta tgccgtcttc tgcttgttgt cgactc 646

<210> SEQ ID NO 162
<211> LENGTH: 646
<212> TYPE: DNA
<213> ORGANISM: Artificial
<220> FEATURE:
<223> OTHER INFORMATION: Polynucleotide

<400> SEQUENCE: 162
cggatctctt ggttctcgca tcgatgaaga acgcagtgaa atgcgatacg taatgtgaat 60
tgcagaattc cgtgaatcat cgaatcgcct ttgaacgcac attgcgcccc ttggtattcc 120
agggggcatg cctgtttgag cgtcatttcc ttctcaaaca ttctgtttgg tagtgagtga 180
tactctttgg agttaacttg aaattgctgg ccttttcatt ggatgttttt tttccaaaga 240
gaggtttctc tgcgtgcttg aggtataatg caagtacggt cgttttaggt tttaccaact 300
gcggctaatc tttttttata ctgagcgtat tggaacgtta tcgataagaa gagagcgtct 360
aggcgaacaa tgttcttaaa gtttgacctc aaatcaggta ggagtacccg ctgaacttaa 420
gcatatcaat aagcggagga aaagaaacca accgggattg tagggataac agggtaatga 480
gtcgacaaaa tgatacggcg accaccgaga tctacactct ttccctacac gacgctcttc 540
cgatctgact gtgtgttact gctgacagat cggaagagca cacgtctgaa ctccagtcac 600
aatcagtctc gtatctcgta tgccgtcttc tgcttgttgt cgactc 646

<210> SEQ ID NO 163
<211> LENGTH: 646
<212> TYPE: DNA
<213> ORGANISM: Artificial
<220> FEATURE:
<223> OTHER INFORMATION: Polynucleotide

<400> SEQUENCE: 163
cggatctctt ggttctcgca tcgatgaaga acgcagggaa atgcgatacg taatgtgaat 60
tgcagaattc cgtgaatcat cgaatcgcct ttgaacgcac attgcgcccc ttggtattcc 120
agggggcatg cctgtttgag cgtcatttcc ttctcaaaca ttctgtttgg tagtgagtga 180
tactctttgg agttaacttg aaattgctgg ccttttcatt ggatgttttt tttccaaaga 240
gaggtttctc tgcgtgcttg aggtataatg caagtacggt cgttttaggt tttaccaact 300
gcggctaatc ttttttata ctgagcgtat tggaacgtta tcgataagaa gagagcgtct 360
aggcgaacaa tgttcttaaa gtttgacctc aaatcaggta ggagtacccg ctgaacttaa 420
gcatatcaat aagcggagga aaagaaacca accgggattg tagggataac agggtaatga 480
gtcgacaaaa tgatacggcg accaccgaga tctacactct ttccctacac gacgctcttc 540
cgatctaaat actgtttata cggttgagat cggaagagca cacgtctgaa ctccagtcac 600
aatcagtctc gtatctcgta tgccgtcttc tgcttgttgt cgactc 646

<210> SEQ ID NO 164
<211> LENGTH: 646
<212> TYPE: DNA
<213> ORGANISM: Artificial
<220> FEATURE:
<223> OTHER INFORMATION: Polynucleotide

<400> SEQUENCE: 164
cggatctctt ggttctcgca tcgatgaaga acgcagcaaa atgcgatacg taatgtgaat 60
tgcagaattc cgtgaatcat cgaatcgcct ttgaacgcac attgcgcccc ttggtattcc 120
agggggcatg cctgtttgag cgtcatttcc ttctcaaaca ttctgtttgg tagtgagtga 180
tactctttgg agttaacttg aaattgctgg ccttttcatt ggatgttttt tttccaaaga 240
gaggtttctc tgcgtgcttg aggtataatg caagtacggt cgttttaggt tttaccaact 300
gcggctaatc ttttttata ctgagcgtat tggaacgtta tcgataagaa gagagcgtct 360
aggcgaacaa tgttcttaaa gtttgacctc aaatcaggta ggagtacccg ctgaacttaa 420
gcatatcaat aagcggagga aaagaaacca accgggattg tagggataac agggtaatga 480
gtcgacaaaa tgatacggcg accaccgaga tctacactct ttccctacac gacgctcttc 540
cgatctgtaa acagtaagga ggcatcagat cggaagagca cacgtctgaa ctccagtcac 600
aatcagtctc gtatctcgta tgccgtcttc tgcttgttgt cgactc 646

<210> SEQ ID NO 165
<211> LENGTH: 646
<212> TYPE: DNA
<213> ORGANISM: Artificial
<220> FEATURE:
<223> OTHER INFORMATION: Polynucleotide

<400> SEQUENCE: 165
cggatctctt ggttctcgca tcgatgaaga acgcagctaa atgcgatacg taatgtgaat 60
tgcagaattc cgtgaatcat cgaatcgcct ttgaacgcac attgcgcccc ttggtattcc 120
agggggcatg cctgtttgag cgtcatttcc ttctcaaaca ttctgtttgg tagtgagtga 180
tactctttgg agttaacttg aaattgctgg ccttttcatt ggatgttttt tttccaaaga 240
gaggtttctc tgcgtgcttg aggtataatg caagtacggt cgttttaggt tttaccaact 300
gcggctaatc ttttttata ctgagcgtat tggaacgtta tcgataagaa gagagcgtct 360
aggcgaacaa tgttcttaaa gtttgacctc aaatcaggta ggagtacccg ctgaacttaa 420
gcatatcaat aagcggagga aaagaaacca accgggattg tagggataac agggtaatga 480
gtcgacaaaa tgatacggcg accaccgaga tctacactct ttccctacac gacgctcttc 540
cgatctttgc agacaggtgc gggatgagat cggaagagca cacgtctgaa ctccagtcac 600
aatcagtctc gtatctcgta tgccgtcttc tgcttgttgt cgactc 646

<210> SEQ ID NO 166
<211> LENGTH: 646

<212> TYPE: DNA
<213> ORGANISM: Artificial
<220> FEATURE:
<223> OTHER INFORMATION: Polynucleotide

<400> SEQUENCE: 166
cggatctctt ggttctcgca tcgatgaaga acgcagccaa atgcgatacg taatgtgaat 60
tgcagaattc cgtgaatcat cgaatcgcct ttgaacgcac attgcgcccc ttggtattcc 120
agggggcatg cctgtttgag cgtcatttcc ttctcaaaca ttctgtttgg tagtgagtga 180
tactctttgg agttaacttg aaattgctgg ccttttcatt ggatgttttt tttccaaaga 240
gaggtttctc tgcgtgcttg aggtataatg caagtacggt cgttttaggt tttaccaact 300
gcggctaatc ttttttata ctgagcgtat tggaacgtta tcgataagaa gagagcgtct 360
aggcgaacaa tgttcttaaa gtttgacctc aaatcaggta ggagtacccg ctgaacttaa 420
gcatatcaat aagcggagga aaagaaacca accgggattg tagggataac agggtaatga 480
gtcgacaaaa tgatacggcg accaccgaga tctacactct ttccctacac gacgctcttc 540
cgatctctca ttcagctttg ttaaagagat cggaagagca cacgtctgaa ctccagtcac 600
aatcagtctc gtatctcgta tgccgtcttc tgcttgttgt cgactc 646

<210> SEQ ID NO 167
<211> LENGTH: 517
<212> TYPE: DNA
<213> ORGANISM: Artificial
<220> FEATURE:
<223> OTHER INFORMATION: Polynucleotide

<400> SEQUENCE: 167
cggatctctt ggttctcgca tcgatgaaga acgcagcgta tgaaggttga aagcgtaatt 60
aggaattatt gatagtaaag tgcacactag cgttttgtta aatcttaagt gtaatccccg 120
agctaaaaca aggaataaca tctgataatt acaagattga aaatcgtatt tggaggtaga 180
attccaggag taaaggagaa attaatagtg ttctgtaata atacaagtat cgtatgcagc 240
aactaggtcg aagactgatg atcaggtgag aaagtgttgg gagctaactg agcatatcaa 300
taagcggagg aaaagaaacc aaccgggatt gtagggataa cagggtaatg agtcgacaaa 360
atgatacggc gaccaccgag atctacactc tttccctaca cgacgctctt ccgatctggc 420
catactcgca gtggctcaga tcggaagagc acacgtctga actccagtca caatcagtct 480
cgtatctcgt atgccgtctt ctgcttgttg tcgactc 517

<210> SEQ ID NO 168
<211> LENGTH: 517
<212> TYPE: DNA
<213> ORGANISM: Artificial
<220> FEATURE:
<223> OTHER INFORMATION: Polynucleotide

<400> SEQUENCE: 168
cggatctctt ggttctcgca tcgatgaaga acgcagcgta tggaggattc aaacataaat 60
cagaattact gggcttaaaa taatcgcatt ctgtttgtta agtaatatgt gtaatccccg 120
ggctaatcct gggaaatgca tttaatactg gcaatctaga gtataataaa ggagaatagt 180
attttagtag aaacagagaa ttgtttagat atttggagga ataaagttag catttgctgc 240
cccatggacg aaaaatgatg ctcatatgca aaagcgtggt gtacaaacag ggcatatcaa 300
taagcggagg aaaagaaacc aaccgggatt gtagggataa cagggtaatg agtcgacaaa 360
atgatacggc gaccaccgag atctacactc tttccctaca cgacgctctt ccgatctgtg 420
tcctaccgct ataccgcaga tcggaagagc acacgtctga actccagtca caatcagtct 480
cgtatctcgt atgccgtctt ctgcttgttg tcgactc 517

<210> SEQ ID NO 169
<211> LENGTH: 517
<212> TYPE: DNA
<213> ORGANISM: Artificial
<220> FEATURE:
<223> OTHER INFORMATION: Polynucleotide

<400> SEQUENCE: 169
cggatctctt ggttctcgca tcgatgaaga acgcagcgaa tgaagaatga atgctttaat 60
cggtattatt ggtcgtaaaa cgcacgcagg aggattgtta aattagatgt gaaatccact 120
ggcttaacat tagataagca tctgatacag gatagcttga ttttcatata agaggtttga 180
aatccagata tagctttgta attcgtagaa atctggatga ttaccggtta tgaaggcggt 240
ctcatggatg aaatctgatg ctaaaatacg aatgcgtggt tatcaaataa tgcatatcaa 300
taagcggagg aaaagaaacc aaccgggatt gtagggataa cagggtaatg agtcgacaaa 360
atgatacggc gaccaccgag atctacactc tttccctaca cgacgctctt ccgatctgct 420
cgaacacaca gccggtaaga tcggaagagc acacgtctga actccagtca caatcagtct 480
cgtatctcgt atgccgtctt ctgcttgttg tcgactc 517

<210> SEQ ID NO 170
<211> LENGTH: 517
<212> TYPE: DNA
<213> ORGANISM: Artificial
<220> FEATURE:
<223> OTHER INFORMATION: Polynucleotide

<400> SEQUENCE: 170
cggatctctt ggttctcgca tcgatgaaga acgcagcgaa ctgatggtgt aaacgttttt 60
cggtttaact gaacataatg ttcacgaaag ataaatgtta ttacatttga tatttatctt 120
gactcaacat gggaacagca tatgatacag gaaaacttga gtctcgtaga agggagttta 180
attccaggtt aagctattat atgataatag aactggagaa aatccggtgt tgatggcggt 240
tacttggatt tagacttacg ttcaggaaca aaatcttgtg gtgctaacag ggcatatcaa 300
taagcggagg aaaagaaacc aaccgggatt gtagggataa cagggtaatg agtcgacaaa 360
atgatacggc gaccaccgag atctacactc tttccctaca cgacgctctt ccgatctcca 420
ggtgggtagg tctttggaga tcggaagagc acacgtctga actccagtca caatcagtct 480
cgtatctcgt atgccgtctt ctgcttgttg tcgactc 517

<210> SEQ ID NO 171
<211> LENGTH: 517
<212> TYPE: DNA
<213> ORGANISM: Artificial
<220> FEATURE:
<223> OTHER INFORMATION: Polynucleotide

<400> SEQUENCE: 171
cggatctctt ggttctcgca tcgatgaaga acgcagcgta cggagggtga tagtgttaat 60
cgtaattact aggcgttaag cacaaacagg tggattgtta agacagatat gatatcccag 120
ggcttaaaca ggaaactgca aatgatacta gctagcttga gactcgaata tgggggtaga 180
ataccaggat taaagatgat ttacgtagag ataaggagta ttaccgttgt taaaggcggc 240
aacctgaatt aatactaact aacaggaaag aaagcgtggt aagaaaacag ggcatatcaa 300
taagcggagg aaaagaaacc aaccgggatt gtagggataa cagggtaatg agtcgacaaa 360
atgatacggc gaccaccgag atctacactc tttccctaca cgacgctctt ccgatctgtc 420
tcactcagtc agtacgaaga tcggaagagc acacgtctga actccagtca caatcagtct 480
cgtatctcgt atgccgtctt ctgcttgttg tcgactc 517

<210> SEQ ID NO 172
<211> LENGTH: 517
<212> TYPE: DNA
<213> ORGANISM: Artificial
<220> FEATURE:
<223> OTHER INFORMATION: Polynucleotide

<400> SEQUENCE: 172
cggatctctt ggttctcgca tcgatgaaga acgcagcgta cggagggtgc aaattttaat 60
cggaattact ggtaataaag cgcacgtagt cggtttgtta attcatattt gaattcctaa 120
gtctaaacct agtaactaca tctgatactg gtaaacttga gtctcttaga gggggataga 180
attatagttg tagcggtgaa attcgaagag ttctggagta ataccggtag caaagacgac 240
caactggacg aagtctgacg ttaagataag aaagtatggg gagcaaacag ggcatatcaa 300
taagcggagg aaaagaaacc aaccgggatt gtagggataa cagggtaatg agtcgacaaa 360
atgatacggc gaccaccgag atctacactc tttccctaca cgacgctctt ccgatcttga 420
tctcgagtgt cgtcacaaga tcggaagagc acacgtctga actccagtca caatcagtct 480
cgtatctcgt atgccgtctt ctgcttgttg tcgactc 517

<210> SEQ ID NO 173
<211> LENGTH: 517
<212> TYPE: DNA
<213> ORGANISM: Artificial
<220> FEATURE:
<223> OTHER INFORMATION: Polynucleotide

<400> SEQUENCE: 173
cggatctctt ggttctcgca tcgatgaaga acgcagcgta cagagggtgt aagcgttaat 60
agaaattact gggcgtaaaa agcacgcagg cggtttgtaa agttagatat aaattcattg 120
gactctaact gagaactgca tttgatactt tcaagctttt gtctcgttga ggagggtaga 180
aattcaggag ttgcgatgat atgcttagag atcttgagga attccggtgt cgaatgcaaa 240
ctcctggacg aagactaacg ttcagttgca aaagagtgga aattaaacat tgcatatcaa 300
taagcggagg aaaagaaacc aaccgggatt gtagggataa cagggtaatg agtcgacaaa 360
atgatacggc gaccaccgag atctacactc tttccctaca cgacgctctt ccgatctgtg 420
tagctaactt aaggtggaga tcggaagagc acacgtctga actccagtca caatcagtct 480
cgtatctcgt atgccgtctt ctgcttgttg tcgactc 517

<210> SEQ ID NO 174
<211> LENGTH: 517
<212> TYPE: DNA
<213> ORGANISM: Artificial
<220> FEATURE:
<223> OTHER INFORMATION: Polynucleotide

<400> SEQUENCE: 174
cggatctctt ggttctcgca tcgatgaaga acgcagcgta aggaatgagc tagcgttaat 60

-continued

```
cgaaattact gggtgttttg ctcatgcagg agattagttt attcagatgt aaaaaacccg    120

ggtacaacct gggaattgca tctgatactt ataagctaaa tactcgtaga gggaggtagt    180

attcctggtg ttgtggtgaa atgtgtagag atctatataa ttacatgttg cgaaggcgga    240

cccaaggacg aagactgatg ctcagaaatt aaaacgtgga aatcaaactt ggcatatcaa    300

taagcggagg aaaagaaacc aaccgggatt gtagggataa cagggtaatg agtcgacaaa    360

atgatacggc gaccaccgag atctacactc tttccctaca cgacgctctt ccgatctaac    420

gttgtccagc cgtatgtaga tcggaagagc acacgtctga actccagtca caatcagtct    480

cgtatctcgt atgccgtctt ctgcttgttg tcgactc                             517
```

```
<210> SEQ ID NO 175
<211> LENGTH: 517
<212> TYPE: DNA
<213> ORGANISM: Artificial
<220> FEATURE:
<223> OTHER INFORMATION: Polynucleotide

<400> SEQUENCE: 175

cggatctctt ggttctcgca tcgatgaaga acgcagcgtt cagaatgtgt aagcgtaatt     60

cgaaatttct gagagtaaag cgaatgcaga tggtttattt tgttagaagt gaaatccccg    120

ggctatacct ggttactgca tctgttactg gtaaacttga aactcgaaga gggtgataat    180

attccaggta tttaggttaa atgtgtagat atctggatga atactagtgt ctaaggcagt    240

ccactggacg tagacttact ctcaggttcg aaagcgtggg gaacattcat agcatatcaa    300

taagcggagg aaaagaaacc aaccgggatt gtagggataa cagggtaatg agtcgacaaa    360

atgatacggc gaccaccgag atctacactc tttccctaca cgacgctctt ccgatctacc    420

cggacggcgg tcaataaaga tcggaagagc acacgtctga actccagtca caatcagtct    480

cgtatctcgt atgccgtctt ctgcttgttg tcgactc                             517
```

```
<210> SEQ ID NO 176
<211> LENGTH: 517
<212> TYPE: DNA
<213> ORGANISM: Artificial
<220> FEATURE:
<223> OTHER INFORMATION: Polynucleotide

<400> SEQUENCE: 176

cggatctctt ggttctcgca tcgatgaaga acgcagcgta aggagggtgc ttgcgttaaa     60

cagaaatact gggtgtaaaa cgtacgtaga cggtttatta agtaagatgt gaaatccccg    120

tgctcaacct aggaactgca tatgatattg gaaaacttga gacatataga gggagataga    180

atacttggag tagcgttgta atgcgtatag atttggagga ataccggtgg cgaaggcggc    240

cccctggacg aagacagacg ctcaggtgcg aaatcgttgt gatcaaatag ggcatatcaa    300

taagcggagg aaaagaaacc aaccgggatt gtagggataa cagggtaatg agtcgacaaa    360

atgatacggc gaccaccgag atctacactc tttccctaca cgacgctctt ccgatcttca    420

ctcgggttct cggcacgaga tcggaagagc acacgtctga actccagtca caatcagtct    480

cgtatctcgt atgccgtctt ctgcttgttg tcgactc                             517
```

```
<210> SEQ ID NO 177
<211> LENGTH: 517
<212> TYPE: DNA
<213> ORGANISM: Artificial
<220> FEATURE:
<223> OTHER INFORMATION: Polynucleotide
```

<400> SEQUENCE: 177
cggatctctt ggttctcgca tcgatgaaga acgcagcgta cgaagtgtga aaacgttatt 60
aagaattact gggcgtaaag cgttcgcagg cggtttgtta agtcataagt gaaatccccg 120
ggcacaaact gggaactgaa tctgtaactg acaagcttga gtatcttata atgggataga 180
atttaatgtg tagctgtgaa atgcgtagag atctggagat ataccggtga ctaaggcggc 240
cccctggacg aagactgacg ctcaggtgct aaatcgtggg gaacaaaaag ggcatatcaa 300
taagcggagg aaaagaaacc aaccgggatt gtagggataa cagggtaatg agtcgacaaa 360
atgatacggc gaccaccgag atctacactc tttccctaca cgacgctctt ccgatctaaa 420
caactctggc tcgataaaga tcggaagagc acacgtctga actccagtca caatcagtct 480
cgtatctcgt atgccgtctt ctgcttgttg tcgactc 517

<210> SEQ ID NO 178
<211> LENGTH: 517
<212> TYPE: DNA
<213> ORGANISM: Artificial
<220> FEATURE:
<223> OTHER INFORMATION: Polynucleotide

<400> SEQUENCE: 178
cggatctctt ggttctcgca tcgatgaaga acgcagcgaa ctgagggtgc aagcgttaat 60
cggaattact gtgcataaag ctcacgcatt cgttttgtta agtcagataa taaatcctcg 120
agttaaacct gggaaatgca tctgatactg aaaagcttga ttctcgtaga ggggtgtaga 180
attccaggtg tagcagtaaa atacgtagag atcagaatga attccggtgg tgaagtcggc 240
ctactggacg aagactgacg ctaaggtgcg aaagcgtggg gagcaaacag ggcatatcaa 300
taagcggagg aaaagaaacc aaccgggatt gtagggataa cagggtaatg agtcgacaaa 360
atgatacggc gaccaccgag atctacactc tttccctaca cgacgctctt ccgatctcga 420
cagtccgacc gcaacagaga tcggaagagc acacgtctga actccagtca caatcagtct 480
cgtatctcgt atgccgtctt ctgcttgttg tcgactc 517

<210> SEQ ID NO 179
<211> LENGTH: 517
<212> TYPE: DNA
<213> ORGANISM: Artificial
<220> FEATURE:
<223> OTHER INFORMATION: Polynucleotide

<400> SEQUENCE: 179
cggatctctt ggttctcgca tcgatgaaga acgcagcgta cggagtgtta aatcgttaat 60
aggaattact gggcgaaaag tgctagcagg cggtttgtta aatcagttgt gaaatccctg 120
ggcacaacct gggatctgca tctgattttg gcaagcttta gtctattaga ggggggtaaa 180
tttccatgtg tagatttgaa atgcgtttag atctggagga ataccggagg tgaaggcgat 240
cccctggacg tagactgaag ctcaagtgag aaagcttgga gtgcaaacta ggcatatcaa 300
taagcggagg aaaagaaacc aaccgggatt gtagggataa cagggtaatg agtcgacaaa 360
atgatacggc gaccaccgag atctacactc tttccctaca cgacgctctt ccgatctaca 420
gatacgaggg agcaggtaga tcggaagagc acacgtctga actccagtca caatcagtct 480
cgtatctcgt atgccgtctt ctgcttgttg tcgactc 517

<210> SEQ ID NO 180

<211> LENGTH: 517
<212> TYPE: DNA
<213> ORGANISM: Artificial
<220> FEATURE:
<223> OTHER INFORMATION: Polynucleotide

<400> SEQUENCE: 180
cggatctctt ggttctcgca tcgatgaaga acgcagcgta cggagggtgc aagcgataat 60
agtatttact gtgcgaaaag catacttagg aagattttta tgtcagatgt gaaatccccg 120
ggcttaacct gggaactgca tctgatactg acaagtttga gactcgtata gggggtaga 180 attccaggtg ttgcagtgaa aagtgtagag atctggaaga ataccggtgg cgaaggttgc 240
cccctgtacg aataatgacg ctatggtgcg aaagcattgt gtgcaaacaa ggcatatcaa 300
taagcggagg aaaagaaacc aaccgggatt gtagggataa cagggtaatg agtcgacaaa 360
atgatacggc gaccaccgag atctacactc tttccctaca cgacgctctt ccgatctagt 420
ttccagtcgg ttctcacaga tcggaagagc acacgtctga actccagtca caatcagtct 480
cgtatctcgt atgccgtctt ctgcttgttg tcgactc 517

<210> SEQ ID NO 181
<211> LENGTH: 517
<212> TYPE: DNA
<213> ORGANISM: Artificial
<220> FEATURE:
<223> OTHER INFORMATION: Polynucleotide

<400> SEQUENCE: 181
cggatctctt ggttctcgca tcgatgaaga acgcagcgta cggaaggtgc aagtgttaat 60
cggaattact gggcataaag cgcacgaagg cggtatgtta agttagatgt gaaatccccg 120
ggctcaatct gtgaactgca tctgatactg gcaagcttga gtctcgtaga gggggtaga 180 attcaaggtg tagcggtgaa atgcgtagag atctagatga ataccggtgg cgaaggaggt 240
cccctggacg aagactgaca ctctggtgcg aaatagtggg gagcaaacag agcatatcaa 300
taagcggagg aaaagaaacc aaccgggatt gtagggataa cagggtaatg agtcgacaaa 360
atgatacggc gaccaccgag atctacactc tttccctaca cgacgctctt ccgatctcac 420
gtttactgac acgaagcaga tcggaagagc acacgtctga actccagtca caatcagtct 480
cgtatctcgt atgccgtctt ctgcttgttg tcgactc 517

<210> SEQ ID NO 182
<211> LENGTH: 517
<212> TYPE: DNA
<213> ORGANISM: Artificial
<220> FEATURE:
<223> OTHER INFORMATION: Polynucleotide

<400> SEQUENCE: 182
cggatctctt ggttctcgca tcgatgaaga acgcagcgta cggagggtgc aatcgttaat 60
cggatttact gggcttaaat cgcacgcagg cggtttgtta agtcatatgt gaaaaccccg 120
ggctcaacct gggaactgca tctgatactt gcaagcttga gtctcgtata gggaggtaga 180
attccaggtg tagcggtgaa atgcgtagag atctgaagta ataccggtag ctaatacggc 240
ccactggacg aagactgacg cacaggtgct aaagcgtgtg gagcaaacag ggcatatcaa 300
taagcggagg aaaagaaacc aaccgggatt gtagggataa cagggtaatg agtcgacaaa 360
atgatacggc gaccaccgag atctacactc tttccctaca cgacgctctt ccgatctgat 420
ataagcagcc tccgcaaaga tcggaagagc acacgtctga actccagtca caatcagtct 480
cgtatctcgt atgccgtctt ctgcttgttg tcgactc 517

<210> SEQ ID NO 183
<211> LENGTH: 517
<212> TYPE: DNA
<213> ORGANISM: Artificial
<220> FEATURE:
<223> OTHER INFORMATION: Polynucleotide

<400> SEQUENCE: 183
cggatctctt ggttctcgca tcgatgaaga acgcagcgta cggagtgtgc aagcgttaat 60
cggaattact ggtcgtaaag cgcacgtaga cggtttgtta attcagatgt taaattccag 120
ggcaaaacct gggaactgca tcttatactg gcaagcttga gtctcgtaga gggggttaga 180
attccaggtg tagcggtgaa atgtgtaaag atctggagga ataccggtgt tgaaggcggc 240
ctcctggacg aagactgacg ctcaggtgcg aaagcgtggg gagcaaacag ggcatatcaa 300
taagcggagg aaaagaaacc aaccgggatt gtagggataa cagggtaatg agtcgacaaa 360
atgatacggc gaccaccgag atctacactc tttccctaca cgacgctctt ccgatctgaa 420
tttagtgagc acgaaggaga tcggaagagc acacgtctga actccagtca caatcagtct 480
cgtatctcgt atgccgtctt ctgcttgttg tcgactc 517

<210> SEQ ID NO 184
<211> LENGTH: 517
<212> TYPE: DNA
<213> ORGANISM: Artificial
<220> FEATURE:
<223> OTHER INFORMATION: Polynucleotide

<400> SEQUENCE: 184
cggatctctt ggttctcgca tcgatgaaga acgcagcgta cggagggaac aagcgttaat 60
cgaaataact gggcgtaaag cgctcgtagg ttgtttgtta agtcagatgt gaaatccccg 120
ggttcaacct gggaactgca tctgattatg gcaagcttga gtctcgtaga ggggggtata 180
attccagttg aagcggtaaa atgcgttgag atctggaggt ataccggtgg cgaaagcggc 240
cccatggacg aagactgacg ctcatttgcg aaatcgttgg gagcaaacag ggcatatcaa 300
taagcggagg aaaagaaacc aaccgggatt gtagggataa cagggtaatg agtcgacaaa 360
atgatacggc gaccaccgag atctacactc tttccctaca cgacgctctt ccgatctatt 420
taagtgcagc tatgtccaga tcggaagagc acacgtctga actccagtca caatcagtct 480
cgtatctcgt atgccgtctt ctgcttgttg tcgactc 517

<210> SEQ ID NO 185
<211> LENGTH: 517
<212> TYPE: DNA
<213> ORGANISM: Artificial
<220> FEATURE:
<223> OTHER INFORMATION: Polynucleotide

<400> SEQUENCE: 185
cggatctctt ggttctcgca tcgatgaaga acgcagcgtt cttcgggtac tagcgttaat 60
taggatttct gcgcgtaaag tgaacgcagg cttgttggtc agtgagatgt gtattacagg 120
tacttaacct gtgaaccgca tctgatactc gcaagcctga ggctcctagt ggggggtaga 180
aatctatgtg tatcgttgga acccgtaaac atctgtagga tggcatgtgt ccaaggcagc 240
cccctggtct gagactgaca atcagtttcg aaagcgtggg gagcaaacag cgcatatcaa 300

-continued taagcggagg aaaagaaacc aaccgggatt gtagggataa cagggtaatg agtcgacaaa 360
atgatacggc gaccaccgag atctacactc tttccctaca cgacgctctt ccgatctaag 420
aggataactc cagtctgaga tcggaagagc acacgtctga actccagtca caatcagtct 480
cgtatctcgt atgccgtctt ctgcttgttg tcgactc 517

<210> SEQ ID NO 186
<211> LENGTH: 517
<212> TYPE: DNA
<213> ORGANISM: Artificial
<220> FEATURE:
<223> OTHER INFORMATION: Polynucleotide

<400> SEQUENCE: 186
cggatctctt ggttctcgca tcgatgaaga acgcagcgga cggagggtgc aagcgttaat 60
cggaataact gggcgtaaag cggtcgcagg cggtttgtta agtcagatgt gaattccccg 120
ggctcaacgt gggaacttca cctaatacgg gcaagcttta gaatcgtaga gggggggtaga 180 attataggta tagcggtgca atgcgaagag agctggagga atcccggtgg agaaggcagc 240
cccctggacg aagacagaag ctcaggggcg aaaccgtggg gagcaaacag ggcatatcaa 300
taagcggagg aaaagaaacc aaccgggatt gtagggataa cagggtaatg agtcgacaaa 360
atgatacggc gaccaccgag atctacactc tttccctaca cgacgctctt ccgatcttgg 420
gcaaggtaat ccgtgcaaga tcggaagagc acacgtctga actccagtca caatcagtct 480
cgtatctcgt atgccgtctt ctgcttgttg tcgactc 517

<210> SEQ ID NO 187
<211> LENGTH: 517
<212> TYPE: DNA
<213> ORGANISM: Artificial
<220> FEATURE:
<223> OTHER INFORMATION: Polynucleotide

<400> SEQUENCE: 187
cggatctctt ggttctcgca tcgatgaaga acgcagcgta cggagggtgc aagcgtttat 60
cggaattact gggcgtaaag cgcacgtagg cggtttgtta agtcagaagt gaaatccccg 120
ggctcaacct gggaactgca tctgatactg gctagcatga gtatcgtaga gggggggtaga 180 attccaggtg tagcggtgta atgcgtagag atctagagga ataccggtgg cgaaggcggc 240
cccctggacg aagactgacg ctcaggtgtg aaagcgaggg gagcaaacag ggcatatcaa 300
taagcggagg aaaagaaacc aaccgggatt gtagggataa cagggtaatg agtcgacaaa 360
atgatacggc gaccaccgag atctacactc tttccctaca cgacgctctt ccgatctctt 420
ccgtctttat ctaactaaga tcggaagagc acacgtctga actccagtca caatcagtct 480
cgtatctcgt atgccgtctt ctgcttgttg tcgactc 517

<210> SEQ ID NO 188
<211> LENGTH: 517
<212> TYPE: DNA
<213> ORGANISM: Artificial
<220> FEATURE:
<223> OTHER INFORMATION: Polynucleotide

<400> SEQUENCE: 188
cggatctctt ggttctcgca tcgatgaaga acgcagcgta ctgagggtgc aagcgtaaat 60
cggaattact gggcgtaaag cgcaagcagg cagtttgtta agtcagatgt gaaatccccg 120
ggctcaacct gggaactgca tcagatactg gcaagcttga gtctcgttga gggggggtaga 180 attccatgtg tagcggtgaa ttgcgtagag aactggagga ataccggtgg cgaaggcggc 240
cccctggacg aagactgacg ctcaggtgcg aaagcgtggg gtgcaaacag ggcatatcaa 300
taagcggagg aaaagaaacc aaccgggatt gtagggataa cagggtaatg agtcgacaaa 360
atgatacggc gaccaccgag atctacactc tttccctaca cgacgctctt ccgatctatg 420
taggtggaat acccaaaaga tcggaagagc acacgtctga actccagtca caatcagtct 480
cgtatctcgt atgccgtctt ctgcttgttg tcgactc 517

<210> SEQ ID NO 189
<211> LENGTH: 517
<212> TYPE: DNA
<213> ORGANISM: Artificial
<220> FEATURE:
<223> OTHER INFORMATION: Polynucleotide

<400> SEQUENCE: 189
cggatctctt ggttctcgca tcgatgaaga acgcagcgta ctgagggtgc aagcgttagt 60
cggaattact gggcgtaaag cgcactcagg cggtttgtta agtcagatgt gaaatccccg 120
ggctcaacct ggggactgca tctgatactg gcaagcctga gtctcgtagt ggggggtata 180
attccaggtg tagcggtgaa atgcgtagag atcaggaaga agtccagttg tgaaggcggc 240
cccctggacg aagactgagg ctcaggtgcg aaagcgtggg gagcaaacaa ggcatatcaa 300
taagcggagg aaaagaaacc aaccgggatt gtagggataa cagggtaatg agtcgacaaa 360
atgatacggc gaccaccgag atctacactc tttccctaca cgacgctctt ccgatcttgg 420
atacctagac ccgaggaaga tcggaagagc acacgtctga actccagtca caatcagtct 480
cgtatctcgt atgccgtctt ctgcttgttg tcgactc 517

<210> SEQ ID NO 190
<211> LENGTH: 517
<212> TYPE: DNA
<213> ORGANISM: Artificial
<220> FEATURE:
<223> OTHER INFORMATION: Polynucleotide

<400> SEQUENCE: 190
cggatctctt ggttctcgca tcgatgaaga acgcagcgta ccgagggtgc aagagttaag 60
cggaattgct ggccgtaaag cgcacacagg cgctttgtca agttagatgc gaaatcccca 120
ggttcaacct gggaactgca tctgatactg gcaagcttaa ctctcgtaga gggggttaca 180
attccaggtg gagcgctgaa atgcgtagac atctggagga ataccggtgg cgaaggcgac 240
cccctggacg aagactcccg cttaggttcg caagcggggg gagcaaacag agcatatcaa 300
taagcggagg aaaagaaacc aaccgggatt gtagggataa cagggtaatg agtcgacaaa 360
atgatacggc gaccaccgag atctacactc tttccctaca cgacgctctt ccgatctttg 420
tgctaacaag ccgcggaaga tcggaagagc acacgtctga actccagtca caatcagtct 480
cgtatctcgt atgccgtctt ctgcttgttg tcgactc 517

<210> SEQ ID NO 191
<211> LENGTH: 517
<212> TYPE: DNA
<213> ORGANISM: Artificial
<220> FEATURE:
<223> OTHER INFORMATION: Polynucleotide

<400> SEQUENCE: 191

```
cggatctctt ggttctcgca tcgatgaaga acgcagcgta cggagggggc aagcgttgat     60

cggaattacc cggcgtgaag cgcacgcagg cggtttgtta agtcagatgt gaaatccccg    120

ggctcaacgt gggaactgca tgtgatactg gcacgcttga gtctcgcaga ggggggggaga    180

attgcagggg tagcggtgaa aggcgtagag atctggagga ataccggtgg cgagggcggc    240

cccctggagg aagactgacg ctcaggtgcg aaagcgtggc gagcaaacac ggcatatcaa    300

taagcggagg aaaagaaacc aaccgggatt gtagggataa cagggtaatg agtcgacaaa    360

atgatacggc gaccaccgag atctacactc tttccctaca cgacgctctt ccgatctgaa    420

tttgtccagt cacgcataga tcggaagagc acacgtctga actccagtca caatcagtct    480

cgtatctcgt atgccgtctt ctgcttgttg tcgactc                             517
```

<210> SEQ ID NO 192
<211> LENGTH: 517
<212> TYPE: DNA
<213> ORGANISM: Artificial
<220> FEATURE:
<223> OTHER INFORMATION: Polynucleotide

<400> SEQUENCE: 192

```
cggatctctt ggttctcgca tcgatgaaga acgcagcgta cggagggtgc aagcgttaat     60

cggaatgact gggcgtaaag cgcacgcagg cgctgtgtta agtcagatgt ggaatccccg    120

ggctcaacct gggaactgca tctgatactg gcaaggttga gtctggtgga ggggggggaga    180

atcccaggtg tggcggtgaa atgcggagag agctggagga ataccggtgg cgaaggcggc    240

cccctggacg gagactgacg ctcaggtgcg aaagcgtggg gagcaaacag ggcatatcaa    300

taagcggagg aaaagaaacc aaccgggatt gtagggataa cagggtaatg agtcgacaaa    360

atgatacggc gaccaccgag atctacactc tttccctaca cgacgctctt ccgatctagg    420

gaagatagga ggctcccaga tcggaagagc acacgtctga actccagtca caatcagtct    480

cgtatctcgt atgccgtctt ctgcttgttg tcgactc                             517
```

<210> SEQ ID NO 193
<211> LENGTH: 517
<212> TYPE: DNA
<213> ORGANISM: Artificial
<220> FEATURE:
<223> OTHER INFORMATION: Polynucleotide

<400> SEQUENCE: 193

```
cggatctctt ggttctcgca tcgatgaaga acgcagcgta cggagggtgc aagcggtaat     60

cggaattact gggcgtaaac cgcacgcagg cggtctgtta agtcagatgt gaaatccccg    120

ggctcaaccg gggaactgca tctgatactg gcaagcttga gcctcgtaga gggggtaga     180

agtccgggtg tagcggtgaa ctgcgtagac atctggagga ataccggggg cgaaggcggc    240

cccctggacg aagactgacg ggcaggtgcg acagcgtggg gagcaaacag ggcatatcaa    300

taagcggagg aaaagaaacc aaccgggatt gtagggataa cagggtaatg agtcgacaaa    360

atgatacggc gaccaccgag atctacactc tttccctaca cgacgctctt ccgatcttat    420

tgtacggtac aggttcaaga tcggaagagc acacgtctga actccagtca caatcagtct    480

cgtatctcgt atgccgtctt ctgcttgttg tcgactc                             517
```

<210> SEQ ID NO 194
<211> LENGTH: 517
<212> TYPE: DNA
<213> ORGANISM: Artificial
<220> FEATURE:
<223> OTHER INFORMATION: Polynucleotide

<400> SEQUENCE: 194
cggatctctt ggttctcgca tcgatgaaga acgcagcgtc cggagggtgc gagcgttaat 60
cggaattact gcgcgtaaag cgcacgcagg cggtttctta agtcagctgt gaaatccccg 120
ggctcacccc gggaactgca tctgatactc gcaaccttga gtctcgtaga gggggccaga 180
attccaggtg tagcggtgaa atgcgtagag atccggagga ataccggggg cgaaggcggc 240
cccctggacg aagactgacg ctcaggtgcg aaagcgcggg gagcaaaccg ggcatatcaa 300
taagcggagg aaaagaaacc aaccgggatt gtagggataa cagggtaatg agtcgacaaa 360
atgatacggc gaccaccgag atctacactc tttccctaca cgacgctctt ccgatctaag 420
aaggcacctg aagctcaaga tcggaagagc acacgtctga actccagtca caatcagtct 480
cgtatctcgt atgccgtctt ctgcttgttg tcgactc 517

<210> SEQ ID NO 195
<211> LENGTH: 517
<212> TYPE: DNA
<213> ORGANISM: Artificial
<220> FEATURE:
<223> OTHER INFORMATION: Polynucleotide

<400> SEQUENCE: 195
cggatctctt ggttctcgca tcgatgaaga acgcagcgtc cggagcgtgc aagcgtcaat 60
ccgcattagt gggcgtaaag cgcacgcagg cgggttgtta agtcagatgt gaaatcccgg 120
ggctcaacct gggaactgca tctgagactg gcaagcttga gtctcgtaca ggggggtaga 180
attccaggtc tggcgctgaa atgcgtagag atctggaggc agaccggtcg cgaaggcggc 240
cccctgcacg acgagtgacc ctcaggcgcg aaagcgtggg gagcaaacag ggcatatcaa 300
taagcggagg aaaagaaacc aaccgggatt gtagggataa cagggtaatg agtcgacaaa 360
atgatacggc gaccaccgag atctacactc tttccctaca cgacgctctt ccgatcttgc 420
cgacgttcga cccgttaaga tcggaagagc acacgtctga actccagtca caatcagtct 480
cgtatctcgt atgccgtctt ctgcttgttg tcgactc 517

<210> SEQ ID NO 196
<211> LENGTH: 517
<212> TYPE: DNA
<213> ORGANISM: Artificial
<220> FEATURE:
<223> OTHER INFORMATION: Polynucleotide

<400> SEQUENCE: 196
cggatctctt ggttctcgca tcgatgaaga acgcagcgta cgcagggtgc aagcgttaat 60
cggaattact gggcggaagg cgcacgcacg cggcctgtca agtgagatgt gacatccccg 120
ggctcaacct cggaactgcg tctgatactg gcacgcttgc gtcgcgtaca gggggcgaga 180
attccagggg gaggggtgaa atgcgtggcg atccggagga ataccggtgg cgaaggcggc 240
ccccgggacg aagacggccg ctcaggggcc aaagcgtggg gggcagacac ggcatatcaa 300
taagcggagg aaaagaaacc aaccgggatt gtagggataa cagggtaatg agtcgacaaa 360
atgatacggc gaccaccgag atctacactc tttccctaca cgacgctctt ccgatcttaa 420
atgatccgcc tggtcagaga tcggaagagc acacgtctga actccagtca caatcagtct 480
cgtatctcgt atgccgtctt ctgcttgttg tcgactc 517

<210> SEQ ID NO 197
<211> LENGTH: 517
<212> TYPE: DNA
<213> ORGANISM: Artificial
<220> FEATURE:
<223> OTHER INFORMATION: Polynucleotide

<400> SEQUENCE: 197
cggatctctt ggttctcgca tcgatgaaga acgcagcgta cggggggtgc aagcgtggat 60
cggaattgct gggcgtcaag ggcacgcagg cggtttgtga agtcagacgc gagagccccg 120
ggctccaccg gggaactgca tctgatactg gcaagcttga gtctcgtaga cgggggcaga 180
atcccgggtg tggcggggaa atgcgtagag atctggaggg atcccggtgg cgaaggcggc 240
cccctggacg gagactgacg ctcaggtgcg gaagcggggg gaccaaacag ggcatatcaa 300
taagcggagg aaaagaaacc aaccgggatt gtagggataa cagggtaatg agtcgacaaa 360
atgatacggc gaccaccgag atctacactc tttccctaca cgacgctctt ccgatctgca 420
gctccgcact aagcgacaga tcggaagagc acacgtctga actccagtca caatcagtct 480
cgtatctcgt atgccgtctt ctgcttgttg tcgactc 517

<210> SEQ ID NO 198
<211> LENGTH: 517
<212> TYPE: DNA
<213> ORGANISM: Artificial
<220> FEATURE:
<223> OTHER INFORMATION: Polynucleotide

<400> SEQUENCE: 198
cggatctctt ggttctcgca tcgatgaaga acgcagcgta cgcagggtgc cagcgttaat 60
cggaattact gggcgtgaag cgcacgcggg cggtttgtta agtcagacgt gaaatccccg 120
cgctcaacct gggagccgca cctgagagtg gcgagcttgg gtgtcgtaga ggggggtaga 180
cttccaggtg tagcggtgaa atgcgcagcg ctctggcggg ataccgctgg cgaaggcggc 240
cccccgggcg aagcctgccg ctcaggggcg aaagcgtggg gagcacacag ggcatatcaa 300
taagcggagg aaaagaaacc aaccgggatt gtagggataa cagggtaatg agtcgacaaa 360
atgatacggc gaccaccgag atctacactc tttccctaca cgacgctctt ccgatcttac 420
ttgggtccta gggaccaaga tcggaagagc acacgtctga actccagtca caatcagtct 480
cgtatctcgt atgccgtctt ctgcttgttg tcgactc 517

<210> SEQ ID NO 199
<211> LENGTH: 517
<212> TYPE: DNA
<213> ORGANISM: Artificial
<220> FEATURE:
<223> OTHER INFORMATION: Polynucleotide

<400> SEQUENCE: 199
cggatctctt ggttctcgca tcgatgaaga acgcagcgta cggagcgtgc aagcgctaac 60
cggaattact gcgcgtcaag cggacgcagg cggttcgtta agtcaggtgt gagatccccg 120
gggtcaaccg gggacctgca tctgacaccg gcacgcttga gtcccgtagg ggcgggtaga 180
atccccggtg tagcggtgcg agccgtagcg atccggagga ataccggtgg cgacggccgc 240
cccctggacg aaggctgacg ctgaggtgcg aaagcgtggg gagcaaacag ggcatatcaa 300
taagcggagg aaaagaaacc aaccgggatt gtagggataa cagggtaatg agtcgacaaa 360
atgatacggc gaccaccgag atctacactc tttccctaca cgacgctctt ccgatctcgg 420

```
atttacgata gtaggacaga tcggaagagc acacgtctga actccagtca caatcagtct    480

cgtatctcgt atgccgtctt ctgcttgttg tcgactc                            517


<210> SEQ ID NO 200
<211> LENGTH: 517
<212> TYPE: DNA
<213> ORGANISM: Artificial
<220> FEATURE:
<223> OTHER INFORMATION: Polynucleotide

<400> SEQUENCE: 200

cggatctctt ggttctcgca tcgatgaaga acgcagcgta ccgccggtgc acgcgttaat     60

cggaattact gggggtacag cgcgcgcggg cggtttgtta gctccggtgt gaagtcccgg    120

ggctcaacct gggaactcca gcggacactg gcaagcctga gtctcgtccc ggggggggaga    180

gttccagctg tagcggtgac gtccctggag atctcgggga atacgggtgg ccaaggccgc    240

cccctcgagg aggagtcacg ctgaggcgcg aaagcgtggg gagcaaacag ggcatatcaa    300

taagcggagg aaaagaaacc aaccgggatt gtagggataa cagggtaatg agtcgacaaa    360

atgatacggc gaccaccgag atctacactc tttccctaca cgacgctctt ccgatcttta    420

tcactgtaga cgggaataga tcggaagagc acacgtctga actccagtca caatcagtct    480

cgtatctcgt atgccgtctt ctgcttgttg tcgactc                            517


<210> SEQ ID NO 201
<211> LENGTH: 517
<212> TYPE: DNA
<213> ORGANISM: Artificial
<220> FEATURE:
<223> OTHER INFORMATION: Polynucleotide

<400> SEQUENCE: 201

cggatctctt ggttctcgca tcgatgaaga acgcagcgtg cggggggtgg aagcggcgag     60

cggactggcg gggcgccaag cgcgcgccgg cggcttgcta ggtcagatgt gaggtgcccg    120

gcctcaacct gggaactgca ggtgatactg ggcagccgga gtcgggtaga cgggggtaca    180

atgccaggtg tagcggggca acgggtagcg atgtggggga ataccggtgg cgaacggggc    240

cccccggacg aaggctggcg ctcgggtgcc acagcgtggg gagcaaacag ggcatatcaa    300

taagcggagg aaaagaaacc aaccgggatt gtagggataa cagggtaatg agtcgacaaa    360

atgatacggc gaccaccgag atctacactc tttccctaca cgacgctctt ccgatcttaa    420

gttcttatgc agctattaga tcggaagagc acacgtctga actccagtca caatcagtct    480

cgtatctcgt atgccgtctt ctgcttgttg tcgactc                            517


<210> SEQ ID NO 202
<211> LENGTH: 517
<212> TYPE: DNA
<213> ORGANISM: Artificial
<220> FEATURE:
<223> OTHER INFORMATION: Polynucleotide

<400> SEQUENCE: 202

cggatctctt ggttctcgca tcgatgaaga acgcagcgtg cggagggtgc acggggtaac     60

gggaatgcct gggcgcccag ccgacggagc cggttcggta agtcagaggt gaacgcgccg    120

ggctcaaccc gcgaactgcc gctgataccg gggcgcttcc gtctcgtaga ggggggtcga    180

attccaggtg tggcgctgaa gtcccgagag ctctggagga agcgcggtgg cgagggcgcc    240
```

```
cgcccggacc aagactggcg gccaggtgcg aaagcgcggg gagcgaacgg ggcatatcaa    300

taagcggagg aaaagaaacc aaccgggatt gtagggataa cagggtaatg agtcgacaaa    360

atgatacggc gaccaccgag atctacactc tttccctaca cgacgctctt ccgatcttga    420

cagagagacc tccctacaga tcggaagagc acacgtctga actccagtca caatcagtct    480

cgtatctcgt atgccgtctt ctgcttgttg tcgactc                             517
```

<210> SEQ ID NO 203
<211> LENGTH: 517
<212> TYPE: DNA
<213> ORGANISM: Artificial
<220> FEATURE:
<223> OTHER INFORMATION: Polynucleotide

<400> SEQUENCE: 203

```
cggatctctt ggttctcgca tcgatgaaga acgcagcgca cggagggcgc aagcgttaat     60

cggaaccact ggccctaaag cggccccagg cgggtcgtga ggtcagatgt gaaaccgccg    120

gggtcaaccg gggggggcg gctgacactg gcgagcctgg gtctcgtaca cgggggcaga    180

cctccaggtg tcccgctgag gcgcgtggag atccggagga gtaccggtgg ggacgccggc    240

cccctcgagg cagactgacg cgcaggtgcg aaagcgcggg gagcaaacgg ggcatatcaa    300

taagcggagg aaaagaaacc aaccgggatt gtagggataa cagggtaatg agtcgacaaa    360

atgatacggc gaccaccgag atctacactc tttccctaca cgacgctctt ccgatctcct    420

acgttaatgc gcaaattaga tcggaagagc acacgtctga actccagtca caatcagtct    480

cgtatctcgt atgccgtctt ctgcttgttg tcgactc                             517
```

<210> SEQ ID NO 204
<211> LENGTH: 517
<212> TYPE: DNA
<213> ORGANISM: Artificial
<220> FEATURE:
<223> OTHER INFORMATION: Polynucleotide

<400> SEQUENCE: 204

```
cggatctctt ggttctcgca tcgatgaaga acgcagcgta cggcgggtgc cagccttaat     60

cggaatgccc gggcgcacag cggacgcggg cggttcgtta agccgcaggc gagatccccg    120

ggcccaacct cggcacggcg tctgacactg gcgaggttga gtctcggaga ggggggtagg    180

attccaggtc caccggtgga accccctagag ctctgggggga ctaccggtgg cccaggccgc    240

ggcctggacg aacgctggcg ctcaggtccg caagcctgcg gcgcacacgg ggcatatcaa    300

taagcggagg aaaagaaacc aaccgggatt gtagggataa cagggtaatg agtcgacaaa    360

atgatacggc gaccaccgag atctacactc tttccctaca cgacgctctt ccgatctaac    420

ccatgtaaag agttatcaga tcggaagagc acacgtctga actccagtca caatcagtct    480

cgtatctcgt atgccgtctt ctgcttgttg tcgactc                             517
```

<210> SEQ ID NO 205
<211> LENGTH: 517
<212> TYPE: DNA
<213> ORGANISM: Artificial
<220> FEATURE:
<223> OTHER INFORMATION: Polynucleotide

<400> SEQUENCE: 205

```
cggatctctt ggttctcgca tcgatgaaga acgcagcgta ccgcgggtgc aagcgttaat     60

gcggcttact gggcgtaaag cggaccccgg cggtttgtga ggtcacatgt gaagcccccg    120
```

```
cccctccgcct gggaactgcg tctgatactg gcgggctcgg ggcccgtaca ggggggtaga    180

atcccaggtg gagggcggaa ccgggtgccg agctgcagga aggccggcgg cgaagccggc    240

cccccgggcg gagactgacg cccaggggcg cgaccgtggg gagcaagcag ggcatatcaa    300

taagcggagg aaaagaaacc aaccgggatt gtagggataa cagggtaatg agtcgacaaa    360

atgatacggc gaccaccgag atctacactc tttccctaca cgacgctctt ccgatctcgt    420

gtgtatctct agccttcaga tcggaagagc acacgtctga actccagtca caatcagtct    480

cgtatctcgt atgccgtctt ctgcttgttg tcgactc                             517
```

<210> SEQ ID NO 206
<211> LENGTH: 477
<212> TYPE: DNA
<213> ORGANISM: Artificial
<220> FEATURE:
<223> OTHER INFORMATION: Polynucleotide

<400> SEQUENCE: 206

```
cggatctctt ggttctcgca tcgatgaaga acgcagcgaa atgcgatacg taatgtgaat     60

tgcagaattc cgtgaatcat cgaatcgcct ttgaacgcac attgcgcccc ttggtattcc    120

agggggcatg cctgtttgag cgtcatttcc ttctcaaaca ttctgtttgg tagtgagtga    180

tactctttgg agttaacttg aaattgctgg ccttttcatt ggatgttttt tttccaaaga    240

gaggtttctc tgcatatcaa taagcggagg aaaagaaacc aaccgggatt gtagggataa    300

cagggtaatg agtcgacaaa atgatacggc gaccaccgag atctacactc tttccctaca    360

cgacgctctt ccgatctgtt gtctcttagg ccctcagaga tcggaagagc acacgtctga    420

actccagtca caatcagtct cgtatctcgt atgccgtctt ctgcttgttg tcgactc       477
```

<210> SEQ ID NO 207
<211> LENGTH: 507
<212> TYPE: DNA
<213> ORGANISM: Artificial
<220> FEATURE:
<223> OTHER INFORMATION: Polynucleotide

<400> SEQUENCE: 207

```
cggatctctt ggttctcgca tcgatgaaga acgcagcgaa atgcgatacg taatgtgaat     60

tgcagaattc cgtgaatcat cgaatcgcct ttgaacgcac attgcgcccc ttggtattcc    120

agggggcatg cctgtttgag cgtcatttcc ttctcaaaca ttctgtttgg tagtgagtga    180

tactctttgg agttaacttg aaattgctgg ccttttcatt ggatgttttt tttccaaaga    240

gaggtttctc tgcgtgcttg aggtataatg caagtacggt cgcatatcaa taagcggagg    300

aaaagaaacc aaccgggatt gtagggataa cagggtaatg agtcgacaaa atgatacggc    360

gaccaccgag atctacactc tttccctaca cgacgctctt ccgatctacg caatgtttcg    420

atgagctaga tcggaagagc acacgtctga actccagtca caatcagtct cgtatctcgt    480

atgccgtctt ctgcttgttg tcgactc                                        507
```

<210> SEQ ID NO 208
<211> LENGTH: 537
<212> TYPE: DNA
<213> ORGANISM: Artificial
<220> FEATURE:
<223> OTHER INFORMATION: Polynucleotide

<400> SEQUENCE: 208

```
cggatctctt ggttctcgca tcgatgaaga acgcagcgaa atgcgatacg taatgtgaat     60
tgcagaattc cgtgaatcat cgaatcgcct ttgaacgcac attgcgcccc ttggtattcc    120
agggggcatg cctgtttgag cgtcatttcc ttctcaaaca ttctgtttgg tagtgagtga    180
tactctttgg agttaacttg aaattgctgg ccttttcatt ggatgttttt tttccaaaga    240
gaggtttctc tgcgtgcttg aggtataatg caagtacggt cgttttaggt tttaccaact    300
gcggctaatc tgcatatcaa taagcggagg aaaagaaacc aaccgggatt gtagggataa    360
cagggtaatg agtcgacaaa atgatacggc gaccaccgag atctacactc tttccctaca    420
cgacgctctt ccgatctcac ctttggagaa tgtcaccaga tcggaagagc acacgtctga    480
actccagtca caatcagtct cgtatctcgt atgccgtctt ctgcttgttg tcgactc       537
```

<210> SEQ ID NO 209
<211> LENGTH: 567
<212> TYPE: DNA
<213> ORGANISM: Artificial
<220> FEATURE:
<223> OTHER INFORMATION: Polynucleotide

<400> SEQUENCE: 209

```
cggatctctt ggttctcgca tcgatgaaga acgcagcgaa atgcgatacg taatgtgaat     60
tgcagaattc cgtgaatcat cgaatcgcct ttgaacgcac attgcgcccc ttggtattcc    120
agggggcatg cctgtttgag cgtcatttcc ttctcaaaca ttctgtttgg tagtgagtga    180
tactctttgg agttaacttg aaattgctgg ccttttcatt ggatgttttt tttccaaaga    240
gaggtttctc tgcgtgcttg aggtataatg caagtacggt cgttttaggt tttaccaact    300
gcggctaatc tttttttata ctgagcgtat tggaacgtta tgcatatcaa taagcggagg    360
aaaagaaacc aaccgggatt gtagggataa cagggtaatg agtcgacaaa atgatacggc    420
gaccaccgag atctacactc tttccctaca cgacgctctt ccgatctagg acccgacaag    480
cacacgtaga tcggaagagc acacgtctga actccagtca caatcagtct cgtatctcgt    540
atgccgtctt ctgcttgttg tcgactc                                        567
```

<210> SEQ ID NO 210
<211> LENGTH: 597
<212> TYPE: DNA
<213> ORGANISM: Artificial
<220> FEATURE:
<223> OTHER INFORMATION: Polynucleotide

<400> SEQUENCE: 210

```
cggatctctt ggttctcgca tcgatgaaga acgcagcgaa atgcgatacg taatgtgaat     60
tgcagaattc cgtgaatcat cgaatcgcct ttgaacgcac attgcgcccc ttggtattcc    120
agggggcatg cctgtttgag cgtcatttcc ttctcaaaca ttctgtttgg tagtgagtga    180
tactctttgg agttaacttg aaattgctgg ccttttcatt ggatgttttt tttccaaaga    240
gaggtttctc tgcgtgcttg aggtataatg caagtacggt cgttttaggt tttaccaact    300
gcggctaatc tttttttata ctgagcgtat tggaacgtta tcgataagaa gagagcgtct    360
aggcgaacaa tgcatatcaa taagcggagg aaaagaaacc aaccgggatt gtagggataa    420
cagggtaatg agtcgacaaa atgatacggc gaccaccgag atctacactc tttccctaca    480
cgacgctctt ccgatctttt agcggtgcga gtgatcaaga tcggaagagc acacgtctga    540
actccagtca caatcagtct cgtatctcgt atgccgtctt ctgcttgttg tcgactc       597
```

<210> SEQ ID NO 211
<211> LENGTH: 627
<212> TYPE: DNA
<213> ORGANISM: Artificial
<220> FEATURE:
<223> OTHER INFORMATION: Polynucleotide

<400> SEQUENCE: 211
cggatctctt ggttctcgca tcgatgaaga acgcagcgaa atgcgatacg taatgtgaat 60
tgcagaattc cgtgaatcat cgaatcgcct ttgaacgcac attgcgcccc ttggtattcc 120
agggggcatg cctgtttgag cgtcatttcc ttctcaaaca ttctgtttgg tagtgagtga 180
tactctttgg agttaacttg aaattgctgg ccttttcatt ggatgttttt tttccaaaga 240
gaggtttctc tgcgtgcttg aggtataatg caagtacggt cgttttaggt tttaccaact 300
gcggctaatc ttttttttata ctgagcgtat tggaacgtta tcgataagaa gagagcgtct 360
aggcgaacaa tgttcttaaa gtttgacctc aaatcaggta ggcatatcaa taagcggagg 420
aaaagaaacc aaccgggatt gtagggataa cagggtaatg agtcgacaaa atgatacggc 480
gaccaccgag atctacactc tttccctaca cgacgctctt ccgatcttct cgcaatcgac 540
atgaccgaga tcggaagagc acacgtctga actccagtca caatcagtct cgtatctcgt 600
atgccgtctt ctgcttgttg tcgactc 627

<210> SEQ ID NO 212
<211> LENGTH: 667
<212> TYPE: DNA
<213> ORGANISM: Artificial
<220> FEATURE:
<223> OTHER INFORMATION: Polynucleotide

<400> SEQUENCE: 212
cggatctctt ggttctcgca tcgatgaaga acgcagcgaa atgcgatacg taatgtgaat 60
tgcagaattc cgtgaatcat cgaatcgcct ttgaacgcac attgcgcccc ttggtattcc 120
agggggcatg cctgtttgag cgtcatttcc ttctcaaaca ttctgtttgg tagtgagtga 180
tactctttgg agttaacttg aaattgctgg ccttttcatt ggatgttttt tttccaaaga 240
gaggtttctc tgcgtgcttg aggtataatg caagtacggt cgttttaggt tttaccaact 300
gcggctaatc ttttttttata ctgagcgtat tggaacgtta tcgataagaa gagagcgtct 360
aggcgaacaa tgttcttaaa gtttgacctc aaatcaggta gccttagtaa cggcgagtga 420
agcggcaaaa gctcaaattt ggcatatcaa taagcggagg aaaagaaacc aaccgggatt 480
gtagggataa cagggtaatg agtcgacaaa atgatacggc gaccaccgag atctacactc 540
tttccctaca cgacgctctt ccgatctagt gacagtgttg agaggataga tcggaagagc 600
acacgtctga actccagtca caatcagtct cgtatctcgt atgccgtctt ctgcttgttg 660
tcgactc 667

<210> SEQ ID NO 213
<211> LENGTH: 697
<212> TYPE: DNA
<213> ORGANISM: Artificial
<220> FEATURE:
<223> OTHER INFORMATION: Polynucleotide

<400> SEQUENCE: 213
cggatctctt ggttctcgca tcgatgaaga acgcagcgaa atgcgatacg taatgtgaat 60
tgcagaattc cgtgaatcat cgaatcgcct ttgaacgcac attgcgcccc ttggtattcc 120
agggggcatg cctgtttgag cgtcatttcc ttctcaaaca ttctgtttgg tagtgagtga 180
tactctttgg agttaacttg aaattgctgg ccttttcatt ggatgttttt tttccaaaga 240
gaggtttctc tgcgtgcttg aggtataatg caagtacggt cgttttaggt tttaccaact 300
gcggctaatc tttttttata ctgagcgtat tggaacgtta tcgataagaa gagagcgtct 360
aggcgaacaa tgttcttaaa gtttgacctc aaatcaggta gccttagtaa cggcgagtga 420
agcggcaaaa gctcaaattt gaaatctggt accttcggtg cccgagttgt agcatatcaa 480
taagcggagg aaaagaaacc aaccgggatt gtagggataa cagggtaatg agtcgacaaa 540
atgatacggc gaccaccgag atctacactc tttccctaca cgacgctctt ccgatctcca 600
aagcacgtac gggaagtaga tcggaagagc acacgtctga actccagtca caatcagtct 660
cgtatctcgt atgccgtctt ctgcttgttg tcgactc 697

<210> SEQ ID NO 214
<211> LENGTH: 727
<212> TYPE: DNA
<213> ORGANISM: Artificial
<220> FEATURE:
<223> OTHER INFORMATION: Polynucleotide

<400> SEQUENCE: 214
cggatctctt ggttctcgca tcgatgaaga acgcagcgaa atgcgatacg taatgtgaat 60
tgcagaattc cgtgaatcat cgaatcgcct ttgaacgcac attgcgcccc ttggtattcc 120
agggggcatg cctgtttgag cgtcatttcc ttctcaaaca ttctgtttgg tagtgagtga 180
tactctttgg agttaacttg aaattgctgg ccttttcatt ggatgttttt tttccaaaga 240
gaggtttctc tgcgtgcttg aggtataatg caagtacggt cgttttaggt tttaccaact 300
gcggctaatc tttttttata ctgagcgtat tggaacgtta tcgataagaa gagagcgtct 360
aggcgaacaa tgttcttaaa gtttgacctc aaatcaggta gccttagtaa cggcgagtga 420
agcggcaaaa gctcaaattt gaaatctggt accttcggtg cccgagttgt aatttggaga 480
gggcaacttt ggggccgttc cgcatatcaa taagcggagg aaaagaaacc aaccgggatt 540
gtagggataa cagggtaatg agtcgacaaa atgatacggc gaccaccgag atctacactc 600
tttccctaca cgacgctctt ccgatctgta cccgaggttc catactcaga tcggaagagc 660
acacgtctga actccagtca caatcagtct cgtatctcgt atgccgtctt ctgcttgttg 720
tcgactc 727

<210> SEQ ID NO 215
<211> LENGTH: 1727
<212> TYPE: DNA
<213> ORGANISM: Artificial
<220> FEATURE:
<223> OTHER INFORMATION: Polynucleotide

<400> SEQUENCE: 215
ttacaatgaa gagtttgatc ctggctcagg atgaacgcta gctacaggct taacacatgc 60
aagtcgaggg gcagcatttt agtttgcttg caaactgaag atggcgaccg gcgcacgggt 120
gagtaacacg tatccaacct gccgataact ccggaatagc ctttcgaaag aaagattaat 180
accggatagc atacgaatat cgcatgatat ttttattaaa gaatttcggt tatcgatggg 240
gatgcgttcc attagtttgt tggcggggta acggcccacc aagactacga tggatagggg 300
ttctgagagg aaggtccccc acattggaac tgagacacgg tccaaactcc tacgggaggc 360
agcagtgagg aatattggta caatagtggg cgagagcctg aaccagccaa gtagcgtgaa 420

```
ggatgaaggc tctatgggtc gtaaacttct tttatatggg aataaagttt tccacgtgtg    480
gaattttgta tgtaccatat gaataaggat cggctaactc cgtgccagca gccgcggtaa    540
tacggaggat ccgagcgtta tccggattta ttgggtttaa atctgggagc gtaggtggat    600
tgttaagtca gttgtgaaag tttgcggctc aaccgtaaaa ttgcagttga aactggcagt    660
cttgagtaca gtagaggtgg gcggaattcg tggtgtagcg gtgaaatgct tagatatcac    720
gaagaactcc gattgcgaag gcagctcact agactgttac tgacactgat gctcgaaagt    780
gtaggtatca aacaggatta gataccctgg tagtccacac agtaaacgat gaatactcgc    840
tgtttgcgat atacagtaag cggccaagcg aaagcattaa gtattccacc tggcatggta    900
cgccggcaac ggtgaaactc aaaggaattg acgggggccc gcacaagcgg aggaacatgt    960
ggtttaattc gatgatacgc gaggaacctt acccgggctt aaattgcaac agaatatatt   1020
ggaaacagta tagccgtaag gctgttgtga aggtgctgca tggttgtcgt cagctcgtgc   1080
cgtgaggtgt cggcttaagt gccataacga gcgcaaccct tatctttagt tactaacagg   1140
ttatgctgag gactctagag agactgccgt cgtaagatgt gaggaaggtg gggatgacgt   1200
caaatcagca cggcccttac gtccggggct acacacgtgt tacaatgggg ggtacagaag   1260
gcagctacac ggcgacgtga tgctaatccc aaaaacctct ctcagttcgg atcgaagtct   1320
gcaacccgac ttcgtgaagc tggattcgct agtaatcgcg catcagccat ggcgcggtga   1380
atacgttccc gggccttgta cacaccgccc gtcaagccat gaaagccggg ggtacctgaa   1440
gtacgtaacc gcaaggagcg tcctagggta aaactggtaa ttggggctaa gtcgtaacaa   1500
ggtagccgta ccggaaggtg cggctggaac acctcctttc ttagggataa caggtaatg    1560
agtcgacaaa atgatacggc gaccaccgag atctacactc tttccctaca cgacgctctt   1620
ccgatctctc agccaatgag aaggagcaga tcggaagagc acacgtctga actccagtca   1680
caatcagtct cgtatctcgt atgccgtctt ctgcttgttg tcgactc                 1727
```

<210> SEQ ID NO 216
<211> LENGTH: 1720
<212> TYPE: DNA
<213> ORGANISM: Artificial
<220> FEATURE:
<223> OTHER INFORMATION: Polynucleotide

<400> SEQUENCE: 216

```
acaacgaaga gtttgatcct ggctcaggat gaacgctagc gacaggctta acacatgcaa     60
gtcgaggggc agcggggtgt agcaatacac cgccggcgac cggcgcacgg gtgagtaacg    120
cgtatgcaac ttgcctatca gagggggata acccggcgaa agtcggacta ataccgcatg    180
aagcagggat cccgcatggg aatatttgct aaagattcat cgctgataga taggcatgcg    240
ttccattagg cagttggcgg ggtaacggcc caccaaaccg acgatggata ggggttctga    300
gaggaaggtc cccacattg gtactgagac acggaccaaa ctcctacggg aggcagcagt     360
gaggaatatt ggtacaatag tgggcgtaag cctgaaccag ccaagtcgcg tgagggatga    420
aggttctatg gatcgtaaac ctcttttata agggaataaa gtgcgggacg tgtcccgttt    480
tgtatgtacc ttatgaataa ggatcggcta actccgtgcc agcagccgcg gtaatacgga    540
ggatccgagc gttatccgga tttattgggt ttaaatctgg gtgcgtaggc ggcctttttaa   600
gtcagcggtg aaagtctgtg gctcaaccat agaattgccg ttgaaactgg ggggcttgag    660
tatgtttgag gcaggcggaa tgcgtggtgt agcggtgaaa tgcatagata tcacgcagaa    720
```

```
ccccgattgc gaaggcagcc tgccaagcca ttactgacgc tgatgcacga aagcgtgggg    780
atcaaacagg attagatacc ctggtagtcc acgcagtaaa cgatgatcac tagctgtttg    840
cgatacactg taagcggcac agcgaaagcg ttaagtgatc cacctggcat ggtacgccgg    900
caacggtgaa actcaaagga attgacgggg gcccgcacaa gcggaggaac atgtggttta    960
attcgatgat acgcgaggaa ccttacccgg gtttgaacgc attcggaccg aggtggaaac   1020
accttttcta gcaatagccg tttgcgaggt gctgcatggt tgtcgtcagc tcgtgccgtg   1080
aggtgtcggc ttaagtgcca taacgagcgc aacccttgcc actagttact aacaggttag   1140
gctgaggact ctggtgggac tgccagcgta agctgcgagg aaggcgggga tgacgtcaaa   1200
tcagcacggc ccttacatcc ggggcgacac acgtgttaca atggcgtgga caaagggagg   1260
ccacctggcg acagggagcg aatccccaaa ccacgtctca gttcggatcg gagtctgcaa   1320
cccgactccg tgaagctgga ttcgctagta atcgcgcatc agccatggcg cggtgaatac   1380
gttcccgggc cttgtacaca ccgcccgtca agccatggga gccgggggta cctgaagtcc   1440
gtaaccgcga ggatcggcct agggtaaaac tggtgactgg ggctaagtcg taacaaggta   1500
gccgtaccgg aaggtgcggc tggaacacct cctttaggga taacagggta atgagtcgac   1560
aaaatgatac ggcgaccacc gagatctaca ctctttccct acacgacgct cttccgatct   1620
cccacaaaga tcgcgccggc agatcggaag agcacacgtc tgaactccag tcacaatcag   1680
tctcgtatct cgtatgccgt cttctgcttg ttgtcgactc                         1720
```

<210> SEQ ID NO 217
<211> LENGTH: 1693
<212> TYPE: DNA
<213> ORGANISM: Artificial
<220> FEATURE:
<223> OTHER INFORMATION: Polynucleotide

<400> SEQUENCE: 217

```
gagagtttga ttctggctca ggacgaacgc tggcggcgcg cctaacacat gcaagtcgaa     60
cgagcgagag aggagcttgc tttctcaagc gagtggcgaa cgggtgagta acgcgtgagg    120
aacctgcctc aaagaggggg acaacagttg gaaacgactg ctaataccgc ataagcccac    180
gacctggcat cgggtagagg gaaaaggagc aatccgcttt gagatggcct cgcgtccgat    240
tagctagttg gtgaggtaac ggcccaccaa ggcgacgatc ggtagccgga ctgagaggtt    300
gaacggccac attgggactg agacacggcc cagactccta cgggaggcag cagtggggaa    360
tattgcaaca atagtggggg aaaccctgat gcagcgacgc cgcgtggagg aagaaggtct    420
tcggattgta aactcctgtt gttgaggaag ataatgacgg tactcaacaa ggaagtgacg    480
gctaactacg tgccagcagc cgcggtaaaa cgtaggtcac aagcgttgtc cggaattact    540
gggtgtaaat ctgggagcgc aggcgggaag gcaagttgga agtgaaatcc atgggctcaa    600
cccatgaact gctttcaaaa ctgtttttct tgagtagtgc agaggtaggc ggaattcccg    660
gtgtagcggt ggaatgcgta gatatcggga ggaacaccag tggcgaaggc ggcctactgg    720
gcaccaactg acgctgaggc tcgaaagtgt gggtagcaaa caggattaga taccctggta    780
gtccacactg taaacgatga ttactaggtg ttggaggatt gaccccttca gtgccgcagt    840
taacacaata agtaatccac ctggcatggt acgaccgcaa ggttgaaact caaaggaatt    900
gacgggggcc cgcacaagca gtggagtatg tggtttaatt cgacgcaacg cgaagaacct    960
taccaagtct tgacatcctg cgacgcgcat agaaatatgt gtttcttcgg gaccagagac   1020
aggtggtgca tggttgtcgt cagctcgtgt cgtgagatgt tgggttaagt cccgcaacga   1080
```

gcgcaaccct tatggtcagt tactacgcaa gaggactctg gccagactgc cgttgacaaa 1140
acggaggaag gtggggatga cgtcaaatca tcatgccctt tatgacttgg gctacacacg 1200
tactacaatg gcgttaaaca aagagaagca agaccgcgag gcgagcaaaa ctcagaaact 1260
tcgtcccagt tcggactgca ggctgcaact cgcctgcacg aagtcggaat tgctagtaat 1320
cgcagatcag catgctgcgg tgaatacgtt cccgggcctg tacacaccgc ccgtcacacc 1380
atgagagccg gggggacccg aagtcggtag tctaaccgca aggaggacgc cgccgaagta 1440
aaactggtga ttggggtgaa gtcgtaacaa ggtagccgta gagaacctgc ggctggatca 1500
cctcctttag ggataacagg gtaatgagtc gacaaaatga tacggcgacc accgagatct 1560
acactctttc cctacacgac gctcttccga tctcaagtca atgaaagcgc atgagatcgg 1620
aagagcacac gtctgaactc cagtcacaat cagtctcgta tctcgtatgc cgtcttctgc 1680
ttgttgtcga ctc 1693

<210> SEQ ID NO 218
<211> LENGTH: 1648
<212> TYPE: DNA
<213> ORGANISM: Artificial
<220> FEATURE:
<223> OTHER INFORMATION: Polynucleotide

<400> SEQUENCE: 218
ttgatcctgg ctcaggatga acgctggcgg cgtgcttaac acatgcaagt cgaacgaagc 60
acttttacag atttcttcgg aatgaagttt tagtgactga gtggcggacg ggtgagtaac 120
gcgtgggtaa cctgcctcac acaggggggat aacagttgga aacggctgct aataccgcat 180
aagcgcacag taccgcatgg tacagtgtga aaaactccgg tggtgtgaga tggacccgcg 240
tctgattagc tagttggcag ggcaacggcc taccaaggcg acgatcagta gccgacctga 300
gagggtgacc ggccacattg ggactgagac acggcccaaa ctcctacggg aggcagcagt 360
ggggaatatt gcaacaatag tgggggaaac cctgatgcag cgacgccgcg tgagcgaaga 420
agtatttcgg tatgtaaagc tctatcagca gggaagaaga aatgacggta cctgactaag 480
aagcaccggc taaatacgtg ccagcagccg cggtaatacg tatggtgcaa gcgttatccg 540
gatttactgg gtgtaaatct gggagcgcag gcggaaggct aagtctgatg tgaaagcccg 600
gggctcaacc ccggtactgc attggaaact ggtcatctag agtgtcggag gggtaagtgg 660
aattcctagt gtagcggtga aatgcgtaga tattaggagg aacaccagtg gcgaaggcgg 720
cttactggac gataactgac gctgaggctc gaaagcgtgg ggagcaaaca ggattagata 780
ccctggtagt ccacgccgta aacgatgaat actaggtgtc ggaaagcaca gcttttcggt 840
gccgccgcaa acgcattaag tattccacct ggcatggtac gttcgcaaga atgaaactca 900
aaggaattga cggggacccg cacaagcggt ggagcatgtg gtttaattcg aagcaacgcg 960
aagaacctta ccaagtcttg acatccttct gaccggacag taatgtgtcc tttccttcgg 1020
gacagaagtg acaggtggtg catggttgtc gtcagctcgt gtcgtgagat gttgggttaa 1080
gtcccgcaac gagcgcaacc cttatcccca gtagccagcg gttcggacgg gcactctgag 1140
gagactgcca gggataacct ggaggaaggt ggggatgacg tcaaatcatc atgcccctta 1200
tgacttgggc tacacacgtg ctacaatggc gtaaacaaag ggaagcgaga ccgtgaggtg 1260
gagcaaatcc caaaaaataac gtctcagttc ggactgtagt ctgcaacccg actacacgaa 1320
gctggaatcg ctagtaatcg cagatcagaa tgctgcggtg aatacgttcc cgggtcttgt 1380

```
acacaccgcc cgtcacacca tgggagttgg aaatgcccga agtcagtgac ccaaccgcaa   1440

ggagggagct gcgaaggcag gttagggata acagggtaat gagtcgacaa aatgatacgg   1500

cgaccaccga gatctacact ctttccctac acgacgctct tccgatctgt tagggagcta   1560

gtttaggcag atcggaagag cacacgtctg aactccagtc acaatcagtc tcgtatctcg   1620

tatgccgtct tctgcttgtt gtcgactc                                      1648
```

<210> SEQ ID NO 219
<211> LENGTH: 1732
<212> TYPE: DNA
<213> ORGANISM: Artificial
<220> FEATURE:
<223> OTHER INFORMATION: Polynucleotide

<400> SEQUENCE: 219

```
tttttgtgga gggttcgatt ctggctcagg atgaacgctg gcggcgtgct taacacatgc     60

aagtcgaacg ggatccatca agcttgcttg gtggtgagag tggcgaacgg gtgagtaatg    120

cgtgaccgac ctgccccatg ctccggaata gctcctggaa acgggtggta atgccggatg    180

ttccacatga tcgcatgtga ttgtgggaaa gattctatcg gcgtgggatg gggtcgcgtc    240

ctatcagctt gttggtgagg taacggctca ccaaggcttc gacgggtagc cggcctgaga    300

gggcgaccgg ccacattggg actgagatac ggcccagact cctacgggag gcagcagtgg    360

ggaatattgc aacaatagtg ggcgcaagcc tgatgcagcg acgccgcgtg agggatggag    420

gccttcgggt tgtaaacctc ttttgtttgg gagcaagcct tcgggtgagt gtacctttcg    480

aataagcgcc ggctaactac gtgccagcag ccgcggtaat acgtagggcg caagcgttat    540

ccggatttat tgggcgtaaa tctgggctcg taggcggctc gtcgcgtccg gtgtgaaagt    600

ccatcgctta acggtggatc tgcgccgggt acgggcgggc tggagtgcgg taggggagac    660

tggaattccc ggtgtaacgg tggaatgtgt agatatcggg aagaacaccg atggcgaagg    720

caggtctctg ggccgtcact gacgctgagg agcgaaagcg tggggagcga acaggattag    780

ataccctggt agtccacgcc gtaaacggtg gacgctggat gtggggcacg ttccacgtgt    840

tccgtgtcgg agctaacgcg ttaagcgtcc cgcctggcat ggtacggccg caaggctaaa    900

actcaaagaa attgacgggg gcccgcacaa gcggcggagc atgcggatta attcgatgca    960

acgcgaagaa ccttacctgg gcttgacatg ttcccgacga cgccagagat ggcgtttccc   1020

ttcggggcgg gttcacaggt ggtgcatggt cgtcgtcagc tcgtgtcgtg agatgttggg   1080

ttaagtcccg caacgagcgc aaccctcgcc ccgtgttgcc agcacgttat ggtgggaact   1140

cacgggggac cgccggggtt aactcggagg aaggtgggga tgacgtcaga tcatcatgcc   1200

ccttacgtcc agggcttcac gcatgctaca atggccggta cagcgggatg cgacatggcg   1260

acatggagcg gatccctgaa aaccggtctc agttcggatc ggagcctgca acccggctcc   1320

gtgaaggcgg agtcgctagt aatcgcggat cagcaacgcc gcggtgaatg cgttcccggg   1380

ccttgtacac accgcccgtc aagtcatgaa agtgggcagc acccgaagcc ggtggcctaa   1440

ccccttgtgg gatggagccg tctaaggtga ggctcgtgat tgggactaag tcgtaacaag   1500

gtagccgtac cggaaggtgc ggctggatca cctcctttct acggagtagg gataacaggg   1560

taatgagtcg acaaaatgat acggcgacca ccgagatcta cactctttcc ctacacgacg   1620

ctcttccgat ctgagcacgg gaattactcc gaagatcgga agagcacacg tctgaactcc   1680

agtcacaatc agtctcgtat ctcgtatgcc gtcttctgct tgttgtcgac tc           1732
```

<210> SEQ ID NO 220
<211> LENGTH: 1660
<212> TYPE: DNA
<213> ORGANISM: Artificial
<220> FEATURE:
<223> OTHER INFORMATION: Polynucleotide

<400> SEQUENCE: 220
cagattgaac gctggcggca ggcttaacac atgcaagtcg aacggtaaca ggaagaagct 60
tgcttctttg ctgacgagtg gcggacgggt gagtaatgct tgggtatctg gcttatggag 120
ggggataact acgggaaact gtagctaata ccgcgtagta tcggaagatg aaagtgtggg 180
accgcaaggc cacatgccat aggatgagcc caagtgggat taggtagttg gtgaggtaat 240
ggctcaccaa gccgacgatc tctagctggt ctgagaggat gaccagccac accgggactg 300
agacacggcc cggactccta cgggaggcag cagtggggaa tattgcgaca atagtggggg 360
caaccctgac gcagccatgc cgcgtgaatg aagaaggcct tcgggttgta aagttctttc 420
ggtagcgagg aaggcattta gtttaataga ctagatgatt gacgttaact acagaagaag 480
caccggctaa ctccgtgcca gcagccgcgg taatacggag ggtgcgagcg ttaatcggaa 540
taactgggcg taaatctggg cacgcaggcg gacttttaag tgaggtgtga aagccccggg 600
cttaacctgg gaattgcatt tcagactggg agtctagagt actttaggga ggggtagaat 660
tccacgtgta gcggtgaaat gcgtagagat gtggaggaat accgaaggcg aaggcagccc 720
cttgggaatg tactgacgct catgtgcgaa agcgtgggga gcaaacagga ttagataccc 780
tggtagtcca cgctgtaaac gctgtcgatt tggggattgg gcttaatgct tggtgcccgt 840
agctaacgtg ataaatcgac cgcctggcat ggtacggccg caaggttaaa actcaaatga 900
attgacgggg gcccgcacaa gcggtggagc atgtggttta attcgatgca acgcgaagaa 960
ccttacctac tcttgacatc cagagaactt tccagagatg gattggtgcc ttcgggagct 1020
ctgagacagg tgctgcatgg ctgtcgtcag ctcgtgttgt gaaatgttgg gttaagtccc 1080
gcaacgagcg caacccttat cctttgttgc cagcgatttg gtcgggaact caaaggagac 1140
tgccggtgat aaaccggagg aaggtgggga tgacgtcaag tcatcatggc ccttacgagt 1200
agggctacac acgtgctaca atggcgtata cagagggagg cgaagcagcg atgtggagcg 1260
aatcccagaa agtgcgtcta agtccggatt ggagtctgca actcgactcc atgaagtcgg 1320
aatcgctagt aatcgcgaat cagaatgtcg cggtgaatac gttcccgggc cttgtacaca 1380
ccgcccgtca caccatggga gtgggttgta ccagaagtag atagcttaac cttcgggagg 1440
gcgtttacca cggtatgatt catgactggg gtgataggga taacagggta atgagtcgac 1500
aaaatgatac ggcgaccacc gagatctaca ctctttccct acacgacgct cttccgatct 1560
gagccataaa ccagctcgga agatcggaag agcacacgtc tgaactccag tcacaatcag 1620
tctcgtatct cgtatgccgt cttctgcttg ttgtcgactc 1660

<210> SEQ ID NO 221
<211> LENGTH: 1654
<212> TYPE: DNA
<213> ORGANISM: Artificial
<220> FEATURE:
<223> OTHER INFORMATION: Polynucleotide

<400> SEQUENCE: 221
tgatcctggc tcaggacgaa cgctggcggc gtgcctaata catgcaagta gaacgctgaa 60
gagaggagct tgctcttctt ggatgagttg cgaacgggtg agtaacgcgt aggtaacctg 120

-continued

```
cctggtagcg ggggataact attggaaacg atagctaata ccgcataaaa ttgattattg    180
catgataatt aattgaaaga tgcaattgca tcactaccag atggacctgc gttgtattag    240
ctagttggtg aggtaacggc tcaccaaggc gacgatacat agccgacctg agagggtgat    300
cggccacact gggactgaga cacggcccag actcctacgg gaggcagcag tagggaatct    360
tcggacaata gtggggggaa ccctgaccga gcaacgccgc gtgagtgaag aaggttttcg    420
gatcgtaaag ctctgttgta agagaagaac gggtgtgaga gtggaaagtt cacactgtga    480
cggtatctta ccagaaaggg acggctaact acgtgccagc agccgcggta atacgtaggt    540
cccgagcgtt gtccggattt attgggcgta aatctgcgag cgcaggcggt tagataagtc    600
tgaagttaaa ggctgtggct taaccatagt atgctttgga aactgtttaa cttgagtgca    660
gaaggggaga gtggaattcc atgtgtagcg gtgaaatgcg tagatatatg gaggaacacc    720
ggtggcgaaa gcggctctct ggtctgtaac tgacgctgag gctcgaaagc gtggggagca    780
aacaggatta gataccctgg tagtccacgc cgtaaacgat gagtgctagg tgttaggccc    840
tttccggggc ttagtgccgc agctaacgca ttaagcactc cgcctggcat ggtacgaccg    900
caaggttgaa actcaaagga attgacgggg gcccgcacaa gcggtggagc atgtggttta    960
attcgaagca acgcgaagaa ccttaccagg tcttgacatc cctctgaccg ctctagagat   1020
agagttttcc ttcgggacag aggtgacagg tggtgcatgg ttgtcgtcag ctcgtgtcgt   1080
gagatgttgg gttaagtccc gcaacgagcg caacccctat tgttagttgc catcattcag   1140
ttgggcactc tagcgagact gccggtaata aaccggagga aggtggggat gacgtcaaat   1200
catcatgccc cttatgacct gggctacaca cgtgctacaa tggctggtac aacgagtcgc   1260
aagccggtga cggcaagcta atctctgaaa gccagtctca gttcggattg taggctgcaa   1320
ctcgcctaca tgaagtcgga atcgctagta atcgcggatc agcacgccgc ggtgaatacg   1380
ttcccgggcc ttgtacacac cgcccgtcac accacgagag tttgtaacac ccgaagtcgg   1440
tgaggtaacc gtaaggagcc agccgcctta gggataacag ggtaatgagt cgacaaaatg   1500
atacggcgac caccgagatc tacactcttt ccctacacga cgctcttccg atctttggcc   1560
ggagtacagt atcaagatcg gaagagcaca cgtctgaact ccagtcacaa tcagtctcgt   1620
atctcgtatg ccgtcttctg cttgttgtcg actc                                1654
```

```
<210> SEQ ID NO 222
<211> LENGTH: 1691
<212> TYPE: DNA
<213> ORGANISM: Artificial
<220> FEATURE:
<223> OTHER INFORMATION: Polynucleotide

<400> SEQUENCE: 222

gctggcggcg tgcttaacac atgcaagtcg aacgaagagc gatggaagct tgcttctatc     60
aatcttagtg gcgaacgggt gagtaacgcg taatcaacct gcccttcaga gggggacaac    120
agttggaaac gactgctaat accgcatacg atctaacctc ggcatcgagg aaagatgaaa    180
ggtggcctct atttataagc tatcactgaa ggaggggatt gcgtctgatt agctagttgg    240
aggggtaacg gcccaccaag gcgatgatca gtagccggtc tgagaggatg aacggccaca    300
ttgggactga gacacggccc agactcctac gggaggcagc agtggggaat cttccgacaa    360
tagtggacga aagtctgacg gagcaacgcc gcgtgagtga tgacggcctt cgggttgtaa    420
agctctgtta atcgggacga aaggccttct tgcgaacagt tagaaggatt gacggtaccg    480
gaatagaaag ccacggctaa ctacgtgcca gcagccgcgg taatacgtag gtggcaagcg    540
```

ttgtccggaa ttattgggcg taaatctgcg cgcgcaggcg gatcagtcag tctgtcttaa 600
aagttcgggg cttaaccccg tgatgggatg gaaactgctg atctagagta tcggagagga 660
aagtggaatt cctagtgtag cggtgaaatg cgtagatatt aggaagaaca ccagtggcga 720
aggcgacttt ctggacgaaa actgacgctg aggcgcgaaa gccaggggag cgaacgggat 780
tagatacccc ggtagtcctg gccgtaaacg atgggtacta ggtgtaggag gtatcgaccc 840
cttctgtgcc ggagttaacg caataagtac cccgcctggc atggtacgac cgcaaggttg 900
aaactcaaag gaattgacgg gggcccgcac aagcggtgga gtatgtggtt taattcgacg 960
caacgcgaag aaccttacca ggtcttgaca ttgatggaca gaaccagaga tggttcctct 1020
tcttcggaag ccagaaaaca ggtggtgcac ggttgtcgtc agctcgtgtc gtgagatgtt 1080
gggttaagtc ccgcaacgag cgcaacccct atcttatgtt gccagcactt tgggtgggaa 1140
ctcatgagag actgccgcag acaatgcgga ggaaggcggg gatgacgtca aatcatcatg 1200
ccccttatga cctgggctac acacgtacta caatgggagt taatagacgg aagcgagatc 1260
gcgagatgga gcaaacccga gaaacactct ctcagttcgg atcgtaggct gcaactcgcc 1320
tacgtgaagt cggaatcgct agtaatcgca ggtcagcata ctgcggtgaa tacgttcccg 1380
ggccttgtac acaccgcccg tcacaccacg aaagtcggaa gtgcccaaag ccggtggggt 1440
aaccttcggg agccagccgt ctaaggtaaa gtcgatgatt ggggtgaagt cgtaacaagg 1500
tagcctaggg ataacagggt aatgagtcga caaaatgata cggcgaccac cgagatctac 1560
actctttccc tacacgacgc tcttccgatc tgtcccgcta ttcggcttgt cagatcggaa 1620
gagcacacgt ctgaactcca gtcacaatca gtctcgtatc tcgtatgccg tcttctgctt 1680
gttgtcgact c 1691

<210> SEQ ID NO 223
<211> LENGTH: 1694
<212> TYPE: DNA
<213> ORGANISM: Artificial
<220> FEATURE:
<223> OTHER INFORMATION: Polynucleotide

<400> SEQUENCE: 223
agagtttgat cctggctcag gatgaacgct ggcggcgtgc ctaacacatg caagtcgaac 60
gatgaaaccg ccctcgggcg gacatgaagt ggcgaacggg tgagtaacac gtgaccaacc 120
tgccccttgc tccgggacaa ccttgggaaa ccgaggctaa taccggatac tcctcgcccc 180
cctcctgggg ggcccgggaa agcccagacg gcaagggatg ggtcgcggc ccattaggta 240 gtaggcgggg taacggccca cctagcccgc gatgggtagc cgggttgaga gaccgaccgg 300
ccacattggg actgagatac ggcccagact cctacgggag gcagcagtgg ggaattttgc 360
gacaatagtg ggggaaaccc tgacgcagca acgccgcgtg cgggacgacg gccttcgggt 420
tgtaaaccgc tttcagcagg gaagaaattc gacggtacct gcagaagaag ctccggctaa 480
ctacgtgcca gcagccgcgg taatacgtag ggagcgagcg ttatccggat tcattgggcg 540
taaatctgag cgcgtaggcg gcctctcaag cgggatctct aatccgaggg ctcaaccccc 600
ggccggatcc cgaactggga ggctcgagtt cggtagaggc aggcggaatt cccggtgtag 660
cggtggaatg cgcagatatc gggaagaaca ccgatggcga aggcagcctg ctgggccgca 720
actgacgctg aggcgcgaaa gctaggggag cgaacaggat tagataccct ggtagtccta 780
gccgtaaacg atggatacta ggtgtggggc tccgccctcc gtgccgcagc caacgcatta 840
agtatcccgc ctggcatggt acggccgcaa ggctaaaact caaaggaatt gacgggggcc 900
cgcacaagca gcggagcatg tggcttaatt cgaagcaacg cgaagaacct taccagggct 960
tgacatggac gtgaagccgg ggaaacccgg tggccgagag gagcgtccgc aggtggtgca 1020
tggctgtcgt cagctcgtgt cgtgagatgt tgggttaagt cccgcaacga gcgcaacccc 1080
tgccccatgt tgccagcatt aggttgggga ctcatggggg actgccggcg tcaagccgga 1140
ggaaggtggg gacgacgtca agtcatcatg ccctttatgc cctgggctgc acacgtgcta 1200
caatggccgg tacaacgggc tgcgagaccg cgaggtcgag cgaatccctc aaagccggcc 1260
ccagttcgga tcggaggctg caacccgcct ccgtgaagtc ggagttgcta gtaatcgcgg 1320
atcagcatgc cgcggtgaat acgttcccgg gccttgtaca caccgcccgt cacaccaccc 1380
gagtcgtatg cacccgaagc cgccggccga acccgcaagg ggcggaggcg tcgaaggtgt 1440
ggagggtaag gggggtgaag tcgtaacaag gtagccgtac cggaaggtgc ggctggatca 1500
cctcctttta gggataacag ggtaatgagt cgacaaaatg atacggcgac caccgagatc 1560
tacactcttt ccctacacga cgctcttccg atctcttcgt gttggtgccg gtctagatcg 1620
gaagagcaca cgtctgaact ccagtcacaa tcagtctcgt atctcgtatg ccgtcttctg 1680
cttgttgtcg actc 1694

<210> SEQ ID NO 224
<211> LENGTH: 1744
<212> TYPE: DNA
<213> ORGANISM: Artificial
<220> FEATURE:
<223> OTHER INFORMATION: Polynucleotide

<400> SEQUENCE: 224
tgaactggag agtttgattc tggctcagat tgaacgctgg cggcgtgctt aacacatgca 60
agtcgaacgc gaaagggact tcggtcctga gtaaagtggc gcacgggtga gtaacgcgtg 120
gataatctgc ccttatgatc gggataacag ttggaaacgg ctgctaatac cggatacgct 180
caaaatgaac tttttgagga aagatggcct ctgcttgcat gctatcacgt aaggatgagt 240
ccgcgtccca ttagcttgtt ggcggggtaa cggcccacca aggcatcgat gggtagccga 300
tttgagagga tgatcggcca cactggaact gaaacacggt ccagactcct acgggaggca 360
gcagtgggga atattgcgac aatagtgggc gaaagcctga cgcagcgacg ccgcgtgagg 420
gatgaaggtt ttcggatcgt aaacctctgt cagaagggaa gaaactacgt tgtgctaatc 480
agcagcgtac tgacggtacc ttcaaaggaa gcaccggcta actccgtgcc agcagccgcg 540
gtaatacgga gggtgcaagc gttaatcgga attactgggc gtaaatctgc gcacgtaggc 600
tgtagtgtaa gtcaggggtg aaatcccacg gctcaaccgt ggaactgcct ttgatactgc 660
acaacttgaa tccgggagag ggtggcggaa ttccaggtgt aggagtgaaa tccgtagata 720
tctggaggaa catcagtggc gaaggcggcc acctggaccg gtattgacgc tgaggtgcga 780
aagcgtgggg agcaaacagg attagatacc ctggtagtcc acgctgtaaa cgatggatgc 840
tagatgtcgg ggagtattct tcggtgtcgt agttaacgcg ttaagcatcc cgcctggcat 900
ggtacggtcg caaggctgaa actcaaagaa attgacgggg gcccgcacaa gcggtggagt 960
atgtggttta attcgatgca acgcgaagaa ccttacctag gtttgacatc cacggaaccc 1020
tcccgaaaag gaggggtgcc cttcggggag ccgtgagaca ggtgctgcat ggctgtcgtc 1080
agctcgtgtc gtgagatgtt gggttaagtc ccgcaacgag cgcaacccct atggatagtt 1140
gccagcaagt aatgttgggc actctattca gactgcccgg gttaaccggg aggaaggtgg 1200

```
ggacgacgtc aagtcatcat ggcccttacg cctagggcta cacacgtact acaatggcgc   1260
gcacaaaggg gagcgagacc gcgaggtgga gccaatccca aaaaacgcgt cccagtccgg   1320
attgcagtct gcaactcgac tgcatgaagt tggaatcgct agtaattcga gatcagcatg   1380
ctcgggtgaa tgcgttcccg ggccttgtac acaccgcccg tcacaccacg aaagtcggtt   1440
ttacccgaag ccggtgagcc aaccagcaat ggaggcagcc gtctacggta gggccgatga   1500
ttggggtgaa gtcgtaacaa ggtagccgta ggggaacctg cggctggatc acctccttta   1560
gggataacag ggtaatgagt cgacaaaatg atacggcgac caccgagatc tacactcttt   1620
ccctacacga cgctcttccg atctgtccga tcagtcgcgt gcacagatcg gaagagcaca   1680
cgtctgaact ccagtcacaa tcagtctcgt atctcgtatg ccgtcttctg cttgttgtcg   1740
actc                                                                1744
```

<210> SEQ ID NO 225
<211> LENGTH: 1711
<212> TYPE: DNA
<213> ORGANISM: Artificial
<220> FEATURE:
<223> OTHER INFORMATION: Polynucleotide

<400> SEQUENCE: 225

```
atggagagtt cgatcctggc tcaggatgaa cgctggcggc gcgcctaaca catgcaagtc     60
gaacgattaa agcaccttcg ggtgtgtata aagtggcgaa cggctgagta acacgtgggc    120
aacctgcccc tttcattggg atagccacgg gaaaccgtgg ataataccga atacttcgag    180
acttccgcat ggaagactcg agaaagctcc ggcggagagg gatgggcccg cggcctgtta    240
gcttgttggt ggggtaacgg cctaccaagg caatgatggg tagctgggtt gagagaccga    300
ccagccagat tgggactgag acacggccca gactcctacg ggaggcagca gtggggaatc    360
ttgcaacaat agtgggcgaa agcctgatgc agcgacgccg cgtgcgggat gaaggccttc    420
gggttgtaaa ccgctttcag cagggacgag gcgaaagtga cggtacctgc agaagaagcc    480
ccggctaact acgtgccagc agccgcggta atacgtaggg ggcaagcgtt atccggattc    540
attgggcgta aatctgcgct cgtaggcggt ctgttaggtc gggagttaaa tccgggggct    600
caacccccgc tcgctctcga taccggcaga cttgagtttg gtaggggaag gtggaattcc    660
tagtgtagcg gtggaatgcg cagatattag gaagaacacc agtggcgaag gcggccttct    720
gggccataac tgacgctgag gagcgaaagc taggggagca aacaggatta gataccctgg    780
tagtcctagc cgtaaacgat ggacactagg tgtgggggag tatttcttcc gtgccgcagc    840
taacgcatta agtgtcccgc ctggcatggt acggccgcaa ggctaaaact caaaggaatt    900
gacgggggcc cgcacaagca gcggagcatg tggtttaatt cgaagcaacg cgaagaacct    960
taccagggct tgacatttag gtgaagcggc ggaaacgtcg tggccgaaag gagcctaaac   1020
aggtggtgca tggctgtcgt cagctcgtgt cgtgagatgt taggttaagt cctgcaacga   1080
gcgcaaccct cgtcgtatgt tgccagcggt taggccgggc acccatacga gaccgccggc   1140
gtcaagccgg aggaaggtgg ggacgacgtc aagtcatcat gccccttatg tcctgggcta   1200
cacacgtgct acaatggccg gcacaatggg ctgccaaccc gcgagggtga gcgaatccct   1260
aaagccggtc ccagttcgga ttggaggctg caacccgcct ccatgaagtc ggagttgcta   1320
gtaatcgcgg atcagcacgc cgcggtgaat gcgttcccgg gccttgtaca caccgcccgt   1380
cacaccaccc gagtcgattg cacccgaagt cgtcggccta accttttagg agggagacgc   1440
```

```
cgaaggtgtg gttggtaagg ggggtgaagt cgtaacaagg tagccgtacc ggaaggtgcg   1500

gctggatcac ctcctttcta gggagtaggg ataacagggt aatgagtcga caaaatgata   1560

cggcgaccac cgagatctac actctttccc tacacgacgc tcttccgatc tacacgtcaa   1620

gcagcagtgg aagatcggaa gagcacacgt ctgaactcca gtcacaatca gtctcgtatc   1680

tcgtatgccg tcttctgctt gttgtcgact c                                  1711
```

```
<210> SEQ ID NO 226
<211> LENGTH: 1706
<212> TYPE: DNA
<213> ORGANISM: Artificial
<220> FEATURE:
<223> OTHER INFORMATION: Polynucleotide

<400> SEQUENCE: 226

agtttgatca tggctcagga cgaacgctgg cggcgtgcct aatacatgca agtcgaacga     60

gagcgaccgg tgcttgcact ggtcaatcta gtggcgaacg ggtgagtaac acgtgggtaa    120

cctgcccatc agagggggat aacatccgga aacggatgct aaaaccgcat aggtcttcga    180

gccgcatggc ttgaagagga aaagaggcgc aagcttctgc tgatggatgg acccgcggtg    240

cattagctag ttggtgaggt aacggctcac caaggccgtg atgcatagcc gacctgagag    300

ggtgatcggc cacattggga ctgagacacg gcccaaactc ctacgggagg cagcagtagg    360

gaatcttccg acaatagtgg acgcaagtct gacggagcaa cgccgcgtga gtgaagaagg    420

ttttcggatc gtaaaactct gttgttagag aagaacaagt gctagagtaa ctgttagcgc    480

cttgacggta tctaaccaga aagccacggc taactacgtg ccagcagccg cggtaatacg    540

taggtggcaa gcgttgtccg gatttattgg gcgtaaatct gcgagcgcag gcggttcctt    600

aagtctgatg tgaaagcccc cggctcaacc ggggagggtc attggaaact ggggaacttg    660

agtgcagaag aggagagtgg aattccatgt gtagcggtga aatgcgtaga tatatggagg    720

aacaccagtg gcgaaggcga ctctctggtc tgtaactgac gctgaggctc gaaagcgtgg    780

gtagcaaaca ggattagata ccctggtagt ccacgccgta aacgatgagt gctaagtgtt    840

ggagggtttc cgcccttcag tgctgcagtt aacgcattaa gcactccgcc tggcatggta    900

cgaccgcaag gttgaaactc aaaggaattg acggggaccc gcacaagcgg tggagcatgt    960

ggtttaattc gaagcaacgc gaagaacctt accaagtctt gacatccttt gaccactcta   1020

gagatagagc tttcccttcg ggacaaagt gacaggtggt gcatggttgt cgtcagctcg   1080

tgtcgtgaga tgttgggtta agtcccgcaa cgagcgcaac ccttattact agttgccagc   1140

attcagttgg gcactctagt gagactgccg gtgacaaacc ggaggaaggt ggggatgacg   1200

tcaaatcatc atgcccctta tgacttgggc tacacacgtg ctacaatgga tggtacaacg   1260

agcagcgaac tcgcgagggt aagcgaatct cttaaagcca ttctcagttc ggattgtagg   1320

ctgcaactcg cctacatgaa gccggaatcg ctagtaatcg cggatcagca cgccgcggtg   1380

aatacgttcc cgggtcttgt acacaccgcc cgtcacacca cgagagtttg taacacccaa   1440

agtcggtgag gtaaccattt ggagccagcc gcctaaggtg ggatagatga ttggggtgaa   1500

gtcgtaacaa ggtagccgta tagggataac agggtaatga gtcgacaaaa tgatacggcg   1560

accaccgaga tctacactct ttccctacac gacgctcttc cgatctatcc ttgcgcaggt   1620

cacctgagat cggaagagca cacgtctgaa ctccagtcac aatcagtctc gtatctcgta   1680

tgccgtcttc tgcttgttgt cgactc                                        1706
```

<210> SEQ ID NO 227
<211> LENGTH: 1697
<212> TYPE: DNA
<213> ORGANISM: Artificial
<220> FEATURE:
<223> OTHER INFORMATION: Polynucleotide

<400> SEQUENCE: 227
agagtttgat ccatggctca ggatgaacgc tggcggcgtg cttaacacat gcaagtcgaa 60
cgaagcattt aggattgaag ttttcggatg gatttcctat atgactgagt ggcggacggg 120
tgagtaacgc gtggggaacc tgccctatac agggggataa cagctggaaa cggctgctaa 180
taccgcataa gcgcacagaa tcgcatgatt cagtgtgaaa agccctggca gtataggatg 240
gtcccgcgtc tgattagctg gttggtgagg taacggctca ccaaggcgac gatcagtagc 300
cggcttgaga gagtgaacgg ccacattggg actgagacac ggcccaaact cctacgggag 360
gcagcagtgg ggaatattgc aacaatagtg ggggaaaccc tgatgcagcg acgccgcgtg 420
agtgaagaag tatttcggta tgtaaagctc tatcagcagg gaagaaaaca gacggtacct 480
gactaagaag ccccggctaa ctacgtgcca gcagccgcgg taatacgtag ggggcaagcg 540
ttatccggaa ttactgggtg taaatctggg tgcgtaggtg gcatggtaag tcagaagtga 600
aagcccgggg cttaaccccg ggactgcttt tgaaactgtc atgctggagt gcaggagagg 660
taagcggaat tcctagtgta gcggtgaaat gcgtagatat taggaggaac accagtggcg 720
aaggcggctt actggactgt cactgacact gatgcacgaa agcgtgggga gcaaacagga 780
ttagataccc tggtagtcca cgccgtaaac gatgaatact aggtgtcggg gccgtagagg 840
cttcggtgcc gcagcaaacg cagtaagtat tccacctggc atggtacgtt cgcaagaatg 900
aaactcaaag gaattgacgg ggacccgcac aagcggtgga gcatgtggtt taattcgaag 960
caacgcgaag aaccttacct ggtcttgaca tcccaatgac cgaaccttaa ccggtttttt 1020
ctttcgagac attggagaca ggtggtgcat ggttgtcgtc agctcgtgtc gtgagatgtt 1080
gggttaagtc ccgcaacgag cgcaacccct atctttagta gccagcattt gaggtgggca 1140
ctctagagag actgccaggg ataacctgga ggaaggtggg gacgacgtca aatcatcatg 1200
ccccttatgg ccagggctac acacgtgcta caatggcgta aacaaaggga agcgaagtcg 1260
tgaggcgaag caaatcccag aaataacgtc tcagttcgga ttgtagtctg caactcgact 1320
acatgaagct ggaatcgcta gtaatcgtga atcagaatgt cacggtgaat acgttcccgg 1380
gtcttgtaca caccgcccgt cacaccatgg gagtcagtaa cgcccgaagt cagtgaccca 1440
accgcaagga gggagctgcc gaaggtggga ccgataactg gggtgaagtc gtaacaaggt 1500
agccgtatcg gtagggataa cagggtaatg agtcgacaaa atgatacggc gaccaccgag 1560
atctacactc tttccctaca cgacgctctt ccgatctggc acctagaata gccgttgaga 1620
tcggaagagc acacgtctga actccagtca caatcagtct cgtatctcgt atgccgtctt 1680
ctgcttgttg tcgactc 1697

<210> SEQ ID NO 228
<211> LENGTH: 1684
<212> TYPE: DNA
<213> ORGANISM: Artificial
<220> FEATURE:
<223> OTHER INFORMATION: Polynucleotide

<400> SEQUENCE: 228
agagtttgat catggctcag gacgaacgct ggcggcgtgc ttaacacatg caagtcgaac 60
gatgaagcct agcttgctag gtggattagt ggcgaacggg tgagtaatac gtgagtaacc 120
tacctttaac tctgggataa gcctgggaaa ctgggtctaa taccggatac gaccaatctc 180
cgcatggggt gttggtggaa agcgttatgt agtggttata gatgggctca cggcctatca 240
gctcgttggt gaggtaacgg ctcaccaagg cgacgacggg tagccggcct gagagggtga 300
ccggccacac tgggactgag acacggccca gactcctacg ggaggcagca gtggggaata 360
ttgcaacaat agtgggcgca agcctgatgc agcgacgccg cgtgagggat gacggccttc 420
gggttgtaaa cctctgttag cagggaagaa gagagattga cggtacctgc agagaaagcg 480
ccggctaact acgtgccagc agccgcggta atacgtaggg cgcgagcgtt gtccggaatt 540
attgggcgta aatctgagct tgtaggcggt ttgtcgcgtc tgctgtgaaa ggccggggct 600
taactccgtg tattgcagtg ggtacgggca gactagagtg cagtagggga gactggaatt 660
cctggtgtag cggtggaatg cgcagatatc aggaggaaca ccgatggcga aggcaggtct 720
ctgggctgta actgacgctg agaagcgaaa gcatggggag cgaacaggat tagataccct 780
ggtagtccat gccgtaaacg ttgggcacta ggtgtggggg acattccacg ttttccgcgc 840
cgtagctaac gcattaagtg ccccgcctgg catggtacgg ccgcaaggct aaaactcaaa 900
gaaattgacg gggcccgca caagcggcgg agcatgcgga ttaattcgat gcaacgcgaa 960
gaaccttacc aaggcttgac atatactgga ccgcatcaga gatggtgttt cccttcgggg 1020
ctggtataca ggtggtgcat ggttgtcgtc agctcgtgtc gtgagatgtt gggttaagtc 1080
ccgcaacgag cgcaaccctc gttctatgtt gccagcacgt tatggtgggg actcatagga 1140
gactgccggg gtcaactcgg aggaaggtgg ggatgacgtc aaatcatcat gccccttatg 1200
tcttgggctt cacgcatgct acaatggccg gtacagaggg ttgcgatact gtgaggtgga 1260
gctaatccct aaaagccggt ctcagttcgg attggggtct gcaactcgac cccatgaagt 1320
cggagtcgct agtaatcgca gatcagcaac gctgcggtga atacgttccc gggccttgta 1380
cacaccgccc gtcaagtcac gaaagttggt aacacccaaa gccggtggcc taacccttttt 1440 gggagggagc cgtctaaggt gggattggcg attgggacta agtcgtaaca aggtagccta 1500
gggataacag ggtaatgagt cgacaaaatg atacggcgac caccgagatc tacactcttt 1560
ccctacacga cgctcttccg atctacacct attagaggtc agacagatcg gaagagcaca 1620
cgtctgaact ccagtcacaa tcagtctcgt atctcgtatg ccgtcttctg cttgttgtcg 1680
actc 1684

<210> SEQ ID NO 229
<211> LENGTH: 1646
<212> TYPE: DNA
<213> ORGANISM: Artificial
<220> FEATURE:
<223> OTHER INFORMATION: Polynucleotide

<400> SEQUENCE: 229
tgaacgctgg cggcaggcct aacacatgca agtcgagcgg tagcacagag agcttgctct 60
cgggtgacga gcggcggacg ggtgagtaat gtctgggaaa ctgcctgatg gagggggata 120
actactggaa acggtagcta ataccgcata acgtcgcaag accaaagtgg gggaccttcg 180
ggcctcatgc catcagatgt gcccagatgg gattagctag taggtggggt aacggctcac 240
ctaggcgacg atccctagct ggtctgagag gatgaccagc cacactggaa ctgagacacg 300
gtccagactc ctacgggagg cagcagtggg gaatattgca acaatagtgg gcgcaagcct 360
gatgcagcca tgccgcgtgt gtgaagaagg ccttcgggtt gtaaagcact ttcagcgggg 420
aggaaggcga taaggttaat aaccttgtcg attgacgtta cccgcagaag aagcaccggc 480
taactccgtg ccagcagccg cggtaatacg gagggtgcaa gcgttaatcg gaattactgg 540
gcgtaaatct gcgcacgcag gcggtctgtc aagtcggatg tgaaatcccc gggctcaacc 600
tgggaactgc attcgaaact ggcaggctag agtcttgtag aggggggtag aattccaggt 660
gtagcggtga aatgcgtaga gatctggagg aataccggtg gcgaaggcgg ccccctggac 720
aaagactgac gctcaggtgc gaaagcgtgg ggagcaaaca ggattagata ccctggtagt 780
ccacgccgta aacgatgtcg atttggaggt tgtgcccttg aggcgtggct tccggagcta 840
acgcgttaaa tcgaccgcct ggcatggtac ggccgcaagg ttaaaactca aatgaattga 900
cgggggcccg cacaagcggt ggagcatgtg gtttaattcg atgcaacgcg aagaacctta 960
cctggtcttg acatccacag aacttagcag agatgctttg gtgccttcgg gaactgtgag 1020
acaggtgctg catggctgtc gtcagctcgt gttgtgaaat gttgggttaa gtcccgcaac 1080
gagcgcaacc cttatccttt gttgccagcg gttaggccgg gaactcaaag gagactgcca 1140
gtgataaact ggaggaaggt ggggatgacg tcaagtcatc atggccctta cgaccagggc 1200
tacacacgtg ctacaatggc atatacaaag agaagcgacc tcgcgagagc aagcggacct 1260
cataaagtat gtcgtagtcc ggattggagt ctgcaactcg actccatgaa gtcggaatcg 1320
ctagtaatcg tagatcagaa tgctacggtg aatacgttcc cgggccttgt acacaccgcc 1380
cgtcacacca tgggagtggg ttgcaaaaga agtaggtagc ttaaccttcg ggagggcgct 1440
taccactttg tgattcatga tagggataac agggtaatga gtcgacaaaa tgatacggcg 1500
accaccgaga tctacactct ttccctacac gacgctcttc cgatcttttg tatgcacctt 1560
gtaaatagat cggaagagca cacgtctgaa ctccagtcac aatcagtctc gtatctcgta 1620
tgccgtcttc tgcttgttgt cgactc 1646

<210> SEQ ID NO 230
<211> LENGTH: 1726
<212> TYPE: DNA
<213> ORGANISM: Artificial
<220> FEATURE:
<223> OTHER INFORMATION: Polynucleotide

<400> SEQUENCE: 230
tacaatggag agtttgatcc tggctcagga tgaacgctag ctacaggctt aacacatgca 60
agtcgagggg aaacgacatc gaaagcttgc ttttgatggg cgtcgaccgg cgcacgggtg 120
agtaacgcgt atccaacctg cccaccactt ggggataacc ttgcgaaagt aagactaata 180
cccaatgata tctctagaag acatctgaaa gagattaaag atttatcggt gatggatggg 240
gatgcgtctg attagcttgt tggcggggta acggcccacc aaggcgacga tcagtagggg 300
ttctgagagg aaggtccccc acattggaac tgagacacgg tccaaactcc tacgggaggc 360
agcagtgagg aatattggta caatagtggg cgagagcctg aaccagccaa gtagcgtgca 420
ggatgacggc cctatgggtt gtaaactgct tttataaggg aataaagtta gtctcgtgag 480
actttttgca tgtaccttat gaataaggac cggctaattc cgtgccagca gccgcggtaa 540
tacggaaggt ccgggcgtta tccggattta ttgggtttaa atctgggagc gtaggccgga 600
gattaagcgt gttgtgaaat gtaggcgctc aacgtctgca ctgcagcgcg aactggtttc 660
cttgagtacg cacaaagtgg gtggaattcg tggtgtagcg gtgaaatgct tagatatcac 720
gaagaactcc gattgcgaag gcagctcact ggagcgcaac tgacgctgaa gctcgaaagt 780
gcgggtatcg aacaggatta gataccctgg tagtccgcac ggtaaacgat ggatgcccgc 840
tgttggtctg aacaggtcag cggccaagcg aaagcattaa gcatcccacc tggcatggta 900
cgccggcaac ggtgaaactc aaaggaattg acgggggccc gcacaagcgg aggaacatgt 960
ggtttaattc gatgatacgc gaggaacctt acccgggctt gaattgcaga ggaaggattt 1020
ggagacaatg acgcccttcg gggcctctgt gaaggtgctg catggttgtc gtcagctcgt 1080
gccgtgaggt gtcggcttaa gtgccataac gagcgcaacc cctctcctta gttgccatca 1140
ggttatgctg ggcactctgg ggacactgcc accgtaaggt gtgaggaagg tggggatgac 1200
gtcaaatcag cacggccctt acgtccgggg ctacacacgt gttacaatgg caggtacaga 1260
gagacggttg tacgtaagta cgatcaaatc cttaaagcct gtctcagttc ggattggggt 1320
ctgcaacccg accccacgaa gctggattcg ctagtaatcg cgcatcagcc atggcgcggt 1380
gaatacgttc ccgggccttg tacacaccgc ccgtcaagcc atgaaagccg gggcgcccta 1440
aagtccgtga ccgtaaggag cggcctaggg cgaaactggt aattggggct aagtcgtaac 1500
aaggtagccg taccggaagg tgcggctgga acacctcctt tagggataac agggtaatga 1560
gtcgacaaaa tgatacggcg accaccgaga tctacactct ttccctacac gacgctcttc 1620
cgatctggaa cgggtgttgc ccagatagat cggaagagca cacgtctgaa ctccagtcac 1680
aatcagtctc gtatctcgta tgccgtcttc tgcttgttgt cgactc 1726

<210> SEQ ID NO 231
<211> LENGTH: 1717
<212> TYPE: DNA
<213> ORGANISM: Artificial
<220> FEATURE:
<223> OTHER INFORMATION: Polynucleotide

<400> SEQUENCE: 231
gagagtttga tcctggctca ggatgaacgc tagcggcagg cttaacacat gcaagtcgag 60
gggcagcata atggatagca atatctatgg tggcgaccgg cgcacgggtg cgtaacgcgt 120
atgcaaccta cctttaacag gggggataaca ctgagaaatt ggtactaata ccccataata 180
tcatagaagg catcttttat ggttgaaaat tccgatggtt agagatgggc atgcgttgta 240
ttagctagtt ggtggggtaa cggctcacca aggcgacgat acatagggg actgagaggt 300 taaccccca cactggtact gagacacgga ccagactcct acgggaggca gcagtgagga 360
atattggtac aatagtggac gcaagtctga accagccatg ccgcgtgcag gatgacggct 420
ctatgagttg taaactgctt ttgtacgagg gtaaacgcag atacgtgtat ctgtctgaaa 480
gtatcgtacg aataaggatc ggctaactcc gtgccagcag ccgcggtaat acggaggatt 540
caagcgttat ccggatttat tgggtttaaa tctgggtgcg taggcggttt gataagttag 600
aggtgaaatt tcggggctca accctgaacg tgcctctaat actgttgagc tagagagtag 660
ttgcggtagg cggaatgtat ggtgtagcgg tgaaatgctt agagatcata cagaacaccg 720
attgcgaagg cagcttacca aactatatct gacgttgagg cacgaaagcg tggggagcaa 780
acaggattag ataccctggt agtccacgca gtaaacgatg ataactcgtt gtcggcgata 840
cacagtcggt gactaagcga aagcgataag ttatccacct ggcatggtac gttcgcaaga 900
atgaaactca aaggaattga cgggggcccg cacaagcgga ggaacatgtg gtttaattcg 960
atgatacgcg aggaacctta cccgggcttg aaagttagcg acgattcttg aaagaggatt 1020
tcccttcggg gcgcgaaact aggtgctgca tggttgtcgt cagctcgtgc cgtgaggtgt 1080
cgggttaagt cccataacga gcgcaacccc taccgttagt tgccatcagg tgaagctggg 1140

```
cactctggcg ggactgccgg tgtaagccga gaggaaggtg gggatgacgt caaatcagca   1200
cggcccttac gtccggggct acacacgtgt tacaatggta ggtacagagg gcagctaccc   1260
agcgatggga tgcgaatctc gaaagcctat ctcagttcgg attggaggct gaaacccgcc   1320
tccatgaagt tggattcgct agtaatcgcg catcagccat ggcgcggtga atacgttccc   1380
gggccttgta cacaccgccc gtcaagccat gggagccggg ggtgcctgaa gttcgtgacc   1440
gcaaggagcg acctagggca aaactggtga ctggggctaa gtcgtaacaa ggtagccgta   1500
ccggaaggtg cggctggaac acctcctttc ttagggataa cagggtaatg agtcgacaaa   1560
atgatacggc gaccaccgag atctacactc tttccctaca cgacgctctt ccgatctcag   1620
tgctcgaccc gacacccaga tcggaagagc acacgtctga actccagtca caatcagtct   1680
cgtatctcgt atgccgtctt ctgcttgttg tcgactc                            1717
```

<210> SEQ ID NO 232
<211> LENGTH: 1686
<212> TYPE: DNA
<213> ORGANISM: Artificial
<220> FEATURE:
<223> OTHER INFORMATION: Polynucleotide

<400> SEQUENCE: 232

```
agagtttgat cctggctcag gatgaacgct ggcggcgtgc ttaacacatg caagtcgaac     60
gaagcacttt atttgatttc cttcgggact gattattttg tgactgagtg gcggacgggt    120
gagtaacgcg tgggtaacct gccttgtaca gggggataac agttggaaac gactgctaat    180
accgcataag cgcacagtat cgcatgatgc agtgtgaaaa actccggtgg tataagatgg    240
acccgcgttg gattagctag ttggtgaggt gacggcccac caaggcgacg atccatagcc    300
gacctgagag ggtgaccggc cacattggga ctgagacacg gcccaaactc ctacgggagg    360
cagcagtggg gaatattgca acaatagtgg gcgaaagcct gatgcagcga cgccgcgtga    420
gcgaagaagt atttcggtat gtaaagctct atcagcaggg aagataatga cggtacctga    480
ctaagaagca ccggctaaat acgtgccagc agccgcggta atacgtatgg tgcaagcgtt    540
atccggattt actgggtgta aatctgggag cgcaggcggt gcggcaagtc tgatgtgaaa    600
gcccggggct caaccccggt actgcattgg aaactgtcgt actagagtgt cggaggggta    660
agcggaattc ctagtgtagc ggtgaaatgc gtagatatta ggaggaacac cagtggcgaa    720
ggcggcttac tggacgataa ctgacgctga ggctcgaaag cgtggggagc aaacaggatt    780
agataccctg gtagtccacg ccgtaaacga tgaatactag gtgttgggaa gcattgcttc    840
tcggtgccgt cgcaaacgca gtaagtattc cacctggcat ggtacgttcg caagaatgaa    900
actcaaagga attgacgggg acccgcacaa gcggtggagc atgtggttta attcgaagca    960
acgcgaagaa ccttaccaag tcttgacatc cttctgaccg gtacttaacc gtaccttctc   1020
ttcggagcag gagtgacagg tggtgcatgg ttgtcgtcag ctcgtgtcgt gagatgttgg   1080
gttaagtccc gcaacgagcg caacccttat ctttagtagc cagcggttcg gccgggcact   1140
ctagagagac tgccagggat aacctggagg aaggcgggga tgacgtcaaa tcatcatgcc   1200
ccttatgact tgggctacac acgtgctaca atggcgtaaa caaagggaag caaagctgtg   1260
aagccgagca aatctcaaaa ataacgtctc agttcggact gtagtctgca acccgactac   1320
acgaagctgg aatcgctagt aatcgcagat cagaatgctg cggtgaatac gttcccgggt   1380
cttgtacaca ccgcccgtca caccatggga gttgggaatg cccgaaccag tgacctaacc   1440
```

```
gtaaggaagg agctgtcgaa ggcaggctcg ataactgggg tgaagtctaa caaggtaacc   1500

tagggataac agggtaatga gtcgacaaaa tgatacggcg accaccgaga tctacactct   1560

ttccctacac gacgctcttc cgatctgagt ttacctgcgc ccagttagat cggaagagca   1620

cacgtctgaa ctccagtcac aatcagtctc gtatctcgta tgccgtcttc tgcttgttgt   1680

cgactc                                                              1686


<210> SEQ ID NO 233
<211> LENGTH: 1646
<212> TYPE: DNA
<213> ORGANISM: Artificial
<220> FEATURE:
<223> OTHER INFORMATION: Polynucleotide

<400> SEQUENCE: 233

gacgaacgct ggcggcgtgc ctaacacatg caagtcgaac ggaactgttt tgaaagattt     60

cttcggaatg aatttgattt agtttagtgg cggacgggtg agtaacgcgt gagtaacctg    120

ccttcaagag gggataaca ttctgaaaag aatgctaata ccgcatgaca tatcggaacc     180

acatggtttt gatatcaaag attttatcgc ttgaagatgg actcgcgtcc gattagttag    240

ttggtgaggt aacggctcac caagaccgcg atcggtagcc ggactgagag gttgaacggc    300

cacattggga ctgagacacg gcccagactc ctacgggagg cagcagtggg ggatattgcg    360

acaatagtgg gggcaaccct gacgcagcaa cgccgcgtga aggatgaagg ttttcggatt    420

gtaaacttct tttattaagg acgaaacttg acggtactta atgaataagc tccggctaac    480

tacgtgccag cagccgcggt aatacgtagg gagcaagcgt tgtccggatt tactgggtgt    540

aaatctgggt gcgtaggcgg ctttgcaagt cagatgtgaa atctatgggc tcaacccata    600

aactgcattt gaaactgtag agcttgagtg aagtagaggc aggcggaatt ccccgtgtag    660

cggtgaaatg cgtagagatg gggaggaaca ccagtggcga aggcggcctg ctgggcttta    720

actgacgctg aggcacgaaa gcgtgggtag caaacaggat tagataccct ggtagtccac    780

gctgtaaacg atgattacta ggtgtggggg gtctgacccc ttccgtgccg gagttaacac    840

aataagtaat ccacctggca tggtacggcc gcaaggttga aactcaaagg aattgacggg    900

ggcccgcaca agcagtggag tatgtggttt aattcgaagc aacgcgaaga accttaccag    960

gtcttgacat ccaactaacg aagtagagat acattaggtg cccttcgggg aaagttgaga   1020

caggtggtgc atggttgtcg tcagctcgtg tcgtgagatg ttgggttaag tcccgcaacg   1080

agcgcaaccc ttgctattag ttgctacgca agagcactct aataggactg ccgttgacaa   1140

aacggaggaa ggtggggacg acgtcaaatc atcatgcccc ttatgacctg ggctacacac   1200

gtactacaat ggatgttaac agagggaagc aagacagcga tgtggagcaa accccctaaaa   1260

acattctcag ttcagattgc aggctgcaac ccgcctgcat gaagatggaa ttgctagtaa   1320

tcgcggatca gcatgccgcg gtgaatacgt tcccgggcct tgtacacacc gcccgtcaca   1380

ccatgggagc cggtaatacc cgaagtcagt agtccaacct cgtgaggacg ctgccgaagg   1440

taggattggc gactggggtg tagggataac agggtaatga gtcgacaaaa tgatacggcg   1500

accaccgaga tctacactct ttccctacac gacgctcttc cgatctaaga tgcatacgag   1560

gagcaaagat cggaagagca cacgtctgaa ctccagtcac aatcagtctc gtatctcgta   1620

tgccgtcttc tgcttgttgt cgactc                                        1646


<210> SEQ ID NO 234
<211> LENGTH: 1670
```

<212> TYPE: DNA
<213> ORGANISM: Artificial
<220> FEATURE:
<223> OTHER INFORMATION: Polynucleotide

<400> SEQUENCE: 234
agagtttgat cctggctcag gataacgcta gcgacaggct taacacatgc aagtcgaggg 60
gcatcatgag gtagcaatac cttgatggcg accggcgcac gggtgagtaa cgcgtatgca 120
acctgcctga taccggggta tagcccatgg aaacgtggat taacaccccca tagtactttt 180 atcctgcatg ggatgtgagt taaatgttca aggtatcgga tgggcatgcg tcctattagt 240
tagttggcgg ggtaacagcc caccaagacg atgataggta ggggttctga gaggaaggtc 300
ccccacattg gaactgagac acggtccaaa ctcctacggg aggcagcagt gaggaatatt 360
ggtacaatag tggacgtaag tctgaaccag ccaagtcgcg tgagggaaga ctgccctatg 420
ggttgtaaac ctcttttata agggaagaat aagttctacg tgtagaatga tgcctgtacc 480
ttatgaataa gcatcggcta actccgtgcc agcagccgcg gtaatacgga ggatgcgagc 540
gttatccgga tttattgggt ttaaatctgg gtgcgtaggc ggtttattaa gttagtggtt 600
aaatatttga gctaaactca attgtgccat taatactggt aaactggagt acagacgagg 660
taggcggaat aagttaagta gcggtgaaat gcatagatat aacttagaac tccgatagcg 720
aaggcagctt accagactgt aactgacgct gaagcacgag agcgtgggta gcgaacagga 780
ttagataccc tggtagtcca cgccgtaaac gatgctcact ggttctgtgc gatatattgt 840
acgggattaa gcgaaagtat taagtgagcc acctggcatg gtacgtcggc aacgatgaaa 900
ctcaaaggaa ttgacggggg cccgcacaag cggaggaaca tgtggtttaa ttcgatgata 960
cgcgaggaac cttacctggg tttaaatggg aaatgtcgta tttggaaaca gatattctct 1020
tcggagcgtt tttcaaggtg ctgcatggtt gtcgtcagct cgtgccgtga ggtgtcgggt 1080
taagtcccat aacgagcgca acccttaccg ttagttgcta gcatgtaatg atgagcactc 1140
taacgggact gccaccgtaa ggtgagagga aggcggggat gacgtcaaat cagcacggcc 1200
cttacaccca gggctacaca cgtgttacaa tggccggtac agagggccgc taccaggtga 1260
ctggatgcca atctcaaaag ccggtcgtag ttcggattgg agtctgtaac ccgactccat 1320
gaagttggat tcgctagtaa tcgcgcatca gccatggcgc ggtgaatacg ttcccgggcc 1380
ttgtacacac cgcccgtcaa gccatggaag ccgggggtgc ctgaagtccg taaccgcgag 1440
gatcggccta gggcaaaact ggtaactggg gctaagtcgt aacataggga taacagggta 1500
atgagtcgac aaaatgatac ggcgaccacc gagatctaca ctctttccct acacgacgct 1560
cttccgatct atcatgatac tgccgtttcg agatcggaag agcacacgtc tgaactccag 1620
tcacaatcag tctcgtatct cgtatgccgt cttctgcttg ttgtcgactc 1670

<210> SEQ ID NO 235
<211> LENGTH: 1627
<212> TYPE: DNA
<213> ORGANISM: Artificial
<220> FEATURE:
<223> OTHER INFORMATION: Polynucleotide

<400> SEQUENCE: 235
aacgaacgct ggcggcgtgg ataagacatg caagtcgaac gagagaattg ctagcttgct 60
aataattctc tagtggcgca cgggtgagta acacgtgagt aacctgcccc cgagagcggg 120
atagccctgg gaaactggga ttaataccgc atagtatcga aagattaaag cagcaatgcg 180

```
cttggggatg ggctcgcggc ctattagtta gttggtgagg taacggctca ccaaggcgat    240
gacgggtagc cggtctgaga ggatgtccgg ccacactgga actgagacac ggtccagaca    300
cctacgggtg gcagcagtcg agaatcattc aacaatagtg ggggaaaccc tgatggtgcg    360
acgccgcgtg ggggaatgaa ggtcttcgga ttgtaaaccc ctgtcatgtg ggagcaaatt    420
aaaaagatag taccacaaga ggaagagacg gctaactctg tgccagcagc cgcggtaata    480
cagaggtctc aagcgttgtt cggaatcact gggcgtaaat ctgcgtgcgt aggctgtttc    540
gtaagtcgtg tgtgaaaggc gcgggctcaa cccgcggacg gcacatgata ctgcgagact    600
agagtaatgg agggggaacc ggaattctcg gtgtagcagt gaaatgcgta gatatcgaga    660
ggaacactcg tggcgaaggc gggttcctgg acattaactg acgctgaggc acgaaggcca    720
ggggagcgaa agggattaga taccccctgta gtcctggcag taaacggtgc acgcttggtg    780
tgcggggaat cgaccccctg cgtgccggag taacgcgtta agcgtgccgc ctggcatggt    840
acggtcgcaa gattaaaact caaagaaatt gacggggacc cgcacaagcg gtggagtatg    900
tggcttaatt cgatgcaacg cgaagaacct tacctgggct tgacatgtaa tgaacaacat    960
gtgaaagcat gcgactcttc ggaggcgtta cacaggtgct gcatggccgt cgtcagctcg   1020
tgtcgtgaga tgtttggtta agtccagcaa cgagcgcaac ccctgttgcc agttaccagc   1080
acgtgaaggt ggggactctg gcgagactgc ccagatcaac tgggaggaag gtggggacga   1140
cgtcaggtca gtatggccct tatgcccagg gctgcacacg tactacaatg cccagtacag   1200
agggggccga agccgcgagg cggaggaaat cctaaaaact gggcccagtt cggactgtag   1260
gctgcaaccc gcctacacga agccggaatc gctagtaatg gcgcatcagc tacggcgccg   1320
tgaatacgtt cccgggtctt gtacacaccg cccgtcacat catggaagct ggtcgcaccc   1380
gaagtatctg aagccaaccg caaggaggca gggtcctaag gtgagactgg taactgggat   1440
gtagggataa cagggtaatg agtcgacaaa atgatacggc gaccaccgag atctacactc   1500
tttccctaca cgacgctctt ccgatcttgt cttatctgaa tacagagaga tcggaagagc   1560
acacgtctga actccagtca caatcagtct cgtatctcgt atgccgtctt ctgcttgttg   1620
tcgactc                                                             1627
```

<210> SEQ ID NO 236
<211> LENGTH: 1718
<212> TYPE: DNA
<213> ORGANISM: Artificial
<220> FEATURE:
<223> OTHER INFORMATION: Polynucleotide

<400> SEQUENCE: 236

```
gacgaacgct ggcggcgtgc ttaacacatg caagtcgaac gaaaagacgg aaagagcttg     60
ctcttttcag aattgagtgg caaacgggtg agtaacacgt aaacaacctg ccttcaggat    120
ggggacaaca gacggaaacg actgctaata ccgaataagt tccaagagcc gcatggccca    180
tggaagaaaa ggtggcctct acctgtaagc tatcgcctga agaggggttt gcgtctgatt    240
agctggttgg aggggtaacg gcccaccaag gcgacgatca gtagccggtc tgagaggatg    300
aacggccaca ctggaactga gacacggtcc agactcctac gggaggcagc agtggggaat    360
cttccgacaa tagtgggcga aagcctgacg gagcaacgcc gcgtgagtga tgacggcctt    420
cgggttgtaa aactctgtga tccgggacga aaaggcagag tgcgaagaac aaactgcatt    480
gacggtaccg gaaaagcaag ccacggctaa ctacgtgcca gcagccgcgg taatacgtag    540
gtggcaagcg ttgtccggaa ttattgggcg taaatctgcg cgcgcaggcg gcttcccaag    600
```

tccctcttaa aagtgcgggg cttaaccccg tgatgggaag gaaactggga agctggagta 660
tcggagagga aagtggaatt cctagtgtag cggtgaaatg cgtagagatt aggaagaaca 720
ccggtggcga aggcgacttt ctggacgaaa actgacgctg aggcgcgaaa gcgtggggca 780
aacaggatta gataccctgg tagtccacgc cgtaaacgat ggatactagg tgtaggaggt 840
atcgacccct cctgtgccgg agttaacgca ataagtatcc cgcctcatgg gaagtacgat 900
cgcaagatta aaactcaaag gaattgacgg gggcccgcac aagcggtgga gtatgtggtt 960
taattcgacg caacgcgaag aaccttacca ggtcttgaca ttgatcgcga tctgcagaaa 1020
tgcggagttc ttcttcggaa gacgagaaaa caggtggtgc acggctgtcg tcagctcgtg 1080
tcgtgagatg ttgggttaag tcccgcaacg agcgcaaccc ctatcatttg ttaccagcac 1140
gtaaaggtgg ggactcaaat gagaccgccg cggacaacgc ggaggaaggc ggggacgacg 1200
tcaagtcatc atgcccctta tgacctgggc tacacacgta ctacaatggg tgtcaacaaa 1260
gagaagcgaa cccgcgagga agagcaaacc tcaaaaacac acccccagtt cagatcgcag 1320
gctgcaaccc gcctgcgtga agtaggaatc gctagtaatc gcgggtcagc ataccgcggt 1380
gaatacgttc ccgggccttg tacacaccgc ccgtcacact atgagagtca gaaacacccg 1440
aagccggtga ggtaaccgca aggagccagc cgtcgaaggc ggagctgatg attggagtga 1500
agtcgtaaca aggtagccgt atcggaaggt gctagggata acagggtaat gagtcgacaa 1560
aatgatacgg cgaccaccga gatctacact ctttccctac acgacgctct tccgatcttg 1620
gcagccataa catagtccag atcggaagag cacacgtctg aactccagtc acaatcagtc 1680
tcgtatctcg tatgccgtct tctgcttgtt gtcgactc 1718

<210> SEQ ID NO 237
<211> LENGTH: 1660
<212> TYPE: DNA
<213> ORGANISM: Artificial
<220> FEATURE:
<223> OTHER INFORMATION: Polynucleotide

<400> SEQUENCE: 237
tttgatcatg gctcaggatg aacgctagct acaggcttaa cacatgcaag tcgaggggca 60
gcatgaactt agcttgctaa gtttgatggc gaccggcgca cgggtgagta acacgtatcc 120
aacctgccga tgactcgggg atagcctttc gaaagaaaga ttaatacccg atggcatagt 180
tcttccgcat ggtggaacta ttaaagaatt tcggtcatcg atggggatgc gttccattag 240
gttgttggcg gggtaacggc ccaccaagcc ttcgatggat aggggttctg agaggaaggt 300
cccccacatt ggaactgaga cacggtccaa actcctacgg gaggcagcag tgaggaatat 360
tggtacaata gtggacgaga gtctgaacca gccaagtagc gtgaaggatg actgccctat 420
gggttgtaaa cttcttttat acgggaataa agtgaggcac gtgtgccttt ttgtatgtac 480
cgtatgaata aggatcggct aactccgtgc cagcagccgc ggtaatacgg aggatccgag 540
cgttatccgg atttattggg tttaaatctg ggagcgtagg cggacgctta agtcagttgt 600
gaaagtttgc ggctcaaccg taaaattgca gttgatactg ggtgtcttga gtacagtaga 660
ggcaggcgga attcgtggtg tagcggtgaa atgcttagat atcacgaaga actccgattg 720
cgaaggcagc ttgctggact gtaactgacg ctgatgctcg aaagtgtggg tatcaaacag 780
gattagatac cctggtagtc cacacagtaa acgatgaata ctcgctgttt gcgatataca 840
gtaagcggcc aagcgaaagc gttaagtatt ccacctggca tggtacgccg gcaacggtga 900

-continued

```
aactcaaagg aattgacggg ggcccgcaca agcggaggaa catgtggttt aattcgatga     960

tacgcgagga acttacccgg gcttgaattg caactgaatg atgtggagac atgtcagccg    1020

caaggcagtt gtgaaggtgc tgcatggttg tcgtcagctc gtgccgtgag gtgtcggctt    1080

aagtgccata acgagcgcaa cccttatcga tagttaccat caggtgatgc tggggactct    1140

gtcgagactg ccgtcgtaag atgtgaggaa ggtggggatg acgtcaaatc agcacggccc    1200

ttacgtccgg ggctacacac gtgttacaat ggggggtaca gaaggcagct acacggcgac    1260

gtgatgctaa tccctaaagc ctctctcagt tcggattgga gtctgcaacc cgactccatg    1320

aagctggatt cgctagtaat cgcgcatcag ccacggcgcg gtgaatacgt tcccgggcct    1380

tgtacacacc gcccgtcaag ccatgaaagc cgggggtacc tgaagtgcgt aaccgcaagg    1440

agcgccctag ggtaaaactg gtgattgggg ctaataggga taacagggta atgagtcgac    1500

aaaatgatac ggcgaccacc gagatctaca ctctttccct acacgacgct cttccgatct    1560

ggcacgcggg tccgacagcc agatcggaag agcacacgtc tgaactccag tcacaatcag    1620

tctcgtatct cgtatgccgt cttctgcttg ttgtcgactc                          1660
```

<210> SEQ ID NO 238
<211> LENGTH: 1728
<212> TYPE: DNA
<213> ORGANISM: Artificial
<220> FEATURE:
<223> OTHER INFORMATION: Polynucleotide

<400> SEQUENCE: 238

```
ttacaatgaa gagtttgatc ctggctcagg atgaacgcta gctacaggct taacacatgc      60

aagtcgaggg gcagcatttc agtttgcttg caaactggag atggcgaccg gcgcacgggt     120

gagtaacacg tatccaacct gccgataact cggggatagc ctttcgaaag aaagattaat     180

acccgatggt ataatcagac cgcatggtct tgttattaaa gaatttcggt tatcgatggg     240

gatgcgttcc attaggcagt tggtgaggta acggctcacc aaaccttcga tggatagggg     300

ttctgagagg aaggtccccc acattggaac tgagacacgg tccaaactcc tacgggaggc     360

agcagtgagg aatattggta caatagtggg cgcaggcctg aaccagccaa gtagcgtgaa     420

ggatgactgc cctatgggtt gtaaacttct tttatatggg aataaagttt tccacgtgtg     480

gaattttgta tgtaccatat gaataaggat cggctaactc cgtgccagca gccgcggtaa     540

tacggaggat ccgagcgtta tccggattta ttgggtttaa atctgggagc gtaggtggac     600

agttaagtca gttgtgaaag tttgcggctc aaccgtaaaa ttgcagttga tactggctgt     660

cttgagtaca gtagaggtgg gcggaattcg tggtgtagcg gtgaaatgct tagatatcac     720

gaagaactcc gattgcgaag gcagctcact ggactgcaac tgacactgat gctcgaaagt     780

gtgggtatca aacaggatta gataccctgg tagtccacac agtaaacgat gaatactcgc     840

tgtttgcgat atacagtaag cggccaagcg aaagcattaa gtattccacc tggcatggta     900

cgccggcaac gggtgaaact caaaggaatt gacgggggcc cgtacaagcg gaggaacatg     960

tggtttaatt cgatgatacg cgaggaacct tacccgggct taaattgcat ttgaatatat    1020

tggaaacagt atagccgtaa ggcaaatgtg aaggtgctgc atggttgtcg tcagctcgtg    1080

ccgtgaggtg tcggcttaag tgccataacg agcgcaaccc ttatctttag ttactaacag    1140

gtcatgctga ggactctaga gagactgccg tcgtaagatg tgaggaaggt ggggatgacg    1200

tcaaatcagc acggccctta cgtccggggc tacacacgtg ttacaatggg gggtacagaa    1260

ggcagctacc tggtgacagg atgctaatcc caaaagcctc tctcagttcg gatcgaagtc    1320
```

```
tgcaacccga cttcgtcaag ctggattcgc tagtaatcgc gcatcagcca tggcgcggtg   1380

aatacgttcc cgggccttgt acacaccgcc cgtcaagcca tgaaagccgg gggtacctga   1440

agtacgtaac cgcaaggagc gtcctagggt aaaactggta attggggcta agtcgtaaca   1500

aggtagccgt accggaaggt gcggctggaa cacctccttt cttagggata acagggtaat   1560

gagtcgacaa aatgatacgg cgaccaccga gatctacact ctttccctac acgacgctct   1620

tccgatctca agtcgcatcc gaatattaag atcggaagag cacacgtctg aactccagtc   1680

acaatcagtc tcgtatctcg tatgccgtct tctgcttgtt gtcgactc                1728
```

<210> SEQ ID NO 239
<211> LENGTH: 1630
<212> TYPE: DNA
<213> ORGANISM: Artificial
<220> FEATURE:
<223> OTHER INFORMATION: Polynucleotide

<400> SEQUENCE: 239

```
atgaacgcta gctacaggct taacacatgc aagtcgaggg gcatcaggaa gaaagcttgc     60

tttctttgct ggcgaccggc gcacgggtga gtaacacgta tccaacctgc cctttactcg    120

gggatagcct ttcgaaagaa agattaatac ccgatagcat aatgattccg catggtttca    180

ttattaaagg attccggtaa aggatgggga tgcgttccat taggttgttg gtgaggtaac    240

ggctcaccaa gccttcgatg gataggggtt ctgagaggaa ggtcccccac attggaactg    300

agacacggtc caaactccta cgggaggcag cagtgaggaa tattggtaca atagtgggcg    360

ctagcctgaa ccagccaagt agcgtgaagg atgaaggctc tatgggtcgt aaacttcttt    420

tatataagaa taaagtgcag tatgtatact gttttgtatg tattatatga ataaggatcg    480

gctaactccg tgccagcagc cgcggtaata cggaggatcc gagcgttatc cggatttatt    540

gggtttaaat ctgggagcgt aggtggactg gtaagtcagt tgtgaaagtt tgcggctcaa    600

ccgtaaaatt gcagttgata ctgtcagtct tgagtacagt agaggtgggc ggaattcgtg    660

gtgtagcggt gaaatgctta gatatcacga agaactccga ttgcgaaggc agctcactgg    720

actgcaactg acactgatgc tcgaaagtgt gggtatcaaa caggattaga taccctggta    780

gtccacacag taaacgatga atactcgctg tttgcgatat acagtaagcg gccaagcgaa    840

agcattaagt attccacctg gcatggtacg ccggcaacgg tgaaactcaa aggaattgac    900

gggggcccgc acaagcggag gaacatgtgg tttaattcga tgatacgcga ggaaccttac    960

ccgggcttaa attgcagtgg aatgatgtgg aaacatgtca gtgagcaatc accgctgtga   1020

aggtgctgca tggttgtcgt cagctcgtgc cgtgaggtgt cggcttaagt gccataacga   1080

gcgcaaccct tatctttagt tactaacagg ttatgctgag gactctagag agactgccgt   1140

cgtaagatgt gaggaaggtg gggatgacgt caaatcagca cggcccttac gtccggggct   1200

acacacgtgt tacaatgggg ggtacagaag gcagctagcg ggtgaccgta tgctaatccc   1260

aaaatcctct ctcagttcgg atcgaagtct gcaacccgac ttcgtgaagc tggattcgct   1320

agtaatcgcg catcagccac ggcgcggtga atacgttccc gggccttgta cacaccgccc   1380

gtcaagccat gggagccggg ggtacctgaa gtacgtaacc gcaaggatcg tcctagggta   1440

aaactaggga taacagggta atgagtcgac aaaatgatac ggcgaccacc gagatctaca   1500

ctctttccct acacgacgct cttccgatct cgcgccgcgg cagcaatcca agatcggaag   1560

agcacacgtc tgaactccag tcacaatcag tctcgtatct cgtatgccgt cttctgcttg   1620
```

ttgtcgactc 1630

<210> SEQ ID NO 240
<211> LENGTH: 372
<212> TYPE: DNA
<213> ORGANISM: Artificial
<220> FEATURE:
<223> OTHER INFORMATION: Polynucleotide

<400> SEQUENCE: 240
gagtcgacaa aatgatacgg cgaccaccga gatctacact ctttccctac acgacgctct 60
tccgatctga gcatgccgat ggtttgttaa agatcggaag agcacacgtc tgaactccag 120
tcacaatcag tctcgtatct cgtatgccgt cttctgcttg ttgtcgactc tagggataac 180
agggtaatga gtcgacaaca agcagaagac ggcatacgag attggtcaac gatagtctcg 240
tgggctcgga gatgtgtata agagacaggc cgcccgtcac agcacgtact gtctcttata 300
cacatctgac gctgccgacg aatcaccagg tgtgtgtaga tctcggtggt cgccgtatca 360
ttttgtcgac tc 372

<210> SEQ ID NO 241
<211> LENGTH: 522
<212> TYPE: DNA
<213> ORGANISM: Artificial
<220> FEATURE:
<223> OTHER INFORMATION: Polynucleotide

<400> SEQUENCE: 241
gagtcgacaa aatgatacgg cgaccaccga gatctacact ctttccctac acgacgctct 60
tccgatctag actatcgcct ttagcctcaa attgaagagt ttgatcatgg ctcagattga 120
acgctggcgg caggcctaac acatgcaagt cgaacggtaa caggaagaag cttgctcttt 180
gctgacgagt ggcggacggg tgagtaatgt ctgggaaact gcctgatgga gggggataac 240
agatcggaag agcacacgtc tgaactccag tcacaatcag tctcgtatct cgtatgccgt 300
cttctgcttg ttgtcgactc tagggataac agggtaatga gtcgacaaca agcagaagac 360
ggcatacgag attggtcaac gatagtctcg tgggctcgga gatgtgtata agagacaggc 420
agctgttaga gacgaatcct gtctcttata cacatctgac gctgccgacg aatcaccagg 480
tgtgtgtaga tctcggtggt cgccgtatca ttttgtcgac tc 522

<210> SEQ ID NO 242
<211> LENGTH: 672
<212> TYPE: DNA
<213> ORGANISM: Artificial
<220> FEATURE:
<223> OTHER INFORMATION: Polynucleotide

<400> SEQUENCE: 242
gagtcgacaa aatgatacgg cgaccaccga gatctacact ctttccctac acgacgctct 60
tccgatcttg atgtatatag ccggcggcaa attgaagagt ttgatcatgg ctcagattga 120
acgctggcgg caggcctaac acatgcaagt cgaacggtaa caggaagaag cttgctcttt 180
gctgacgagt ggcggacggg tgagtaatgt ctgggaaact gcctgatgga gggggataac 240
tactggaaac ggtagctaat accgcataac gtcgcaagac caaagagggg gaccttcggg 300
cctcttgcca tcggatgtgc ccagatggga ttagctagta ggtggggtaa cggctcacct 360
aggcgacgat ccctagctgg tctgagagga agatcggaag agcacacgtc tgaactccag 420
tcacaatcag tctcgtatct cgtatgccgt cttctgcttg ttgtcgactc tagggataac 480

```
agggtaatga gtcgacaaca agcagaagac ggcatacgag attggtcaac gatagtctcg    540

tgggctcgga gatgtgtata agagacaggg acaaacagaa atatcacgct gtctcttata    600

cacatctgac gctgccgacg aatcaccagg tgtgtgtaga tctcggtggt cgccgtatca    660

ttttgtcgac tc                                                        672
```

<210> SEQ ID NO 243
<211> LENGTH: 822
<212> TYPE: DNA
<213> ORGANISM: Artificial
<220> FEATURE:
<223> OTHER INFORMATION: Polynucleotide

<400> SEQUENCE: 243

```
gagtcgacaa aatgatacgg cgaccaccga gatctacact ctttccctac acgacgctct     60

tccgatctca acggaacgtg cactgcagaa attgaagagt ttgatcatgg ctcagattga    120

acgctggcgg caggcctaac acatgcaagt cgaacggtaa caggaagaag cttgctcttt    180

gctgacgagt ggcggacggg tgagtaatgt ctgggaaact gcctgatgga gggggataac    240

tactggaaac ggtagctaat accgcataac gtcgcaagac caaagagggg gaccttcggg    300

cctcttgcca tcggatgtgc ccagatggga ttagctagta ggtggggtaa cggctcacct    360

aggcgacgat ccctagctgg tctgagagga tgaccagcca cactggaact gagacacggt    420

ccagactcct acgggaggca gcagtgggga atattgcaca atgggcgcaa gcctgatgca    480

gccatgccgc gtgtatgaag aaggccttcg ggttgtaaag tactttcagc ggggaggaag    540

agatcggaag agcacacgtc tgaactccag tcacaatcag tctcgtatct cgtatgccgt    600

cttctgcttg ttgtcgactc tagggataac agggtaatga gtcgacaaca agcagaagac    660

ggcatacgag attggtcaac gatagtctcg tgggctcgga gatgtgtata agagacaggg    720

ccaccgtaaa cagtgcgact gtctcttata cacatctgac gctgccgacg aatcaccagg    780

tgtgtgtaga tctcggtggt cgccgtatca ttttgtcgac tc                       822
```

<210> SEQ ID NO 244
<211> LENGTH: 972
<212> TYPE: DNA
<213> ORGANISM: Artificial
<220> FEATURE:
<223> OTHER INFORMATION: Polynucleotide

<400> SEQUENCE: 244

```
gagtcgacaa aatgatacgg cgaccaccga gatctacact ctttccctac acgacgctct     60

tccgatctaa tgtgagcgta tcaggagaaa attgaagagt ttgatcatgg ctcagattga    120

acgctggcgg caggcctaac acatgcaagt cgaacggtaa caggaagaag cttgctcttt    180

gctgacgagt ggcggacggg tgagtaatgt ctgggaaact gcctgatgga gggggataac    240

tactggaaac ggtagctaat accgcataac gtcgcaagac caaagagggg gaccttcggg    300

cctcttgcca tcggatgtgc ccagatggga ttagctagta ggtggggtaa cggctcacct    360

aggcgacgat ccctagctgg tctgagagga tgaccagcca cactggaact gagacacggt    420

ccagactcct acgggaggca gcagtgggga atattgcaca atgggcgcaa gcctgatgca    480

gccatgccgc gtgtatgaag aaggccttcg ggttgtaaag tactttcagc ggggaggaag    540

ggagtaaagt taataccttt gctcattgac gttacccgca gaagaagcac cggctaactc    600

cgtgccagca gccgcggtaa tacggagggt gcaagcgtta atcggaatta ctgggcgtaa    660
```

```
agcgcacgca ggcggtttgt taagtcagat agatcggaag agcacacgtc tgaactccag    720

tcacaatcag tctcgtatct cgtatgccgt cttctgcttg ttgtcgactc tagggataac    780

agggtaatga gtcgacaaca agcagaagac ggcatacgag attggtcaac gatagtctcg    840

tgggctcgga gatgtgtata agagacagta gcgcccacag caagtgatct gtctcttata    900

cacatctgac gctgccgacg aatcaccagg tgtgtgtaga tctcggtggt cgccgtatca    960

ttttgtcgac tc                                                        972
```

<210> SEQ ID NO 245
<211> LENGTH: 1122
<212> TYPE: DNA
<213> ORGANISM: Artificial
<220> FEATURE:
<223> OTHER INFORMATION: Polynucleotide

<400> SEQUENCE: 245

```
gagtcgacaa aatgatacgg cgaccaccga gatctacact ctttccctac acgacgctct     60

tccgatctcg gcgggtagta cctgtaccaa attgaagagt ttgatcatgg ctcagattga    120

acgctggcgg caggcctaac acatgcaagt cgaacggtaa caggaagaag cttgctcttt    180

gctgacgagt ggcggacggg tgagtaatgt ctgggaaact gcctgatgga gggggataac    240

tactggaaac ggtagctaat accgcataac gtcgcaagac caaagagggg gaccttcggg    300

cctcttgcca tcggatgtgc ccagatggga ttagctagta ggtggggtaa cggctcacct    360

aggcgacgat ccctagctgg tctgagagga tgaccagcca cactggaact gagacacggt    420

ccagactcct acgggaggca gcagtgggga atattgcaca atgggcgcaa gcctgatgca    480

gccatgccgc gtgtatgaag aaggccttcg ggttgtaaag tactttcagc ggggaggaag    540

ggagtaaagt taatacettt gctcattgac gttacccgca gaagaagcac cggctaactc    600

cgtgccagca gccgcggtaa tacggagggt gcaagcgtta atcggaatta ctgggcgtaa    660

agcgcacgca ggcggtttgt taagtcagat gtgaaatccc cgggctcaac ctgggaactg    720

catctgatac tggcaagctt gagtctcgta gaggggggta gaattccagg tgtagcggtg    780

aaatgcgtag agatctggag gaataccggt ggcgaaggcg gccccctgga cgaagactga    840

agatcggaag agcacacgtc tgaactccag tcacaatcag tctcgtatct cgtatgccgt    900

cttctgcttg ttgtcgactc tagggataac agggtaatga gtcgacaaca agcagaagac    960

ggcatacgag attggtcaac gatagtctcg tgggctcgga gatgtgtata agagacagac   1020

aagccctaat gatgatagct gtctcttata cacatctgac gctgccgacg aatcaccagg   1080

tgtgtgtaga tctcggtggt cgccgtatca ttttgtcgac tc                      1122
```

<210> SEQ ID NO 246
<211> LENGTH: 1272
<212> TYPE: DNA
<213> ORGANISM: Artificial
<220> FEATURE:
<223> OTHER INFORMATION: Polynucleotide

<400> SEQUENCE: 246

```
gagtcgacaa aatgatacgg cgaccaccga gatctacact ctttccctac acgacgctct     60

tccgatctgt tctcctgcta cagaggttaa attgaagagt ttgatcatgg ctcagattga    120

acgctggcgg caggcctaac acatgcaagt cgaacggtaa caggaagaag cttgctcttt    180

gctgacgagt ggcggacggg tgagtaatgt ctgggaaact gcctgatgga gggggataac    240

tactggaaac ggtagctaat accgcataac gtcgcaagac caaagagggg gaccttcggg    300
```

```
cctcttgcca tcggatgtgc ccagatggga ttagctagta ggtggggtaa cggctcacct    360
aggcgacgat ccctagctgg tctgagagga tgaccagcca cactggaact gagacacggt    420
ccagactcct acgggaggca gcagtgggga atattgcaca atgggcgcaa gcctgatgca    480
gccatgccgc gtgtatgaag aaggccttcg ggttgtaaag tactttcagc ggggaggaag    540
ggagtaaagt taataccttt gctcattgac gttacccgca gaagaagcac cggctaactc    600
cgtgccagca gccgcggtaa tacggagggt gcaagcgtta atcggaatta ctgggcgtaa    660
agcgcacgca ggcggtttgt taagtcagat gtgaaatccc cgggctcaac ctgggaactg    720
catctgatac tggcaagctt gagtctcgta gaggggggta gaattccagg tgtagcggtg    780
aaatgcgtag agatctggag gaataccggt ggcgaaggcg gccccctgga cgaagactga    840
cgctcaggtg cgaaagcgtg gggagcaaac aggattagat accctggtag tccacgccgt    900
aaacgatgtc gacttggagg ttgtgccctt gaggcgtggc ttccggagct aacgcgttaa    960
gtcgaccgcc tggggagtac ggccgcaagg agatcggaag agcacacgtc tgaactccag   1020
tcacaatcag tctcgtatct cgtatgccgt cttctgcttg ttgtcgactc tagggataac   1080
agggtaatga gtcgacaaca agcagaagac ggcatacgag attggtcaac gatagtctcg   1140
tgggctcgga gatgtgtata agagacagac gctgataaat atcgagttct gtctcttata   1200
cacatctgac gctgccgacg aatcaccagg tgtgtgtaga tctcggtggt cgccgtatca   1260
ttttgtcgac tc                                                       1272
```

```
<210> SEQ ID NO 247
<211> LENGTH: 1422
<212> TYPE: DNA
<213> ORGANISM: Artificial
<220> FEATURE:
<223> OTHER INFORMATION: Polynucleotide

<400> SEQUENCE: 247
```

```
gagtcgacaa aatgatacgg cgaccaccga gatctacact ctttccctac acgacgctct     60
tccgatctcc cacatgccgg aacgcaccaa attgaagagt ttgatcatgg ctcagattga    120
acgctggcgg caggcctaac acatgcaagt cgaacggtaa caggaagaag cttgctcttt    180
gctgacgagt ggcggacggg tgagtaatgt ctgggaaact gcctgatgga gggggataac    240
tactggaaac ggtagctaat accgcataac gtcgcaagac caaagagggg gaccttcggg    300
cctcttgcca tcggatgtgc ccagatggga ttagctagta ggtggggtaa cggctcacct    360
aggcgacgat ccctagctgg tctgagagga tgaccagcca cactggaact gagacacggt    420
ccagactcct acgggaggca gcagtgggga atattgcaca atgggcgcaa gcctgatgca    480
gccatgccgc gtgtatgaag aaggccttcg ggttgtaaag tactttcagc ggggaggaag    540
ggagtaaagt taataccttt gctcattgac gttacccgca gaagaagcac cggctaactc    600
cgtgccagca gccgcggtaa tacggagggt gcaagcgtta atcggaatta ctgggcgtaa    660
agcgcacgca ggcggtttgt taagtcagat gtgaaatccc cgggctcaac ctgggaactg    720
catctgatac tggcaagctt gagtctcgta gaggggggta gaattccagg tgtagcggtg    780
aaatgcgtag agatctggag gaataccggt ggcgaaggcg gccccctgga cgaagactga    840
cgctcaggtg cgaaagcgtg gggagcaaac aggattagat accctggtag tccacgccgt    900
aaacgatgtc gacttggagg ttgtgccctt gaggcgtggc ttccggagct aacgcgttaa    960
gtcgaccgcc tggggagtac ggccgcaagg ttaaaactca aatgaattga cgggggcccg   1020
```

```
cacaagcggt ggagcatgtg gtttaattcg atgcaacgcg aagaacctta cctggtcttg   1080

acatccacgg aagttttcag agatgagaat gtgccttcgg gaaccgtgag acaggtgctg   1140

agatcggaag agcacacgtc tgaactccag tcacaatcag tctcgtatct cgtatgccgt   1200

cttctgcttg ttgtcgactc tagggataac agggtaatga gtcgacaaca agcagaagac   1260

ggcatacgag attggtcaac gatagtctcg tgggctcgga gatgtgtata agagacagtc   1320

gttctaagag ggtgccagct gtctcttata cacatctgac gctgccgacg aatcaccagg   1380

tgtgtgtaga tctcggtggt cgccgtatca ttttgtcgac tc                       1422
```

<210> SEQ ID NO 248
<211> LENGTH: 1572
<212> TYPE: DNA
<213> ORGANISM: Artificial
<220> FEATURE:
<223> OTHER INFORMATION: Polynucleotide

<400> SEQUENCE: 248

```
gagtcgacaa aatgatacgg cgaccaccga gatctacact ctttccctac acgacgctct     60

tccgatctcc caaacgtcgg aaaggtctaa attgaagagt ttgatcatgg ctcagattga    120

acgctggcgg caggcctaac acatgcaagt cgaacggtaa caggaagaag cttgctcttt    180

gctgacgagt ggcggacggg tgagtaatgt ctgggaaact gcctgatgga gggggataac    240

tactggaaac ggtagctaat accgcataac gtcgcaagac caaagagggg gaccttcggg    300

cctcttgcca tcggatgtgc ccagatggga ttagctagta ggtggggtaa cggctcacct    360

aggcgacgat ccctagctgg tctgagagga tgaccagcca cactggaact gagacacggt    420

ccagactcct acgggaggca gcagtgggga atattgcaca atgggcgcaa gcctgatgca    480

gccatgccgc gtgtatgaag aaggccttcg ggttgtaaag tactttcagc ggggaggaag    540

ggagtaaagt taataccttt gctcattgac gttacccgca gaagaagcac cggctaactc    600

cgtgccagca gccgcggtaa tacggagggt gcaagcgtta atcggaatta ctgggcgtaa    660

agcgcacgca ggcggtttgt taagtcagat gtgaaatccc cgggctcaac ctgggaactg    720

catctgatac tggcaagctt gagtctcgta gaggggggta gaattccagg tgtagcggtg    780

aaatgcgtag agatctggag gaataccggt ggcgaaggcg gccccctgga cgaagactga    840

cgctcaggtg cgaaagcgtg gggagcaaac aggattagat accctggtag tccacgccgt    900

aaacgatgtc gacttggagg ttgtgccctt gaggcgtggc ttccggagct aacgcgttaa    960

gtcgaccgcc tggggagtac ggccgcaagg ttaaaactca aatgaattga cgggggcccg   1020

cacaagcggt ggagcatgtg gtttaattcg atgcaacgcg aagaacctta cctggtcttg   1080

acatccacgg aagttttcag agatgagaat gtgccttcgg gaaccgtgag acaggtgctg   1140

catggctgtc gtcagctcgt gttgtgaaat gttgggttaa gtcccgcaac gagcgcaacc   1200

cttatccttt gttgccagcg gtccggccgg gaactcaaag gagactgcca gtgataaact   1260

ggaggaaggt ggggatgacg tcaagtcatc agatcggaag agcacacgtc tgaactccag   1320

tcacaatcag tctcgtatct cgtatgccgt cttctgcttg ttgtcgactc tagggataac   1380

agggtaatga gtcgacaaca agcagaagac ggcatacgag attggtcaac gatagtctcg   1440

tgggctcgga gatgtgtata agagacagtg caactcaacg gtcccaggct gtctcttata   1500

cacatctgac gctgccgacg aatcaccagg tgtgtgtaga tctcggtggt cgccgtatca   1560

ttttgtcgac tc                                                        1572
```

<210> SEQ ID NO 249
<211> LENGTH: 1722
<212> TYPE: DNA
<213> ORGANISM: Artificial
<220> FEATURE:
<223> OTHER INFORMATION: Polynucleotide

<400> SEQUENCE: 249
gagtcgacaa aatgatacgg cgaccaccga gatctacact ctttccctac acgacgctct 60
tccgatctaa ccagaggatg agacacgtaa attgaagagt ttgatcatgg ctcagattga 120
acgctggcgg caggcctaac acatgcaagt cgaacggtaa caggaagaag cttgctcttt 180
gctgacgagt ggcggacggg tgagtaatgt ctgggaaact gcctgatgga gggggataac 240
tactggaaac ggtagctaat accgcataac gtcgcaagac caaagagggg gaccttcggg 300
cctcttgcca tcggatgtgc ccagatggga ttagctagta ggtggggtaa cggctcacct 360
aggcgacgat ccctagctgg tctgagagga tgaccagcca cactggaact gagacacggt 420
ccagactcct acgggaggca gcagtgggga atattgcaca atgggcgcaa gcctgatgca 480
gccatgccgc gtgtatgaag aaggccttcg ggttgtaaag tactttcagc ggggaggaag 540
ggagtaaagt taataccttt gctcattgac gttacccgca gaagaagcac cggctaactc 600
cgtgccagca gccgcggtaa tacggagggt gcaagcgtta atcggaatta ctgggcgtaa 660
agcgcacgca ggcggtttgt taagtcagat gtgaaatccc cgggctcaac ctgggaactg 720
catctgatac tggcaagctt gagtctcgta gaggggggta gaattccagg tgtagcggtg 780
aaatgcgtag agatctggag gaataccggt ggcgaaggcg gccccctgga cgaagactga 840
cgctcaggtg cgaaagcgtg gggagcaaac aggattagat accctggtag tccacgccgt 900
aaacgatgtc gacttggagg ttgtgccctt gaggcgtggc ttccggagct aacgcgttaa 960
gtcgaccgcc tggggagtac ggccgcaagg ttaaaactca aatgaattga cgggggcccg 1020
cacaagcggt ggagcatgtg gtttaattcg atgcaacgcg aagaacctta cctggtcttg 1080
acatccacgg aagttttcag agatgagaat gtgccttcgg gaaccgtgag acaggtgctg 1140
catggctgtc gtcagctcgt gttgtgaaat gttgggttaa gtcccgcaac gagcgcaacc 1200
cttatccttt gttgccagcg gtccggccgg gaactcaaag gagactgcca gtgataaact 1260
ggaggaaggt ggggatgacg tcaagtcatc atggccctta cgaccagggc tacacacgtg 1320
ctacaatggc gcatacaaag agaagcgacc tcgcgagagc aagcggacct cataaagtgc 1380
gtcgtagtcc ggattggagt ctgcaactcg actccatgaa gtcggaatcg ctagtaatcg 1440
agatcggaag agcacacgtc tgaactccag tcacaatcag tctcgtatct cgtatgccgt 1500
cttctgcttg ttgtcgactc tagggataac agggtaatga gtcgacaaca agcagaagac 1560
ggcatacgag attggtcaac gatagtctcg tgggctcgga gatgtgtata agagacagtg 1620
gctccttctg ttaaggcact gtctcttata cacatctgac gctgccgacg aatcaccagg 1680
tgtgtgtaga tctcggtggt cgccgtatca ttttgtcgac tc 1722

<210> SEQ ID NO 250
<211> LENGTH: 372
<212> TYPE: DNA
<213> ORGANISM: Artificial
<220> FEATURE:
<223> OTHER INFORMATION: Polynucleotide

<400> SEQUENCE: 250
gagtcgacaa aatgatacgg cgaccaccga gatctacact ctttccctac acgacgctct 60
tccgatctcc acctaacaga cacttgttag agatcggaag agcacacgtc tgaactccag 120
tcacaatcag tctcgtatct cgtatgccgt cttctgcttg ttgtcgactc tagggataac 180
agggtaatga gtcgacaaca agcagaagac ggcatacgag attggtcaac gatagtctcg 240
tgggctcgga gatgtgtata agagacaggg taagtagtgc gtgagggtct gtctcttata 300
cacatctgac gctgccgacg aatcaccagg tgtgtgtaga tctcggtggt cgccgtatca 360
ttttgtcgac tc 372

<210> SEQ ID NO 251
<211> LENGTH: 522
<212> TYPE: DNA
<213> ORGANISM: Artificial
<220> FEATURE:
<223> OTHER INFORMATION: Polynucleotide

<400> SEQUENCE: 251
gagtcgacaa aatgatacgg cgaccaccga gatctacact ctttccctac acgacgctct 60
tccgatctgc gccctggcgc cggccaggtt tttaaggcgc ttatataatc aaaccctttg 120
taaaaattaa agttttaaat ggaattctaa tcgatttatt tcacattagc tttatttaag 180
tgtgacctac gcagaaagct agcgaaatac tcatcaaccc tcccccgcca tcgcagcgcc 240
agatcggaag agcacacgtc tgaactccag tcacaatcag tctcgtatct cgtatgccgt 300
cttctgcttg ttgtcgactc tagggataac agggtaatga gtcgacaaca agcagaagac 360
ggcatacgag attggtcaac gatagtctcg tgggctcgga gatgtgtata agagacagac 420
ggagtagtac ggtcaaatct gtctcttata cacatctgac gctgccgacg aatcaccagg 480
tgtgtgtaga tctcggtggt cgccgtatca ttttgtcgac tc 522

<210> SEQ ID NO 252
<211> LENGTH: 672
<212> TYPE: DNA
<213> ORGANISM: Artificial
<220> FEATURE:
<223> OTHER INFORMATION: Polynucleotide

<400> SEQUENCE: 252
gagtcgacaa aatgatacgg cgaccaccga gatctacact ctttccctac acgacgctct 60
tccgatctct actaaacaat aatgggaatt tttaaggcgc ttatataatc aaaccctttg 120
taaaaattaa agttttaaat ggaattctaa tcgatttatt tcacattagc tttatttaag 180
tgtgacctac gcagaaagct agcgaaatac tcatcaaccc tcccccgcca tcgcagcgcc 240
attctcctaa tttgcgaaaa aagctccggg aaaaggaaaa agcggcagtc gtaatagcga 300
actgaaactg aacgagagta aaagtgaaaa gacagcagga actcagccat gtcgaagatc 360
ggaattaacg gatttggccg catcggccgc agatcggaag agcacacgtc tgaactccag 420
tcacaatcag tctcgtatct cgtatgccgt cttctgcttg ttgtcgactc tagggataac 480
agggtaatga gtcgacaaca agcagaagac ggcatacgag attggtcaac gatagtctcg 540
tgggctcgga gatgtgtata agagacaggg attgccacac gcgatagact gtctcttata 600
cacatctgac gctgccgacg aatcaccagg tgtgtgtaga tctcggtggt cgccgtatca 660
ttttgtcgac tc 672

<210> SEQ ID NO 253
<211> LENGTH: 822
<212> TYPE: DNA
<213> ORGANISM: Artificial
<220> FEATURE:
<223> OTHER INFORMATION: Polynucleotide

<400> SEQUENCE: 253
gagtcgacaa aatgatacgg cgaccaccga gatctacact ctttccctac acgacgctct 60
tccgatctct gtgttcggcc ttcgagattt tttaaggcgc ttatataatc aaaccctttg 120
taaaaattaa agttttaaat ggaattctaa tcgatttatt tcacattagc tttatttaag 180
tgtgacctac gcagaaagct agcgaaatac tcatcaaccc tcccccgcca tcgcagcgcc 240
attctcctaa tttgcgaaaa aagctccggg aaaaggaaaa agcggcagtc gtaatagcga 300
actgaaactg aacgagagta aaagtgaaaa gacagcagga actcagccat gtcgaagatc 360
ggaattaacg gatttggccg catcggccgc ttggtgctcc gcgccgccat cgataagggc 420
gcctccgtgg tggccgtcaa cgatcccttc atcgatgtca actacatggt ttacctgttt 480
aaattcgact cgactcacgg tcgtttcaag ggcaccgttg cggctgaggg cggattcctg 540
agatcggaag agcacacgtc tgaactccag tcacaatcag tctcgtatct cgtatgccgt 600
cttctgcttg ttgtcgactc tagggataac agggtaatga gtcgacaaca agcagaagac 660
ggcatacgag attggtcaac gatagtctcg tgggctcgga gatgtgtata agagacagta 720
gtgtttaagt gcgaacctct gtctcttata cacatctgac gctgccgacg aatcaccagg 780
tgtgtgtaga tctcggtggt cgccgtatca ttttgtcgac tc 822

<210> SEQ ID NO 254
<211> LENGTH: 972
<212> TYPE: DNA
<213> ORGANISM: Artificial
<220> FEATURE:
<223> OTHER INFORMATION: Polynucleotide

<400> SEQUENCE: 254
gagtcgacaa aatgatacgg cgaccaccga gatctacact ctttccctac acgacgctct 60
tccgatctta tgaaatcgga gtatcagttt tttaaggcgc ttatataatc aaaccctttg 120
taaaaattaa agttttaaat ggaattctaa tcgatttatt tcacattagc tttatttaag 180
tgtgacctac gcagaaagct agcgaaatac tcatcaaccc tcccccgcca tcgcagcgcc 240
attctcctaa tttgcgaaaa aagctccggg aaaaggaaaa agcggcagtc gtaatagcga 300
actgaaactg aacgagagta aaagtgaaaa gacagcagga actcagccat gtcgaagatc 360
ggaattaacg gatttggccg catcggccgc ttggtgctcc gcgccgccat cgataagggc 420
gcctccgtgg tggccgtcaa cgatcccttc atcgatgtca actacatggt ttacctgttt 480
aaattcgact cgactcacgg tcgtttcaag ggcaccgttg cggctgaggg cggattcctg 540
gtggtgaacg gccagaagat caccgtgttc agcgagcgcg acccggccaa catcaactgg 600
gccagtgctg gagccgagta tgtggtggag tccaccggag tgttcaccac cattgacaag 660
gcgtccaccc acttgaaggg cggcgccaag agatcggaag agcacacgtc tgaactccag 720
tcacaatcag tctcgtatct cgtatgccgt cttctgcttg ttgtcgactc tagggataac 780
agggtaatga gtcgacaaca agcagaagac ggcatacgag attggtcaac gatagtctcg 840
tgggctcgga gatgtgtata agagacagaa gagccctgcc tcaagtccct gtctcttata 900
cacatctgac gctgccgacg aatcaccagg tgtgtgtaga tctcggtggt cgccgtatca 960
ttttgtcgac tc 972

<210> SEQ ID NO 255

<211> LENGTH: 1122
<212> TYPE: DNA
<213> ORGANISM: Artificial
<220> FEATURE:
<223> OTHER INFORMATION: Polynucleotide

<400> SEQUENCE: 255

```
gagtcgacaa aatgatacgg cgaccaccga gatctacact ctttccctac acgacgctct     60
tccgatctag ccaaacgtct gaacagattt tttaaggcgc ttatataatc aaaccctttg    120
taaaaattaa agttttaaat ggaattctaa tcgatttatt tcacattagc tttatttaag    180
tgtgacctac gcagaaagct agcgaaatac tcatcaaccc tcccccgcca tcgcagcgcc    240
attctcctaa tttgcgaaaa aagctccggg aaaaggaaaa agcggcagtc gtaatagcga    300
actgaaactg aacgagagta aaagtgaaaa gacagcagga actcagccat gtcgaagatc    360
ggaattaacg gatttggccg catcggccgc ttggtgctcc gcgccgccat cgataagggc    420
gcctccgtgg tggccgtcaa cgatcccttc atcgatgtca actacatggt ttacctgttt    480
aaattcgact cgactcacgg tcgtttcaag ggcaccgttg cggctgaggg cggattcctg    540
gtggtgaacg gccagaagat caccgtgttc agcgagcgcg acccggccaa catcaactgg    600
gccagtgctg gagccgagta tgtggtggag tccaccggag tgttcaccac cattgacaag    660
gcgtccaccc acttgaaggg cggcgccaag aaggtcatca tctcggcccc atccgccgat    720
gcgcccatgt tcgtgtgcgg cgttaacctg gacgcctaca gccccgacat gaaggtggtc    780
tccaacgcct cgtgcaccac caactgcctg gctcccctgg ccaaggtcat caatgacaac    840
agatcggaag agcacacgtc tgaactccag tcacaatcag tctcgtatct cgtatgccgt    900
cttctgcttg ttgtcgactc tagggataac agggtaatga gtcgacaaca agcagaagac    960
ggcatacgag attggtcaac gatagtctcg tgggctcgga gatgtgtata agagacagcc   1020
gtgtcgaacg ccactcgact gtctcttata cacatctgac gctgccgacg aatcaccagg   1080
tgtgtgtaga tctcggtggt cgccgtatca ttttgtcgac tc                      1122
```

<210> SEQ ID NO 256
<211> LENGTH: 1272
<212> TYPE: DNA
<213> ORGANISM: Artificial
<220> FEATURE:
<223> OTHER INFORMATION: Polynucleotide

<400> SEQUENCE: 256

```
gagtcgacaa aatgatacgg cgaccaccga gatctacact ctttccctac acgacgctct     60
tccgatctca agtccagggc actcgccttt tttaaggcgc ttatataatc aaaccctttg    120
taaaaattaa agttttaaat ggaattctaa tcgatttatt tcacattagc tttatttaag    180
tgtgacctac gcagaaagct agcgaaatac tcatcaaccc tcccccgcca tcgcagcgcc    240
attctcctaa tttgcgaaaa aagctccggg aaaaggaaaa agcggcagtc gtaatagcga    300
actgaaactg aacgagagta aaagtgaaaa gacagcagga actcagccat gtcgaagatc    360
ggaattaacg gatttggccg catcggccgc ttggtgctcc gcgccgccat cgataagggc    420
gcctccgtgg tggccgtcaa cgatcccttc atcgatgtca actacatggt ttacctgttt    480
aaattcgact cgactcacgg tcgtttcaag ggcaccgttg cggctgaggg cggattcctg    540
gtggtgaacg gccagaagat caccgtgttc agcgagcgcg acccggccaa catcaactgg    600
gccagtgctg gagccgagta tgtggtggag tccaccggag tgttcaccac cattgacaag    660
gcgtccaccc acttgaaggg cggcgccaag aaggtcatca tctcggcccc atccgccgat    720
```

gcgcccatgt tcgtgtgcgg cgttaacctg gacgcctaca gccccgacat gaaggtggtc 780
tccaacgcct cgtgcaccac caactgcctg gctcccctgg ccaaggtcat caatgacaac 840
ttcgagatcg tcgagggtct gatgaccacc gtgcacgcca ccactgccac ccagaagacc 900
gtcgacggtc cctctggcaa actgtggcgc gatggacgtg gcgccgccca gaacatcatc 960
ccggccgcca ccggagccgc caaggctgtg agatcggaag agcacacgtc tgaactccag 1020
tcacaatcag tctcgtatct cgtatgccgt cttctgcttg ttgtcgactc tagggataac 1080
agggtaatga gtcgacaaca agcagaagac ggcatacgag attggtcaac gatagtctcg 1140
tgggctcgga gatgtgtata agagacagta tgccatgggc tttcgaacct gtctcttata 1200
cacatctgac gctgccgacg aatcaccagg tgtgtgtaga tctcggtggt cgccgtatca 1260
ttttgtcgac tc 1272

<210> SEQ ID NO 257
<211> LENGTH: 1422
<212> TYPE: DNA
<213> ORGANISM: Artificial
<220> FEATURE:
<223> OTHER INFORMATION: Polynucleotide

<400> SEQUENCE: 257
gagtcgacaa aatgatacgg cgaccaccga gatctacact ctttccctac acgacgctct 60
tccgatctat ttctactcat aggttcattt tttaaggcgc ttatataatc aaaccctttg 120
taaaaattaa agttttaaat ggaattctaa tcgatttatt tcacattagc tttatttaag 180
tgtgacctac gcagaaagct agcgaaatac tcatcaaccc tcccccgcca tcgcagcgcc 240
attctcctaa tttgcgaaaa aagctccggg aaaaggaaaa agcggcagtc gtaatagcga 300
actgaaactg aacgagagta aaagtgaaaa gacagcagga actcagccat gtcgaagatc 360
ggaattaacg gatttggccg catcggccgc ttggtgctcc gcgccgccat cgataagggc 420
gcctccgtgg tggccgtcaa cgatcccttc atcgatgtca actacatggt ttacctgttt 480
aaattcgact cgactcacgg tcgtttcaag ggcaccgttg cggctgaggg cggattcctg 540
gtggtgaacg gccagaagat caccgtgttc agcgagcgcg acccggccaa catcaactgg 600
gccagtgctg gagccgagta tgtggtggag tccaccggag tgttcaccac cattgacaag 660
gcgtccaccc acttgaaggg cggcgccaag aaggtcatca tctcggcccc atccgccgat 720
gcgcccatgt tcgtgtgcgg cgttaacctg gacgcctaca gccccgacat gaaggtggtc 780
tccaacgcct cgtgcaccac caactgcctg gctcccctgg ccaaggtcat caatgacaac 840
ttcgagatcg tcgagggtct gatgaccacc gtgcacgcca ccactgccac ccagaagacc 900
gtcgacggtc cctctggcaa actgtggcgc gatggacgtg gcgccgccca gaacatcatc 960
ccggccgcca ccggagccgc caaggctgtg ggcaaggtca tccccgccct gaacggcaag 1020
ctgaccggca tggctttccg cgtgcccacg cccaatgtct ccgttgtgga tcttaccgtc 1080
cgcttgggca agggagccac ctatgacgaa atcaaggcta aggtcgagga ggcctccaag 1140
agatcggaag agcacacgtc tgaactccag tcacaatcag tctcgtatct cgtatgccgt 1200
cttctgcttg ttgtcgactc tagggataac agggtaatga gtcgacaaca agcagaagac 1260
ggcatacgag attggtcaac gatagtctcg tgggctcgga gatgtgtata agagacagtt 1320
agatcagata gaaggtacct gtctcttata cacatctgac gctgccgacg aatcaccagg 1380
tgtgtgtaga tctcggtggt cgccgtatca ttttgtcgac tc 1422

<210> SEQ ID NO 258
<211> LENGTH: 1572
<212> TYPE: DNA
<213> ORGANISM: Artificial
<220> FEATURE:
<223> OTHER INFORMATION: Polynucleotide

<400> SEQUENCE: 258
gagtcgacaa aatgatacgg cgaccaccga gatctacact ctttccctac acgacgctct 60
tccgatcttt aagactgtta gttcgaggtt tttaaggcgc ttatataatc aaaccctttg 120
taaaaattaa agttttaaat ggaattctaa tcgatttatt tcacattagc tttatttaag 180
tgtgacctac gcagaaagct agcgaaatac tcatcaaccc tcccccgcca tcgcagcgcc 240
attctcctaa tttgcgaaaa aagctccggg aaaaggaaaa agcggcagtc gtaatagcga 300
actgaaactg aacgagagta aaagtgaaaa gacagcagga actcagccat gtcgaagatc 360
ggaattaacg gatttggccg catcggccgc ttggtgctcc gcgccgccat cgataagggc 420
gcctccgtgg tggccgtcaa cgatcccttc atcgatgtca actacatggt ttacctgttt 480
aaattcgact cgactcacgg tcgtttcaag ggcaccgttg cggctgaggg cggattcctg 540
gtggtgaacg gccagaagat caccgtgttc agcgagcgcg acccggccaa catcaactgg 600
gccagtgctg gagccgagta tgtggtggag tccaccggag tgttcaccac cattgacaag 660
gcgtccaccc acttgaaggg cggcgccaag aaggtcatca tctcggcccc atccgccgat 720
gcgcccatgt tcgtgtgcgg cgttaacctg gacgcctaca gccccgacat gaaggtggtc 780
tccaacgcct cgtgcaccac caactgcctg gctcccctgg ccaaggtcat caatgacaac 840
ttcgagatcg tcgagggtct gatgaccacc gtgcacgcca ccactgccac ccagaagacc 900
gtcgacggtc cctctggcaa actgtggcgc gatggacgtg gcgccgccca gaacatcatc 960
ccggccgcca ccggagccgc caaggctgtg ggcaaggtca tccccgccct gaacggcaag 1020
ctgaccggca tggctttccg cgtgcccacg cccaatgtct ccgttgtgga tcttaccgtc 1080
cgcttgggca agggagccac ctatgacgaa atcaaggcta aggtcgagga ggcctccaag 1140
ggacccctga agggaatcct gggctacacc gatgaggagg tggtctccac cgacttcttc 1200
agcgacaccc attcgtctgt gttcgacgcc aaggctggca tttcgctgaa cgataagttc 1260
gtcaagctaa tctcgtggta cgacaacgag agatcggaag agcacacgtc tgaactccag 1320
tcacaatcag tctcgtatct cgtatgccgt cttctgcttg ttgtcgactc tagggataac 1380
agggtaatga gtcgacaaca agcagaagac ggcatacgag attggtcaac gatagtctcg 1440
tgggctcgga gatgtgtata agagacagtt tatattgttc tgcctcacct gtctcttata 1500
cacatctgac gctgccgacg aatcaccagg tgtgtgtaga tctcggtggt cgccgtatca 1560
ttttgtcgac tc 1572

<210> SEQ ID NO 259
<211> LENGTH: 1722
<212> TYPE: DNA
<213> ORGANISM: Artificial
<220> FEATURE:
<223> OTHER INFORMATION: Polynucleotide

<400> SEQUENCE: 259
gagtcgacaa aatgatacgg cgaccaccga gatctacact ctttccctac acgacgctct 60
tccgatctag ttactggctt tgtaggattt tttaaggcgc ttatataatc aaaccctttg 120
taaaaattaa agttttaaat ggaattctaa tcgatttatt tcacattagc tttatttaag 180

```
tgtgacctac gcagaaagct agcgaaatac tcatcaaccc tcccccgcca tcgcagcgcc    240
attctcctaa tttgcgaaaa aagctccggg aaaaggaaaa agcggcagtc gtaatagcga    300
actgaaactg aacgagagta aaagtgaaaa gacagcagga actcagccat gtcgaagatc    360
ggaattaacg gatttggccg catcggccgc ttggtgctcc gcgccgccat cgataagggc    420
gcctccgtgg tggccgtcaa cgatcccttc atcgatgtca actacatggt ttacctgttt    480
aaattcgact cgactcacgg tcgtttcaag ggcaccgttg cggctgaggg cggattcctg    540
gtggtgaacg gccagaagat caccgtgttc agcgagcgcg acccggccaa catcaactgg    600
gccagtgctg gagccgagta tgtggtggag tccaccggag tgttcaccac cattgacaag    660
gcgtccaccc acttgaaggg cggcgccaag aaggtcatca tctcggcccc atccgccgat    720
gcgcccatgt tcgtgtgcgg cgttaacctg gacgcctaca gccccgacat gaaggtggtc    780
tccaacgcct cgtgcaccac caactgcctg gctcccctgg ccaaggtcat caatgacaac    840
ttcgagatcg tcgagggtct gatgaccacc gtgcacgcca ccactgccac ccagaagacc    900
gtcgacggtc cctctggcaa actgtggcgc gatggacgtg gcgccgccca gaacatcatc    960
ccggccgcca ccggagccgc caaggctgtg ggcaaggtca tccccgccct gaacggcaag   1020
ctgaccggca tggctttccg cgtgcccacg cccaatgtct ccgttgtgga tcttaccgtc   1080
cgcttgggca agggagccac ctatgacgaa atcaaggcta aggtcgagga ggcctccaag   1140
ggacccctga agggaatcct gggctacacc gatgaggagg tggtctccac cgacttcttc   1200
agcgacaccc attcgtctgt gttcgacgcc aaggctggca tttcgctgaa cgataagttc   1260
gtcaagctaa tctcgtggta cgacaacgag ttcggttact ccaaccgcgt catcgacctg   1320
atcaagtata tgcagagcaa ggactaaact agccaaaact atcgtacaaa cccggcgccc   1380
agcagctggt cgggaatcac tgttgcataa tccgcaaggg gcgcaattga ggatgctttt   1440
agatcggaag agcacacgtc tgaactccag tcacaatcag tctcgtatct cgtatgccgt   1500
cttctgcttg ttgtcgactc tagggataac agggtaatga gtcgacaaca agcagaagac   1560
ggcatacgag attggtcaac gatagtctcg tgggctcgga gatgtgtata agagacagtg   1620
tggctccaat tgctgcaact gtctcttata cacatctgac gctgccgacg aatcaccagg   1680
tgtgtgtaga tctcggtggt cgccgtatca ttttgtcgac tc                      1722
```

<210> SEQ ID NO 260
<211> LENGTH: 372
<212> TYPE: DNA
<213> ORGANISM: Artificial
<220> FEATURE:
<223> OTHER INFORMATION: Polynucleotide

<400> SEQUENCE: 260

```
gagtcgacaa aatgatacgg cgaccaccga gatctacact ctttccctac acgacgctct     60
tccgatctaa cggttgatgg gcctggtatc agatcggaag agcacacgtc tgaactccag    120
tcacaatcag tctcgtatct cgtatgccgt cttctgcttg ttgtcgactc tagggataac    180
agggtaatga gtcgacaaca agcagaagac ggcatacgag attggtcaac gatagtctcg    240
tgggctcgga gatgtgtata agagacagca cgcgtacgtg ctatcttcct gtctcttata    300
cacatctgac gctgccgacg aatcaccagg tgtgtgtaga tctcggtggt cgccgtatca    360
ttttgtcgac tc                                                        372
```

<210> SEQ ID NO 261

<211> LENGTH: 522
<212> TYPE: DNA
<213> ORGANISM: Artificial
<220> FEATURE:
<223> OTHER INFORMATION: Polynucleotide

<400> SEQUENCE: 261
gagtcgacaa aatgatacgg cgaccaccga gatctacact ctttccctac acgacgctct 60
tccgatctcg ttgtgtttgc tggcgcaatc atattcgttt tacgtttgtc aagcctcata 120
gccggcagtt cgaacgtata cgctctctga gtcagacctc gaaatcgtag ctctacacaa 180
ttctgtgaat tttccttgtc gcgtgtgaaa cacttccaat aaaaactcaa tatgcgtgaa 240
agatcggaag agcacacgtc tgaactccag tcacaatcag tctcgtatct cgtatgccgt 300
cttctgcttg ttgtcgactc tagggataac agggtaatga gtcgacaaca agcagaagac 360
ggcatacgag attggtcaac gatagtctcg tgggctcgga gatgtgtata agagacagtc 420
gcgaccaaat ggtcagtcct gtctcttata cacatctgac gctgccgacg aatcaccagg 480
tgtgtgtaga tctcggtggt cgccgtatca ttttgtcgac tc 522

<210> SEQ ID NO 262
<211> LENGTH: 672
<212> TYPE: DNA
<213> ORGANISM: Artificial
<220> FEATURE:
<223> OTHER INFORMATION: Polynucleotide

<400> SEQUENCE: 262
gagtcgacaa aatgatacgg cgaccaccga gatctacact ctttccctac acgacgctct 60
tccgatctgg ctgacggttg agagggattc atattcgttt tacgtttgtc aagcctcata 120
gccggcagtt cgaacgtata cgctctctga gtcagacctc gaaatcgtag ctctacacaa 180
ttctgtgaat tttccttgtc gcgtgtgaaa cacttccaat aaaaactcaa tatgcgtgaa 240
tgtatctcta tccatgttgg tcaggctggt gtccagattg gaaacgcctg ctgggagctc 300
tactgcttgg agcacggcat ccagcccgat ggccagatgc cgtctgacaa gaccgtgggc 360
ggaggtgatg actcgttcaa caccttcttc agatcggaag agcacacgtc tgaactccag 420
tcacaatcag tctcgtatct cgtatgccgt cttctgcttg ttgtcgactc tagggataac 480
agggtaatga gtcgacaaca agcagaagac ggcatacgag attggtcaac gatagtctcg 540
tgggctcgga gatgtgtata agagacagtt cggcaatcag aaagggtact gtctcttata 600
cacatctgac gctgccgacg aatcaccagg tgtgtgtaga tctcggtggt cgccgtatca 660
ttttgtcgac tc 672

<210> SEQ ID NO 263
<211> LENGTH: 822
<212> TYPE: DNA
<213> ORGANISM: Artificial
<220> FEATURE:
<223> OTHER INFORMATION: Polynucleotide

<400> SEQUENCE: 263
gagtcgacaa aatgatacgg cgaccaccga gatctacact ctttccctac acgacgctct 60
tccgatcttt cacatcgcct tgaccttatc atattcgttt tacgtttgtc aagcctcata 120
gccggcagtt cgaacgtata cgctctctga gtcagacctc gaaatcgtag ctctacacaa 180
ttctgtgaat tttccttgtc gcgtgtgaaa cacttccaat aaaaactcaa tatgcgtgaa 240
tgtatctcta tccatgttgg tcaggctggt gtccagattg gaaacgcctg ctgggagctc 300
tactgcttgg agcacggcat ccagcccgat ggccagatgc cgtctgacaa gaccgtgggc 360
ggaggtgatg actcgttcaa caccttcttc agcgagactg gagctggcaa gcacgtgccc 420
cgcgccgtgt ttgtggatct ggaacccact gtggtcgatg aggtccgtac cggaacctac 480
cgtcagctgt tccaccccga gcagctgatc actggtaagg aggatgcggc caacaactac 540
agatcggaag agcacacgtc tgaactccag tcacaatcag tctcgtatct cgtatgccgt 600
cttctgcttg ttgtcgactc tagggataac agggtaatga gtcgacaaca agcagaagac 660
ggcatacgag attggtcaac gatagtctcg tgggctcgga gatgtgtata agagacagtt 720
aggaccggat taggttcact gtctcttata cacatctgac gctgccgacg aatcaccagg 780
tgtgtgtaga tctcggtggt cgccgtatca ttttgtcgac tc 822

<210> SEQ ID NO 264
<211> LENGTH: 972
<212> TYPE: DNA
<213> ORGANISM: Artificial
<220> FEATURE:
<223> OTHER INFORMATION: Polynucleotide

<400> SEQUENCE: 264
gagtcgacaa aatgatacgg cgaccaccga gatctacact ctttccctac acgacgctct 60
tccgatcttg gtactgcctc ctggcctctc atattcgttt tacgtttgtc aagcctcata 120
gccggcagtt cgaacgtata cgctctctga gtcagacctc gaaatcgtag ctctacacaa 180
ttctgtgaat tttccttgtc gcgtgtgaaa cacttccaat aaaaactcaa tatgcgtgaa 240
tgtatctcta tccatgttgg tcaggctggt gtccagattg gaaacgcctg ctgggagctc 300
tactgcttgg agcacggcat ccagcccgat ggccagatgc cgtctgacaa gaccgtgggc 360
ggaggtgatg actcgttcaa caccttcttc agcgagactg gagctggcaa gcacgtgccc 420
cgcgccgtgt ttgtggatct ggaacccact gtggtcgatg aggtccgtac cggaacctac 480
cgtcagctgt tccaccccga gcagctgatc actggtaagg aggatgcggc caacaactac 540
gcccgtggcc actacaccat cggcaaggag atcgtcgatc tggttctgga caggatccgc 600
aagctggccg atcagtgcac cggtctgcag ggcttcctca tcttccactc gttcggtgga 660
ggtaccggct ccggcttcac ctcgctgctg agatcggaag agcacacgtc tgaactccag 720
tcacaatcag tctcgtatct cgtatgccgt cttctgcttg ttgtcgactc tagggataac 780
agggtaatga gtcgacaaca agcagaagac ggcatacgag attggtcaac gatagtctcg 840
tgggctcgga gatgtgtata agagacagag acctcggacg aggctcacct gtctcttata 900
cacatctgac gctgccgacg aatcaccagg tgtgtgtaga tctcggtggt cgccgtatca 960
ttttgtcgac tc 972

<210> SEQ ID NO 265
<211> LENGTH: 1122
<212> TYPE: DNA
<213> ORGANISM: Artificial
<220> FEATURE:
<223> OTHER INFORMATION: Polynucleotide

<400> SEQUENCE: 265
gagtcgacaa aatgatacgg cgaccaccga gatctacact ctttccctac acgacgctct 60
tccgatctcg accgtcattg acggcccttc atattcgttt tacgtttgtc aagcctcata 120
gccggcagtt cgaacgtata cgctctctga gtcagacctc gaaatcgtag ctctacacaa 180

```
ttctgtgaat tttccttgtc gcgtgtgaaa cacttccaat aaaaactcaa tatgcgtgaa    240

tgtatctcta tccatgttgg tcaggctggt gtccagattg gaaacgcctg ctgggagctc    300

tactgcttgg agcacggcat ccagcccgat ggccagatgc cgtctgacaa gaccgtgggc    360

ggaggtgatg actcgttcaa caccttcttc agcgagactg gagctggcaa gcacgtgccc    420

cgcgccgtgt ttgtggatct ggaacccact gtggtcgatg aggtccgtac cggaacctac    480

cgtcagctgt tccaccccga gcagctgatc actggtaagg aggatgcggc caacaactac    540

gcccgtggcc actacaccat cggcaaggag atcgtcgatc tggttctgga caggatccgc    600

aagctggccg atcagtgcac cggtctgcag ggcttcctca tcttccactc gttcggtgga    660

ggtaccggct ccggcttcac ctcgctgctg atggagcgtc tctccgtgga ctacggcaag    720

aagtccaagc tggagttcgc catctaccca gccccccagg tgtccactgc cgtggtcgag    780

ccctacaact ccatcctgac cacccacacc accctggagc attccgactg cgccttcatg    840

agatcggaag agcacacgtc tgaactccag tcacaatcag tctcgtatct cgtatgccgt    900

cttctgcttg ttgtcgactc tagggataac agggtaatga gtcgacaaca agcagaagac    960

ggcatacgag attggtcaac gatagtctcg tgggctcgga gatgtgtata agagacagac   1020

ctgaaataca cagtaaccct gtctcttata cacatctgac gctgccgacg aatcaccagg   1080

tgtgtgtaga tctcggtggt cgccgtatca ttttgtcgac tc                      1122
```

<210> SEQ ID NO 266
<211> LENGTH: 1272
<212> TYPE: DNA
<213> ORGANISM: Artificial
<220> FEATURE:
<223> OTHER INFORMATION: Polynucleotide

<400> SEQUENCE: 266

```
gagtcgacaa aatgatacgg cgaccaccga gatctacact ctttccctac acgacgctct     60

tccgatctta tcaccaggga tgcattgatc atattcgttt tacgtttgtc aagcctcata    120

gccggcagtt cgaacgtata cgctctctga gtcagacctc gaaatcgtag ctctacacaa    180

ttctgtgaat tttccttgtc gcgtgtgaaa cacttccaat aaaaactcaa tatgcgtgaa    240

tgtatctcta tccatgttgg tcaggctggt gtccagattg gaaacgcctg ctgggagctc    300

tactgcttgg agcacggcat ccagcccgat ggccagatgc cgtctgacaa gaccgtgggc    360

ggaggtgatg actcgttcaa caccttcttc agcgagactg gagctggcaa gcacgtgccc    420

cgcgccgtgt ttgtggatct ggaacccact gtggtcgatg aggtccgtac cggaacctac    480

cgtcagctgt tccaccccga gcagctgatc actggtaagg aggatgcggc caacaactac    540

gcccgtggcc actacaccat cggcaaggag atcgtcgatc tggttctgga caggatccgc    600

aagctggccg atcagtgcac cggtctgcag ggcttcctca tcttccactc gttcggtgga    660

ggtaccggct ccggcttcac ctcgctgctg atggagcgtc tctccgtgga ctacggcaag    720

aagtccaagc tggagttcgc catctaccca gccccccagg tgtccactgc cgtggtcgag    780

ccctacaact ccatcctgac cacccacacc accctggagc attccgactg cgccttcatg    840

gtcgacaacg aggctatcta cgacatctgc cgccgcaatc tggacattga gcgccccacg    900

tacaccaacc tgaaccgtct gattggccag atcgtgtcct cgattaccgc ctctctgcga    960

ttcgatggtg cccttaacgt ggatctgact agatcggaag agcacacgtc tgaactccag   1020

tcacaatcag tctcgtatct cgtatgccgt cttctgcttg ttgtcgactc tagggataac   1080

agggtaatga gtcgacaaca agcagaagac ggcatacgag attggtcaac gatagtctcg   1140
```

tgggctcgga gatgtgtata agagacagta ttgtgtaaga cattaccgct gtctcttata 1200
cacatctgac gctgccgacg aatcaccagg tgtgtgtaga tctcggtggt cgccgtatca 1260
ttttgtcgac tc 1272

<210> SEQ ID NO 267
<211> LENGTH: 1422
<212> TYPE: DNA
<213> ORGANISM: Artificial
<220> FEATURE:
<223> OTHER INFORMATION: Polynucleotide

<400> SEQUENCE: 267
gagtcgacaa aatgatacgg cgaccaccga gatctacact ctttccctac acgacgctct 60
tccgatctgg accatattta gttatgactc atattcgttt tacgtttgtc aagcctcata 120
gccggcagtt cgaacgtata cgctctctga gtcagacctc gaaatcgtag ctctacacaa 180
ttctgtgaat tttccttgtc gcgtgtgaaa cacttccaat aaaaactcaa tatgcgtgaa 240
tgtatctcta tccatgttgg tcaggctggt gtccagattg gaaacgcctg ctgggagctc 300
tactgcttgg agcacggcat ccagcccgat ggccagatgc cgtctgacaa gaccgtgggc 360
ggaggtgatg actcgttcaa caccttcttc agcgagactg gagctggcaa gcacgtgccc 420
cgcgccgtgt ttgtggatct ggaacccact gtggtcgatg aggtccgtac cggaacctac 480
cgtcagctgt tccaccccga gcagctgatc actggtaagg aggatgcggc caacaactac 540
gcccgtggcc actacaccat cggcaaggag atcgtcgatc tggttctgga caggatccgc 600
aagctggccg atcagtgcac cggtctgcag ggcttcctca tcttccactc gttcggtgga 660
ggtaccggct ccggcttcac ctcgctgctg atggagcgtc tctccgtgga ctacggcaag 720
aagtccaagc tggagttcgc catctaccca gccccccagg tgtccactgc cgtggtcgag 780
ccctacaact ccatcctgac cacccacacc accctggagc attccgactg cgccttcatg 840
gtcgacaacg aggctatcta cgacatctgc cgccgcaatc tggacattga gcgccccacg 900
tacaccaacc tgaaccgtct gattggccag atcgtgtcct cgattaccgc ctctctgcga 960
ttcgatggtg cccttaacgt ggatctgact gagttccaga ccaacttggt gccctaccca 1020
cgtattcact tccctctggt gacctacgcc cccgttatct ccgccgagaa ggcctaccac 1080
gagcagctgt cggtggctga gatcaccaac gcctgcttcg agccggccaa ccagatggtc 1140
agatcggaag agcacacgtc tgaactccag tcacaatcag tctcgtatct cgtatgccgt 1200
cttctgcttg ttgtcgactc tagggataac agggtaatga gtcgacaaca agcagaagac 1260
ggcatacgag attggtcaac gatagtctcg tgggctcgga gatgtgtata agagacagtg 1320
gaggtattgc taataatgct gtctcttata cacatctgac gctgccgacg aatcaccagg 1380
tgtgtgtaga tctcggtggt cgccgtatca ttttgtcgac tc 1422

<210> SEQ ID NO 268
<211> LENGTH: 1572
<212> TYPE: DNA
<213> ORGANISM: Artificial
<220> FEATURE:
<223> OTHER INFORMATION: Polynucleotide

<400> SEQUENCE: 268
gagtcgacaa aatgatacgg cgaccaccga gatctacact ctttccctac acgacgctct 60
tccgatctcg atttctaggt gttacttgtc atattcgttt tacgtttgtc aagcctcata 120
gccggcagtt cgaacgtata cgctctctga gtcagacctc gaaatcgtag ctctacacaa 180
ttctgtgaat tttccttgtc gcgtgtgaaa cacttccaat aaaaactcaa tatgcgtgaa 240
tgtatctcta tccatgttgg tcaggctggt gtccagattg gaaacgcctg ctgggagctc 300
tactgcttgg agcacggcat ccagcccgat ggccagatgc cgtctgacaa gaccgtgggc 360
ggaggtgatg actcgttcaa caccttcttc agcgagactg gagctggcaa gcacgtgccc 420
cgcgccgtgt ttgtggatct ggaacccact gtggtcgatg aggtccgtac cggaacctac 480
cgtcagctgt tccaccccga gcagctgatc actggtaagg aggatgcggc caacaactac 540
gcccgtggcc actacaccat cggcaaggag atcgtcgatc tggttctgga caggatccgc 600
aagctggccg atcagtgcac cggtctgcag ggcttcctca tcttccactc gttcggtgga 660
ggtaccggct ccggcttcac ctcgctgctg atggagcgtc tctccgtgga ctacggcaag 720
aagtccaagc tggagttcgc catctaccca gccccccagg tgtccactgc cgtggtcgag 780
ccctacaact ccatcctgac cacccacacc accctggagc attccgactg cgccttcatg 840
gtcgacaacg aggctatcta cgacatctgc cgccgcaatc tggacattga gcgccccacg 900
tacaccaacc tgaaccgtct gattggccag atcgtgtcct cgattaccgc ctctctgcga 960
ttcgatggtg cccttaacgt ggatctgact gagttccaga ccaacttggt gccctaccca 1020
cgtattcact tccctctggt gacctacgcc cccgttatct ccgccgagaa ggcctaccac 1080
gagcagctgt cggtggctga gatcaccaac gcctgcttcg agccggccaa ccagatggtc 1140
aagtgcgatc cccgtcacgg caagtacatg gcctgctgca tgctgtaccg cggtgatgtt 1200
gtgcccaagg acgtcaacgc cgctattgcc accatcaaga ccaagcgcac cattcaattc 1260
gtcgactggt gccccactgg cttcaaggtt agatcggaag agcacacgtc tgaactccag 1320
tcacaatcag tctcgtatct cgtatgccgt cttctgcttg ttgtcgactc tagggataac 1380
agggtaatga gtcgacaaca agcagaagac ggcatacgag attggtcaac gatagtctcg 1440
tgggctcgga gatgtgtata agagacagcc tgcgtgtgcc gtgtaggact gtctcttata 1500
cacatctgac gctgccgacg aatcaccagg tgtgtgtaga tctcggtggt cgccgtatca 1560
ttttgtcgac tc 1572

<210> SEQ ID NO 269
<211> LENGTH: 1722
<212> TYPE: DNA
<213> ORGANISM: Artificial
<220> FEATURE:
<223> OTHER INFORMATION: Polynucleotide

<400> SEQUENCE: 269
gagtcgacaa aatgatacgg cgaccaccga gatctacact ctttccctac acgacgctct 60
tccgatcttt tgagggtcgc tacagaattc atattcgttt tacgtttgtc aagcctcata 120
gccggcagtt cgaacgtata cgctctctga gtcagacctc gaaatcgtag ctctacacaa 180
ttctgtgaat tttccttgtc gcgtgtgaaa cacttccaat aaaaactcaa tatgcgtgaa 240
tgtatctcta tccatgttgg tcaggctggt gtccagattg gaaacgcctg ctgggagctc 300
tactgcttgg agcacggcat ccagcccgat ggccagatgc cgtctgacaa gaccgtgggc 360
ggaggtgatg actcgttcaa caccttcttc agcgagactg gagctggcaa gcacgtgccc 420
cgcgccgtgt ttgtggatct ggaacccact gtggtcgatg aggtccgtac cggaacctac 480
cgtcagctgt tccaccccga gcagctgatc actggtaagg aggatgcggc caacaactac 540
gcccgtggcc actacaccat cggcaaggag atcgtcgatc tggttctgga caggatccgc 600

```
aagctggccg atcagtgcac cggtctgcag ggcttcctca tcttccactc gttcggtgga    660

ggtaccggct ccggcttcac ctcgctgctg atggagcgtc tctccgtgga ctacggcaag    720

aagtccaagc tggagttcgc catctaccca gccccccagg tgtccactgc cgtggtcgag    780

ccctacaact ccatcctgac cacccacacc accctggagc attccgactg cgccttcatg    840

gtcgacaacg aggctatcta cgacatctgc cgccgcaatc tggacattga gcgccccacg    900

tacaccaacc tgaaccgtct gattggccag atcgtgtcct cgattaccgc ctctctgcga    960

ttcgatggtg cccttaacgt ggatctgact gagttccaga ccaacttggt gccctaccca   1020

cgtattcact tccctctggt gacctacgcc cccgttatct ccgccgagaa ggcctaccac   1080

gagcagctgt cggtggctga gatcaccaac gcctgcttcg agccggccaa ccagatggtc   1140

aagtgcgatc cccgtcacgg caagtacatg gcctgctgca tgctgtaccg cggtgatgtt   1200

gtgcccaagg acgtcaacgc cgctattgcc accatcaaga ccaagcgcac cattcaattc   1260

gtcgactggt gccccactgg cttcaaggtt ggcatcaact accagccacc caccgtggtg   1320

cctggaggtg atttggccaa ggtgcagcgt gccgtgtgca tgttgtccaa caccacggcc   1380

atcgccgagg cctgggcccg tctggaccac aagttcgatc tgatgtacgc caagcgtgcc   1440

agatcggaag agcacacgtc tgaactccag tcacaatcag tctcgtatct cgtatgccgt   1500

cttctgcttg ttgtcgactc tagggataac agggtaatga gtcgacaaca agcagaagac   1560

ggcatacgag attggtcaac gatagtctcg tgggctcgga gatgtgtata agagacagtg   1620

gtttcacctc acgacaagct gtctcttata cacatctgac gctgccgacg aatcaccagg   1680

tgtgtgtaga tctcggtggt cgccgtatca ttttgtcgac tc                      1722
```

<210> SEQ ID NO 270
<211> LENGTH: 22
<212> TYPE: DNA
<213> ORGANISM: Artificial
<220> FEATURE:
<223> OTHER INFORMATION: Polynucleotide

<400> SEQUENCE: 270

```
cgactctaga ggatcgagca ca                                              22
```

<210> SEQ ID NO 271
<211> LENGTH: 20
<212> TYPE: DNA
<213> ORGANISM: Artificial
<220> FEATURE:
<223> OTHER INFORMATION: Polynucleotide

<400> SEQUENCE: 271

```
ttcgagctcg gtacccgcat                                                 20
```

<210> SEQ ID NO 272
<211> LENGTH: 52
<212> TYPE: DNA
<213> ORGANISM: Artificial
<220> FEATURE:
<223> OTHER INFORMATION: Polynucleotide

<400> SEQUENCE: 272

```
tcgtcggcag cgtcagatgt gtataagaga caggtgccag cagccgcggt aa             52
```

<210> SEQ ID NO 273
<211> LENGTH: 54
<212> TYPE: DNA

<213> ORGANISM: Artificial
<220> FEATURE:
<223> OTHER INFORMATION: Polynucleotide

<400> SEQUENCE: 273
gtctcgtggg ctcggagatg tgtataagag acagggacta ccagggtatc taat 54

<210> SEQ ID NO 274
<211> LENGTH: 51
<212> TYPE: DNA
<213> ORGANISM: Artificial
<220> FEATURE:
<223> OTHER INFORMATION: Polynucleotide
<220> FEATURE:
<221> NAME/KEY: misc_feature
<222> LOCATION: (30)..(37)
<223> OTHER INFORMATION: n is a, c, g, or t

<400> SEQUENCE: 274
aatgatacgg cgaccaccga gatctacacn nnnnnnntcg tcggcagcgt c 51

<210> SEQ ID NO 275
<211> LENGTH: 47
<212> TYPE: DNA
<213> ORGANISM: Artificial
<220> FEATURE:
<223> OTHER INFORMATION: Polynucleotide
<220> FEATURE:
<221> NAME/KEY: misc_feature
<222> LOCATION: (25)..(32)
<223> OTHER INFORMATION: n is a, c, g, or t

<400> SEQUENCE: 275
caagcagaag acggcatacg agatnnnnnn nngtctcgtg ggctcgg 47

<210> SEQ ID NO 276
<211> LENGTH: 52
<212> TYPE: DNA
<213> ORGANISM: Artificial
<220> FEATURE:
<223> OTHER INFORMATION: Polynucleotide

<400> SEQUENCE: 276
tcgtcggcag cgtcagatgt gtataagaga caggtgccag cmgccgcggt aa 52

<210> SEQ ID NO 277
<211> LENGTH: 54
<212> TYPE: DNA
<213> ORGANISM: Artificial
<220> FEATURE:
<223> OTHER INFORMATION: Polynucleotide

<400> SEQUENCE: 277
gtctcgtggg ctcggagatg tgtataagag acagggacta chvgggtwtc taat 54

<210> SEQ ID NO 278
<211> LENGTH: 53
<212> TYPE: DNA
<213> ORGANISM: Artificial
<220> FEATURE:
<223> OTHER INFORMATION: Polynucleotide

<400> SEQUENCE: 278
tcgtcggcag cgtcagatgt gtataagaga cagagagttt gatcmtggct cag 53

<210> SEQ ID NO 279
<211> LENGTH: 50

<212> TYPE: DNA
<213> ORGANISM: Artificial
<220> FEATURE:
<223> OTHER INFORMATION: Polynucleotide

<400> SEQUENCE: 279
tcgtcggcag cgtcagatgt gtataagaga cagcctacgg gaggcagcag 50

<210> SEQ ID NO 280
<211> LENGTH: 52
<212> TYPE: DNA
<213> ORGANISM: Artificial
<220> FEATURE:
<223> OTHER INFORMATION: Polynucleotide

<400> SEQUENCE: 280
tcgtcggcag cgtcagatgt gtataagaga caggtgccag cmgccgcggt aa 52

<210> SEQ ID NO 281
<211> LENGTH: 47
<212> TYPE: DNA
<213> ORGANISM: Artificial
<220> FEATURE:
<223> OTHER INFORMATION: Polynucleotide

<400> SEQUENCE: 281
tcgtcggcag cgtcagatgt gtataagaga cagrggatta gataccc 47

<210> SEQ ID NO 282
<211> LENGTH: 51
<212> TYPE: DNA
<213> ORGANISM: Artificial
<220> FEATURE:
<223> OTHER INFORMATION: Polynucleotide

<400> SEQUENCE: 282
gtctcgtggg ctcggagatg tgtataagag acagattacc gcggctgctg g 51

<210> SEQ ID NO 283
<211> LENGTH: 54
<212> TYPE: DNA
<213> ORGANISM: Artificial
<220> FEATURE:
<223> OTHER INFORMATION: Polynucleotide

<400> SEQUENCE: 283
gtctcgtggg ctcggagatg tgtataagag acagggacta chvgggtwtc taat 54

<210> SEQ ID NO 284
<211> LENGTH: 54
<212> TYPE: DNA
<213> ORGANISM: Artificial
<220> FEATURE:
<223> OTHER INFORMATION: Polynucleotide

<400> SEQUENCE: 284
gtctcgtggg ctcggagatg tgtataagag acagggacta chvgggtwtc taat 54

<210> SEQ ID NO 285
<211> LENGTH: 53
<212> TYPE: DNA
<213> ORGANISM: Artificial
<220> FEATURE:
<223> OTHER INFORMATION: Polynucleotide
<220> FEATURE:
<221> NAME/KEY: misc_feature
<222> LOCATION: (48)..(48)

<223> OTHER INFORMATION: n is a, c, g, or t

<400> SEQUENCE: 285
gtctcgtggg ctcggagatg tgtataagag acagcgacrr ccatgcanca cct 53

<210> SEQ ID NO 286
<211> LENGTH: 20
<212> TYPE: DNA
<213> ORGANISM: Artificial
<220> FEATURE:
<223> OTHER INFORMATION: Polynucleotide

<400> SEQUENCE: 286
aatgatacgg cgaccaccga 20

<210> SEQ ID NO 287
<211> LENGTH: 21
<212> TYPE: DNA
<213> ORGANISM: Artificial
<220> FEATURE:
<223> OTHER INFORMATION: Polynucleotide

<400> SEQUENCE: 287
caagcagaag acggcatacg a 21

<210> SEQ ID NO 288
<211> LENGTH: 19
<212> TYPE: DNA
<213> ORGANISM: Artificial
<220> FEATURE:
<223> OTHER INFORMATION: Polynucleotide

<400> SEQUENCE: 288
gtgccagcag ccgcggtaa 19

<210> SEQ ID NO 289
<211> LENGTH: 19
<212> TYPE: DNA
<213> ORGANISM: Artificial
<220> FEATURE:
<223> OTHER INFORMATION: Polynucleotide

<400> SEQUENCE: 289
gtgccagcaa ccgcggtaa 19

<210> SEQ ID NO 290
<211> LENGTH: 19
<212> TYPE: DNA
<213> ORGANISM: Artificial
<220> FEATURE:
<223> OTHER INFORMATION: Polynucleotide

<400> SEQUENCE: 290
gtgccagcat ccgcggtaa 19

<210> SEQ ID NO 291
<211> LENGTH: 19
<212> TYPE: DNA
<213> ORGANISM: Artificial
<220> FEATURE:
<223> OTHER INFORMATION: Polynucleotide

<400> SEQUENCE: 291
gtgccagcac ccgcggtaa 19

<210> SEQ ID NO 292
<211> LENGTH: 19
<212> TYPE: DNA
<213> ORGANISM: Artificial
<220> FEATURE:
<223> OTHER INFORMATION: Polynucleotide

<400> SEQUENCE: 292
gtgccagcag acgcggtaa 19

<210> SEQ ID NO 293
<211> LENGTH: 19
<212> TYPE: DNA
<213> ORGANISM: Artificial
<220> FEATURE:
<223> OTHER INFORMATION: Polynucleotide

<400> SEQUENCE: 293
gtgccagcag tcgcggtaa 19

<210> SEQ ID NO 294
<211> LENGTH: 19
<212> TYPE: DNA
<213> ORGANISM: Artificial
<220> FEATURE:
<223> OTHER INFORMATION: Polynucleotide

<400> SEQUENCE: 294
gtgccagcag gcgcggtaa 19

<210> SEQ ID NO 295
<211> LENGTH: 19
<212> TYPE: DNA
<213> ORGANISM: Artificial
<220> FEATURE:
<223> OTHER INFORMATION: Polynucleotide

<400> SEQUENCE: 295
gtgccagcag cagcggtaa 19

<210> SEQ ID NO 296
<211> LENGTH: 19
<212> TYPE: DNA
<213> ORGANISM: Artificial
<220> FEATURE:
<223> OTHER INFORMATION: Polynucleotide

<400> SEQUENCE: 296
gtgccagcag ctgcggtaa 19

<210> SEQ ID NO 297
<211> LENGTH: 19
<212> TYPE: DNA
<213> ORGANISM: Artificial
<220> FEATURE:
<223> OTHER INFORMATION: Polynucleotide

<400> SEQUENCE: 297
gtgccagcag cggcggtaa 19

<210> SEQ ID NO 298
<211> LENGTH: 19
<212> TYPE: DNA
<213> ORGANISM: Artificial
<220> FEATURE:
<223> OTHER INFORMATION: Polynucleotide

<400> SEQUENCE: 298
gtgccagcag ccacggtaa 19

<210> SEQ ID NO 299
<211> LENGTH: 19
<212> TYPE: DNA
<213> ORGANISM: Artificial
<220> FEATURE:
<223> OTHER INFORMATION: Polynucleotide

<400> SEQUENCE: 299
gtgccagcag cctcggtaa 19

<210> SEQ ID NO 300
<211> LENGTH: 19
<212> TYPE: DNA
<213> ORGANISM: Artificial
<220> FEATURE:
<223> OTHER INFORMATION: Polynucleotide

<400> SEQUENCE: 300
gtgccagcag ccccggtaa 19

<210> SEQ ID NO 301
<211> LENGTH: 19
<212> TYPE: DNA
<213> ORGANISM: Artificial
<220> FEATURE:
<223> OTHER INFORMATION: Polynucleotide

<400> SEQUENCE: 301
gtgccagcag ccgaggtaa 19

<210> SEQ ID NO 302
<211> LENGTH: 19
<212> TYPE: DNA
<213> ORGANISM: Artificial
<220> FEATURE:
<223> OTHER INFORMATION: Polynucleotide

<400> SEQUENCE: 302
gtgccagcag ccgtggtaa 19

<210> SEQ ID NO 303
<211> LENGTH: 19
<212> TYPE: DNA
<213> ORGANISM: Artificial
<220> FEATURE:
<223> OTHER INFORMATION: Polynucleotide

<400> SEQUENCE: 303
gtgccagcag ccggggtaa 19

<210> SEQ ID NO 304
<211> LENGTH: 19
<212> TYPE: DNA
<213> ORGANISM: Artificial
<220> FEATURE:
<223> OTHER INFORMATION: Polynucleotide

<400> SEQUENCE: 304
gtgccagcag ccgcagtaa 19

<210> SEQ ID NO 305
<211> LENGTH: 19

<212> TYPE: DNA
<213> ORGANISM: Artificial
<220> FEATURE:
<223> OTHER INFORMATION: Polynucleotide

<400> SEQUENCE: 305
gtgccagcag ccgctgtaa 19

<210> SEQ ID NO 306
<211> LENGTH: 19
<212> TYPE: DNA
<213> ORGANISM: Artificial
<220> FEATURE:
<223> OTHER INFORMATION: Polynucleotide

<400> SEQUENCE: 306
gtgccagcag ccgccgtaa 19

<210> SEQ ID NO 307
<211> LENGTH: 19
<212> TYPE: DNA
<213> ORGANISM: Artificial
<220> FEATURE:
<223> OTHER INFORMATION: Polynucleotide

<400> SEQUENCE: 307
gtgccagcag ccgcgataa 19

<210> SEQ ID NO 308
<211> LENGTH: 19
<212> TYPE: DNA
<213> ORGANISM: Artificial
<220> FEATURE:
<223> OTHER INFORMATION: Polynucleotide

<400> SEQUENCE: 308
gtgccagcag ccgcgttaa 19

<210> SEQ ID NO 309
<211> LENGTH: 19
<212> TYPE: DNA
<213> ORGANISM: Artificial
<220> FEATURE:
<223> OTHER INFORMATION: Polynucleotide

<400> SEQUENCE: 309
gtgccagcag ccgcgctaa 19

<210> SEQ ID NO 310
<211> LENGTH: 19
<212> TYPE: DNA
<213> ORGANISM: Artificial
<220> FEATURE:
<223> OTHER INFORMATION: Polynucleotide

<400> SEQUENCE: 310
gtgccagcag ccgcggaaa 19

<210> SEQ ID NO 311
<211> LENGTH: 19
<212> TYPE: DNA
<213> ORGANISM: Artificial
<220> FEATURE:
<223> OTHER INFORMATION: Polynucleotide

<400> SEQUENCE: 311
gtgccagcag ccgcgggaa 19

<210> SEQ ID NO 312
<211> LENGTH: 19
<212> TYPE: DNA
<213> ORGANISM: Artificial
<220> FEATURE:
<223> OTHER INFORMATION: Polynucleotide

<400> SEQUENCE: 312
gtgccagcag ccgcggcaa 19

<210> SEQ ID NO 313
<211> LENGTH: 19
<212> TYPE: DNA
<213> ORGANISM: Artificial
<220> FEATURE:
<223> OTHER INFORMATION: Polynucleotide

<400> SEQUENCE: 313
gtgccagcag ccgcggtta 19

<210> SEQ ID NO 314
<211> LENGTH: 19
<212> TYPE: DNA
<213> ORGANISM: Artificial
<220> FEATURE:
<223> OTHER INFORMATION: Polynucleotide

<400> SEQUENCE: 314
gtgccagcag ccgcggtga 19

<210> SEQ ID NO 315
<211> LENGTH: 19
<212> TYPE: DNA
<213> ORGANISM: Artificial
<220> FEATURE:
<223> OTHER INFORMATION: Polynucleotide

<400> SEQUENCE: 315
gtgccagcag ccgcggtca 19

<210> SEQ ID NO 316
<211> LENGTH: 19
<212> TYPE: DNA
<213> ORGANISM: Artificial
<220> FEATURE:
<223> OTHER INFORMATION: Polynucleotide

<400> SEQUENCE: 316
gtgccagcag ccgcggtat 19

<210> SEQ ID NO 317
<211> LENGTH: 19
<212> TYPE: DNA
<213> ORGANISM: Artificial
<220> FEATURE:
<223> OTHER INFORMATION: Polynucleotide

<400> SEQUENCE: 317
gtgccagcag ccgcggtag 19

<210> SEQ ID NO 318
<211> LENGTH: 19
<212> TYPE: DNA
<213> ORGANISM: Artificial

<220> FEATURE:
<223> OTHER INFORMATION: Polynucleotide

<400> SEQUENCE: 318
gtgccagcag ccgcggtac 19

<210> SEQ ID NO 319
<211> LENGTH: 19
<212> TYPE: DNA
<213> ORGANISM: Propionibacterium acnes

<400> SEQUENCE: 319
gtgccagcag ccgcggtga 19

<210> SEQ ID NO 320
<211> LENGTH: 19
<212> TYPE: DNA
<213> ORGANISM: Artificial
<220> FEATURE:
<223> OTHER INFORMATION: Polynucleotide

<400> SEQUENCE: 320
gtgccagcmg ccgcggtaa 19

<210> SEQ ID NO 321
<211> LENGTH: 20
<212> TYPE: DNA
<213> ORGANISM: Propionibacterium acnes

<400> SEQUENCE: 321
ggactaccag ggtatctaag 20

<210> SEQ ID NO 322
<211> LENGTH: 20
<212> TYPE: DNA
<213> ORGANISM: Artificial
<220> FEATURE:
<223> OTHER INFORMATION: Polynucleotide

<400> SEQUENCE: 322
ggactachvg ggtwtctaat 20

<210> SEQ ID NO 323
<211> LENGTH: 10
<212> TYPE: DNA
<213> ORGANISM: Artificial
<220> FEATURE:
<223> OTHER INFORMATION: Polynucleotide

<400> SEQUENCE: 323
actgatcgct 10

<210> SEQ ID NO 324
<211> LENGTH: 10
<212> TYPE: DNA
<213> ORGANISM: Artificial
<220> FEATURE:
<223> OTHER INFORMATION: Polynucleotide

<400> SEQUENCE: 324
tgactgtcgc 10

<210> SEQ ID NO 325
<211> LENGTH: 10
<212> TYPE: DNA

-continued

```
<213> ORGANISM: Artificial
<220> FEATURE:
<223> OTHER INFORMATION: Polynucleotide

<400> SEQUENCE: 325

atggctaggg                                                              10


<210> SEQ ID NO 326
<211> LENGTH: 10
<212> TYPE: DNA
<213> ORGANISM: Artificial
<220> FEATURE:
<223> OTHER INFORMATION: Polynucleotide

<400> SEQUENCE: 326

ctacttatcg                                                              10


<210> SEQ ID NO 327
<211> LENGTH: 10
<212> TYPE: DNA
<213> ORGANISM: Artificial
<220> FEATURE:
<223> OTHER INFORMATION: Polynucleotide

<400> SEQUENCE: 327

gccgcggtaa                                                              10


<210> SEQ ID NO 328
<211> LENGTH: 32
<212> TYPE: DNA
<213> ORGANISM: Artificial
<220> FEATURE:
<223> OTHER INFORMATION: Polynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (6)..(8)
<223> OTHER INFORMATION: n is a, c, g, or t
<220> FEATURE:
<221> NAME/KEY: misc_feature
<222> LOCATION: (23)..(25)
<223> OTHER INFORMATION: n is a, c, g, or t
<220> FEATURE:
<221> NAME/KEY: misc_feature
<222> LOCATION: (28)..(30)
<223> OTHER INFORMATION: n is a, c, g, or t

<400> SEQUENCE: 328

nnnwwnnnww ggataagtgc aannnwwnnn ww                                     32
```